(12) United States Patent
Loosmore et al.

(10) Patent No.: US 6,432,669 B1
(45) Date of Patent: Aug. 13, 2002

(54) **PROTECTIVE RECOMBINANT *HAEMOPHILUS INFLUENZAE* HIGH MOLECULAR WEIGHT PROTEINS**

(75) Inventors: Sheena M. Loosmore, Aurora; Yan-Ping Yang; Michel H. Klein, both of Willowdale, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/206,942

(22) Filed: Dec. 8, 1998

Related U.S. Application Data

(63) Continuation-in-part of application No. 09/167,568, filed on Oct. 7, 1998, now abandoned.

(51) Int. Cl.$^7$ ................................................ C12P 21/06
(52) U.S. Cl. ..................... 435/69.1; 435/69.3; 435/69.7; 435/71.1; 435/243; 435/252.3; 435/320.1; 536/23.1; 536/23.7; 536/24.1; 424/256.1
(58) Field of Search .............................. 435/320.1, 69.1, 435/243, 252.3, 69.3, 71.1, 69.7; 424/256.1; 536/23.1, 23.7, 24.1

(56) References Cited

U.S. PATENT DOCUMENTS

| | | | |
|---|---|---|---|
| 4,496,538 A | 1/1985 | Gordon | 424/92 |
| 5,194,254 A | 3/1993 | Barber et al. | 424/85.8 |
| 5,603,938 A | 2/1997 | Barenkamp | 424/256.1 |

FOREIGN PATENT DOCUMENTS

| | | |
|---|---|---|
| EP | 0502637 | 9/1992 |
| WO | WO 92/17167 | 10/1992 |
| WO | WO 93/19090 A | 9/1994 |
| WO | WO 94/21290 A | 9/1994 |
| WO | WO 97/36914 | 10/1997 |
| WO | WO 97/36914 A | 10/1997 |

OTHER PUBLICATIONS

Murphy et al. Pedatr. Infect. Dis. J., 1989, 8(1): S66–S68, 1989.*
Yamanaka et al. J. Pediatrics. 1993. 122(2): 212–218, 1993.*
Barenkamp, S.J.: Inf. Immun., vol. 64, No. 4, Apr. 1996, pp. 1245–1251.
Barenkamp, S.J. et al, Infection and Immunity, U.S., American Society for Microbiology, Washington, vol. 62, No. 8, Aug. 1, 1994, pp. 3320–3328.
St. Geme III, J.W. et al, Mol. Microbiol., vol. 27, No. 3, Feb. 1998 pp. 617–630.
Dawid, S.R. et al, Abstracts of the 1998 General Meeting of The American Society for Microbiology, vol. 98, May 17, 1998, p. 74.
St. Geme III, J.W. et al, Infection and Immunity, vol. 66, No. 1, Jan. 1998, pp. 364–368.
Berkowitz et al. 1987. J. Pediatr. 110:509.
Claesson et al. 1989. J. Pediatr. 114:97.

Black, S.B., H.R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97–104.
Madore, D.V. 1996. Impact of immunization on *Haemophilus influenzae* type b disease. Infectious Agents and Disease 5:8–20.
Bluestone, C.D. 1982. Current concepts in otolaryngology. Otitis media in children: to treat or not to treat? N. Engl. J. Med. 306:1399–1404.
Barenkamp, S.J., and F.F. Bodor. 1990. Development of serum bactericidal activity following nontypable *Haemophilus influenzae* acute otitis media. Pediatr. Infect. Dis. 9:333–339.
Barenkamp, S.J., and E. Leininger. 1992. Cloning, expression, and DNA sequence analysis of genes encoding nontypeable *Haemophilus influenzae* high–molecular–weight surface–exposed proteins related to filamentous hemagglutinin of *Bordetella pertussis*. Infect. Immun. 60:1302–1313.
Barenkamp, S.J., and J.W. St. Geme III. 1994. Genes encoding high–molecular–weight adhesion proteins of nontypeable *Haemophilus influenzae* are part of gene clusters. Infect. Immun. 62:3320–3328.
St. Geme III, J.W. and S. Grass. 1998. Secretion of the *Haemophilus influenzae* HMW1 and HMW2 adhesins involves a periplasmic intermediate and requires the HMWB and HMWC proteins. Molec. Microbiol. 27:617–630.
St. Geme III, J.W., S. Falkow, and S.J. Barenkamp. 1993. High–molecular–weight proteins of nontypeable *Haemophilus influenzae* mediate attachment to human epithelial cells. Proc. Natl. Acad. Sci. USA 90:2875–2879.
Barenkamp, S.J. 1996. Immunization with high–molecular–weight adhesion proteins of nontypeable *Haemophilus influenzae* modifies experimental otitis media in chinchillas. Infect. Immun. 64:1246–1251.
Tabor, S., and C.C. Richardson. 1985. A bacteriophage T7 RNA polymerase/promoter system for controlled exclusive expression of specific genes. Proc. Natl. Acad. Sci. USA 82:1074–1078.

(List continued on next page.)

Primary Examiner—Jennifer E. Graser
(74) Attorney, Agent, or Firm—Sim & McBurney

(57) ABSTRACT

Protective high molecular weight (HMW) proteins are produced recombinantly by expression from *E. coli* by using a promoter effective in *E. coli* and a nucleic acid molecule which contains a modified operon of a non-typeable strain of Haemophilus. The modified operon contains the portion only of the A region which encodes the mature HMW protein and the complete B and C regions of the operon. Enhanced levels of expression of the HMW proteins can be achieved by including the *E. coli* cer gene, a further copy of the portion of the A region of the operon encoding the mature protein or both in the expression vector. Nucleotide and deduced amino acid sequences of the hmw1 and hmw2 genes and HMW1 and HMW2 proteins, respectively of several non-typeable *Haemophilus influenzae* strain have been identified.

21 Claims, 235 Drawing Sheets

OTHER PUBLICATIONS

Patient, M.E., and D.K. Summers. 1993. ColE1 multimer formation triggers inhibition of *Escherichia coli* cell division. Molec. Microbiol. 9:1089–1095.

Barenkamp, S. 1986. Protection by serum antibodies in experimental nontypeable *Haemophilus influenzae* otitis media. Infect. Immun. 52:572–578.

Yang, Y.–P., S.M. Loosmore, B. Underdown, and M.H. Klein. 1998. Nasopharyngeal colonization with nontypeable H. influenzae in chinchillas. Infect. Immun. 66:1973–1980.

Fleischmann et al. 1995. Whole–genome random sequencing and assembly of *Haemophilus influenzae* Rd. Science 269:496–512.

O'Hagan, DT. 1992. Oral delivery of vaccines. Formulation and clinical pharmaco kinetic considerations. Clin. Pharmacokinet 22(t): 1–10.

Ulmer et al. 1993. Curr. Opinion Invest. Drugs 2:983–989.

Lockhoff, O., 1991. Glycolipids as immunomodulators: Synthesis and properties.

Nixon–George A., et al., 1990. The adjuvant effect of stearyl tyrosine on a recombinant subunit hepatitis B surface antigen. J. Immunol 144 (12):4798–4802.

* cited by examiner

FIG.1B

Oligonucleotides to re-create the N-terminus of the full-length HMW1A protein in plasmid DS-1091-2 or the N-terminus of the full-length HMW2A protein in plasmid DS-1094-2.

|  | SEQ ID NO |
|---|---|
| M N K I Y R L K F S K R L N A BsmI | 1 |
| CTAGAAATAATTTGTTTAACTTTAAGAAGGAGATATACATATGAACAAGATATATCGTCTCAAATTCAGCAAACGCCTGAATGCT | 2 |
| TTTATTAAACAAATTGAAATTCTTCCTCTATATGTATACTTGTTCTATATAGCAGAGTTTAAGTCGTTTGCGGACTTAC | 3 |

Xba I →
← BsmI

Construction of DS-1094-2, a T7 *hmw2ABC (155)* plasmid.

FIG.3B

Oligonucleotides to re-create the N-terminus of the mature HMW1A protein in plasmid DS-1046-1-1.

|  | SEQ ID NO |
|---|---|
| Xba I →<br>CTAGAAATAATTTGTTAACTTTAAGAAGAGATATACATATGCCGGATAATGTAT...<br>TTTATTAAACAATTGAAATTCTTCTCTATATGTATACGGCTATTACATA...<br>     M  P  D  N  V ...<br>...S  I  N  A  E  T  A  G  R  S  N  T  S  E  D  D  E  Y  T  BamH I→<br>...CTATTAATGCAGAAACAGCAGGACGCAGCAATACTTCAGAAGACGATGAATACACG<br>...GATAATTAGCGTCTTTGTCGTCCGTCGTTATGAAGTCTTCTGCTACTTATGTGCCCTAG | 4<br>5<br>6 |

FIG. 4B

Oligonucleotides used to re-create the N-terminus of the HMW2A protein in plasmid DS-1200-3.

| | SEQ ID NO |
|---|---|
| Xba I → | |
| CTAGAAATAATTTGTTAACTTTAAGAAGAGATATACATATGCCTGATGATG... | 7 |
|    TTTATTAAACAATTGAAATTCTTCTCTATATGTATACGGACTACTAC... | 8 |
|                            M  P  D  D ... | |
| | |
|                         ...V  T  I  E  A  E  D  P  L  R  N  N  T  G  I  N  D  EcoR I → | |
| ...TAACAATTGAAGCGGAAGACCCCCTTCGCAATAATACGGTATAAATGATG | 9 |
| ...ATTGTTAACTTCGCCTTCTGGGGGAAGGTTATTATGCCATATTTACTACTTAA | |

Construction of JB-2330-7, a T7 hmw1A (125) plasmid.

FIG. 6B

Oligonucleotides used to PCR amplify the 3'-end of *hmw1A*.

|  | SEQ ID NO |
|---|---|
| sense | |

```
              Kpn I
        T  S  G  T  L  V  I  N  A  K  D  A  E
5' CAACCAGCGGTACCTTGGTTATTAATCGCAAAGACGCTGAG 3'     5358.JS    10
                                                               11
``` antisense

```
        V  N  I  A  D  N  G  R  *
   GGGTTAATATCCTGATAACCGGCGGTAG                                12
3' CCCAATTATAGGACTATTGCCGCCATCGAGCTCTTCGAACCGG 5'   5359.JS    13
                                  Xho I Hind III               14
```

FIG. 8B

Oligonucleotides used to PCR amplify the 3'-end of *hmM2A*.

SEQ ID NO sense

EcoR I

↓      K  R  V  L  E  K  V  K

5'  CCGGAATTCCGAAACGCGTCCTTGAAAAAGTAAAAG  3'    5360.DC    15
                                                                        16 antisense

T  N  V  A  D  D  D  G  Q  P  *

3'  TACCAATGTTGCTGACGATGGACAGCCGTAG
    ATGGTTACAACGACTGCTACCTGTGGCATCCTAGGCGC  5'    5361.DC    17
                                  ↑                                       18
                              BamH I                                    19

Construction of BK-86-1-1, a *T7 hmw1A/T7 hmw1ABC/KanR* plasmid.

Extraction of rHMW1 from *E. coli*

FIG.15.

The Stability of rHMW1 (abc/cer)

-20C (+ 20% glycerol)

Kinetics of Antibody Response to rHMW1 in Mice

FIG. 17

Oligonucleotides used to PCR amplify hmwA genes from NTHi strains.

sense

```
          EcoR I      K   E   W   L   L   D   P
5'   GGGAATTCCAAAGAGTGGTTGTTAGACCCCGGA   3'     5522.SL
```

| | SEQ ID NO |
|---|---|
| | 20 |
| | 21 | antisense

```
      M   K   N   I   K   S   R   L   K   L
      ATGAAAAATATAAAGCAGATTAAAACTC
3'  TACTTTTTATATTTCGTCTAATTTTGAGGCTTAAGG   5'    5523.SL
                                        ↑
                                      EcoR I
```

| | SEQ ID NO |
|---|---|
| | 22 |
| | 23 |
| | 24 |

FIG. 18A  Joyc hmw1A sequence

```
          LYS GLU TRP LEU LEU ASP PRO ASP ASN VAL  ...
          A A A G A A T G G T T G T T A G A C C C G G A C A A T G T A T ...
                         10                      20                      30

ASP ALA SER PRO THR GLU ASP PHE PRO THR         ...SER ILE ASN ALA GLY THR SER GLU ARG ASN
G A C G C T T C A C C A A C A G A A G A T T T C C C T A C C G...  C C A T T A A C G C A G G C A C A T C A G A A C G T A A C
                  70                      80                      90              40                                          50                      60

...GLY ALA GLY GLY LYS ASP ASN PRO LYS LYS
                                                 ...G A G C A G G A G G A A A A G G A T A A C C C C A A A A A A
                                                                100                        110                      120

ASN ALA HIS ASN LYS PRO THR LEU ILE ASN         ...THR THR LEU GLU ARG ILE LEU SER GLY ASN
A A C G C T C A C A A C A A A C C G A C A T T A A T A A A C A...  C A A C T C T T G A G C G T A T A T T A A G T G G C A A C
                  130                     140                     150             160                     170                     180

THR PHE VAL ASN ILE THR ALA ARG LYS ARG         ...
A C C T T T G T T A A T A T C A C T G C C A G A A A A A G A A ...
                  190                     200                     210
```

FIG.18B

```
                              ...ILE THR VAL ASN SER ASP ILE ASN ILE LYS
                              ...T C A C A G T T A A T A G T G A T A T C A A C A T C A A A
                                                        220           230           240
                              ...

ASP SER SER HIS LEU ILE LEU TRP SER GLU      ...ASN ASP ASN SER SER GLY VAL ASP ILE LYS
G A C A G C T C C C A T C T A A T A C T C T G G A G C G A A A ... A T G A T A A C A G C A G C G G C G T T G A T A T T A A A
              250           260           270 ...                 280           290           300
                                             ...

GLY ASN ILE THR SER THR THR GLY GLY SER      ...LEU THR ILE TYR SER SER GLY TRP ILE ASP
G G C A A T A T C A C T T C T A C T A C T G G C G G A A G C T ... T A A C T A T T T A C T C C A G C G G C T G G A T T G A T
              310           320           330 ...                 340           350           360
                                             ...

ILE HIS LYS ASN ILE THR LEU ASN SER GLY      ...LEU LEU ASN ILE THR THR LYS GLN GLY ASP
A T T C A T A A A A A C A T T A C G C T T A A T T C A G G G C ... T C T T A A A C A T T A C A A C T A A A C A A G G A G A T
              370           380           390 ...                 400           410           420
                                             ...
```

FIG. 18C

```
ILE ALA PHE GLU LYS GLY ASN ASN PRO THR              ...ILE THR GLY GLN GLY THR ILE THR ALA GLY
ATCGCCTTCGAAAAAGGGAATAACCCAACCA...           ...TTACAGGTCAAGGGACTATTACCGCAGGC
          430            440            450            460            470            480

ASN GLY LYS GLY PHE ARG PHE GLU ASN ALA              ...SER LEU ASN GLY ILE GLY THR GLY LEU LEU
AATGGTAAAGGTTTTAGGTTTGAAAACGCCT...           ...CCCTAAACGGTATTGGAACAGGGTTACTT
          490            500            510            520            530            540

PHE ASN ILE LYS ARG ASP LEU GLY ASN ASN              ...PHE GLN ILE ILE ASN PHE PHE ASN GLY THR
TTTAACATCAAAAGGGATTTAGGAAATAATT...           ...TCCAAATCATAAACTTTTTTAACGGAACT
          550            560            570            580            590            600

LEU ASN ILE SER GLY LYS VAL ASN ILE SER
TTAAATATTTCAGGGAAAGTAAACATCTCAA...
          610            620            630
```

FIG. 18D

```
                        ...MET VAL ILE PRO LYS LYS TRP ASP TYR SER
                        ...T G G T C A T A C C T A A A A A A T G G G A T T A T A G T
                                              640           650           660

LYS PHE ARG GLY ARG THR TYR TRP ASN VAL  ...
A A A T T C A G G G G G C G A A C C T A T T G G A A C G T A A...
              670           680           690

PHE ASN LEU THR ILE ASP SER ARG GLY ASP  ...THR HIS LEU ASN VAL SER GLU GLY SER LYS
T T T A A C C T C A C T A T C G A C T C C A G A G G A G A T G... C C C A T T T A A A T G T T T C C G A A G G C A G T A A G
              730           740           750                         700           710           720

...ASP THR ALA GLY THR LEU ASN THR PRO TYR
                        ...A C A C T G C A G G C A C C C T T A A C A C C C C T T A T
                                              760           770           780

ASN LEU ASN GLY ILE SER PHE ASN LYS ASP  ...THR ILE PHE ASP VAL LYS GLN ASN GLY ALA
A A T T T A A A C G G T A T A T C A T T C A A C A A A G A C A... C T A T C T T T G A T G T T A A A C A A A A C G G G G C A
              790           800           810                         820           830           840
```

FIG.18E

```
VAL THR PHE ASP ILE LYS ALA PRO ILE GLY ...
GTCACCTTTGACATCAAGGCGCCAATAGGGG...
         850              860          870

...VAL ASN ASN ARG ASN LEU ASN TYR ALA
                       ...TAAATAATAATCGTAATTTGAATTACGCA
                                   880              890              900

SER PHE ASN GLY ASN ILE SER VAL SER GLY ...
TCATTCAATGGAAATATTTCAGTTTCAGGAG...
         910              920          930

...GLY GLY ASN VAL THR PHE LYS LEU ALA
                       ...GAGGGAATGTCACTTTCAAACTTCTCGCC
                                   940              950              960

SER SER SER THR ALA GLN THR PRO GLY VAL ...
TCATCCCTCTACCGCTCAAACTCCCGGTGTAT...
         970              980          990

...PHE ILE ASN SER LYS HIS PHE ASN ALA SER
                       ...TTATAAATTCTAAACACTTTAATGCTTCA
                                   1000             1010             1020

GLY GLY SER SER LEU GLU PHE ARG THR GLU ...
GGAGGGTCGAGTTTAGAATTTAGAAACTGAAG...
         1030             1040         1050
```

FIG. 18F

```
                                        ...GLY SER THR LYS VAL GLY PHE LEU ILE ASN
                                        ...G C T C A A C A A A A G T C G G C T T C T T G A T A A A T
                                                            1060                1070              1080

ASN ASP LEU THR LEU ASN ALA THR GLY GLY ...
A A T G A T T T A A C C C T A A A T G C C A C C G G A G G T A ...
              1090                1100              1110
                                        ...ASN ILE SER LEU LEU GLN VAL GLU GLY ILE
                                        ...A C A T A T C G C T C T T G C A A G T T G A A G G C A T T
                                                            1120                1130              1140

ASP GLY MET ILE GLY LYS GLY VAL VAL ALA ...
G A C G G G A T G A T T G G T A A A G G C G T T G T A G C T A ...
              1150                1160              1170
                                        ...LYS LYS ASN ILE THR PHE ALA GLY GLY ASN
                                        ...A A A A A A C A T A A C C T T T G C T G G A G G C A A T
                                                            1180                1190              1200

ILE THR PHE GLY SER LYS LYS ALA ILE THR ...
A T C A C C T T T G G C T C C A A G A A A G C C A T A A C A G ...
              1210                1220              1230
                                        ...GLU ILE GLU GLY ASN ALA THR ILE ASN ASN
                                        ...A A A T C G A A G G C A A T G C T A C T A T C A A T A A C
                                                            1240                1250              1260
```

FIG.18G

```
ASN ALA ASN VAL THR LEU ILE GLY SER ASP ...
A A C G C T A A C G T C A C T C T T A T C G G T T C G G A T T ...
                    1270                    1280                    1290
                                                        ...PHE ASP ASN HIS GLN LYS PRO LEU THR ILE
                                                        ...T T G A C A A C C A T C A A A A C C T T T A A C T A T T
                                                                            1300        1310        1320

LYS LYS ASP VAL ILE ILE ASN SER GLY ASN ...
A A A A A G A T G T C A T C A T T A A T A G C G G C A A C C ...
                    1330                    1340                    1350
                                                        ...LEU THR ALA GLY GLY ASN VAL ILE ASN ILE
                                                        ...T T A C C G C T G G C G G C A A T G T T A T C A A T A T A
                                                                            1360        1370        1380

ASN GLY ASN LEU THR VAL ASN ASN GLY ALA ...
A A C G G A A A T C T T A C C G T T A A C A A T G G C G C C A ...
                    1390                    1400                    1410
                                                        ...ASN LEU LYS ALA ILE THR ASN PHE THR PHE
                                                        ...A T C T T A A A G C T A T C A C A A A T T T C A C T T T T
                                                                            1420        1430        1440

ASN VAL GLY GLY LEU PHE ASP ASN LYS GLY ...
A A T G T A G G C G G C T T G T T T G A C A A C A A A G G C A ...
                    1450                    1460                    1470
```

FIG.18H

```
ALA LYS PHE LYS ASP ILE ASN ASN THR SER ...ASN SER ASN ILE SER ILE ALA ARG GLY GLY
GCTAAATTTAAAGATATCAATAACACCAGTA... ATTCAAATATCTCCATTGCTAGAGGAGGG
          1510              1520    1530        1480         1490        1500

THR TYR ARG THR ILE ILE GLU GLY ASN ILE ...SER LEU ASN ILE THR THR ASN SER ASP THR
ACTTACCGTACCATTATAGAAGGTAATATAA... GCTTAAATATTACCACCAACTCCGACACC
          1570              1580    1590        1540         1550        1560

ASP ASN LYS GLY ASN ALA GLU ILE GLN ILE ...THR ASN LYS ALA GLY ASP LEU ASN ILE ILE
GATAATAAAGGTAACGCTGAAATCCAAATTG... CCAACAAAGCAGGTGATTTGAATATCATT
          1630              1640    1650        1600         1610        1620

...GLY GLY ASN ILE SER GLN LYS GLU GLY ASN
                                            GCGGCAATATCTCGCAAAAGAAGGTAAT
                                                 1660         1670        1680
```

FIG.18I

LEU THR ILE SER SER ASP LYS ILE ASN ILE ...  ...THR ASN GLN ILE THR ILE LYS LYS GLY VAL
CTCACGATTTCTTCCGATAAAATTAATATCA...      ...CTAACCAGATAACAATCAAGAAGGGTGTT
       1690          1700          1710              1720          1730          1740

ASN LYS GLU ASP SER ASP SER SER THR ALA ...  ...ASN ASN ALA ASN LEU THR ILE LYS THR LYS
AATAAAGAGGATTCTGATTCAAGCACGGCAA...      ...ACAATGCTAATCTAACCATTAAAACCAAA
       1750          1760          1770              1780          1790          1800

GLU LEU GLN LEU THR GLY ASP LEU ASN ILE ...  ...SER GLY PHE ASP LYS ALA GLU ILE THR ALA
GAATTGCAATTAACGGGAGACCTAAATATTT...      ...CAGGCTTCGATAAAGCAGAAATCACAGCC
       1810          1820          1830              1840          1850          1860

LYS GLU GLY ALA ASP LEU ILE ILE GLY ASN ....
AAAGAGGGTGCCGATTTAATCATCGGTAATA....
       1870          1880          1890

FIG.18J

```
                                              ...SER ASP ASN ASN ASN ALA ASN ALA LYS
LYS VAL THR PHE ASN GLN VAL LYS ASP SER... ...GTGATAATAACAAACAATGCTAATGCTAAA
AAAGTAACCTTTAACCAGGTTAAAGATTCGA...                                          1910              1920
                1930                1940                    1950
                                              ...LYS ILE SER ALA GLY SER HIS ASN VAL THR
LEU ASN SER LYS VAL GLU THR SER ASN GLY... ...AAATCTCTGCTGGCAGTCACAATGTAACA
CTAAACAGTAAAGTAGAAACCTCTAATGGCA...                                          1970              1980
                1990                2000                    2010
                                              ...ASN ASN ASP ALA GLU SER ASN GLY ASP
SER THR SER LEU THR ILE ASN ALA LYS ASN... ...ATAATGACGCTGAAAGCAATAATGGCGAT
AGCACCAGCTTAACTATTAATGCAAAAAATG...                                          2030              2040
                2050                2060                    2070
                                              ...VAL THR VAL ASN ASN ILE THR SER HIS
                                              ...TAACAGTAAACAACAATATTACTTCTCAC
                                                                            2090              2100
                2080
```

FIG.18K

```
LYS  THR  VAL  ASN  ILE  THR  ALA  SER  GLU  ASN          ...VAL  THR  THR  LYS  ALA  GLY  THR  THR  ILE  ASN
A A A A C A G T A A A T A T C A C T G C G T C A G A A A A T G...    T T A C C A C C A A A G C G G G C A C A A C C A T T A A T
                    2110                    2120                    2130                    2140                    2150                    2160

ALA  THR  ILE  GLY  SER  VAL  GLU  VAL  THR  ALA          ...LYS  THR  GLY  ASP  ILE  THR  ALA          ...LYS  GLY  GLY  ILE  GLU
G C A A C C A T A G G T A G C G T A G A A G T A A C A G C C A...    A A A C A G G T G A T A T T A C A G C G A...    A A A G G T G G A A T T G A A
                    2170                    2180                    2190                    2200                    2210                    2220

SER  ASN  SER  GLY  ASN  VAL  ASN  ILE  THR  ALA          ...SER  GLY  ASP  THR  LEU  ASN  VAL  SER  ASN  ILE
T C C A A T T C C G G T A A T G T A A A T A T T A C A G C G A...    G C G G G C G A C A C G C T T A A T G T A A G T A A C A T C
                    2230                    2240                    2250                    2260                    2270                    2280

THR  GLY  GLN  ASN  VAL  THR  VAL  ALA  ALA  ALA          ...
A C A G G T C A A A A T G T G A C A G T G G C A G C A G C C T...
                    2290                    2300                    2310
```

FIG. 18L

```
                                    ...SER GLY ALA VAL THR THR LYS GLY SER
                                    ...C A G G T G C C G T A A C C A A C C A C A A A A G G A T C A
                                    ...                                              2340
                                       2320                2330

THR ILE ASN ALA THR THR GLY ASN ALA ASN                ...ILE THR THR LYS THR GLY GLU ILE ASN GLY
A C T A T T A A T G C A A C A A C T G G T A A T G C A A A T A...   T T A C A A C A A A A C A G G T G A A A T T A A T G G C
                    2350                2360                ...         2380                2390                2400
                                                            ...                                              2370

GLU VAL LYS SER ALA SER GLY ASN VAL ASN                ...ILE THR ALA SER GLY ASN THR LEU ASN VAL
G A A G T T A A A T C A G C T T C C G G T A A T G T A A A T A...   T T A C A G C G A G C G G C A A T A C A C T T A A T G T A
                    2410                2420                ...         2440                2450                2460
                                                            ...                                              2430

SER ASN ILE THR GLY GLN ASN VAL THR VAL                ...THR ALA ASN SER GLY ALA ILE THR THR THR
A G T A A C A T C A C T G G T C A A A A T G T A A C A G T A A...   C A G C A A A C T C A G G T G C C A T A A C A A C C A C A
                    2470                2480                ...         2500                2510                2520
                                                            ...                                              2490
```

FIG.18M

GLU GLY SER THR ILE ASN ALA THR THR GLY ...
GAAGGCTCAACTATTAACGCGACAACAGGTG...
        2530                    2540                    2550

...ASP ALA ASN ILE THR THR GLN THR GLY ASN
...ATGCAAATATTACAACCCAAACAGGTAAT
        2560                    2570                    2580

ILE ASN GLY LYS VAL GLU SER SER GLY ...
ATTAATGGTAAAGTTGAATCCAGTTCTGGTT...
        2590                    2600                    2610

...SER VAL THR LEU ILE ALA THR GLY GLN THR
...CTGTGAACGCTTATTGCAACTGGACAAACT
        2620                    2630                    2640

LEU ALA VAL GLY ASN ILE SER GLY ASP THR ...
CTTGCTGTAGGTAATATTTCAGGTGACACTG...
        2650                    2660                    2670

...VAL THR ILE THR ALA ASP LYS GLY LYS LEU
...TTACCATTACTGCGGATAAAGGTAAATTA
        2680                    2690                    2700

THR THR GLN THR SER SER LYS ILE ASN GLY ...
ACCACACAAACAAGCTCTAAGATTAACGGAA...
        2710                    2720                    2730

FIG. 18N

```
                          ...THR LYS SER VAL THR THR SER SER GLN SER
                          ...C T A A G A G T G T A A C C A C C T C A A G C C A A T C A
                                                    2750                          2760
                              2740

GLY ASP ILE SER GLY THR ILE SER GLY ASN ...         ...THR VAL SER VAL SER ALA THR GLY SER LEU
G G T G A T A T T A G T G G C A C A A T T T C T G G T A A T A... ...C G G T A A G C G T T A G T G C G A C C G G T A G C T T G
                  2770                          2790                          2800                          2820
                                                                                        2810

THR THR GLN ALA GLY SER LYS ILE GLU ALA ...         ...LYS THR GLY GLU ALA ASN VAL THR SER ALA
A C C A C T C A A G C A G G C T C A A A A A T T G A A G C A A... ...A A A C A G G T G A G G C T A A T G T A A C A A G C G C A
                  2830                          2850                                        2860                          2880
                        2840                                                                      2870

THR GLY THR ILE GLY GLY THR ILE SER GLY ...         ...ASN THR ALA ASN VAL THR ALA ASN THR ASP
A C A G G T A C A A T T G G C G G T A C A A T C T C T G G C A... ...A T A C A G T A A A T G T T A C A G C A A A T A C T G A T
                  2890                          2910                                        2920                          2940
                        2900                                                                      2930
```

FIG. 18O

```
ASN LEU THR ILE LYS ASP GLY ALA ARG ILE ...
AATTTAACTATTAAAGATGGCGCAAGAATTA...
            2950              2960              2970    ...

...LYS ALA THR GLY GLY ALA VAL THR LEU THR
                              ...AAGCAACGGGCGGAGCTGTGACTTTAACC
                                        2980              2990              3000

ALA THR GLY GLY THR LEU THR THR GLU THR ...
GCAACAGGAGGTACTTTAACCACCGAAACAA...
            3010              3020              3030    ...

...SER SER ASP ILE THR SER SER ASN GLY GLN
                              ...GTTCTGATATTACCTCAAGCAATGGTCAG
                                        3040              3050              3060

THR LEU THR ALA LYS ASP SER ILE ...
ACAACTCTCACGGCCAAGGATAGCAGTATCG...
            3070              3080              3090    ...

...ALA GLY SER ILE ASN ALA ALA ASN VAL THR
                              ...CAGGAAGCATCAATGCCGCCAATGTGACA
                                        3100              3110              3120

LEU ASN THR THR GLY THR LEU THR THR VAL ...
TTAAATACCACCAGGCACTTTAACTACTGTGG...
            3130              3140              3150    ...
```

FIG.18P

...ALA GLY SER LYS ILE GLU ALA ALA SER GLY
...C A G G T T C A A A A A T C G A G G C A G C C A G T G G C
            3160              3170              3180

THR LEU VAL ILE ASN ALA LYS ASP ALA GLN ...
A C C C T G G T T A T T A A T G C A A A A G A T G C T C A G T ...
        3190              3200              3210

...LEU ASP GLY ALA ALA LEU GLY ASP ARG THR
...T G G A C G G C G C G G C A T T A G G T G A C C G T A C A
            3220              3230              3240

GLU VAL ASN VAL THR ASN ALA ASN GLY SER ...
G A A G T A A A T G T A A C T A A C G C A A A T G G C T C C G ...
        3250              3260              3270

...GLY SER VAL ILE ALA THR THR SER SER ARG
...G C A G C G T A A T C G C G A C A A C C T C A A G C A G A
            3280              3290              3300

VAL ASN ILE THR GLY ASP LEU ILE THR ILE ...
G T G A A C A T C A C T G G G G A T T T A A T C A C A A T A A ...
        3310              3320              3330

...ASN GLY LEU ASN ILE ILE SER LYS ASN GLY
...A T G G A T T A A A T A T C A T T T C A A A A A C G G T
            3340              3350              3360

FIG.18Q

```
LYS ASN THR VAL LEU LEU LYS GLY VAL GLU ...
A A A A A C A C C G T G C T G T T A A A A G G T G T T G A A A...
            3370                3380             3390

...ILE ASP VAL LYS TYR ILE GLN PRO GLY ILE
            ...T T G A T G T G A A A T A C A T T C A A C C G G G C A T A
                            3400              3410              3420

ALA SER VAL TYR GLU VAL ILE GLU VAL LYS ...
G C G A G C G T A T A T G A A G T A A T T G A A G C A A A A C...
            3430                3440             3450

...ARG ALA LEU GLU LYS VAL LYS ASP LEU SER
            ...G C G C T C T T G A G A A A G T G A A A G A T T T A T C T
                            3460              3470              3480

ASP GLU ARG GLU ALA LEU ALA LYS LEU ...
G A T G A A A G A G A A G C A T T A G C T A A G C T T G...
            3490                3500             3510

...GLY VAL SER ALA VAL ARG PHE ILE GLU PRO
            ...G T G T G A G C G C T G T A C G T T T A T T G A G C C A
                            3520              3530              3540

ASN ASN THR ILE THR VAL ASP THR GLN ASN ...
A A T A A T A C A A T T A C A G T C G A T A C A C A A A A T G...
            3550                3560             3570
```

FIG.18R

```
                               ...GLU PHE ALA THR ARG PRO LEU SER ARG ILE
                               ...A A T T T G C A A C C A G A C C A T T A A G T C G A A T A
                               ...                  3580                  3590                  3600

CYS PHE SER...
                                   T G T T T C T C A A...
                                   3630              ...

VAL ILE SER GLU GLY ARG ALA
G T G A T T T C T G A A G G C A G G G C A
                  3610

...ASN SER ASP GLY ALA THR VAL CYS VAL ASN
                               ...A C A G T G A T G G C G A C G G T G T G C G T T A A T
                                                     3640                  3650                  3660

ILE ALA ASP ASN GLY ARG ***
A T C G C T G A T A A C G G G C G G T A G
                  3670                  3680
```

FIG.19A

Joyc hmw2A sequence

```
       LYS GLU TRP LEU LEU ASP PRO ASP ASN VAL ....
       A A A G A G T G G T T G T T A G A C C C G G A T A A T G T A ....
                               10                      20                      30....

ASP SER ASN GLU GLU ASP LEU GLU TYR THR GLY ....
       G A T T C C A A T G A A G A C C T A G A G T A T A C A G G A ....
                               70                      80                      90....

ASN ASN GLN SER LYS LYS THR LYS LYS THR LEU THR SER ....
       A A T A A T C A G T C T A A A A A A A C A C T A A C A A G C ....
                              130                     140                     150....

SER ILE GLU ASN PRO SER THR GLU ARG ASN
                ... T C C A T T G A A A A T C C T T C A A C T G A A C G C A A T
                                       40                      50                      60

THR GLY GLU ASN ILE ASN ASN PRO LYS VAL
                ... A C A G G G G A A A A T A T A A A C A A C C C T A A G G T A
                                      100                     110                     120

SER ILE LEU GLU ASN ILE LEU LYS LYS GLY
                ... T C A A T C C C T T G A G A A C A T C C T G A A A A A G G C
                                      160                     170                     180
```

FIG. 19B

```
SER PHE VAL ASN ILE THR ALA THR ASP ASN ...       ILE TYR VAL ASN SER SER ILE ASN ILE GLY
T C T T T T G T T A A C A T T A C T G C C A C T G A T A A C ... ... A T C T A C G T T A A T A G C T C T A T C A A C A T C G G A
                    190                     200                     210                     220                     230                     240

ASP SER GLY HIS LEU ILE LEU SER GLY GLY ...       GLY ARG ASN GLY GLY VAL GLY GLY VAL LYS ILE ASN
G A C A G T G G T C A C T T A A T T C T C T C A G G T G G A ... ... G G C A G G A A C G G C G G T G T T G T T A A G A T T A A T
                    250                     260                     270                     280                     290                     300

LYS ASN ILE THR SER THR GLY GLY GLY SER LEU ...   THR ILE ASN SER LYS GLY TRP VAL ASP ILE
A A A A A T A T T A C T T C C A C G G G C G G G A A G T T T A ... ... A C C A T T A A T T C C A A A G G A T G G G T T G A T A T T
                    310                     320                     330                     340                     350                     360

HIS SER ASN ILE SER LEU GLY THR GLY PHE ...
C A C T C C A A T A T T T C A C T T G G T A C G G G T T T T ...
                    370                     380                     390
```

FIG. 19C

```
            LEU ASN ILE THR SER ASN GLY SER VAL ALA
         ...T T G A A C A T T A C C T C T A A T G G T T C C G T G G C T
         ...                              410                    420
                                  400

PHE GLU LYS ALA ASP LYS ASP LYS ALA ARG ...
T T T G A G A A G G C A G A C A A A G A T A A G G C A C G T...
                    430                      450...
                                440

SER ALA ALA ASP ALA GLN ILE VAL ALA GLN
         ...A G C G C G G C A G A T G C T C A A A T T G T C G C A C A A
         ...                              470                    480
                                  460

GLY ILE ILE ASN LEU THR GLY GLU ASN LYS ...
G G C A T C A T A A A C C T C A C A G G G G A A A A C A A A...
                    490                      510...
                                500

THR PHE ARG LEU ASN ASN VAL SER LEU ASN
         ...A C C T T T A G G C T T A A C A A T G T G T C T T T A A A T
         ...                              530                    540
                                  520

GLY VAL GLY GLN GLY LEU SER ILE THR SER ...
G G A G T G G G T C A A G G T C T A T C C A T C A C G T C A...
                    550                      570...
                                560

ASN VAL GLY ASN GLN THR HIS LYS PHE ASP
         ...A A T G T G G G C A A T C A A A C T C A T A A A T T C G A T
         ...                              590                    600
                                  580
```

FIG. 19D

```
GLY GLU ILE ASN ILE THR GLY ASN VAL THR ...
GGTGAAATTAACATAACTGGAAATGTAACA...
         610               620         630...

ILE ASN GLN THR ALA PRO ALA THR THR ALA
      ...ATTAATCAAACTGCACCTGCGACAACCGCA
                640               650              660

TYR TRP ASN PHE SER TYR ASP SER TYR TRP ...
TATTGGAAATTTTAGCTACGATTCATATTGG...
         670               680         690...

ASN VAL SER THR LEU ASN VAL GLN LYS ASN
      ...AACGTCAGTACTCTTAACGTACAAAAAAAC
                700               710              720

SER PHE THR PHE ILE LYS ARG THR GLU ...
TCAAGCTTTACCTTTATTAAGCGCACTGAA...
         730               740         750...

SER ASN ARG PHE GLY PRO THR THR PRO LEU
      ...AGTAAATCGCTTTGGCCCAACAACACCACTT
                760               770              780

ARG SER SER GLY GLY VAL PHE PHE ASN GLY ...
CGAAGCTCCGGAGGGGTATTCTTTAACGGC...
         790               800         810...
```

FIG.19E

```
                            THR ASN GLY ASN MET VAL LEU ASN VAL GLY
                        ...ACGAATGGCAACATGGTGCTTAACGTCGGA
                        ...                       830          840
THR ASN SER ARG VAL LEU PHE ASN LEU LYS ....
ACTAATTCGAGAGTTTTGTTTAATTTGAAG....
              850                 860
                            PRO ASN GLU ASN THR ASN ASN SER LYS PRO
                        ...CCAAATGAGAATACAAACAACAGCAAGCCT
                        ...            880           890          900
LEU PRO LEU GLN PHE ASN ALA ASN ILE THR ....
TTACCGCTTCAATTTAACGCCAATATTACA....
              910                 920           930
                            ALA ILE GLY GLY SER VAL SER PHE ASP
                        ...GCCATTGGTGGAGGCTCTGTGTCTTTTGAT
                        ...            940           950          960
ILE HIS ALA ASN HIS SER GLY ARG GLY ALA ....
ATACACGCCAATCATTCCGGCAGAGGGGCT....
              970                 980           990
                            GLU LEU LYS MET ASN THR ILE ASN ILE SER
                        ...GAATTAAAAATGAACACAATTAATATCTCT
                        ...           1000          1010         1020
```

FIG.19F

```
ASP GLY THR SER LEU THR LEU GLN SER HIS ....
GACGGCACCAGCCCTCACCCTACAATCCCAT...
              1030                1040          1050....

VAL ARG LYS ASP SER ALA PHE ILE ILE SER
                   ...GTTCGCAAAGATAGTGCTTTTATAATCAGT
                                1060                  1070           1080

LYS ASP LEU THR ILE ASN ALA THR GLY SER ....
AAAGATTTAACAATAAACGCAACCGGTTCA....
              1090                1100          1110....

ASN PHE LEU THR LEU GLU GLN SER PRO ASP SER
                   ...AATTTTACTCTTGAGCAATCACCAGACAGT
                                1120                  1130           1140

PHE THR ASP LYS TYR PRO GLY ARG ALA ILE ....
TTTACTGACAAATACCCCGGAAGAGCTATT....
              1150                1160          1170....

SER SER THR LYS ASN ILE THR ILE SER GLY
                   ...AGTTCAACTAAAAATATAACCATCTCAGGT
                                1180                  1190           1200

GLY ASN VAL SER LEU GLY GLY GLN ASN SER ....
GGCAACGTCTCTCTTGGTGGGCAAAATTCA....
              1210                1220          1230....
```

FIG. 19G

```
        SER SER ASP ILE LYS GLY ASN ILE THR ILE
     ...AGCAGTGACATCAAGGGAAATATTACCATC
                    1240          1250          1260

LYS SER SER THR ASN VAL THR LEU LYS ALA ....    HIS ASN SER PRO ARG ASP PHE ALA SER ARG
AAAAGCTCAACAAATGTTACACTGAAAGCC....           ...CATAACAGCCCCTCGCGACTTTGCTTCCAGA
         1270          1280          1290                    1300          1310          1320

THR LEU THR LEU GLY ASN LEU ASN VAL GLU ....    GLY ASN LEU THR LEU THR GLY SER VAL ALA
ACCTTAACCCTTGGCAACTTGAATGTTGAA....            ...GGAAATTTAACCCTAACCGGCTCAGTTGCG
         1330          1340          1350                    1360          1370          1380

ASP ILE LYS GLY ASN LEU SER ILE LEU ASN ....    ASP ALA THR PHE LYS PHE LYS GLU THR SER GLU
GATATTAAAGGTAACCTTTCCATTCTTAAC....            ...GATGCTACTTTTAAAGGAGAGACCAGTGAA
         1390          1400          1410                    1420          1430          1440
```

FIG. 19H

```
ASN LEU ASN ILE THR GLY ASN PHE THR ASN....                                    ASN
AACCTAAACATCACCGGCAACTTCACCAAT...                                              CAA
          1450                1460                1470....                     1500
                              ...ASN GLY THR ALA ASP ILE ASN ILE LYS GLN
                              ...AATGGCACCGCCGACATTAATATAAAACAA
                                     1480                1490

GLY VAL VAL ASN ILE GLN GLY ASN ILE THR....                                    ASN
GGGGTGGTAAACATCCAAGGTAATATTACC...                                              ACT
          1510                1520                1530....                     1560
                              ...ASN LYS GLY LEU ASN ILE THR THR ASN
                              ...AATAAAGGTGGTTTAAACATTACCACTAAT
                                     1540                1550

ALA GLN ASN ASN GLN LYS THR ILE ILE ASN....                                    ASP LEU
GCCCAAAACAATCAAAAAACCATTATTAAC...                                              GATTTA
          1570                1580                1590....                     1620
                              ...GLY ASN ILE THR ASN GLU GLY GLY
                              ...GGAAATATAACTAACGAAGGCGGAGA
                                     1600                1610

ASN ILE LYS ASP SER ASN ASN ASN ALA GLU....
AACATCAAGGATAGTAATAACAATAATGCTGAA...
          1630                1640                1650
```

FIG. 19I

```
                                    ... ILE GLN ILE GLY GLY ASN ILE SER GLN LYS
                                    ... ATC CAA ATT GGC GGC AAT ATC TCG CAA AAA
                                            1660              1670              1680

LYS GLY ASN LEU THR ILE SER SER SER ASP LYS ...
AAA GGC AAT CTC ACA ATT TCT TCT GAT AAA ...
        1690              1700        1710 ...

... ILE ASN ILE THR LYS LYS ILE THR ILE LYS
                                    ... ATC AAT ATT ACC AAG AAG ATA ACA ATC AAA
                                            1720              1730              1740

ALA GLY VAL ASP GLU GLY SER GLY GLY SER ...
GCA GGC GTT GAT GAA GGT TGG TTC TGA CTC A...
        1750              1760        1770 ...

... SER PRO ALA SER ASN ALA ASN LEU THR ILE
                                    ... AGC CCC AGC AAG TAA TGC TAA TCT AAC CAT T
                                            1780              1790              1800

LYS THR LYS THR LEU GLU LEU THR GLY ASP ...
AAA CCA AAA ACG CTA GAA TTA ACA GGA GAC ...
        1810              1820        1830 ...

... LEU ASN ILE PHE SER GLY PHE ASN LYS ALA GLU
                                    ... CTA AAA TAT TTC AGG CTT TAA TAA AAG CAG AA
                                            1840              1850              1860
```

FIG. 19J

```
ILE THR ALA LYS ASN GLY ASN ASP LEU THR                ILE GLY LYS ALA SER ASP GLY ASN ALA ASN
ATTACAGCTAAAAATGGCAATGATTTAACT...    ...ATTGGCAAGGCTAGTGATGGTAATGCTAAT
             1870               1880           1890         1900              1910             1920

ALA LYS LYS VAL THR PHE ASP LYS VAL LYS                ASP SER LYS ILE SER ALA ASN GLY HIS ASN
GCTAAAAAAGTGACTTTTGACAAGGTTAAA...    ...GATTCAAAATCTCAGCTAACGGTCACAAT
             1930               1940           1950         1960              1970             1980

VAL THR LEU ASN SER LYS VAL GLU THR SER                ASN SER ASP SER SER ALA ASP ASP SER ASN
GTAACACTAAATAGCAAAGTGGAAACGTCT...    ...AATAGTGATAGTGCTGATGATAGTAAT
             1990               2000           2010         2020              2030             2040

ASP ASN ASN THR GLY LEU THR ILE SER ALA
GATAACAACACTGGTTTAACCATTTCCGCA...
             2050               2060           2070
```

FIG.19K

```
                           ...    LYS ASP VAL THR VAL ASN ASN ASP VAL THR
                           ...    AAA GAT GTA ACA GTA AAC AAT GAC GTC ACC
                                  2080              2090              2100

SER HIS LYS THR ILE ASN ALA THR ...
TCC CAC AAG ACA ATA AAT ATC TCT GCC ACA...
        2110              2120          2130....

...    THR GLY ASN VAL THR THR LYS GLU SER THR
                           ...    ACA GGA AAT GTA ACC AAA GAA AGC ACA
                                  2140              2150              2160

THR ILE ASN ALA ALA THR GLY SER VAL GLU ...
ACC ATT AAT GCG GCC ACA GGT AGC GTG GAA...
        2170              2180          2190....

...    VAL THR ALA LYS THR GLY ASP ILE SER GLY
                           ...    GTA ACT GCT AAA ACA GGC GAT ATT AGT GGC
                                  2200              2210              2220

THR ILE SER GLY ASN THR VAL ASN VAL THR ...
ACA ATT TCT GGT AAT ACA GTA AAT GTT ACA...
        2230              2240          2250....

...    ALA THR ASP SER LEU THR THR GLN ALA SER
                           ...    GCA ACT GAT AGC TTA ACC ACC CAA GCA AGC
                                  2260              2270              2280
```

FIG.19L

```
SER SER ILE THR SER SER ASN GLY GLN THR ...
TCTAGCATTACCTCAAGTAATGGTCAGACA...
         2290              2300              2310....
                    THR LEU THR ALA LYS ASN GLY SER ILE ALA
                  ...ACTCTTACAGCCAAGAATGGCAGTATCGCA
                              2320              2330              2340

GLY SER ILE ASP ALA ALA ALA VAL THR LEU ...
GGAAGTATTGATGCCGCTAATGTGACATTA...
         2350              2360              2370....
                    THR GLY THR LEU THR THR VAL ALA
                  ...CACCAGGCACCTTAACTACTGTAGCG
                              2380              2390              2400

GLY SER ASN ILE LYS ALA THR SER GLY THR ...
GGTTCAAACATTAAGGCAACCAGTGGCACT...
         2410              2420              2430....
                    LEU ALA ILE ASN ALA LYS ASP ALA LYS LEU
                  ...TTAGCTATTAACGCAAAAGATGCTAAGTTA
                              2440              2450              2460

ASP GLY THR ALA SER GLY ASP ARG THR VAL ...
GATGGTACTGCATCAGGTGACCGCACAGTA...
         2470              2480              2490....
```

FIG. 19M

```
                              ...  VAL  ASN  ALA  THR  ASN  ALA  SER  GLY  SER  GLY
                              ...  G T A A A T G C A A C T A A C G C A A G T G G C T C T G G T
                              ...                        2500                2510                2520

SER  VAL  THR  ALA  ALA  THR  SER  SER  ASN  VAL  ...
A G T G T G A C T G C G G C A A C C T C A A G T A A C G T G ...
                  2530                2540                2550 ...

...  ASN  ILE  THR  GLY  ASP  LEU  SER  THR  ILE  ASN
              ...  A A T A T C A C T G G A G A T T T A A G C A C A A T A A A T
                                2560                2570                2580

GLY  LEU  ASN  ILE  ILE  SER  LYS  ASN  GLY  LYS  ...
G G A T T A A A T A T C A T T T C G A A A A A T G G T A A A ...
              2590                2600                2610 ...

...  ASN  THR  VAL  VAL  LEU  LYS  GLY  ALA  GLU  ILE
              ...  A A C A C C G T A G T G T T A A A A G G T G C T G A A A T T
                                2620                2630                2640

ASP  VAL  LYS  TYR  ILE  GLN  PRO  GLY  VAL  ALA  ...
G A T G T G A A A T A T A T T C A A C C A G G T G T A G C A ...
              2650                2660                2670 ...

...  SER  ALA  ASN  GLU  VAL  ILE  GLU  ALA  LYS  ARG
              ...  A G T G C G A A T G A G G T T A T T G A A G C G A A G C G T
                                2680                2690                2700
```

FIG.19N

```
ALA LEU GLU LYS VAL LYS ASP LEU SER ASP....
GCCCTTGAAAAAGTAAAAGATTTATCTGAT...
           2710              2720        2730....
           ...GLU GLU ARG GLU THR LEU ALA LYS LEU GLY
           ...GAAGAAAGAGAAACATTAGCTAAACTTGGT
                       2740          2750         2760

VAL SER ALA VAL ARG PHE VAL GLU PRO ASN....
GTAAGTGCTGTACGTTTTGTTGAGCCAAAT...
           2770              2780        2790....
           ...ASN THR ILE THR VAL ASN THR GLN ASN GLU
           ...AATACAATTACAGTCAATACACAAAATGAA
                       2800          2810         2820

PHE THR THR ARG PRO SER SER GLN VAL THR....
TTTACAACCAGACCGTCAAGTCAAGTGACA...
           2830              2840        2850....
           ...ILE SER GLU ASP LYS ALA CYS PHE SER SER
           ...ATTTCTGAAGACAAGGCGTGTTTCTCAAGT
                       2860          2870         2880
```

FIG.190

```
GLY ASN GLY ALA ALA VAL CYS THR ASN VAL ...  THR ASP ARG GLN ***
G G T A A T G G T G C A G C A G T A T G T A C T A A T G T T ...  A C T G A C G A T A G A C A G T A A
          2890                              2900            2910              2920
```

FIG. 20A

K1 hmw1A sequence

```
    LYS GLU TRP LEU LEU ASP PRO ASP ASN VAL....
    A A A G A G T G G T T G T T A G A C C C G G A T A A T G T A....
                        10                    20                    30....
                                                                                SER ILE ASN ALA PRO ALA LEU GLY ARG THR
                                                                            ...T C T A T T A A T G C A C C C G C A C T T G G A C G T A C T
                                                                        ...                    40                    50                    60

GLU SER THR PRO ASN ASN ASN GLU TYR ASP....
    G A G A G T A C C C C A A A T A A C A A T G A G T A C G A C....
                        70                    80                    90....
                                                                                SER PRO ASN GLN ILE ASN TYR LYS ASN LYS
                                                                            ...T C G C C A A A T C A A A T T A A C T A T A A A A A C A A A
                                                                        ...                    100                   110                   120

PRO SER LEU SER THR LEU THR ASN THR THR....
    C C A T C C C T A A G T A C A C T A A C A A A C A A C A....
                        130                   140                   150....
                                                                                LEU GLU ARG ILE LEU LYS ARG ASN THR SER
                                                                            ...C T T G A G A G A A T A T T A A A A A G A A A C A C C T C T
                                                                        ...                    160                   170                   180
```

FIG.20B

```
VAL ASN ILE THR ALA THR LYS THR ILE THR ...
GTTAATATCACTGCCACCAAAACAATCACA...
               190              200              210...

VAL ASN SER ASP ILE ASN ILE GLY ASP SER
                     ...GTTAATAGTGATATCAATATTGGAGACAGC
                              220              230              240

SER HIS LEU THR LEU TRP SER GLU GLY GLN ....
TCCCACTTAACCCTTTGGAGTGAGGGTCAG....
              250              260              270....

GLY ARG GLY VAL ASN VAL THR GLY ASN
                     ...GGGAGAGGCGGCGTTAATGTTACAGGCAAT
                              280              290              300

ILE THR SER THR THR ASN GLY ASN LEU THR ....
ATTACTTCTACTACCAACGGAAACTTAACC....
              310              320              330....

ILE TYR SER GLY GLY TRP VAL ASP VAL HIS
                     ...ATTTACTCTGGCGGATGGGTTGATGTTCAT
                              340              350              360

LYS ASN ILE THR LEU LYS SER GLY TYR LEU ....
AAAAACATTACACTTAAAATCAGGGTACTTA....
              370              380              390...
```

FIG. 20C

```
          ...ASN ILE THR THR LYS GLN GLY ASP ILE ALA
          ...A A C A T T A C A A C T A A A C A A G G A G A C A T C G C C
                      400                     410                     420

PHE GLU ASP LYS PRO GLY LEU SER ASN LEU...
T T C G A A G A C A A A C C A G G G C T G A G C A A C C T A...
            430                     440                     450...

...THR ILE THR ALA LYS GLY THR ILE ALA VAL
          ...A C C A T T A C A G C T A A A G G G A C C A T T G C C G T G
                      460                     470                     480

ASN ASN LYS LYS GLY PHE ARG PHE ASP ASN...
A A C A A C A A G A A A G G C T T T A G G T T T G A T A A T...
            490                     500                     510...

...VAL THR LEU ASN GLY THR GLY GLY LEU
          ...G T C A C T C T A A A T G G A A C G G G A G G G G C T C
                      520                     530                     540

SER PHE LYS TYR ILE GLU THR PHE GLU THR ARG...
T C T T T T A A A T A C A T C G A A A C C T T C G A A A C T A G A...
            550                     560                     570...

...ASP SER ASN PHE GLU THR HIS PHE ARG GLY
          ...G A T A G C A A T T T C G A A A C C C A T T T T A G A G G A
                      580                     590                     600
```

FIG. 20D

```
ARG  LEU  ASN  ILE  SER  GLY  LYS  VAL  ASP  ILE ....
A G A T T A A A T A T T T C A G G G A A A G T A G A T A T C...
                       610                           620                           630....

LEU  MET  GLN  ALA  ARG  GLN  GLU  ASN  TRP  ASN
                                   ...T T A A T G C A A G C A A G G C A G G A G A A C T G G A A C
                                                            640                           650                           660

ARG  ARG  HIS  TRP  GLY  ARG  SER  HIS  TRP  ASN ....
C G C A G A C A C T G G G G A C G C T C C C A C T G G A A T...
                       670                           680                           690....

VAL  THR  ARG  LEU  ASN  VAL  SER  GLU  ASN  SER
                                   ...G T A A C C C G A T T G A A C G T T T C T G A A A C A G T
                                                            700                           710                           720

TYR  PHE  ASN  VAL  THR  ILE  ASP  SER  SER  GLY ....
T A T T T T A A C G T C A C T A T T G A T A G C A G T G G C...
                       730                           740                           750....

SER  ALA  SER  SER  PRO  GLY  ALA  GLY  PRO  LEU
                                   ...A G T G C C T C T T C C C C T G G C G C T G G C C C T C T G
                                                            760                           770                           780

ASN  ALA  GLN  SER  GLY  LEU  ASN  GLY  ILE  SER ....
A A T G C C C A A T C G G G T T T A A A T G G C A T A T C G...
                       790                           800                           810....
```

FIG.20E

```
                                    ...  PHE ASN ASN ASP THR VAL PHE ASN ILE ALA
                                    ...  TTTAATAATGACACTGTTTTAATATTGCA
                                    ...           820         830         840

ALA SER ALA VAL ASN   PHE ASN ILE LYS ...
GCAAGTTCGGCGGGTTAA    CTTTAAACATCAAA...
         850                  860           870

...  PRO PRO ILE VAL ASP LYS VAL THR ASN GLY
                                    ...  CCACCAATAGTAGACAAAGTAACCAACGGG
                                    ...          880         890         900

ASN HIS THR LEU PHE LYS GLY ASN ILE SER ...
AATCACACATTATTCAAAGGGAATATTTCA...
         910         920         930

...  VAL LEU GLY GLY GLY                  THR PHE ILE
                                                       GLY  GLY ASP VAL ASN PHE HIS P
                                 ...  GTTTTAGGGGGGGGGATGTCAACTTTCATT
                                 ...          940         950         960

HE ASN ALA SER SER SER ASN TYR GLN THR ...
TTAACGCCTCCTCCAGCAACTACCAGACTT...
         970         980         990
```

FIG. 20F

```
                                              ...TYR GLY VAL ILE ILE GLU SER GLN ASN PHE S
                                              ...A T G G C G T G A T T A T A G A G T C A C A A A A C T T T A
                                                                          1000            1010            1020

ER  ALA SER GLY GLY GLY SER SER SER LEU LYS PHE ...          ...LYS SER GLU GLY SER THR HIS ALA ALA PHE T
G T G C C C T C A G G A G G G T C A A G C T T A A A A T T C A ...    ...A A A G C G A A G G T T C G A C A C G C C G C T T T A
                     1030            1040            1050....                1060            1070            1080

HR  ILE LYS ASN ASP LEU ILE LEU ASN ALA ...                  ...THR GLY GLY ASN ILE SER LEU ASN GLN VAL A
C A A T A A A A A A T G A T T T A A T T T A A A T G C C A ...         ...C T G G G G G C A A T A T C A T T G A A C C A A G T T G
                     1090            1100            1110....               1120            1130            1140

LA  GLY ILE ASP SER ASN LEU LYS LYS SER ...                  ...LEU ILE ALA ASN LYS ASN ILE THR PHE GLU G
C A G G T A T T G A T A G T A A T C T C A A A A A A G C C ...        ...T T A T A G C C A A T A A A A C A T A A C C T T T G A A G
                     1150            1160            1170....               1180            1190            1200
```

FIG. 20G

```
LY  GLY ASN ILE THR LEU ALA ALA ASP LYS ...
    G G G C A A T A T C A C C C T T G C A G C C G A T A A A A ....
                          1210                      1220                  1230....

...LYS PRO ILE GLU ILE LYS GLY ASN ILE THR V
                                           ...A A C C A A T A G A A A T C A A A G G T A A T A T T A C T G
                                                     1240                      1250                     1260

AL  LYS GLU GLY ALA ASN VAL THR LEU ARG ...
    T T A A A G A A G G A G C C A A T G T C A C C C T T C G T A....
                          1270                      1280                    1290....

...SER ALA ASN TYR GLY ASN ASP LYS SER ALA L
                                           ...G C G C G A A T T A T G G T A A T G A C A A A T C A G C T T
                                                    1300                     1310                      1320

EU  SER ILE ARG GLY ASN VAL THR ASN LYS ...
    T A A G T A T A A G A G G A A A T G T C A C T A A T A A A G....
                        1330                       1340                     1350....

...GLY ASN LEU THR VAL THR GLY SER ALA ILE A
                                           ...G C A A T C T C A C C G T T A C C G G C T C C G C T A T C A
                                                    1360                    1370                       1380

SN  ILE GLU LYS ASN LEU THR VAL GLU GLY ...
    A T A T A G A A A A A A T C T T A C C G T T G A A G G T A....
                        1390                      1400                     1410....
```

FIG. 20H

```
ER  PHE ASN VAL SER GLY LEU PHE ASP ASN ...SER ALA LYS PHE LEU ALA ASN PRO ASN TYR  S
GCTTTAACGTATCCGGCCTATTTGACAACC....GTGCTAAGTTTTTAGCTAATCCAAATTACA
         1450              1470....          1420                1440

...GLN GLY LYS SER ASN ILE SER ILE ALA LYS  G
                    ....AAGGCAAGTCAAACATTTCCATCGCTAAGG
                              1480              1490              1500

LY  GLY ALA ILE PHE LYS ASP ILE GLU ASN ...THR GLY SER LEU ASN ILE THR THR LYS SER  A
GAGGAGCTATTTTTAAAGATATCGAGAATA....CTGGCAGTCTGAATATTACCACTAAATCCG
         1510              1530....          1540              1550              1560

SP  SER ASN HIS HIS THR ILE ILE LYS GLY ...ASN ILE THR ASN ARG LYS GLY ASP LEU ASN  I
ACTCCAACCACCACCATACTATTATAAAGGGTA....ATATAACTAACAGAAAAGGTGATTTAAATA
         1570              1590....          1600              1610              1620
```

FIG. 20I

```
LE  THR ASN ASN GLY ASP ASN THR GLU ILE                                    ...
T C A C G A A T A A T G G T G A T A A T A C T G A A A T C C ...
                    1630                    1640                    1650

...GLN ILE GLY GLY ASN ILE SER GLN LYS GLU G
                            ...A A A T T G G C G G C A A T A T C T C G C A A A A G A A G
                                        1660                    1670                    1680

LY  ASN LEU THR ILE SER SER ASP LYS VAL                                    ...
G C A A T C T C A C A A T T T C T T C T G A T A A A G T C A ...
                    1690                    1700                    1710

...ASN ILE THR GLU ARG ILE THR ILE LYS ALA G
                            ...A T A T T A C C G A G C G G A T A A C A A T C A A A G C A G
                                        1720                    1730                    1740

LY  VAL ASN GLY ASP ASN SER ASP SER ASN                                    ...
G C G T T A A T G G G G A T A A C T C T G A T T C A A A T G ...
                    1750                    1760                    1770

...GLU ALA THR SER ALA ASN LEU THR ILE LYS T
                            ...A G G C A A C A A G T G C T A A C C A T T A A A A
                                        1780                    1790                    1800

HR  LYS GLU LEU LYS LEU THR ASN ASP LEU                                    ...
C C A A A G A G T T A A A A T T A A C A A A A C G A C C T A A ...
                    1810                    1820                    1830
```

FIG.20J

```
                ...ASN ILE SER GLY PHE ASN LYS ALA GLU ILE T
                ...A T A T T T C A G G T T T T A A T A A A G C A G A A A T T A
                     1840                1850                1860

HR  ALA LYS ASP ASN SER ASN LEU THR ILE ...
C A G C T A A A A G A T A A C A G T A A A T T T A A C T A T T G....
        1870                1880              1890....

...GLY ASP ASN SER ASP ALA GLY ASN THR ASP A
                ...G C G A T A A C A G T G A C G C T G G C A A T A C T G A C G
                      1900               1910                1920

LA  LYS LYS VAL THR PHE SER ASN VAL LYS ...
C T A A A A A A G T A A C C T T T A G C A A T G T T A A A G....
        1930                1940              1950....

...ASP SER LYS ILE SER ALA SER ASP HIS ASN V
                ...A T T C A A A A T C T C T G C T A G C G A C C A T A A T G
                      1960                1970               1980

AL  THR LEU ASN SER LYS VAL GLU THR SER ...
T A A C G C T A A A C A G C A A A G T G G A A A C A T C T G....
        1990                2000              2010....

...GLY ASP THR ASP SER THR GLU ASP GLY GLY A
                ...G C G A T A C T G A C A G C A C T G A A G A T G G C G G C A
                      2020                2030              2040
```

FIG.20K

```
SN  ASN  ASN  THR  GLY  LEU  THR  ILE  THR  ALA  ...
A C A A T A A C A C C G G C T T A A C T A T T A C T G C A A...
                              2050                2060                2070....

...LYS  ASN  VAL  THR  VAL  ASN  ASN  ILE  THR  S
                    ...A A A A T G T A A C A G T A A A C A A T A T T A C T T
                                   2080                2090                2100

ER  HIS  LYS  THR  VAL  ASN  ILE  THR  ALA  SER  ...
C T C A C A A A A C A G T A A A T A T C A C T G C G T C A G...
                              2110                2120                2130....

...GLU  ASN  VAL  THR  THR  LYS  ALA  GLY  THR  THR  I
                    ...A A A A T G T T A C C A C C A A A G C G G G C A C A A C C A
                                   2140                2150                2160

LE  ASN  ALA  THR  THR  GLY  SER  VAL  GLU  VAL  ...
T T A A T G C A A C C A C C A G G T A G C G T A G A A G T A A...
                              2170                2180                2190....

...THR  ALA  LYS  THR  GLY  ASP  ILE  LYS  GLY  GLY  I
                    ...C A G C C A A A A C A G G T G A T A T T A A A G G T G G A A
                                   2200                2210                2220

LE  GLU  SER  ASN  SER  GLY  ASN  VAL  ASN  ILE  ...
T T G A A T C C A A T T C C G G T A A T G T A A A T A T T A....
                              2230                2240                2250
```

FIG.20L

```
SN  ILE THR GLY GLN ASN VAL THR VAL ALA ...THR ALA SER GLY ASP THR LEU ASN VAL SER A
ACATCACAGGTCAAAATGTGACAGTGGCAG....CAGCGAGCGGCGACACGCTTAAATGTAAGTA
        2290              2300              2310              2260              2270              2280

LY  SER THR ILE ASN ALA THR THR GLY ASN ...ALA ALA SER GLY ALA VAL THR THR LYS G
GATCAACTATTAATGCAACAACTGGTAATG....CAGCCTCAGGTGCCGTAACCACAAAAG
        2350              2360              2370              2320              2330              2340

SN  GLY GLU VAL LYS SER ALA SER GLY ASN ...ALA ASN ILE THR THR LYS THR GLY GLU ILE A
ATGGCGAAGTTAAATCAGCTTCCGGTAATG....CAAATATTACAACCAAAACAGGTGAAATTA
        2410              2420              2430              2380              2390              2400

...VAL ASN ILE THR ALA SER GLY ASN THR LEU A
                                          TAAATATTACAGCGAGCGGCAATACACTTA
                                                  2440              2450              2460
```

FIG.20M

```
SN  VAL SER ASN ILE THR GLY GLN ASN VAL ...
    A T G T A A G T A A C A T C A C T G G T C A A A A T G T A A ...
                    2470                      2480                      2490
    ...THR VAL THR ALA ASN SER GLY ALA ILE THR T
    ...C A G T A A C A G C A A A C T C A G G T G C C A T A A C A A
                          2500                      2510                      2520

HR  THR GLU GLY SER THR ILE ASN ALA THR ...
    C C A C A G A A G G C T C A A C T A T T A A C G C G A C A A ...
                    2530                      2540                      2550
    ...THR GLY ASP ALA ASN ILE THR THR GLN THR G
    ...C A G G T G A T G C A A A T A T T A C A A C C C A A A C A G
                          2560                      2570                      2580

LY  ASN ILE ASN GLY LYS VAL GLU SER SER ...
    G T A A T A T T A A T G G T A A A G T T G A A T C C A G T T ...
                    2590                      2600                      2610
    ...SER GLY SER VAL THR LEU ILE ALA THR GLY G
    ...C T G G T T C T G T G A C G C T T A T T G C A A C T G G A C
                          2620                      2630                      2640

LN  THR LEU ALA VAL GLY ASN ILE SER GLY ...
    A A C T C T T G C T G T T A G G T A A T A T T T C A G G T G ...
                    2650                      2660                      2670
```

FIG.20N

```
                                                    ...ASP THR VAL THR ILE THR ALA ASP LYS GLY L
                                                    ...A C A C T G T T A C C A T T A C T G C G G A T A A A G G T A
                                                                              2680              2690              2700
                                                    ...

YS  LEU THR THR GLN THR SER SER LYS ILE   ...       ...ASN GLY THR LYS SER VAL THR THR SER SER G
A A T T A A C C A C A C A A A C A A G C T C T A A G A T T A.... A C G G A A C T A A G A G T G T A A C C A C C T C A A G C C
                    2710                        2720                              2740              2750              2760
                                                    ...                                                             ...

LN  SER GLY ASP ILE SER GLY THR ILE SER   ...       ...GLY ASN THR VAL SER ALA THR GLY S
A A T C A G G T G A T A T T A G T G G C A C A A T T T C T G.... G T A A T A C G G T A A G C G T T A G T G C G A C C G G T A
                    2770                        2780                              2800              2810              2820
                                                    ...                                                             ...

ER  LEU THR THR GLN ALA GLY SER LYS ILE   ...       ...GLU ALA LYS THR GLY GLU ALA ASN VAL THR S
G C T T G A C C A C T C A A G C A G G C T C A A A A A T T G.... A A G C A A A A A C A G G T G A G G C T A A T G T A A C A A
                    2830                        2840                              2860              2870              2880
                                                    ...                                                             ...
```

FIG. 20O

```
ER  ALA THR GLY THR ILE GLY GLY THR ILE ...      ...SER GLY ASN THR VAL ASN VAL THR ALA ASN T
G C G C A A C A G G T A C A A T T G G C G G T A C A A T C T...  ...C T G G C A A T A C A G T A A A T G T T A C A G C A A A T A
                        2890                2900                2910                    2920                2930                2940

HR  ASP ASN LEU THR ILE LYS ASP GLY ALA ...      ...ARG ILE LYS ALA THR GLY GLY ALA VAL THR L
C T G A T A A T T T A A C T A T T A A A G A T G G C G C A A...  ...G A A T T A A A G C A A C G G G C G G A G C T G T G A C T T
                        2950                2960                2970                    2980                2990                3000

EU  THR ALA THR GLY GLY THR LEU THR THR ...      ...GLU THR SER SER ASP ILE SER SER ASN G
T A A C C G C A A C A G G A G G T A C T T T A A C C A C C G...  ...A A A C A A G T T C T G A T A T T A C C T C A A G C A A T G
                        3010                3020                3030                    3040                3050                3060

LY  GLN THR THR LEU THR ALA LYS ASP SER ...
G T C A G A C A A C T C T T C A C G G C C A A G G A T A G C A...
                        3070                3080                3090
```

FIG.20P

```
                                                 ...SER  ILE  ALA  GLY  SER  ILE  ASN  ALA  ALA  ALA  ASN  V
                                                 ...G    T    A    T    C    G    C    A    G    G    A    A   G  C  A  T  C  A  A  T  G  C  C  G  C  C  A  A  T  G
                                                 ...                                                                                                               3120
                                                    3100                                                 3110

AL   THR  LEU  ASN  THR  THR  GLY  THR  LEU  THR  ...                   THR  VAL  ALA  GLY  SER  LYS  ILE  GLU  ALA  ALA  S
T G  A    C    A    T    T    A    A    A    T    A    C    C    A    C    A    G    G    C    A    C    T    T    T    A    A    C    T    A    ...             ...C  T  G  T  G  G  C  A  G  G  T  T  C  A  A  A  A  A  T  C  G  A  G  G  C  A  G  C  C  A
         3130                                              3140                                3150    ...                                                           3180
                                                                                                                                  3160                  3170

ER   GLY  THR  LEU  VAL  ILE  ASN  ALA  LYS  ASP  ...                   ALA  GLN  LEU  ASP  GLY  ALA  ALA  SER  GLY  ASP  H
G T  G    G    C    A    C    C    C    C    T    G    G    T    T    A    T    T    A    A    T    G    C    A    A    A    A    G    A    T    G    ...         ...C  T  C  A  G  T  T  G  G  A  C  G  G  C  G  C  A  T  C  A  G  G  T  G  A  C  C
              3190                                         3200                                3210    ...                                                           3240
                                                                                                                                  3220                  3230

IS   THR  VAL  VAL  ASN  ALA  THR  ASN  ALA  ASN  ...                   GLY  SER  GLY  SER  VAL  ILE  ALA  THR  THR  SER  S
A C  A    C    A    G    T    A    G    T    A    A    A    T    G    C    A    A    C    C    A    A    C    G    C    A    A    A    C    G    ...             ...G  C  T  C  C  G  G  C  A  G  C  G  T  A  A  T  C  G  C  G  A  C  A  A  C  C  T  C  A  A
              3250                                         3260                                3270    ...                                                           3300
                                                                                                                                  3280                  3290
```

FIG.20Q

```
ER  ARG VAL ASN ILE THR GLY ASP LEU ILE                     THR ILE ASN GLY LEU ASN ILE ILE SER LYS A
GCAGAGTGAACATCACTGGGATTTAATCA....         ...CAATAAAATGGATTAAATCATTTCAAAAA
     3310         3320         3330                  3340         3350         3360

SN  GLY LYS ASN THR VAL LEU LEU LYS GLY                     VAL GLU ILE ASP VAL LYS TYR ILE GLN PRO G
ACGGTAAAAACACCGTGCTAAAAGGTG....           ...TTGAAATTGATGTGAAATACATTCAACCGG
     3370         3380         3390                  3400         3410         3420

LY  ILE ALA SER VAL ASN GLU VAL ILE GLU                     ALA LYS ARG ALA LEU GLU LYS VAL LYS ASP L
GCATAGCGAGCGTAAATGAAGTAATTGAAG....        ...CGAAACGCGCCCTTGAGAAAGTAAAAGATT
     3430         3440         3450                  3460         3470         3480

EU  SER ASP GLU GLU ARG GLU THR LEU ALA
TATCTGACGAAGAGAGAAACATTAGCTA....
     3490         3500         3510
```

FIG. 20R

```
         ...LYS LEU GLY VAL SER ALA VAL ARG PHE ALA G
         ...A A C T T G G C G T G A G C G C T G T A C G T T T T G C T G
                          3520                    3530              3540

LU  PRO ASN ASN ALA ILE THR ILE ASN THR                                  ...
    A G C C A A A T A A T G C C A T T A C G A T T A A T A C A C ...
                 3550                    3560            3570....

...GLN ASN GLU PHE THR THR ARG PRO LEU SER G
                       ...A A A A T G A G T T T A C A A C C A G A C C A T T A A G T C
                                        3580                    3590              3600

LN  VAL THR ILE SER GLU GLY LYS VAL CYS                                  ...
    A A G T G A C A A T T T C T G A A G G T A A G G T A T G T T ...
                 3610                    3620            3630....

...PHE LEU ILE GLY ASN GLY ALA THR ILE CYS T
                       ...T C T T A A T C G G C A A T G G C G C A A C A A T A T G C A
                                        3640                    3650              3660

HR  ASN ILE ALA ASP ILE GLU ARG ***
    C C A A T A T T G C T G A T A T T G A G C G G G T A G
                 3670                    3680
```

FIG.21A

K21 hmw1A sequence

```
     LYS GLU TRP LEU LEU ASP PRO ASP ASP ILE ....
     AAAGAGTGGTTGTTAGACCCGGATGATATA....
                      10              20              30....

... ASN ILE VAL ASN GLY SER ASN ILE ASP ALA
     ...AATATTGTCAACGGAAGTAATATTGATGCT
                      40              50              60

GLN LEU GLN PRO GLY ARG GLY ASP THR PRO ....
     CAATTACAGCCAGGTAGAGGCGATACACCC....
                      70              80              90....

... ASN LYS VAL SER ALA GLU GLY LEU THR SER
     ...AACAAGGTTTCAGCAGAAGGCTTAACATCC
                     100             110             120

ILE ASN ASN ALA THR LEU SER THR ALA LEU ....
     ATTAACAATGCCACATTATCCACCGCTTTA....
                     130             140             150....

... GLN LYS GLY ILE GLU VAL ASN ILE SER ALA
     ...CAAAAGGGTATTGAGGTCAACATTTCTGCC
                     160             170             180
```

FIG. 21B

```
THR LYS ASN VAL THR VAL ASN ALA ASP VAL ...
A C A A A A A A T G T A A C C G T C A A C G C G G A T G T T ...
                    190                         200                        210...

...ASP VAL LYS ASN GLY THR LEU VAL LEU HIS
                        ...G A T G T T A A A A A C G G A A C A T T A G T A T T A C A T   240
                                   220                       230
                        ...

SER GLN ARG ASN GLY VAL LYS ILE ASN GLY ....
T C A C A A A G G A A T G G A G T T A A A A T T A A C G G T ....
                    250                         260                        270...

... ASN ILE THR SER THR GLN ASN GLY ASN LEU
                        ... A A T A T T A C C T C A A C A C A A A A T G G T A A T T T A   300
                                   280                       290
                        ...

THR ILE LYS THR GLY GLY LYS VAL ASP VAL ....
A C C A T T A A A A C A G G T G G C A A G G T T G A T G T T ....
                    310                         320                        330...

... HIS LYS ASN ILE THR LEU GLY MET GLY PHE
                        ... C A T A A A A A T A T C A C A C T T G G T A T G G G T T T T   360
                                   340                       350
                        ...

LEU ASN ILE THR SER ASP ASN ASN ILE THR ....
T T G A A T A T T A C T T C C G A T A A T A A C A T C A C C ....
                    370                         380                        390...
```

FIG.21C

```
ALA GLN GLY ASN ILE ILE SER ASN GLN GLU...     ...PHE GLU LYS GLY ASP ASN LEU THR ILE THR
GCCCAAGGAAATATAATCTCTAATCAAGAG...               ...TTTGAAAAAGGTGATAATCTAACCATTACC
            430                  450....           400                              420
                                  ...
                                  ...ASN LYS GLN LEU ARG PHE ...                   ...PHE SER ASN VAL SER
                                  ...AATAAACAACTTAGATTTAG...                       ...AGTAATGTATCT
                                     460                                           470            480
                                                                                                  ...
                                                                                                  ...
LEU ASN GLY MET GLY ALA GLY LEU ...              ...THR ALA ASN LYS GLY ASN HIS THR HIS LYS
TTAAATGGGATGGGTGCGGGGTTTAACTTTT...                ...ACTGCAAATAAAGGTAATCATACCCATAAG
            490                 510....              520                              540
                                 ...
PHE ASP GLY THR LEU ASN ILE SER GLY LYS...       ...VAL VAL ILE ASN GLN THR THR PRO HIS ASN
TTTGATGGCACGCTTAACATTTCCGGAAAG...                ...GTAGTAATTAATCAAACCACACCTCACAAC
            550                  570....            580                              600
                                  ...                                                  ...
```

FIG.21D

```
ILE ALA PRO TRP ASN ALA SER ALA ASP SER....
ATTGCTCCATGGAATGCAAGTGCAGACTCT...
        610                 620           630...

TYR TRP ASN VAL THR THR LEU GLY
                ...TACTGGAATGTAACTACTCTTACTTTAGGT
                             640          650           660

ASN ASN ALA GLN PHE THR PHE ILE LYS PHE....
AATAATGCGCAATTTACCTTTATTAAATTT...
        670                  680...

VAL ASP SER ASN ARG SER VAL ALA LEU ASN
                ...GTCGATAGCAACCGCTCGGTAGCTCTTAAT
                             690          700           710          720

SER GLY SER ARG SER PHE ALA GLY VAL LYS....
AGCGGTTCAAGAAGTTTTGCGGGGGTAAAG...
        730                  740           750...

PHE TYR GLY LYS ASN ASN GLU MET LYS PHE
                ...TTCTACGGCAAGAATAATGAAATGAAATTT
                             760          770           780

ASN ILE GLY ASP ASN ALA ASN VAL GLU PHE....
AATATTGGTGATAATGCTAATGTTGAATTC...
        790                  800           810...
```

FIG. 21E

```
                                              ... LYS LEU LYS SER ASN ASP ASN THR SER ASN
                                              ... A A G T T A A A A T C A A A T G A T A A T A C A A G C A A C
                                                   820              830              840

ASN LYS PRO LEU PRO ILE GLN PHE LEU SER ...
A A C A A A C C A C T A C C A A T T C A G T T T T T A T C T ...
         850              860              870 ...

... ASN ILE SER ALA THR GLY ASN GLY THR VAL
                       ... A A T A T C T C A G C C A C T G G T A A T G G C A C T G T A
                                880              890              900

SER PHE ASP ILE HIS ALA ASN LEU SER ALA ...
T C T T T T G A T A T A C A T G C C A A C T T G T C A G C A ...
         910              920              930 ...

... ARG SER THR GLU LEU ASN MET SER LEU ILE
                       ... A G G T C A A C T G A G T T A A A T A T G A G T T T A A T T
                                940              950              960

ASN ILE SER ASN GLY VAL ASN PHE SER ILE ...
A A C A T T T C T A A T G G G G T T A A T T T T T C C A T A ...
         970              980              990 ...

... ASN SER HIS VAL ARG GLY ASN ASN ALA PHE
                       ... A A C T C C C A T G T T C G C G G T A A T A A T G C T T T T
                                1000             1010             1020
```

FIG.21F

```
GLU ILE LYS LYS ASP LEU ILE ILE ASN ALA ....
GAAATCAAAAAAGATTTAATTATAAATGCA...
         1030              1040           1050...

... THR GLY SER ASN PHE ASN LEU LYS GLN THR
                    ...ACTGGCTCGAATTTTAAGCAAACG
                              1060          1070          1080

LYS ASP LYS PHE ASP ASN SER TYR GLU LYS ....
AAAGATAAATTTGACAATAGTTACGAAAAA...
         1090              1100           1110...

... ASN ALA ILE PHE SER THR HIS ASN LEU THR
                    ...AACGCCATTTCTCAACTCATAACCTAACC
                              1120          1130          1140

ILE LEU GLY GLY ASN VAL THR LEU GLY GLY ....
ATTCTTGGCGGCAATGTTACTCTAGGTGGG...
         1150              1160           1170...

... GLU ASN SER SER ASN ILE LYS GLY ASN
                    ...GAAAATTCAAGTAGTAATATTAAAGGAAAT
                              1180          1190          1200

ILE ASN ILE ASN SER LYS ALA ASN VAL THR ....
ATCAACATCAATAGCAAGGCAAATGTTACA...
         1210              1220           1230...
```

FIG. 21G

```
                        ... LEU GLN ALA HIS ALA GLY THR SER HIS LEU
                        ... T T A C A A G C T C A T G C C G G C A C G A G T C A C C T T
                            ...                                                      1260
                                     1240                    1250

ASP LYS GLU ARG THR LEU GLY ...           ... ASN VAL GLY GLY ASN LEU ASN ILE
G A T A A A A A G A A C C C T T G G C ... ... A A T G T A T C T G T T G G G G A A A T T T A A A C A T A
                    1270         1280 ...             1300         1310         1320
                                                1290

ILE GLY SER ASN ALA HIS ILE ASP GLY ASN ...           ... LEU SER ILE ALA GLU SER ALA LYS PHE GLN
A T T G G C T C A A A T G C A C A T A T T G A C G G C A A T ... ... C T T T C T A T T G C A G A A A G T G C T A A A T T T C A A
                    1330                     1340   1350 ...                 1360         1370         1380

GLY LYS THR ASN ASN ASN LEU ASN ILE THR ...             ... GLY THR PHE THR ASN ASN GLY THR ALA ASP
G G A A A A A C C A A T A A C A A C C T A A A T A T T A C C ... ... G G C A C C T T T A C C A A C A A C G G C A C C G C C G A C
                    1390                    1400         1410 ...             1420                     1430         1440
```

FIG.21H

```
ILE ASN ILE LYS GLN GLY VAL VAL LYS LEU ...
A T T A A T A T A A A A C A A G G A G T G G T A A A A C T C ...
                        1450                        1460                        1470 ...

... GLN GLY ASP ILE THR ASN ASN GLY ASN LEU
                                ... C A A G G T G A T A T T A C C A A T A A C G G T A A T T T A
                                         1480                        1490                        1500

ASN ILE THR THR ASN ALA SER VAL ASN GLN ...
A A T A T C A C T A C T A A C G C C T C A G T C A A T C A A ...
                        1510                        1520                        1530 ...

... LYS THR ILE ILE ASN GLY ASN ILE THR ASN
                                ... A A A A C C A T T A T T A A C G G A A A T A T A A C T A A C
                                         1540                        1550                        1560

LYS LYS GLY ASP LEU ASN ILE LYS ASP ILE ...
A A A A A A G G C G A C T T A A A C A T C A A G G A T A T T ...
                        1570                        1580                        1590 ...

... LYS ALA ASN ALA GLU ILE GLN ILE GLY GLY
                                ... A A A G C C A A C G C C G A A A T C C A A A T T G G C G G C
                                         1600                        1610                        1620

ASN ILE SER GLN LYS GLU GLY ASN LEU THR ...
A A T A T C T C G C A A A A A G A A G G T A A T C T C A C G ...
                        1630                        1640                        1650 ...
```

FIG. 21I

```
                                            ILE SER SER ASP LYS ILE ASN ILE THR LYS
                                        ... A T T T C T T C T G A C A A A A T T A A T A T C A C C A A A
                                        ...                 1660              1670              1680

ARG ILE GLU ILE LYS ALA ASP THR ASP GLN ...          GLY ASN SER ASP SER GLY VAL ALA SER ASN
C G G A T A G A A A T T A A G G C A G A T A C T G A T C A A ...     G G G A A T T C T G A T T C A G G C G T A G C A A G T A A T
             1690              1700              1710...                       1720              1730              1740

ALA ASN LEU THR ILE LYS THR LYS GLU LEU ...          THR LEU THR ASP ASN LEU ASN ILE SER GLY
G C T A A T C T A A C C A T T A A A A C C A A A G A G T T A ...     A C A T T A A C A G A C A A T C T A A A C A T T T C A G G T
             1750              1760              1770...                       1780              1790              1800

PHE ASN LYS ALA GLU ILE THR ALA LYS ASP ...          ASN SER ASP LEU ILE ILE GLY LYS ALA SER
T T T A A T A A A G C A G A A A T T A C A G C T A A A G A T ...     A A C A G T G A T T T A A T T A T T G G C A A G G C T A G C
             1810              1820              1830...                       1840              1850              1860
```

FIG.21J

SER ASP ASN SER ASN ALA LYS GLN ILE THR ...
AGTGACAACAGTAATGCTAAACAAATAACC...
       1870                1880           1890...

... PHE ASP LYS VAL LYS ASP SER LYS ILE SER
...TTTGACAAGGTTAAAGATTCAAAATCTCA
                1900           1910          1920

ALA GLY ASN HIS ASN VAL THR LEU ASN SER ...
GCTGGCAATCACAATGTAAACACTAAATAGC...
       1930              1940           1950...

... LYS VAL GLU THR SER ASN SER ASP GLY SER
...AAAGTGGAAACGTCTAATAGCGATGGTAGC
                1960           1970          1980

THR GLY ASN GLY SER ASP ASP ASN ASN ILE ...
ACCGGAAACGGTAGCGATGACAACAATATC...
       1990               2000          2010...

... GLY LEU THR ILE SER ALA LYS ASP VAL THR
...GGCTTAACTATTTCCGCAAAAGATGTAACG
              2020          2030          2040

VAL ASN SER ASN ILE THR SER HIS LYS THR ...
GTAAATAGTAATATCACCTCTCACAAAACA...
       2050              2060          2070...

FIG.21K

```
THR THR LYS ALA GLY THR THR ILE ASN ALA...    ...VAL ASN ILE SER ALA SER GLU GLY GLY ILE
ACTACTAAAGCAGGCACAACCATTAATGCG...              ...GTAAATATCTCTGCATCAGAAGGAGGTATC
         2110              2120    2130...                2080              2090         2100

THR GLY ASP ILE SER GLY THR ILE SER GLY....    ...THR THR GLY SER VAL GLU VAL THR ALA LYS
ACAGGCGATATTAGCGGTACGATTTCCGGT....              ...ACCACAGGTAGCGTGGAAGTAACTGCTAAA
         2170              2180    2190....               2140              2150         2160

SER LEU THR VAL LYS GLY ALA LYS ILE....         ...LYS THR VAL SER VAL THR ALA THR THR ASP
AGTTTAACTGTTAAAGGTGCGCAAAAATT....               ...AAGACAGTAAGTGTTACAGCAACCACCGAC
         2230              2240    2250....              2200              2210          2220

...ASN ALA THR GLU GLY THR ALA THR LEU THR
                                                ...AATGCGACAGAAGGAACTGCAACCTTAACT
                                                         2260              2270        2280
```

FIG. 21L

```
ALA SER GLY LYS LEU THR THR GLU ALA ...        ALA SER GLY LYS LEU THR THR GLU ALA ...
GCATCATCGGGCAAATTAACCACCGAGGCC...              
         2290                   2300              2310...

THR ALA SER SER GLN SER GLY    ...ASN SER ALA ILE SER GLY ALA ASN GLY VAL
         ACTGCCTCAAGTCAATCAGGCGATATTAGC...   ...AACTCTGCGATTAGCGGGGCTAACGGTGTA
                  2350                2360         2320           2330        2340

THR ALA SER SER GLY SER LEU THR VAL GLY ...    ...GLY THR ILE SER GLY LYS THR VAL SER VAL
         ACAGCAAGCTCTGGCAGTTTAACTGTTGGA...              ...GGTACGATTTCCGGTAAGACAGTAAGTGTT
                  2410                  2420               2380                  2390         2400

ALA ALA THR LEU THR ALA THR LYS GLY THR ...    ...GLY ASP ALA LYS ILE ASN ALA THR GLU GLY
         GCTGCGACTTTAACTGCAACAAAAGGCACT...              ...GGTGACGCAAAAATTAATGCGACAGAAGGA
                  2470                 2480                  2440                 2450        2460
```

FIG. 21M

```
    ALA ASN GLU GLY THR LEU VAL ILE LEU VAL ASN ALA ... LEU THR THR VAL LYS GLY SER ASN ILE ASP
... GCAAACGAAGGCACCCTTAGTTATTAACGCA... ...TTAACTACCGTGAAGGGTTCAAACATTGAC
            2530              2540              2550              2500              2510              2520

GLY ASP ARG THR GLU VAL ASN ALA VAL ASN ... GLN ASP ALA THR LEU ASN GLY ASP ALA SER
... GGCGACCGTACAGAAGTGAATGCAGTCAAC... ...CAAGACGCCACACTAAATGGTGATGCATCA
            2590              2600              2610              2560              2570              2580

THR SER SER VAL ASN ILE THR GLY ASP ... ALA SER GLY SER GLY ASN VAL THR ALA LYS
... ACCTCAAGCAGTGTGAATATCACTGGAGAT... ...GCAAGCGGCTCTGGTAACGTAACTGCGAAA
            2650              2660              2670              2620              2630              2640

... LEU SER THR ILE ASN GLY LEU ASN ILE ILE
                                        ...TTAAGCACAATAAATGGATTAAATATCATT
                                                    2680              2690              2700
```

FIG.21N

SER LYS ASN GLY LYS ASN THR VAL VAL LEU ...
TCGAAAAATGGTAAAAACACCGTAGTGTTA....
         2710              2720              2730....

... LYS GLY ALA GLU ILE ASP VAL LYS TYR ILE
                  ...AAAGGTGCTGAAATTGATGTGAAATATATT
                                2740              2750              2760

GLN PRO GLY VAL ALA SER ALA ASN GLU VAL ....
CAACCAGGTGTAGCAAGTGCGAATGAGGTT....
         2770              2780              2790....

... ILE GLU ALA LYS ARG ALA LEU GLU LYS VAL
                  ...ATTGAAGCGAAGCGTGCCCTTGAAAAAGTA
                                2800              2810              2820

LYS ASP LEU SER ASP GLU ARG GLU THR ....
AAAGATTTATCTGATGAAAGAGAAACA....
         2830              2840              2850....

... LEU ALA LYS LEU GLY VAL SER ALA VAL ARG
                  ...TTAGCTAAACTTGGTGTAAGTGCTGTACGT
                                2860              2870              2880

PHE ILE GLU PRO ASN ASN THR ILE THR VAL ....
TTTATTGAACCAAATAATACCATTACGGTT....
         2890              2900              2910....

FIG.210

```
              ASN THR GLN ASN GLU PHE THR THR ARG PRO
          ... A A C A C A C A A A A T G A G T T T A C A A C C A G A C C A
          ...                             2930                    2940
                                2920

SER SER GLN VAL THR ILE SER GLU GLY LYS ...    ALA CYS PHE SER SER GLY ASN GLY ALA ALA
T C A A G T C A A G T G A C A A T T T C T G A A G G T A A G ... G C G T G T T T C T C A A G T G G T A A T G G G C A G C A
                  2950                    2970...                          2990                    3000
                                                              2980

VAL CYS THR ASN VAL ALA ASP ASP GLY GLN ...    GLN ***
G T A T G T A C C A A T G T T G C T G A C G A T G G A C A G ... C A G T A G
                  3010                    3030
                                3020
```

FIG.22A

LCDC2 *hmw1A* sequence

```
LYS GLU TRP LEU LEU ASP PRO ASP GLU ...
A A A G A G T G G C T A C T G G A C C C T G A T G A A G ...
                    10                      20
                                                    ...VAL THR ILE GLY ALA GLY ASP VAL GLY ARG SER
                                                    ... T A A C T A T T G G A G C A G G T G A C G T A G C
                                                            30                      40                      50                      60

ASP ASP SER SER ASP THR ALA PHE PRO ...
G A T G A T T C A A G T G A C A C T G C T T T C C C T A ...
                    70                      80
                                                    ...THR GLY THR GLY GLU ARG ASN SER PRO LYS THR
                                                    ... C C G G A A C A G G G G A A A G A A A C A G C C C C A A A A C A
                                                            90                      100                     110                     120

ASN ALA GLN ASN ARG PRO THR ILE THR ...
A A C G C T C A A A A C A G A C C A A C A A T A A C A A ...
                    130                     140
                                                    ...ASN THR SER LEU GLU GLN ILE LEU LYS ASN GLY
                                                    ... A C A C A T C T C T T G A G C A A A T A T T A A A A A A T G G C
                                                            150                     160                     170                     180
```

FIG.22B

```
THR PHE VAL ASN ILE THR ALA LYS ASN                                                 ...
ACC TTT GTT AAC ATA ACC GCC AAA AAT A...
                190                    200
                                             ...LYS ILE LEU VAL ASN SER ASP ILE ASN ILE LYS
                                             ...AAA TCT TAG TTA ATA GCG ACA TCA ATA TCA AAA
                                                 210              220              230              240

GLU ASN SER HIS LEU ILE LEU TRP SER                                                 ...
GAG AAC TCC CAC CTA ATC CTC TGG AGC G...
                250                    260
                                             ...GLU ARG ASP GLY ASN SER GLY VAL GLN ILE ASP
                                             ...AAA GAG ATG GCA ACA GCG GCG TTC AGA TTG AT
                                                 270              280              290              300

GLY ASN ILE THR SER ALA THR GLY GLY                                                 ...
GGC AAT ATT ACT TCC GCT ACT GGC GGA A...
                310                    320
                                             ...SER LEU THR VAL TYR SER SER GLY TRP VAL ASP
                                             ...GCT TAA CCG TTT ACT CTA GTG GCT GGG TTG AT
                                                 330              340              350              360

VAL HIS LYS ASN ILE THR LEU ASN SER                                                 ...
GTT CAT AAA AAC ATT ACA CTT AAT TCA G...
                370                    380
```

FIG.22C

```
...GLY TYR LEU ASN ILE THR THR LYS SER GLY ASP
...G G T A C T T A A A C A T T A C G A C T A A A A G T G G A G A T
   ...390             400             410             420

VAL ALA PHE GLU GLN GLY ASN ASP LEU...       ...ILE THR GLY GLN GLY THR ILE THR ALA SER
G T C G C C T T C G A A C A A G G G A A T G A C C T A A...   ...C C A T T A C A G G T C A A G G A A C T A T T A C C G C A A G C
          430             440                      450             460             470             480

LYS LYS GLY PHE ARG PHE ASP ASN VAL...       ...THR LEU SER GLY VAL LYS LYS GLY PHE LEU PHE
A A A A A G G T T T T A G A T T T G A T A A T G T T A...   ...C T C T A A G T G G A G T G A A A A A G G G G T T C C T T T T
          490             500                      510             520             530             540

LYS TYR SER GLN THR ASN ASN LYS...       ...ASP SER ASN PHE GLU ASN HIS PHE ARG GLY THR
A A A T A C A G C C A A A C C A A C A A T A A A G...   ...A T A G C A A T T T C G A A A A C C A T T T T A G A G G A A C T
          550             560                      570             580             590             600
```

FIG.22D

```
LEU  ASN  ILE  SER  GLY  LYS  VAL  ASP  ILE   ...
T T A A A T A T T T C A G G G A A A G T A G A T A T C T ...
                    610                  620

...LEU  MET  GLN  ALA  ARG  GLN  GLU  ASN  TRP  ASN  ARG
      ... T A A T G C A A G C A G G A G A A C T G G A A C C G C
                       630            640               650            660

ARG  HIS  SER  GLY  ARG  SER  HIS  TRP  ASN   ...
A G A C A C T C G G G A C G C T C C C A C T G G A A T G ...
                    670                  680

...VAL  THR  ARG  LEU  ASN  VAL  SER  THR  ASN  SER  TYR
      ... T A A C C C G A T T G A A T G T T T C T A C A A A T A G T T A T
                       690            700               710            720

LEU  ASN  ILE  THR  ILE  ASP  ASN  SER  GLY   ...
C T C A A C A T C A C T A T T G A T A A C A G T G G C A ...
                    730                  740

...SER  ARG  PRO  SER  PRO  GLY  ALA  GLY  PRO  LEU  TYR
      ... G C C G T C C A T C C C C T G G T G C C G G C C C T C T A T A T
                       750            760               770            780

ARG  ARG  SER  GLY  LEU  ASN  GLY  ILE  SER   ...
A G A C G T T C G G G T T T A A A T G G C A T A T C G T ...
                    790                  800
```

FIG. 22E

```
                ...PHE ASN ASN ASP THR VAL PHE ASN VAL ALA SER
                ...T T A A C A A T G A C A C T G T T T T T A A T G T T G C G T C A
                ....810                        820                        830                        840

GLY SER ALA VAL ASN PHE SER ILE LYS                            ...PRO PRO ILE VAL SER ASN VAL HIS ASP GLY ASN
G G T T C G G C A G T T A A C T T T T A G C A T C A A G C...   ...C A C C A A T A G T A A G C A A T G T A C A C G A C G G G A A T
                        850                        860                                890                        900

HIS THR LEU PHE ASN GLY ASN VAL SER                            ...VAL LEU GLY GLY GLY ASP VAL ASN PHE HIS PHE
C A C A C A T T A T T C A A T G G G A A T G T T T C A G...    ...T T T T A G G G G G A G G G G A T G T C A A C T T T C A T T T T
                        910                        920                                940                        960

ASN ALA SER SER SER ASN HIS TRP THR                            ...HIS GLY VAL VAL ILE LYS SER GLN ASN PHE ASN
A A C G C C T C C T C C A G C A A C C A C T G G A C T C...    ...A T G G C G T G G T T A T A A A G T C T C A A A A C T T T A A T
                        970                        980                                1000                       1020
```

```
ALA SER GLU GLY SER SER LEU ARG PHE ...
GCCTCAGAAGGGTCAAGCTTAAGATTCA...
                1040
                            ...LYS SER GLU GLY SER THR ARG THR ALA PHE THR
                            ...AAAGCGAAGGTTCAACACGAACCGCTTTTACA
                               ...1050            1060           1070            1080

ILE GLU SER ASP LEU THR LEU ASN ALA ...
ATAGAAAGTGATTTAACTTTAAATGCCA...
                1090
                            ...GLY GLY ASN ILE SER LEU ASN GLN VAL ALA
                            ...CTGGGGCAATATATCATTGAACCAAGTTGCA
                               ...1110           1120            1130           1140

GLY ILE ASP GLY ASN LEU GLN LYS SER ...
GGTATTGATGGTAATCTCCAAAAAGCC...
                1150                1160
                            ...LEU VAL ALA ASN LYS ASN ILE THR PHE GLU GLY
                            ...TTGTAGCCAATAAAAACATAACCTTTGAAGGG
                               ...1170           1180            1190           1200

GLY ASN ILE THR LEU ALA ALA ASP LYS ...
GGCAATATCACCCTTGCAGCCGATAAAA...
                1210                1220
```

FIG.22G

```
                              ...LYS PRO ILE GLU ILE LYS GLY ASN ILE THR VAL
                              ...A A C C A A T A G A A A T C A A A G G T A A T A T T A C T G T T
                                 ...1230              1240              1250              1260

LYS GLU GLY ALA ALA ASN VAL THR LEU ARG ...
A A A G A A G G A G C C A A T G T C A C C C T T C G T A...
                  1270              1280

...SER ALA ASN TYR GLY ASN ASP LYS SER ALA LEU
                              ...G C G C G A A T T A T G G T A A T G A C A A A T C A G C T T T A
                                 ...1290              1300              1310              1320

SER ILE ARG GLY ASN VAL THR ASN LYS ...
A G T A T A A G A G G A A A T G T C A C T A A T A A A G...
                  1330              1340

...GLY ASN LEU THR VAL THR GLY SER ALA ILE ASN
                              ...G C A A T C T C A C C G T T A C C G G C T C C G C T A T C A A T
                                 ...1350              1360              1370              1380

ILE GLU LYS ASN LEU THR VAL GLU GLY ...
A T A G A A A A A A A T C T T A C C G T T G A A G G T A...
                  1390              1400

...SER ALA LYS PHE LEU ALA ASN PRO ASN TYR SER
                              ...G T G C T A A G T T T T T A G C T A A T C C A A A T T A C A G C
                                 ...1410              1420              1430              1440
```

FIG.22H

```
PHE ASN VAL SER GLY LEU PHE ASP ASN ...
TTTAACGTATCCGGCCTATTTGACAACC...
        1450              1460        ...1470

...GLN GLY LYS SER ASN ILE SER ILE ALA LYS GLY
                                    ...AAGGCAAGTCAAACATTTCCATTGCCAAGGA
                                        ...1480              1490              1500

GLY ALA HIS PHE LYS ASP ILE ASN ASN ...
GGGGCTCACTTTAAAGACATTAATAACA...
        1510              1520        ...1530

...THR LYS SER LEU ASN ILE THR THR ASN SER ASP
                                    ...CTAAGAGTTTAAACATTACTACCAACTCCGAC
                                        ...1540              1550              1560

SER ALA TYR ARG THR ILE ILE GLU GLY ...
TCCGCTTACCGCACTATTATAGAAGGCA...
        1570              1580        ...1590

...ASN ILE THR ASN SER ASN GLY ASP LEU ASN ILE
                                    ...ATATAACCAACAGTAACGGGGATTTAAATATC
                                        ...1600              1610              1620

THR ASP ASN LYS ASN ASN ALA GLU ILE ...
ACTGATAATAAAAATAACGCTGAAATCC...
        1630              1640
```

FIG. 22I

```
ASN LEU THR ILE SER SER ASP SER SER ASP SER SER    ...GLN ILE GLY GLY ASN ILE SER GLN LYS GLU GLY
AATCTCACGATTTCTTCCGA                               ...AAATTGGCGGCAATATCTCGCAAAAGAAGGT
         1690                                         ...1650      1660          1670          1680

...ASN ILE THR ASN GLN ILE THR ILE LYS LYS GLY
                                                   ...ATATCACTAACCAGATAACAATCAAGAAGGT
         1700                                         ...1710      1720          1730          1740

VAL ASN LYS GLU ASP SER                            ...THR ALA ASN ALA ASN LEU THR ILE LYS THR
GTTAATAAAGAGGATTCTGATTCAAGCA                       ...CGGCAAACAATGCTAATCTAACCATTAAAACC
         1750                                         ...1770      1780          1790          1800
                   1760

LYS GLU LEU GLN LEU THR GLY ASP LEU                ...ASN ILE SER GLY PHE ASP LYS ALA GLU ILE THR
AAAGAATTGCAATTAACGGGAGACCTAA                       ...ATATTTCAGGCTTCGATAAAGCAGAAATCACA
         1810                                         ...1830      1840          1850          1860
                   1820
```

FIG.22J

```
ALA LYS GLU GLY ALA ASP LEU ILE ILE ...
GCC AAA GAG GGG TGC CGA TTT AAT CAT CG...
            1870                    1880
                                            ...GLY ASN SER ASP ASN ASN ASN ALA ASN ALA
                                            ....GTA ATA GTG ATA ATA ACA ACA ATG CTA ATG CT
                                                    ...1890              1900              1910              1920

LYS LYS VAL THR PHE ASN GLN VAL LYS ...
AAA AAA GTA ACC TTT AAC CAG GTT AAA G...
            1930                    1940
                                            ...ASP SER LYS ILE SER ALA ASP SER HIS ASN VAL
                                            ...ATT CGA AAA TCT CTG CTG ACA GTC ACA ATG TA
                                                    ...1950              1960              1970              1980

THR LEU ASN SER LYS VAL GLU THR SER ...
ACA CTA AAC AGT AAA GTA GAA ACC TCT A...
            1990                    2000
                                            ...ASN GLY ASN ASP ALA GLU SER ASN ASN GLY
                                            ...ATG GCA ATA ATG ACG CTG AAA GCA ATA ATG GC
                                                    ...2010              2020              2030              2040

ASP GLY THR SER LEU THR ILE ASN ALA ...
GAT GGC ACC AGC TTA ACT ATT AAT GCA A...
            2050                    2060
```

FIG.22K

```
                     ...LYS ASN ILE THR VAL ASN ASN ASN ILE THR SER
                     ...A A A T A T A A C A G T A A A C A A C A A T A T T A C T T C T
                        ...2070              2080              2090              2100

HIS LYS THR VAL ASN ILE THR ALA SER         ...GLU ASN VAL THR THR LYS ALA GLY THR ILE
C A C A A A A C A G T A A A T A T C A C T G C G T C A G...   ...A A A T G T T A C C A C C A A A G C G G G C A C A A C C A T T
         2110              2120                                  2130              2140              2150              2160

ASN ALA THR THR GLY SER VAL GLU VAL         ...THR ALA LYS THR GLY ASP ILE LYS GLY LYS VAL
A A T G C A A C C A C A G G T A G C G T A G A A G T A A...   ...C A G C C A A A A C A G G T G A T A T T A A A G G T A A A G T T
         2170              2180                                  2190              2200              2210              2220

GLU SER THR SER GLY SER VAL THR LEU         ...THR ALA THR GLY GLU ALA LEU ALA VAL SER ASN
G A A T C C A C T T C C G G C T C T G T A A C A C T T A...   ...C T G C A A C C G G A G A A G C T C T T G C T G T A A G C A A C
         2230              2240                                  2250              2260              2270              2280
```

FIG.22L

```
ILE SER GLY ASN THR VAL THR ILE THR ...
ATTTCAGGCAACACTGTTACCATCACTG...
         2290                    2300

...ALA ASN LYS GLY LYS LEU THR THR GLN ALA GLY
                              ...CAAATAAGGGTAAATTAACAACTCAAGCAGGC
                                   ...2310              2320             2330         2340

SER THR VAL SER ALA ILE ASN GLY VAL ...
TCTACGGTTAGCGCGATTAACGGTGTAA....
         2350                    2360

...THR ALA SER GLN SER GLY ASP ILE SER GLY
                              ...CTGCCCTCAAGCCAATCAGGCGATATTAGCGGT
                                   ...2370              2380             2390         2400

THR ILE SER GLY ASN THR VAL LYS VAL ...
ACGATTTCCGGTAACACAGTAAAAGTTA...
         2410                    2420

...SER ALA ILE GLY ASP LEU THR LYS SER GLY
                              ...GTGCGATCGGTGATTTGACTACTAAATCCGGC
                                   ...2430              2440             2450         2460

SER GLU ILE LYS ALA LYS THR GLY GLU ...
TCGGAAATCAAGGCAAAAACAGGTGAGG...
         2470                    2480
```

FIG.22M

```
        ...ALA ASN VAL THR SER ALA THR GLY THR ILE GLY
        ...CTAACGTGACAAGTGCGACAGGTACAATTGGT
        ...2490           2500          2510          2520

GLY THR ILE SER GLY ASN ALA VAL ASN ...VAL THR ALA ASN THR GLY ASP LEU THR VAL GLU
GGTACGATTTCTGGTAATGCAGTAAATG...  TTACAGCAAATACTGGCGATTTAACTGTTGAA
          2530                2540     ...2550         2560          2570          2580

ASP ALA ALA LYS ILE ASP ALA THR GLY ...GLY ALA ALA THR LEU THR ALA THR SER GLY LYS
GATGCCGCAAAAATTGATGCGACAGGAG...  GAGCCGCGACCCTAACTGCAACATCGGGCAAA
          2590                2600     ...2610         2620          2630          2640

LEU THR THR LYS ALA SER SER ILE ...THR SER ALA ASN ASN GLN VAL ASN LEU SER ALA
TTAACCACTAAGGCTAGTTCAAGCATTA...  CTTCAGCTAATAACCAGGTAAACCTTTCAGCT
          2650                2660     ...2670          2680          2690          2700
```

FIG.22N

```
LYS ASP GLY SER ILE GLY GLY ASN ILE  ...                                    THR THR GLY
AAG GAT GGT AGC ATT GGG GGA AAT ATC A...    ...ASN ALA ALA ASN VAL THR LEU ASN THR THR GLY
          2710               2720           ...ATG CTG CTA ATG TAA CAC TGA ATA CTA CAG GC
                                                  2730              2740              2750              2760

ALA LEU THR THR VAL LYS GLY SER SER  ...                                    VAL ILE ASN
GCT CTA ACT ACC GTG AAG GGT TCA AGC A...    ...ILE ASN ALA ASN SER GLY THR LEU VAL ILE ASN
          2770               2780           ...TTA ACG CAA ACA GCG GCA CCT TGG TTA TTA AAC
                                                  2790              2800              2810              2820

ALA LYS ASP ALA GLU LEU ASN GLY GLU  ...                                    ASN ALA THR
GCA AAA GAC GCT GAG CTA AAT GGT GAG G...    ...ALA SER GLY ASN HIS THR VAL VAL ASN ALA THR
          2830               2840           ...CAT CAG GTA ACC ATA CAG TAG TGA ATG CAA CC
                                                  2850              2860              2870              2880

ASN ALA ASN GLY SER GLY SER VAL ILE  ...
AAC GCA AAT GGC TCC GGC AGC GTA ATC G...
          2890               2900
```

FIG.220

```
                                  ...ALA THR THR SER SER ARG VAL ASN ILE THR GLY
                                  ...C G A C A A C C T C A A G C A G A G T G A A C A T C A C T G G G
                                     ...2910      2920           2930           2940

ASP LEU ILE THR ILE ASN GLY LEU ASN                                                  ...
G A T T T A A T C A C A A T A A A T G G A T T A A A T A...
            2950                    2960

...ILE ILE SER LYS ASN GLY ILE ASN THR VAL LEU
                                  ...T C A T T T C A A A A A A C G G T A T A A A C A C C G T A C T G
                                     ...2970      2980           2990           3000

LEU LYS GLY VAL LYS ILE ASP VAL LYS                                                  ...
T T A A A A G G C G T T A A A A T T G A T G T G A A A T...
            3010                    3020

...TYR ILE GLN PRO GLY ILE ALA SER VAL ASP GLU
                                  ...A C A T T C A A C C G G G T A T A G C A A G C G T A G A T G A A
                                     ...3030      3040           3050           3060

VAL ILE GLU ALA LYS ARG ILE LEU GLU                                                  ...
G T A A T T G A A G C G A A A C G C A T C C T T G A G A...
            3070                    3080

...LYS VAL LYS ASP LEU SER ASP GLU GLU ARG GLU
                                  ...A G G T A A A A G A T T T A T C T G A T G A A G A A A G A G A A
                                     ...3090      3100           3110           3120
```

FIG.22P

```
ALA LEU ALA LYS LEU GLY VAL SER ALA ...
GCGTTAGCTAAACTTGGCGTAAGCGCTG...
         3130                 3140

...VAL ARG PHE ALA GLU PRO ASN ASN ALA ILE THR
...TACGTTTTGCTGAGCCAAATAATGCCATTACG
       3150            3160            3170         3180

ILE ASN THR GLN ASN GLU PHE THR THR ...
ATTAATACACAAAATGAGTTTACAACCA...
         3190                 3200

...ARG PRO SER SER GLN VAL THR ILE SER GLU GLY
...GACCATCAAGTGACAATTTCTGAAGGT
       3210            3220            3230         3240

LYS VAL CYS PHE LEU ILE GLY ASN GLY ...
AAGGTATGTTTCTTAATCGGCAATGGTG...
         3250                 3260

...ALA THR ILE CYS THR ASN ILE ALA ASP ILE GLU
...CAACAAATATGCACCAATATTGCTGATATTGAG
       3270            3280            3290         3300

ARG ***
CGGTAG
```

FIG. 23A

LCDC2 hmw2A sequence

```
LYS GLU TRP LEU LEU ASP PRO ASP ASP ...
A A A G A G T G G T T G T T A G A C C C G G A T G ...
                    10                  20

...VAL SER ILE ASP ALA PRO SER ALA GLU ARG THR
       ...T A T C C A T T G A C G C A C C T T C G G C T G A A C G C A C T
              30                      40                      50                      60

ASP THR GLY GLU ASP VAL GLU TYR THR ...
G A C A C T G G C G A A G A C G T G G A A T A C A C C G ...
                    70                      80

...GLY THR GLY ALA ASP ILE ASN HIS GLN LYS GLN
       ...G A A C A G G G G C T G A T A T T A A C C A T C A A A A A C A A
              90                      100                     110                     120

ASN SER GLU THR LYS SER THR LEU THR ...
A A C A G C G A A A C C A A G T C A A C A T T A A C A A ...
                    130                     140

...ASN THR THR LEU GLU GLY MET LEU LYS ARG GLY
       ...A C A C A A C T C T T G A G G G G A T G T T A A A A A G G G G G
              150                     160                     170                     180
```

FIG.23B

```
LEU PHE VAL ASN ILE THR ALA ARG ASN ...
CTTTTTGTTAATATCACCGCCAGAAATA...
                190              200

...LYS ILE ARG VAL ASN SER THR ILE ASN ILE GLY
                              ...AAATCCGAGTTAATAGCACCATCAATATCGGG
                                    210              220              230              240

ASP SER GLY HIS LEU THR LEU TYR LYS ...
GATAGCGGGCCATTTAACCCTTTACAAAA...
                250              260

...LYS ARG LYS ASN ARG SER ASP GLY ILE GLN ILE
                              ...AAAGAAAAAATCGTAGCGATGGTATTCAAATT
                                    270              280              290              300

ASN LYS ASP ILE THR SER THR GLY GLY ...
AACAAGGATATTACTTCTACAGGCGGAA...
                310              320

...SER LEU THR ILE ASN SER ASP ASP TRP VAL ASP
                              ...GTTAACTATTAACTCCGACGACTGGGTTGAT
                                    330              340              350              360

ILE HIS GLY ASN ILE THR LEU GLY GLU ...
ATTCATGGAAATATCACGCTTGGTGAGG...
                370              380
```

FIG.23C

```
                                        ...GLY PHE LEU ASN ILE THR SER SER ASP SER VAL
                                        ...G C T T T T A A A T A T T A C C T C T A G T G A T T C C G T G
                                        ...390                     400                     410                     420

ALA PHE GLU GLY GLY ASN GLY ASN LYS ...GLY ARG SER SER ALA GLN ILE ILE ALA
G C T T T C G A G G G T G G A A A C G G C A A T A A A G... ...G A C G T A G C T C A G C A A G T G C T C A A A T T A T C G C G
                    430                     440                                             450                     460                     470                     480

GLN GLY THR ILE THR LEU THR GLY GLU ...ASN LYS THR PHE ARG LEU ASN ASN VAL SER LEU
C A G G G T A C T A T A A C T C T T A C T G G A G A A A... ...A T A A A A C C T T T A G A C T C A A C A A T G T C T T T A
                    490                     500                                             510                     520                     530                     540

ASN GLY THR GLY ASN GLY LEU SER ILE ...ILE SER THR ALA SER ASN LEU SER HIS ARG LEU
A A T G G G A C G G G T A A T G G T C T A A G T A T T A... ...T T T C A A C A G C A A T T T A T C T C A T A G A C T T
                    550                     560                                             570                     580                     590                     600
```

FIG.23D

ASP GLY GLU ILE ASN VAL SER GLY ASN ...VAL THR ILE ASN GLN THR THR GLN GLN ASN ILE
GACGGTGAAATTAATGTATCTGGAAATG...TAACAATTAATCAAACCACGCAGCAAACATT
        610              620      ...630                640           650           660

GLU TYR TRP LYS ALA SER SER ASP SER ...TYR TRP ASN VAL THR SER PHE ASN LEU ARG GLU
GAATACTGGAAGGCTAGCAGCGATTCTT...ATTGGAATGTCACTTCTTTTAATTTGAGAGAA
        670              680      ...690                700           710           720

ASP SER LYS PHE THR PHE ILE LYS TYR ...VAL ASN SER ALA ARG ASN GLY ASP VAL ARG GLY
GATTCAAAGTTTACCTTTATCAAATACG...TTAACTCTGCCAGAAATGGTGATGTAAGAGGA
        730              740      ...750                760           770           780

ARG SER PHE ALA GLY VAL ILE PHE ASN ...
AGAAGTTTTGCAGGTGTGATATTTAATG...
        790              800

FIG. 23E

```
                     ...ALA LYS GLY LEU THR THR SER PHE ASN VAL LYS
                     ...C T A A A G G T C T C A C T A C A A G C T T T A A C G T C A A G
                        ...810                  820                  830                 840

LYS GLY SER THR VAL ASP PHE LYS LEU...
A A A G G C T C G A C A G T T G A T T T T A A A T T A A...
            850                  860

...LYS PRO ASN SER GLY TYR ASN SER GLN LYS ARG
                     ...A G C C A A A T T C A G G C T A T A A T T C A C A A A A A G G
                        ...870                  880                  890                 900

ILE PRO ILE GLN PHE GLN SER ASN ILE...
A T T C C A A T T C A A T T C C A A T C C A A C A T C T...
            910                  920

...SER VAL SER GLY GLY ARG GLY ARG VAL ASN ILE ASN
                     ...C G G T C T C A G G A G G A G G A A G G G T A A A C A T T A A C
                        ...930                  940                  950                 960

THR LEU ALA ASN LEU THR GLY GLY GLY...
A C G C T C G C C A A T C T T A C A G G C G G G A G G A G...
            970                  980

...VAL GLU ILE ARG SER SER ILE ASN VAL SER
                     ...T T G A G A T A A G A T C G A G T T C A A T T A A T G T T T C T
                        ...990                 1000                 1010                1020
```

FIG.23F

```
ASP GLY SER THR LEU SER MET THR ALA                    ...
GATGGCTCAACCCTCTCTATGACAGCTC...
                1030             1040

...GLN ALA ARG ASP ARG ASN ALA PHE GLU ILE THR
                         ...AGGCTCGCGACAGGAATGCCTTTGAAATTACC
                            ...1050             1060             1070             1080

LYS ASP LEU VAL ILE ASN ALA SER ASN                    ...
AAAGATTTAGTTATAAACGCAAGCAATT...
                1090             1100

...SER ASN LEU SER ILE ILE GLN GLN ASN ASP GLY
                         ...CAAACCTATCTTATTATACAGCAAAATGATGGA
                            ...1110             1120             1130             1140

PHE ASP ASN ASN GLN LYS ALA ASN ALA                    ...
TTTGATAATAATCAAAAGGCAAATGCCA...
                1150             1160

...ILE ASN SER LYS TYR ASN VAL THR ILE GLN GLY
                         ...TTAACTCAAAATATAACGTAACTATTCAAGGT
                            ...1170             1180             1190             1200

GLY ASN VAL THR LEU GLY GLY GLN ASN                    ...
GGTAATGTTACCCTTGGCGGGCAAAATT...
                1210             1220
```

FIG. 23G

```
          ...SER SER SER THR ILE THR GLY SER VAL ASN ILE
          ...C A A G C A G T A C A A T C A C A G G G A G T G T T A A T A T T
                 ...1230            1240            1250            1260

GLY ALA ALA ASN VAL THR LEU GLN ...
G G C G C T A A T G C A A A T G T T A C T T T G C A A G ...
           1270            1280            ...1290

THR PHE GLY ASN VAL SER VAL GLU GLY ...ALA HIS ASN GLY ASN ASP ARG ASN LYS LEU
A C C T T C G G T A A T G T A T C T G T T G A A G G A G ...C C C A C A A T G G C A A T G A T A G A A A T A A A A G C T A
           1330            1340            ...            ...1290  1300            1310            1320

...GLU LEU ARG LEU VAL GLY ALA SER ALA ASN ILE
                                              ...A A T T A A G G C T A G T T G G C G C A A G T G C A A A C A T T
                                                      ...1350            1360            1370            1380

ASN ASN ASN LEU SER VAL LYS SER GLY ...ALA LYS PHE LYS ALA GLU THR ASN ASP ASN LEU
A A C A A C A A T C T T A G T G T T A A G A G C G G G T G ...C T A A A T T C A A A G C A G A A A C A A A T G A C A A C C T A
           1390            1400            ...1410            1420            1430            1440
```

FIG.23H

```
ASN ILE THR GLY THR PHE THR ASN ASN
AACATTACCGGCACCTTTACCAACAACG...
            1450       1460       ...1470

...GLY THR SER ILE ILE ASP VAL LYS LYS GLY ALA
                           ...GCACCTCCATAATTGATGTAAAAAAGGGGCG
                              ...1480       1490       1500

ALA LYS LEU GLY ASN ILE THR ASN ASP
GCAAAACTAGGCAATATTACCAATGATG...
            1510       1520       ...1530

...GLY ASN LEU ASN ILE THR THR ASN ALA LYS ASN
                           ...GTAATTTAAATATCACTACTAATGCTAAAAAC
                              ...1540       1550       1560

GLY GLN LYS SER VAL ILE ASN GLY ASN
GGTCAAAAAGCGTTATCAACGGAAATA...
            1570       1580       ...1590

...ILE THR ASN ASN LYS GLY ALA LEU ASN ILE THR
                           ...TAACTAACAATAAAGGTGCTTTAAATATTACG
                              ...1600       1610       1620

ASN ASN GLY ASN ASP THR GLU ILE GLN
AATAATGGTAATGACACTGAAATCCAAA...
            1630       1640
```

FIG.23I

```
        LEU THR ILE SER SER ASP LYS      ...ILE GLY GLY ASN ILE SER GLN LYS GLU GLY ASN
        CTCACGATTTCTTCTCTGACAAA          ...TTGGCGGCAATATCTCGCAAAAAGAAGGTAAT
                  1690                   ...1650              1660              1670              1680

...ILE ASN
                                         ...TTAATA...
                                         ...1700

LEU THR ILE SER SER ASP LYS      ...ILE THR LYS ARG ILE GLU ILE LYS ALA GLY THR
                                         ...TCACCAAACGGATAGAAATTAAGGCAGGTACT
                                         ...1710              1720              1730              1740

ASP GLN GLY ASN SER ASP SER      ...ALA SER ASN ALA ASN LEU THR ILE LYS THR LYS
        GATCAAGGGAATTCTGATTCAGG          ...CAAGTAATGCTAATCTAACCATTAAAACCAAA
                  1750                   ...1770              1780              1790              1800

...GLY VAL
                                         ...GCGTAG...
                                         ...1760

GLU LEU LYS LEU THR GLU ASN      ...ILE SER GLY PHE ASP LYS ALA GLU ILE VAL ALA
        GAATTGAAATTAACAGAAAAC             ...TTTCAGGTTTTGATAAAGCAGAAATTGTAGCC
                  1810                   ...1830              1840              1850              1860

...LEU ASN
                                         ...CCTAAATA...
                                         ...1820
```

FIG.23J

```
LYS GLU ASN ASN ASN LEU ILE ILE GLY ...
A A A G A G A A T A A C A A T T T A A T T A T T G G C A...
            1870                1880
                                        ...ASN ASN GLY ASP ASN ALA ASN ALA LYS THR
                                        ...A T A A T A A T G G C G A C A A T G C T A A C G C C A A A A C A
                                              1890          1900          1910          1920

VAL THR PHE ASN ASN VAL LYS ASP SER ...
G T A A C T T T T A A C A A T G T T A A A G A T T C A A...
            1930                1940
                                        ...LYS ILE SER ALA ASN GLY HIS ASN VAL THR LEU
                                        ...A A A T C T C T G C T A A C G G T C A C A A T G T G A C A C T A
                                              1950          1960          1970          1980

ASN SER LYS VAL GLU THR SER ASP GLY ...
A A T A G C A A A G T G G A A A C A T C T G A T G G A A...
            1990                2000
                                        ...ASN SER ASN THR GLU GLY ASN SER ASP ASN ASN
                                        ...A C A G T A A C A C T G A A G G T A A T A G T G A C A A T A A C
                                              2010          2020          2030          2040

ALA GLY LEU THR ILE ASP ALA LYS ASN ...
G C C G G C T T A A C T A T C G A T G C A A A A A A T G...
            2050                2060
```

FIG.23K

```
                                          ...VAL THR VAL ASN ASN ASP ILE THR SER HIS LYS
                                          ....T A A C A G T A A A C A A C G A T A T C A C T T C T C A C A A A
                                          ...2070                            2080                       2090                       2100

THR VAL ASN ILE THR ALA SER GLU ARG ...                    ...ILE ASP THR LYS ALA ASP THR THR ILE ASN ALA
A C A G T A A A T A T C A C T G C G T C A G A A A G G A   ...T T G A T A C T A A A G C T G A T A C A A C C A T T A A T G C A
                   2110                           2120    ...2130                          2140                        2150                     2160

THR THR GLY ASN VAL LYS LEU THR ALA ...                    ...VAL THR SER ASP ILE GLN GLY GLY ILE LYS SER
A C C A C C G G C A A C G T G A A A C T A A C A G C T G   ....T A A C A A G T G A T A T C C A A G G T G G A A T T A A A T C T
                   2170                           2180    ...2190                          2200                        2210                     2220

ASN SER GLY ASP VAL ASN ILE THR THR ...                    ...SER THR GLY SER ILE ASN GLY LYS ILE GLU SER
A A T T C T G G T G A T G T A A A T A T C A C A A C C A   ...G C A C A G G T A G C A T T A A C G G T A A A A T T G A A T C C
                   2230                           2240    ...2250                          2260                        2270                     2280
```

FIG.23L

LYS SER GLY SER VAL THR LEU THR ALA
A A G T C T G G C T C T G T A A C A C T T A C C G C A A...
                2290                                     2300

...THR GLU LYS THR LEU THR VAL GLY ASN VAL SER
...C C G A A A A A C T C T T A C T G T A G G C A A T G T T T C G
      2310                  2320                  2330                  2340

GLY ASN THR VAL THR VAL THR ALA ASN
G G C A A C A C C G T T A C T G T T A C T G C A A A T A...
                2350                                     2360

...ARG GLY ALA LEU THR THR LEU ALA GLY SER THR
...G A G G T G C A T T A A C C A C T T T G G C A G G C T C T A C G
      2370                  2380                  2390                  2400

ILE ASN GLY THR ASN GLY VAL THR THR
A T T A A C G G G A C T A A C G G T G T A A C T A C C T...
                2410                                     2420

...SER SER GLN SER GLY GLU ILE GLY GLU VAL
...C A A G T C A A T C A G G C G A G A T T G G C G A G G T T
      2430                  2440                  2450                  2460

THR GLY LYS THR VAL SER VAL THR ALA
A C T G G T A A G A C A G T A A G T G T T A C A G C A A...
                2470                                     2480

FIG.23M

```
                                    ...THR ALA GLY SER LEU THR VAL LYS GLY GLY ALA
                                    ...C T G C C G G C A G C T T A A C T G T T A A A G G T G G C G C A
                                        ..2490                         2500                         2510                         2520

LYS ILE ASN ALA THR GLU GLY                                     ...THR LEU THR ALA SER GLY LYS LEU THR THR
A A A A T T A A T G C G A C A G A A G G A A C T G C A A ...    ...C C T T A A C T G C A T C G G G C A A A T T A A C C A C C
                    2530                                 2540      ...2550                         2560                         2570                         2580

GLU ALA SER SER ASN ILE THR SER ALA                             ...LYS GLY GLN VAL ASP LEU SER ALA GLN ASP GLY
G A G G C T A G C T C A A A C A T C A C T T C A G C C A ...    ...A A G G T C A G G T A G A C C T T T C A G C T C A G G A T G G T
                    2590                                 2600      ...2610                         2620                         2630                         2640

SER ILE ALA GLY GLN ILE SER ALA ALA                             ...ASN VAL THR LEU ASN THR THR GLY THR LEU THR
A G C A T T G C A G G A C A A A T T A G T G C A G C T A ...    ...A T G T A A C A C T G A A T A C T A C A G G C A C T C T A A C T
                    2650                                 2660      ...2670                         2680                         2690                         2700
```

FIG.23N

```
THR VAL GLU GLY SER SER ILE ASN ALA                         ILE ASN ALA ASN ASP
ACCGTAGAGGGTTCAAGCATTAACGCAA...        ...ACGAAGGCACCCTTGGTTATTAACGCAAACGAC
              2710                                                        2760
                                  ...ASN GLU GLY THR LEU VAL
                                  ...ACGAAGGCACCCTTGG...
                                        2730              2740

ALA LYS LEU ASP GLY LYS ALA SER GLY                         VAL ASN ALA THR ASN ALA SER
GCCAAGTTAGATGGTAAGGCATCAGGTA...        ...ACCGTACAGAAGTAAATGCAACTAACGCAAGC
              2770                                                        2820
                                  ...ASN ARG THR GLU
                                  ...ACCGTACAGAAGTA...
                                        2790    2800

GLY SER GLY SER VAL THR ALA LYS THR                         SER VAL ASN ILE THR GLY ASP LEU ASN
GGCTCTGGTAGCGTGACTGCGAAAACCT...        ...CAAGCAGCGTGAATATCACCGGGGATTTAAAC
              2830                                                        2880
                                  ...SER SER VAL
                                  ...CAAGCAGCGTGAATATCACC...
                                        2850      2860

THR ILE ASN GLY LEU ASN ILE ILE SER
ACAATAAATGGGTTAAATATCATTTCGG...
              2890              2900
```

FIG.230

```
                      ...GLU ASN GLY ARG ASN THR VAL ARG LEU ARG GLY
                      ....A A A A T G G T A G A A A C A C T G T G C G C T T A A G A G G C
                         ...2910              2920              2930              2940

LYS GLU ILE GLU VAL LYS TYR ILE GLN...           ...PRO GLY VAL ALA SER VAL GLU VAL ILE GLU
A A G G A A A T T G A G G T G A A A T A T C C A G C...  ...C A G G T G T A G C A A G T G T A G A A G T A A T T G A A
          2950              2960                               2970              2980              2990              3000

ALA LYS ARG VAL LEU GLU LYS VAL LYS...           ...ASP LEU SER ASP GLU ARG GLU THR LEU ALA
G C G A A A C G C G T C C T T G A G A A A G T G A A A G...  ...A T T T A T C T G A T G A A A G A G A A A C A T T A G C T
          3010              3020                               3030              3040              3050              3060

LYS LEU GLY VAL SER ALA VAL ARG PHE...           ...ILE GLU PRO ASN ASN THR ILE THR VAL ASN THR
A A A C T T G G T G T A A G T G C T G T A C G T T T T A...  ...T T G A A C C A A A A T A A T A C C A T T A C G G T T A A C A C A
          3070              3080                               3090              3100              3110              3120
```

FIG.23P

```
GLN ASN GLU PHE THR THR ARG PRO SER ...
C A A A A T G A G T T T A C A A C C A G A C C A T C A A ...
                  3130                    3140
                                                   ...3150

...SER GLN VAL THR ILE SER GLU GLY LYS ALA CYS
    ...G T C A A G T G A C A A T T T C T G A A G G T A A G G C G T G T
                        3160                    3170              3180

PHE SER SER GLY ASN GLY ALA ALA VAL ...
T T C T C A A G T G G T A A T G G C G C A G C A G T A T ...
                  3190                    3200
                                                   ...3210

...CYS THR ASN VAL ALA ASP ASP GLY GLN GLN ***
    ...G T A C C A A T G T T G C T G A C G A T G G A C A G C A G T A G
                        3220                    3230              3240
```

FIG. 24A

PMH1 hmw1A sequence

→

LYS GLU TRP LEU LEU ASP PRO ASP ASN ...
A A A G A G T G G T T G T T A G A C C C G G A T A A T G ...
              10                    20

...VAL ASN ILE VAL LYS GLY THR GLU LEU GLN ASN ...
...T C A A T A T T G T T A A A G G A A C C G A A T T A C A G A A T
    30                40                  50                  60

ASP LEU VAL VAL ARG GLY ASP SER ILE ...
G A T T T G G T T G T T A G G G G C G A T A G T A T T G ...
              70                    80

...GLU LYS LYS ASN ALA PRO THR LYS THR ILE
...A G A A A A A G A A T G C C C C T A C C A A G A C T A C A A T T
    90                100              110              120

HIS ALA GLY SER ILE GLU GLN SER LEU ...
C A T G C A G G C T C T A T A G A A C A A T C T T T G A ...
              130                  140

...MET LYS GLY GLY ALA VAL ASN ILE SER ALA THR
...T G A A G G G G T G G T G C A G T T A A T A T T T C T G C T A C A
    150                160              170              180

FIG.24B

```
ASN LYS VAL ASN VAL THR THR ASP ILE   ...
A A T A A A G T A A A T G T T A C T A C A G A T A T T A...
                      190                     200
                                                    ...ASN VAL TYR ASN GLY ALA LEU THR LEU HIS SER
                                                    ...A T G T T T A T A A T G G A G C A T T A A C G T T A C A C T C A
                                                       210                     220                     230                     240
GLU ARG ASP GLY VAL GLU ILE ASN GLY   ...
G A A C G A G A T G G A G T T G A A A T T A A C G G T A...
                      250                     260
                                                    ...ASN ILE THR SER GLU LYS ASN GLY ASN LEU THR
                                                    ...A T A T T A C C T C A G A A A A A A T G G T A A T T T A A C C
                                                       270                     280                     290                     300
ILE LYS ALA GLY SER TRP VAL ASP VAL   ...
A T T A A A G C A G G T A G C T G G G T T G A T G T T C...
                      310                     320
                                                    ...HIS LYS ASN ILE THR LEU GLY GLU GLY PHE LEU
                                                    ...A T A A A A A A T A T C A C A C T T G G C G A G G G T T T T T G
                                                       330                     340                     350                     360
ASN ILE THR SER GLY ASP ILE ALA PHE   ...
A A T A T T A C T T C C G G T G A T A T C G C C T T C G...
                      370                     380
```

FIG.24C

...GLU LYS GLY ASN ASN LEU THR ILE THR ALA GLN
...A A A A A G G T A A T C T A A C C A T T A C C G C T C A A
...390          400          410          420

GLY ASN ILE THR SER ASN LYS ASP GLY...
G G A A A T A T A A C C T C T A A T A A A G A C G G A A...
         430          440

...LYS GLN LEU ARG LEU ASN ASN VAL SER LEU ASN
...A A C A A C T T A G A C T T A A T A A T G T A T C T T T A A A T
   450          460          470          480

GLY THR GLY ALA GLY LEU ASN PHE ILE...
G G A A C A G G T G C A G G T T T A A A C T T T A T T G...
         490          500

...ALA ASN GLN ASN ASN PHE THR HIS ASN ILE SER
...C A A A T C A A A A T A A T T T T A C A C A C A A C A T T A G T
   510          520          530          540

GLY ALA ILE ASN ILE SER GLY VAL VAL...
G G C G C G A T T A A C A T T T C C G G A G T A G T A A...
         550          560

...THR ILE ASN GLN THR THR LYS LYS ASN ALA LYS
...C G A T T A A T C A A A C T A C G A A A A A A C G C T A A G
   570          580          590          600

FIG.24D

```
ALA TRP ASN THR SER TYR ASP SER TYR ...TRP ASN VAL SER THR LEU THR LEU SER ASN ASP
GCATGGAATACAAGCTATGACTCTTACT......GGAACGTATCTTACTCTTACTTTAAGCAATGAT
            610                 620            630            640            650            660

ALA LYS PHE THR PHE ILE LYS TYR VAL ...ASP SER ASN HIS SER THR ASN SER SER ASP SER
GCGAAATTTACCTTTATTAAATATGTCG......ACAGCAATCATTCGACAAACTCCAGTGATTCA
            670                 680            690            700            710            720

ARG SER PHE ALA GLY VAL LYS PHE HIS ...GLY LYS ASN ASN GLU MET LYS PHE ASN ILE GLY
CGAAGTTTTGCGGGAGTAAAGTTCCACG......GCAAGAATAAATGAAATGAAATTTAATATTGGT
            730                 740            750            760            770            780

ASN ASN ALA LYS ALA GLU PHE ARG LEU ...
AATAATGCCAAGGCTGAATTTAGGTTAA...
            790                 800
```

FIG. 24E

```
                                          ...LYS  PRO  ASN  GLU  LYS  THR  THR  PRO  ASN  ARG  PRO
                                          ...A A C C A A A T G A G A A G A C A A C T C C T A A C A G A C C A
                                             ...810                  820                  830           840

LEU  PRO  ILE  GLN  PHE  LEU  SER  ASN  ILE...
C T A C C A A T T C A G T T T T T A T C T A A T A T T T...
              850                  860

...SER  VAL  THR  GLY  GLY  SER  VAL  PHE  PHE  ASP
                                          ...C G G T C A C T G G C G G A G G T T C T G T T T T T C G A T
                                             ...870                  880                  890           900

ILE  TYR  ALA  ASN  LEU  TRP  GLY  LYS  GLY...
A T A T A C G C T A A C C T T T G G G G T A A A G G G A...
              910                  920

...THR  GLU  LEU  LYS  MET  ASP  SER  ILE  ASN  VAL  SER
                                          ...C T G A G C T A A A G A T G G A T T C A A T T A A C G T T T C T
                                             ...930                  940                  950           960

SER  GLY  SER  ASN  LEU  THR  LEU  ASN  SER...
A G C G G C T C T A A T C T T A C C T T A A A T T C C C...
              970                  980

...HIS  VAL  ARG  LYS  TYR  ASN  ALA  PHE  GLU  ILE  ASN
                                          ...A T G T T C G C A A G T A T A A T G C T T T T G A A A T C A A T
                                             ...990                  1000                 1010          1020
```

FIG.24F

```
LYS ASP LEU THR ILE ASN ALA THR ASN ...      ...SER ASN PHE ASN LEU ARG GLN THR SER ASP SER
A A A G A C T T A A C T A T A A A C G C A A C T A A T T ... ... C A A A T T T C A A C C T C A G A C A G A C G T C A G A T A G T
                        1030                        1040              ...1050            1060                  1070                  1080

PHE ARG ASN GLY TYR ARG ASN ASN ALA ...      ...ILE ASN SER THR HIS ASN ILE SER ILE LEU GLY
T T T C G T A A C G G G T A C C G C A A T A A T G C C A ... ... T C A A T T C A A C C A C A C A T A T C C A T C T T G G G C
                        1090                        1100              ...1110            1120                  1130                  1140

GLY ASN VAL THR LEU GLY GLY GLN ASN ...      ...SER SER SER ILE MET GLY ASN ILE ILE ILE
G G C A A C G T C A C T C T C G G C G G A C A A A A C T ... ... C A A G C A G C A G C A T T A T G G G A A T A T C A T C A T C
                        1150                        1160              ...1170            1180                  1190                  1200

LYS ARG ALA ALA ASN VAL THR LEU GLU ...
A A G C G A G C A G C A A A T G T T A C G C T A G A A G ...
                        1210                        1220
```

FIG. 24G

```
                              ...ALA ASP ASN SER HIS ASN SER ASP ASN VAL LYS
                              ...CCGATAATAGTCACAATTCTGACAACGTAAAG
                              ...1230              1240              1250              1260

ASP ARG THR ILE ASN LEU GLY ASN LEU ...    ...THR VAL GLU GLY ASN LEU SER LEU ILE GLY GLU
GATAGAACTATAAATCTTGGCAACTTGA...            ...CCGTTGAGGGGAATTTAAGTTTAATTGGCGAA
          1270               1280                  1290              1300              1310              1320

ASN ALA ASN ILE ASN GLY ASN LEU SER ...    ...ILE GLU LYS GLU ALA ILE PHE LYS GLY LYS THR
AATGCAAATATTAACGGCAATCTCTCCA...            ...TTGAAAAAGAAGCCATCTTTAAAGGAAAAACC
          1330               1340                  1350              1360              1370              1380

LYS ASP SER LEU ASN ILE THR GLY ASN ...    ...PHE THR ASN ASN GLY THR ALA GLU ILE ASN ILE
AAGGACAGCCTAAACATCACCGGCAACT...            ...TTACCAATAATGGCACTGCCGAATTAATATA
          1390               1400                  1410              1420              1430              1440
```

FIG.24H

SER GLN GLY VAL VAL SER LEU GLY ASP ...
AGCCAAGGAGTGGTAAGTCTTGGCGATA...
        1450                    1460

...ILE THR ASN ASP GLY LYS LEU ASN ILE THR THR
...TTACCAATGATGGCAAATTAAACATCACCACT
        ...1470      1480              1490           1500

HIS ALA LYS SER GLY GLN LYS SER ILE ...
CACGCCAAGAGCGGTCAAAAAGCATTA...
        1510                    1520

...ILE ARG GLY ASP ILE ILE ASN LYS GLN GLY ASN
...TCCCGGGAGATATAATTAACAAAGGGAAT
        ...1530      1540              1550           1560

LEU ASN ILE THR ASP ASN SER ASN ...
TTAAATATTACGGACAATAATAGTAATG...
        1570                    1580

...ALA GLU ILE GLU ILE GLY GLY ASN ILE SER GLN
...CTGAAATTGAAATTGGCGGCAATATCTCGCAA
        ...1590      1600              1610           1620

LYS GLU GLY ASN LEU THR ILE SER SER ...
AAAGAAGGTAATCTCACCATTTCTTCTG...
        1630                    1640

FIG.24I

```
                    ...ASP LYS VAL ASN ILE THR LYS GLN ILE THR ILE
                    ...A T A A A G T C A A T A T T A C C A A A A C A G A T A A C A A T C
                       ...1650                1660              1670              1680

LYS ALA GLY VAL ASP GLY SER SER...      SER SER THR ALA SER ASP ALA SER ASN LEU THR
A A A G C A G G C G T T G A T G G G A G A G T T C T A...   G T T C A A G C A C A G C A A G T G A T G C C A A T C T A A C C
                   1690             1700           ...1710              1720              1730             1740

ILE LYS THR LYS GLU LEU THR LEU THR...   ASP ASN LEU ASN ILE SER GLY PHE ASN LYS ALA
A T T A A A A C C A A A G A G T T A A C A T T A A C A G...  A C A A T C T A A A C A T T T C A G G T T T T A A T A A A G C A
                1750              1760            ...1770              1780              1790             1800

GLU ILE THR ALA LYS ASP ASN SER ASP...   LEU ILE ILE GLY LYS ALA SER SER ASP ASN SER
G A A A T T A C A G C T A A A G A T A A C A G T G A T T...  T A A T T A T T G G C A A G G C T A G C A G T G A C A A C A G T
                1810              1820            ...1830              1840              1850             1860
```

FIG. 24J

```
ASN ALA LYS GLN VAL THR PHE ASP LYS
AATGCTAAACAAGTAACCTTTGACAAGG...
                1870                1880

...VAL LYS ASP SER LYS ILE SER ALA GLY ASN HIS
         ...TTAAAGATTCAAAAATCTCAGCTGGCAATCAC
             ...1890           1900           1910           1920

ASN VAL THR LEU ASN SER LYS VAL GLU
AATGTAACACTAAATAGCAAAGTGGAAA...
                1930                1940

...THR SER ASN SER ASP GLY SER THR GLY ASN GLY
         ...CGTCTAATAGCGATGGTAGCACCGGAAACGGT
             ...1950           1960           1970           1980

SER ASP ASP ASN ASN ILE GLY LEU THR
AGCGATGACAACAATATCGGCTTAACTA...
                1990                2000

...ILE SER ALA LYS ASP VAL THR VAL ASN SER ASN
         ...TTTCCGCAAAAGATGTAACGGTAAATAGTAAT
             ...2010           2020           2030           2040

ILE THR SER HIS LYS THR VAL ASN ILE
ATCACCCTCTCACAAAACAGTAAATATCT...
                2050                2060
```

FIG.24K

```
                                ...SER ALA SER GLU GLY GLY ILE THR THR LYS ALA
                                ...CTGCAATCAGAAGGAGGTATCACTACTAAAGCA
                                   ...2070              2080              2090          2100

GLY THR ILE ASN ALA THR THR GLY                    ...SER VAL GLU VAL THR ALA LYS THR GLY ASP ILE
GGCACAACCATTAATGCGACCACAGGTA...                    ...GCGTGGAAGTAACTGCTAAAACAGGCGATATT
            2110              2120                    ...2130              2140              2150          2160

SER GLY THR ILE SER GLY LYS THR VAL                ...SER VAL THR ALA SER THR GLY ASP LEU THR VAL
AGCGGGTACGATTTCCGGTAAGACAGTAA...                   ...GTGTTACAGCAAGCACTGGCGATTTAACTGTT
            2170              2180                    ...2190              2200              2210          2220

ARG LYS ALA ALA ALA THR ILE SER ALA THR            ...GLU GLY ALA ALA THR LEU THR ALA THR GLY ASN
AGGAAAGCTGCAACCATTAGTGCGACAG...                    ...AAGGAGCTGCAACCTTAACCGCAACAGGGAAT
            2230              2240                    ...2250              2260              2270          2280
```

FIG.24L

```
THR LEU THR THR GLU ALA GLY SER SER ...     ILE THR SER THR LYS GLY GLN VAL ASP LEU SER
ACCTTGACTACTGAAGCCGGTTCTAGCA...     TCACTTCAACTAAGGGTCAGGTAGACCTTTCA
          2290              2300    ...2310      2320              2330              2340

ALA GLN ASP GLY SER ILE ALA GLY GLN ...     ILE SER ALA ALA ASN VAL THR LEU ASN THR THR
GCTCAGGATGGTAGCATTGCAGGACAAA...     TTAGTGCAGCTAATGTGACATTAAATACCACA
          2350              2360    ...2370      2380              2390              2400

GLY THR LEU THR THR VAL GLU GLY SER ...     ASN ILE LYS ALA THR SER GLY THR LEU ALA ILE
GGCACCTTAACTACTGTAGAAGGTTCAA...     ACATTAAAGGCAACCAGTGGCACCTTAGCTATT
          2410              2420    ...2430      2440              2450              2460

ASN ALA LYS ASP ALA LYS LEU ASP GLY ...
AACGCAAAAGACGCTAAGCTAGATGGTA...
          2470              2480
```

FIG.24M

```
         ...THR ALA SER GLY ASN ARG THR GLU VAL ASN ALA
         ...CGG CAT CAG GTA ACC CGT ACA GAA GTA AAT GCA
         ...2490      2500      2510      2520

THR ASN ALA SER GLY SER VAL ...THR ALA LYS THR SER SER ASN VAL ASN ILE THR
ACT AAC GCA AGT GGT TCT GGT AGC GTG A ...CTG CGA AAA ACC TCA AGT AAT GTG AAT ATC ACC
         2530                  2540       ...2550      2560      2570      2580

GLY ASP LEU SER THR ILE ASN GLY LEU ...ASN ILE ILE SER GLU ASN GLY ARG ASN THR VAL
GGG GAT TTA AGC ACA ATA AAT GGG TTA A ...ATA TCA TTT CGG AAA ATG GTA GAA ACA CTG TG
         2590                  2600       ...2610      2620      2630      2640

ARG LEU ARG GLY LYS GLU ILE ASP VAL ...LYS TYR ILE GLN PRO GLY VAL ALA SER VAL GLU
CGC TTA AGA GGC AAG GAA ATT GAT GTG A ...AAT ATA TCC AAC CAG GTG TAG CAA GCG TAG AA
         2650                  2660       ...2670      2680      2690      2700
```

FIG.24N

```
GLU VAL ILE GLU ALA LYS ARG VAL LEU             LYS ASP LEU SER ASP GLU ARG
GAG GTA ATT GAA GCG AAA CGC GTC CTT G...      ...AGA AAG ATT TAT CTG ACG AAG AAA GA
         2710                                      2740           2750         2760
                                    ...GLU LYS VAL
                                 ...AGA AAG TAA GTG
                                    ...2730
               2720

GLU THR LEU ALA LYS LEU GLY VAL SER             ALA VAL ARG PHE VAL GLU PRO ASN ASN ALA ILE
GAA ACA CTA GCC AAA CTT GGT GTA AGT G...      ...CTG TAC GTT TCG TTG AGC CCA AAT AAT GCC ATT
         2770                                      2790            2800            2810        2820
                        2780                 ...2790

THR ILE ASN THR GLN ASN GLU PHE THR              THR ARG PRO SER SER GLN VAL ILE ILE SER GLU
ACG ATT AAT ACA CAA AAT GAA TTT ACA A...      ...CCA GAC CGT CAA GTC AAG TGA TAA TTT CTG AA
         2830                                      2850          2860            2870        2880
                        2840                 ...2850

GLY LYS ALA CYS PHE SER SER GLY ASN
GGT AAG GCG TGT TTC TCA AGT GGT AAT G...
         2890
                        2900
```

FIG. 24O

...GLY ALA ALA VAL CYS THR ASN VAL ALA ASP ASP
...GCGCAGCAGTATGTACCAATGTTGCTGACGAT
...2910      2920      2930      2940

GLY GLN PRO ***
GGACAGCCCGTAG
        2950

FIG. 25A

PMH1 hmw2A sequence

```
LYS GLU TRP LEU LEU ASP PRO ASP ASP ...
A A A G A G T G G T T G T T A G A C C C G G A T G A T G ...
                    10                   20
  ...VAL THR ILE ALA ALA GLY ALA PRO GLY ARG ASN
  ...T A A C T A T T G C C G C A G G C G C C A G G A C G T A A C
              30                   40                   50                   60

ASP GLY SER VAL ASP ASP PHE PRO   ...THR GLY ARG GLY ASP ASP ALA SER ASN ALA LYS
G A T G G T T C A G T A G A C G A C T T T T T T C C C A ...C T G G A A G A G G G G A T G A T G C T A G T A A T G C A A A A
                    70                   80                   90                   100                  110                  120

THR ASN HIS PRO ASP LYS PRO THR LEU   ...THR ASN THR THR VAL GLU ASN ALA LEU LYS ASN
A C A A A C C A T C C A G A C A A G C C G A C A T T A A ...C A A A C A C A A C T G T T G A G A A C G C A T T A A A A A A C
                    130                  140                  150                  160                  170                  180
```

FIG.25B

```
ASN THR PHE VAL ASN ILE THR ALA LYS
AACACCCTTTGTTAACATAACCGCCAAAA...
          190        200

ASN LYS ILE THR VAL ASN SER ASP ILE ASN ILE
         ...ATAAAATCACAGTTAATAGCGACATCAATATC
              210        220        230        240

LYS GLY GLY ALA HIS LEU THR LEU TYR
AAAGGTGGGCGCCCACCTAACCCCTCTATA...
          250        260

SER LYS ASN LYS LYS SER SER VAL LYS ILE
         ...GCAAAAACAATAAAAAAGTAGCGTTAAGATT
              270        280        290        300

ASN GLY ASN ILE THR SER THR THR ASN
AATGGCAATATTACTTCTACCACTAACG...
          310        320

GLY ASN LEU THR ILE TYR SER SER GLY TRP VAL
         ...GAAACTTAACTATTTACTTCCAGCGGGCTGGGTT
              330        340        350        360

ASP ILE HIS LYS ASN ILE THR LEU ASN
GATATCCATAAAAACATTACGCTTAACA...
          370        380
```

FIG. 25C

```
            ...THR GLY TYR LEU ASN ILE THR ALA GLY GLY SER
            ...C A G G T T A C C T G A A T A T T A C C G C T G G G G G T T C T
               ...390             400             410             420

VAL ALA PHE GLU LYS ALA GLY ASN GLU...
G T A G C C T T C G A G A A A G C C G G A A A T G A G A...
                430             440

...LYS GLY ARG GLN VAL SER GLU SER VAL ILE LYS
            ...A A G G G C G C C A A G T A T C A G A A T C T G T A A T C A A A
               ...450             460             470             480

ALA GLN GLY VAL ILE THR SER GLY VAL...
G C C C A G G G A G T T A T C A C C T C A G G T G T A G...
                490             500

...GLY GLU GLY PHE ARG PHE ASN VAL SER LEU
            ...G G G A A G G C T T T A G G T T T A A T A A C G T C T C C C T A
               ...510             520             530             540

ASN GLY VAL GLY ALA GLY LEU ARG PHE...
A A T G G C G T T G G C G C A G G A C T G C G C T T C G...
                550             560

...VAL GLY GLN LYS ASN ILE SER SER ASN SER TRP
            ...T T G G T C A G A A A A A T A T C A G T A G C A A C T C T T G G
               ...570             580             590             600
```

FIG.25D

```
ARG GLU ASN THR ILE LYS ASN ARG PHE ...
A G A G A A A C A C C A T C A A A A A C A G A T T C G ...
                    610                 620

ASP GLY ASN LEU ASN ILE SER GLY LYS VAL ASN
...A T G G G A A T T A A A T A T C T C A G G A A A G G T A A A T
            630                 640                 650                 660

VAL SER MET ASP VAL SER GLY THR LYS ...
G T T T C A A T G G A T G T A T C C G G G A C A A A G T ...
                    670                 680

TRP HIS THR ARG ILE ASN GLY ARG THR TYR TRP
...G G C A T A C A A G A A T T A A C G G G C A C C T A C T G G
            690                 700                 710                 720

ASN VAL THR THR LEU ASN VAL ALA SER ...
A A T G T A A C C A C T C T A A A C G T T G C C T C A G ...
                    730                 740

GLY SER SER PHE ASN LEU SER ILE ASP ALA SER
...G T A G T A G T T T C A A T C T C A G T A T C G A C G C C A G T
            750                 760                 770                 780

GLY ILE SER SER GLY ASN GLN ASP ASP ...
G G A A T T T C T T C A G G T A A C C A G G A C G A C A ...
                    790                 800
```

FIG.25E

...ILE THR ASN ARG GLY LEU ASN GLY ILE THR PHE
...T A A C A A A T A G G G G T T T A A A T G G C A T A A C A T T T
...810              820              830              840

ASN GLY GLU ASN THR PHE ASN ILE ALA ...
A A T G G A G A A A A C A C T T T T A A T A T C G C A C...
                850              860

...GLN GLY SER THR ALA ASN PHE HIS ILE LYS THR
...A G G G C T C A A C A G C T A A C T T T C A T A T C A A A A C G
    870              880              890              900

SER VAL MET THR PRO LYS PRO ASN SER ...
T C A G T A A T G A C C C C T A A A C C C A A C T C G A...
              910              920

...ASN TYR ALA LEU PHE ASN GLY ASN ILE SER VAL
...A C T A C G C A T T A T T T A A T G G A A A T A T T T C A G T T
        930              940              950              960

LEU GLY GLY GLY THR VAL ASN PHE GLU ...
T T A G G A G G A G G A A C T G T C A A C T T T G A A C...
              970              980

...LEU ASN ALA SER SER SER THR HIS THR THR SER
...T T A A T G C C T C A T C T A G C A C C C A C A A C T T C T
            990              1000             1010             1020

FIG.25F

```
GLY ALA ILE ILE ASN SER GLN ASN PHE ...
GGCGCAATTATAAATTCTCAAAATTTTA...
              1030              1040

...ASN VAL SER GLY GLY SER LYS LEU ASN LEU LYS
          ...ATGTCTCAGGTGGGTCAAAATTAAATCTCAAG
             ...1050              1060              1070              1080

ALA SER GLY SER THR ASN THR ALA PHE ...
GCTTCAGGCTCAACAAATACCGCTTTT....
              1090              1100

...LEU ILE LYS ASN ASN LEU THR LEU ASN ALA THR
          ...TAATAAAAAATAATTAACTTTAAACGCTACT
             ...1110              1120              1130              1140

GLY GLY ASN ILE GLU ILE LYS GLN VAL ...
GGAGGTAATATAGAAATTAAACAGGTTG....
              1150              1160

...GLU GLY THR ASP SER ARG ILE GLN LYS GLY VAL
          ...AGGGTACCGATTCGCGCATTCAAAAGGTGTT
             ...1170              1180              1190              1200

VAL ALA GLU GLN ASN ILE ILE PHE GLU ...
GTAGCCGAACAAAACATAATTTTTGAAG....
              1210              1220
```

FIG.25G

```
                                    ...GLY GLY ASN ILE THR LEU GLY SER GLN LYS ALA
                                    ...GGGGTAACATCACCCTTGGCTCCCAAAAGCC
                                    ...1230                1240            1250            1260

PRO THR GLU ILE LYS GLY ASP VAL THR                       ...VAL LYS GLN GLY THR ASN ALA THR LEU ARG SER
CCAACAGAAATAAAAGGCGATGTTACCG...                           ...TCAAACAAGGAACCAACGCCACTCTCAGAAGC
            1270                1280                      ...1290            1300            1310            1320

ALA ASN PHE ASP ASN HIS LYS GLY ALA                       ...LEU ILE VAL ASN GLY ASN VAL THR ALA ASN GLY
GCGAATTTTGACAACCACAAAGGTGCCT...                           ...TAATTGTGAATGGAAACGTTACCGCCAATGGC
            1330                1340                      ...1350            1360            1370            1380

ASN LEU THR ALA ASP GLY ASP THR ILE                       ...LYS ILE LYS GLY ASN LEU ASP VAL ALA GLN GLY
AACCTTACTGCGGACGGCGACACTATTA...                           ...AAATAAAAGGCAATCTTGATGTTGCACAAGGC
            1390                1400                      ...1410            1420            1430            1440
```

FIG.25H

```
ALA  LYS  PHE  ASN  GLY  SER  THR  LYS  ASN  ...
GCTAAATTTAACGGCAGCACAAAAACA...
              1450            1460

...ASN  LEU  ASN  ILE  THR  GLY  THR  PHE  THR  ASN  ASN
                                ....ACCTAAACATTACTGGCACCTTTACCAACAAC
                                        1470            1480            1490            1500

GLY  THR  SER  ILE  ILE  ASP  ILE  THR  GLN  ...
GGCACTTCTATAATCGATATAACACAAG...
              1510            1520

...GLY  VAL  VAL  ASN  LEU  GLY  ASN  VAL  THR  ASN  ASP
                                ...GGGTGGTAAACCTTGGTAATGTTACCAATGAC
                                        1530            1540            1550            1560

GLY  LYS  LEU  ASN  ILE  THR  THR  HIS  ALA  ...
GGCAAATTAAACATCACCACTCACGCCA...
              1570            1580

...LYS  SER  GLY  GLN  LYS  SER  ILE  ILE  ARG  GLY  ASP
                                ...AGAGCGGTCAAAAAAGCATTATCCGCGGAGAT
                                        1590            1600            1610            1620

ILE  ILE  ASN  LYS  GLN  GLY  ASN  LEU  ASN  ...
ATAATTAACAAACAAGGAATTTAAATA...
              1630            1640
```

FIG.25I

```
                                    ...ILE  THR  ASP  ASN  ASN  SER  ASN  ALA  GLU  ILE  GLU
                                    ...T T A C G G A C A A T A A T A G T A A T G C T G A A A T T G A A
                                    ...1650                    1660                   1670                  1680

ILE  GLY  GLY  ASN  ILE  SER  GLN  LYS  GLU                 ...GLY  ASN  LEU  THR  ILE  SER  SER  ASP  LYS  VAL  ASN
A T T G G C G G C A A T A T C T C G C A A A A A G A A G     ...G T A A T C T T C A C C A T T T C T T C T G A T A A A G T C A A T
              1690                    1700                   ...1710                 1720                   1730                   1740

ILE  THR  LYS  GLN  ILE  THR  ILE  LYS  ALA                 ...GLY  VAL  ASP  GLY  GLU  SER  SER  SER  THR
A T T A C C A A A C A G A T A A C A A T C A A A G C A G     ...G C G T T G A T G G G G A G A G T T C T A G T T C A A G C A C A
              1750                    1760                   ...1770                 1780                  1790                   1800

ALA  SER  ASP  ALA  ASN  LEU  THR  LEU  THR  ILE  LYS       ...THR  LYS  GLU  LEU  THR  PHE  THR  ASP  ASN  LEU  ASN
G C A A G T G A T G C C A A T C T A A C C A T T A A A A     ...C C A A A G A G T T A A C A T T C A C A G A C A A T C T A A A C
              1810                    1820                   ...1830                  1840                  1850                  1860
```

FIG. 25J

```
ILE SER GLY PHE ASN LYS ALA GLU ILE ...
ATTTCAGGTTTTAATAAAGCAGAAATTA...
                          1870                    ...1880

THR ALA LYS ASP ASN SER ASP LEU ILE ILE GLY
   ...CAGCTAAAGATAACAGTGATTTAATTATTGGC
       ...1890                   1900                    1910                    1920

LYS ALA SER SER ASP ASN SER ASN ALA ...
AAGGCTAGCAGTGACAACAGTAATGCTA...
                          1930                    ...1940

...LYS GLN VAL THR PHE ASP LYS VAL LYS ASP SER
       ...AACAAGTAACCTTTGACAAGGTAAAGATTCA
          ...1950                   1960                    1970                    1980

LYS ILE SER ALA GLY ASN HIS ASN VAL ...
AAAATCTCAGCTGGCAATCACAATGTAA...
                          1990                    ...2000

...THR LEU ASN SER LYS VAL GLU THR SER ASN SER
       ...CACTAAATAGCAAAGTGGAACGTCTAATAGC
          ...2010                   2020                    2030                    2040

ASP GLY SER THR GLY ASN GLY SER ASP ...
GATGGTAGCACCGGAAACGGTAGCGATG...
                          2050                    ...2060
```

FIG. 25K

```
                                  ...ASP ASN ASN ILE GLY LEU THR ILE SER ALA LYS
                                  ....A C A A C A A T A T C G G C T T A A C T A T T T C C G C A A A A
                                    ...2070                        2080                        2090                       2100

ASP VAL THR VAL ASN SER ASN ILE THR ...
G A T G T A A C G G T A A A T A G T A A T A T C A C C T...
                          2110                         2120

...SER HIS LYS THR VAL ASN ILE SER ALA SER GLU
                                  ...C T C A C A A A A C A G T A A A T A T C T C T G C A T C A G A A
                                    ...2130                        2140                        2150                       2160

GLY GLY ILE THR THR LYS ALA GLY THR ...
G G A G G T A T C A C T A C T A A A G C A G G C A C A A...
                          2170                         2180

...THR ILE ASN ALA THR THR GLY SER VAL GLU VAL
                                  ...C C A T T A A T G C G A C C A C A G G T A G C G T G G A A G T A
                                    ...2190                        2200                        2210                       2220

THR ALA LYS THR GLY ASP ILE SER GLY ...
A C T G C T A A A A C A G G C G A T A T T A G C G G T A...
                          2230                         2240

...THR ILE SER GLY LYS THR VAL SER VAL THR ALA
                                  ...C G A T T T C C G G T A A G A C A G T A A G T G T T A C A G C A
                                    ...2250                        2260                        2270                       2280
```

FIG.25L

```
SER THR GLY ASP LEU THR VAL ARG LYS   ...
AGCACTGGCGATTTAACTGTTAGGAAAG...
                           2300  ...2310
        2290

ALA ALA THR ILE SER VAL THR GLU GLY ALA ALA
                 ...CTGCAACCATTAGTGTGACAGAAGGAGCTGCA
                              2320        2330              2340

THR LEU THR ALA THR GLY ASN THR LEU   ...
ACCTTAACCGCAACAGGGAATACCCTTGA...
              2350             ...2370
                         2360

THR THR GLU ALA GLY SER SER ILE THR SER THR
                 ...CTACTGAAGCCGGTTCTAGCATCACTTCAACT
                              2380        2390              2400

LYS GLY GLN VAL ASP LEU SER ALA GLN   ...
AAGGGTCAGGTAGACCTTTCAGCTCAGG...
              2410            ...2430
                         2420

ASP GLY SER ILE ALA GLY GLN ILE SER ALA ALA
                 ...ATGGTAGCATTGCAGGACAAATTAGTGCAGCT
                              2440        2450              2460

ASN VAL THR LEU ASN THR THR GLY THR   ...
AATGTGACATTAAATACCACAGGCACCT...
              2470             ...
                         2480
```

FIG.25M

```
THR SER GLY THR LEU ALA ILE ASN ALA ...LEU THR THR VAL GLU GLY SER ASN ILE LYS ALA
ACCAGTGGCACCTTAGCTATTAACGCAA... ...TAACTACTGTAGAAGGTTCAAACATTAAGGCA
          2530                 2540       ...2490        2500         2510         2520

ASN ARG THR GLU VAL ASN ALA THR ASN ...LYS ASP ALA LYS LEU ASP GLY THR ALA SER GLY
AACCGTACAGAAGTAAATGCAACTAACG... ...AAGACGCTAAGCTAGATGGTACGGCATCAGGT
          2590                 2600       ...2550        2560         2570         2580

SER SER ASN VAL ASN ILE THR GLY ASP ...ALA SER GLY PHE SER GLY SER VAL ALA LYS THR
TCAAGTAATGTGAATATCACCGGGGATT... ...CAAGTGGGTTCTCTGGTAGCGTGACTGCGAAAACC
          2650                 2660       ...2610        2620         2630         2640

...LEU SER THR ILE ASN GLY LEU ASN ILE ILE SER
                                        ...TAAGCACAATAAATGGGTTAAATATCATTTCG
                                           ...2670        2680         2690         2700
```

FIG.25N

```
GLU ASN GLY ARG ASN THR VAL ARG LEU                    ...
GAAAATGGTAGAAACACTGTGCGCTTAA...
           2710

...ARG GLY LYS GLU ILE ASP VAL LYS TYR ILE GLN
            ...GAGGCAAGGAAATTGATGTGAAATATCCAA
                    2730              2750

PRO GLY VAL ALA SER VAL GLU GLU VAL                    ...
CCAGGTGTAGCAAGCGTAGAAGAGGTAA...
           2770

...ILE GLU ALA LYS ARG VAL LEU GLU LYS VAL LYS
            ...TTGAAGCGAAACGCGTCCTTGAGAAAGTAAAA
                    2790              2810

ASP LEU SER ASP GLU GLU ARG GLU THR                    ...
GATTTATCTGACGAAGAAAGAGAAACAC...
           2830

...LEU ALA LYS LEU GLY VAL SER ALA VAL ARG PHE
            ...TAGCCAAACTTGGTGTAAGTGCTGTACGTTTC
                    2850              2870

VAL GLU PRO ASN ASN ALA ILE THR ILE                    ...
GTTGAGCCAAATAATGCCATTACGATTA...
           2890
```

FIG. 250

```
                              ...ASN THR GLN ASN GLU PHE THR THR ARG PRO SER
                              ...A T A C A C A A A A T G A A T T T A C A A C C A G A C C G T C A
                                 ...2910                2920              2930              2940

SER GLN VAL ILE ILE SER GLU GLY LYS ...     ...ALA CYS PHE SER SER GLY ASN GLY ALA ALA VAL
A G T C A A G T G A T A A T T T C T G A A G G T A A G G... ...C G T G T T T C T C A A G T G G T A A T G G C A G C A G T A
               2950                2960                  ...2970             2980              2990              3000

CYS THR ASN VAL ALA ASP ASP GLY GLN ...     ...PRO ***
T G T A C C A A T G T T G C T G A C G A T G G A C A G C... ...C G T A G
               3010                3020                  ...3030
```

FIG. 26A

Strain 15 *hmw1A* sequence

→

```
LYS GLU TRP LEU LEU ASP PRO ASP ASN VAL      ...
A A A G A G T G G T T G T T A G A C C C G G A T A A T G T A A ...
                    10                  20                  30
```

```
                                                       SER TYR SER ARG GLY
                         ...THR ILE GLU ALA PRO                          60
                         ...C A A T T G A A G C C C C C T T C C T A T T C T C G C G G T
                                                40                  50
```

```
ASN ALA GLY ILE ASP SER GLU PHE PRO GLY             ...
A A T G C C G G T A T A G A T A G T G A A T T C C C G G G C G ...
                    70                  80                  90
```

```
                                                       GLU SER PRO LYS THR
                         ...GLY SER GLY THR LYS                          120
                         ...G T T C G G G C A C A A A G G A A A G C C C T A A A A C A
                                                100                 110
```

```
ASN GLY GLU GLN PRO THR VAL LEU THR ASN             ...
A A C G G C G A A C A G C C G A C A G T A T T A A C C A A T G ...
                    130                 140                 150
```

```
                                                       LEU LYS SER GLY
                         ...GLU THR ILE SER ASN TYR                      180
                         ...A A A C C A T T T C A A T T A T C T G A A A A G C G G C
                                                160                 170
```

FIG.26B

```
THR TRP VAL MET ASN ILE THR ALA LYS LYS           ASN LEU THR VAL ASN SER SER ILE ASN ILE
ACCTGGGTAATGAATATAACAGCCAAGAAAA...      ...ATCTTACCGTTAACAGCTCAATTAACATT
              190            210         220            230            240

GLY ASP SER SER HIS LEU ILE LEU HIS SER           GLU GLY LYS ASN GLY GLY VAL LYS ILE
GGAGACAGCTCCCACTTAATCCTTCATAGTG...      ...AAGGCAAGAATAACGGGCGGTGTTAAGATT
              250            270         280            290            300

LYS GLU ASP ILE THR SER ASN GLY GLY ASN           LEU THR ILE GLN SER GLY GLY TRP VAL ASP
AAAGAAGACATTACCTCTAATGGCGGAAACT...      ...TAACCATTCAATCCGGCGGATGGGTTGAT
              310            330         340            350            360

VAL HIS LYS ASN ILE THR LEU GLY THR GLY
GTTCACAAAAATATTACGCTTGGCACAGGCA...
              370            390
              380
```

FIG.26C

```
             ...THR LEU ASN ILE THR ALA LYS GLY SER ILE
             ...C C T T G A A T A T T A C A G C T A A A G G A T C C A T A
                  400                 410                 420

ALA PHE GLU GLY ASN GLY THR GLU LYS ALA             ...ARG ASN ALA SER SER ALA GLN ILE THR ALA
G C C T T T G A G G G A A A C G G T A C A G A A A A A G C C C...  ...G C A A C G C A T C A A G C G C T C A A A T C A C C G C G
          430                 440                 450                      460                 470                 480

GLN GLY THR ILE THR ASN THR GLY ASP GLN             ...LYS GLN LEU ARG LEU ASN ASN VAL SER ILE
C A G G G A A C T A T A A C C A A T A C T G G C G A T C A A A...  ...A A C A A C T C A G A C T T A A T A A T G T A T C T A T T
          490                 500                 510                      520                 530                 540

ASN GLY THR GLY ILE GLY LEU ASN PHE VAL             ...SER ILE GLN PRO ASN THR SER HIS ARG PHE
A A T G G G A C G G G T A T A G G T T T A A A T T T T G T T T...  ...C A A T T C A G C C T A A C A C T T C T C A C A G A T T T
          550                 560                 570                      580                 590                 600
```

FIG.26D

```
ASP GLY GLU LEU ILE ILE SER GLY ARG VAL ...
GAT GGG GAG CTT ATT ATT TCA GGG AGA GTA C...
                    610            620            630

...HIS VAL ASN GLN THR THR PRO LYS ASN LEU
...A TGT TAA TCA AAC CAC ACC TAA AAA CCT G
                640            650            660

SER PHE TRP LYS VAL SER ASP GLU SER TYR ...
TCT TTT TGG AAG GTA TCC GAT GAA TCT TAT T...
                670            680            690

...TRP ASN VAL SER HIS LEU THR VAL LYS GLU
...GG AAT GTC AGC CAT CTT ACC GTA AAA GAG
                700            710            720

LYS SER ALA PHE SER PHE THR LYS PHE ALA ...
AAG TCA GCA TTC TCA TTT ACC AAG TTT GCG T...
                730            740            750

...LEU ASN ASN ASN HIS GLY ARG GLU THR SER
...T AAA TAA CAA TCA TGG CCG AGA GAC TTC C
                760            770            780

ARG TYR ARG LYS GLY GLY VAL ILE PHE ...
AGA TAC CGC AAA GGT GGA GGT GTA ATC TTT C...
                790            800            810
```

FIG. 26E

```
         ...ARG SER PRO THR GLY HIS THR ASN PHE THR
         ...G C T C A C C T A C C G G T C A C A A A T T T C A C A
         ...                 820             830             840
         ...

VAL LYS GLN GLY SER VAL ALA ASN PHE SER
G T T A A A C A A G G C T C A G T G G C T A A T T T T T C A T...
                850             860             870 ...
                                                    ...

...PHE LYS ALA LYS ASN ASP THR ASN HIS ALA
                     ...T C A A G G C A A A A A T G A T A C A A A T C A T G C A
                     ...             880             890             900
                     ...

ASN GLN LEU PRO ILE GLN PHE ASN SER ASN
A A T C A A C T C C C G A T T C A G T T T A A C T C T A A T A...
                910             920             930 ...
                                                    ...

...ILE SER VAL ASP GLY GLY LYS VAL LEU
                     ...T C T C A G T C G A T G G A G G A G G G A A A G T C C T T
                     ...             940             950             960
                     ...

PHE CYS ILE THR SER ASN TYR SER GLY ARG
T T T T G T A T A A C C T C C A A C T A C T C C G G C A G A T...
                970             980             990 ...
                                                    ...

...SER VAL GLY ILE GLY MET SER SER ILE ASN
                     ...C A G T G G G G A T A G G A A T G T C T A G C A T T A A T
                     ...             1000            1010            1020
                     ...
```

FIG. 26F

```
VAL  SER  ASP  GLY  SER  ASN  LEU  THR  PHE  ASN                                  ...
GTTTCTGATGGCTCAAAACCTTACTTTTAATT...
         1030              1040              1050       ...
                        ...SER  ILE  ASN  ALA  THR                                  ...
                        ...CTTCCATTCGCGGAAGCCTTTAAT
                                     1060              1070              1080

ILE  SER  LYS  ASP  LEU  THR  ILE  ASN  ALA  THR                                  ...
ATCAGTAAAGATTTAACCATAAATGCAACCG...
         1090              1100              1110       ...
                        ...GLY  SER  PHE  PHE  GLU  LEU  GLY  GLN  TYR  SER         ...
                        ...GTTCATTTTTTGAACTTGGGCAATACTCG
                                     1120              1130              1140

ASP  THR  ILE  ASN  GLY  ASN  GLY  PHE  ASN  HIS                                  ...
GATACCTTTAATGGTAATGGCTTTAACCACG...
         1150              1160              1170       ...
                        ...ASP  ALA  ILE  LYS  SER  THR  HIS  ASN  ILE  SER         ...
                        ...ACGCCATTAAATCAACTCACAATATATCC
                                     1180              1190              1200

ILE  LEU  GLY  GLY  ASN  VAL  THR  LEU  GLY  GLY                                  ...
ATCTTAGGTGGCAAATGTTACCCTTGGCGGGC...
         1210              1220              1230       ...
```

FIG. 26G

```
                          ...GLN   ASP   SER   SER   SER   THR   ILE   THR   GLY   ASN
                          ...A A G A T T C A A G C A G T A C C A T T A C A G G T A A T
                          ...                 1240              1250              1260

ILE   ASN   ILE   SER   GLN   ALA   ALA   ALA   ASN   VAL   THR   ...
A T C A A T A T C T C T C A G G C A G C A A A T G T T A C C T   ...
              1270              1280              1290           ...

...LEU   ARG   ALA   TYR   ASN   GLY   ASN   GLY   ARG   ASN
                          ...T G C G A G C T T A T A A T G G T A A C G G T C G A A A C
                                            1300              1310              1320

LYS   GLN   LEU   THR   LEU   GLY   ASN   VAL   SER   ILE   ...
A A A C A A C T A A C C C T T G G C A A T G T A T C T A T T G   ...
              1330              1340              1350           ...

...GLU   GLY   ASN   LEU   LYS   SER   LEU   ILE   GLY   ALA   SER
                          ...A A G G G A A T T A A G T T T A A T C G G T G C A A G T
                                            1360              1370              1380

ALA   ASN   ILE   ASN   GLY   ASN   LEU   SER   VAL   LYS   ...
G C A A A T A T T A A C G G C A A C C T T T C C G T T A A A G   ...
              1390              1400              1410           ...

...GLU   ASN   ALA   LYS   PHE   LYS   GLY   GLU   THR   GLN
                          ...A A A A T G C T A A A T T T A A A G G G A A A C C C A A
                                            1420              1430              1440
```

FIG. 26H

```
ASP ASN LEU ASN ILE THR GLY THR PHE ILE                                           ...
GACAACTTGAACATCACCGGCACCTTTATCA...
              1450              1460              1470
                        ...ASN ASN GLY ASP SER LYS ILE ASN ILE SER
                        ...ATAACGGCGACTCTAAAATCAATATATCT
                                      1480              1490              1500

GLN GLY VAL VAL LYS LEU GLY ASN VAL THR                                           ...
CAAGGAGTGGTAAAACTTGGCAATGTTACCA...
              1510              1520              1530
                        ...ASN ASP GLY ASP LEU ASN ILE THR THR HIS
                        ...ATGATGGTGATTTAAACATTACCACTCAC
                                      1540              1550              1560

ALA LYS HIS ASN GLN ARG SER ILE ILE GLY                                           ...
GCTAAACACAACCAAAGAAGCATCATCGGCG...
              1570              1580              1590
                        ...GLY ASP ILE ILE ASN LYS LYS GLY SER LEU
                        ...GAGATATAATCAACAAAAAGGAAGCTTA
                                      1600              1610              1620

ASN ILE THR ASP SER ASN LYS ASN ALA GLU                                           ...
AATATTACAGACAGTAATAAGAATGCTGAAA...
              1630              1640              1650
```

FIG.26I

```
                                    ...ILE  GLN  ILE  GLY  GLY  ASN  ILE  SER  GLN  LYS
GLU  GLY  ASN  LEU  THR  ILE  SER  SER  ASP  LYS                         1680
                                    ...T    C    C    A    A    A    T    T    G    G    C    G    G    C    A    A    T    A    T    C    T    C    G    C    A    A    A    A
G    A    A    G    G    C    A    A    T    C    T    C    A    C    G    A    T    T    T    C    T    T    C    C    G    A    T    A    A    A    A...      1670
                      1690                                                1700                               1710

...ILE  ASN  ILE  THR  ASN  GLN  ILE  THR  ILE  LYS
ALA  GLY  VAL  ASP  GLY  GLU  ASN  SER  ASP  SER                         1740
                                    ...T    C    A    A    T    A    T    T    A    C    C    A    A    T    C    A    G    A    T    A    A    C    A    A    T    C    A    A    A
G    C    A    G    G    T    G    T    T    G    A    T    G    G    G    G    A    G    A    A    T    T    C    C    G    A    T    T    C    A    G...      1730
                      1750                                                1760                               1770

...ASP  ALA  THR  ASN  ALA  ASN  LEU  THR  ILE
LYS  THR  LYS  GLU  LEU  LYS  LEU  THR  GLN  ASP                         1800
                                    ...A    C    G    C    G    A    C    A    A    A    C    A    A    T    G    C    C    A    A    T    C    T    A    A    C    C    A    T    T
A    A    A    A    C    C    A    A    A    G    A    A    T    T    G    A    A    A    T    T    A    A    C    G    C    A    A    G    A    C    C...      1790
                      1810                                                1820                               1830

...LEU  ASN  ILE  SER  GLY  PHE  ASN  LYS  ALA  GLU
                                                                         1860
                                    ...T    A    A    A    T    A    T    T    T    C    A    G    G    T    T    T    C    A    A    T    A    A    A    G    C    A    G    A    G
                                                                         1850
                      1840
```

FIG.26J

```
ILE THR ALA LYS ASP GLY SER ASP LEU THR                   ...
ATTACAGCTAAAGATGGTAGTGATTTAACTA...
        1870           1880           1890

ILE GLY ASN THR PHE ASN SER ALA ASP SER THR
...TTGGTAACACCAATAGTGCTGATAGTACT
          1900           1910           1920

ASN ALA LYS LYS VAL THR PHE ASN GLN VAL                   ...
AATGCCAAAAAAGTAACCTTTAACCAGGTTA...
        1930           1940           1950

...LYS ASP SER LYS ILE SER ALA GLY ASP HIS
       AAGATTCAAAAATCTCTGCTGGCGACCAT
          1960           1970           1980

ASN VAL THR LEU ASN SER LYS VAL GLU THR                   ...
AATGTGACACTAAATAGCAAAGTGGAAACAT...
        1990           2000           2010

...SER GLY ASN THR ASP ASN THR GLY ASP GLY
       CTGGTAATACTGACAACACTGGAGACGGC
          2020           2030           2040

SER GLY ASN ASN ALA GLY LEU THR ILE ALA                   ...
AGTGGCAATAATGCCGGCTTAACTATTGCCG...
        2050           2060           2070
```

FIG. 26K

```
           ...ALA LYS ASN VAL GLU VAL LYS ASN ASN ILE
           ...CGA AAA AAT GTA GAA GTA AAA AAC AAC ATT
                                   2090              2100
              ...
THR SER ASN LYS THR VAL ASN ILE THR ALA...
ACT TCT AAC AAA ACA GTA AAT ATC ACC GCT...
             2110                    2120       2130
...SER GLU LYS THR THR LYS ALA ASP ALA...
...CAG AAA AAC TTA CCA CCA AAG CGG ATG CA
                       2140               2150       2160
              ...
THR ILE ASN ALA THR THR GLY ASN VAL GLU...
ACC ATT AAT GCA ACC ACT GGT AAC GTA GAA G...
             2170                    2180       2190
...VAL THR ALA LYS THR GLY ASP ILE LYS GLY
...TGA CAG CCA AAA ACA GGT GAT ATT AAA GGT
                       2200               2210       2220
              ...
GLU VAL LYS SER THR SER GLY ASN VAL ASN...
GAA GTC AAA TCC ACT TCC GGT AAT GTA AAT A...
             2230                    2240       2250
...ILE THR ALA ASN GLY ASP THR LEU ASN VAL
...TTA CAG CAA ACG GCG ACA CGC TTA AAT GTA
                       2260               2270       2280
              ...
```

FIG. 26L

```
SER ASN VAL SER GLY ASN ALA VAL THR ILE
AGTAATGTTTCAGGCAATGCTGTTACCATCA...
         2290              2300              2310

THR ALA ASP LYS GLY LYS LEU THR THR GLN
               ...CTGCAGATAAGGGCAAATTAACCACCCAA
                         2320              2330              2340

ALA SER SER ILE THR SER ASN ASN GLY
GCAAGCTCTAGCATTACCTCAAACAATGGCC...
         2350              2360              2370

GLN THR THR LEU THR ALA LYS ASP GLY SER
               ...AGACAACTCTTACAGCCAAGGATGGCAGT
                         2380              2390              2400

ILE ALA GLY SER ILE ASN ALA ALA ASN VAL
ATCGCAGGAAGCATCAATGCCGCCAATGTGA...
         2410              2420              2430

THR LEU ASN THR THR GLY THR LEU THR THR
               ...CATTAAATACCACAGGCACTTTAACTACT
                         2440              2450              2460

VAL GLU GLY SER ASN ILE ASN ALA ALA SER
GTAGAAGGTTCAAACATTAACGCCAGCCAGTG...
         2470              2480              2490
```

FIG.26M

```
         LYS LEU ASN GLY ALA ALA ALA SER GLY ASP HIS  ...GLY THR LEU VAL ILE ASN ALA LYS ASP ALA
         AAGTTGAACGGCGCGGCGGCATCAGGTGACCACA...         ...GTACCTTGGTTATTAATGCAAAAGATGCT
              2530              2540      2550                  2500      2510      2520

SER GLY SER VAL THR ALA VAL THR SER SER  ...THR VAL ASN ALA THR ASN ALA SER GLY
         TCTGGTAGTGTGACTGCGGTAACCTCAAGTA...        ...CAGTAGTAAATGCAACTAACGCAAGTGGC
              2590              2600      2610              2560      2570      2580

...ASN VAL ASN ILE THR GLY ASP LEU SER THR
                                                   ...ATGTGAATATCACCGGGGATTTAAGTACA
                                                           2620      2630      2640

VAL ASN GLY LEU ASN ILE ILE SER LYS ASN  ...GLY ARG ASN THR VAL VAL LEU LYS GLY THR
         GTAAATGGATTAAATATCATTTCGAAAATG...         ...GTAGAAACACCGTAGTGTTAAAGGTACT
              2650              2660      2670            2680      2690      2700
```

FIG. 26N

```
GLU ILE GLU VAL LYS TYR ILE GLN PRO GLY          ...VAL ALA SER VAL GLU VAL ILE GLU ALA
GAAATTGAGGTGAAATATATCCAGCCAGGTG...             ...TAGCAAGTGTAGAAGAAGTAATTGAAGCG
          2710              2720              2730              2740              2750              2760

LYS ARG VAL LEU GLU LYS VAL LYS ASP LEU          ...SER ASP GLU GLU ARG GLU THR LEU ALA LYS
AAACGCGTCCTTGAGAAAGTGAAAGATTTAT...             ...CTGATGAAAGAGAAACATTAGCTAAA
          2770              2780              2790              2800              2810              2820

LEU GLY VAL SER ALA VAL ARG PHE ILE GLU          ...PRO ASN ASN THR ILE THR VAL ASN THR GLN
CTTGGTGTAAGTGCTGTACGTTTTATTGAAC...             ...CAAATAATACCATTACGGTTAACACACAAA
          2830              2840              2850              2860              2870              2880
```

FIG. 260

```
ASN GLU PHE THR THR ARG PRO SER SER GLN ...
A A T G A G T T T A C A A C C A G A C C A T C A A G T C A A G...
                           2890                    2900              2910

...VAL THR ILE SER GLU GLY LYS ALA CYS PHE
     ...T G A C A A T T T C T G A A G G T A A G G C G T G T T T C
                2920                    2930                    2940
     ...

SER SER GLY ASN GLY ALA ALA VAL CYS THR ...
T C A A G T G G T A A T G G C G C A G C A G T A T G T A C C A...
                2950                    2960              2970

...ASN VAL ALA ASP ASP GLY GLN GLN ***
     ...A T G T T G C T G A C G A T G G A C A G C A G T A G
                2980                    2990
     ...
```

FIG. 27A

NTHi strain 15 *hmw2A* sequence

```
          ASN SER ALA SER GLY SER HIS MET PRO ....
          G A A T T C G G C T T C G G G A T C C C A T G C C G ...
                                    10              20
          .... GLU ASN VAL TYR ILE ASN ALA GLY ASP ALA GLY
          ... G A G A A T G T A T A T A T T A A T G C A G G A G A C G C A G G
                    30              40              50              60
          ARG SER ASP THR ASN LEU GLU ASN GLU ....
          G C G T A G T G A C A C T A A T T T A G A A A A C G A A ...
                    70              80
          .... GLU TYR THR GLY THR GLY GLU SER ALA ASP THR
          ... G A A T A C A C A G G A A C A G G A G A G A G T G C T G A T A C
                    90              100             110             120
          PRO LYS ARG ASN ASN THR LYS THR ....
          T C C A A A A C G A A A C A A T A A C A C A A A G A C A ...
                    130             140
          .... THR LEU THR ASN SER THR LEU GLU LYS ILE LEU
          ... A C A C T A A C A A A C T C A A C G C T T G A G A A G A T A T T
                    150             160             170             180
```

FIG.27B

```
ALA ARG GLY SER PHE VAL ASN ILE THR ...
AGCAAGAGGCTCTTTTGTTAATATCACT...
            190                 200

ALA ASN ASN GLU ILE ARG VAL ASN SER ASP ILE
        ...GCCAACAATGAAATCAGAGAGTTAATAGTGATAT
           210                 220                 230                 240

ASN ILE GLY GLY ASN SER HIS LEU THR ...
CAATATCGGAGGCAAACTCCCACCTAACC...
            250                 260

LEU TRP SER SER LYS ASN LYS ASN LEU THR ILE TYR SER GLY VAL
        ...CTCTGGAGCAGCAAAAATAAAACAGTGGCGT
           270                 280                 290                 300

LEU ILE ASN GLY ASN ILE THR SER THR ...
TCTGATTAATGGCAATATCACTTCTACT...
            310                 320

ALA ASN GLY ASN LEU THR ILE TYR SER SER GLY
        ...GCTAACGGAAACTTAACCATTTACTCTAGCGG
           330                 340                 350                 360

TRP VAL ASP ILE HIS LYS ASN ILE THR ...
ATGGGTTGATATTCATAAAAATATTACG...
            370                 380
```

FIG.27C

```
        ... LEU GLU SER GLY ARG LEU ASN ILE THR THR LYS
        ... CTT GAA TCA GGA CGC TTA AAC ATT ACA ACT AA A
            ...390             400             410         420

GLU GLY ASP VAL ALA PHE GLU LYS GLY ...    ASN LEU THR ILE THR GLY GLN GLY THR ILE
A G A A G G A G A T G T C G C C T T T G A A A A A G G G ...    A A T A A C C T A A C C A T T A C A G G T C A A G G A A C T A T
                430                 440                 ...450             460             470             480

THR ALA GLY ASN ASN LYS GLY PHE ARG ....    PHE GLU ASN VAL SER LEU ASN GLY THR GLY THR
T A C A G C A G G C A A T A A T A A A G G C T T T A G A ....    T T T G A A A A T G T C T C T C T A A A T G G C A C T G G G A C
                490                 500                 ...510             520             530             540

GLY LEU LEU PHE ASN LEU SER ARG PRO ....    GLN LYS ASN ASN SER LEU VAL THR ASN TYR PHE
T G G C T T G C T T T T T A A T C T C A G T A G A C C A ....    C A A A A A A A C A A T A G T C T C G T C A C A A A C T A T T T
                550                 560                 ...570             580             590             600
```

FIG.27D

```
ASN GLY THR LEU ASN ILE SER GLY SER ...     VAL ASN ILE SER MET ILE PRO PRO ASN ALA THR
TAATGGGACTTTAAATATTTCAGGAAGC... ...GTAAATATCTCAATGATTCCACCTAATGCTAC
              610                                    630                    640                   650                   660

SER ASN TRP TYR SER ARG TYR LYS GLY ...     ARG THR TYR TRP ASN ILE THR HIS LEU ASN ALA
AAGCAATTGGTACAGCAGATACAAAGGG... ...CGAACCTATTGGAATATAACCCACTTAAATGC
              670                                    680                     690                   700                   710                   720

SER GLU ASP SER ASN PHE ASN LEU THR ...     ILE ASP SER SER ALA GLU ASP GLY SER ALA PRO
CTCCGAAGATAGCAACTTTAACCTTACT... ...ATTGACTCCTCGGCAGAGGATGGCTCAGCCCC
              730                                    740                    750                   760                   770                   780

LEU LEU SER SER TYR THR LEU ASN GLY ...
TCTTTTATCCAGTTATACCTTAAACGGC
              790                                    800
```

FIG.27E

```
            ... ILE SER PHE THR THR ASP THR THR PHE ASN VAL
            ... A T A T C A T T C A C C A C A G A T A C C A C C T T T A A T G T
                        810           820           830           840

ASN LYS ASN ALA LYS VAL ASN PHE ASN ....
T A A T A A A A A T G C A A A A G T C A A C T T T A A C ....
            850           860

... ILE LYS ALA PRO ILE GLY THR ILE ASN GLN TYR
            ... A T C A A A G C A C C A A T A G G G A C T A T A A A T C A A T A
                        870           880           890           900

ASN ASN LEU ASN TYR ALA LEU PHE ASN ....
C A A T A A C C T G A A T T A C G C A T T A T T C A A T ....
            910           920

... GLY ASN ILE SER VAL SER GLY GLY GLY ASN VAL
            ... G G G A A C A T T T C A G T T T C A G G A G G G G G A A T G T
                        930           940           950           960

THR PHE ARG LEU ASN ALA SER SER SER ....
C A C C T T C A G G C T T A A C G C T T C A T C C T C T ....
            970           980

... ASN GLN GLN THR PRO GLY VAL ILE ILE ASN SER
            ... A A C C A G C A A A C C C C T G G C G T A A T T A T A A A T T C
                        990          1000          1010          1020
```

FIG. 27F

```
LYS HIS LEU ASN ALA SER LYS GLY SER ....     LEU ARG PHE GLU THR THR GLY SER THR LYS
T AAA CAC CTT AAT GCT TCA AAA GGG TCG... ...A GCT TAA GA T TT GAA ACT ACA GGT TCA ACA AAA
              1030                   1040       ...1050          1060              1070            1080

VAL GLY PHE LEU ILE ASN ASN ASP LEU ....      THR LEU ASN ALA THR GLY GLY ASN ILE SER LEU
A GTC GGG TTT TTA ATA AAT AAT GAT TTA... ...A CTT TAA ACG CCA CTG GAG GCA ATA TCG CT
              1090                   1100       ...1110          1120              1130            1140

LEU GLN VAL GLU GLY ILE ASP GLY MET ....      ILE GLY GLY VAL VAL ALA LYS LYS ASN ILE
C TTG CAG GTT GAA GGC ATT GAC GGG ATG... ...A TTG GTG AAG GCG TTG TAG CTA AAA AAA CAT
              1150                   1160       ...1170          1180              1190            1200

THR PHE THR GLY GLY ASN ILE THR PHE ....
A ACC TTT ACT GGA GGC AAT ATC ACC TTT...
              1210                   1220
```

FIG.27G

```
                          ... GLY SER LYS LYS ALA ILE THR GLU ILE LYS GLY
                          ... G G C T C C A A G A A A A G C C A T A A C A G A A A T C A A A G G
                                                                                          1260
                              1230                    1240                    1250

ASN VAL THR ILE ASN GLU ASN THR ASN ...               ... ALA THR LEU ILE GLY SER ASP PHE ASN ASP HIS
C A A T G T T A C T A T C A A T G A A A A C A C C A A C...    G C C A C T C T T A T C G G T T C G G A T T T T A A C G A T C A
                  1270                    1280                          1290                   1300                   1310                   1320

LYS LYS PRO LEU ASN ILE LYS GLY ASP ...               ... VAL VAL ASN ARG GLY ASN LEU THR ALA GLY GLY
T A A A A A A C C T T T A A A T A T A A A A G G A G A T...    G T C G T C A A T A G A G G C A A C C T T A C C G C T G G C G G
                  1330                    1340                         1350                   1360                    1370                   1380

ASN VAL ILE ASN ILE GLY GLY ASN LEU ...               ... THR VAL GLU ASN GLY ALA ASN LEU LYS ALA ILE
C A A T G T T A T C A A T A T A G G C G G A A A T C T T...    A C C G T T G A A A A T G G C G C C A A T C T T A A A G C T A T
                  1390                    1400                         1410                   1420                    1430                   1440
```

FIG.27H

```
THR ASN PHE THR PHE ASN VAL GLY GLY ...      LEU PHE ASN ASN LYS GLY ASN SER ASN ILE SER
CACAAATTTCACTTTTAATGTAGGCGGC...        ...TTGTTTTAACAACAAAGGCAATTCAAATATCTC
                1450          1460       ...1470        1480          1490         1500

ILE ALA ARG GLY GLY GLY ALA LYS PHE LYS ...        ASP ILE ASN ASN THR SER SER LEU ASN ILE THR
CATTGCTAGAGGAGGGGCTAAATTTAAA...             GATATCAATAACACCAGTAGCTTAAATATTAC
                1510                  1520       ...1530           1540          1550          1560

THR ASN SER ASP THR THR TYR ARG THR ...         ILE ILE GLU GLY ASN ILE THR ASN LYS ALA GLY
CACCAAACTCCGACACCACTTACCGTACC...              ATTATAGAAGGTAATATAACCAACAAAGCAGG
                1570                 1580      ...1590          1600           1610          1620

ASP LEU ASN ILE ILE ASP ASN LYS GLY ...
TGATTTGAATATCATTGATAATAAAGGT...
                1630                1640
```

FIG.27I

```
             ... ASN ALA GLU ILE GLN ILE GLY GLY ASN ILE SER
             ... A A C G C T G A A A T C C A A A T T G G G C G G C A A C A T C T C
                ...1650                     1660                    1670                   1680

GLN LYS GLU GLY ASN LEU THR ILE SER ....
G C A A A A G A A G G T A A C C T C A C G A T T T C C ....
                     1690                     1700

... SER ASP LYS ILE ASN ILE THR LYS GLN ILE THR
                                           ... T C C G A T A A A A T C A A T A T T A C C A A A C A G A T A A C
                                             ...1710                    1720                    1730                     1740

ILE LYS LYS GLY VAL ASN GLY GLU ASN ....
A A T C A A G A A G G G T G T T A A C G G A G A G A A C ....
                     1750                     1760

... SER ASP SER SER THR LYS SER GLN ALA ASN LEU
                                           ... T C T G A T T C A A G T A C G A A A A G T C A A G C C A A T C T
                                             ...1770                    1780                    1790                     1800

THR ILE LYS THR LYS GLU LEU LYS LEU ....
A A C C A T T A A A A C C A A A G A A T T G A A A T T A ....
                     1810                     1820

... THR GLN ASP LEU ASN ILE SER GLY PHE ASN LYS
                                           ... A C A C A A G A C C T A A A T A T T T C A G G C T T C A A C A A
                                             ...1830                    1840                    1850                     1860
```

FIG.27J

```
ALA LYS ILE VAL ALA LYS ASP SER SER ...
A G C A A A G A T T G T A G C T A A A G A T A G T A G T...
                    1870                1880         ...1890

... ASN LEU THR ILE GLY ASN SER ASP ASP SER GLY
            ...A A T T T A A C T A T T G G T A A T A G T G A T G A T A G C G G
                          1900                1910                1920

ASN THR SER ALA LYS THR VAL THR PHE ...
C A A T A C T A G C G C T A A A A C A G T A A C T T T T...
              1930                1940         ...1950

... ASN VAL LYS ASP SER LYS ILE SER ALA ASP
            ...A A C A A T G T T A A A G A T T C A A A A T C T C T G C T G A
                          1960                1970                1980

GLY HIS LYS VAL THR LEU SER LYS ...
C G G T C A C A A G G T G A C A C T A A G C A A A...
              1990                2000         ...2010

... VAL LYS THR LEU SER ASP ASN ASN THR
            ...G T G A A A A C A C T T A G T G A T A A T A A C A C
                          2020                2030                2040

GLU GLY GLY SER ASP ASN ASN THR GLY ...
T G A A G G T G G C A G T G A C A A C A A T A C C G G T...
              2050                2060         ...
```

FIG.27K

```
          ...  LEU  THR  ILE  THR  ALA  LYS  ASP  VAL  GLU  VAL  ASN
          ...  T T A A C T A T T A C T G C A A A A G A T G T A G A A G T A A A
          ...2070.              2080              2090              2100

ASN  ASN  ILE  THR  SER  HIS  LYS  THR  VAL  ...
C A A C A A T A T T A C T T C T C A C A A A A C A G T G ...
                    2110              2120         ...2130

...  ASN  VAL  SER  ALA  ALA  ASN  GLY  GLY  ILE  THR  THR
          ...  A A C G T C T C T G C G G C A A A T G G A G G A T T A C C A C
                                  2140              2150              2160

LYS  THR  GLY  THR  THR  ILE  ASN  ALA  THR  ...
T A A A A C A G G T A C A A C C A T T A A T G C A A C C ...
               2170              2180         ...2190

...  ALA  GLY  ASN  VAL  GLU  ILE  THR  ALA  HIS  THR  GLY
          ...  G C C G G T A A C G T G G A G A T A A C C G C T C A T A C A G G
                                  2200              2210              2220

SER  ILE  GLN  GLY  GLY  ILE  GLU  SER  LYS  ...
C A G T A T C C A A G G C G G A A T T G A G T C C A A G ...
               2230              2240         ...2250

...  PRO  GLY  SER  VAL  THR  ILE  VAL  ALA  GLY  GLY  ASP
          ...  C C T G G C T C T G T G A C A A T T G T G G C A G G C G G C G A
                                  2260              2270              2280
```

FIG.27L

```
THR LEU ALA VAL GLY ASN ILE SER GLY ...
TACTCTTGCTGTAGGTAATATTTCAGGC...
            2290               2300

ASN ALA VAL THR VAL THR ALA ASN SER GLY ALA
                ...AACGCCGTTACTGTTACTGCAAATAGCGGTGC
                   ...2310            2320            2330      2340

LEU THR THR LEU ALA GLY SER THR ILE ...
ATTAACCACTTTGGCAGGCTCTACAATT...
            2350               2360

LYS GLY THR GLU SER ILE THR THR SER SER GLN
                ...AAAGGAACCGAGAGTATAACCACTTCAAGTCA
                   ...2370            2380            2390      2400

SER GLY ASN ILE GLY GLY LYS ILE SER ...
ATCAGGTAATATCGGCGGTAAAATTTCC...
            2410               2420

GLY LYS THR VAL ASN VAL LYS ALA THR ASN SER
                ...GGCAAGACAGTAAACGTTAAAGCAACTAATAG
                   ...2430            2440            2450      2460

LEU THR THR GLN ALA ASP SER LYS ILE ...
TTTAACCACCCAAGCAGACTCAAAAATT...
            2470               2480
```

FIG.27M

```
                                    ...  GLU  ALA  THR  GLU  GLY  GLU  ALA  ASN  VAL  THR  SER
                                    ....G A A G C G A C T G A A G G C G A G G C T A A T G T A A C A A G
                                    ...2490                          2500                         2510                         2520

LYS  THR  SER  ILE  ILE  GLY  GLY  THR  ILE  ...        ...  SER  GLY  THR  VAL  GLU  VAL  THR  ALA  THR  GLU
C A A A A C A A G C A T A A T T G G C G G T A C A A T T...  ...T C T G G T G G C A C A G T A G A A G T T A C C G C G A C C G A
                     2530                          2540      ...2550                         2560                         2570                         2580

GLY  LEU  THR  THR  GLN  ALA  GLY  SER  THR  ...        ...  ILE  THR  GLY  THR  GLU  SER  VAL  THR  THR  SER  SER
A G G T T T A A C C A C C C A A G C A G G C T T C T A C G... ...A T T A C T G G A A C C G A G A G C G T G A C C A C T T C A A G
                     2590                          2600      ...2610                         2620                         2630                         2640

GLN  SER  GLY  ASN  ILE  GLY  GLY  MET  ILE  ...        ...  SER  GLY  GLY  LYS  VAL  GLU  VAL  SER  ALA  THR  LYS
C C A A T C A G G T A A T A T C G G C G G C A T G A T T... ...T C T G G T G G C A A A G T A G A A G T T A G C G C A A C C A A
                     2650                          2660      ...2670                         2680                         2690                         2700
```

FIG.27N

```
ASP LEU ILE THR LYS SER GLY SER GLU ...      ILE LYS ALA THR ALA GLY GLU VAL ASN VAL THR
AGATTTAAATTACTAAATCCGGTTCAGAG...      ...ATTAAAGCAACAGGGCGAGGTGAATGTAAC
            2710                                  ...2730                              2750                 2760
                                                  ...2720

SER ALA THR GLY THR ILE ASP GLY THR ...      ILE SER GLY ASN THR VAL ASN VAL THR GLY ALA ALA ASN
AAGTGCAACAGGTACAATTGACGGTACG...      ...ATTTCCGGTAATACGGTAAATGTTACAGCAAA
            2770                                  ...2790                              2810                 2820
                                                  ...2780                              2800

THR GLY ASP LEU THR VAL GLU ASP ALA ...      ALA LYS ILE ASP ALA THR GLY ALA ALA THR
TACTGGCGATTTAACTGTTGAAGATGCC...      ...GCAAAAATTGATGCGACAGGAGGAGCCGCGAC
            2830                                  ...2850                              2870                 2880
                                                  ...2840                              2860

LEU THR ALA THR SER GLY LYS LEU THR ...
CCTAACTGCAACATCGGGCAAATTAACC...
            2890                                  ...2900
```

FIG. 270

```
            ...   THR   LYS   ALA   SER   SER   ILE   THR   SER   ALA   ASN
            ...A  C T A A G G C T A G T T C A A G C A T T A C T T T C A G C T A A
               ...2910              2920              2930              2940

ASN   GLN   VAL   ASN   LEU   SER   ALA   LYS   ASP   ...
T A A C C A G G T A A A C C T T T C A G C T A A G G A T...
                  2950              2960                  ...

...   GLY   SER   ILE   GLY   GLY   ASN   ILE   ALA   ALA   ASN
            ...G G T A G C A T T G G G G G A A A T C A A T G C T G C T A A
               ...2970              2980              2990              3000

VAL   THR   LEU   ASN   THR   THR   GLY   ALA   LEU   ...
T G T A A C A C T G A A T A C T A C A G G C G C T C T A...
                  3010              3020                  ...

...   THR   THR   VAL   LYS   GLY   SER   SER   ILE   ASN   ALA   ASN
            ...A  C T A C C G T G A A A G G G T T C A A G C A T T A A C G C A A A
               ...3030              3040              3050              3060

SER   GLY   THR   LEU   VAL   ILE   ASN   ALA   LYS   ...
C A G C G G G C A C C T T G G T T A T T A A C G C A A A A...
                  3070              3080                  ...

...   ASP   ALA   GLU   LEU   ASN   GLY   ALA   SER   GLY   ASN
            ...G  A C G C T G A G C T A A A T G G T G A G G C A T C A G G T A A
               ...3090              3100              3110              3120
```

FIG.27P

```
HIS THR VAL VAL ASN ALA THR ASN ALA ...
CCATACAGTAGTGAATGCAACCAACGCA...
         3130                        3140
                    ... ASN GLY SER GLY SER VAL ILE ALA THR THR SER
                    ...AATGGCTCCGGCAGCGTAATCGCGACAACCTC
                       ...3150          3160          3170          3180

SER ARG VAL ASN ILE THR GLY ASP LEU ....
AAGCAGAGTGAACATCACTGGGGATTTA....
         3190                        3200
                    ... ILE THR ILE ASN GLY LEU ASN ILE ILE SER LYS
                    ...ATCACAATAAAATGGATTAAATATCATTTCAAA
                       ...3210          3220          3230          3240

ASN GLY ILE ASN THR VAL LEU LEU LYS ....
AAACGGTATAAACACCGTACTGTTAAAA....
         3250                        3260
                    ... GLY VAL LYS ILE ASP VAL LYS TYR ILE GLN PRO
                    ...GGCGTTAAAATTGATGTGAAATACATTCAACC
                       ...3270          3280          3290          3300

GLY ILE ALA SER VAL ASP GLU VAL ILE ...
GGGTATAGCAAGCGTAGATGAAGTAATT...
         3310                        3320
```

FIG. 27Q

```
         ...  GLU ALA LYS ARG ILE LEU GLU LYS VAL LYS ASP
         ...  G A A G C G A A A A C G C A T C C T T G A G A A G G T A A A A G A
                                                                              3360
                                       ...3330                      3350

LEU SER ASP GLU GLU ARG GLU ALA LEU ...
T T T A T C T G A T G A A G A A A G A G A A G C G T T A...
                3370                    3380           ...3390

...  ALA LYS LEU GLY VAL SER ALA VAL ARG PHE ALA
         ...  G C T A A A C T T G G C G T A A G C G C T G T A C G T T T T G C
                                                                              3420
                     ...3400                       3410

GLU PRO ASN ASN ALA ILE THR ILE ASN ...
T G A G C C A A A T A A T G C C A T T A C G A T T A A T...
                3430                    3440           ...3450

...  THR GLN ASN GLU PHE THR THR ARG PRO SER SER
         ...  A C A C A A A A T G A G T T T A C A A C C A G A C C A T C A A G
                                                                              3480
                    ...3460                        3470

GLN VAL THR ILE SER GLU GLY LYS VAL ...
T C A A G T G A C A A T T T C T G A A G G T A A G G T A...
                3490                    3500           ...3510

...  CYS PHE LEU ILE GLY ASN GLY ALA THR ILE CYS
         ...  T G T T T C T T A A T C G G C A A T G G T G C A A C A A T A T G
                                                                              3540
                      ...3520                      3530
```

FIG.27R

THR ASN ILE ALA ASP ILE GLU ARG ***
CACCAATATTGCTGATATTGAGCGGTAG
         3550               3560

FIG.28A

```
ACAGGTTCT CTTAATACTA GTACAAACCC ACAATAAAAT ATGACAAACA ACAATTACAA      60

CACCTTTTTT GCAGTCTATA TGCAAATATT TTAAAAAATA GTATAAATCC GCCATATAAA    120

ATGTATAAT CTTTCATCTT TCATCTTTCA TCTTTCATCT TTCATCTTTC ATCTTTCATC    180

TTTCATCTTT CATCTTTCAT CTTTCATCT TCATCTTTCA TCTTTCATCT TTCATCTTTC     240

ACATGCCCTG ATGAACCGAG ATGAACCGAG GGAAGGGAAG GAGGGGCAAG AATGAAGAAG GAGCTGAACG    300

AACGCAAATG ATAAAGTAAT TTAATTGTTC AACTAACCTT AGGAGAAAAT ATG AAC    356
                                                      Met Asn
                                                       1

AAG CTA TAT CGT CTC AAA TTC AGC AAA CGC CTG AAT GCT TTG GTT GCT    404
Lys Leu Tyr Arg Leu Lys Phe Ser Lys Arg Leu Asn Ala Leu Val Ala
 5                          10                          15

GTG TCT GAA TTG GCA CGG GGT TGT GAC CAT TCC ACA GAA AAA GGC AGC    452
Val Ser Glu Leu Ala Arg Gly Cys Asp His Ser Thr Glu Lys Gly Ser
 20                         25                          30
```

FIG.28B

```
GAA AAA CCT GCT CGC ATG AAA GTG CGT CAC TTA GCG TTA AAG CCA CTT    500
Glu Lys Pro Ala Arg Met Lys Val Arg His Leu Ala Leu Lys Pro Leu
 35                  40                  45                  50

TCC GCT ATG TTA CTA TCT TTA GGT GTA ACA TCT ATT CCA CAA TCT GTT    548
Ser Ala Met Leu Leu Ser Leu Gly Val Thr Ser Ile Pro Gln Ser Val
             55                  60                  65

TTA GCA AGC GGC TTA CAA GGA ATG GAT GTA GTA CAC GGC ACA GCC ACT    596
Leu Ala Ser Gly Leu Gln Gly Met Asp Val Val His Gly Thr Ala Thr
         70                  75                  80

ATG CAA GTA GAT GGT AAT AAA ACC ATT ATC CGC AAC AGT GTT GAC GAT    644
Met Gln Val Asp Gly Asn Lys Thr Ile Ile Arg Asn Ser Val Asp Asp
     85                  90                  95

ATC ATT AAT TGG AAA CAA TTT AAC ATC GAC CAA AAT GAA ATG GTG CAG    692
Ile Ile Asn Trp Lys Gln Phe Asn Ile Asp Gln Asn Glu Met Val Gln
100                 105                 110

TTT TTA CAA GAA AAC AAC AAC TCC GCC GTA TTC AAC CGT GTT ACA TCT    740
Phe Leu Gln Glu Asn Asn Asn Ser Ala Val Phe Asn Arg Val Thr Ser
115                 120                 125                 130
```

FIG. 28C

```
AAC CAA ATC TCC CAA TTA AAA GGG ATT TTA GAT TCT AAC GGA CAA GTC    788
Asn Gln Ile Ser Gln Leu Lys Gly Ile Leu Asp Ser Asn Gly Gln Val
            135                 140                 145

TTT TTA ATC AAC CCA AAT GGT ATC ACA ATA GGT AAA GAC GCA ATT ATT    836
Phe Leu Ile Asn Pro Asn Gly Ile Thr Ile Gly Lys Asp Ala Ile Ile
        150                 155                 160

AAC ACT AAT GGC TTT ACG GCT TCT ACG CTA GAC ATT TCT AAC GAA AAC    884
Asn Thr Asn Gly Phe Thr Ala Ser Thr Leu Asp Ile Ser Asn Glu Asn
    165                 170                 175

ATC AAG GCG CGT AAT TTC ACC TTC GAG CAA ACC AAA GAT AAA GCG CTC    932
Ile Lys Ala Arg Asn Phe Thr Phe Glu Gln Thr Lys Asp Lys Ala Leu
180                 185                 190

GCT GAA ATT GTG AAT CAC GGT TTA ATT ACT GTC GGT AAA GAC GGC AGT    980
Ala Glu Ile Val Asn His Gly Leu Ile Thr Val Gly Lys Asp Gly Ser
            195                 200                 205                 210

GTA AAT CTT ATT GGT GGC AAA GTG AAA AAC GAG GGT GTG ATT AGC GTA   1028
Val Asn Leu Ile Gly Gly Lys Val Lys Asn Glu Gly Val Ile Ser Val
        215                 220                 225
```

FIG.28D

```
AAT GGT GGC AGC ATT TCT TTA CTC GCA GGG CAA AAA ATC ACC ATC AGC        1076
Asn Gly Gly Ser Ile Ser Leu Leu Ala Gly Gln Lys Ile Thr Ile Ser
            230                 235                 240

GAT ATA ATA AAC CCA ACC ATT ACT TAC AGC ATT GCC GCG CCT GAA AAT        1124
Asp Ile Ile Asn Pro Thr Ile Thr Tyr Ser Ile Ala Ala Pro Glu Asn
            245                 250                 255

GAA GCG GTC AAT CTG GGC GAT ATT TTT GCC AAA GGC GGT AAC ATT AAT        1172
Glu Ala Val Asn Leu Gly Asp Ile Phe Ala Lys Gly Gly Asn Ile Asn
            260                 265                 270

GTC CGT GCT GCC ACT ATT CGA AAC CAA GGT AAA CTT TCT GCT GAT TCT        1220
Val Arg Ala Ala Thr Ile Arg Asn Gln Gly Lys Leu Ser Ala Asp Ser
            275                 280                 285                 290

GTA AGC AAA GAT AAA AGC GGC AAT ATT GTT CTT TCC GCC AAA GAG GGT        1268
Val Ser Lys Asp Lys Ser Gly Asn Ile Val Leu Ser Ala Lys Glu Gly
            295                 300                 305

GAA GCG GAA ATT GGC GGT GTA ATT TCC GCT CAA AAT CAG CAA GCT AAA        1316
Glu Ala Glu Ile Gly Gly Val Ile Ser Ala Gln Asn Gln Gln Ala Lys
            310                 315                 320
```

FIG. 28E

```
GGC GGC AAG CTG ATG ATT ACA GGC GAT AAA GTC ACA TTA AAA ACA GGT      1364
Gly Gly Lys Leu Met Ile Thr Gly Asp Lys Val Thr Leu Lys Thr Gly
                325                 330                 335

GCA GTT ATC GAC CTT TCA GGT AAA GAA GGG GGA GAA ACT TAC CTT GGC      1412
Ala Val Ile Asp Leu Ser Gly Lys Glu Gly Gly Glu Thr Tyr Leu Gly
                340                 345                 350

GGT GAC GAG CGC GGC GAA GGT AAA AAG GGC ATT CAA TTA GCA AAG AAA      1460
Gly Asp Glu Arg Gly Glu Gly Lys Lys Gly Ile Gln Leu Ala Lys Lys
                355                 360                 365                 370

ACC TCT TTA GAA AAA GGC TCA ACC ATC AAT GTA TCA GGC AAA GAA AAA      1508
Thr Ser Leu Glu Lys Gly Ser Thr Ile Asn Val Ser Gly Lys Glu Lys
                375                 380                 385

GGC GGA CGC GCT ATT GTG TGG GGC GAT ATT GCG TTA ATT GAC GGC AAT      1556
Gly Gly Arg Ala Ile Val Trp Gly Asp Ile Ala Leu Ile Asp Gly Asn
                390                 395                 400

ATT AAC GCT CAA GGT AGT GGT GAT ATC GCT AAA ACC GGT GGT TTT GTG      1604
Ile Asn Ala Gln Gly Ser Gly Asp Ile Ala Lys Thr Gly Gly Phe Val
                405                 410                 415
```

FIG.28F

```
GAG ACG TCG GGG CAT GAT TTA TTC ATC AAA GAC AAT GCA ATT GTT GAC    1652
Glu Thr Ser Gly His Asp Leu Phe Ile Lys Asp Asn Ala Ile Val Asp
420                         425                         430

GCC AAA GAG TGG TTG TTA GAC CCG GAT AAT GTA TCT ATT AAT GCA GAA    1700
Ala Lys Glu Trp Leu Leu Asp Pro Asp Asn Val Ser Ile Asn Ala Glu
435                         440                         445                 450

ACA GCA GGA CGC AGC AAT ACT TCA GAA GAC GAT GAA TAC ACG GGA TCC    1748
Thr Ala Gly Arg Ser Asn Thr Ser Glu Asp Asp Glu Tyr Thr Gly Ser
                455                         460                         465

GGG AAT AGT GCC AGC ACC CCA AAA CGA AAC AAA GAA AAG ACA ACA TTA    1796
Gly Asn Ser Ala Ser Thr Pro Lys Arg Asn Lys Glu Lys Thr Thr Leu
470                         475                         480

ACA AAC ACA ACT CTT GAG AGT ATA CTA AAA AAA GGT ACC TTT GTT AAC    1844
Thr Asn Thr Thr Leu Glu Ser Ile Leu Lys Lys Gly Thr Phe Val Asn
        485                         490                         495

ATC ACT GCT AAT CAA CGC ATC TAT GTC AAT AGC TCC ATT AAT TTA TCC    1892
Ile Thr Ala Asn Gln Arg Ile Tyr Val Asn Ser Ser Ile Asn Leu Ser
500                         505                         510
```

FIG. 28G

```
AAT GGC AGC TTA ACT CTT TGG AGT GAG GGT CGG AGC GGT GGC GTT      1940
Asn Gly Ser Leu Thr Leu Trp Ser Glu Gly Arg Ser Gly Gly Val
515                 520                 525                 530

GAG ATT AAC AAC GAT ATT ACC ACC GGT GAT GAT ACC AGA GGT GCA AAC  1988
Glu Ile Asn Asn Asp Ile Thr Thr Gly Asp Asp Thr Arg Gly Ala Asn
            535                 540                 545

TTA ACA ATT TAC TCA GGC GGC TGG GTT GAT GTT CAT AAA AAT ATC TCA  2036
Leu Thr Ile Tyr Ser Gly Gly Trp Val Asp Val His Lys Asn Ile Ser
        550                 555                 560

CTC GGG GCG CAA GGT AAC ATA AAC ATT ACA GCT AAA CAA GAT ATC GCC  2084
Leu Gly Ala Gln Gly Asn Ile Asn Ile Thr Ala Lys Gln Asp Ile Ala
    565                 570                 575

TTT GAG AAA GGA AGC AAC CAA GTC ATT ACA GGT CAA GGG ACT ATT ACC  2132
Phe Glu Lys Gly Ser Asn Gln Val Ile Thr Gly Gln Gly Thr Ile Thr
580                 585                 590

TCA GGC AAT CAA AAA GGT TTT AGA TTT AAT AAT GTC TCT CTA AAC GGC  2180
Ser Gly Asn Gln Lys Gly Phe Arg Phe Asn Asn Val Ser Leu Asn Gly
            595                 600                 605                 610
```

FIG.28H

```
ACT GGC AGC GGA CTG CAA TTC ACC ACT AAA AGA ACC AAT AAA TAC GCT    2228
Thr Gly Ser Gly Leu Gln Phe Thr Thr Lys Arg Thr Asn Lys Tyr Ala
615                              620                      625

ATC ACA AAT AAA TTT GAA GGG ACT TTA AAT ATT TCA GGG AAA GTG AAC    2276
Ile Thr Asn Lys Phe Glu Gly Thr Leu Asn Ile Ser Gly Lys Val Asn
        630                      635                      640

ATC TCA ATG GTT TTA CCT AAA AAT GAA AGT GGA TAT GAT AAA TTC AAA    2324
Ile Ser Met Val Leu Pro Lys Asn Glu Ser Gly Tyr Asp Lys Phe Lys
645                      650                      655

GGA CGC ACT TAC TGG AAT TTA ACC TCC TTA AAT GTT TCC GAG AGT GGC    2372
Gly Arg Thr Tyr Trp Asn Leu Thr Ser Leu Asn Val Ser Glu Ser Gly
660                      665                      670

GAG TTT AAC CTC ACT ATT GAC TCC AGA GGA AGC GAT AGT GCA GGC ACA    2420
Glu Phe Asn Leu Thr Ile Asp Ser Arg Gly Ser Asp Ser Ala Gly Thr
675                      680                      685                690

CTT ACC CAG CCT TAT AAT TTA AAC GGT ATA TCA TTC AAC AAA GAC ACT    2468
Leu Thr Gln Pro Tyr Asn Leu Asn Gly Ile Ser Phe Asn Lys Asp Thr
            695                      700                      705
```

FIG. 28I

```
ACC TTT AAT GTT GAA CGA AAT GCA AGA GTC AAC TTT GAC ATC AAG GCA    2516
Thr Phe Asn Val Glu Arg Asn Ala Arg Val Asn Phe Asp Ile Lys Ala
              710                 715                 720

CCA ATA GGG ATA AAT AAG TAT TCT AGT TTG AAT TAC GCA TCA TTT AAT    2564
Pro Ile Gly Ile Asn Lys Tyr Ser Ser Leu Asn Tyr Ala Ser Phe Asn
              725                 730                 735

GGA AAC ATT TCA GTT TCG GGA GGG AGT GTT GAT TTC ACA CTT CTC        2612
Gly Asn Ile Ser Val Ser Gly Gly Gly Ser Val Asp Phe Thr Leu Leu
              740                 745                 750

GCC TCA TCC TCT AAC GTC CAA ACC CCC GGT GTA GTT ATA AAT TCT AAA    2660
Ala Ser Ser Ser Asn Val Gln Thr Pro Gly Val Val Ile Asn Ser Lys
              755                 760                 765                 770

TAC TTT AAT GTT TCA ACA GGG TCA AGT TTA AGA TTT AAA ACT TCA GGC    2708
Tyr Phe Asn Val Ser Thr Gly Ser Ser Leu Arg Phe Lys Thr Ser Gly
              775                 780                 785

TCA ACA AAA ACT GGC TTC TCA ATA GAG AAA GAT TTA ACT TTA AAT GCC    2756
Ser Thr Lys Thr Gly Phe Ser Ile Glu Lys Asp Leu Thr Leu Asn Ala
              790                 795                 800
```

FIG.28J

ACC GGA GGC AAC ATA ACA CTT TTG CAA GTT GAA GGC ACC GAT GGA ATG    2804
Thr Gly Gly Asn Ile Thr Leu Leu Gln Val Glu Gly Thr Asp Gly Met
805                             810                             815

ATT GGT AAA GGC ATT GTA GCC AAA AAC ACC TTT GAA GGA GGT             2852
Ile Gly Lys Gly Ile Val Ala Lys Asn Ile Thr Phe Glu Gly Gly
    820                             825                         830

AAC ATC ACC TTT GGC TCC AGG AAA GCC GTA ACA GAA ATC GAA GGC AAT    2900
Asn Ile Thr Phe Gly Ser Arg Lys Ala Val Thr Glu Ile Glu Gly Asn
835                             840                             845                     850

GTT ACT ATC AAT AAC AAC GCT AAC GTC ACT CTT ATC GGT TCG GAT TTT    2948
Val Thr Ile Asn Asn Asn Ala Asn Val Thr Leu Ile Gly Ser Asp Phe
                855                             860                             865

GAC AAC CAT CAA AAA CCT TTA ACT ATT AAA AAA GAT GTC ATC ATT AAT    2996
Asp Asn His Gln Lys Pro Leu Thr Ile Lys Lys Asp Val Ile Ile Asn
870                             875                             880

AGC GGC AAC CTT ACC GCT GGA GGC AAT ATT GTC AAT ATA GCC GGA AAT    3044
Ser Gly Asn Leu Thr Ala Gly Gly Asn Ile Val Asn Ile Ala Gly Asn
            885                             890                             895

FIG.28K

```
CTT ACC GTT GAA AGT AAC GCT AAT TTC AAA GCT ATC ACA AAT TTC ACT    3092
Leu Thr Val Glu Ser Asn Ala Asn Phe Lys Ala Ile Thr Asn Phe Thr
900                         905                         910

TTT AAT GTA GGC GGC TTG TTT GAC AAC AAA GGC AAT TCA AAT ATT TCC    3140
Phe Asn Val Gly Gly Leu Phe Asp Asn Lys Gly Asn Ser Asn Ile Ser
915                         920                         925                         930

ATT GCC AAA GGA GGG GCT CGC TTT AAA GAC ATT GAT AAT TCC AAG AAT    3188
Ile Ala Lys Gly Gly Ala Arg Phe Lys Asp Ile Asp Asn Ser Lys Asn
935                         940                         945

TTA AGC ATC ACC AAC TCC AGC TCC ACT TAC CGC ACT ATT ATA AGC        3236
Leu Ser Ile Thr Thr Asn Ser Ser Thr Tyr Arg Thr Ile Ile Ser
950                         955                         960

GGC AAT ATA ACC AAT AAA AAC GGT GAT TTA AAT ATT ACG AAC GAA GGT    3284
Gly Asn Ile Thr Asn Lys Asn Gly Asp Leu Asn Ile Thr Asn Glu Gly
965                         970                         975

AGT GAT ACT GAA ATG CAA ATT GGC GGC GAT GTC TCG CAA AAA GAA GGT    3332
Ser Asp Thr Glu Met Gln Ile Gly Gly Asp Val Ser Gln Lys Glu Gly
980                         985                         990
```

FIG.28L

```
AAT CTC ACG ATT TCT TCT GAC AAA ATC AAT ATT ACC AAA CAG ATA ACA        3380
Asn Leu Thr Ile Ser Ser Asp Lys Ile Asn Ile Thr Lys Gln Ile Thr
995                 1000                1005                1010

ATC AAG GCA GGT GTT GAT GGG GAG AAT TCC GAT TCA GAC GCG ACA AAC        3428
Ile Lys Ala Gly Val Asp Gly Glu Asn Ser Asp Ser Asp Ala Thr Asn
            1015                1020                1025

AAT GCC AAT CTA ACC ATT AAA ACC AAA GAA TTG AAA TTA ACG CAA GAC        3476
Asn Ala Asn Leu Thr Ile Lys Thr Lys Glu Leu Lys Leu Thr Gln Asp
                1030                1035                1040

CTA AAT ATT TCA GGT TTC AAT AAA GCA GAG ATT ACA GCT AAA GAT GGT        3524
Leu Asn Ile Ser Gly Phe Asn Lys Ala Glu Ile Thr Ala Lys Asp Gly
            1045                1050                1055

AGT GAT TTA ACT ATT GGT AAC ACC AAT AGT GCT GAT GGT ACT AAT GCC        3572
Ser Asp Leu Thr Ile Gly Asn Thr Asn Ser Ala Asp Gly Thr Asn Ala
        1060                1065                1070

AAA AAA GTA ACC TTT AAC CAG GTT AAA GAT TCA AAA ATC TCT GCT GAC        3620
Lys Lys Val Thr Phe Asn Gln Val Lys Asp Ser Lys Ile Ser Ala Asp
1075                1080                1085                1090
```

FIG.28M

```
GGT CAC AAG GTG ACA CTA CAC AGC AAA GTG GAA ACA TCC GGT AGT AAT    3668
Gly His Lys Val Thr Leu His Ser Lys Val Glu Thr Ser Gly Ser Asn
              1095                    1100                   1105

AAC AAC ACT GAA GAT AGC AGT GAC AAT AAT GCC GGC TTA ACT ATC GAT    3716
Asn Asn Thr Glu Asp Ser Ser Asp Asn Asn Ala Gly Leu Thr Ile Asp
              1110                    1115                   1120

GCA AAA AAT GTA ACA AAC AAT ATT ACT TCT CAC AAA GCA GTG            3764
Ala Lys Asn Val Thr Asn Asn Ile Thr Ser His Lys Ala Val
              1125                    1130              1135

AGC ATC TCT GCG ACA AGT GGA GAA ATT ACC ACT AAA ACA GGT ACA ACC    3812
Ser Ile Ser Ala Thr Ser Gly Glu Ile Thr Thr Lys Thr Gly Thr Thr
              1140                    1145                   1150

ATT AAC GCA ACC ACT GGT AAC GTG GAG ATA ACC GCT CAA ACA GGT AGT    3860
Ile Asn Ala Thr Thr Gly Asn Val Glu Ile Thr Ala Gln Thr Gly Ser
              1155                    1160                   1165
                                                             1170

ATC CTA GGT GGA ATT GAG TCC AGC TCT GTA ACA CTT ACT GCA            3908
Ile Leu Gly Gly Ile Glu Ser Ser Ser Val Thr Leu Thr Ala
              1175                    1180              1185
```

FIG.28N

```
ACC GAG GGC GCT CTT GCT GTA AGC AAT ATT TCG GGC AAC ACC GTT ACT        3956
Thr Glu Gly Ala Leu Ala Val Ser Asn Ile Ser Gly Asn Thr Val Thr
                1190                    1195                    1200

GTT ACT GCA AAT AGC GGT GCA TTA ACC ACT TTG GCA GGC TCT ACA ATT        4004
Val Thr Ala Asn Ser Gly Ala Leu Thr Thr Leu Ala Gly Ser Thr Ile
                1205                    1210                    1215

AAA GGA ACC GAG AGT GTA ACC ACT TCA AGT CAA TCA GGC GAT ATC GGC        4052
Lys Gly Thr Glu Ser Val Thr Thr Ser Ser Gln Ser Gly Asp Ile Gly
                1220                    1225                    1230

GGT ACG ATT TCT GGT GGC ACA GTA GAG GTT AAA GCA ACC GAA AGT TTA        4100
Gly Thr Ile Ser Gly Gly Thr Val Glu Val Lys Ala Thr Glu Ser Leu
                1235                    1240                    1245    1250

ACC ACT CAA TCC AAT TCA AAA ATT AAA GCA ACA ACA GGC GAG GCT AAC        4148
Thr Thr Gln Ser Asn Ser Lys Ile Lys Ala Thr Thr Gly Glu Ala Asn
                1255                    1260                    1265

GTA ACA AGT GCA ACA GGT ACA ATT GGT ACG ATT TCC GGT AAT ACG            4196
Val Thr Ser Ala Thr Gly Thr Ile Gly Thr Ile Ser Gly Asn Thr
                1270                    1275                    1280
```

FIG.28O

```
GTA AAT GTT ACG GCA AAC GCT GGC GAT TTA ACA GTT GGG AAT GGC GCA      4244
Val Asn Val Thr Ala Asn Ala Gly Asp Leu Thr Val Gly Asn Gly Ala
                1285                    1290                1295

GAA ATT AAT GCG ACA GAA GGA GCT GCA ACC TTA ACT ACA TCA TCG GGC      4292
Glu Ile Asn Ala Thr Glu Gly Ala Ala Thr Leu Thr Thr Ser Ser Gly
        1300                    1305                    1310

AAA TTA ACT ACC GAA GCT AGT TCA CAC ATT ACT TCA GCC AAG GGT CAG      4340
Lys Leu Thr Thr Glu Ala Ser Ser His Ile Thr Ser Ala Lys Gly Gln
1315                    1320                    1325                1330

GTA AAT CTT TCA GCT CAG GAT GGT AGC GTT GCA GGA AGT ATT AAT GCC      4388
Val Asn Leu Ser Ala Gln Asp Gly Ser Val Ala Gly Ser Ile Asn Ala
            1335                    1340                    1345

GCC AAT GTG ACA CTA AAT ACT ACA GGC ACT TTA ACT ACC GTG AAG GGT      4436
Ala Asn Val Thr Leu Asn Thr Thr Gly Thr Leu Thr Thr Val Lys Gly
                1350                    1355                1360

TCA AAC ATT AAT GCA ACC AGC GGT ACC TTG GTT ATT AAC GCA AAA GAC      4484
Ser Asn Ile Asn Ala Thr Ser Gly Thr Leu Val Ile Asn Ala Lys Asp
        1365                    1370                    1375
```

FIG.28P

```
GCT GAG CTA AAT GGC GCA GCA TTG GGT AAC CAC ACA GTG GTA AAT GCA    4532
Ala Glu Leu Asn Gly Ala Ala Leu Gly Asn His Thr Val Val Asn Ala
1380                              1385                         1390

ACC AAC GCA AAT GGC TCC GGC AGC GTA ATC GCG ACA ACC TCA AGC AGA    4580
Thr Asn Ala Asn Gly Ser Gly Ser Val Ile Ala Thr Thr Ser Ser Arg
       1395                         1400                         1410

GTG AAC ATC ACT GGG GAT TTA ATC ACA ATA AAT GGA TTA AAT ATC ATT    4628
Val Asn Ile Thr Gly Asp Leu Ile Thr Ile Asn Gly Leu Asn Ile Ile
                 1415                         1420                1425

TCA AAA AAC GGT ATA AAC ACC GTA CTG TTA AAA GGC GTT AAA ATT GAT    4676
Ser Lys Asn Gly Ile Asn Thr Val Leu Leu Lys Gly Val Lys Ile Asp
             1430                         1435                    1440

GTG AAA TAC ATT CAA CCG GGT ATA GCA AGC GTA GAT GAA GTA ATT GAA    4724
Val Lys Tyr Ile Gln Pro Gly Ile Ala Ser Val Asp Glu Val Ile Glu
         1445                         1450                         1455

GCG AAA CGC ATC CTT GAG AAG GTA AAA GAT TTA TCT GAT GAA GAA AGA    4772
Ala Lys Arg Ile Leu Glu Lys Val Lys Asp Leu Ser Asp Glu Glu Arg
     1460                         1465                         1470
```

FIG. 28Q

```
GAA GCG TTA GCT AAA CTT GGA GTA AGT GCT GTA CGT TTT ATT GAG CCA         4820
Glu Ala Leu Ala Lys Leu Gly Val Ser Ala Val Arg Phe Ile Glu Pro
1475                    1480                    1485            1490

AAT AAT ACA ATT ACA GTC GAT ACA CAA AAT GAA TTT GCA ACC AGA CCA         4868
Asn Asn Thr Ile Thr Val Asp Thr Gln Asn Glu Phe Ala Thr Arg Pro
        1495                    1500                    1505

TTA AGT CGA ATA GTG ATT TCT GAA GGC AGG GCG TGT TTC TCA AAC AGT         4916
Leu Ser Arg Ile Val Ile Ser Glu Gly Arg Ala Cys Phe Ser Asn Ser
1510                    1515                    1520

GAT GGC GCG ACG GTG TGC GTT AAT ATC GCT GAT AAC GGG CGG                 4958
Asp Gly Ala Thr Val Cys Val Asn Ile Ala Asp Asn Gly Arg
        1525                    1530                1535

TAGCGGTCAG TAATTGACAA GGTAGATTTC ATCCTGCAAT GAAGTCATTT TATTTTCGTA       5018

TTATTTACTG TGTGGGTTAA AGTTCAGTAC GGGCTTTACC CATCTTGTAA AAAATTACGG      5078

AGAATACAAT AAAGTATTTT TAACAGTTA TTATTATG                                5116
```

FIG.29A

```
TAAATATACA AGATAATAAA AATAAATCAA GATTTTTGTG ATGACAAACA ACAATTACAA      60
CACCTTTTTT GCAGTCTATA TGCAAATATT TTAAAAAAAT AGTATAAATC CGCCATATAA     120
AATGTATAA TCTTTCATCT TTCATCTTTA ATCTTTCATC TTTCATCTTT CATCTTTCAT     180
CTTTCATCTT TCATCTTTCA TCTTTCATCT TTCATCTTTC ATCTTTCATC TTTCATCTTT     240
CACATGAAAT GATGAACCGA GGGAAGGGAG GGAAGGGCAA GAATGAAGAG GGAGCTGAAC     300
GAAGCAAAT GATAAAGTAA TTTAATTGTT CAACTAACCT TAGGAGAAAA T ATG AAC     357
                                                        Met Asn
                                                        1

AAG ATA TAT CGT CTC AAA TTC AGC AAA CGC CTG AAT GCT TTG GTT GCT     405
Lys Ile Tyr Arg Leu Lys Phe Ser Lys Arg Leu Asn Ala Leu Val Ala
    5                   10                  15

GTG TCT GAA TTG GCA CGG GGT TGT GAC CAT TCC ACA GAA AAA GGC TTC     453
Val Ser Glu Leu Ala Arg Gly Cys Asp His Ser Thr Glu Lys Gly Phe
20                  25                  30

CGC TAT GTT ACT ATC TTT AGG TGT AAC CAC TTA GCG TTA AAG CCA CTT     501
Arg Tyr Val Thr Ile Phe Arg Cys Asn His Leu Ala Leu Lys Pro Leu
35                  40                  45                  50
```

FIG. 29B

```
TCC GCT ATG TTA CTA TCT TTA GGT GTA ACA TCT ATT CCA CAA TCT GTT          549
Ser Ala Met Leu Leu Ser Leu Gly Val Thr Ser Ile Pro Gln Ser Val
             55                      60                      65

TTA GCA AGC GGC TTA CAA GGA ATG GAT GTA GTA CAC GGC ACA GCC ACT          597
Leu Ala Ser Gly Leu Gln Gly Met Asp Val Val His Gly Thr Ala Thr
             70                      75                      80

ATG CAA GTA GAT GGT AAT AAA ACC ATT ATC CGC AAC AGT GTT GAC GCT          645
Met Gln Val Asp Gly Asn Lys Thr Ile Ile Arg Asn Ser Val Asp Ala
             85                      90                      95

ATC ATT AAT TGG AAA CAA TTT CAA AAT GAC CAA AAT GAA ATG GTG CAG          693
Ile Ile Asn Trp Lys Gln Phe Gln Asn Asp Gln Asn Glu Met Val Gln
             100                     105                     110

TTT TTA CAA GAA AAC AAC TCC GCC GTA TTC AAC CGT GTT ACA TCT              741
Phe Leu Gln Glu Asn Asn Ser Ala Val Phe Asn Arg Val Thr Ser
115                     120                     125             130

AAC CAA ATC TCC CAA TTA AAA GGG ATT TTA GAT TCT AAC GGA CAA GTC          789
Asn Gln Ile Ser Gln Leu Lys Gly Ile Leu Asp Ser Asn Gly Gln Val
             135                     140                     145

TTT TTA ATC AAC CCA AAT GGT ATC ACA ATA GGT AAA GAC GCA ATT ATT          837
Phe Leu Ile Asn Pro Asn Gly Ile Thr Ile Gly Lys Asp Ala Ile Ile
             150                     155                     160
```

FIG.29C

```
AAC ACT AAT GGC TTT ACG GCT TCT ACG CTA GAC ATT TCT AAC GAA AAC    885
Asn Thr Asn Gly Phe Thr Ala Ser Thr Leu Asp Ile Ser Asn Glu Asn
165                 170                 175

ATC AAG GCG CGT AAT TTC ACC GAG CAA ACC AAA GAT AAA GCG CTC        933
Ile Lys Ala Arg Asn Phe Thr Glu Gln Thr Lys Asp Lys Ala Leu
        180                 185                 190

GCT GAA ATT GTG AAT CAC GGT TTA ATT ACT GTC GGT AAA GAC GGC AGT    981
Ala Glu Ile Val Asn His Gly Leu Ile Thr Val Gly Lys Asp Gly Ser
195                 200                 205                 210

GTA AAT CTT ATT GGT GGC AAA GTG AAA AAC GAG GGT GTG ATT AGC GTA   1029
Val Asn Leu Ile Gly Gly Lys Val Lys Asn Glu Gly Val Ile Ser Val
            215                 220                 225

AAT GGT GCC AGC ATT TCT TTA CTC GCA GGG CAA AAA ATC ACC ATC AGC   1077
Asn Gly Gly Ser Ile Ser Leu Leu Ala Gly Gln Lys Ile Thr Ile Ser
        230                 235                 240

GAT ATA ATA AAC CCA ACC ATT ACT TAC AGC ATT GCC CCT GAA AAT       1125
Asp Ile Ile Asn Pro Thr Ile Thr Tyr Ser Ile Ala Pro Glu Asn
245                 250                 255

GAA GCG GTC AAT CTG GGC GAT ATT TTT GCC AAA GGT AAC ATT AAT       1173
Glu Ala Val Asn Leu Gly Asp Ile Phe Ala Lys Gly Asn Ile Asn
        260                 265                 270
```

FIG.29D

```
GTC CGT GCT GCC ACT ATT CGA AAC CAA GGT AAA CTT TCT GCT GAT TCT      1221
Val Arg Ala Ala Thr Ile Arg Asn Gln Gly Lys Leu Ser Ala Asp Ser
275                 280                 285                 290

GTA AGC AAA GAT AAA AGC GGC AAT GTT CTT TCC GCC AAA GAG GGT          1269
Val Ser Lys Asp Lys Ser Gly Asn Ile Val Leu Ser Ala Lys Glu Gly
        295                 300                 305

GAA GCG GAA ATT GGC GGT GTA ATT TCC GCT CAA AAT CAG CAA GCT AAA      1317
Glu Ala Glu Ile Gly Gly Val Ile Ser Ala Gln Asn Gln Gln Ala Lys
310                 315                 320

GGC AAG CTG ATG ATT ACA GGC GAT AAA GTC ACA TTA AAA ACA GGT          1365
Gly Gly Leu Met Ile Thr Gly Asp Lys Val Thr Leu Lys Thr Gly
325                 330                 335

GCA GTT ATC GAC CTT TCA GGT GAA GAA GGG GGA GAA ACT TAC CTT GGC      1413
Ala Val Ile Asp Leu Ser Gly Lys Glu Gly Gly Glu Thr Tyr Leu Gly
340                 345                 350

GGT GAC GAG CGC GGC GAA GGT GGT AAA AAC GGC ATT CAA TTA GCA AAG AAA  1461
Gly Asp Glu Arg Gly Glu Gly Gly Lys Asn Gly Ile Gln Leu Ala Lys Lys
355                 360                 365                 370

ACC TCT TTA GAA AAA GTA TCA ACC ATC AAT GTA TCA GGC AAA GAA AAA      1509
Thr Ser Leu Glu Lys Val Ser Thr Ile Asn Val Ser Gly Lys Glu Lys
375                 380                 385
```

FIG.29E

```
GGC GGA CGC GCT ATT GTG TGG GAT ATT GCG TTA ATT GAC GGC AAT        1557
Gly Gly Arg Ala Ile Val Trp Gly Asp Ile Ala Leu Ile Asp Gly Asn
            390                 395                 400

ATT AAC GCT CAA GGT AGT GAT GAT ATC GCT AAA ACC GGT TTT GTG        1605
Ile Asn Ala Gln Gly Ser Gly Asp Ile Ala Lys Thr Gly Phe Val
        405                 410                 415

GAG ACA TCG GGG CAT TAT TTA TCC ATT GAC AGC AAT GCA ATT GTT AAA    1653
Glu Thr Ser Gly His Tyr Leu Ser Ile Asp Ser Asn Ala Ile Val Lys
            420                 425                 430

ACA AAA GAG TGG TTG CTA GAC CCT GAT GAT GTA ACA ATT GAA GCC GAA    1701
Thr Lys Glu Trp Leu Leu Asp Pro Asp Asp Val Thr Ile Glu Ala Glu
            435                 440                 445                 450

GAC CCC CTT CGC AAT AAT ACC GGT ATA AAT GAT GAA TTC CCA ACA GGC    1749
Asp Pro Leu Arg Asn Asn Thr Gly Ile Asn Asp Glu Phe Pro Thr Gly
            455                 460                 465

ACC GGT GAA GCA AGC GAC CCT AAA AAT AGC GAA CTC AAA ACA ACG        1797
Thr Gly Glu Ala Ser Asp Pro Lys Asn Ser Glu Leu Lys Thr Thr
        470                 475                 480

CTA ACC AAT ACA ACT ATT TCA AAT TAT CTG AAA AAC GCC TGG ACA ATG    1845
Leu Thr Asn Thr Thr Ile Ser Asn Tyr Leu Lys Asn Ala Trp Thr Met
            485                 490                 495
```

FIG.29F

```
AAT ATA ACG GCA TCA AGA AAA CTT ACC GTT AAT AGC TCA ATC AAC ATC    1893
Asn Ile Thr Ala Ser Arg Lys Leu Thr Val Asn Ser Ser Ile Asn Ile
        500                 505                 510

GGA AGC AAC TCC CAC TTA ATT CTC CAT AGT AAA GGT CAG CGT GGC GGA    1941
Gly Ser Asn Ser His Leu Ile Leu His Ser Lys Gly Gln Arg Gly Gly
    515                 520                 525                 530

GGC GTT CAG ATT GAT GGA GAT ATT ACT AAA GGC GGA AAT TTA ACC        1989
Gly Val Gln Ile Asp Gly Asp Ile Thr Lys Gly Gly Asn Leu Thr
        535                 540                 545

ATT TAT TCT GGC GGA TGG GTT GAT GTT CAT AAA AAT ATT ACG CTT GAT    2037
Ile Tyr Ser Gly Gly Trp Val Asp Val His Lys Asn Ile Thr Leu Asp
    550                 555                 560

CAG GGT TTT TTA AAT ATT ACC GCC GCT ACA TCC GTA GCT TTT GAA GGT GGA 2085
Gln Gly Phe Leu Asn Ile Thr Ala Ala Ser Val Ala Phe Glu Gly Gly
        565                 570                 575

AAT AAC AAA GCA CGC GAC GCG GCA AAT GCT AAA GTC GCC CAG GGC        2133
Asn Asn Lys Ala Arg Asp Ala Ala Asn Ala Lys Val Ala Gln Gly
    580                 585                 590

ACT GTA ACC ATT ACA GGA GAG GGA AAA GAT TTC AGG GCT AAC AAC GTA    2181
Thr Val Thr Ile Thr Gly Glu Gly Lys Asp Phe Arg Ala Asn Asn Val
        595                 600                 605                 610
```

FIG. 29G

| | | | | | | | | | | | | | | | | |
|---|---|---|---|---|---|---|---|---|---|---|---|---|---|---|---|---|
| TCT | TTA | AAC | GGA | ACG | GGT | AAA | GGT | CTG | AAT | ATC | ATT | TCA | GTG | AAT | | 2229 |
| Ser | Leu | Asn | Gly | Thr | Gly | Lys | Gly | Leu | Asn | Ile | Ile | Ser | Val | Asn | | |
| | | | 615 | | | | | | | 620 | | | | 625 | | |
| AAT | TTA | ACC | CAC | AAT | CTT | AGT | GGC | ACA | ATT | AAC | ATA | TCT | GGG | AAT | ATA | 2277 |
| Asn | Leu | Thr | His | Asn | Leu | Ser | Gly | Thr | Ile | Asn | Ile | Ser | Gly | Asn | Ile | |
| | | | 630 | | | | | 635 | | | | | | 640 | | |
| ACA | ATT | AAC | CAA | ACT | ACG | AGA | AAG | AAC | ACC | TCG | TAT | TGG | CAA | ACC | AGC | 2325 |
| Thr | Ile | Asn | Gln | Thr | Thr | Arg | Lys | Asn | Thr | Ser | Tyr | Trp | Gln | Thr | Ser | |
| | | | 645 | | | | 650 | | | | | 655 | | | | |
| CAT | GAT | TCG | CAC | TGG | AAC | GTC | AGT | GCT | CTT | AAT | CTA | GAG | ACA | GGC | GCA | 2373 |
| His | Asp | Ser | His | Trp | Asn | Val | Ser | Ala | Leu | Asn | Leu | Glu | Thr | Gly | Ala | |
| | | 660 | | | | | 665 | | | | 670 | | | | | |
| AAT | TTT | ACC | TTT | ATT | AAA | TAC | ATT | TCA | AGC | AAT | AGC | AAA | GGC | TTA | ACA | 2421 |
| Asn | Phe | Thr | Phe | Ile | Lys | Tyr | Ile | Ser | Ser | Asn | Ser | Lys | Gly | Leu | Thr | |
| | | 675 | | | | 680 | | | | 685 | | | | | 690 | |
| ACA | CAG | TAT | AGA | AGC | TCT | GCA | GGG | GTG | AAT | TTT | AAC | GCC | GTA | AAT | GGC | 2469 |
| Thr | Gln | Tyr | Arg | Ser | Ser | Ala | Gly | Val | Asn | Phe | Asn | Ala | Val | Asn | Gly | |
| | | 695 | | | | | 700 | | | | | 705 | | | | |
| AAC | ATG | TCA | TTC | AAT | CTC | AAA | GAA | GGA | GCG | AAA | GTT | AAT | TTC | AAA | TTA | 2517 |
| Asn | Met | Ser | Phe | Asn | Leu | Lys | Glu | Gly | Ala | Lys | Val | Asn | Phe | Lys | Leu | |
| | | 710 | | | | 715 | | | | | 720 | | | | | |

FIG.29H

```
AAA CCA AAC GAG AAC ATG AAC ACA AGC AAA CCT TTA CCA ATT CGG TTT    2565
Lys Pro Asn Glu Asn Met Asn Thr Ser Lys Pro Leu Pro Ile Arg Phe
725                         730                         735

TTA GCC AAT ATC ACA GCC ACT GGT GGC TCT GTT TTT GAT ATA            2613
Leu Ala Asn Ile Thr Ala Thr Gly Gly Gly Ser Val Phe Asp Ile
        740                         745                 750

TAT GCC AAC CAT TCT GGC AGA GGG GCT GAG TTA AAA ATG AGT GAA ATT    2661
Tyr Ala Asn His Ser Gly Arg Gly Ala Glu Leu Lys Met Ser Glu Ile
755                         760                         765                 770

AAT ATC TCT AAC GGC GCT AAT TTT ACC TTA AAT TCC CAT GTT CGC GGC    2709
Asn Ile Ser Asn Gly Ala Asn Phe Thr Leu Asn Ser His Val Arg Gly
        775                         780                         785

GAT GAC GCT TTT AAA ATC AAC AAA GAC TTA ACC ATA AAT GCA ACC AAT    2757
Asp Asp Ala Phe Lys Ile Asn Lys Asp Leu Thr Ile Asn Ala Thr Asn
790                         795                         800

TCA AAT TTC AGC CTC AGA CAG ACG AAA GAT GAT TTT TAT GAC GGG TAC    2805
Ser Asn Phe Ser Leu Arg Gln Thr Lys Asp Asp Phe Tyr Asp Gly Tyr
        805                         810                         815

GCA CGC AAT GCC ATC AAT TCA ACC TAC AAC ATA TCC ATT CTG GGC GGT    2853
Ala Arg Asn Ala Ile Asn Ser Thr Tyr Asn Ile Ser Ile Leu Gly Gly
820                         825                         830
```

FIG. 29I

```
AAT GTC ACC CTT GGT GGA CAA AAC TCA AGC AGC ATT ACG GGG AAT      2901
Asn Val Thr Leu Gly Gly Gln Asn Ser Ser Ser Ile Thr Gly Asn
835                 840                 845                 850

ATT ACT ATC GAG AAA GCA GCA AAT GTT ACG CTA GAA GCC AAT AAC GCC  2949
Ile Thr Ile Glu Lys Ala Ala Asn Val Thr Leu Glu Ala Asn Asn Ala
            855                 860                 865

CCT AAT CAG CAA CAA AAC ATA AGG GAT AGA GTT ATA AAA CTT GGC AGC TTG  2997
Pro Asn Gln Gln Gln Asn Ile Arg Asp Arg Val Ile Lys Leu Gly Ser Leu
        870                 875                 880

CTC GTT AAT GGG AGT TTA ACT GGG AGT TTA ACT GGC GAA AAT GCA GAT ATT AAA  3045
Leu Val Asn Gly Ser Leu Ser Leu Thr Gly Glu Asn Ala Asp Ile Lys
            885                 890                 895

GGC AAT CTC ACT ATT TCA GAA AGC GCC ACT TTT AAA GGA AAG ACT AGA  3093
Gly Asn Leu Thr Ile Ser Glu Ser Ala Thr Phe Lys Gly Lys Thr Arg
900                 905                 910

GAT ACC CTA AAT ATC ACC GGC AAT TTT ACC AAT AAT GGC ACT GCC GAA  3141
Asp Thr Leu Asn Ile Thr Gly Asn Phe Thr Asn Asn Gly Thr Ala Glu
915                 920                 925                 930

ATT AAT ATA ACA CAA GGA GTG GTA AAA CTT GGC AAT GTT ACC AAT GAT  3189
Ile Asn Ile Thr Gln Gly Val Val Lys Leu Gly Asn Val Thr Asn Asp
            935                 940                 945
```

FIG. 29J

```
GGT GAT TTA AAC ATT ACC ACT CAC GCT AAA CGC AAC CAA AGA AGC ATC    3237
Gly Asp Leu Asn Ile Thr Thr His Ala Lys Arg Asn Gln Arg Ser Ile
            950                 955                 960

ATC GGC GGA GAT ATA ATC AAC AAA GGA AGC TTA AAT ATT ACA GAC        3285
Ile Gly Gly Asp Ile Ile Asn Lys Lys Gly Ser Leu Asn Ile Thr Asp
        965                 970                 975

AGT AAT GCT GAA ATC CAA ATT GGC GGC AAT ATC TCG CAA AAA            3333
Ser Asn Ala Glu Ile Gln Ile Gly Gly Asn Ile Ser Gln Lys
    980                 985                 990

GAA GGC AAC CTC ACG ATT TCT TCC GAT AAA ATT AAT ATC ACC AAA CAG    3381
Glu Gly Asn Leu Thr Ile Ser Ser Asp Lys Ile Asn Ile Thr Lys Gln
995                 1000                1005                1010

ATA ACA ATC AAA AAG ATT GAT GGA GAG GAC TCT AGT TCA GAT GCG        3429
Ile Thr Ile Lys Lys Gly Ile Asp Gly Glu Asp Ser Ser Asp Ala
        1015                1020                1025

ACA AGT AAT GCC AAC CTA ACT ATT AAA ACC AAA GAA TTG AAA TTG ACA    3477
Thr Ser Asn Ala Asn Leu Thr Ile Lys Thr Lys Glu Leu Lys Leu Thr
            1030                1035                1040

GAA GAC CTA AGT ATT TCA GGT TTC AAT AAA GCA GAG ATT ACA GCC AAA    3525
Glu Asp Leu Ser Ile Ser Gly Phe Asn Lys Ala Glu Ile Thr Ala Lys
            1045                1050                1055
```

FIG.29K

```
GAT GGT AGA GAT TTA ACT ATT GGC AAC AGT AAT GAC GGT AAC AGC GGT    3573
Asp Gly Arg Asp Leu Thr Ile Gly Asn Ser Asn Asp Gly Asn Ser Gly
1060                     1065                    1070

GCC GAA GCC AAA ACA GTA ACT TTT AAC AAT GTT AAA GAT TCA AAA ATC    3621
Ala Glu Ala Lys Thr Val Thr Phe Asn Asn Val Lys Asp Ser Lys Ile
      1075                    1080                    1085    1090

TCT GCT GAC GGT CAC AAT GTG ACA CTA AAT AGC AAA GTG AAA ACA TCT    3669
Ser Ala Asp Gly His Asn Val Thr Leu Asn Ser Lys Val Lys Thr Ser
                 1095                    1100                    1105

AGC AGC AAT GGC GGA CGT GAA AGC GAT AGC AAT AGC GAC AAC GAT ACC GGC TTA    3717
Ser Ser Asn Gly Gly Arg Glu Ser Asp Ser Asn Ser Asp Asn Asp Thr Gly Leu
         1110                    1115                    1120

ACT ATT ACT GCA AAA AAT GTA GAA GTA AAC AAA GAT ATT ACT TCT CTC    3765
Thr Ile Thr Ala Lys Asn Val Glu Val Asn Lys Asp Ile Thr Ser Leu
         1125                    1130                    1135

AAA ACA GTA AAT ATC ACC GCG TCG GAA AAG GTT ACC ACA GCA GGC    3813
Lys Thr Val Asn Ile Thr Ala Ser Glu Lys Val Thr Thr Thr Ala Gly
         1140                    1145                    1150

TCG ACC ATT AAC GCA ACA AAT GGC AAA GCA AGT ATT ACA ACC AAA ACA    3861
Ser Thr Ile Asn Ala Thr Asn Gly Lys Ala Ser Ile Thr Thr Lys Thr
1155                    1160                    1165                    1170
```

FIG.29L

```
GGT GAT ATC AGC GGT ACG ATT TCC GGT AAC ACG GTA AGT GTT AGC GCG    3909
Gly Asp Ile Ser Gly Thr Ile Ser Gly Asn Thr Val Ser Val Ser Ala
            1175                    1180                    1185

ACT GGT GAT TTA ACC ACT AAA TCC GGC TCA AAA ATT GAA GCG AAA TCG    3957
Thr Gly Asp Leu Thr Thr Lys Ser Gly Ser Lys Ile Glu Ala Lys Ser
            1190                    1195                    1200

GGT GAG GCT AAT GTA ACA AGT GCA ACA GGT GGC ACA ATT GGC GGT ACA ATT    4005
Gly Glu Ala Asn Val Thr Ser Ala Thr Gly Thr Ile Gly Gly Thr Ile
            1205                    1210                    1215

TCC GGT AAT ACG GTA AAT GTT ACG GCA AAC GCT GGC GAT TTA ACA GTT    4053
Ser Gly Asn Thr Val Asn Val Thr Ala Asn Ala Gly Asp Leu Thr Val
            1220                    1225                    1230

GGG AAT GGC GCA GAA ATT AAT GCG ACA GAA GGA GCT GCA ACC TTA ACC    4101
Gly Asn Gly Ala Glu Ile Asn Ala Thr Glu Gly Ala Ala Thr Leu Thr
            1235                    1240                    1245                    1250

GCA ACA GGG AAT ACC TTG ACT ACT GAA GCC TCT AGC ATC ACT TCA    4149
Ala Thr Gly Asn Thr Leu Thr Thr Glu Ala Gly Ser Ile Thr Ser
            1255                    1260                    1265

ACT AAG GGT GTA CAG GAC CTC TTG GCT CAG AAT GGT AGC ATC GCA GGA    4197
Thr Lys Gly Val Gln Val Asp Leu Leu Ala Gln Asn Gly Ser Ile Ala Gly
            1270                    1275                    1280
```

FIG.29M

AGC ATT AAT GCT AAT GTG ACA TTA AAT ACT ACA GGC ACC TTA ACC          4245
Ser Ile Asn Ala Asn Val Thr Leu Asn Thr Thr Gly Thr Leu Thr
                1285              1290             1295

ACC GTG GCA GGC TCG GAT ATT AAA GCA ACC AGC GGC TTG GTT ATT          4293
Thr Val Ala Gly Ser Asp Ile Lys Ala Thr Ser Gly Leu Val Ile
        1300             1305              1310

AAC GCA AAA GAT GCT AAG CTA AAT GGT GAT GCA TCA GGT GAT AGT ACA      4341
Asn Ala Lys Asp Ala Lys Leu Asn Gly Asp Ala Ser Gly Asp Ser Thr
    1315              1320             1325              1330

GAA GTG AAT GCA GTC AAC GCA AGC GGC TCT AGT GTG ACT GCG GCA          4389
Glu Val Asn Ala Val Asn Ala Ser Gly Ser Ser Val Thr Ala Ala
            1335             1340             1345

ACC TCA AGC AGT GTG AAT ATC ACT GGG GAT TTA AAC ACA GTA AAT GGG      4437
Thr Ser Ser Ser Val Asn Ile Thr Gly Asp Leu Asn Thr Val Asn Gly
        1350             1355             1360

TTA AAT ATC ATT TCG AAA GAT GGT AGA AAC ACT GTG CGC TTA AGA GGC      4485
Leu Asn Ile Ile Ser Lys Asp Gly Arg Asn Thr Val Arg Leu Arg Gly
        1365             1370             1375

AAG GAA ATT GAG GTG AAA TAT ATC CAG CCA GGT GTA GCA AGT GTA GAA      4533
Lys Glu Ile Glu Val Lys Tyr Ile Gln Pro Gly Val Ala Ser Val Glu
    1380              1385             1390

FIG.29N

```
GAA GTA ATT GAA GCG AAA CGC GTC CTT GAA AAA GTA AAA GAT TTA TCT    4581
Glu Val Ile Glu Ala Lys Arg Val Leu Glu Lys Val Lys Asp Leu Ser
1395                        1400                     1405      1410

GAT GAA GAA AGA GAA ACA TTA GCT AAA CTT GGT GTA AGT GCT GTA CGT    4629
Asp Glu Glu Arg Glu Thr Leu Ala Lys Leu Gly Val Ser Ala Val Arg
             1415                        1420                 1425

TTT GTT GAG CCA AAT AAT ACA ATT ACA GTC AAT ACA CAA AAT GAA TTT    4677
Phe Val Glu Pro Asn Asn Thr Ile Thr Val Asn Thr Gln Asn Glu Phe
         1430                        1435                     1440

ACA ACC AGA CCG TCA AGT CAA GTG ATA ATT TCT GAA GGT AAG GCG TGT    4725
Thr Thr Arg Pro Ser Ser Gln Val Ile Ile Ser Glu Gly Lys Ala Cys
     1445                        1450                     1455

TTC TCA AGT GGT AAT GCC GCA CGA GTA TGT ACC AAT GTT GCT GAC GAT    4773
Phe Ser Ser Gly Asn Ala Arg Val Cys Thr Asn Val Ala Asp Asp
 1460                        1465                     1470

GGA CAG CCG TAGTCAGTAA TTGACAAGT AGATTCATC CTGCAATGAA              4822
Gly Gln Pro
1475

GTCATTTTAT TTTGTATTA TTTACTGTGT GGGTTAAAGT TCAGTACGGG CTTTACCCAT   4882

CTTGTAAAAA ATTACGGAGA ATACAATAAA GTATTTTTAA CAGGTTATTA TTATG       4937
```

FIG.30A  Alignment of HMW proteins

```
          10        20        30        40        50
MNKIYRLKFSKRLNALVAVSELARGCDHSTEKGSEKPARMKVRHLALKPLSAMLLS
.......................................................

110       120       130       140       150
NWKQFNIDQNEMVQFLQENNNSAVFNRVTSNQISQLKGILDSNGQVFLINPNGITI
.......................................................

210       220       230       240       250
GLITVGKDGSVNLIGGKVKNEGVISVNGGSISLLAGQKITISDIINPTITYSIAAP
.......................................................

310       320       330       340       350
LSAKEGEAEIGGVISAQNQQAKGGKLMITGDKVTLKTGAVIDLSGKEGGETYLGGD
.......................................................

410       420       430       440▼      450
GNINAQGSGDIAKTGGFVETSGHDLFIKDNAIVDAKEWLLDPDNVSINAETAGRSN
........................Y.S.DS....KT........D.T.E..DPL.N.
..........T.E.PSYS.G.
........E..Y...GD....D
.............G.SE.ND
.............ENPSTE.ND
..........E.T.G.GDV...D
........D...D.PS.E.TD
..........N.VKG.ELQND
........D.T.A.GAP..ND
...............PAL..TE
........DIN.VNGSNIDAQ 510       520       530       540       550
ANQRIYVNSSINL-SNGSLTLWSEGRSGG-GVEINNDITTGDDTRGANLTIYSGGW
.SRKLT......IG..SH.I.H.K.QR..-..Q.DG...S----K.G.........
.KKNLT......IGDSSH.I.H...KNN.-..K.KE...S----N.G....Q....
..NE.R...D..IGG.SH.....SKNKNS-..L..GN..S---.ANG......S..
.RK..T...D..IKDSSH.I....NDNSS-..D.KGN..S----.T.GS.....S.
.TDN........IGDS.H.I.SGG..N.-..K..KN..S----T.GS...N.K..
.KNK.L...D..IKE.SH.I.W..RDGNS-..Q.DGN..S---AT.GS..V..S..
```

FIG.30B

```
           60         70         80         90        100
    LGVTSIPQSVLASGLQGMDVVHGTATMQVDGNKTIIRNSVDAII              12-1
    ...........................................              12-2

160        170        180        190        200
    GKDAIINTNGFTASTLDISNENIKARNFTFEQTKDKALAEIVNH              12-1
    ...........................................              12-2

260        270        280        290        300
    ENEAVNLGDIFAKGGNINVRAATIRNQGKLSADSVSKDKSGNIV              12-1
    ...........................................              12-2

360        370        380        390        400
    ERGEGKNGIQLAKKTSLEKGSTINVSGKEKGGRAIVWGDIALID              12-1
    ...........................................              12-2

460        470        480        490        500
    TS-EDDEY-TGSGNSASTPKRNKE--KTTLTNTTLESILKKGTFV-NIT          12-1
    .G-IN..FP..TGE-...D..K.S.L-.........ISNY..NAWIM-...       12-2
    AG-I.S.FPG...TKE.-...T.G.Q-P.V...E.ISNY...S..W.M...       15-1
    .NL.NE..-..T.E..D.....NNT-.......S...K..AR.S..-...        15-2
    A.-PTEDFP...A.GKDN-...K.AHN-.P...I.....R...SGN...-...     Joyc-1
    SN-...L..-..T.ENINN..V.NQS-.K...SSI..N.....S..-...        Joyc-2
    D.-S.TAFP..T.ERN.-..T.AQN-RP.I...S...Q...N....-...        LCDC2-1
    .G-..V...-.T.ADINHQ.Q.S.T-.S........GM..R.L..-...         LCDC2-2
    LV-V-------R.D--.IE.K.APT-...IHAGSI.QS.M..GA.-...S        PMH1-1
    G.-V..FFP..R.DD..NA.T.HPD-.P......V.NA..NN...-...         PMH1-2
    STPNNN..—-D.P.QINY--K..PS-LS........R...RN.S.-...         K1-1
    LQP-------.R.D---..NKVSAEGL.SIN.A...STA.Q..IE.-...S       K21-1

560        570        580        590
    VDVHKNISLGAQGNININITAKQ-DIAFEKGS-N-------QVITGQ           12-1
    .......T.D-..FL....AS--V...G.N-.KARDAANAK.VA.            12-2
    .......T..T-.TL.....G-S.T..GNGTEKARNASSAQ..A.            15-1
    ..I....T.ES-.RL...T.EG.V.....N-.-------LT....            15-2
    I.I....T.NS-.LL...T..G.......N-.-------PT....            Joyc-1
    ..I.S.....T-.FL...SNG-SV....ADKDKARSAADAQ.VA.            Joyc-2
```

FIG.30C

```
.RNK.R...T..IGDS.H...YKKRKNRSD.IQ..K...S----.G.S-...N.DD.
.TNKVN.TTD..V-Y..A...H..RD----.....GN..S---EKNG....KA.S.
.KNK.T...D..IKGGAH...Y.KNNKKS-S.K...GN..S---.TNG......S..
.TKT.T...D..IGDSSH.......QGR.-..NVTGN..S---.TNG.........
.TKNVT..ADVDV-K..T.V.H.QRN----...K..GN..S---.QNG....KT..K 600       610       620       630
G--TITSGNQ-KGFRFNNVSLNGTGSGLQFTTKRIN------KYAITNKFEGTLNI
.TV...GEG--.D..A.........K..NIISSVN.---------L.HNLS..I..
.--...NTGDQ.QL.L....I....I..N.VSIQP.---------TSHR.D.E.I.
.--...A..N-......E........T..L.NLS.PQ----KNNSLV..Y.N.....
.--...A..G-......E.A....I.T..L.NI..DL----GNNFQ.I.F.N.....
.--I.NLTGEN.T..L.......V.Q..SI.SNVG.---------Q.H..D.EI..
.--...ASK--......D..T.S.VKK.FL.KYSQ..---NNKDSNFE.H.R.....
.--...LTGEN.T..L.........N..SIISTAS.---------LSHRLD.EI.V
.--N...NKDG.QL.L..........A..N.IANQN.---------F.HNIS.AI..
.--V....VG-E..........V.A..R.VGQKNISSNSWRENT.K.R.D.N...
.--..AVN.K-......D..T.....G..S.KYIE.G---NRDSNFE.H-.R.R...
.--N.I.NQEN.QL..S......M.A..T..ANKG.---------H.H..D.....

690       700       710       720       730
DSRGS-----DSAGTLTQPYNLNGISFNKDTTFNVERNARVNFDIKAPIG-INKYS
S.---NSKGLTTQYRSSA.V.F..VNG.M-S-..LKEG.K...KL.-.NE-NMNT.
LNNNH-GRETSR-YRKGGGVIFRSPTGHTN--.T.KQGSVA...SF..KND-T.HAN
..-----SAE.GSAP.LSS.T......TT......NK..K...N......T...Q.N
....D-----.T.....NT............I.D.KQ.GA.T.........-V.NNR
E.NRFGPTTPLRS---SGGVFF..TNG.MVL--..GT.S..L.NL.-.NE-NT.N.
.NS.SRP--SPG..P.YRRSG.......N..V...ASGSA...S..P..V-S.VHD
N.ARNGDVR----GRSFAGVIF.AKGLTTS--...KKGST.D.KL.-.NSGYNSQK
..NHS---TNSSDSRSFAGVKFH.KNNEMK--..IGN..KAE.RL.-.NEKTTPNR
.AS.ISSGNQDDITNRG----....T..GEN...IAQGSTA..H..TSVMTP.PN.
..SGSAS--SPG..P.NAQSG.......N..V..IAASSA...N..P..V-DKVTN

..NRSVA--LNSGSRSFAGVKFY.KNNEMK--..IGD..N.E.KL.SNDNTSNNKP 790       800       810       820       830
RFKTSGSTKTGFSIEKDLTLNATGGNITLLQVEGT--DGMIGK-GIVAKKNITFEG
TLNSHVRGDDA.K.N....I...NS.FS.R.TKDDFY..YARN-A.NSTY..SIL.
```

FIG.30D

```
........T.NS-.YL...T.SG.V...Q.N--------DLT....          LCDC2-1
..I.G..T..E-.FL...SSD-SV...G.NG.KGRSSASAQ.IA.           LCDC2-2
........T..E-.FL...SG--........N-.-------LT..A.        PMH1-1
..I....T.NT-.YL....GG-SV....AGNEKGRQVSES...KA.          PMH1-2
........T.KS-.YL...T..G.....DKPGLS-----NLT..AK          K1-1
........T..M-.FL...SDN-N.T....D-.-------LT..A.          K21-1

640       650       660       670       680
SGKVNISMVLPKNESG-YDKFKGRTYWNLTSLNVSESGEFNLT--I           12-1
..NIT.NQTTR..T.--.WQTSHDSH..VSA..LETGAN.TFIKY.          12-2
..R.HVNQTT...L.--FW.VSDES...VSH.T.K.KSA.SF.KFA          15-1
..S.....IP.NAT.NW.SRY.......I.H..A..DSN....--.          15-2
.........I..-KWD-.S..R......V.H.....GSK....--.          Joyc-1
T.N.T.NQTA.ATTA--.WN.SYDS...VST...QKNSS.TFIKRT          Joyc-2
....D.L.QARQENWN-RRHS-..SH..V.R....TNSYL.I.--.          LCDC2-1
..N.T.NQTTQQ.IE--.W.ASSDS...V..F.LR.DSK.TFIKYV          LCDC2-2
..V.T.NQTTK..AK--AWNTSYDS...VST.TL.NDAK.TFIKYV          PMH1-1
.....V..DVSGTKWH-TRIN-......V.T...ASGSS...S--.          PMH1-2
....D.L.QARQENWN-RRHW-..SH..V.R.....NSY..V.--.          K1-1
....V.NQTT.H.-IA-PWNASADS...V.T.TLGNNAQ.TFIKFV          K21-1

740       750       760       770       780
SLNYASFNGNISVSGGGSVDFTLLASSSNVQTPGVVINSKYFNVSTGSSL       12-1
KPLPIR.LA..TAT.....F.DIY.NH.---GR.AELKMSEI.I.N.ANF       12-2
-QLPIQ..S....D...K.L.CITSNY.---GRS.G.GMSSI...D..N.      15-1
N....L..........N.T.R.N.....Q.....I....HL.A.K....       15-2
N..............N.T.K......TA.....F....H..A.G....        Joyc-1
KP.PLQ..A..TAI.....S.DIH.NH.---GR.AELKMNTI.I.D.T..      Joyc-2
G-.HTL....V..L....D.N.HFN.....HW.H....K.QN..A.E....     LCDC2-1
RIPIQ.QS........R.NINT..NLT---GG..E.R.SSI...D..T.       LCDC2-2
PLPIQ.LS....T.....F.DIY.NLW---GK.TELKMDSI...S..N.       PMH1-1
-...L.......L...T.N.E.N....THT.S.AI...QN....G..K.       PMH1-2
G-.HTL.K.....L...                                       K1-1
              ..D.N.HFN.....Y..Y..I.E.QNFSA.G....       K1-1
-LPIQ.LS...AT.N.T.S.DIH.NL.---ARSTEL.MSLI.I.N.VNF       K21-1

840       850       860       870       880
GNITFGSRKAVTEIEGNVTINNNANVTLIGSDFDNHQ--KPLTIKK-DVI       12-1
```

FIG.30E

```
T.NS.IRGQEA.N.S....I....SFFE.G.YSD.FNGNGFNHDA.KSTH..SIL.
..E.T....V..L.NN..........S......I--.....E-.V........T.
E.RAE....V..L.NN..........S......I--........-.V........A.
TLQSHVRKDSA.I.S....I....S.F..E.SPDSFT.KYP.R-A.SST....IS.
...SE...R.A.T...S...........S.N..A.I--..NLQ.-SL..N.......
SMTAQARDRNA.E.T...VI..SNS.LSII.QNDGFDNNQKAN-A.NS.Y.V.IQ.
TLNSHVRKYNA.E.N....I...NS.FN.R.TSDSFRN.YRNN-A.NSTH..SIL.
NL.A....N.A.L.KNN..........EIK......--.SR.Q.-.V..EQ..I...
K..SE...HAA.T.KN..I........S.N..A.I--.SNLK.-SLI.N.......
SINSHVRGNNA.E.K...II....S.FN.K.TKDKFDNSYEKN-A.FSTH.L.IL.

890       900       910       920       930
INSGNLTAGGNIVNIAGNLTVESNANFKAITNFTFNVGGLFDNKGNSNISIAKGGA
LVN.S.SLT.ENAD.K....ISES.T..GK.RD.L.IT.N.T.N.TAE.N.TQ.VV
.E-...SLI.ASA..N...S.KE..K..GE.QDNL.IT.T.I.N.D.K.N.SQ.VV
NR-........VI..G......NG..L..............N..........R...
...........VI..N.....NNG..L..........................R...
V-E....LT.SVAD.K...SILND.T..GE.SENL.IT.N.T.N.TAD.N.KQ.VV
-.K....VT.SAI..EK.....GS.K.L.NP.YS...S.....Q.K..........
VE-.E.RLV.ASA..NN..S.K.G.K...E..DNL.IT.T.T.N.T.I.DVK..A.
VE-...SLI.ENA..N...SI.KE.I..GK.KDSL.IT.T.N.TAE.N.SQ.VV
TAN......D.DTIK.K...D.AQG.K.NGS.KNNL.IT.T.N.T.I.D.TQ.VV
NK-....VT.SAI..EK.....GS.K.L.NP.YS...S.....Q.K..........
SVG...NII.SNAH.D...SIAES.K.QGK..NNL.IT.T.T.N.TAD.N.KQ.VV 990      1000      1010      1020      1030
TEMQIGGDVSQKEGNLTISSDKINITKQITIKAGVDGENSDSDATNNANLTIKTKE
A.I....NI....................K.I...D.S....S..........
A.I....NI.....................N.......................
A.I....NI.....................K..N......STKSQ..........
A.I....NI.....................N.....K..NK.D...STA......
A.I....NI...K.................K........EGG...SPAS.......T
A.I....NI.....................N.....K..NK.D...STA......
..I....NI.....................R.E....T.QG....GVAS......
A.IE...NI............V..................S.S.STASD......
A.IE...NI............V..................S.S.STASD......
..I....NI............V...ER.......N.D....NEATS.........
A.I....NI.....................R.E...DT.QG....GVAS......
```

FIG.30F

```
..V.L.GQNSSSS.T...I..EKA.....EANNAP.Q.NIRDRV..LG-SL      12-2
..V.L.GQDSSST.T...IN.SQA.....RAYNGNGRN--.Q..--LGN.S      15-1
.......K..I...K......E.T.A.......ND.K--...N..G-..V      15-2
.......K..I......A........................--........-...  Joyc-1
..VSL.GQNSSSD.K..I..KSST....KAHNSPRDFASRT...--LGNLN      Joyc-2
....LAAD.KPI..K..I.VKEG.....RSANYG.DK--SA.S.R-GN.T       LCDC2-1
..V.L.GQNSSST.T.S.N.GA......QAHNGNDRN--.K..--FGN.S       LCDC2-2
..V.L.GQNSSSS.M..II.KRA.....EADNSH.SDNV.DR..NLGNLT       PMH1-1
....L..Q..P...K.D..VKQGT.A...RSAN.......---.GAL.VNGN.-   PMH1-2
....LAAD.KPI..K..I.VKEG.....RSANYG.DK--SA.S.-RGN.T       K1-1
..V.L.GENSSSN.K..IN..SK.....QAHAGTS.LDK.ER.LTLGN.-       K21-1

940       950       960       970       980
RFK-DIDNSKNLSITTNSSSTYRTIISGNITNKNGDLNITNEGSD            12-1
KLG-NVT.DGD.N...HAKRNQ.S...G.D.I..K.S....DSNN.           12-2
KLG-NVT.DGD.N...HAKHNQ.S...G.D.I..K.S....DSNKN           15-1
K..-..N.TSS.N.....DT......E.....A.....IDNKGN            15-2
K..-..N.TSS.N.....DT......E.....A.....IDNKGN            Joyc-1
NIQGN.T.KGG.N....AQNNQK...N.....EG.....KDSNNN            Joyc-2
H..-..N.T.S.N.....D.A.....E....S.......DNKNN            LCDC2-1
KLG-N.T.DG..N....AKNGQKSV.N.....NK.A.....N.N.            LCDC2-2
SLG-..T.DGK.N...HAK.GQKS..R.D.I..Q.N....DNN.N            PMH1-1
NLG-NVT.DGK.N...HAK.GQKS..R.D.I..Q.N....DNN.N            PMH1-2
I..-..E.TGS.N...K.D.NHH...K.....RK.......N.DN            K1-1
KLQG..T.NG..N....A.VNQK...N......K.....KDIKAN            K21-1

1040      1050      1060      1070      1080
LKLTQDLNISGFNKAEITAKDGSDLTIGNIN-SADGTNAKKVTFN            12-1
....E...S...............R......S.DGNS.AE..T....         12-2
...........................................-...S........  15-1
..............K.V...S.N.....SDD.GN-.S..T....            15-2
.Q..G......D.......E.A..I...SDNNNNA-........             Joyc-1
.E..G..............N.N.....KASDGNA--.......D            Joyc-2
.Q..G......D.......E.A..I...SDNNNNA-........            LCDC2-1
....EN......D....V..ENNN.I...N.--G.NA...T....           LCDC2-2
.T..DN..............N...I..KA--.S.NS...Q...D            PMH1-1
.TF.DN..............N...I..KA--.S.NS...Q...D            PMH1-2
```

FIG.30G

```
              1090        1100        1110        1120        1130
QVKDSKISADGHKVTLHSKVET-SGSNNNTEDSSDNNA-GLTIDAKNVTVNNNITS
N...........N...K.-.S..GGR.SN...DT-....T....E..KD...
.........GD.N...N.....-..NTD..G.G.G...-....A....E.K.....
N...........N...K.L.DND....GG....T-....T..D.E.......
.........GS.N...N.....-.NG...DA.SNNGDST-S...N...........
K........N..N...N.....-.N.DSSAD..N...T-....S..D.....DV..
...........S.N...N....-.NG...DA.SNNGDGT-S...N...I........
N........N..N...N.....-.DG.S...GN.....-.............D...
K........GN.N...N.....-.N.DGS.GNG..D.NI....S..D....S....
K........GN.N...N.....-.N.DGS.GNG..D.NI....S..D....S....
N........SD.N...N.....-.GDTDS...GGN..T-....T.............
K........GN.N...N.....-.N.DGS.GNG..D.NI....S..D....S....

1190        1200        1210
SVTLTATEGALAVSNISGNTVTVTANSGALTTLAGSTI------------------
--------------------------------------------------------
--------------------------------------------------------
...IV.GGDT...G.....A.................------------------
N.NI..SGDT.N....T.QN...A.A...V..TK....NATTGSANITTKTGEING
--------------------------------------------------------
.......GE............I...K.K...Q....V------------------
--------------------------------------------------------
--------------------------------------------------------
N.NI..SGDT.N....T.QN...A.A...V..TK....NATTGNANITTKTGEING
...A.---------------------------------------------------
--------------------------------------------------------
--------------------------------------------------------
--------------------------------------------------------
NATTGDANITTQTGNINGKVESSSGSVTLIATGQTLAVGNISGDTVTITADKGKLT
--------------------------------------------------------
--------------------------------------------------------
-----DVNITTSTGSINGKIESKSGSVTLTATEKTLTVGNVSGNTVTVTANRGALT
--------------------------------------------------------
```

FIG.30H

```
....N................N.N....DNSD-.GN.D......S           K1-1
.T..DN...............N...I..KA--.S.NS...QI..D           K21-1

1140      1150      1160      1170      1180
HKAVSISATSGEITTKTGTTINATTGNVEITAQTGSILGGIESSSG           12-1
L.T.N.T.SEK-V..TA.S.....N.KAS..TK..D.S.-------          12-2
N.T.N.T.SEK-L...ADA.........V...K..D.K.EVK.T--          15-1
..T.NV..AN.G...........A.......H....Q.....KP.           15-2
..T.N.T.SEN-V...A.......I.S..V..K..D.K.....N..          Joyc-1
..TIN....T.NV...ES.....A..S..V..K..D.S.-------          Joyc-2
..T.N.T.SEN-V...A.........S..V..K..D.K.KV..T..          LCDC2-1
..T.N.T.SER-.D..AD.........KL..V.SD.-...K.N..           LCDC2-2
..T.N...SE.G....A.........S..V..K.------------          PMH1-1
..T.N...SE.G....A.........S..V..K.------------          PMH1-2
..T.N.T.SEN-V...A.........S..V..K..D.K.....N..          K1-1
..T.N...SE.G....A.........S..V..K..D.S.T.SGKTV          K21-1

---------------------------------------------           12-1
---------------------------------------------           12-2
---------------------------------------------           15-1
---------------------------------------------           15-2
EVKSASGNVNITASGNTLNVSNITGQNVTVTANSGAITTTEGSTI            Joyc-1
---------------------------------------------           Joyc-2
---------------------------------------------           LCDC2-1
---------------------------------------------           LCDC2-2
---------------------------------------------           PMH1-1
---------------------------------------------           PMH1-2
EVKSASGNVNITASGNTLNVSNITGQNVTVTANSGAITTTEGSTI            K1-1
---------------------------------------------           K21-1

1220      1230      1240      1250
-------KGTESVTTSSQSGDIGGTISGGIVEVKAT-ESL                 12-1
-----------------------....N...S.S..-GD.                 12-2
----------------------------------------                 15-1
-------.....I.......N...K...K..N....-N..                 15-2
TQTSSKIN..K..........S.....N..S.S..-G..                  Joyc-1
--------------------....N..N.T..D.--                     Joyc-2
```

FIG. 30I

```
------------------------------------------------------------
NATTGDANITTQTGNINGKVESSSGSVTLIATGQTLAVGNISGDIVTITADKGKLT
---------------------------TDLTTVKGGAKINATEGTATLTASSGKLT
------------------------------------------------------------
------------------------------------------------------------
------------------------------------------------------------
TTQADSKIEATEGEANVTSKTSIIGGTISGGTVEVTATEGLTTQAGSTITGTESVT
------------------------------------------------------------
------------------------------------------------------------
------------------------------------------------------------
------------------------------------------------------------
------------------------------------------------------------
------------------------------------------------------------
------------------------------------------------------------
------------------------------------------------------------

1260      1270      1280      1290      1300
TTQSNSKIKATTGEANVTSATGTIGGTISGNTVNVTANAGDLTVGNGAEINATEGA
..K.G...E.KS............................................
------------------------------...-..I...-..TLNVS----.VSGN.
I.K.G.E....A..V.........D.............T.....EDA.K.D..G..
...AG...E.K........................TDN..IKD..R.K..G..
------------------------------------------------------------
..K.G.E...K..................A......T.....EDA.K.D..G..
----------------------------------------..KG..K......T
--------------------.D.S.....K..S...ST.....RKA.T.S.....
--------------------.D.S.....K..S...ST.....RKA.T.S.....
...AG...E.K........................TDN..IKD..R.K..G..
-----------------------------------------...GD.K.......

1360      1370      1380      1390      1400
LNTTGTLTTVKGSNINATSGTLVINAKDAELNGAALGNHTVVNATNANGSGSVIAT
..........A..D.K..........K...D.S.DS.E...V..S.....T.A
..........E......A..........K.....S.D.........S.....T.V
.....A........S..N.............E.S.....................
..........A..K.E.A.............Q.D.....DR.E..V..........
..........A...K......A......K.D.T.S.DR........S.....T.A
```

FIG.30J

```
-------SAING..A........S.....N..K.S.I-GD.              LCDC2-1
TLAGSTIN..NG........E...EVT.K..S.T..AG..               LCDC2-2
----------------------------------------               PMH1-1
----------------------------------------               PMH1-2
TQTSSKIN..K...........S.....N..S.S..G-..               K1-1
TEANSAIS.ANG..A........S.....K..S.T.SSG..              K21-1

------------------------                               12-1
------------------------                               12-2
------------------------                               15-1
TSSQSGNIGGMISGGKVEVSATKDL                              15-2
------------------------                               Joyc-1
------------------------                               Joyc-2
------------------------                               LCDC2-1
------------------------                               LCDC2-2
------------------------                               PMH1-1
------------------------                               PMH1-2
------------------------                               K1-1
------------------------                               K21-1

1310      1320      1330      1340      1350
ATLTTSSGKLTTEASSHITSAKGQVNLSAQDGSVAGSINAANVT            12-1
....ATGNT.....G.S...T....D.L..N..I..........            12-2
V.I.ADK.....Q...S...NN..TT.T.K...I..........            15-1
....AT......K...S....NN......K...IG.N.......            15-2
V...ATG.T....T..D...SN..TT.T.K.S.I..........            Joyc-1
---------...Q...S...SN..TT.T.KN..I....D.....            Joyc-2
....AT......K...S....NN......K...IG.N.......            LCDC2-1
....A..........N........D......I..Q.S.......            LCDC2-2
....ATGNT.....G.S...T....D......I..Q.S.......           PMH1-1
....ATGNT.....G.S...T....D......I..Q.S.......           PMH1-2
V...ATG.T....T..D...SN..TT.T.K.S.I..........            K1-1
....ATK.T...--------------------------------            K21-1

1410      1420      1430      1440      1450
TSSRVNITGDLITINGLNIISKNGINTVLLKGVKIDVKYIQPGI            12-1
...S.......N.V........D.R...R.R.KE.E.......V           12-2
...N.......S.V...........R...V...TE.E.......V          15-1
```

FIG.30K

```
.....A........S...N................E.S.....................
..........E..S...NE.......N..K.D.K.S..R.E......S.....T.K
..........E....K.....A.....K.D.T.S..R.E......S.....T.K
..........E....K.....A.....K.D.T.S..R.E......S.....T.K
..........A..K.E.A...........Q.D...S.D...................
---------......D.NE.......Q..T...D.S.DR.E...V..S...N.T.K 1460      1470      1480      1490      1500
ASVDEVIEAKRILEKVKDLSDEEREALAKLGVSAVRFIEPNNTITVDTQNEFATRP
...E.......V............T..............V........N.....T...
...E.......V............T........................N....T...
.........................................A....A..IN.....T...
...Y....A...................................................
..AN.......A............T..............V........N.....T...
.........................................A....A..IN.....T...
..E.......V............T.........................N.....T...
...E.......V............T..............V....A..IN.....T...
...E.......V............T..............V....A..IN.....T...
...N.......A............T..............A....A..IN.....T...
..AN.......A............T.........................N.....T...
```

FIG.30L

```
..............................................        15-2
................K........E..........           Joyc-1
...N......S..........K...V...AE........V        Joyc-2
..............................................        LCDC2-1
...S......N......E..R...R.R.KE.E......V         LCDC2-2
...N......S......E..R...R.R.KE........V         PMH1-1
...N......S......E..R...R.R.KE.........V        PMH1-2
................K........E..........           K1-1
...S......S..........K...V...AE........V        K21-1

1510      1520      1530
LSRIVISEGRACFSNSDGATVCVNIADNGR-*                 12-1
S.QVI....K....SGN..R..T.V..D.QP*                 12-2
S.QVT....K....SGN..A..T.V..D.QQ*                 15-1
S.QVT....KV..LIGN...I.T....IE.*                  15-2
.............................*                  Joyc-1
S.QVT...DK....SGN..A..T.VT.DRQ*                  Joyc-2
S.QVT....KV..LIGN...I.T....IE.*                  LCDC2-1
S.QVT....K....SGN..A..T.V..D.QQ*                 LCDC2-2
S.QVI....K....SGN..A..T.V..D.QP*                 PMH1-1
S.QVI....K....SGN..A..T.V..D.QP*                 PMH1-2
..QVT....KV..LIGN...I.T....IE.-*                 K1-1
S.QVT....K....SGN..A..T.V..D.QQ*                 K21-1
```

FIG.31

Oligonucleotides used to determine whether PCR amplified hmwA genes were hmw1 or hmw2.

| | | | SEQ ID NO |
|---|---|---|---|
| 5' TCTTTTGCTGTGGCTGATGCCCCTA 3' | 5672.SL | | 74 |
| 5' CACTGATAGTTGCTCATATATTCGCC 3' | 5676.SL | | 75 |
| | V G V H K N | | 76 |
| | GGTTGATGTTCATAAAATAT | | 77 |
| 3' CCAACTACAAGTATTTTATA 5' | 5742.SL | | 78 |
| | G G S L T I N S | | 79 |
| | GGCGGAAGTTTAACTATTAACTC | | 80 |
| 3' CCGCCTTCAAATTGATAATTGAG 5' | 5743.SL | | 81 | pT7 hmw1BC(12)/cer/KanR

FIG. 32B

Oligonucleotides used to PCR amplify the 3'-end of *hmw1A* and 5'-end of *hmw1B* to construct a generic expression vector.

| | | | SEQ ID NO |
|---|---|---|---|
| 3'-end of *hmw1A* | | | 82 |
| | EcoR I ↓ | | 83 |
| | G V D G E N S D S D | | |
| 5' | GGTGTTGATGGGGAGAATTCCGATTCAGACG | 3' | |
| | | 5947.SL | |
| | | | 84 |
| | V C V N I A D N G R * | | 85 |
| | GTGTGCGTTAATATCGCTGATAACGGGCGGTAG | | 86 |
| 3' | CACACGCAATTATAGCGACTATTGCCCGCCATCAGATCTCCGG | 5' | |
| | ↑ Xba I | 5948.SL | |

FIG.33B

Oligonucleotides used to PCR amplify the LCDC2 hmw2A gene for expression sense

```
     BamH I  Nde I
            ↓   M  P  D  D  V  S  I  D  A  P  S  A  E
5' CGGGATCCCATATGCCGGATGATGTATCCATTGACGCACCTTCGGCTGAA 3'   5972.SL   SEQ ID NO 91
                                                                            92
``` antisense

```
        A  A  V  C  T  N  V  A  D  D  G  Q  Q  *
5' GCAGCAGTAGTACCAATGTTGCTGACGATGGACAGCAGTAGT 3'            93
3' CGTCGTCATACATGGTTACAACGACTGCTACCTGTCGTCATCAGATCTG 5'   5973.SL   94
                                            ↑ XBA I                    95
```

Construction of DS-2400-13, a pBR T7 hmwA/T7 hmwABC/cer/KanRplasmid

PROTECTIVE RECOMBINANT *HAEMOPHILUS INFLUENZAE* HIGH MOLECULAR WEIGHT PROTEINS

REFERENCE TO RELATED APPLICATION

This application is a continuation-in-part of application Ser. No. 09/167,568 filed Oct. 7, 1998 now abandoned.

FIELD OF INVENTION

The present invention relates to the field of molecular genetics and, in particular, to the production of recombinant *Haemophilus influenzae* high molecular weight proteins and nucleic acid molecules and vectors employed therein.

BACKGROUND TO THE INVENTION

Encapsulated *Haemophilus influenzae* type b strains are a major cause of bacterial meningitis and other invasive infections in young children. However, the non-encapsulated or nontypeable *H. influenzae* (NTHi) are responsible for a wide range of human diseases, including otitis media, epiglottitis, pneumonia and tracheobronchitis. Vaccines based upon *H. influenzae* type b capsular polysaccharide conjugated to diphtheria toxoid (ref. 1. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure), tetanus toxoid (ref. 2 and U.S. Pat. No. 4,496,538), or *Neisseria meningitidis* outer membrane protein (ref. 3) have been effective in reducing *H. influenzae* type b-induced meningitis, but not NTHi-induced disease (ref. 4).

Otitis media is the most common illness of early childhood, with 60 to 70% of all children, of less than 2 years of age, experiencing between one and three ear infections (ref. 5). Chronic otitis media is responsible for hearing, speech and cognitive impairments in children. *H. influenzae* infections account for about 30% of the cases of acute otitis media and about 60% of chronic otitis media. In the United States alone, treatment of otitis media costs between 1 and 2 billion dollars per year for antibiotics and surgical procedures, such as tonsillectomies, adenoidectomies and insertion of tympanostomy tubes. It is estimated that an additional $30 billion is spent per annum on adjunct therapies, such as speech therapy and special education classes. Furthermore, many of the causative organisms of otitis media are becoming resistant to antibiotic treatment. An effective prophylactic vaccine against otitis media is thus desirable.

During natural infection by NTHi, surface-exposed outer membrane proteins that stimulate an antibody response are potentially important targets for bactericidal and/or protective antibodies and, therefore, potential vaccine candidates. Barenkamp and Bodor (ref. 6) demonstrated that convalescent sera from children suffering from otitis media due to NTHi contained antibodies to high molecular weight (HMW) proteins. About 70 to 75% of NTHi strains express the HMW proteins and most of these strains contain two gene clusters termed hmw1ABC and hmw2ABC. The hmwA genes encode the structural HMWA proteins and the hmwb and hmwC genes are accessory genes responsible for the processing and secretion of the HMWA proteins (refs. 7, 8, 9; U.S. Pat. No. 5,603,938; Wo 97/36914). The HMWA proteins have been demonstrated to be adhesins mediating attachment to human epithelial cells (ref. 10) and only properly processed HMWA proteins appear to be effective adhesins (ref. 8). Immunization with a mixture of native HMW1A and HMW2A proteins resulted in protection in the chinchilla intrabulla challenge model of otitis media (ref. 11; WO 97/36914). The prototype hmw1A gene from NTHi strain 12 encodes a 160 kDa HMW1A protein that is processed by cleavage of a 35 kDa amino terminal fragment, generating the mature 125 kDa HMW1A protein. Similarly, the NTHi strain 12 hmw2A gene encodes a 155 kDa HMW2A protein that is processed by cleavage of a nearly identical 35 kDa amino terminal fragment to produce the mature 120 kDa HMW2A protein.

Plasmid pHMW1-15 (ref. 8) has a pT7-7 backbone (ref. 12) and contains the complete NTHi strain 12 hmw1ABC operon with 5'- and 3'-flanking regions. There are about 400 bp of 5'-flanking sequences located between the T7 promoter and the start of the hmw1A structural gene. Plasmid pHMW2-21 (ref. 10) has a pT7-7 backbone and contains the complete hmw2ABC operon with 5'- and 3'-flanking sequences. There are about 800 bp of 5'-flanking sequences located between the T7 promoter and the start of the hmw2A structural gene. The rHMW1A and rHMW2A proteins are produced in relatively low yield from plasmids pHMW1-15 and pHMW2-21.

The *H. influenzae* hmw1 ABC or hmw2 ABC genes can be genetically engineered to produce the mature recombinant HMW1A or HMW2A proteins by deleting the sequence encoding the 35 kDa leader sequence, that is normally removed by processing in *H. influenzae*. Since the leader sequence has been deleted, there should be no necessity for the hmw1BC or hmw2BC genes which serve to process and secrete the mature HMW1A and HMW2A structural proteins in *H. influenzae* (ref. 9). The yield of rHMW1A or rHMW2A protein can be significantly increased by deletion of the leader sequence and processing genes, however, the purified recombinant proteins are not protective. As set forth herein, the hmw1BC and hmw2BC genes or their protein products apparently contribute to the protective ability of rHMW1A and rHMW2A proteins. Such a requirement for otherwise redundant accessory genes, is unexpected.

The *E. coli* cer gene is thought to stabilize plasmids by preventing multimerization (ref. 13). For expression vectors with large inserts, the cer gene may be used to stabilize the plasmids.

SUMMARY OF THE INVENTION

The present invention is directed towards the provision of recombinant non-typeable *H. influenzae* high molecular weight proteins that are protective by providing certain nucleic acid molecules and vectors containing the same.

It has now been found that, in order to obtain recombinant high molecular weight (HMW) proteins of non-typeable Haemophilus which are protective, it is necessary to provide a vector containing only the segment of the A portion of the operon which encodes the mature HMW protein, i.e. lacking the segment of the A gene which encodes the leader sequence, and the B and C portions of the operon. It has also been found that the level of expression of the mature protein may be enhanced by including in the vector at least one additional segment which encodes the mature protein, the cer gene from *E. coli* or both. Accordingly, in one aspect of the present invention, there is provided a nucleic acid molecule comprising a promoter functional in *E. coli* and operatively coupled to a modified operon of a non-typeable strain of Haemophilus comprising A, B and C genes, wherein the A gene of the operon contains only a nucleic acid sequence which encodes a mature high molecular weight protein of the non-typeable strain of Haemophilus, and hence from which the portion of the A gene encoding the leader sequence is absent.

Any suitable promoter may be used to effect expression of the mature HMW protein in *E. coli*. However, it is preferred to use the T7 promoter.

The encoded mature high molecular weight protein may be HMW1 or HMW2 protein of the non-typeable Haemophilus strain. The non-typeable Haemophilus strain may be selected from the group consisting of strains 12, Joyc, K21, LCDC2, PMH1 and 15 of non-typeable *Haemophilus influenzae*.

The present invention also provides the nucleotide sequences for the hmw1A and/or hmw2A genes of certain non-typeable strains of *Haemophilus influenzae* which have not been previously isolated, purified and expressed, along with the deduced amino acid sequences of the corresponding HMW1 and HMW2 proteins of the non-typeable Haemophilus strains.

Accordingly, in another aspect of the invention, there is provided an isolated and purified nucleic acid molecule encoding a high molecular weight (HMW) protein of a non-typeable strain of *Haemophilus influenzae* having:

(a) a DNA sequence selected from the group consisting of those shown in FIGS. 18, 19, 20, 21, 22, 23, 24, 25, 26 and 27 (SEQ ID NOS: 25, 27, 29, 32, 33, 36, 38, 40, 42, 44, 46, 48, 50, 52, 54, 56, 58, 60 62, 64), or a sequence complementary thereto; or (b) a DNA sequence encoding a high molecular weight protein having an amino acid sequence selected from the group consisting of those shown in FIGS. 18, 19, 20, 21, 22, 23, 24, 25, 26 and 27 (SEQ ID NOS: 26, 28, 30, 32, 34, 35, 37, 39, 41, 43, 45, 47, 49, 51, 53, 55, 57, 59, 61, 63, 65), or a sequence complementary thereto.

The modified operon in the first aspect of the invention may include the mature protein encoding sequences (SEQ ID NOS: 27, 31, 36, 40, 44, 48, 52, 56, 60, 64, 68, 72) or a DNA molecule encoding the mature protein having the amino acid sequences (SEQ ID NOS: 28, 32, 37, 41, 45, 49, 53, 57, 61, 65, 69, 73) shown in such FIGS. 18, 19, 20, 21, 22, 23, 24, 25, 26, 27, 28 and 29.

The nucleic acid molecule provided in accordance with the first aspect of the invention may further comprise a sequence containing at least one additional copy of the mature encoding region only of the operon of a non-typeable strain of Haemophilus, the cer gene of *E. coli* or both such segments.

The nucleic acid molecules provided in accordance with the first aspect of the invention may be incorporated into a vector, usually a plasmid vector, for transformation of *E. coli* for the purpose of expression of the mature protective high molecular protein of a non-typeable strain of Haemophilus.

Plasmid vectors for the latter purpose may have the identifying characteristics of a plasmid which is selected from the group consisting of:

DS-1046-1-1
JB-2507-7
BK-86-1-1
BK-35-4
BK-76-1-1
DS-2334-5
DS-2400-13

Details of the structures and preparation of such plasmid is provided in the Figures and Examples.

The present invention extends, in a further aspect thereof, to a strain of *E. coli* transformed by the vectors provided herein and expressing a protective high molecular weight protein of a non-typeable strain of Haemophilus. The present invention further includes an isolated and purified recombinant protective high molecular weight protein of a non-typeable strain of Haemophilus immunogenic segment or analog thereof producible by the transformed *E. coli*.

The present invention further includes, in an additional aspect therein, a recombinant method for a production of a protective high molecular weight protein of a non-typeable strain of Haemophilus, which comprises:

transforming *E. coli* with a vector comprising the nucleic acid molecule provided in the first aspect of the invention, growing *E. coli* to express the encoded mature high molecular weight (HMW) protein, and isolating and purifying the expressed HMW protein.

The non-typeable strain of Haemophilus may be any of the strains referred to above and the high molecular weight protein may be the HMW1 protein or HMW2 protein, which is provided in a form free from contamination by the other protein. The purification steps may include separating the HMW A protein from the B and C protein.

The present invention, in an additional aspect thereof provides an isolated and purified protective HMW 1 protein of a strain of non-typeable Haemophilus which is free from contamination by the HMW2 protein of the same strain of non-typeable Haemophilus.

In a yet further aspect, the present invention provides an isolated and purified protective HMW2 protein of a strain of non-typeable Haemophilus which is free from contamination by the HMW 1 protein of the same strain of non-typeable Haemophilus.

The HMW1 or HMW2 protein may be from any of the non-typeable strain of Haemophilus mentioned above and may be one having SEQ ID NO: 28, 32, 37, 41, 45, 49, 53, 57, 61, 65, 69 or 73.

In accordance with another aspect of the invention, an immunogenic composition is provided which comprises at least one immunologically-active component selected from the group consisting of at least one nucleic acid molecule as provided herein, at least one recombinant HMW protein as provided herein or at least one novel HMW protein as provided herein, and a pharmaceutically acceptable carrier therefor. The at least one active component produces an immune response when administered to a host.

The immunogenic compositions provided herein may be formulated as a vaccine for in vivo administration to a host to provide protection against disease caused by *H. influenzae*. For such purpose, the compositions may be formulated as a microparticle, ISCOM or liposome preparation. The immunogenic composition may be provided in combination with a targeting molecule for delivery to specific cells of the immune system or to mucosal surfaces. The immunogenic compositions of the invention (including vaccines) may further comprise at least one other immunogenic or immunostimulating material and the immunostimulating material may be at least one adjuvant or at least one cytokine.

Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants. Advantageous combination of adjuvants are described in copending U.S. patent applications Ser. No. 08/261,194 filed Jun. 16, 1994 and U.S. patent application Ser. No. 08/483,856 filed Jun. 7, 1995, assigned to the assignee hereof and the disclosure of which is incorporated herein by reference (WO 95/34308, published Nov. 21, 1995).

In accordance with another aspect of the invention, there is provided a method for generating an immune response in a host, comprising the step of administering to a susceptible host, such as a human, an effective amount of the immunogenic composition as recited above. The immune response may be humoral or a cell-mediated immune response and may provide protection against disease caused by Haemophilus. Hosts in which protection against disease may be conferred include primates, including human.

It has been found that the nucleic acid sequences of the B and C portions of the operon encoding HMW1 and HMW2 proteins are highly conserved in nucleic acid sequence among species of non-typeable Haemophilus, enabling them to be provided on a universal plasmid vector for receipt of the nucleic acid sequence encoding the mature HMW1A or HMW2A protein from a variety of strains of non-typeable Haemophilus for the purpose of expression of the HMW1A or HMW2A from a transformed host, such as *E. coli*.

Accordingly, in a yet further aspect of the invention, there is provided a plasmid vector for expression of a high molecular weight protein of a non-typeable strain of Haemophilus and comprising the T7 promoter, a cloning site and the B and C portions of the hmw operon of a non-typeable Haemophilus strain. The plasmid may also contain the *E. coli* cer gene. The plasmid vector may be plasmid JB-2646-1.

The present invention, in its various aspects, permits the production of protective high molecular weight proteins of non-typeable Haemophilus which are useful in providing immunogenic compositions to confer protection against disease caused by infection by non-typeable Haemophilus strains.

BRIEF DESCRIPTION OF DRAWINGS

The present invention will be further understood from the following description with reference to the drawings, in which:

FIG. 1B shows the sequence of the oligonucleotides used in the construction scheme of FIG. 1A (SEQ ID NOS: 1, 2 and 3).

FIG. 3B shows the sequence of the oligonucleotides used in the construction scheme of FIG. 3A (SEQ ID NOS: 4, 5 and 6).

FIG. 4B shows the oligonucleotides used in the construction scheme of FIG. 4A (SEQ ID NOS: 7, 8 and 9).

FIG. 6B shows the oligonucleotides used to PCR amplify the 3'-end of hmw1A in the construction scheme of FIG. 6A (SEQ ID NOS: 10, 11, 12, 13 and 14).

FIG. 8B shows the oligonucleotides used to PCR amplify the 3'-end of hmw2A in the construction scheme of FIG. 8A (SEQ ID NOS: 15, 16, 17, 18 and 19).

FIG. 15 contains an SDS-PAGE analysis showing the stability of rHMW1 from construct T7 hmwABC/cer/kanR stored at −20° C. in the presence of 20% glycerol.

FIG. 17 shows the sequences of oligonucleotides used to PCR amplify additional hmw genes from non-typable *H. influenzae* chromosomal DNA (SEQ ID NOS: 20, 21, 22, 23 and 24).

FIGS. 18A to 18R show the nucleotide sequence (SEQ ID NO: 25) and deduced amino acid sequence (SEQ ID NO: 26) of the hmw1A gene from NTHi strain Joyc. The arrow marks the predicted start of the mature protein (mature protein: encoding sequence SEQ ID NO: 27; amino acid sequence SEQ ID NO: 28).

FIGS. 19A to 19O show the nucleotide sequence (SEQ ID NO: 29) and deduced amino acid sequence (SEQ ID NO: 30) of the hmw2A gene from NTHi strain Joyc. The arrow marks the predicted start of the mature protein (mature protein: encoding sequence SEQ ID NO: 31; amino acid sequence SEQ ID NO: 32).

FIGS. 20A to 20R show the nucleotide sequence (SEQ ID NO: 33) and deduced amino acid sequences (SEQ ID NO: 34, 35) of the defective hmw1A gene from NTHi strain K1. The arrow marks the predicted start of the mature protein (mature protein: encoding sequence SEQ ID NO: 36; amino acid sequence SEQ ID NOS: 37, 35).

FIGS. 21A to 21O show the nucleotide sequence (SEQ ID NO: 38) and deduced amino acid sequence (SEQ ID NO: 39) of the hmw2A gene from NTHi strain K21. The arrow marks the predicted start of the mature protein (mature protein: encoding sequence SEQ ID NO: 40; amino acid sequence SEQ ID NO: 41).

FIGS. 22A to 22P show the nucleotide sequence (SEQ ID NO: 42) and deduced amino acid sequence (SEQ ID NO: 43) of the hmw1A gene from NTHi strain LCDC2. The arrow marks the predicted start of the mature protein (mature protein: encoding sequence SEQ ID NO: 44; amino acid sequence SEQ ID NO: 45).

FIGS. 23A to 23P shows the nucleotide sequence (SEQ ID NO: 46) and deduced amino acid sequence (SEQ ID NO: 47) of the hmw2A gene from NTHi strain LCDC2. The arrow marks the predicted start of the mature protein (mature protein: encoding sequence SEQ ID NO: 48; amino acid sequence SEQ ID NO: 49).

FIGS. 24A to 24O show the nucleotide sequence (SEQ ID NO: 50) and deduced amino acid sequence (SEQ ID NO: 51) of the hmw1A gene from NTHi strain PMH1. The arrow marks the predicted start of the mature protein (mature protein: encoding sequence SEQ ID NO: 52; amino acid sequence SEQ ID NO: 53).

FIGS. 25A to 25O show the nucleotide sequence (SEQ ID NO: 54) and deduced amino acid sequence (SEQ ID NO: 55) of the hmw2A gene from NTHi strain PMH1. The arrow marks the predicted start of the mature protein (mature protein: encoding sequence SEQ ID NO: 56; amino acid sequence SEQ ID NO: 57).

FIGS. 26A to 26O show the nucleotide sequence (SEQ ID NO: 58) and deduced amino acid sequence (SEQ ID NO: 59) of the hmw1A gene from NTHi strain 15. The arrow marks the predicted start of the mature protein (mature protein: encoding sequence SEQ ID NO: 60; amino acid sequence SEQ ID NO: 61).

FIGS. 27A to 27R show the nucleotide sequence (SEQ ID NO: 62) and deduced amino acid sequence (SEQ ID NO: 63) of the hmw2A gene from NTHi strain 15. The arrow marks the predicted start of the mature protein (mature protein: encoding sequence SEQ ID NO: 64; amino acid sequence SEQ ID NO: 65).

FIGS. 28A to 28Q show the nucleotide sequence (SEQ ID NO: 66) and deduced amino acid sequence (SEQ ID NO: 67) of the hmw1A gene from NTHi strain 12. The arrow marks the predicted start of the mature protein (mature protein: encoding sequence SEQ ID NO: 68; amino acid sequence SEQ ID NO: 69).

FIGS. 29A to 29N show the nucleotide sequence (SEQ ID NO: 70) and deduced amino acid sequence (SEQ ID NO: 71) of the hmw2A gene from NTHi strain 12. The arrow marks the predicted start of the mature protein (mature protein: encoding sequence SEQ ID NO: 72; amino acid sequence SEQ ID NO: 73).

FIGS. 30A to 30L show the alignment of the deduced HMW1A and HMW2A protein sequences (SEQ ID NOS: 26, 30, 34, 35, 39, 43, 47, 51, 55, 59, 63) with the published strain 12 HMW1A and HMW2A protein sequences (U.S. Pat. No. 5,603,938) (SEQ ID NOS: 67, 71).

FIG. 31 shows the oligonucleotides (SEQ ID NOS: 74, 75, 76, 77, 78, 79, 80, 81) used to determine whether the PCR amplified hmwA genes were hmw1 or hmw2.

FIG. 33B shows the oligonucleotides (SEQ ID NOS: 91, 92, 93, 94, 95) used to PCR amplify the LCDC2 hmw2A gene for expression in the generic expression vector constructed as shown in FIG. 33A.

GENERAL DESCRIPTION OF THE INVENTION

Figure 1A:
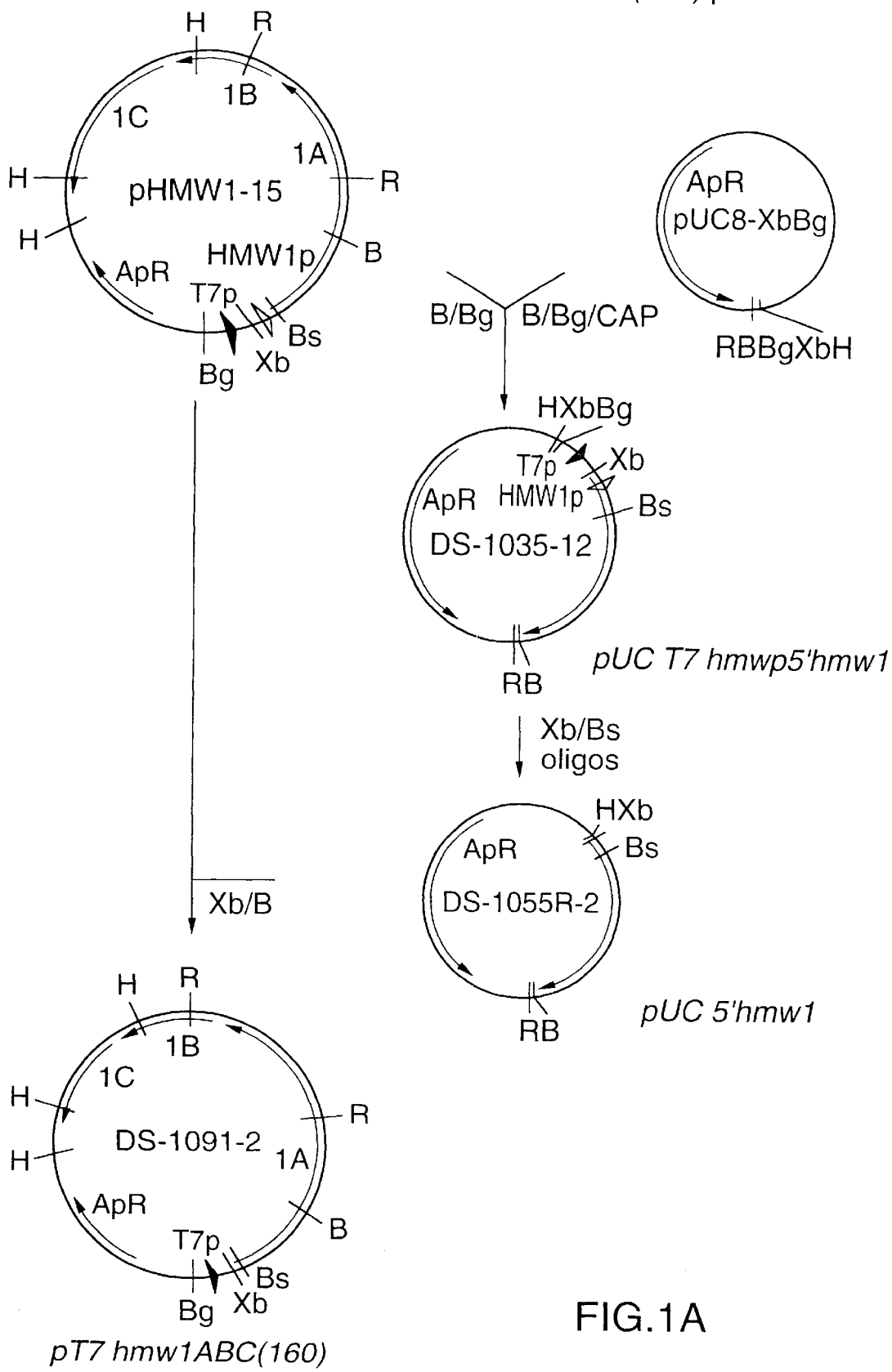
FIG. 1A shows the construction scheme to generate plasmid DS-1091-2 that expresses the hmw1ABC genes encoding the full-length 160 kDa HMW1A protein. Restriction enzyme sites are: B, BamH I; Bg, Bgl II; Bs, Bsm I; H, Hind III; R, EcoR I; Xb, Xba I. Other abbreviations are: T7p, T7 promoter; HMW1p, hmw1 promoter; ApR, ampicillin resistance gene; CAP, calf alkaline phosphatase.

Any Haemophilus strain that has hmw genes may be conveniently used to provide the purified and isolated nucleic acid molecules (which may be in the form of DNA molecules), comprising at least a portion coding for a HMW1A, HMW1B, HMW1C, HMW2A, HMW2B, or HMW2C protein as typified by embodiments of the present invention. Such strains are generally available from clinical sources and from bacterial culture collections, such as the American Type Culture Collection. Appropriate strains of non-typeable Haemophilus include:

Non-typeable *H. influenzae* strain 12

Non-typeable *H. influenzae* strain Joyc;

Non-typeable *H. influenzae* strain K1;

Non-typeable *H. influenzae* strain K21;

Non-typeable *H. influenzae* strain LCDC2;

Non-typeable *H. influenzae* strain PMH1; or

Non-typeable *H. influenzae* strain 15.

In this application, the term "HMW protein" is used to define a family of HMW proteins which includes those having naturally occurring variations in their amino acid sequences as found in various strains of non-typeable Haemophilus and characterized by an apparent molecular weight of about 100 to about 150.

Reference will now be made in detail to the presently preferred embodiments of the invention, which together with the following Examples, serve to explain the principle of the invention. For clarity of disclosure, and not by way of limitation, the detailed description of the invention is divided into the following sections:

1. Iproved Production of Recombinant HMW Proteins from *E. coli.*

The production of native HMW1A or HMW2A proteins in *H. influenzae* is very low. The plasmids pHMW1-15 and pHMW2-21 (refs. 8, 10) contain the complete hmw1ABC and hmw2ABC operons from NTHi strain 12 cloned into the expression vector pT7-7. The production of the recombinant rHMW1A or rHMW2A proteins is low from these plasmids, possibly due to the 5'-flanking and hmw promoter sequences inserted between the T7 promoter and the start codon of the hmwA genes. By removal of the 5'-flanking and hmw promoter sequences, the yield of rHMW1A and rHMW2A proteins produced from plasmids DS-1091-2 and DS-1094-2 (FIGS. 1 and 2), was marginally improved.

When produced in *H. influenzae*, the native HMWA proteins are processed and secreted, with a 35 kDa N-terminal fragment removed. Rather than relying upon the correct processing and secretion of the rHMWA proteins by *E. coli*, the gene sequences encoding the N-terminal 35 kDa fragments were removed genetically from the hmw1ABC and hmw2ABC genes. The production of the mature rHMW1A and rHMW2A proteins was enhanced in the new constructs, DS-1046-1-1 and DS-1174-4 (FIGS. 3 and 4). The rHMW BC proteins were also overproduced. The hmw1ABC and hmw2ABC gene inserts in the pT7-7 vector were still approximately 8.6 kb and approximately 8.3 kb, respectively. Since the HMWA proteins are the structural and protective proteins, it was thought that the size of the gene insert could be reduced by deleting part or all of the hmwBC genes. Expression vectors with smaller inserts are generally more efficient at producing recombinant proteins and the overproduction of the rHMWBC proteins was thought to be undesirable.

The production of rHMWA proteins was marginally improved when the hmwBC genes were deleted in vectors DS-1200-3, DS-1122-2, JB-2330-7 and DS-2084-3 (FIGS. 4, 5, 6 and 8). However, the production of rHMWB and rHMWC proteins was eliminated, which simplified the protein purification process. When tandem copies of T7 hmwA gene cassettes were used to express rHMWA proteins from vectors JB-2369-6 and DS-2084-1 (FIGS. 7 and 8), the production was marginally improved.

The construction of this series of expression vectors demonstrated that it was possible to increase the production of rHMW1 and rHMW2 proteins from *E. coli*. However, when tested in a nasopharyngeal colonization model for protection, the rHMWA proteins produced from the improved vectors were not protective. Only mixtures of native HMW1A+HMW2A proteins or rHMWA proteins produced from the lower yield vectors containing complete hmwABC genes were protective.

2. Modification of Expression Vectors to Produce Protective Recombinant HMW Proteins.

The expression vectors that contained hmwABC genes encoding full-length HMW1A (DS-1091-2) or HMW2A (DS-1094-2) proteins and which relied upon *E. coli* to process them, did not produce enough protein to test in animal models. The expression vectors that contained hmwABC genes encoding mature HMW1A (DS-1046-1-1) or HMW2A (DS-1174-4) proteins, expressed protective rHMWA proteins in moderate yield. The vectors that overproduced rHMWA proteins alone did not yield protective antigens.

Two approaches were tried to enhance the yield of protective rHMWA protein. To the vector that contained the T7 hmwABC gene cassette expressing mature rHMW1A protein, was introduced the *E. coli* cer gene. The cer gene is thought to stabilize plasmids by preventing multimerization and its presence may stabilize expression vectors containing the large hmwABC gene cassettes. We had also found that sometimes the presence of cer also increased the production of recombinant proteins. The rHMW1A antigen that was overproduced from T7 hmw1ABC/cer constructs (FIG. 10) was protective in the nasopharyngeal colonization model (Table 2).

The second approach to overproduce protective rHMWA protein was to construct a vector in which the rHMWA protein was overproduced in the presence of rHMWBC proteins. To the vector that contained the T7 hmwABC gene cassette expressing mature rHMW1A protein, was added an additional T7 hmwA gene cassette. The rHMW1A antigen that was overproduced from T7 hmw1A/T7 hmw1ABC constructs (FIG. 9) was protective in the nasopharyngeal colonization model (Table 2).

Figure 34A:
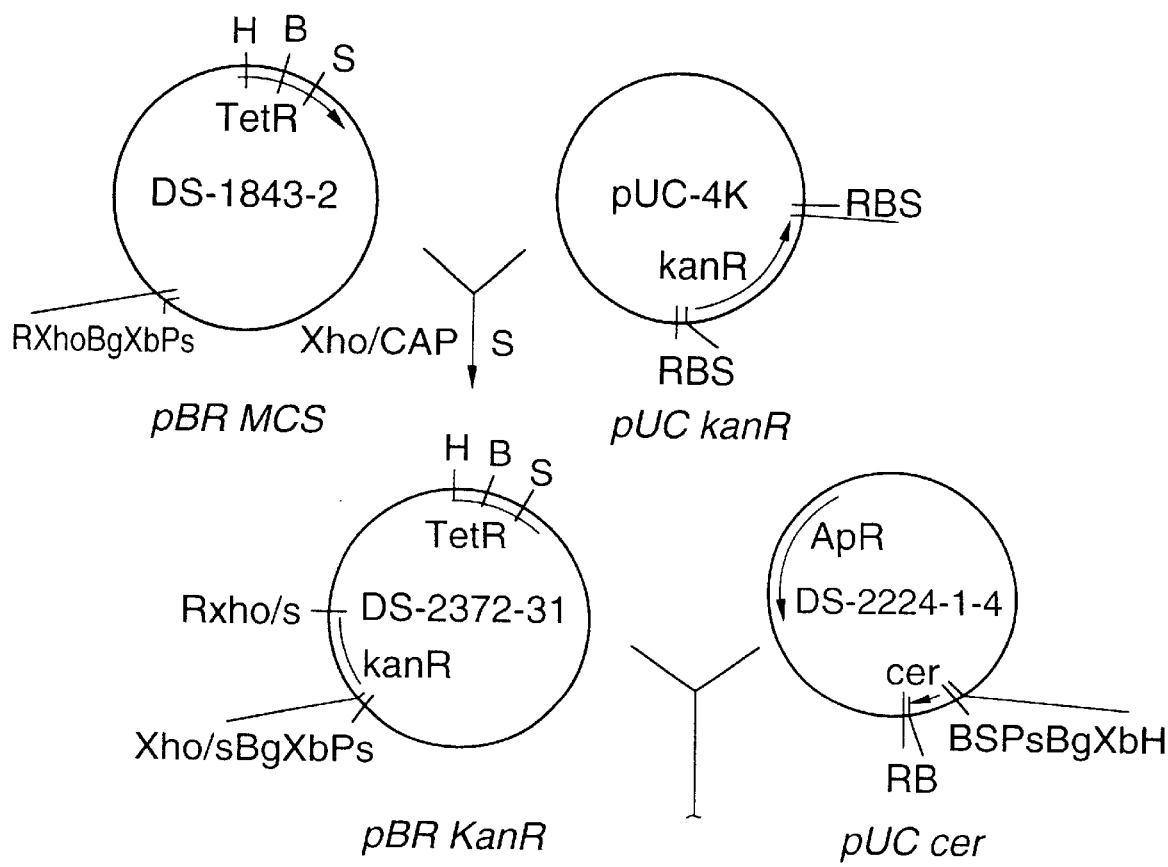
FIGS. 34A and 34A' show the construction of DS-2400-13 that contains the T7 hmwA/T7 hmwABC genes and the *E. coli* cer gene. Restriction enzyme sites are: B, BamH I; Bg, Bgl II; H, Hind III; R, EcoR I; S, Sal I; Xb, Xba I, Xho, Xho I. Other abbreviations are: T7p, T7 promoter; ApR, ampicillin resistance gene; KanR, kanamycin resistance gene; TetR, tetracycline resistance gene; CAP, calf alkaline phosphatase.
Figure 34A:
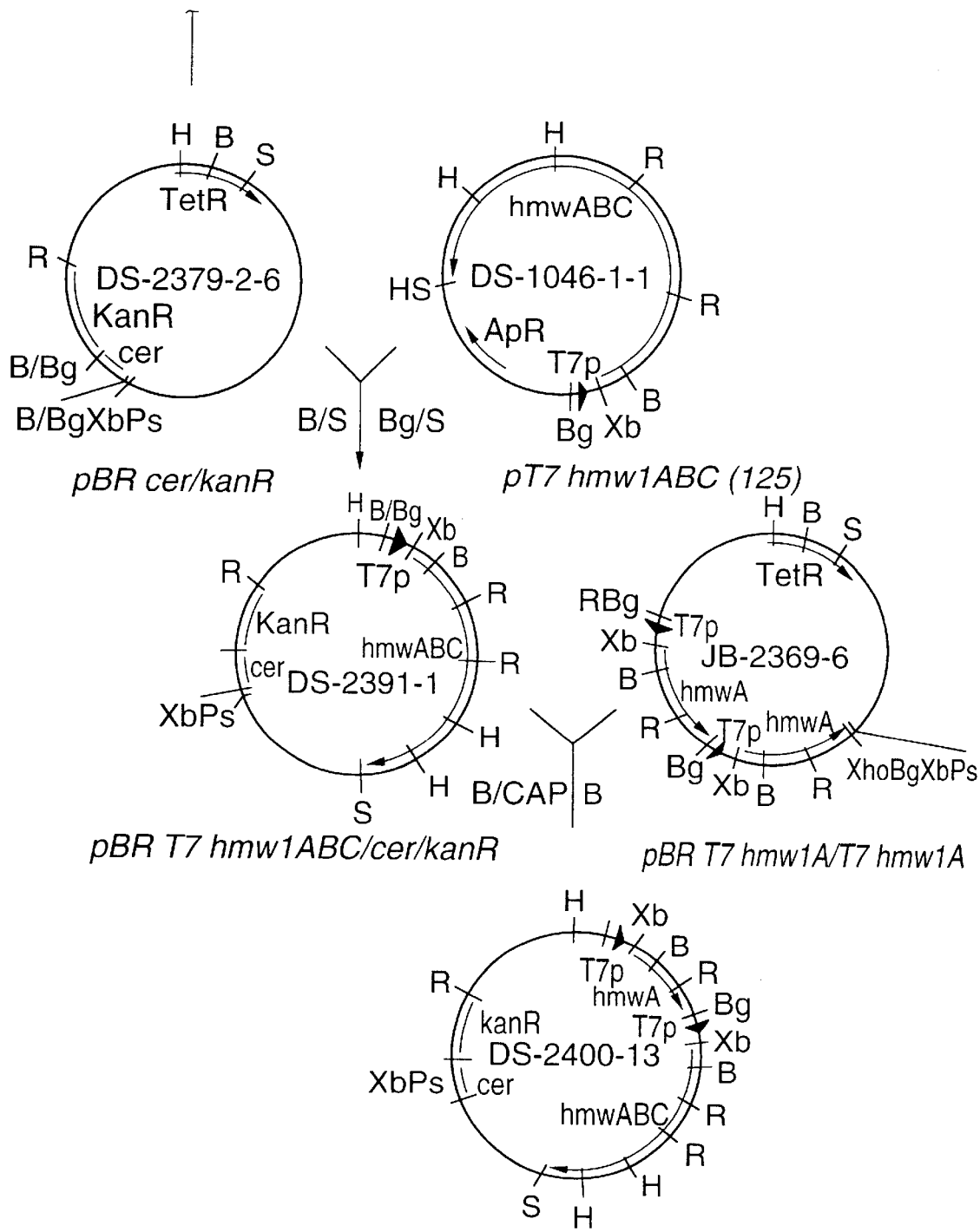

The two approaches can be combined so that tandem copies of the T7 hmwA/T7 hmwABC genes are co-expressed with the *E. coli* cer gene on the same plasmid, DS-2400-13 (FIG. 34).

3. Cloning and Sequence Analysis of Additional hmwA Genes.

The hmwA genes and encoded proteins have variable sequences. In order to produce a completely effective vaccine, it may be necessary to use rHMWA proteins generated from multiple strains of non-typeable Haemophilus. The hmw1A and/or hmw2A genes were PCR amplified and sequenced from several strains of non-typeable *Haemophilus influenzae*. FIGS. 18 to 26 illustrate the nucleotide and deduced amino acid sequences for the hmw1A gene from strain Joyc, the hmw2A gene from strain Joyc, the defective hmw1A gene from strain K1, the hmw2A gene from strain K21, the hmw1A gene from strain LCDC2, the hmw2A gene from strain LCDC2, the hmw1A gene from strain PMH1, the hmw2A gene from strain PMH1, the hmw1A gene from strain 15, and the hmw2A gene from strain 15, respectively. The alignment of the deduced protein sequences with the previously described strain 12 HMW1A and HMW2A protein sequences (FIGS. 28 and 29) identifies both regions of sequence conservation and divergence (FIG. 30). Such information may be useful in the identification of potential epitopes to generate peptides for vaccination or diagnostic purposes. The molecular weights of the mature HMW proteins from the various non-typeable Haemophilus strains is contained in Table 3.

4. Construction of a Generic Expression Vector for Production of Protective Recombinant HMW Proteins.

New hmwA genes can be PCR amplified from strains of non-typeable Haemophilus and sequenced as described above. However, in order to produce protective rHMWA antigens, the hmwA genes must be expressed in the presence of hmwBC genes. The deduced sequences of the accessory HMW1B and HMW2B proteins from the prototype strain 12 were found to be 99% identical, while the deduced HMW1C and HMW2C proteins from the same strain were 96% identical (ref. 8, U.S. Pat. No. 5,603,938). The highly conserved nature of the hmwBC genes lead to the possibility of constructing a generic expression vector using the hmwBC genes from a prototype strain, and introducing any hmwA gene to the vector for expression therein. FIG. 32 illustrates the construction of a generic expression vector (JB-2646-1) that contains the T7 promoter, an Xba I cloning site for introduction of hmwA genes, the strain 12 hmw1BC genes, and the *E. coli* cer gene. FIG. 33 illustrates the construction of a chimeric T7 hmwABC gene cassette in the generic expression vector, wherein a PCR amplified LCDC2 hmw2A gene is combined with the strain 12 hmw1BC genes to produce plasmid DS-2334-5. The expression of the genes from the chimeric construct was as seen for T7 hmw1ABC or T7 hmw2ABC constructs based on NTHi strain 12 hmw1A and hmw2A genes.

It is clearly apparent to one skilled in the art, that the various embodiments of the present invention have use in applications in the fields of vaccination, diagnosis, treatment of Haemophilus infection and the generation of immunological agents. A further non-limiting discussion of such uses is further presented below.

5. Vaccine Preparation and Use

Immunogenic compositions, suitable to be used as vaccines, may be prepared from immunogenic high molecular weight (HMW) proteins of non-typeable Haemophilus strains, immunogenic analogs and fragments thereof and/or immunogenic peptides as disclosed herein. The vaccine elicits an immune response which produces antibodies, including anti-HMW antibodies and antibodies that are opsonizing or bactericidal. Immunogenic compositions, including vaccines, may be prepared as injectables, as liquid solutions or emulsions. The HMW protein, immunogenic analogs and fragments thereof and/or immunogenic peptides may be mixed with pharmaceutically acceptable excipients which are compatible with the HMW protein, immunogenic fragments analogs or immunogenic peptides. Such excipients may include, water, saline, dextrose, glycerol, ethanol and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration including suppositories and oral formulations may be desirable. For suppositories, binders and carriers may include, for example polyalkylene glycols or triglycerides. Oral formulations may include normally employed incipients such as, for example pharmaceutical grades of saccharine, cellulose and magnesium carbonate. These compositions take the form of solutions, suspensions, tablets, pills, capsules, sustained release formulations or powders and contain about 1 to 95% of the HMW protein, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the high molecular weight protein, analogs and fragments thereof and/or peptides. Suitable regimes for initial administration and booster doses are also variable, but may include an initial administration followed by subsequent administrations. The dosage of the vaccine may also depend on the route of administration and will vary according to the size of the host.

The nucleic acid molecules encoding the HMW proteins of non-typeable Haemophilus may also be used directly for immunization by administration of the DNA directly, for example by injection for genetic immunization or by constructing a live vector, such as Salmonella, BCG, adenovirus, poxvirus, vaccinia or poliovirus, containing the nucleic acid molecule. A discussion of some live vectors that have been used to carry heterologous antigens to the immune system are discussed in, for example, O'Hagan (1992) (ref. 17). Processes for the direct injection of DNA into test subjects for genetic immunization are described in, for example, Ulmer et al., 1993 (ref. 18).

Immunogenicity can be significantly improved if the antigens are co-administered with adjuvants, commonly used as an 0.05 to 1.0 percent solution in phosphate—buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvants, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 (ref. 19) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990 (ref. 20), reported that octadecyl esters of aromatic amino acids complexed with a recombinant hepatitis B surface antigen, enhanced the host immune responses against hepatitis B virus.

6. Imunoassays

The HMW protein of a non-typeable strain of Haemophilus, analogs and fragments thereof and/or peptides of the present invention are useful as immunogens, as antigens in immunoassays including enzyme-linked immunosorbent assay (ELISA), RIAs and other non-enzyme linked antibody binding assays or procedures known in the art for the detection of anti-bacterial, Haemophilus, HMW and/or peptide antibodies. In ELISA assays, the HMW protein, analogs, fragments and/or peptides corresponding to portions of HMW protein are immobilized onto a selected surface, for example a surface capable of binding proteins or peptides, such as the wells of a polystyrene microtiter plate. After washing to remove incompletely adsorbed HMW protein, analogs fragments and/or peptides, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents such as BSA, bovine gamma globulin (BGG) and/or phosphate buffered saline (PBS)/Tween. The sample is then allowed to incubate for from about 2 to about 4 hours, at temperature such as of the order of about 25° to about 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound HMW protein, analogs, fragments and/or peptide, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity, such as an enzymatic activity, that will generate, for example, a color development, upon incubating with an appropriate chromogenic substrate. Quantification may then achieved by measuring the degree of color generation using, for example, a visible spectra spectrophotometer.

7. Use of Sequences as Hybridization Probes

The nucleotide sequences of the present invention, comprising the newly-isolated and characterized sequences of the hmw genes, allow for the identification and cloning of the hmw genes from other non-typeable strains of Haemophilus.

The nucleotide sequences comprising the sequence of hmw genes of the present invention are useful for their ability to selectively from duplex molecules with complementary stretches of other hmw genes. Depending on the application, a variety of hybridization conditions may be employed to achieve varying degrees of selectivity of the probe toward the other hmw genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between 20° C. to 55° C. Hybridization conditions can also be rendered more stringent by the addition of increasing amount of formamide, to destabilize the hybrid duplex. Thus, particular hybridization conditions can be readily manipulated, and will generally be a method of choice depending on the desired results. In general convenient hybridization temperatures in the presence of 50% formamide and 0.15 M NaCl are: 42° C. for an hmw gene which is about 95 to 100% homologous to the target nucleic acid fragment, 37° C. for about 90 to 95 homology and 32° C. for about 85 to 90% homology.

In a clinical diagnostic embodiment, the nucleic acid sequences of the hmw genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing hmw genes sequences.

The nucleic acid sequences of hmw genes of the present invention are useful as hybridization probes in solution hybridizations and in embodiments employing solid-phase procedures. In embodiments involving solid-phase procedures the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the hmw genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Haemophilus. The selected probe may be at least 18 bp in length and may be in the range of 30 bp to 90 bp long.

8. Expression of the High Molecular Weight Protein Genes

Plasmid vectors containing replicon and control sequences which are derived from species compatible with the host cell may be used for the expression of the high molecular weight protein genes in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems and other microbial promoters such as the T7 promoter system employed herein in preferred embodiments (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the HMW protein and immunological fragments or analogs thereof include E. coli, Bordetella species, Bacillus species, Haemophilus, fungi, yeast or the baculovirus expression system may be used. E. coli is the preferred host used herein.

In accordance with this invention, it is preferred to produce the HMW proteins by recombinant methods, particularly when the naturally occurring HMW protein as purified from a culture of a species of Haemophilus may include trace amounts of toxic materials or other contaminants. This problem can be avoided by using recombinantly produced HMW protein in heterologous systems which can be isolated from the host in a manner to minimize contaminants in the purified materials, specifically employing the constructs described herein. Furthermore, recombinant method of production permit the manufacture of HMW1 or HMW2 or immunogenic fragments and analogs thereof separate from one another and in highly-purified form, which is distinct from the normal combined proteins present in Haemophilus.

9. Cloning and Sequence Analysis of Additional hmwA Genes.

The hmwA genes and encoded proteins have variable sequences. In order to produce a completely effective vaccine, it may be necessary to use rHMWA proteins generated from multiple strains of non-typeable Haemophilus. The hmw1A and/or hmw2A genes were PCR amplified and sequenced from several strains of non-typeable *Haemophilus influenzae*. FIGS. 18 to 27 illustrate the nucleotide and

17 deduced amino acid sequences for the hmw1A gene from strain Joyc, the hmw2A gene from strain Joyc, the defective hmw1A gene from strain Ki, the hmw2A gene from strain K21, the hmw1A gene from strain LCDC2, the hmw2A gene from strain LCDC2, the hmw1A gene from strain PMH1, the hmw2A gene from strain PMH1, the hmw1A gene from strain 15, and the hmw2A gene from strain 15, respectively. The alignment of the deduced protein sequences with the previously described strain 12 HMWLA and HMW2A protein sequences (FIGS. 28 and 29) identifies both regions of sequence conservation and divergence (FIG. 30). Such information may be useful in the identification of potential epitopes to generate peptides for vaccination or diagnostic purposes. The molecular weights of the mature HMW proteins from the various non-typeable Haemophilus strains is contained in Table 3.

Biological Deposits

Certain vectors that contain nucleic acid coding for a high molecular weight protein of a non-typeable strain of Haemophilus that are described and referred to herein have been deposited with the America Type Culture Collection (ATCC) located at 10801 University Boulevard, Manassas, Va. 20110-2209, USA, pursuant the Budapest Treaty and prior to the filing of this application. Samples of the deposited vectors will become available to the public and all restrictions imposed or access to the deposits will be received upon grant of a patent based on this United States patent application. In addition, the deposit will be replaced if viable samples cannot be dispensed by the Depository. The invention described and claimed herein is not limited in scope by the biological materials deposited, since the deposited embodiment is intended only as an illustration of the invention. Any equivalent or similar vectors that contain nucleic acid which encodes equivalent or similar antigens as described in this application are within the scope of the invention.

Deposit Summary

| Plasmid | | ATCC | Date Deposited |
|---|---|---|---|
| DS-1046-1-1 | (pT7 hmw1ABC(125)) | 203263 | 25-Sept-1998 |
| JB-2507-7 | (pT7 hmw1A(125)/ T7 hmw1ABC(125)) | 203262 | 25-Sept-1998 |
| BK-86-1-1 | (pT7 hmw1A(125)/ T7 hmw1ABC(125)/Kan$^R$) | 203258 | 25-Sept-1998 |
| BK-35-4 | (pT7 hmw1ABC(125)/cer) | 203259 | 25-Sept-1998 |
| BK-76-1-1 | (pT7 hmw1ABC(125)/cer/Kan$^R$) | 203263 | 25-Sept-1998 |
| DS-2334-5 | (pT7 hmw2A(LCDC2)/ hmw1BC(12)/cer/Kan$^R$) | 203260 | 25-Sept-1998 |
| JB-2646-1 | (pT7 hmw1BC(12)/cer/Kan$^R$) | 203256 | 25-Sept-1998 |
| DS-2400-13 | (pBRT7 hmw1A/T7 hmw1ABC/ cer/Kan$^R$) | 203263 | 25-Sept-1998 |

EXAMPLES

The above disclosure generally describes the present invention. A more complete understanding can be obtained by reference to the following specific Examples. These Examples are described solely for the purposes of illustration and are not intended to limit the scope of the invention. Changes in form and substitution of equivalents are contemplated as circumstances may suggest or render expedient. Although specific terms have been employed herein, such terms are intended in a descriptive sense and not for the purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

This Example describes the construction of plasmid DS-1091-2 that expresses the hmw1ABC genes encoding the full-length 160 kDa HMW1A protein.

Plasmid pHMW1-15 (ref. 8) contains about 400 bp of 5'-flanking region, including the hmw1promoter, inserted between the T7 promoter and the start of the hmw1ABC coding region (FIG. 1). There is a unique Bgl II site in the multiple cloning site of pHMW1-15 and a unique BamH I site in the coding region of hmw1A. The 2.2 kb Bgl II-BamH I fragment was subcloned for further manipulation, generating plasmid DS-1035-12. A 400 bp Xba I-Bsm I fragment containing the 5'-flanking region was replaced by approximately 86 bp oligonucleotides (FIG. 1B) that joined the T7 promoter directly to the ATG start codon of the hmw1A gene in plasmid DS-1055R-2. The 1.5 kb Xba I-BamH I fragment from DS-1055R-2 was inserted into pHMW1-15 that had been digested with the same enzymes to generate plasmid DS-1091-2.

Example 2

This Example describes the construction of plasmid DS-1094-2 that expresses the hmw2ABC genes encoding the full-length 155 kDa HMW2A protein.

Figure 2:
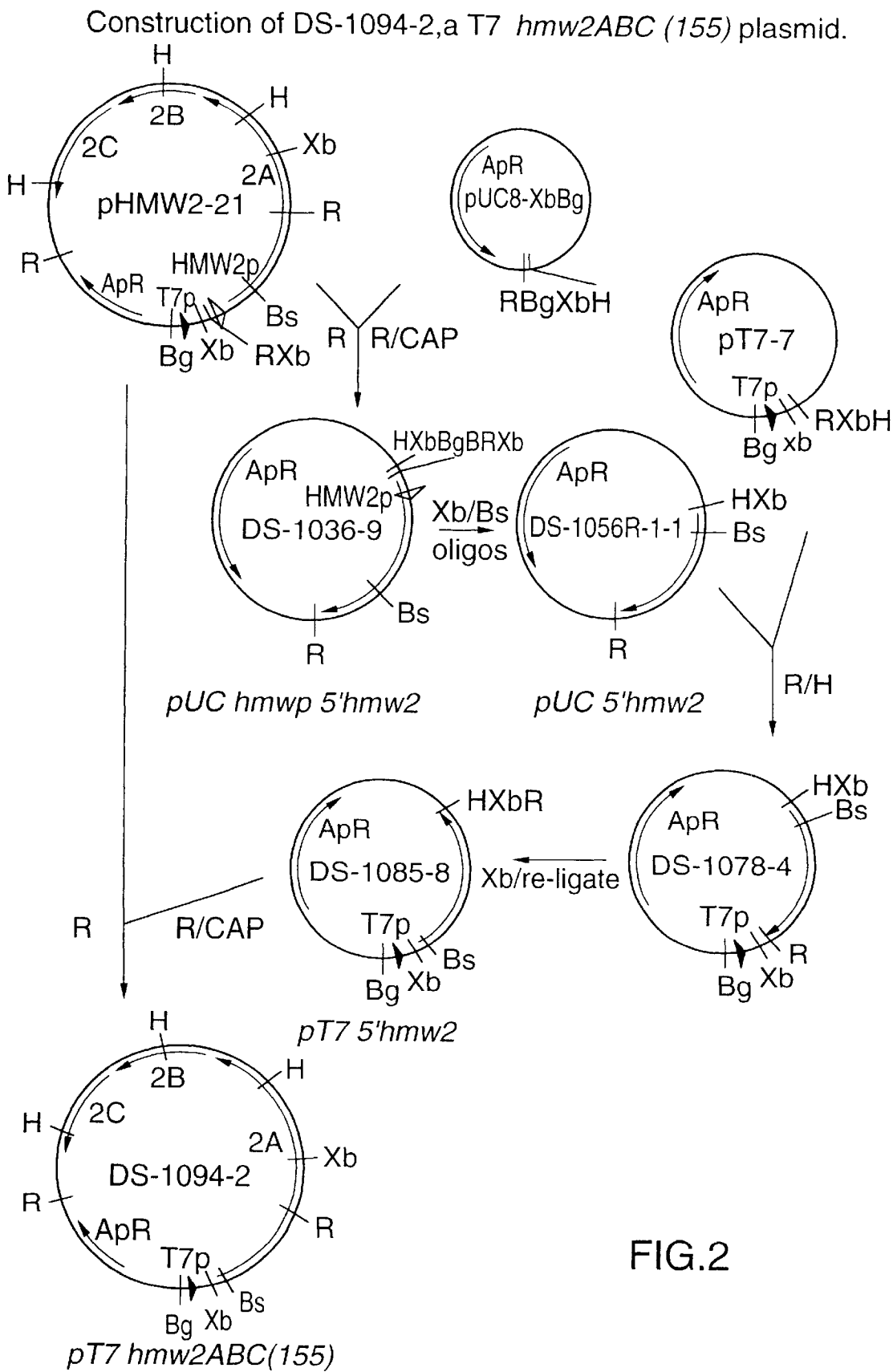
FIG. 2 shows the construction scheme to generate plasmid DS-1094-2 that expresses the hmw2ABC genes encoding the full-length 155 kDa HMW2A protein. Restriction enzyme sites are: Bg, Bgl II; Bs, Bsm I; H, Hind III; R, EcoR I; Xb, Xba I. Other abbreviations are: T7p, T7 promoter; HMW2p, hmw2 promoter; ApR, ampicillin resistance gene; CAP, calf alkaline phosphatase.

Plasmid pHMW2-21 (ref. 10) contains about 800 bp of 5'-flanking sequence, including the hmw2 promoter, between the T7 promoter and the start of the hmw2ABC coding sequence (FIG. 2). Plasmid pHMW2-21 has two EcoR I sites, one in the multiple cloning site, and one within the coding sequence of the hmw2A gene. The 2.5 kb EcoR I fragment was subcloned for further manipulation, generating plasmid DS-1036-9. The approximately 800 bp Xba I-Bsm I fragment containing the 5'-flanking sequences, was replaced by the same approximately 86 bp oligonucleotides that were used for hmw1 (FIG. 1B), to join the T7 promoter directly to the ATG start codon of hmw2A, generating plasmid DS-1056R-1-1. An intermediate plasmid (DS-1078-4) was necessary to introduce convenient restriction enzyme sites, and the Xba I insert was excised, then re-ligated to change orientation for plasmid DS-1085-8. Plasmid DS-1085-8 was linearized with EcoR I, dephosphorylated, and ligated with the 8 kb EcoR I fragment from pHMW2-21, to generate plasmid DS-109t-2 that contains the T7 promoter joined directly to the coding sequence of hmw2ABC.

Example 3

This Example illustrates the construction of plasmid DS-1046-1-1 that expresses the hmw1ABC genes encoding the mature 125 kDa HMW1A protein.

Figure 3A:
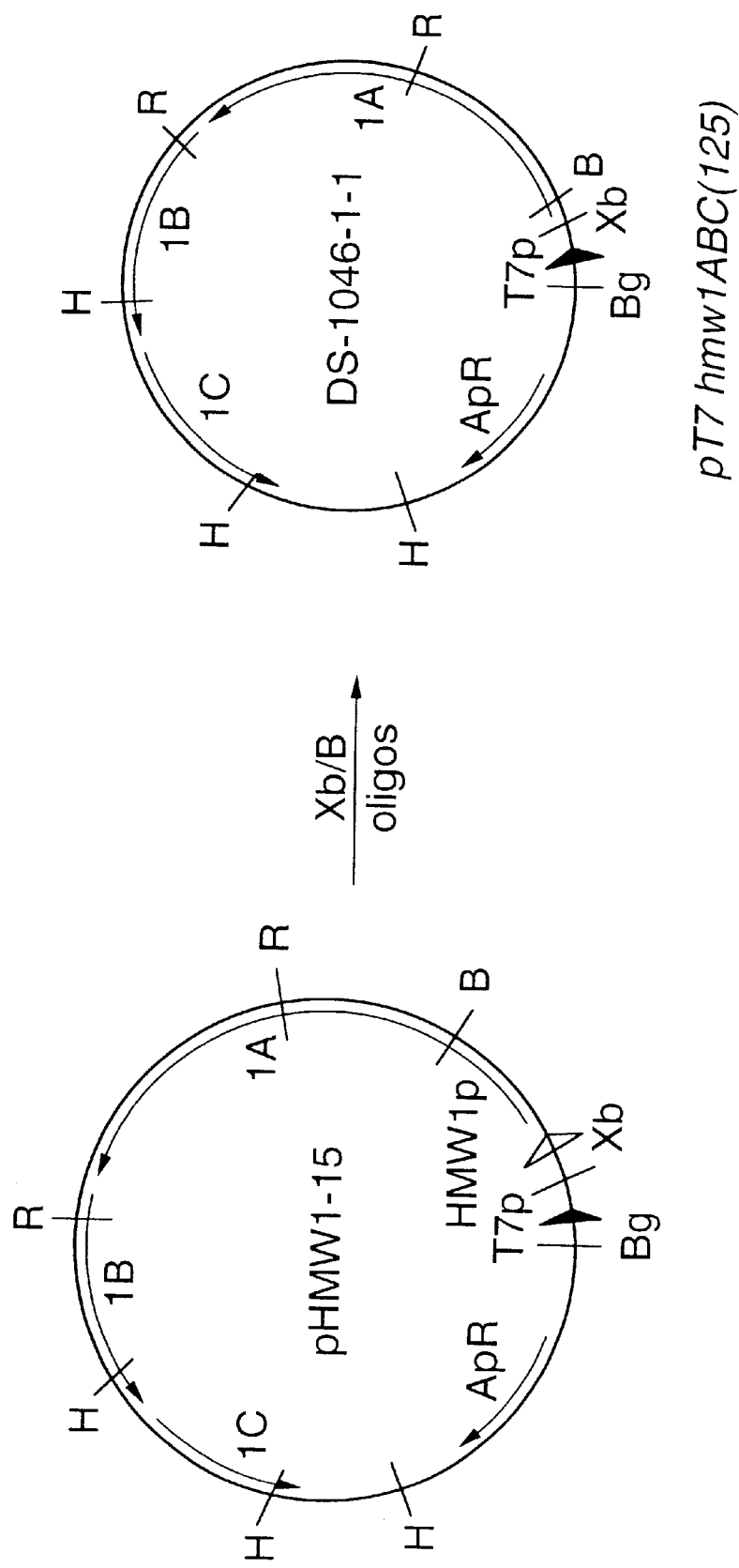
FIG. 3A shows the construction scheme to generate plasmid DS-1046-1-1 that expresses the hmw1ABC genes encoding the mature 125 kDa HMW1A protein. Restriction enzyme sites are: B, BamH I; Bg, Bgl II; H, Hind III; R, EcoR I; Xb, Xba I. Other abbreviations are: T7p, T7 promoter; HMW1p, hmw1 promoter; ApR, ampicillin resistance gene.

Plasmid pHMW1-15 (ref. 8) contains a Xba I site within the T7 promoter sequence and a unique BamH I site within the coding sequence of the mature HMW1A protein (FIG. 3A). The 1.8 kb Xba I-BamH I fragment of pHMW1-15 was deleted and replaced by an approximately 114 bp Xba I-BamH I fragment generated from oligonucleotides (FIG. 3B). The resultant 11.3 kb plasmid, DS-1046-1-1, thus contains the T7 promoter joined in frame with the hmw1ABC operon that encodes the mature 125 kDa HMW1A protein.

Example 4

This Example illustrates the construction of plasmid DS-1200-3 that expresses the hmw2AB partial C genes encoding the mature 120 kDa HMW2A protein.

Figure 4A:
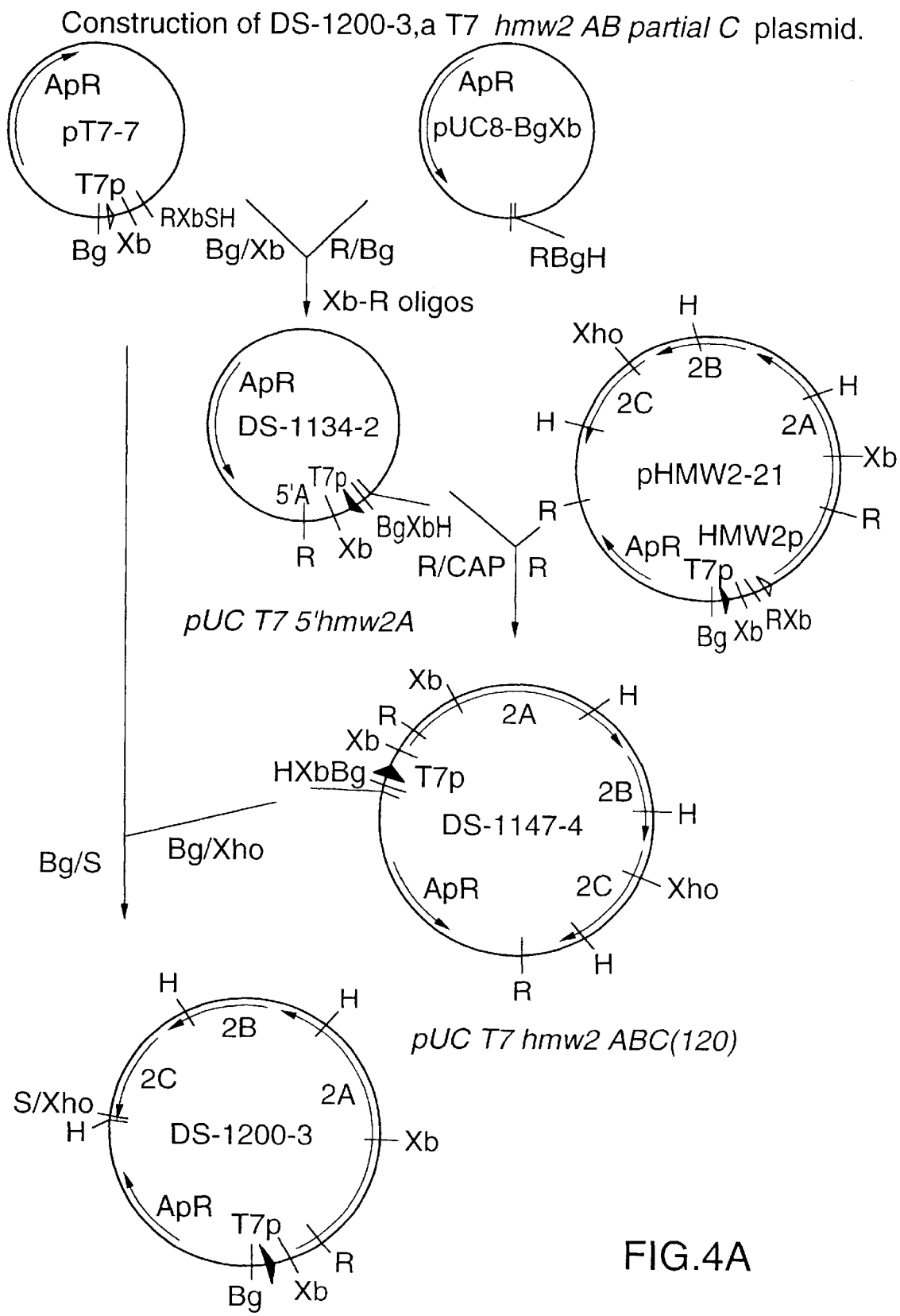
FIG. 4A shows the construction scheme to generate plasmid DS-1200-3 that expresses the hmw2AB genes encoding the mature 120 kDa HMW2A protein. Restriction enzyme sites are: Bg, Bgl II; H, Hind III; R, EcoR I; S, Sal I; Xb, Xba I; Xho, Xho I. Other abbreviations are: T7p, T7 promoter; HMW2p, hmw2 promoter; ApR, ampicillin resistance gene; CAP, calf alkaline phosphatase.

Plasmid pHMW2-21 (ref. 10) contains an EcoR I site within the coding sequence of the mature HMW2A protein. However, it is not unique (FIG. 4A). A multi-step construction process involved first re-creating part of the T7 promoter and the start of the hmw2A gene encoding the mature HMW2A protein, from 105 bp oligonucleotides (FIG. 4B). Plasmid DS-1134-2 contains the complete T7 promoter and the 5'-sequence encoding the mature HMW2A protein. Plasmid DS-1134-2 was linearized with EcoR I, dephosphorylated, and the 8 kb EcoR I fragment from pHMW2-21, containing most of the hmw2A gene and all of the hmw2B and hmw2C genes was inserted. Plasmid DS-1147-4 is a pUC-based plasmid containing the T7 hmw2ABC gene cassette. The entire cassette was removed on a 6.5 kb Bgl II-Xho I fragment and inserted into pT7-7 that had been digested with Bgl II and Sal I, to create plasmid DS-1200-3. Part of the hmw2C gene was deleted in this construct.

Example 5

This Example illustrates the construction of plasmid DS-1122-2 that contains the hmw1A gene encoding the mature 125 kDa HMW1A protein, and part of the hmw1B gene.

Figure 5:
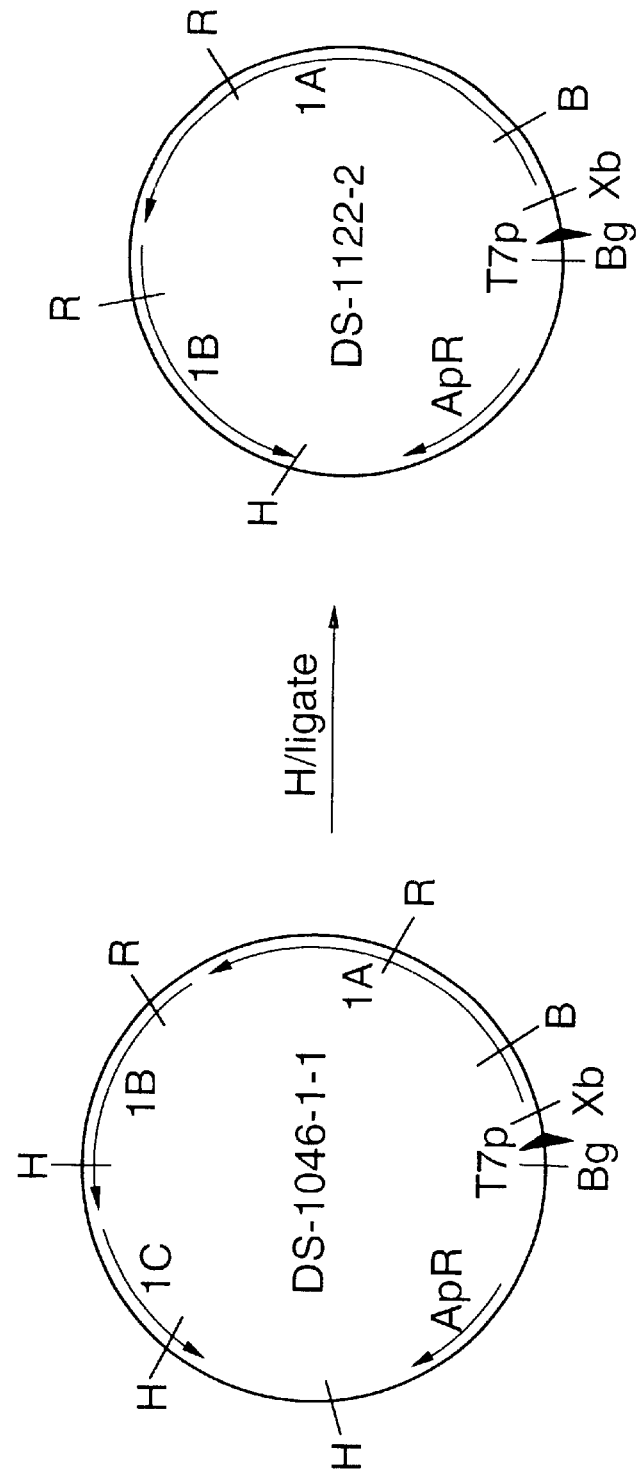
FIG. 5 shows the construction scheme to generate plasmid DS-1122-2 that contains the hmw1A gene encoding the mature 125 kDa HMW1A protein, and part of the hmw1b gene. Restriction enzyme sites are: B, BamH I; Bg, Bgl II; H, Hind III; R, EcoR I; Xb, Xba I. Other abbreviations are: T7p, T7 promoter; ApR, ampicillin resistance gene.

Plasmid DS-1046-1-1 (FIG. 3A; Example 3) contains three Hind III sites, one within the hmw1B gene, one within the hmw1C gene and one in the 3'-region of the multiple cloning site (FIG. 5). When DS-1046-1-1 was digested with Hind III, then re-ligated, plasmid DS-1122-2 was generated that contains a complete hmw1A gene encoding the mature 125 kDa HMW1A protein, part of the hmw1B gene, and no hmw1C gene.

Example 6

This Example illustrates the construction of plasmid JB-2330-7 that contains the hmw1A gene encoding the mature 125 kDa HMW1A protein, with no other hmw genes.

Figure 6A:
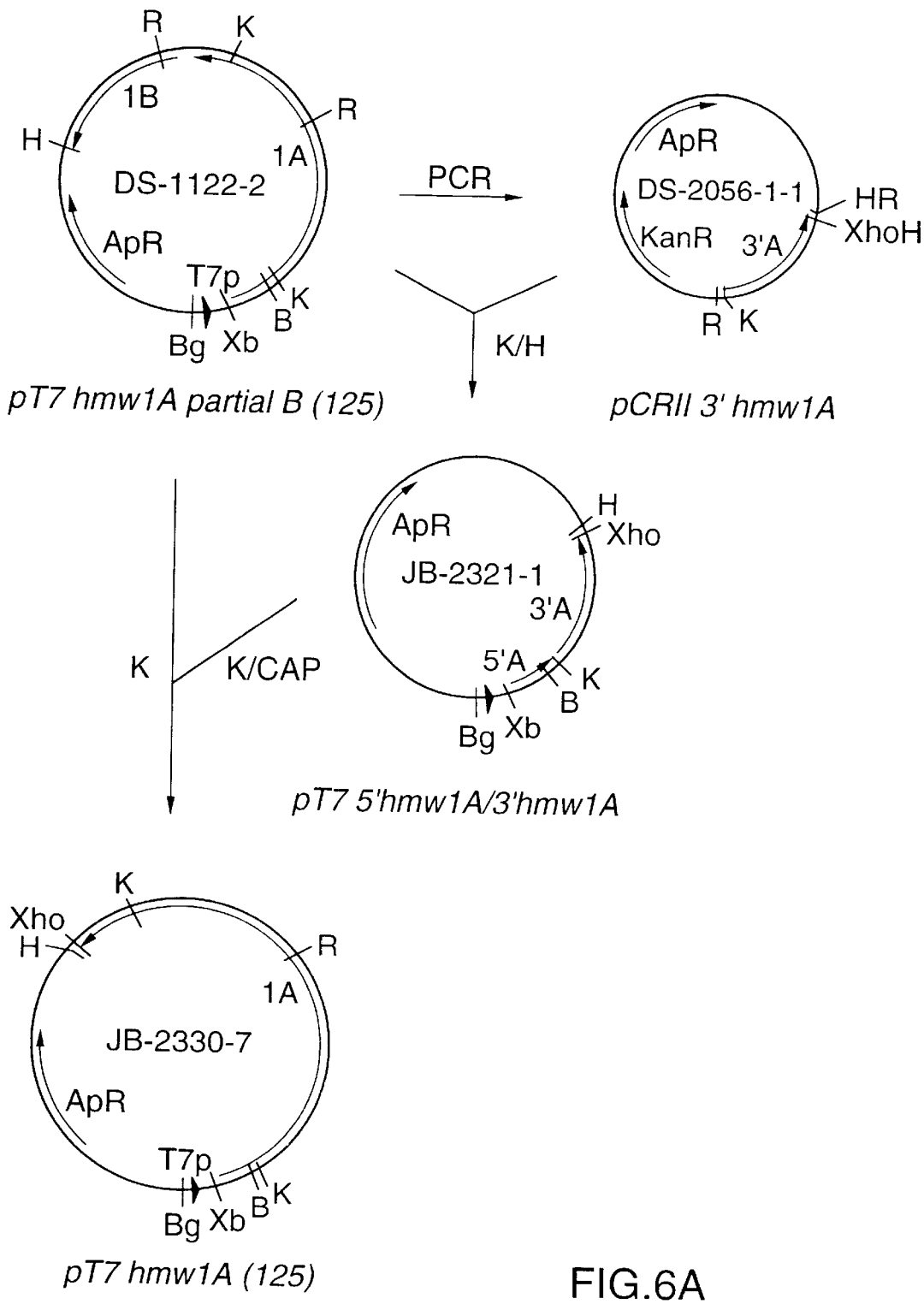
FIG. 6A shows the construction scheme to generate plasmid JB-2330-7 that expresses the hmw1A gene encoding the mature 125 kDa HMW1A protein. Restriction enzyme sites are: B, BamH I; Bg, Bgl II; H, Hind III; K, Kpn I; R, EcoR I; Xho, Xho I. Other abbreviations are: T7p, T7 promoter; ApR, ampicillin resistance gene; KanR, kanamycin resistance gene, CAP, calf alkaline phosphatase.

PCR amplification was performed on plasmid DS-1122-2 (FIG. 5; Example 5) DNA to generate a 500 bp fragment from the Kpn I site near the 3'-end of hmw1A, through the terminator, and introducing restriction enzyme sites for Xho I and Hind III at the 3'-end. The fragment was cloned into pCR II, generating plasmid DS-2056-1-1 (FIG. 6A) and the oligonucleotides used are shown in FIG. 6B. Plasmid DS-1122-2 was digested with Kpn I and Hind III which deletes most of the hmw1A gene and all of the hmw1B gene fragment. The 2.6 kb Kpn I-Hind III vector fragment from DS-1122-2 was ligated with the 0.5 kb Kpn I-Hind III fragment from DS-2056-1-1 to generate plasmid JB-2321-1, that contains approximately 0.2 kb of 5'-hmw1A sequence and approximately 0.5 kb of 3'-hmw1A sequence, joined at the Kpn I site. Plasmid JB-2321-1 was linearized with Kpn I, dephosphorylated, and the internal 2.7 kb Kpn I fragment from DS-1122-2 was inserted to create plasmid JB-2330-7. This plasmid contains a T7 hmw1A gene cassette with no additional hmw1 gene sequences.

Example 7

This Example illustrates the construction of plasmid JB-2369-6 that contains tandem copies of the T7 hmw1A gene cassette encoding the mature 125 kDa HMW1A protein.

Figure 7:
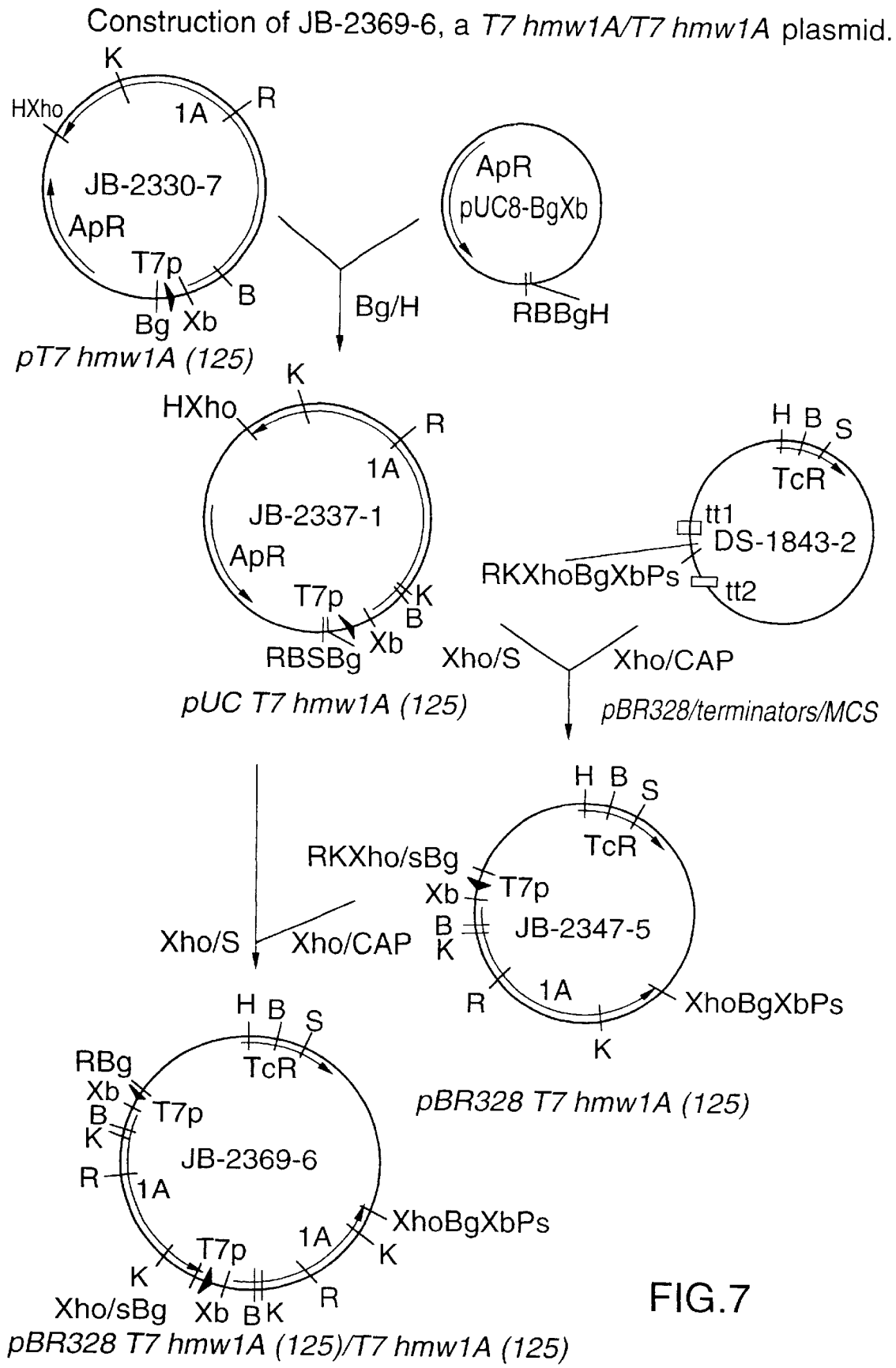
FIG. 7 shows the construction scheme to generate plasmid JB-2369-6 that expresses tandem copies of the T7 hmw1A gene cassette encoding the mature 125 kDa HMW1A protein. Restriction enzyme sites are: B, BamH I; Bg, Bgl II; H, Hind III; K, Kpn I; R, EcoR I; S, Sal I; Xb, Xba I; Xho, Xho I. Other abbreviations are: T7p, T7 promoter; ApR, ampicillin resistance gene; TcR, tetracycline resistance gene; CAP, calf alkaline phosphatase; tt1, transcription terminator 1; tt2 transcription terminator 2; MCS, multiple cloning site.

Plasmid JB-2330-7 (FIG. 6A; Example 6) was digested with Bgl II and Hind III and the T7 hmw1A gene cassette was subcloned into pUC-BgXb that had been digested with Bgl II and Hind III, creating plasmid JB-2337-1 (FIG. 7). Plasmid JB-2337-1 was digested with Sal I and Xho I which released the T7 hmw1A cassette, on a fragment with compatible ends. Vector DS-1843-2 is a pBR328-based plasmid containing transcription terminators and a multiple cloning site with a unique Xho I site. Vector DS-1843-2 was digested with Xho I, dephosphorylated, and then ligated with the 3.5 kb Sal I-Xho I T7 hmw1A gene cassette to generate plasmid JB-2347-5. Because the Sal I and Xho I sites seal, this plasmid contains a unique Xho I site at the 3'-end of the T7 hmw1A gene cassette that can be used to insert additional Sal I-Xho I T7 hmw1A gene cassettes derived from JB-2337-1. Plasmid JB-2369-6 contains two tandem T7 hmw1A genes introduced in this way.

Example 8

This Example illustrates the construction of plasmids DS-2084-3 and DS-2084-1 that contain one or two tandem copies of the T7 hmw2A gene cassette encoding the mature HMW2A protein.

Figure 8A:
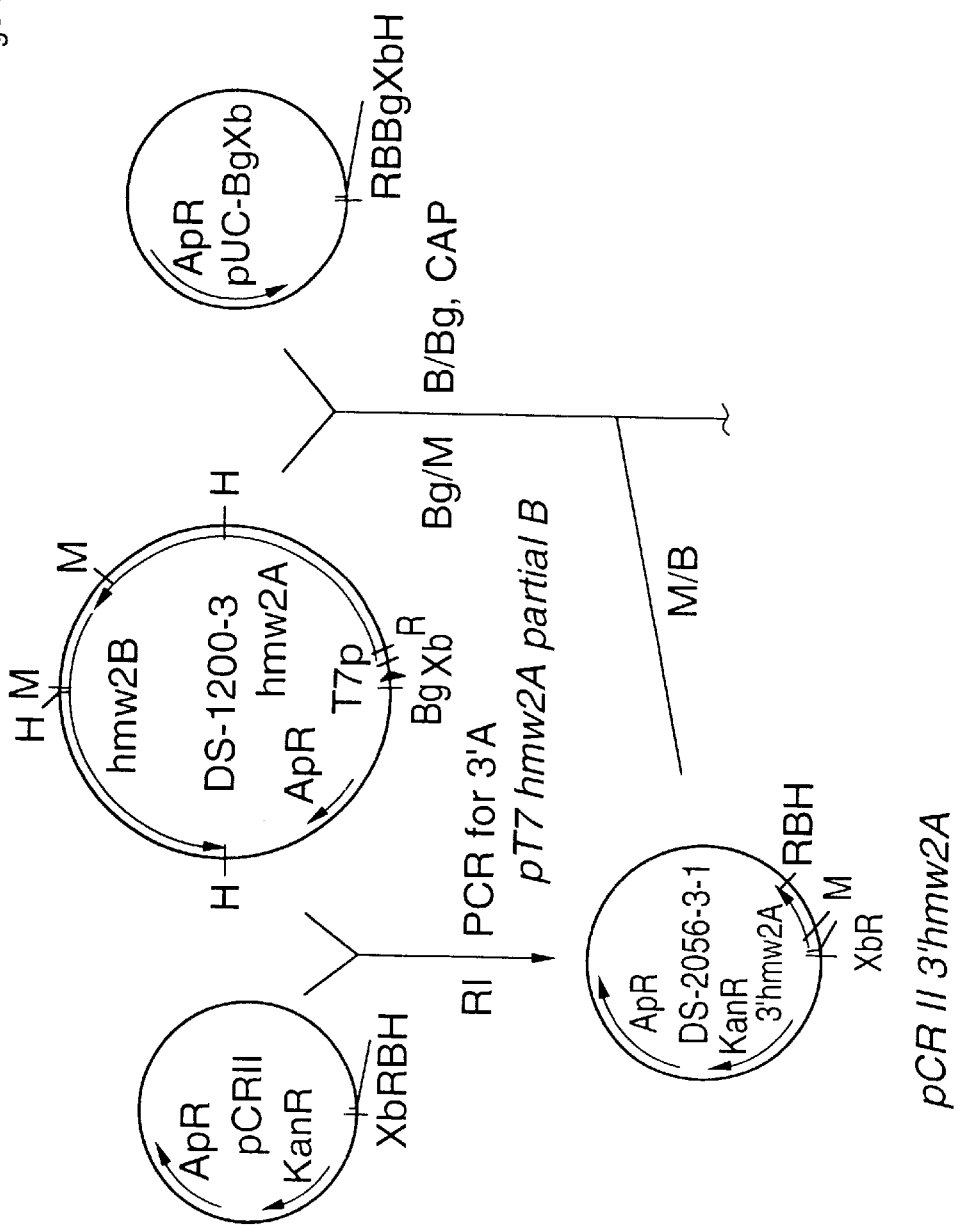
FIGS. 8A and 8A' show the construction scheme to generate plasmids DS-2084-3 and DS-2084-1 that contain one or two copies of the T7 hmw2A gene cassette encoding the mature 120 kDa HMW2A protein. Restriction enzyme sites are: B, BamH I; Bg, Bgl II; H, Hind III; M, Mlu I; R, EcoR I; Xb, Xba I. Other abbreviations are: T7p, T7 promoter; ApR, ampicillin resistance gene; TcR, tetracycline resistance gene; CAP, calf alkaline phosphatase; tt1, transcription terminator 1; tt2, transcription terminator 2; MCS, multiple cloning site.
Figure 8A:
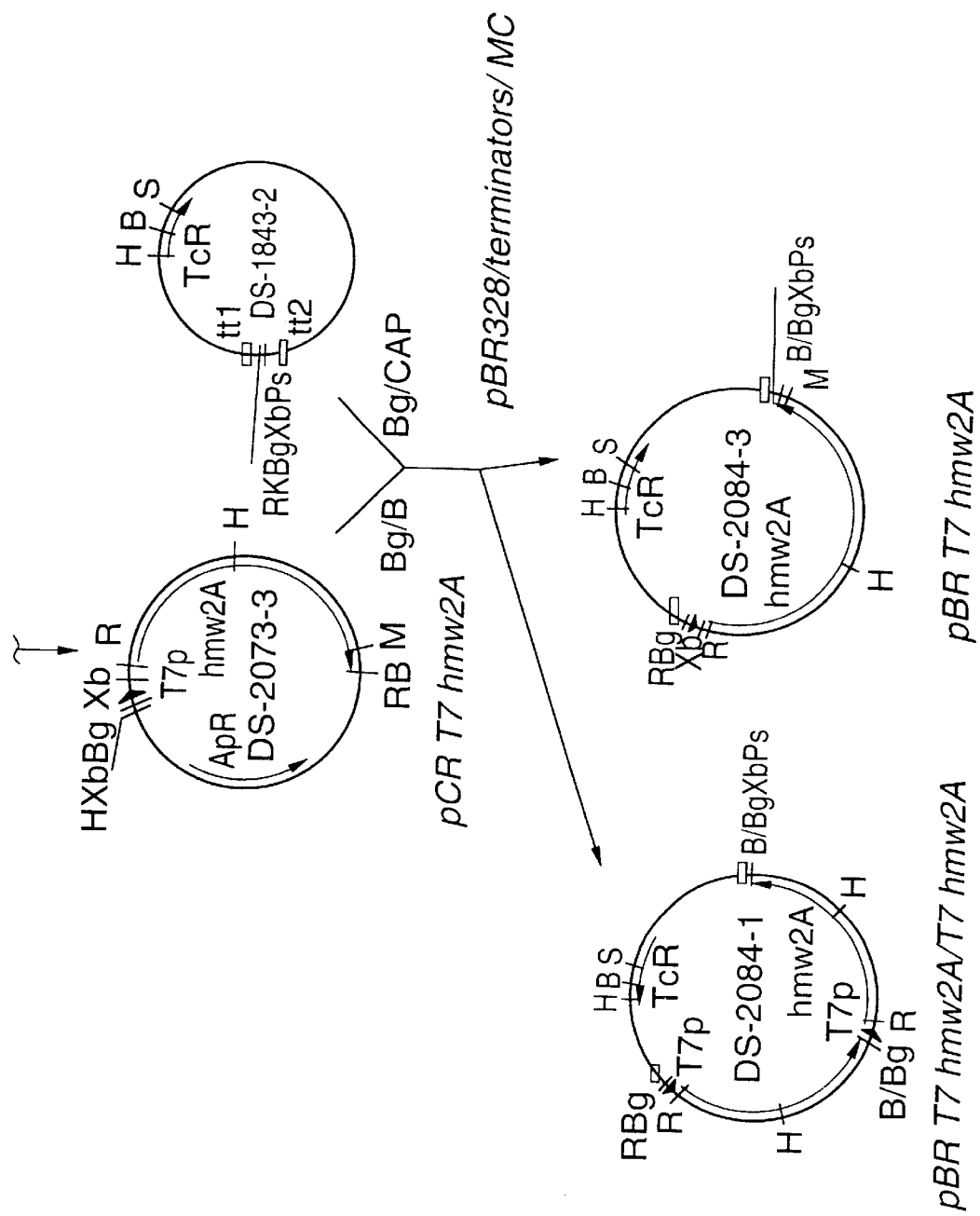

Plasmid DS-1200-3 (FIG. 4A, Example 4) contains the T7 hmw2AB partial C gene cassette. There are two Mlu I sites in DS-1200-3, one located near the 3'-end of hmw2A and the other located near the 5'-end of hmw2B (FIG. 8A). Oligonucleotide primers were used to PCR amplify a 247 bp fragment of the 3'-end of the hmw2A gene from the Mlu I site, and to introduce a unique BamH I site following the termination codon of hmw2A (FIG. 8B). The 247 bp PCR fragment was subcloned into pCRII generating plasmid DS-2056-3-1. Plasmid DS-1200-3 was digested with Bgl II and Mlu I and the 3.2 kb fragment containing the T7 promoter and most of the hmw2A gene was purified. Plasmid pUC-BgXb was digested with Bgl II and BamH I and dephosphorylated. The Bgl II-Mlu I hmw2A gene fragment and the Mlu I-BamH I PCR fragment from DS-2056-3-1 were ligated into the pUC vector to generate plasmid DS-2073-3 which thus contains a 3.4 kb T7 hmw2A gene cassette on a Bgl II-BamH I fragment, with no additional hmw2 genes. Plasmid DS-1843-2 was linearized with Bgl II and the 3.4 kb Bgl II-BamH I cassette was inserted, generating plasmid DS-2084-3 that contains a single T7 hmw2A gene cassette and plasmid DS-2084-1 that contains two tandem T7 hmw2A gene cassettes.

Example 9

This Example illustrates the construction of plasmids JB-2507-7 and BK-86-1-1 that contain tandem T7 hmw1A/T7 hmw1ABC genes encoding the mature 125 kDa HMW1A protein and are resistant to ampicillin or kanamycin, respectively.

Figure 9:
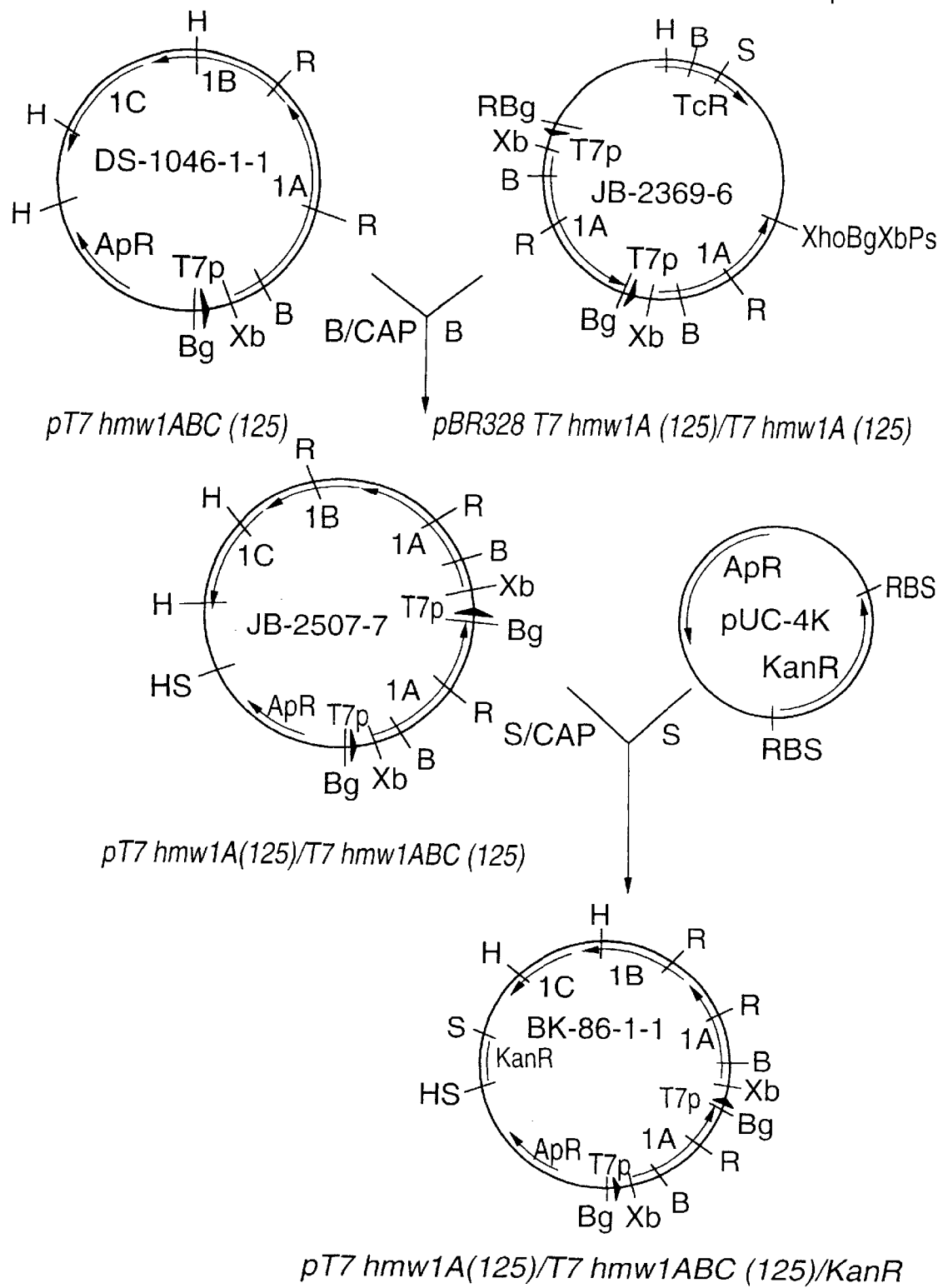
FIG. 9 shows the construction scheme to generate plasmids JB-2507-7 and BK-86-1-1 that contain tandem T7 hmw1A/T7 hmw1ABC genes encoding the mature 125 kDa HMW1A protein, with ampicillin or kanamycin selection, respectively. Restriction enzyme sites are: B, BamH I; Bg, Bgl II; H, Hind III; K, Kpn I; R, EcoR I; S, Sal I; Xb, Xba I; Xho, Xho I. Other abbreviations are: T7p, T7 promoter; ApR, ampicillin resistance gene; KanR, kanamycin resistance gene; TcR, tetracycline resistance gene; CAP, calf alkaline phosphatase.

Plasmid DS-1046-1-1 (FIG. 3A; Example 3) contains the T7 hmw1ABC gene cassette and has a unique BamH I site within the coding region of the mature HMW1A protein. Plasmid JB-2369-6 (FIG. 7; Example 7) contains tandem T7 hmw1A gene cassettes, each of which contains an internal BamH I site within the coding sequence for HMW1A. When plasmid JB-2369-6 was digested with BamH I, a 3.5 kb fragment was generated that contains the 3'-end of the first hmw1A gene and the T7 promoter and 5'-end of the second hmw1A gene. This fragment was ligated into the BamH I site of DS-1046-1-1 to create plasmid JB-2507-7 that contains tandem T7 hmw1A/T7 hmw1ABC gene cassettes (FIG. 9). The unique Sal I site found in the multiple cloning site of the pT7-7 vector backbone, was used to linearize JB-2507-7. The kanamycin resistance cassette was excised from pUC-4K by Sal I digestion, and ligated with the JB-2507-7 vector to generate plasmid BK-86-1-1.

Example 10

This Example illustrates the construction of plasmids BK-35-4 and BK-76-1-1 that contain the T7 hmw1ABC gene cassette and an *E. coli* cer gene and are ampicillin or kanamycin resistant, respectively.

Plasmid DS-2224-1-4 (FIG. 10) contains an *E. coli* cer gene (ref. 13) that was created from approximately 290 bp oligonucleotides cloned into the BamH I site of pUC-BgXb. Plasmid DS-1046-1-1 (FIG. 3; Example 3) contains a unique Bgl II site upstream of the T7 promoter. Plasmid DS-1046-1-1 was linearized with Bgl II, dephosphorylated, and ligated with the 290 bp BamH I fragment containing the cer gene from DS-2224-1-4, to create plasmid BK-35-4. The kanamycin resistance cassette was excised from pUC-4K by Sal I digestion and was inserted at the unique Sal I site of BK-35-4 to create plasmid BK-76-1-1.

Example 11

This Example illustrates the analysis of the production of rHMW1 and rHMW2 proteins from the different constructs produced in the preceding Examples.

Figure 11:
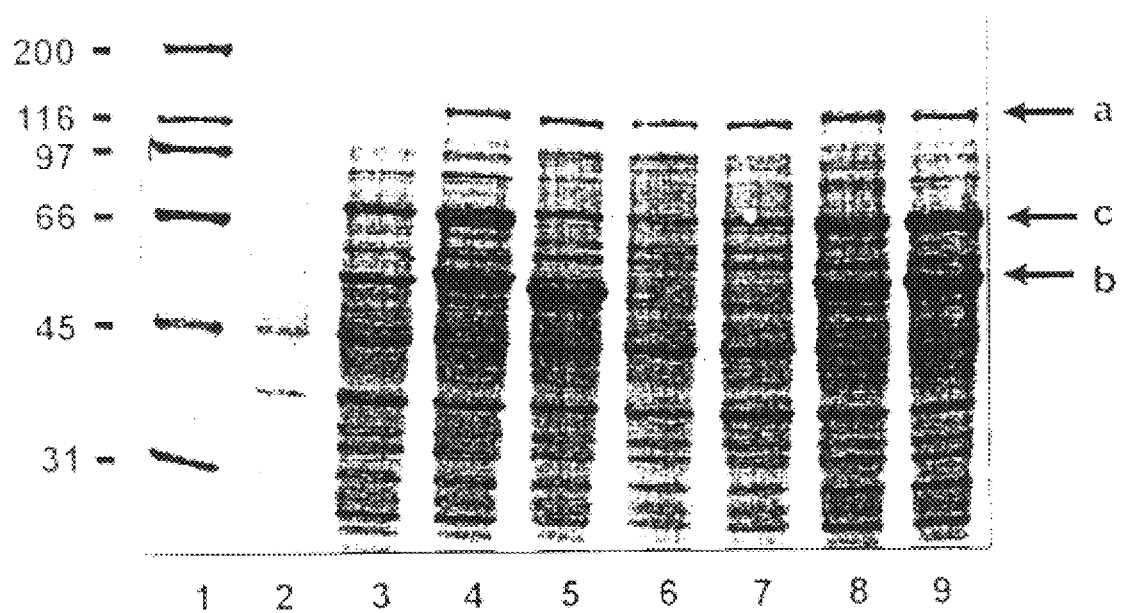
FIG. 11 shows SDS-PAGE analysis of the expression of recombinant HMW1 proteins from various constructs. Lane 1, broad range molecular weight markers; lane 2, DS-1046-1-1 [pT7 hmw1ABC (125)], no induction; lane 3, DS-1091-2 [pT7 hmw1ABC (160)]; lane 4, DS-1046-1-1 [pT7 hmw1ABC (125)]; lane 5, DS-1122-2 [pT7 hmw1A partial B (125)]; lane 6, JB-2330-7 [pT7 hmw1A (125)]; lane 7, JB-2369-6 [pBr328 T7 hmw1A (125)/T7 hmw1A (125)]; lane 8, BK-86-1-1 [pT7 hmw1A (125)/T7 hmw1ABC (125)/kanR]; lane 9, BK-76-1-1 [pT7 hmw1ABC (125)/cer/kanR]; lane 10, broad range molecular weight markers.

Plasmids were introduced into *E. coli* BL21(DE3) cells by electroporation using a BioRad apparatus. Strains were grown at 37° C. in NZCYM medium to an optical density of $A_{578}$=0.3, then induced by the addition of lactose to 1.0% for 4 hours. Samples were adjusted to 0.2 OD/µl with SDS-PAGE lysis+loading buffer and the same amount of protein sample was loaded onto SDS-PAGE gels. FIG. 11 illustrates the relative production of rHMW proteins from various constructs as analysed by SDS PAGE gels. The identification of the lanes in relation to the specific constructs is given in the description of the Figure above. "a" indicates the band for HMWA proteins, "b" indicates the band for HMWB proteins and "c" indicates the band for HMWC proteins.

As may be seen therein, the production of the HMW1A, B, and C proteins from the T7 hmw1ABC(160 construct (lane 3) is negligible. The production of all three proteins is improved in the T7 hmw1ABC(125) construct (lane 4). In lane 5, there is no production of the HMW1C protein and the HMW1B protein is slightly reduced in size due to the truncation of its gene in the T7 hmw1A partial B construct. In lane 6, there is no production of HMW1B or HMW1C protein from the T7 hmw1A(125) construct. Lane 7 shows that there was marginal, if any, improvement in the production of HMW1A from the T7 hmw1A/T7 hmw1A construct. In lane 8, the production of HMW1A, HMW1B and HMW1C proteins is evident when expressed from the T7 hmw1A/T7 hmw1ABC construct. In lane 9, the HMW1A, HMW1B and HMW1C proteins are all produced from the T7 hmw1ABC/cer construct.

Example 12

This Example illustrates the purification of recombinant HMW1 and HMW2 proteins.

Figure 12:
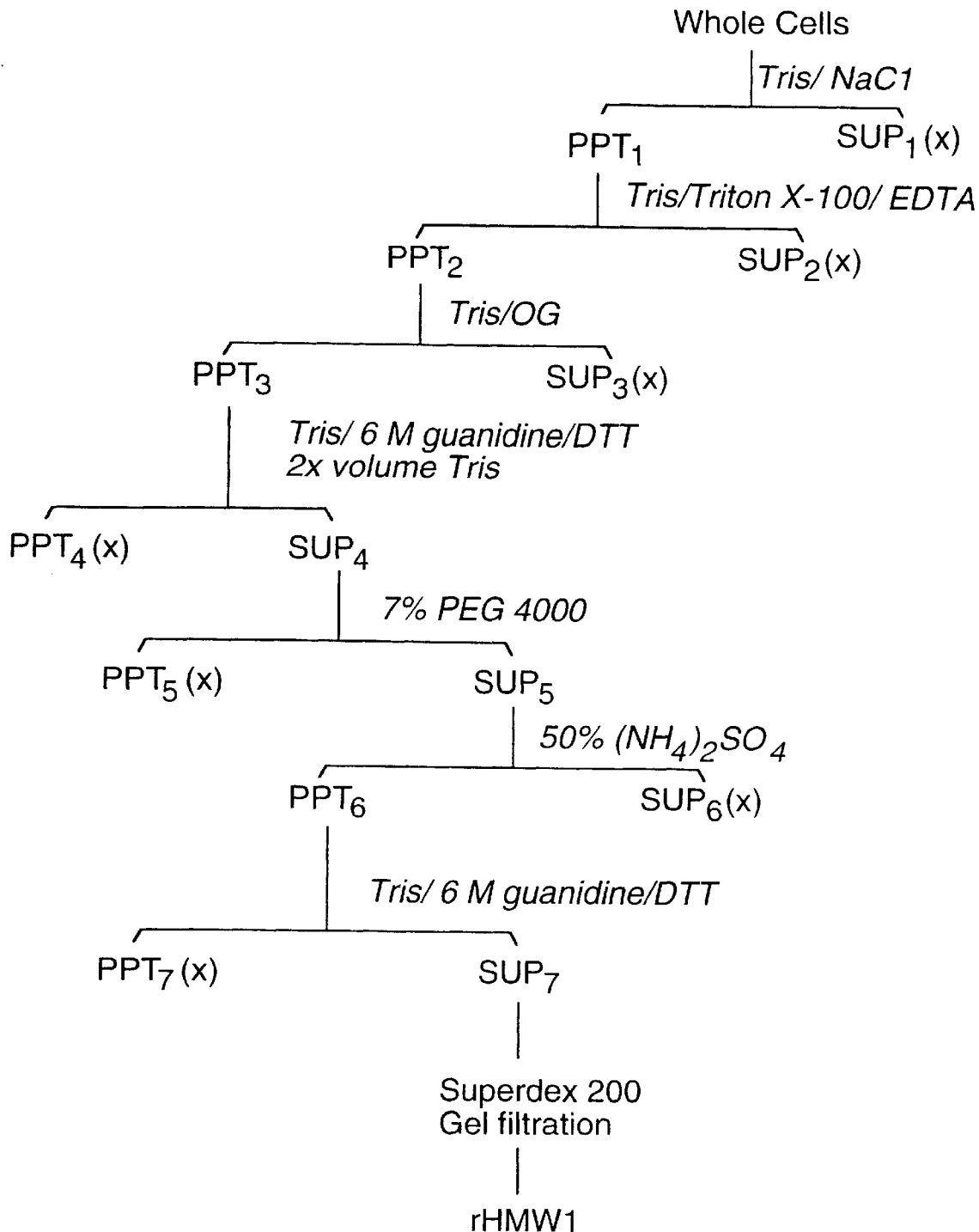
FIG. 12 shows a purification scheme for recombinant HMW1 and HMW2 proteins. Abbreviations are: PPT, pellet; SUP, supernatant; OG, octylglucoside; PEG, polyethylene glycol.

All the recombinant HMW proteins were expressed as inclusion bodies in *E. coli*, regardless of whether there were complete or partial deletion of the B and C genes in the various constructs, and were purified by the same procedure (FIG. 12) *E. coli* cell pellets from 500 ml culture were resuspended in 50 ml of 50 mM Tris-HCl, pH 8.0, containing 0.1 M NaCl, and disrupted by sonication. The extract was centrifuged at 20,000 g for 30 min and the resultant supernatant was discarded. The pellet ($PPT_1$) was further extracted, in 50 ml of 50 mM Tris-$HCl_1$, pH 8.0 containing 0.5% Triton X-100 and 10 mM EDTA, then centrifuged at 20,000 g for 30 min, and the supernatant was discarded. The pellet ($PPT_2$) was further extracted in 50 ml of 50 mM Tris-HCl, pH 8.0, containing 1% octylglucoside, then centrifuged at 20,000 g for 30 min, and the supernatant was discarded.

The resultant pellet ($PPT_3$), obtained after the above extractions, contains the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added to this solution and the mixture was centrifuged at 20,000 g for 30 min. The supernatant ($SUP_4$) was precipitated with polyethylene glycol (PEG) 4000 at a final concentration of 7%. The resultant pellet ($PPT_5$) was removed by centrifugation at 20,000 g for 30 min and the supernatant was precipitated by $(NH_4)_2SO_4$ at 50% saturation. After the addition of $(NH_4)_2SO4$, the solution underwent phase separation with protein going to the upper phase, which was then subjected to centrifugation at 20,000 g for 30 min. The resultant pellet ($PPT_6$) was dissolved in 2 ml of 50 mM Tris-HCl, pH 8.0, containing 6 M guanidine HCl and 5 mM DTT and the clear solution was purified on a Superdex 200 gel filtration column equilibrated in 50 mM Tris-HCl, pH 8.0, containing 2 M guanidine HCl. The fractions were analysed by SDS-PAGE and those containing the purified rHMW1 were pooled and dialysed overnight at 4° C. against PBS, then centrifuged at 20,000 g for 30 min. The protein remained soluble under these conditions and glycerol was added to the rHMW1 preparation at a final concentration of 20% for storage at −20° C.

Figure 13:
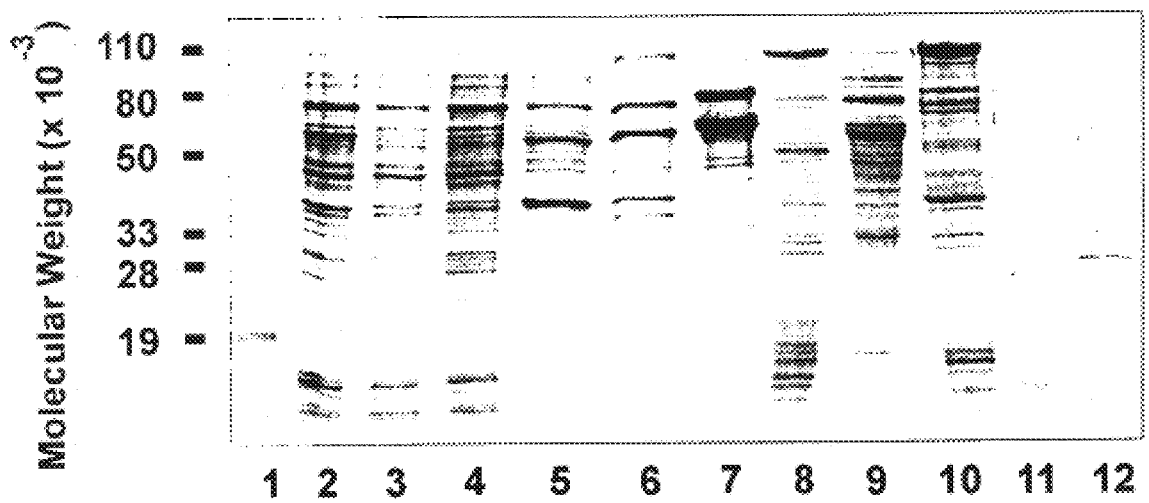
FIG. 13 shows the SDS-PAGE analysis of rHMW1 extractions. Lane 1, prestained protein molecular weight markers; lane 2, *E. coli* whole cell lysates; lane 3, soluble proteins in the Tris-HCl/NaCl extraction; lane 4, soluble proteins in the Tris-HCl/Triton X-100/EDTA extraction; lane 5, soluble proteins in the Tris-HCl/octylglucoside extraction; lane 6, pellet after Tris-HCl/octylglucoside extraction; lane 7, insoluble proteins in 2M guanidine HCl; lane 8, supernatant of 7% PEG precipitation; lane 9, pellet of 7% PEG precipitation; lane 10, interphase pellet of 50% ammonium sulfate precipitation; lane 11, proteins recovered in the lower phase; lane 12, proteins recovered in the upper phase.
Figure 14:
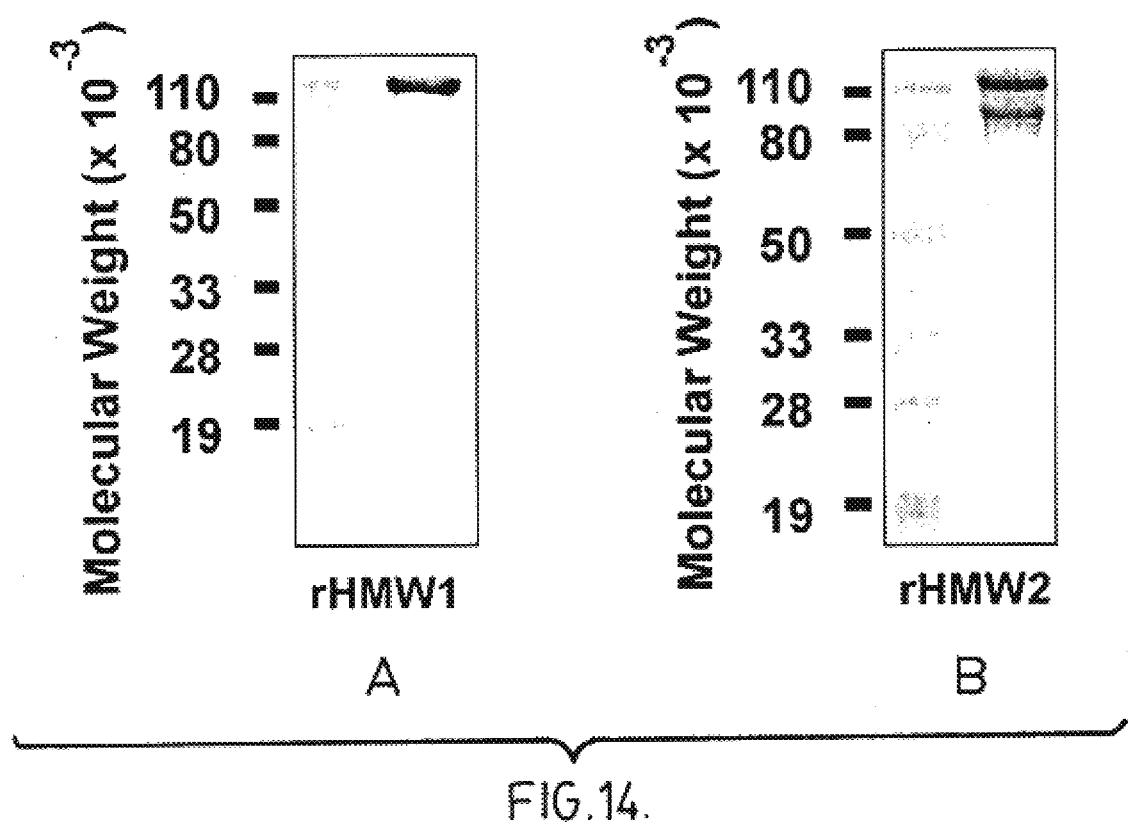
FIG. 14, comprising panels A and B, shows an SDS-PAGE analysis of the purified rHMW1 and rHMW2.

SDS-PAGE analysis of a representative rHMW1 protein (abc/cer) at various stages of purification is shown in FIG. 13. The identification of the lanes is given above in the description of the Figures. Three major protein bands at approximately 110, 80, and 60 kDa, (lane 6) were evident after the initial three extractions with 50 mM Tris-HCl/0.1 M NaCl, pH 8.0 (lane 3); 50 mM Tris-HCl/0.5% Triton X-100, pH 8.0 (lane 4); and 50 mM Tris-HCl/1% octylglucoside, pH 8.0 (lane 5). These three proteins represent the products of hmw1A, C and B genes, respectively, as confirmed by N-terminal amino acid sequencing. The products of the B and C genes were less soluble in the guanidine hydrochloride solution (lane 7), and were easily separated from the gene A product (HMW1, lane 8) by diluting the guanidine HCl concentration from 6 M to 2 M. Precipitation with 7% polyethylene glycol (PEG) 4000 removed other contaminating proteins (lane 9) from the rHMW1 preparation. A final ammonium sulfate precipitation not only concentrated rHMW1 from the PEG soluble fraction (lane 10), but also effectively removed the residual PEG (lane 11) and (NH4)$_2SO_4$ salt (lane 12) through a phase separation that resulted from the mixing of the PEG solution with a high concentration of $(NH_4)_2SO_4$. The rHMW1 pellet was then dissolved in 50 mM Tris-HCl, pH 8.0, containing 6 M guanidine HCl and 5 mM DTT, and purified on a Superdex 200 gel filtration column pre-equilibrated in 50 mM Tris-HCl, pH 8.0, containing 2 M guandine HCl (FIG. 14, panel A). The average yield of the purified rHMW1 is about 10 mg $L^{-1}$ culture. SDS-PAGE analysis of the purification of rHMW2A from construct T7 hmw2A/T7 hmw2A is shown in FIG. 14, panel B.

Example 13

This Example illustrates the stability of the purified rHMW1A protein.

Figure 15:
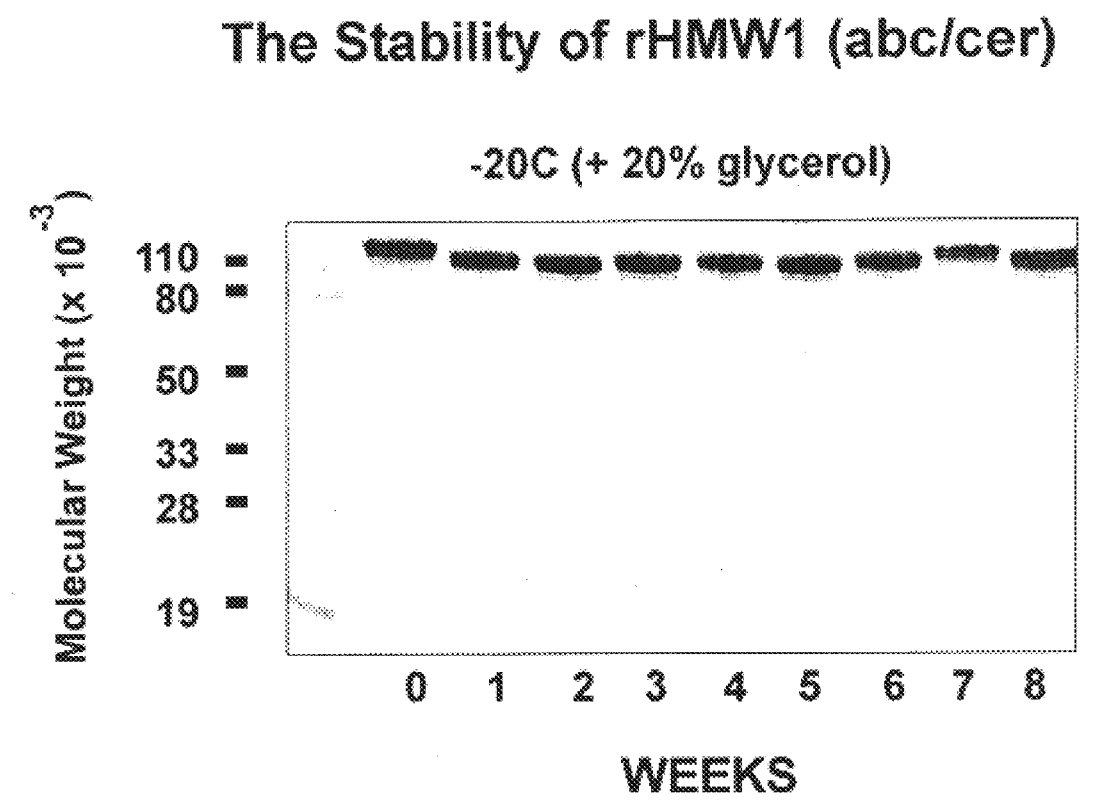

To study the stability of rHMW1A, the purified rHMW1A protein produced in accordance with Example 12 was stored at 4° C. or −20° C. with or without glycerol. In the absence of glycerol, the protein was found to be degraded when stored at 4° C. and tended to precipitate when stored at −20° C. The addition of glycerol to a final concentration of 20% not only significantly enhanced the solubility of rHMW1A, but also increased the stability of the protein when stored at −20° C. The protein remained intact for at least eight weeks even after repeated freezing and thawing (FIG. 15).

Example 14

This Example illustrates the immunogenicity of rHMW1A and rHMW2A proteins produced from different constructs.

Figure 10:
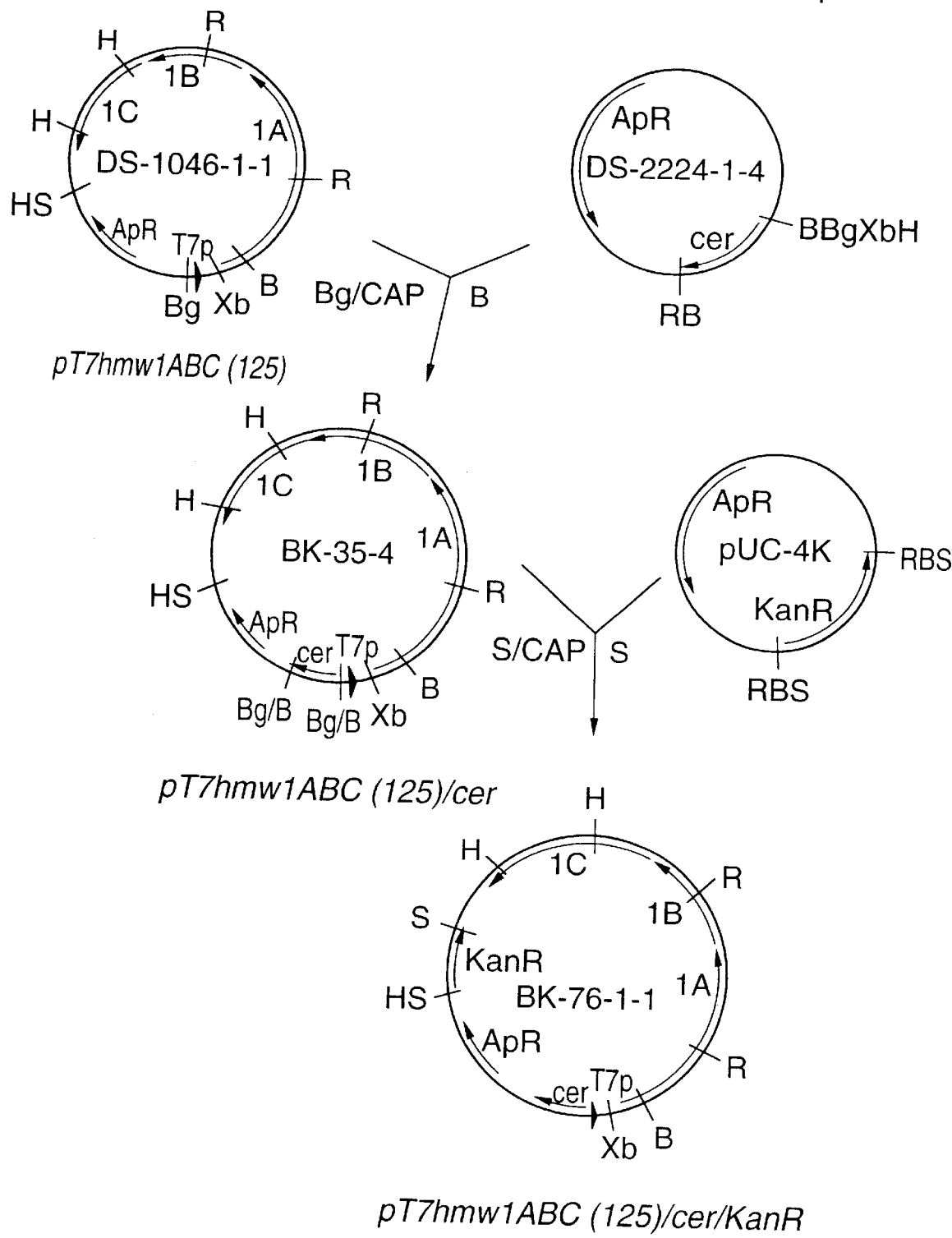
FIG. 10 shows the construction scheme to generate plasmids BK-35-4 and BK-76-1-1 that contain T7 hmw1ABC/cer genes encoding the mature 125 kDa HMW1A protein, utilizing ampicillin or kanamycin selection, respectively. Restriction enzyme sites are: B, BamH I; Bg, Bgl II; H, Hind III; K, Kpn I; R, EcoR I; S, Sal I; Xb, Xba I. Other abbreviations are: T7p, T7 promoter; ApR, ampicillin resistance gene; KanR, kanamycin resistance gene; CAP, calf alkaline phosphatase.

To study the immunogenicity of the rHMW1 protein produced from T7 hmw1ABC (pDS-1046-1-1; FIG. 3A, Example 3) or T7 hmw1ABC/cer (pBK-76-1-1; FIG. 10, Example 10) constructs and purified by the procedure of Example 12, groups of five BALB/c mice (Charles River, Quebec) were immunized s.c. on days 1, 29, and 43 with 0.3, 1, and 3 μg of antigen, in the presence AlPO$_4$ (1.5 mg per dose). Blood samples were collected on days 0, 14, 28, 42 and 56.

Figure 16A:
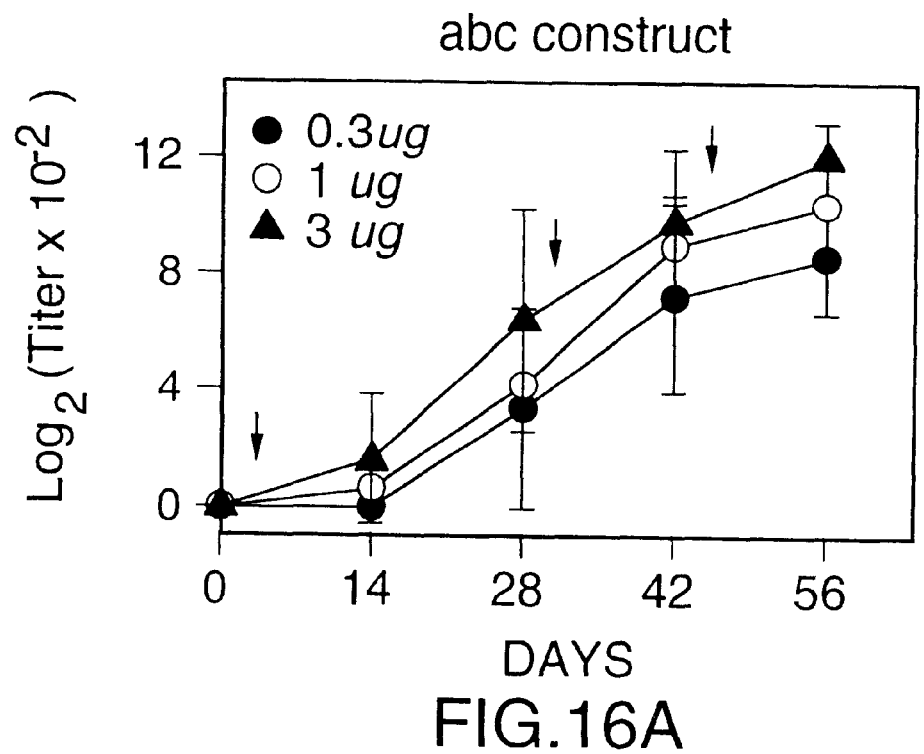
FIGS. 16A and 16B show the immunogenicity of rHMW1A protein produced from various constructs.
Figure 16B:
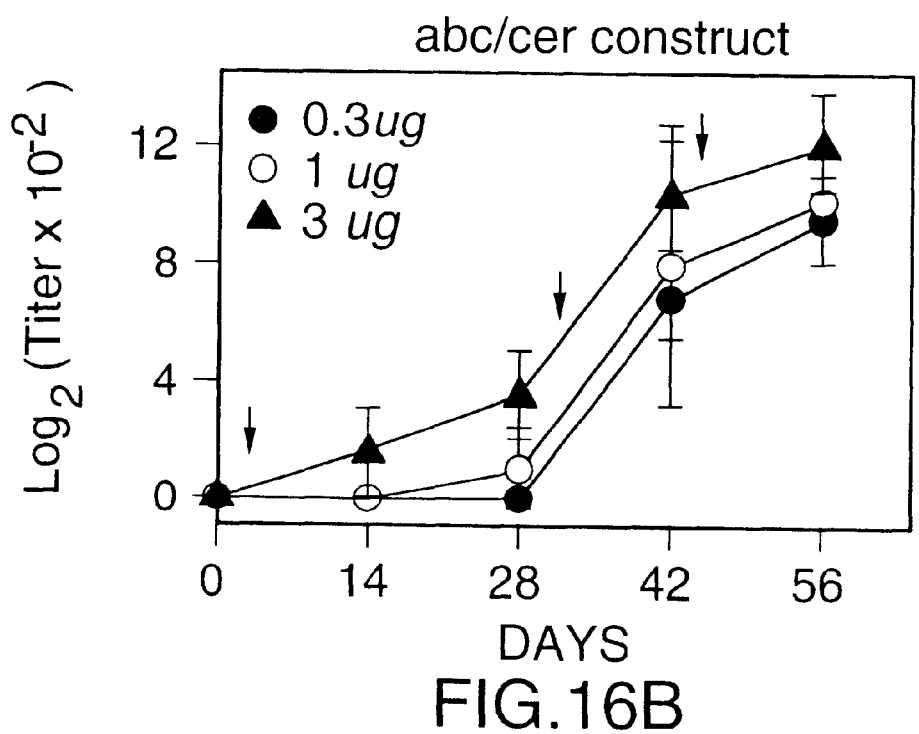

Mice immunized with purified rHMW1 derived from the T7 hmw1ABC or T7 hmw1ABC/cer constructs (0.3 to 3 μg per dose), generated dose-dependent anti-rHMW1 antibody responses (FIG. 16), suggesting that both proteins had remained immunogenic after inclusion body extraction and solubilization. No statistically significant difference was found in the antibody titers induced by the protein from these two constructs in mice.

To compare the immunogenicity of rHMW1 and rHMW2 proteins produced from several different constructs and purified according to Example 12, groups of 9 chinchillas (Moulton Chinchilla Ranch) were immunized i.m. on days 1, 14, and 28 with 30 pg of rHMW protein in the presence AlPO$_4$ (1.5 mg per dose). Blood samples were collected on day 42. Chinchilla anti-HMW antibody responses induced by various forms of rHMW are summarized in Table 1.

It was found that the rHMW1 prepared from the T7 hmw1ABC (abc) (pDS-1046-1-1; FIG. 3A, Example 3), T7 hmw1A/T7 hmw1ABC (a/abc) (pBK-86-1-1; FIG. 9, Example 9), T7 hmw1ABC/cer (abc/cer) (pBK76-1-1; FIG. 10, Example 10), and T7 hmw1A/T7 hmw1A (2xa) (pJB-2369-6; FIG. 7, Example 7) constructs, but not the T7 hmw1AB(125) (abΔ) (pDS-1122-2; FIG. 5, Example 5) construct, induced significant antibody titers in chinchillas after three immunizations. Similarly, the rHMW2 prepared from T7 hmw2ABC (abc) (pDS-1147-4; FIG. 4A, Example 4) or T7 hmw2A/T7 hmw2A (2xa) (pDS-2084-1; FIG. 8A, Example 8) constructs and purified following the procedure of Example 12 elicited significant antibody titers in chinchillas after three immunizations.

Anti-rHMW IgG titers were determined by antigen-specific enzyme-linked immunosorbent assays (EIAs). Microtiter wells (Nunc-MAXISORP, Nunc, Denmark) were coated with 50 μl of protein antigen (0.5 μg ml$^{-1}$). The reagents used in the assays are as follows: affinity-purified F(ab')$_2$ fragments of goat anti-mouse IgG (Fc-specific) conjugated to horseradish peroxidase (Jackson ImmunoResearch Labs, Mississauga, Ontario); affinity-purified guinea pig anti-IgG antibody (1 μg ml$^{-1}$) (prepared by this laboratory); and affinity-purified F(ab')$_2$ fragment of goat anti-guinea pig IgG (H+L) antibodies conjugated to horseradish peroxidase (HRP) (Jackson ImmunoResearch Laboratories) used as a reporter. Chinchilla IgG was purified from chinchilla serum according to Barenkamp (ref. 14). Generation and purification of guinea pig anti-chinchilla IgG antibodies were described earlier (ref. 15). The reactions were developed using tetramethylbenzidine (TMB/H$_2$O$_2$, ADI, Mississauga, Ontario) and absorbancies were measured at 450 nm (using 540 nm as a reference wavelength) in a Flow Multiskan MCC microplate reader (ICN Biomedicals, Mississauga, Ontario). The reactive titer of an antiserum was defined as the reciprocal of the dilution consistently showing a two-fold increase in absorbance over that obtained with the pre-bleed serum sample.

Example 15

This Example illustrates the protective ability of rHMW1A and rHMW2A proteins produced from different constructs.

The immunization and intranasal challenge with freshly grown streptomycin resistant NTHi strain 12 in chinchillas has been described (ref. 15). Briefly, groups of 8 to 9 animals were immunized three times i.m. with one of: 30 μg of purified rHMW1 or rHMW2, 2×10$^9$ cfu of heat inactivated (56° C., 10 min) NTHi whole cells in alum, or alum alone on days 0, 14 and 28. Serum samples and nasal wash samples were taken on day 42 for measurement of anti-HMW1 or anti-rHMW2 antibody titers by EIAs.

On day 44, animals were lightly anesthetized using xylazine/ketamine HCl by intramuscular injection (0.06 mg xylazine and 0.3 mg ketamine HCl per kg body weight). Intranasal inoculations were performed via passive inhalation (50 μl per nares, total 0.1 ml per animal) of freshly cultured streptomycin-resistant NTHi strain 12 in BHI medium supplemented with hemin and NAD both at 2 pg ml$^{-1}$. The dose of bacterial challenge was 1×10$^8$ cfu per animal. Nasopharyngeal lavages were performed 4 days post inoculation on anesthetized chinchillas (xylazine/ketamine HCl, same route and dose as on day 44). Secretions were obtained by irrigating the nasopharynx with 1 ml sterile saline and collecting fluid out of the contralateral nares. Normally, about 500 μl of fluid was collected from each animal and 25 μl of sample was plated on a chocolate agar plate in the presence of 50 μl of streptomycin (20 mg ml$^{-1}$).

The protective effect of parenteral immunization with various rHMW1 and rHMW2 preparations on NP colonization of chinchilla nasopharynx with NTHi strain 12 is summarized in Table 2. 67 to 88% of the control animals immunized with alum only, had culture-positive nasal lavage fluids. In contrast, 67 to 80% of animals immunized with the rHMW1 protein purified from the constructs abc (pDS-1046-1-1), a/abc (pBK86-1-1), or abc/cer (pBK-76-1-1) were largely protected. In animals immunized with the rHMW1 protein derived from either construct abΔ (pDS-1122-2) or construct 2xa (pJB-2369-6), 70 to 90% were infected. These results clearly indicated that, in order to achieve a significant protection against NTHi strain 12 colonization in the chinchilla model, the rHMW1 protein must be derived from a construct with intact ABC genes.

Similar results were also observed with rHMW2 protein. As shown in Table 2, animals immunized with the rHMW2 protein purified from the construct abc (pDS-1147-4), but not from the construct 2xa (pDS-2084-1), were protected against NTHi strain 12 colonization in the chinchilla model. In all cases, significant protection was observed in chinchillas immunized with the heat-inactivated NTHi 12 whole cell preparations, prepared in accordance with Example of U.S. Pat. 5,603,938.

Example 16

This Example illustrates the cloning and sequence analysis of hmwA genes from additional NTHi strains.

Chromosomal DNA was prepared from several NTHi strains and PCR was performed using the oligonucleotide primers shown in FIG. 17. The sense primer (5522.SL, SEQ ID NO: 21) corresponds to the conserved region in the hmwA genes encoding the residues immediately upstream of the processing site for the mature HMW proteins. The antisense primer (5523.SL, SEQ ID NO: 24) corresponds to the start of the hmwB gene that is also conserved.

PCR amplification was performed as follows: each reaction mixture contained 5–100 ng of DNA, 1 μg of each primer, 5 units of taq+ or tsg+ (Sangon) or taq plus long (Stratagene), 2 mM dNTPs, 20 mM Tris-HCl (pH 8.8), 10 mM KCl, 10 mM (NH$_4$)$_2$SO$_4$, 2 mM MgSO$_4$, 0.1% Triton X-100, BSA. Cycling conditions were: 95° C. for 1 min, followed by 25 cycles of 95° C. for 30 sec, 45° C. for 1 min, 72° C. for 2 min; then 72° C. for 10 min.

The nucleotide (SEQ ID NO: 25) and deduced amino acid (SEQ ID NO: 26) sequences of the hmw1A gene from strain Joyc are shown in FIG. 18. The predicted mature HMW1A protein from strain Joyc (encoding sequence SEQ ID NO: 27, amino acid sequence SEQ ID NO: 28) has a molecular weight of 125.9 kDa and a pI of 8.21. There are no RGD motifs found in Joyc HMW1A. The nucleotide (SEQ ID NO: 29) and deduced amino acid (SEQ ID NO: 30) sequences of the hmw2A gene from strain Joyc are shown in FIG. 19. The predicted mature HMW2A protein from strain Joyc (encoding sequence SEQ ID NO: 31, amino acid sequence SEQ ID NO: 32) has a molecular weight of 100.9 kDa and a pI of 6.91. There are no RGD motifs found in Joyc HMW2A.

The nucleotide (SEQ ID NO: 33) and deduced amino acid (SEQ ID NOS: 34, 35) sequences of the defective hmw1A gene from strain K1 are shown in FIG. 20. Although there is a complete hmw1A gene in strain K1, there is a frameshift immediately following a poly G tract, that results in early termination of the HMW1A protein after 326 amino acids.

The nucleotide (SEQ ID NO: 38) and deduced amino acid (SEQ ID NO: 39) sequences of the hmw1A gene from strain K21 are shown in FIG. 21. The predicted mature HMW1A protein from strain K21 (encoding sequence SEQ ID NO: 40, amino acid sequence SEQ ID NO: 41) has a molecular weight of 104.4 kDa and a pI of 8.71. There is a single RGD motif located at residues 20 to 22 in K21 HMW1A.

The nucleotide (SEQ ID No: 42) and deduced amino acid (SEQ ID NO: 43) sequence of the hmw1A gene from strain LCDC2 are shown in FIG. 22. The predicted mature HMW1A protein from strain LCDC2 (encoding sequence SEQ ID NO: 44, amino acid sequence SEQ ID NO: 45) has a molecular weight of 114.0 and a pI of 8.72. There are no RGD motifs found in LCDC2 HMW1A. The nucleotide (SEQ ID NO: 46) and deduced amino acid (SEQ ID NO: 47) sequences of the hmw2A gene from strain LCDC2 are shown in FIG. 23. The predicted mature HMW2A protein from strain LCDC2 (encoding sequence SEQ ID NO: 48, amino acid sequence SEQ ID NO: 49) has a molecular weight of 111.7 kDa and a pI of 8.22. There are no RGD motifs found in LCDC2 HMW2A.

The nucleotide (SEQ ID NO: 50) and deduced amino acid (SEQ ID NO: 51) sequences of the hmw1A gene from strain PMH1 are shown in FIG. 24. The predicted mature HMW1A protein from strain PMH1 (encoding sequence SEQ ID NO: 52, amino acid sequence ID NO: 53) has a molecular weight of 102.4 kDa and a pI of 6.73. There are two RGD motifs found in PMH1 HMW1A, the first at residues 19 to 21 and the second at residues 505 to 507. The nucleotide (SEQ ID NO: 54) and deduced amino acid (SEQ ID NO: 55) sequences of the hmw2A gene from strain PMH1 are shown in FIG. 25. The predicted mature HMW2A protein from strain PMH1 (encoding sequence SEQ ID NO: 56, amino acid sequence SEQ ID NO: 57) has a molecular weight of 103.9 kDa and a pI of 9.07. There are two RGD motifs found in PMH1 HMW2A, the first at residues 26 to 28 and the second at residues 532 to 534.

The nucleotide (SEQ ID NO: 58) and deduced amfino acid (SEQ ID NO: 59) sequences of the hmw1A gene from strain 15 are shown in FIG. 26. The predicted mature HMW1A protein from strain 15 (encoding seqeunce SEQ ID NO: 60, amino acid sequence SEQ ID NO: 61) has a molecular weight of 103.5 kDa and a pI of 8.06. There are no RGD motifs found in strain 15 HMW1A. The nucleotide (SEQ ID NO: 62) and deduced amino acid (SEQ ID NO: 63) sequences of the hmw2A gene from strain 15 are shown in FIG. 27. The predicted mature HMW2A protein from strain 15 (encoding sequence SEQ ID NO: 64, amino acid sequence SEQ ID NO: 65) has a molecular weight of 121.9 kDa and a pI of 8.22. There are no RGD motifs in strain 15 HMW2A.

The nucleotide (SEQ ID NOS: 66, 70) and deduced amino acid sequence (SEQ ID NOS: 67, 71) for the hmw1A and hmw2A genes, from strain 12, as contained in U.S. Pat. No. 5,603,938, are shown in FIGS. 28 and 29 respectively.

An alignment of the deduced HMW1A and HMW2A protein sequences with the published HMW1A and HMW2A protein sequences from strain 12 (SEQ ID NOS: 67, 71) is shown in FIG. 30. The cleavage site for the mature proteins is shown by the arrow. Regions of similarity can be identified especially between residues about 980 to 1168 and, at the carboxyl terminal, from about residue 1360 to the end. There appear to be repeats in some proteins inserted around residue 1219, most notably in Joyc HMW1A and K1 HMW1A, that appear to have two tandem inserted repeats, while K21 HMW1A and LCDC2 HMW2A contain single copies of the repeat. Strain 15 HMW2A contains a different repeat segment located in the same area. There is a short segment of semi-conserved sequence inserted at residue 583 that is found in all of the HMW2A proteins, except strain 15 HMW2A. However, it is found in the strain 15 HMW1A protein.

Example 17

This Example illustrates the PCR amplification used to determine whether hmw1A or hmw2A genes had been amplified.

The hmwA genes were PCR amplified using primers based upon sequences conserved between hmw1 and hmw2 operons and thus amplified genes could be either hmw1 or hmw2. Although the hmw genes do not occur in encapsulated strains, the 5'- and 3'-flanking sequences can be found in the genome sequence of H. influenzae strain Rd (ref. 16). Oligonucleotide sense primers were generated based upon the 5'-hmw1 flanking sequence from strain Rd gene HI1679 (primer 5672.SL, SEQ ID NO: 74) and the 5'-hmw2 flanking region from strain Rd gene HI1598 (primer 5676.SL (SEQ ID NO: 75)). Antisense primers were generated based upon internal sequences of the amplified hmwA genes. The oligonucleotide primers are shown in FIG. 31. Primer 5742.SL (SEQ ID NO: 78) was used to amplify hmwA genes from strains K1, K21, PMH1 and 15, while primer 5743.SL (SEQ ID NO: 81) was used to PCR hmwA genes from strains Joyc and LCDC2. Amplified fragments were directly sequenced using the hmwA-specific primers (5742.SL and 5743.SL)

and the sequence compared to the sequence of the genes cloned in Example 16. After the PCR amplified hmwA genes were identified as hmw1A or hmw2A, specific PCR primers were used to PCR amplify a second copy of the gene with a start codon engineered at the start of the mature protein. A representative pair of PCR primers, used to amplify the LCDC2 hmw2A gene for expression, are illustrated in FIG. 33B (5972.SL, SEQ ID NO: 92; 5973.SL, SEQ ID NO: 95).

Example 18

This Example illustrates the construction of a generic plasmid for expression of hmwABC genes in E. coli.

As shown in Example 16, the hmw1A and hmw2A genes can be PCR amplified from any hmw-containing strain of non-typeable H. influenzae, but to produce protective recombinant antigen, they must be expressed in the presence of hmwBC genes. A generic expression plasmid was constructed that contains the T7 promoter, strain 12 hmw1BC genes, the E. coli cer gene, a kanamycin resistance gene, and a cloning site to insert any hmwA gene.

Figure 32A:
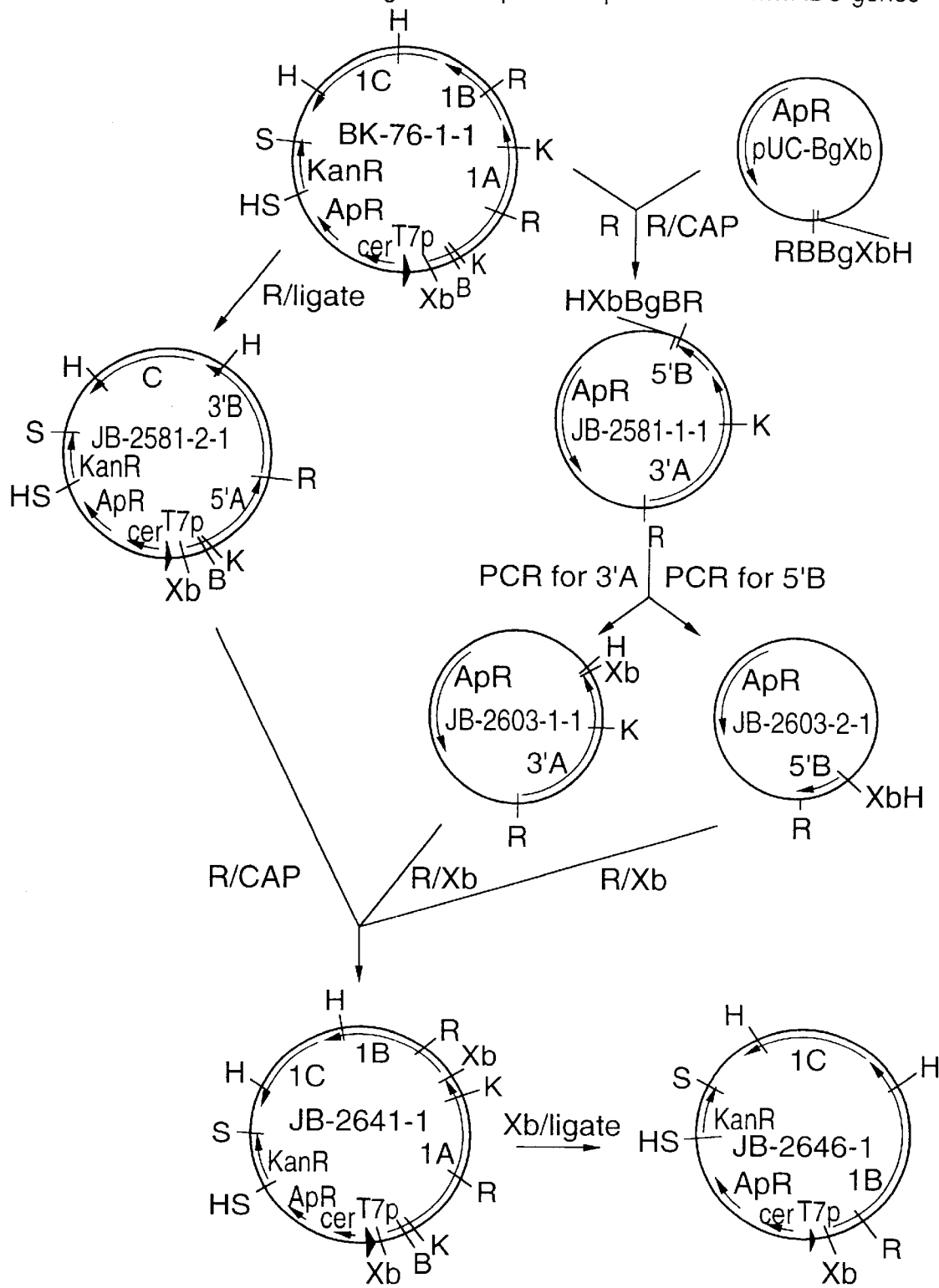
FIG. 32A shows the construction scheme to generate the generic T7 hmwABC expression plasmid JB-2646-1 into which can be inserted any hmwA gene. Restriction enzyme sites are: B, BamH I; Bg, Bgl II; H, Hind III; K, Kpn I; R, EcoR I; S, Sal I; Xb, Xba I. Other abbreviations are: T7p, T7 promoter; ApR, ampicillin resistance gene; KanR, kanamycin resistance gene; CAP, calf alkaline phosphatase.
Figure 32B:
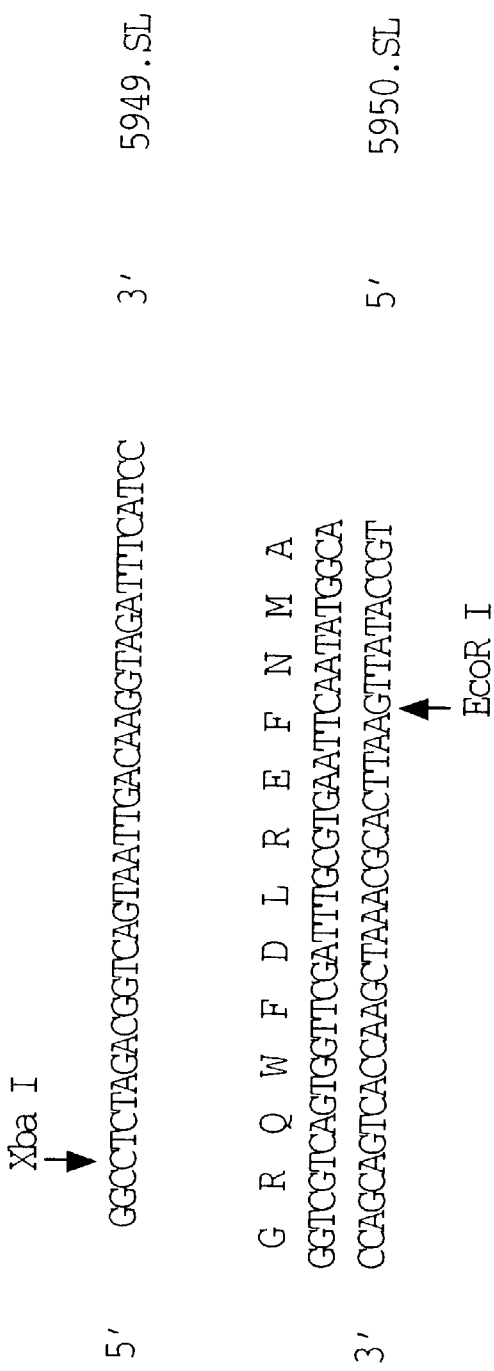
FIGS. 32B and 32B' show the oligonucleotides (SEQ ID NOS: 82, 83, 84, 85, 86, 87, 88, 89, 90) used to PCR amplify the 3'-end of hmw1A and the 5'-end of hmw1B in the construction scheme of FIG. 32A.
Figure 33A:
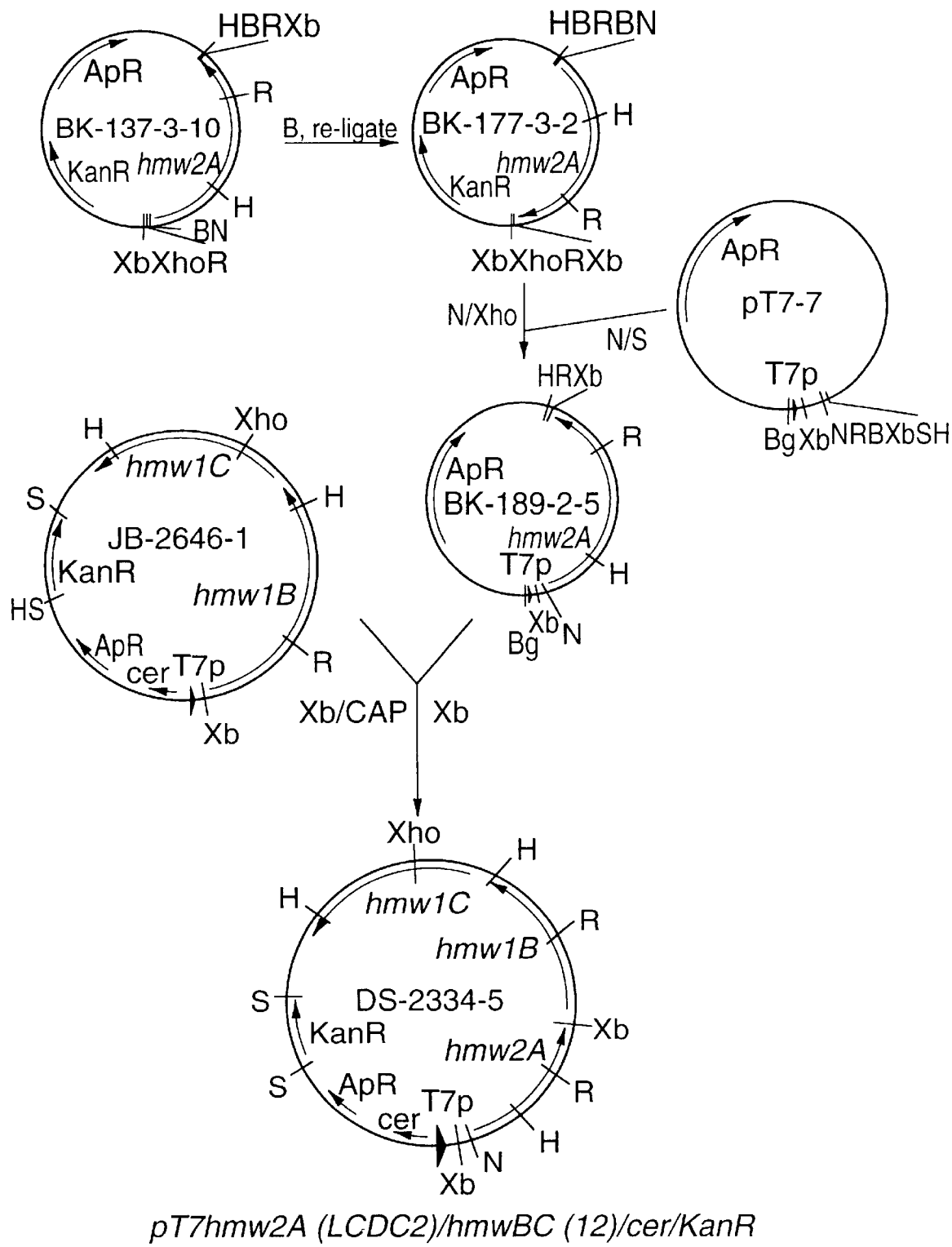
FIG. 33A shows the construction of DS-2334-5 that contains a chimeric T7 hmwABC gene of the LCDC2 hmw2A gene and NTHI 12 hmwBC genes. Restriction enzyme sites are: B, BamH I; Bg, Bgl II; H, Hind III; K, Kpn I; N, Nde I; R, EcoR I; S, Sal I; Xb, Xba I, Xho, Xho I. Other abbreviations are: T7p, T7 promoter; ApR, ampicillin resistance gene; KanR, kanamycin resistance gene; CAP, calf alkaline phosphatase.

Plasmid BK-76-1-1 (FIG. 10, Example 10) was digested with EcoR I and re-ligated to generate plasmid JB-2581-2-1, which has the 2 kb EcoR I fragment containing the 3'-end of hmw1A and the 5'-end of hmw1B deleted (FIG. 32A). The 2 kb EcoR I fragment from BK-76-1-1 was subcloned into pUC-BgXb for further manipulation, creating plasmid JB-2581-1-1. FIG. 32B shows the oligonucleotide primers used to amplify the 3'-end of hmw1A (5947.SL, SEQ ID NO: 83; 5948.SL, SEQ ID NO: 86) and the 5'-end of hmw1B (5949.SL, SEQ ID NO: 87; 5950.SL, SEQ ID NO: 90), introducing a Xba I site at the junction of the two genes. Plasmid JB-2603-1-1 contains a 1.5 kb EcoR I-Xba I 3'-fragment of the hmw1A gene and plasmid JB-2603-2-1 contains the approximately 550 bp Xba I-EcoR I fragment of the hmw A-B intergenic sequence and 5'-end of hmw1B. Plasmid JB-2581-2-1 was linearized with EcoR I, dephosphorylated, and ligated with the EcoR I-Xba I inserts from JB-2603-1-1 and JB-2603-2-1, generating plasmid JB-2641-1. This plasmid is identical to BK-76-1-1, except that it contains an extra Xba I site between the hmw1A and hmw1B genes. Plasmid JB-2641-1 was digested with Xba I which deleted the complete hmw1A gene, but left the hmw1BC genes intact. Re-ligation of the vector fragment generated plasmid JB-2646-1 that is the generic expression vector into which hmwA genes can be cloned at the Xba I site (FIG. 32A).

To demonstrate the utility of the generic expression vector, a chimeric T7 hmwABC gene cassette was generated containing the LCDC2 hmw2A gene combined with the strain 12 hmw1BC genes. The LCDC2 hmw2A gene was PCR amplified using the primers illustrated in FIG. 33B and cloned into pCR II, generating plasmid BK-137-3-10, that contains the hmw2A gene in an anti-clockwise orientation. In order to change the orientation of the hmw2A gene for cloning purposes, the plasmid was digested with BamH I to release the hmw2A insert, then both fragments re-ligated. Plasmid BK-177-3-2 contains the LCDC2 hmw2A gene in a clockwise orientation. Plasmid BK-177-3-2 was digested with Nde I and Xho I and the hmw2A fragment was ligated into pT7-7 that had been digested with Nde I and Sal I, to generate plasmid BK-189-2-5. The generic expression plasmid JB-2646-1 (FIG. 32A) was linearized with Xba I and dephosphorylated. Plasmid BK-189-2-5 was digested with Xba I that released the hmw2A gene ready to be inserted into the expression vector. Plasmid DS2334-5 thus contains a T7 hmwABC gene cassette comprised of the hmw2A gene from LCDC2 and the hmw1BC genes from strain 12.

Example 19

This Example illustrates the construction of plasmid DS-2400-13, that contains a T7 hmwA/T7 hmwABC cassette, the E. coli cer gene, and a kanamycin resistance genes.

Plasmid DS-1843-2 is a tetracycline resistant pBR328-based vector containing a multiple cloning site inserted between the EcoR I and Pst I sites. DS-1843-2 was linearized with Xho I and dephosphorylated and the kanamycin resistance gene from pUC-4K was inserted on a Sal I fragment, generating plasmid DS-2372-31 that is both tetracycline and kanamycin resistant. Plasmid DS-2372-31 was linearized with Bgl II and dephosphorylated, and the synthetic E. coli cer gene from DS-2224-1-4 was inserted on a BamH I fragment, generating plasmid DS-2379-2-6. Plasmid DS-1046-1-1 (FIG. 3A, Example 3) was digested with Bgl II and Sal I and the T7 hmwABC gene fragment was inserted into DS-2379-2-6 that had been digested with BamH I and Sal I. The resulting plasmid (DS-2391-1) is a pBR-based kanamycin resistant and tetracycline sensitive vector containing the T7 hmwABC genes and the E. coli cer gene. JB-2369-6 (FIG. 7, Example 7) was digested with BamH I to release an internal 3' hmwA/T7 5' hmwA fragment that was inserted into the unique BamH I site of the pBR T7 hmwABC/cer/kanR vector. The resulting pBR T7 hmwA/T7 hmwABC/cer/kanR plasmid (DS-2400-13) thus contains multiple hmwA genes (see FIG. 34).

SUMMARY OF THE DISCLOSURE

In summary of this disclosure, the present invention provides nucleic acid molecules and constructs incorporating the same which permit the recombinant production of high molecular weight proteins of non-typeable Haemophilus influenzae which are protective. Modifications are possible within the scope of the invention.

TABLE 1

Immunogenicity of various forms of HMW1 and HMW2 in chinchillas.

| HMW preparations | Anti-HMW antibody titers Log2 (Titers/100) |
|---|---|
| HMW1/HMW2 native | 7.11 ± 0.78 |
|  | 7.75 ± 0.66 |
| HMW1 abc | 9.67 ± 1.12 |
|  | 10.78 ± 0.83 |
| HMW1 a/abc | 8.44 ± 0.88 |
| HMW1 abc/cer | 7.11 ± 0.93 |
|  | 7.44 ± 0.88 |
| HMW1 abΔ | 1.00 ± 0.50 |
|  | 2.17 ± 1.67 |
| HMW1 2xa | 12.29 ± 0.49 |
| HMW2 abc | 9.22 ± 1.48 |
|  | 11.44 ± 0.78 |
| HMW2 2xa | 12.89 ± 0.78 |
| alum | <0.05 |
|  | <0.05 |

Groups of 9 chinchillas were immunized (i.m.) on days 1, 14 and 28 with 30 µg of the indicated antigens adsorbed to alum. Blood samples were collected on day 42. The reactive titer of an antiserum was defined as the reciprocal of the dilution consistently showing a two fold increase in absorbance over that obtained with the prebleed serum sample. Two sets of numbers indicate two sets of experiments.

TABLE 2

Protective abilities of various forms of HMW1 and HMW2 against NP colonization with NTHi strain 12 in chinchillas.

| HMW preparations | # of infected animals/ # of total animals challenged (%) | median cfu/25 µl nasal lavage |
| --- | --- | --- |
| HMW1/HMW2 native + alum | 2/9 (22.2%) | 11* |
| alum | 7/9 (77.8%) | 800 |
| HMW1abc + alum | 2/9 (22.2%) | 6* |
| alum | 7/9 (77.8%) | 800 |
| HMW1 a/abc + alum | 2/9 (22.2%) | 20* |
| alum | 6/9 (66.7%) | 300 |
| HMW1 abc/cer + alum | 3/9 (33.3%) | 60* |
| alum | 7/9 (77.8%) | 1000 |
| HMW1 abΔ + alum | 8/9 (89.9%) | 500 |
| alum | 7/8 (87.5%) | 1270 |
| HMW1 2xa + alum | 5/7 (71.5%) | 400 |
| alum | 7/9 (77.8%) | 630 |
| HMW2 abc + alum | 2/9 (22.2%) | 7* |
| HMW2 2xa + alum | 7/9 (77.8%) | 800 |
| alum | 7/9 (77.8%) | 1000 |

Groups of 9 chinchillas were immunized (i.m.) on days 1, 14 and 28 with 30 µg of indicated antigens adsorbed to alum. Blood samples were collected on day 42. On day 44, animals were challenged by intranasal inoculations with freshly cultured streptomycin-resistant NTHi strain 12. The dose of bacterial challenge was $1 \times 10^8$ cfu per animal. Nasopharyngeal lavages were performed 4 days post inoculation and 25 µl of the nasal lavage were plated on chocolate agar plates.

An animal was defined as infected if >50 cfu of bacteria were recovered from 25 µl nasal lavage fluid. * Statistical significance was found when compared to the control animals by Mann-Whitney Rank Sum Test (p<0.05).

TABLE 3

Molecular weights of Mature HMW Protein from Various H. influenzae non-typeable Strain

| Molecular Weight | Non-typeable H. influenzae Strain | | | | | |
| --- | --- | --- | --- | --- | --- | --- |
| (kDa) | 12 | JoyC | K21 | LCDC2 | PMH1 | 15 |
| Mature Protein | | | | | | |
| HMW1 | 125 | 125.9 | 104.4 | 114.0 | 102.4 | 103.5 |
| HMW2 | 120 | 100.9 | | 111.7 | 103.9 | 121.9 |

REFERENCES

1. Berkowitz et al. 1987. J. Pediatr. 110:509.
2. Claesson et al. 1989. J. Pediatr. 114:97.
3. Black, S. B., H. R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97–104.
4. Madore, D. V. 1996. Impact of immunization on *Haemophilus influenzae* type b disease. Infectious Agents and Disease 5:8–20.
5. Bluestone, C. D. 1982. Current concepts in otolaryngology. Otitis media in children: to treat or not to treat? N. Engl. J. Med. 306:1399–1404.
6. Barenkamp, S. J., and F. F. Bodor. 1990. Development of serum bactericidal activity following nontypable *Haemophilus influenzae* acute otitis media. Pediatr. Infect. Dis. 9:333–339.
7. Barenkamp, S. J., and E. Leininger. 1992. Cloning, expression, and DNA sequence analysis of genes encoding nontypeable *Haemophilus influenzae* high-molecular-weight surface-exposed proteins related to filamentous hemagglutinin of *Bordetella pertussis*. Infect. Immun. 60:1302–1313.
8. Barenkamp, S. J., and J. W. St. Geme III. 1994. Genes encoding high-molecular-weight adhesion proteins of nontypeable *Haemophilus influenzae* are part of gene clusters. Infect. Immun. 62:3320–3328.
9. St. Geme III, J. W. and S. Grass. 1998. Secretion of the *Haemophilus influenzae* HMW1 and HMW2 adhesins involves a periplasmic intermediate and requires the HMWB and HMWC proteins. Molec. Microbiol. 27:617–630.
10. St. Geme III, J. W., S. Falkow, and S. J. Barenkamp. 1993. High-molecular-weight proteins of nontypeable *Haemophilus influenzae* mediate attachment to human epithelial cells. Proc. Natl. Acad. Sci. USA 90:2875–2879.
11. Barenkamp, S. J. 1996. Immunization with high-molecular-weight adhesion proteins of nontypeable *Haemophilus influenzae* modifies experimental otitis media in chinchillas. Infect. Immun. 64:1246–1251.
12. Tabor, S., and C. C. Richardson. 1985. A bacteriophage T7 RNA polymerase/promoter system for controlled exclusive expression of specific genes. Proc. Natl. Acad. Sci. USA 82:1074–1078.
13. Patient, M. E., and D. K. Summers. 1993. ColE1 multimer formation triggers inhibition of *Escherichia coli* cell division. Molec. Microbiol. 9:1089–1095.
14. Barenkamp, S. 1986. Protection by serum antibodies in experimental nontypeable *Haemophilus influenzae* otitis media. Infect. Immun. 52:572–578.
15. Yang, Y. -P., S. M. Loosmore, B. Underdown, and M. H. Klein. 1998. Nasopharyngeal colonization with nontypeable *H. influenzae* in chinchillas. Infect. Immun. 66:1973–1980.
16. Fleischmann et al. 1995. Whole-genome random sequencing and assembly of *Haemophilus influenzae* Rd. Science 269:496–512.
17. O'Hagan, DT. 1992. Oral delivery of vaccines. Formulation and clinical pharmaco kinetic considerations. Clin. Pharmacokinet 22(t): 1–10.
18. Ulmer et al. 1993. Curr. Opinion Invest. Drugs 2:983–989.
19. Lockhoff, O., 1991. Glycolipids as immunomodulators: Synthesis and properties.
20. Nixon-George A., et al., 1990. The adjuvant effect of stearyl tyrosine on a recombinant subunit hepatitis B surface antigen. J. Immunol 144 (12): 4798–4802.

What we claim is:

1. A nucleic acid molecule comprising a promoter functional in *E. coli* and operatively coupled to a modified operon of a non-typeable strain of *Haemophilus influenzae* comprising a modified gene A, a B gene and a C gene and which encodes a high molecular weight (HMW) protein, wherein the modified A gene of the operon contains only a nucleic acid sequence which codes for a mature high molecular weight (HMW) protein of the non-typeable strain of *Haemophilus influenzae* and lacks the segment of the A gene which encodes the leader sequence for the HMW protein.

2. The nucleic acid molecule of claim 1 wherein said promoter is the T7 promoter.

3. The nucleic acid molecule of claim 1 wherein said operon encodes the high molecular weight protein 1 (HMW1) of the non-typeable strain of *Haemophilus influenzae*.

4. The nucleic acid molecule of claim 1 wherein said a non-typeable strain of Haemophilus is selected from the group consisting of strains 12, Joyc, K21, PMH1 and 15 of non-typeable *Haemophilus influenzae*.

5. The nucleic acid molecule of claim 1 wherein said operon encodes the high molecular weight protein 2 (HMW2) of the non-typeable of *Haemophilus influenzae*.

6. The nucleic acid molecule of claim 5 wherein the non-typeable strain of Haemophilus is selected from the group consisting of strains 12, Joyc, K21, LCDC2, PMH1 and 15 of non-typeable *Haemophilus influenzae*.

7. The nucleic acid molecule of claim 1 wherein said nucleic acid sequence which codes for a mature high molecular weight protein has a nucleic acid sequence selected from those having SEQ ID NOS: 27, and 31.

8. The nucleic acid molecule of claim 1 wherein said nucleic acid sequence which codes for a mature high molecular weight protein encodes a HMW1 or HMW2 protein having an amino acid sequence selected from those having SEQ ID NOS: 28, and 32.

9. The nucleic acid molecule of claim I further comprising a further copy of the nucleic acid sequence encoding the mature high molecular weight protein of a non-typeable strain of *Haemophilus influenzae*.

10. The nucleic acid molecule of claim 1 further comprising the cer gene of *E. coli*.

11. The nucleic acid molecule of claim 1 further comprising the cer gene of *E. coli* and a further copy of the nucleic acid sequence encoding the mature high molecular weight protein of a non-typeable strain of *Haemophilus influenzae*.

12. An isolated and purified nucleic acid molecule encoding a high molecular weight (HMW) protein of a non-typeable strain of *Haemophilus influenzae* consisting of:

(a) a DNA sequence selected from the group consisting of SEQ ID NOS: 25, 27, 29, and 31; or (b) a DNA sequence encoding a high molecular weight protein having an amino acid sequence selected from the group consisting of SEQ ID NOS: 26, 28, 30, and 32.

13. A vector for transformation of a host cell comprising the nucleic acid molecule of claim 1.

14. The vector of claim 13 which is a plasmid vector.

15. The vector of claim 14 wherein said plasmid which is selected from group consisting of:

| | |
|---|---|
| DS-1046-1-1 | (ATCC No.: 203263), |
| JB-2507-7 | (ATCC No.: 203262), |
| BK-86-1-1 | (ATCC No.: 203258), |
| BK-35-4 | (ATCC No.: 203259), |
| BK-76-1-1 | (ATCC No.: 203261), |
| DS-2334-5 | (ATCC No.: 203260), and |
| DS-2400-13 | (ATCC No.: 203257). |

16. A strain of *E. coli* transformed by an expression vector of claim 14 and expressing a protective high molecular weight protein of a non-typeable strain of Haemophilus.

17. A method of the production of a protective high molecular weight protein of a non-typeable strain of *Haemophilus influenzae*, which comprises:

transforming *E. coli* with a vector as claimed in claim 14, growing *E. coli* to express the encoded mature high molecular weight (HMW) protein, B, protein and C protein and isolating and purifying the expressed HMW protein.

18. The method of claim 17 wherein said non-typeable strain of Haemophilus is selected from the group consisting of strains 12, Joyc, K21, LCDC2, PMH1 and 15 of non-typeable Haemophilus.

19. The method of claim 17 wherein the high molecular weight protein is an HMW1 protein of the non-typeable strain of Haemophilus.

20. The method of claim 17 wherein the high molecular weight protein is an HMW2 protein of the non-typeable strain of Haemophilus.

21. The method of claim 17 wherein said isolation and purification procedure includes separating the HMWA protein from the B and C proteins.

* * * * *

SEQUENCE LISTING

<160> NUMBER OF SEQ ID NOS: 95

<210> SEQ ID NO 1
<211> LENGTH: 15
<212> TYPE: PRT
<213> ORGANISM: Haemophilus influenzae

<400> SEQUENCE: 1

Met Asn Lys Ile Thr Arg Leu Lys Phe Ser Lys Arg Leu Asn Ala
 1               5                  10                  15

<210> SEQ ID NO 2
<211> LENGTH: 86
<212> TYPE: DNA
<213> ORGANISM: Haemophilus influenzae

<400> SEQUENCE: 2
ctagaaataa ttttgtttaa ctttaagaag gagatataca tatgaacaag atatatcgtc    60
tcaaattcag caaacgcctg aatgct                                        86

<210> SEQ ID NO 3
<211> LENGTH: 80
<212> TYPE: DNA
<213> ORGANISM: Haemophilus influenzae

<400> SEQUENCE: 3
tttattaaaa caaattgaaa ttcttcctct atatgtatac ttgttctata tagcagagtt    60
taagtcgttt gcggacttac                                               80

<210> SEQ ID NO 4
<211> LENGTH: 24
<212> TYPE: PRT
<213> ORGANISM: Haemophilus influenzae

<400> SEQUENCE: 4

Met Pro Asp Asn Val Ser Ile Asn Ala Glu Thr Ala Gly Arg Ser Asn
 1               5                  10                  15

Thr Ser Glu Asp Asp Glu Tyr Thr
                20

<210> SEQ ID NO 5
<211> LENGTH: 114
<212> TYPE: DNA
<213> ORGANISM: Haemophilus influenzae

<400> SEQUENCE: 5
ctagaaataa ttttgtttaa ctttaagaag gagatataca tatgccggat aatgtatcta    60
ttaatgcaga aacagcagga cgcagcaata cttcagaaga cgatgaatac acgg          114

<210> SEQ ID NO 6
<211> LENGTH: 114
<212> TYPE: DNA
<213> ORGANISM: Haemophilus influenzae

<400> SEQUENCE: 6
tttattaaaa caaattgaaa ttcttcctct atatgtatac ggcctattac atagataatt    60
acgtctttgt cgtcctgcgt cgttatgaag tcttctgcta cttatgtgcc ctag          114

<210> SEQ ID NO 7

```
<211> LENGTH: 21
<212> TYPE: PRT
<213> ORGANISM: Haemophilus influenzae

<400> SEQUENCE: 7

Met Pro Asp Asp Val Thr Ile Glu Ala Glu Asp Pro Leu Arg Asn Asn
 1               5                  10                  15

Thr Gly Ile Asn Asp
            20

<210> SEQ ID NO 8
<211> LENGTH: 105
<212> TYPE: DNA
<213> ORGANISM: Haemophilus influenzae

<400> SEQUENCE: 8
ctagaaataa ttttgtttaa ctttaagaag gagatataca tatgcctgat gatgtaacaa      60
ttgaagccga agaccccctt cgcaataata ccggtataaa tgatg                     105

<210> SEQ ID NO 9
<211> LENGTH: 105
<212> TYPE: DNA
<213> ORGANISM: Haemophilus influenzae

<400> SEQUENCE: 9
tttattaaaa caaattgaaa ttcttcctct atatgtatac ggactactac attgttaact      60
tcggcttctg ggggaagcgt tattatggcc atatttacta cttaa                     105

<210> SEQ ID NO 10
<211> LENGTH: 13
<212> TYPE: PRT
<213> ORGANISM: Haemophilus influenzae

<400> SEQUENCE: 10

Thr Ser Gly Thr Leu Val Ile Asn Ala Lys Asp Ala Glu
 1               5                  10

<210> SEQ ID NO 11
<211> LENGTH: 41
<212> TYPE: DNA
<213> ORGANISM: Haemophilus influenzae

<400> SEQUENCE: 11
caaccagcgg taccttggtt attaacgcaa aagacgctga g                          41

<210> SEQ ID NO 12
<211> LENGTH: 8
<212> TYPE: PRT
<213> ORGANISM: Haemophilus influenzae

<400> SEQUENCE: 12

Val Asn Ile Ala Asp Asn Gly Arg
 1               5

<210> SEQ ID NO 13
<211> LENGTH: 29
<212> TYPE: DNA
<213> ORGANISM: Haemophilus influenzae

<400> SEQUENCE: 13
gcgttaatat cgctgataac gggcggtag                                        29
```

```
<210> SEQ ID NO 14
<211> LENGTH: 45
<212> TYPE: DNA
<213> ORGANISM: Haemophilus influenzae

<400> SEQUENCE: 14
ggccaagctt ctcgagctac cgcccgttat cagcgatatt aacgc                45

<210> SEQ ID NO 15
<211> LENGTH: 8
<212> TYPE: PRT
<213> ORGANISM: Haemophilus influenzae

<400> SEQUENCE: 15

Lys Arg Val Leu Glu Lys Val Lys
  1               5

<210> SEQ ID NO 16
<211> LENGTH: 36
<212> TYPE: DNA
<213> ORGANISM: Haemophilus influenzae

<400> SEQUENCE: 16
ccggaattcc gaaacgcgtc cttgaaaaag taaaag                          36

<210> SEQ ID NO 17
<211> LENGTH: 9
<212> TYPE: PRT
<213> ORGANISM: Haemophilus influenzae

<400> SEQUENCE: 17

Thr Asn Val Ala Asp Asp Gly Gln Pro
  1               5

<210> SEQ ID NO 18
<211> LENGTH: 31
<212> TYPE: DNA
<213> ORGANISM: Haemophilus influenzae

<400> SEQUENCE: 18
taccaatgtt gctgacgatg gacagccgta g                               31

<210> SEQ ID NO 19
<211> LENGTH: 39
<212> TYPE: DNA
<213> ORGANISM: Haemophilus influenzae

<400> SEQUENCE: 19
cgcggatcct acggctgtcc atcgtcagca acattggta                       39

<210> SEQ ID NO 20
<211> LENGTH: 7
<212> TYPE: PRT
<213> ORGANISM: Haemophilus influenzae

<400> SEQUENCE: 20

Lys Glu Trp Leu Leu Asp Pro
  1               5

<210> SEQ ID NO 21
<211> LENGTH: 32
<212> TYPE: DNA
<213> ORGANISM: Haemophilus influenzae

<400> SEQUENCE: 21
```

```
gggaattcca aagagtggtt gttagacccg ga                                    32
```

<210> SEQ ID NO 22
<211> LENGTH: 10
<212> TYPE: PRT
<213> ORGANISM: Haemophilus influenzae

<400> SEQUENCE: 22

```
Met Lys Asn Ile Lys Ser Arg Leu Lys Leu
  1               5                  10
```

<210> SEQ ID NO 23
<211> LENGTH: 30
<212> TYPE: DNA
<213> ORGANISM: Haemophilus influenzae

<400> SEQUENCE: 23

```
atgaaaaata taaaaagcag attaaaactc                                       30
```

<210> SEQ ID NO 24
<211> LENGTH: 38
<212> TYPE: DNA
<213> ORGANISM: Haemophilus influenzae

<400> SEQUENCE: 24

```
ggaattcgga gttttaatct gcttttata tttttcat                               38
```

<210> SEQ ID NO 25
<211> LENGTH: 3681
<212> TYPE: DNA
<213> ORGANISM: Haemophilus influenzae

<400> SEQUENCE: 25

```
aaagaatggt tgttagaccc ggacaatgta tccattaacg caggcacatc agaacgtaac      60
gacgcttcac caacagaaga tttccctacc ggagcaggag gaaaggataa ccccaaaaaa     120
aacgctcaca caaaccgac attaataaac caactcttg agcgtatatt aagtggcaac      180
acctttgtta atatcactgc cagaaaaaga atcacagtta atagtgatat caacatcaaa    240
gacagctccc atctaatact ctggagcgaa aatgataaca gcagcggcgt tgatattaaa    300
ggcaatatca cttctactac tggcggaagc ttaactattt actccagcgg ctggattgat   360
attcataaaa acattacgct taattcaggg ctcttaaaca ttacaactaa caaggagat    420
atcgccttcg aaaaagggaa tacccaacc attacaggtc aagggactat taccgcaggc    480
aatggtaaag gttttaggtt tgaaaacgcc tccctaaacg gtattggaac agggttactt   540
tttaacatca aagggatttt aggaaataat ttccaaatca taactttttt taacggaact   600
ttaaatattt cagggaaagt aaacatctca atggtcatac ctaaaaaatg ggattatagt  660
aaattcaggg ggcgaaccta ttggaacgta acccatttaa atgtttccga aggcagtaag  720
tttaacctca ctatcgactc cagaggagat gacactgcag gcacccttaa cacccctat   780
aatttaaacg gtatatcatt caacaaagac actatctttg atgttaaaca aaacggggca   840
gtcacctttg acatcaaggc gccaataggg gtaaataata atcgtaattt gaattacgca   900
tcattcaatg gaaatatttc agtttcagga ggagggaatg tcacttttcaa acttctcgcc   960
tcatcctcta ccgctcaaac tcccggtgta tttataaatt ctaaacactt taatgcttca  1020
ggaggtcga gttagaatt tagaactgaa ggctcaacaa aagtcggctt cttgataaat   1080
aatgatttaa ccctaaatgc caccggaggt aacatatcgc tcttgcaagt tgaaggcatt  1140
```

```
gacgggatga ttggtaaagg cgttgtagct aaaaaaaaca taacctttgc tggaggcaat    1200
atcacctttg gctccaagaa agccataaca gaaatcgaag gcaatgctac tatcaataac    1260
aacgctaacg tcactcttat cggttcggat tttgacaacc atcaaaaacc tttaactatt    1320
aaaaaagatg tcatcattaa tagcggcaac cttaccgctg gcggcaatgt tatcaatata    1380
aacggaaatc ttaccgttaa caatggcgcc aatcttaaag ctatcacaaa tttcactttt    1440
aatgtaggcg gcttgtttga caacaaaggc aattcaaata tctccattgc tagaggaggg    1500
gctaaattta aagatatcaa taacaccagt agcttaaata ttaccaccaa ctccgacacc    1560
acttaccgta ccattataga aggtaatata accaacaaag caggtgattt gaatatcatt    1620
gataataaag gtaacgctga atccaaatt ggcggcaata tctcgcaaaa agaaggtaat    1680
ctcacgattt cttccgataa aattaatatc actaaccaga taacaatcaa gaagggtgtt    1740 aataagagg attctgattc aagcacggca acaatgcta atctaaccat aaaaccaaa     1800 gaattgcaat taacgggaga cctaaatatt tcaggcttcg ataaagcaga aatcacagcc    1860
aaagagggtg ccgatttaat catcggtaat agtgataata caacaatgc taatgctaaa    1920 aaagtaacct ttaaccaggt taaagattcg aaaatctctg ctggcagtca caatgtaaca    1980
ctaaacagta aagtagaaac ctctaatggc aataatgacg ctgaaagcaa taatggcgat    2040
agcaccagct taactattaa tgcaaaaaat gtaacagtaa acaacaatat tactctcac    2100 aaacagtaa atatcactgc gtcagaaat gttaccacca aagcgggcac aaccattaat    2160
gcaaccatag gtagcgtaga agtaacagcc aaaacaggtg atattaaagg tggaattgaa    2220
tccaattccg gtaatgtaaa tattacagcg agcggcgaca cgcttaatgt aagtaacatc    2280
acaggtcaaa atgtgacagt ggcagcagcc tcaggtgccg taacaaccac aaaaggatca    2340
actattaatg caacaactgg taatgcaaat attacaacca aaacaggtga attaatggc    2400 gaagttaaat cagcttccgg taatgtaaat attacagcga gcggcaatac acttaatgta    2460
agtaacatca ctggtcaaaa tgtaacagta acagcaaaact caggtgccat aacaaccaca    2520
gaaggctcaa ctattaacgc gacaacaggt gatgcaaata ttacaaccca aacaggtaat    2580
attaatggta aagttgaatc cagttctggt tctgtgacgc ttattgcaac tggacaaact    2640
cttgctgtag gtaatatttc aggtgacact gttaccatta ctgcggataa agtaaatta    2700 accacacaaa caagctctaa gattaacgga actaagagtg taaccacctc aagccaatca    2760
ggtgatatta gtggcacaat ttctggtaat acggtaagcg ttagtgcgac cggtagcttg    2820
accactcaag caggctcaaa aattgaagca aaaacaggtg aggctaatgt aacaagcgca    2880
acaggtacaa ttggcggtac aatctctggc aatacagtaa atgttacagc aaatactgat    2940
aatttaacta ttaaagatgg cgcaagaatt aaagcaacgg gcggagctgt gactttaacc    3000
gcaacaggag gtactttaac caccgaaaca agttctgata ttacctcaag caatggtcag    3060
acaactctca cggccaagga tagcagtatc gcaggaagca tcaatgccgc caatgtgaca    3120
ttaaatacca caggcacttt aactactgtg gcaggttcaa aaatcgaggc agccagtggc    3180
accctggtta ttaatgcaaa agatgctcag ttggacggcg cggcattagg tgaccgtaca    3240
gaagtaaatg taactaacgc aaatggctcc ggcagcgtaa tcgcgacaac ctcaagcaga    3300
gtgaacatca ctggggattt aatcacaata aatggattaa atatcatttc aaaaaacggt    3360
aaaaacaccg tgctgttaaa aggtgttgaa attgatgtga aatacattca accgggcata    3420
gcgagcgtat atgaagtaat tgaagcaaaa cgcgctcttg agaaagtgaa agatttatct    3480
```

-continued

```
gatgaagaaa gagaagcatt agctaagctt ggtgtgagcg ctgtacgttt tattgagcca    3540
aataatacaa ttacagtcga tacacaaaat gaatttgcaa ccagaccatt aagtcgaata    3600
gtgatttctg aaggcagggc gtgtttctca acagtgatg gcgcgacggt gtgcgttaat     3660
atcgctgata acgggcggta g                                              3681
```

<210> SEQ ID NO 26
<211> LENGTH: 1226
<212> TYPE: PRT
<213> ORGANISM: Haemophilus influenzae

<400> SEQUENCE: 26

```
Lys Glu Trp Leu Leu Asp Pro Asp Asn Val Ser Ile Asn Ala Gly Thr
  1               5                  10                  15

Ser Glu Arg Asn Asp Ala Ser Pro Thr Glu Asp Phe Pro Thr Gly Ala
                 20                  25                  30

Gly Gly Lys Asp Asn Pro Lys Lys Asn Ala His Asn Lys Pro Thr Leu
             35                  40                  45

Ile Asn Thr Thr Leu Glu Arg Ile Leu Ser Gly Asn Thr Phe Val Asn
         50                  55                  60

Ile Thr Ala Arg Lys Arg Ile Thr Val Asn Ser Asp Ile Asn Ile Lys
     65                  70                  75                  80

Asp Ser Ser His Leu Ile Leu Trp Ser Glu Asn Asp Asn Ser Ser Gly
                 85                  90                  95

Val Asp Ile Lys Gly Asn Ile Ser Thr Thr Gly Gly Ser Leu Thr
                100                 105                 110

Ile Tyr Ser Ser Gly Trp Ile Asp Ile His Lys Asn Ile Thr Leu Asn
            115                 120                 125

Ser Gly Leu Leu Asn Ile Thr Thr Lys Gln Gly Asp Ile Ala Phe Glu
        130                 135                 140

Lys Gly Asn Asn Pro Thr Ile Thr Gly Gln Gly Thr Ile Thr Ala Gly
145                 150                 155                 160

Asn Gly Lys Gly Phe Arg Phe Glu Asn Ala Ser Leu Asn Gly Ile Gly
                165                 170                 175

Thr Gly Leu Leu Phe Asn Ile Lys Arg Asp Leu Gly Asn Asn Phe Gln
            180                 185                 190

Ile Ile Asn Phe Phe Asn Gly Thr Leu Asn Ile Ser Gly Lys Val Asn
        195                 200                 205

Ile Ser Met Val Ile Pro Lys Leu Trp Asp Tyr Ser Lys Phe Arg Gly
    210                 215                 220

Arg Thr Tyr Trp Asn Val Thr His Leu Asn Val Ser Glu Gly Ser Lys
225                 230                 235                 240

Phe Asn Leu Thr Ile Asp Ser Arg Gly Asp Asp Thr Ala Gly Thr Leu
                245                 250                 255

Asn Thr Pro Tyr Asn Leu Asn Gly Ile Ser Phe Asn Lys Asp Thr Ile
            260                 265                 270

Phe Asp Val Lys Gln Asn Gly Ala Val Thr Phe Asp Ile Lys Ala Pro
        275                 280                 285

Ile Gly Val Asn Asn Arg Asn Leu Asn Tyr Ala Ser Phe Asn Gly
    290                 295                 300

Asn Ile Ser Val Ser Gly Gly Asn Val Thr Phe Lys Leu Leu Ala
305                 310                 315                 320

Ser Ser Ser Thr Ala Gln Thr Pro Gly Val Phe Ile Asn Ser Lys His
                325                 330                 335
```

```
Phe Asn Ala Ser Gly Gly Ser Ser Leu Glu Phe Arg Thr Glu Gly Ser
            340                 345                 350

Thr Lys Val Gly Phe Leu Ile Asn Asn Asp Leu Thr Leu Asn Ala Thr
            355                 360                 365

Gly Gly Asn Ile Ser Leu Leu Gln Val Glu Gly Ile Asp Gly Met Ile
            370                 375                 380

Gly Lys Gly Val Val Ala Lys Lys Asn Ile Thr Phe Ala Gly Gly Asn
385                 390                 395                 400

Ile Thr Phe Gly Ser Lys Lys Ala Ile Thr Glu Ile Glu Gly Asn Ala
                405                 410                 415

Thr Ile Asn Asn Asn Ala Asn Val Thr Leu Ile Gly Ser Asp Phe Asp
            420                 425                 430

Asn His Gln Lys Pro Leu Thr Ile Lys Lys Asp Val Ile Ile Asn Ser
            435                 440                 445

Gly Asn Leu Thr Ala Gly Gly Asn Val Ile Asn Ile Asn Gly Asn Leu
            450                 455                 460

Thr Val Asn Asn Gly Ala Asn Leu Lys Ala Ile Thr Asn Phe Thr Phe
465                 470                 475                 480

Asn Val Gly Gly Leu Phe Asp Asn Lys Gly Asn Ser Asn Ile Ser Ile
                485                 490                 495

Ala Arg Gly Gly Ala Lys Phe Lys Asp Ile Asn Asn Thr Ser Ser Leu
            500                 505                 510

Asn Ile Thr Thr Asn Ser Asp Thr Thr Tyr Arg Thr Ile Ile Glu Gly
            515                 520                 525

Asn Ile Thr Asn Lys Ala Gly Asp Leu Asn Ile Ile Asp Asn Lys Gly
            530                 535                 540

Asn Ala Glu Ile Gln Ile Gly Gly Asn Ile Ser Gln Lys Glu Gly Asn
545                 550                 555                 560

Leu Thr Ile Ser Ser Asp Lys Ile Asn Ile Thr Asn Gln Ile Thr Ile
                565                 570                 575

Lys Lys Gly Val Asn Lys Glu Asp Ser Asp Ser Ser Thr Ala Asn Asn
            580                 585                 590

Ala Asn Leu Thr Ile Lys Thr Lys Glu Leu Gln Leu Thr Gly Asp Leu
            595                 600                 605

Asn Ile Ser Gly Phe Asp Lys Ala Glu Ile Thr Ala Lys Glu Gly Ala
            610                 615                 620

Asp Leu Ile Ile Gly Asn Ser Asp Asn Asn Asn Ala Asn Ala Lys
625                 630                 635                 640

Lys Val Thr Phe Asn Gln Val Lys Asp Ser Lys Ile Ser Ala Gly Ser
                645                 650                 655

His Asn Val Thr Leu Asn Ser Lys Val Glu Thr Ser Asn Gly Asn Asn
            660                 665                 670

Asp Ala Glu Ser Asn Asn Gly Asp Ser Thr Ser Leu Thr Ile Asn Ala
            675                 680                 685

Lys Asn Val Thr Val Asn Asn Ile Thr Ser His Lys Thr Val Asn
            690                 695                 700

Ile Thr Ala Ser Glu Asn Val Thr Thr Lys Ala Gly Thr Thr Ile Asn
705                 710                 715                 720

Ala Thr Ile Gly Ser Val Glu Val Thr Ala Lys Thr Gly Asp Ile Lys
                725                 730                 735

Gly Gly Ile Glu Ser Asn Ser Gly Asn Val Asn Ile Thr Ala Ser Gly
            740                 745                 750

Asp Thr Leu Asn Val Ser Asn Ile Thr Gly Gln Asn Val Thr Val Ala
```

```
             755                 760                 765
Ala Ala Ser Gly Ala Val Thr Thr Lys Gly Ser Thr Ile Asn Ala
        770                 775                 780

Thr Thr Gly Asn Ala Asn Ile Thr Thr Lys Thr Gly Glu Ile Asn Gly
785                 790                 795                 800

Glu Val Lys Ser Ala Ser Gly Asn Val Asn Ile Thr Ala Ser Gly Asn
                805                 810                 815

Thr Leu Asn Val Ser Asn Ile Thr Gly Gln Asn Val Thr Val Thr Ala
                820                 825                 830

Asn Ser Gly Ala Ile Thr Thr Glu Gly Ser Thr Ile Asn Ala Thr
            835                 840                 845

Thr Gly Asp Ala Asn Ile Thr Thr Gln Thr Gly Asn Ile Asn Gly Lys
        850                 855                 860

Val Glu Ser Ser Gly Ser Val Thr Leu Ile Ala Thr Gly Gln Thr
865                 870                 875                 880

Leu Ala Val Gly Asn Ile Ser Gly Asp Thr Val Thr Ile Thr Ala Asp
                885                 890                 895

Lys Gly Lys Leu Thr Thr Gln Thr Ser Ser Lys Ile Asn Gly Thr Lys
            900                 905                 910

Ser Val Thr Thr Ser Ser Gln Ser Gly Asp Ile Ser Gly Thr Ile Ser
            915                 920                 925

Gly Asn Thr Val Ser Val Ser Ala Thr Gly Ser Leu Thr Thr Gln Ala
    930                 935                 940

Gly Ser Lys Ile Glu Ala Lys Thr Gly Glu Ala Asn Val Thr Ser Ala
945                 950                 955                 960

Thr Gly Thr Ile Gly Gly Thr Ile Ser Gly Asn Thr Val Asn Val Thr
                965                 970                 975

Ala Asn Thr Asp Asn Leu Thr Ile Lys Asp Gly Ala Arg Ile Lys Ala
            980                 985                 990

Thr Gly Gly Ala Val Thr Leu Thr Ala Thr Gly Gly Thr Leu Thr Thr
            995                 1000                1005

Glu Thr Ser Ser Asp Ile Thr Ser Ser Asn Gly Gln Thr Thr Leu Thr
    1010                1015                1020

Ala Lys Asp Ser Ser Ile Ala Gly Ser Ile Asn Ala Ala Asn Val Thr
1025                1030                1035                1040

Leu Asn Thr Thr Gly Thr Leu Thr Thr Val Ala Gly Ser Lys Ile Glu
            1045                1050                1055

Ala Ala Ser Gly Thr Leu Val Ile Asn Ala Lys Asp Ala Gln Leu Asp
            1060                1065                1070

Gly Ala Ala Leu Gly Asp Arg Thr Glu Val Asn Val Thr Asn Ala Asn
        1075                1080                1085

Gly Ser Gly Ser Val Ile Ala Thr Thr Ser Arg Val Asn Ile Thr
    1090                1095                1100

Gly Asp Leu Ile Thr Ile Asn Gly Leu Asn Ile Ile Ser Lys Asn Gly
1105                1110                1115                1120

Lys Asn Thr Val Leu Leu Lys Gly Val Glu Ile Asp Val Lys Tyr Ile
            1125                1130                1135

Gln Pro Gly Ile Ala Ser Val Tyr Glu Val Ile Glu Ala Lys Arg Ala
            1140                1145                1150

Leu Glu Lys Val Lys Asp Leu Ser Asp Glu Glu Arg Glu Ala Leu Ala
            1155                1160                1165

Lys Leu Gly Val Ser Ala Val Arg Phe Ile Glu Pro Asn Asn Thr Ile
        1170                1175                1180
```

Thr Val Asp Thr Gln Asn Glu Phe Ala Thr Arg Pro Leu Ser Arg Ile
1185                1190                1195                1200

Val Ile Ser Glu Gly Arg Ala Cys Phe Ser Asn Ser Asp Gly Ala Thr
            1205                1210                1215

Val Cys Val Asn Ile Ala Asp Asn Gly Arg
            1220                1225

<210> SEQ ID NO 27
<211> LENGTH: 3663
<212> TYPE: DNA
<213> ORGANISM: Haemophilus influenzae

<400> SEQUENCE: 27

| | | | | | |
|---|---|---|---|---|---|
| ccggacaatg | tatccattaa | cgcaggcaca | tcagaacgta | acgacgcttc | accaacagaa | 60 |
| gatttcccta | ccggagcagg | aggaaaggat | aaccccaaaa | aaaacgctca | caacaaaccg | 120 |
| acattaataa | acacaactct | tgagcgtata | ttaagtggca | cacctttgt | taatatcact | 180 |
| gccagaaaaa | gaatcacagt | taatagtgat | atcaacatca | aagacagctc | ccatctaata | 240 |
| ctctggagcg | aaaatgataa | cagcagcggc | gttgatatta | aaggcaatat | cacttctact | 300 |
| actggcggaa | gcttaactat | ttactccagc | ggctggattg | atattcataa | aaacattacg | 360 |
| cttaattcag | ggctcttaaa | cattacaact | aaacaaggag | atatcgcctt | cgaaaaaggg | 420 |
| aataacccaa | ccattacagg | tcaagggact | attaccgcag | gcaatggtaa | aggttttagg | 480 |
| tttgaaaacg | cctccctaaa | cggtattgga | acagggttac | tttttaacat | caaaagggat | 540 |
| ttaggaaata | atttccaaat | cataaacttt | tttaacggaa | ctttaaatat | ttcagggaaa | 600 |
| gtaaacatct | caatggtcat | acctaaaaaa | tgggattata | gtaaattcag | ggggcgaacc | 660 |
| tattggaacg | taacccattt | aaatgtttcc | gaaggcagta | agtttaacct | cactatcgac | 720 |
| tccagaggag | atgacactgc | aggcacccct | aacacccctt | ataatttaaa | cggtatatca | 780 |
| ttcaacaaag | acactatctt | tgatgttaaa | caaaacgggg | cagtcacctt | tgacatcaag | 840 |
| gcgccaatag | gggtaaataa | taatcgtaat | ttgaattacg | catcattcaa | tggaaatatt | 900 |
| tcagtttcag | gaggagggaa | tgtcactttc | aaacttctcg | cctcatcctc | taccgctcaa | 960 |
| actcccggtg | tatttataaa | ttctaaacac | tttaatgctt | caggagggtc | gagtttagaa | 1020 |
| tttagaactg | aaggctcaac | aaaagtcggc | ttcttgataa | ataatgattt | aaccctaaat | 1080 |
| gccaccggag | gtaacatatc | gctcttgcaa | gttgaaggca | ttgacgggat | gattggtaaa | 1140 |
| ggcgttgtag | ctaaaaaaaa | cataaccttt | gctggaggca | atatcacctt | tggctccaag | 1200 |
| aaagccataa | cagaaatcga | aggcaatgct | actatcaata | caacgctaa | cgtcactctt | 1260 |
| atcggttcgg | attttgacaa | ccatcaaaaa | cctttaacta | ttaaaaaaga | tgtcatcatt | 1320 |
| aatagcggca | accttaccgc | tggcggcaat | gttatcaata | taaacggaaa | tcttaccgtt | 1380 |
| aacaatggcg | ccaatcttaa | agctatcaca | aatttcactt | ttaatgtagg | cggcttgttt | 1440 |
| gacaacaaag | gcaattcaaa | tatctccatt | gctagaggag | gggctaaatt | taaagatatc | 1500 |
| aataacacca | gtagcttaaa | tattaccacc | aactccgaca | ccacttaccg | taccattata | 1560 |
| gaaggtaata | taaccaacaa | agcaggtgat | ttgaatatca | ttgataataa | aggtaacgct | 1620 |
| gaaatccaaa | ttggcggcaa | tatctcgcaa | aaagaaggta | atctcacgat | ttcttccgat | 1680 |
| aaaattaata | tcactaacca | gataacaatc | aagaagggtg | ttaataaaga | ggattctgat | 1740 |
| tcaagcacgg | caaacaatgc | taatctaacc | attaaaacca | aagaattgca | attaacggga | 1800 |
| gacctaaata | tttcaggctt | cgataaagca | gaaatcacag | ccaaagaggg | tgccgatta | 1860 |

-continued

```
atcatcggta atagtgataa taacaacaat gctaatgcta aaaagtaac ctttaaccag   1920 gttaaagatt cgaaaatctc tgctggcagt cacaatgtaa cactaaacag taaagtagaa   1980
acctctaatg gcaataatga cgctgaaagc aataatggcg atagcaccag cttaactatt   2040
aatgcaaaaa atgtaacagt aaacaacaat attacttctc acaaaacagt aaatatcact   2100
gcgtcagaaa atgttaccac caaagcgggc acaaccatta atgcaaccat aggtagcgta   2160
gaagtaacag ccaaaacagg tgatattaaa ggtggaattg aatccaattc cggtaatgta   2220
aatattacag cgagcggcga cacgcttaat gtaagtaaca tcacaggtca aaatgtgaca   2280
gtggcagcag cctcaggtgc cgtaacaacc acaaaaggat caactattaa tgcaacaact   2340
ggtaatgcaa atattacaac caaaacaggt gaaattaatg gcgaagttaa atcagcttcc   2400
ggtaatgtaa atattacagc gagcggcaat acacttaatg taagtaacat cactggtcaa   2460
aatgtaacag taacagcaaa ctcaggtgcc ataacaacca cagaaggctc aactattaac   2520
gcgacaacag gtgatgcaaa tattacaacc caaacaggta atattaatgg taaagttgaa   2580
tccagttctg gttctgtgac gcttattgca actggacaaa ctcttgctgt aggtaatatt   2640
tcaggtgaca ctgttaccat tactgcggat aaaggtaaat taaccacaca aacaagctct   2700
aagattaacg gaactaagag tgtaaccacc tcaagccaat caggtgatat tagtggcaca   2760
atttctggta atacggtaag cgttagtgcg accggtagct tgaccactca agcaggctca   2820
aaaattgaag caaaaacagg tgaggctaat gtaacaagcg caacaggtac aattggcggt   2880
acaatctctg gcaatacagt aaatgttaca gcaaatactg ataatttaac tattaaagat   2940
ggcgcaagaa ttaaagcaac gggcggagct gtgactttaa ccgcaacagg aggtacttta   3000
accaccgaaa caagttctga tattacctca agcaatggtc agacaactct cacggccaag   3060
gatagcagta tcgcaggaag catcaatgcc gccaatgtga cattaaatac cacaggcact   3120
ttaactactg tggcaggttc aaaaatcgag gcagccagtg gcaccctggt tattaatgca   3180
aaagatgctc agttggacgg cgcggcatta ggtgaccgta cagaagtaaa tgtaactaac   3240
gcaaatggct ccggcagcgt aatcgcgaca acctcaagca gagtgaacat cactggggat   3300
ttaatcacaa taaatggatt aaatatcatt tcaaaaaacg gtaaaaacac cgtgctgtta   3360
aaaggtgttg aaattgatgt gaaatacatt caaccgggca tagcgagcgt atatgaagta   3420
attgaagcaa aacgcgctct tgagaaagtg aaagatttat ctgatgaaga agagaagca   3480 ttagctaagc ttggtgtgag cgctgtacgt tttattgagc caataatac aattacagtc   3540 gatacacaaa atgaatttgc aaccagacca ttaagtcgaa tagtgatttc tgaaggcagg   3600
gcgtgtttct caaacagtga tggcgcgacg gtgtgcgtta atatcgctga taacgggcgg   3660
tag                                                                3663
```

```
<210> SEQ ID NO 28
<211> LENGTH: 1220
<212> TYPE: PRT
<213> ORGANISM: Haemophilus influenzae

<400> SEQUENCE: 28

Pro Asp Asn Val Ser Ile Asn Ala Gly Thr Ser Glu Arg Asn Asp Ala
 1               5                  10                  15

Ser Pro Thr Glu Asp Phe Pro Thr Gly Ala Gly Gly Lys Asp Asn Pro
            20                  25                  30

Lys Lys Asn Ala His Asn Lys Pro Thr Leu Ile Asn Thr Thr Leu Glu
        35                  40                  45
```

```
Arg Ile Leu Ser Gly Asn Thr Phe Val Asn Ile Thr Ala Arg Lys Arg
 50                  55                  60

Ile Thr Val Asn Ser Asp Ile Asn Ile Lys Asp Ser Ser His Leu Ile
 65                  70                  75                  80

Leu Trp Ser Glu Asn Asp Asn Ser Ser Gly Val Asp Ile Lys Gly Asn
             85                  90                  95

Ile Thr Ser Thr Thr Gly Gly Ser Leu Thr Ile Tyr Ser Ser Gly Trp
            100                 105                 110

Ile Asp Ile His Lys Asn Ile Thr Leu Asn Ser Gly Leu Leu Asn Ile
            115                 120                 125

Thr Thr Lys Gln Gly Asp Ile Ala Phe Glu Lys Gly Asn Asn Pro Thr
130                 135                 140

Ile Thr Gly Gln Gly Thr Ile Thr Ala Gly Asn Gly Lys Gly Phe Arg
145                 150                 155                 160

Phe Glu Asn Ala Ser Leu Asn Gly Ile Gly Thr Gly Leu Leu Phe Asn
                165                 170                 175

Ile Lys Arg Asp Leu Gly Asn Asn Phe Gln Ile Ile Asn Phe Phe Asn
            180                 185                 190

Gly Thr Leu Asn Ile Ser Gly Lys Val Asn Ile Ser Met Val Ile Pro
            195                 200                 205

Lys Lys Trp Asp Tyr Ser Lys Phe Arg Gly Arg Thr Tyr Trp Asn Val
210                 215                 220

Thr His Leu Asn Val Ser Glu Gly Ser Lys Phe Asn Leu Thr Ile Asp
225                 230                 235                 240

Ser Arg Gly Asp Asp Thr Ala Gly Thr Leu Asn Thr Pro Tyr Asn Leu
                245                 250                 255

Asn Gly Ile Ser Phe Asn Lys Asp Thr Ile Phe Asp Val Lys Gln Asn
            260                 265                 270

Gly Ala Val Thr Phe Asp Ile Lys Ala Pro Ile Gly Val Asn Asn Asn
            275                 280                 285

Arg Asn Leu Asn Tyr Ala Ser Phe Asn Gly Asn Ile Ser Val Ser Gly
290                 295                 300

Gly Gly Asn Val Thr Phe Lys Leu Leu Ala Ser Ser Ser Thr Ala Gln
305                 310                 315                 320

Thr Pro Gly Val Phe Ile Asn Ser Lys His Phe Asn Ala Ser Gly Gly
                325                 330                 335

Ser Ser Leu Glu Phe Arg Thr Glu Gly Ser Thr Lys Val Gly Phe Leu
            340                 345                 350

Ile Asn Asn Asp Leu Thr Leu Asn Ala Thr Gly Gly Asn Ile Ser Leu
            355                 360                 365

Leu Gln Val Glu Gly Ile Asp Gly Met Ile Gly Lys Gly Val Val Ala
370                 375                 380

Lys Lys Asn Ile Thr Phe Ala Gly Gly Asn Ile Thr Phe Gly Ser Lys
385                 390                 395                 400

Lys Ala Ile Thr Glu Ile Glu Gly Asn Ala Thr Ile Asn Asn Asn Ala
                405                 410                 415

Asn Val Thr Leu Ile Gly Ser Asp Phe Asp Asn His Gln Lys Pro Leu
            420                 425                 430

Thr Ile Lys Lys Asp Val Ile Asn Ser Gly Asn Leu Thr Ala Gly
            435                 440                 445

Gly Asn Val Ile Asn Ile Asn Gly Asn Leu Thr Val Asn Asn Gly Ala
450                 455                 460
```

-continued

```
Asn Leu Lys Ala Ile Thr Asn Phe Thr Phe Asn Val Gly Gly Leu Phe
465                 470                 475                 480

Asp Asn Lys Gly Asn Ser Asn Ile Ser Ile Ala Arg Gly Gly Ala Lys
            485                 490                 495

Phe Lys Asp Ile Asn Asn Thr Ser Ser Leu Asn Ile Thr Thr Asn Ser
            500                 505                 510

Asp Thr Thr Tyr Arg Thr Ile Ile Glu Gly Asn Ile Thr Asn Lys Ala
            515                 520                 525

Gly Asp Leu Asn Ile Ile Asp Asn Lys Gly Asn Ala Glu Ile Gln Ile
530                 535                 540

Gly Gly Asn Ile Ser Gln Lys Glu Gly Asn Leu Thr Ile Ser Ser Asp
545                 550                 555                 560

Lys Ile Asn Ile Thr Asn Gln Ile Thr Ile Lys Lys Gly Val Asn Lys
                565                 570                 575

Glu Asp Ser Asp Ser Ser Thr Ala Asn Asn Ala Asn Leu Thr Ile Lys
            580                 585                 590

Thr Lys Glu Leu Gln Leu Thr Gly Asp Leu Asn Ile Ser Gly Phe Asp
            595                 600                 605

Lys Ala Glu Ile Thr Ala Lys Glu Gly Ala Asp Leu Ile Ile Gly Asn
610                 615                 620

Ser Asp Asn Asn Asn Ala Asn Ala Lys Lys Val Thr Phe Asn Gln
625                 630                 635                 640

Val Lys Asp Ser Lys Ile Ser Ala Gly Ser His Asn Val Thr Leu Asn
            645                 650                 655

Ser Lys Val Glu Thr Ser Asn Gly Asn Asn Asp Ala Glu Ser Asn Asn
            660                 665                 670

Gly Asp Ser Thr Ser Leu Thr Ile Asn Ala Lys Asn Val Thr Val Asn
            675                 680                 685

Asn Asn Ile Thr Ser His Lys Thr Val Asn Ile Thr Ala Ser Glu Asn
            690                 695                 700

Val Thr Thr Lys Ala Gly Thr Thr Ile Asn Ala Thr Ile Gly Ser Val
705                 710                 715                 720

Glu Val Thr Ala Lys Thr Gly Asp Ile Lys Gly Ile Glu Ser Asn
            725                 730                 735

Ser Gly Asn Val Asn Ile Thr Ala Ser Gly Asp Thr Leu Asn Val Ser
            740                 745                 750

Asn Ile Thr Gly Gln Asn Val Thr Val Ala Ala Ser Gly Ala Val
            755                 760                 765

Thr Thr Thr Lys Gly Ser Thr Ile Asn Ala Thr Thr Gly Asn Ala Asn
770                 775                 780

Ile Thr Thr Lys Thr Gly Glu Ile Asn Gly Glu Val Lys Ser Ala Ser
785                 790                 795                 800

Gly Asn Val Asn Ile Thr Ala Ser Gly Asn Thr Leu Asn Val Ser Asn
            805                 810                 815

Ile Thr Gly Gln Asn Val Thr Val Thr Ala Asn Ser Gly Ala Ile Thr
            820                 825                 830

Thr Thr Glu Gly Ser Thr Ile Asn Ala Thr Thr Gly Asp Ala Asn Ile
            835                 840                 845

Thr Thr Gln Thr Gly Asn Ile Asn Gly Lys Val Glu Ser Ser Ser Gly
            850                 855                 860

Ser Val Thr Leu Ile Ala Thr Gly Gln Thr Leu Ala Val Gly Asn Ile
865                 870                 875                 880

Ser Gly Asp Thr Val Thr Ile Thr Ala Asp Lys Gly Lys Leu Thr Thr
```

| | | | | | | | | | | | |
|---|---|---|---|---|---|---|---|---|---|---|---|
| | | | | 885 | | | 890 | | | 895 | |
| Gln | Thr | Ser | Ser | Lys | Ile | Asn | Gly | Thr | Lys | Ser | Val | Thr | Thr | Ser | Ser |

Gln Thr Ser Ser Lys Ile Asn Gly Thr Lys Ser Val Thr Thr Ser Ser
                              900                 905                 910

Gln Ser Gly Asp Ile Ser Gly Thr Ile Ser Gly Asn Thr Val Ser Val
            915                 920                 925

Ser Ala Thr Gly Ser Leu Thr Thr Gln Ala Gly Ser Lys Ile Glu Ala
        930                 935                 940

Lys Thr Gly Glu Ala Asn Val Thr Ser Ala Thr Gly Thr Ile Gly Gly
945                 950                 955                 960

Thr Ile Ser Gly Asn Thr Val Asn Val Thr Ala Asn Thr Asp Asn Leu
                965                 970                 975

Thr Ile Lys Asp Gly Ala Arg Ile Lys Ala Thr Gly Gly Ala Val Thr
            980                 985                 990

Leu Thr Ala Thr Gly Gly Thr Leu Thr Thr Glu Thr Ser Ser Asp Ile
        995                 1000                1005

Thr Ser Ser Asn Gly Gln Thr Thr Leu Thr Ala Lys Asp Ser Ser Ile
    1010                1015                1020

Ala Gly Ser Ile Asn Ala Ala Asn Val Thr Leu Asn Thr Thr Gly Thr
1025                1030                1035                1040

Leu Thr Thr Val Ala Gly Ser Lys Ile Glu Ala Ala Ser Gly Thr Leu
                1045                1050                1055

Val Ile Asn Ala Lys Asp Ala Gln Leu Asp Gly Ala Ala Leu Gly Asp
            1060                1065                1070

Arg Thr Glu Val Asn Val Thr Asn Ala Asn Gly Ser Gly Ser Val Ile
        1075                1080                1085

Ala Thr Thr Ser Ser Arg Val Asn Ile Thr Gly Asp Leu Ile Thr Ile
    1090                1095                1100

Asn Gly Leu Asn Ile Ile Ser Lys Asn Gly Lys Asn Thr Val Leu Leu
1105                1110                1115                1120

Lys Gly Val Glu Ile Asp Val Lys Tyr Ile Gln Pro Gly Ile Ala Ser
                1125                1130                1135

Val Tyr Glu Val Ile Glu Ala Lys Arg Ala Leu Glu Lys Val Lys Asp
            1140                1145                1150

Leu Ser Asp Glu Glu Arg Glu Ala Leu Ala Lys Leu Gly Val Ser Ala
        1155                1160                1165

Val Arg Phe Ile Glu Pro Asn Asn Thr Ile Thr Val Asp Thr Gln Asn
    1170                1175                1180

Glu Phe Ala Thr Arg Pro Leu Ser Arg Ile Val Ile Ser Glu Gly Arg
1185                1190                1195                1200

Ala Cys Phe Ser Asn Ser Asp Gly Ala Thr Val Cys Val Asn Ile Ala
            1205                1210                1215

Asp Asn Gly Arg
            1220

<210> SEQ ID NO 29
<211> LENGTH: 2928
<212> TYPE: DNA
<213> ORGANISM: Haemophilus influenzae

<400> SEQUENCE: 29
aaagagtggt tgttagaccc ggataatgta tccattgaaa atccttcaac tgaacgcaat    60
gattccaatg aagacctaga gtatacagga acagggaaa atataaacaa ccctaaggta    120
aataatcagt ctaaaaaaac actaacaagc tcaatccttg agaacatcct gaaaaaaggc    180

-continued

| | |
|---|---|
| tcttttgtta acattactgc cactgataac atctacgtta atagctctat caacatcgga | 240 |
| gacagtggtc acttaattct ctcaggtgga ggcaggaacg gcggcggtgt taagattaat | 300 |
| aaaaatatta cttccacggg cggaagttta accattaatt ccaaaggatg ggttgatatt | 360 |
| cactccaata tttcacttgg tacgggtttt ttgaacatta cctctaatgg ttccgtggct | 420 |
| tttgagaagg cagacaaaga taaggcacgt agcgcggcag atgctcaaat tgtcgcacaa | 480 |
| ggcatcataa acctcacagg ggaaaacaaa acctttaggc ttaacaatgt gtctttaaat | 540 |
| ggagtgggtc aaggtctatc catcacgtca aatgtgggca atcaaactca taaattcgat | 600 |
| ggtgaaatta acataactgg aaatgtaaca attaatcaaa ctgcacctgc gacaaccgca | 660 |
| tattggaatt ttagctacga ttcatattgg aacgtcagta ctcttaacgt acaaaaaaac | 720 |
| tcaagcttta cctttattaa gcgcactgaa agtaatcgct ttggcccaac aacaccactt | 780 |
| cgaagctccg gagggtatt ctttaacggc acgaatggca acatggtgct taacgtcgga | 840 |
| actaattcga gagttttgtt taatttgaag ccaaatgaga atacaaacaa cagcaagcct | 900 |
| ttaccgcttc aatttaacgc caatattaca gccattggtg gaggctctgt gtctttttgat | 960 |
| atacacgcca atcattccgg cagaggggct gaattaaaaa tgaacacaat taatatctct | 1020 |
| gacggcacca gcctcaccct acaatcccat gttcgcaaag atagtgcttt tataatcagt | 1080 |
| aaagatttaa caataaacgc aaccggttca aattttactc ttgagcaatc accagacagt | 1140 |
| tttactgaca ataccccgg aagagctatt agttcaacta aaaatataac catctcaggt | 1200 |
| ggcaacgtct ctcttggtgg gcaaaattca agcagtgaca tcaagggaaa tattaccatc | 1260 |
| aaaagctcaa caaatgttac actgaaagcc cataacagcc ctcgcgactt tgcttccaga | 1320 |
| accttaaccc ttggcaactt gaatgttgaa ggaaatttaa ccctaaccgg ctcagttgcg | 1380 |
| gatattaaag gtaacctttc cattcttaac gatgctactt ttaaaggaga gaccagtgaa | 1440 |
| aacctaaaca tcaccggcaa cttcaccaat aatggcaccg ccgacattaa tataaaaacaa | 1500 |
| ggggtggtaa acatccaagg taatattacc aataaggtg gtttaaacat taccactaat | 1560 |
| gcccaaaaca atcaaaaaac cattattaac ggaaatataa ctaacgaagg cggagattta | 1620 |
| aacatcaagg atagtaacaa taatgctgaa atccaaattg gcggcaatat ctcgcaaaaa | 1680 |
| aaaggcaatc tcacaatttc ttctgataaa atcaatatta ccaagaagat aacaatcaaa | 1740 |
| gcaggcgttg atgaaggtgg ttctgactca agcccagcaa gtaatgctaa tctaaccatt | 1800 |
| aaaccaaaa cgctagaatt aacaggagac ctaaatattt caggctttaa taagcagaa | 1860 |
| attacagcta aaaatggcaa cgatttaact attggcaagg ctagtgatgg taatgctaat | 1920 |
| gctaaaaag tgacttttga caaggttaaa gattcaaaaa tctcagctaa cggtcacaat | 1980 |
| gtaacactaa atagcaaagt ggaaacgtct aatagtgata gtagtgctga tgatagtaat | 2040 |
| gataacaaca ctggtttaac catttccgca aaagatgtaa cagtaaacaa tgacgtcacc | 2100 |
| tcccacaaga caataaatat ctctgccaca acaggaaatg taacaaccaa agaaagcaca | 2160 |
| accattaatg cggccacagg tagcgtggaa gtaactgcta aaacaggcga tattagtggc | 2220 |
| acaatttctg gtaatacagt aaatgttaca gcaactgata gcttaaccac ccaagcaagc | 2280 |
| tctagcatta cctcaagtaa tggtcagaca actcttacag ccaagaatgg cagtatcgca | 2340 |
| ggaagtattg atgccgctaa tgtgacatta ataccacag gcaccttaac tactgtagcg | 2400 |
| ggttcaaaca ttaaggcaac cagtggcact ttagctatta cgcaaaaaga tgctaagtta | 2460 |
| gatggtactg catcaggtga ccgcacagta gtaaatgcaa ctaacgcaag tggctctggt | 2520 |
| agtgtgactg cggcaacctc aagtaacgtg aatatcactg gagatttaag cacaataaat | 2580 |

-continued

```
ggattaaata tcatttcgaa aaatggtaaa aacaccgtag tgttaaaagg tgctgaaatt   2640
gatgtgaaat atattcaacc aggtgtagca agtgcgaatg aggttattga agcgaagcgt   2700
gcccttgaaa aagtaaaaga tttatctgat gaagaaagag aaacattagc taaacttggt   2760
gtaagtgctg tacgttttgt tgagccaaat aatacaatta cagtcaatac acaaaatgaa   2820
tttacaacca gaccgtcaag tcaagtgaca atttctgaag acaaggcgtg tttctcaagt   2880
ggtaatggtg cagcagtatg tactaatgtt actgacgata gacagtaa                2928
```

<210> SEQ ID NO 30
<211> LENGTH: 975
<212> TYPE: PRT
<213> ORGANISM: Haemophilus influenzae

<400> SEQUENCE: 30

```
Lys Glu Trp Leu Leu Asp Pro Asp Asn Val Ser Ile Glu Asn Pro Ser
 1               5                  10                  15

Thr Glu Arg Asn Asp Ser Asn Glu Asp Leu Glu Tyr Thr Gly Thr Gly
            20                  25                  30

Glu Asn Ile Asn Asn Pro Lys Val Asn Asn Gln Ser Lys Lys Thr Leu
        35                  40                  45

Thr Ser Ser Ile Leu Glu Asn Ile Leu Lys Lys Gly Ser Phe Val Asn
    50                  55                  60

Ile Thr Ala Thr Asp Asn Ile Tyr Val Asn Ser Ser Ile Asn Ile Gly
65                  70                  75                  80

Asp Ser Gly His Leu Ile Leu Ser Gly Gly Arg Asn Gly Gly Gly
                85                  90                  95

Val Lys Ile Asn Lys Asn Ile Thr Ser Thr Gly Gly Ser Leu Thr Ile
            100                 105                 110

Asn Ser Lys Gly Trp Val Asp Ile His Ser Asn Ile Ser Leu Gly Thr
        115                 120                 125

Gly Phe Leu Asn Ile Thr Ser Asn Gly Ser Val Ala Phe Glu Lys Ala
    130                 135                 140

Asp Lys Asp Lys Ala Arg Ser Ala Ala Asp Ala Gln Ile Val Ala Gln
145                 150                 155                 160

Gly Ile Ile Asn Leu Thr Gly Glu Asn Lys Thr Phe Arg Leu Asn Asn
                165                 170                 175

Val Ser Leu Asn Gly Val Gly Gln Gly Leu Ser Ile Thr Ser Asn Val
            180                 185                 190

Gly Asn Gln Thr His Lys Phe Asp Gly Glu Ile Asn Ile Thr Gly Asn
        195                 200                 205

Val Thr Ile Asn Gln Thr Ala Pro Ala Thr Thr Ala Tyr Trp Asn Phe
    210                 215                 220

Ser Tyr Asp Ser Tyr Trp Asn Val Ser Thr Leu Asn Val Gln Lys Asn
225                 230                 235                 240

Ser Ser Phe Thr Phe Ile Lys Arg Thr Glu Ser Asn Arg Phe Gly Pro
                245                 250                 255

Thr Thr Pro Leu Arg Ser Ser Gly Gly Val Phe Phe Asn Gly Thr Asn
            260                 265                 270

Gly Asn Met Val Leu Asn Val Gly Thr Asn Ser Arg Val Leu Phe Asn
        275                 280                 285

Leu Lys Pro Asn Glu Asn Thr Asn Asn Ser Lys Pro Leu Pro Leu Gln
    290                 295                 300

Phe Asn Ala Asn Ile Thr Ala Ile Gly Gly Gly Ser Val Ser Phe Asp
```

-continued

```
305                 310                 315                 320

Ile His Ala Asn His Ser Gly Arg Gly Ala Glu Leu Lys Met Asn Thr
                325                 330                 335

Ile Asn Ile Ser Asp Gly Thr Ser Leu Thr Leu Gln Ser His Val Arg
                340                 345                 350

Lys Asp Ser Ala Phe Ile Ile Ser Lys Asp Leu Thr Ile Asn Ala Thr
                355                 360                 365

Gly Ser Asn Phe Thr Leu Glu Gln Ser Pro Asp Ser Phe Thr Asp Lys
                370                 375                 380

Tyr Pro Gly Arg Ala Ile Ser Ser Thr Lys Asn Ile Thr Ile Ser Gly
385                 390                 395                 400

Gly Asn Val Ser Leu Gly Gly Gln Asn Ser Ser Asp Ile Lys Gly
                405                 410                 415

Asn Ile Thr Ile Lys Ser Ser Thr Asn Val Thr Leu Lys Ala His Asn
                420                 425                 430

Ser Pro Arg Asp Phe Ala Ser Arg Thr Leu Thr Leu Gly Asn Leu Asn
                435                 440                 445

Val Glu Gly Asn Leu Thr Leu Thr Gly Ser Val Ala Asp Ile Lys Gly
                450                 455                 460

Asn Leu Ser Ile Leu Asn Asp Ala Thr Phe Lys Gly Glu Thr Ser Glu
465                 470                 475                 480

Asn Leu Asn Ile Thr Gly Asn Phe Thr Asn Asn Gly Thr Ala Asp Ile
                485                 490                 495

Asn Ile Lys Gln Gly Val Val Asn Ile Gln Gly Asn Ile Thr Asn Lys
                500                 505                 510

Gly Gly Leu Asn Ile Thr Thr Asn Ala Gln Asn Gln Lys Thr Ile
                515                 520                 525

Ile Asn Gly Asn Ile Thr Asn Glu Gly Gly Asp Leu Asn Ile Lys Asp
                530                 535                 540

Ser Asn Asn Ala Glu Ile Gln Ile Gly Gly Asn Ile Ser Gln Lys
545                 550                 555                 560

Lys Gly Asn Leu Thr Ile Ser Ser Asp Lys Ile Asn Ile Thr Lys Lys
                565                 570                 575

Ile Thr Ile Lys Ala Gly Val Asp Glu Gly Gly Ser Asp Ser Ser Pro
                580                 585                 590

Ala Ser Asn Ala Asn Leu Thr Ile Lys Thr Lys Thr Leu Glu Leu Thr
                595                 600                 605

Gly Asp Leu Asn Ile Ser Gly Phe Asn Lys Ala Glu Ile Thr Ala Lys
                610                 615                 620

Asn Gly Asn Asp Leu Thr Ile Gly Lys Ala Ser Asp Gly Asn Ala Asn
625                 630                 635                 640

Ala Lys Lys Val Thr Phe Asp Lys Val Lys Asp Ser Lys Ile Ser Ala
                645                 650                 655

Asn Gly His Asn Val Thr Leu Asn Ser Lys Val Glu Thr Ser Asn Ser
                660                 665                 670

Asp Ser Ser Ala Asp Asp Ser Asp Asn Asn Thr Gly Leu Thr Ile
                675                 680                 685

Ser Ala Lys Asp Val Thr Val Asn Asn Asp Val Thr Ser His Lys Thr
                690                 695                 700

Ile Asn Ile Ser Ala Thr Thr Gly Asn Val Thr Thr Lys Glu Ser Thr
705                 710                 715                 720

Thr Ile Asn Ala Ala Thr Gly Ser Val Glu Val Thr Ala Lys Thr Gly
                725                 730                 735
```

-continued

```
Asp Ile Ser Gly Thr Ile Ser Gly Asn Thr Val Asn Val Thr Ala Thr
            740                 745                 750
Asp Ser Leu Thr Thr Gln Ala Ser Ser Ile Thr Ser Ser Asn Gly
            755                 760                 765
Gln Thr Thr Leu Thr Ala Lys Asn Gly Ser Ile Ala Gly Ser Ile Asp
            770                 775                 780
Ala Ala Asn Val Thr Leu Asn Thr Thr Gly Thr Leu Thr Thr Val Ala
785                 790                 795                 800
Gly Ser Asn Ile Lys Ala Thr Ser Gly Thr Leu Ala Ile Asn Ala Lys
            805                 810                 815
Asp Ala Lys Leu Asp Gly Thr Ala Ser Gly Asp Arg Thr Val Val Asn
            820                 825                 830
Ala Thr Asn Ala Ser Gly Ser Gly Ser Val Thr Ala Ala Thr Ser Ser
            835                 840                 845
Asn Val Asn Ile Thr Gly Asp Leu Ser Thr Ile Asn Gly Leu Asn Ile
            850                 855                 860
Ile Ser Lys Asn Gly Lys Asn Thr Val Val Leu Lys Gly Ala Glu Ile
865                 870                 875                 880
Asp Val Lys Tyr Ile Gln Pro Gly Val Ala Ser Ala Asn Glu Val Ile
            885                 890                 895
Glu Ala Lys Arg Ala Leu Glu Lys Val Lys Asp Leu Ser Asp Glu Glu
            900                 905                 910
Arg Glu Thr Leu Ala Lys Leu Gly Val Ser Ala Val Arg Phe Val Glu
            915                 920                 925
Pro Asn Asn Thr Ile Thr Val Asn Thr Gln Asn Glu Phe Thr Thr Arg
            930                 935                 940
Pro Ser Ser Gln Val Thr Ile Ser Glu Asp Lys Ala Cys Phe Ser Ser
945                 950                 955                 960
Gly Asn Gly Ala Ala Val Cys Thr Asn Val Thr Asp Asp Arg Gln
            965                 970                 975
```

<210> SEQ ID NO 31
<211> LENGTH: 2910
<212> TYPE: DNA
<213> ORGANISM: Haemophilus influenzae

<400> SEQUENCE: 31

| | | | | | |
|---|---|---|---|---|---|
| ccggataatg | tatccattga | aaatccttca | actgaacgca | atgattccaa | tgaagaccta | 60 |
| gagtatacag | gaacagggga | aaatataaac | aaccctaagg | taataatca | gtctaaaaaa | 120 |
| acactaacaa | gctcaatcct | tgagaacatc | ctgaaaaaag | gctcttttgt | taacattact | 180 |
| gccactgata | acatctacgt | taatagctct | atcaacatcg | gagacagtgg | tcacttaatt | 240 |
| ctctcaggtg | gaggcaggaa | cggcggcggt | gttaagatta | taaaaatat | tacttccacg | 300 |
| ggcggaagtt | taaccattaa | ttccaaagga | tgggttgata | ttcactccaa | tatttcactt | 360 |
| ggtacgggtt | ttttgaacat | tacctctaat | ggttccgtgg | cttttgagaa | ggcagacaaa | 420 |
| gataaggcac | gtagcgcggc | agatgctcaa | attgtcgcac | aaggcatcat | aaacctcaca | 480 |
| ggggaaaaca | aaacctttag | gcttaacaat | gtgtctttaa | atggagtggg | tcaaggtcta | 540 |
| tccatcacgt | caaatgtggg | caatcaaact | cataaattcg | atggtgaaat | taacataact | 600 |
| ggaaatgtaa | caattaatca | aactgcacct | gcgacaaccg | catattgaa | ttttagctac | 660 |
| gattcatatt | ggaacgtcag | tactcttaac | gtacaaaaaa | actcaagctt | tacctttatt | 720 |
| aagcgcactg | aaagtaatcg | ctttggccca | acaacaccac | ttcgaagctc | cggagggta | 780 |

-continued

```
ttctttaacg gcacgaatgg caacatggtg cttaacgtcg gaactaattc gagagttttg      840
tttaatttga agccaaatga gaatacaaac aacagcaagc ctttaccgct tcaatttaac      900
gccaatatta cagccattgg tggaggctct gtgtcttttg atatacacgc caatcattcc      960
ggcagagggg ctgaattaaa aatgaacaca attaatatct ctgacggcac cagcctcacc     1020
ctacaatccc atgttcgcaa agatagtgct tttataatca gtaaagattt aacaataaac     1080
gcaaccggtt caaattttac tcttgagcaa tcaccagaca gttttactga caaataccccc    1140 ggaagagcta ttagttcaac taaaaatata accatctcag gtggcaacgt ctctcttggt     1200
gggcaaaatt caagcagtga catcaaggga atatattacca tcaaaagctc aacaaatgtt    1260
acactgaaag cccataacag ccctcgcgac tttgcttcca gaaccttaac ccttggcaac     1320
ttgaatgttg aaggaaattt aaccctaacc ggctcagttg cggatattaa aggtaacctt     1380
tccattctta acgatgctac ttttaaagga gagaccagtg aaaacctaaa catcaccggc     1440
aacttcacca ataatggcac cgccgacatt aatataaaac aagggggtggt aaacatccaa    1500 ggtaatatta ccaataaagg tggtttaaac attaccacta atgcccaaaa caatcaaaaa     1560
accattatta acggaaatat aactaacgaa ggcggagatt taaacatcaa ggatagtaac    1620
aataatgctg aaatccaaat tggcggcaat atctcgcaaa aaaaaggcaa tctcacaatt     1680
tcttctgata aaatcaatat taccaagaag ataacaatca aagcaggcgt tgatgaaggt     1740
ggttctgact caagcccagc aagtaatgct aatctaacca ttaaaaccaa aacgctagaa    1800
ttaacaggag acctaaatat ttcaggcttt aataaagcag aaattacagc taaaaatggc    1860
aacgatttaa ctattggcaa ggctagtgat ggtaatgcta atgctaaaaa agtgactttt    1920
gacaaggtta aagattcaaa aatctcagct aacggtcaca atgtaacact aaatagcaaa     1980
gtggaaacgt ctaatagtga tagtagtgct gatgatagta atgataacaa cactggttta    2040
accatttccg caaaagatgt aacagtaaac aatgacgtca cctcccacaa gacaataaat     2100
atctctgcca aacaggaaa tgtaacaacc aaagaaagca caaccattaa tgcggccaca      2160
ggtagcgtgg aagtaactgc taaaacaggc gatattagtg gcacaatttc tggtaataca    2220
gtaaatgtta cagcaactga tagcttaacc acccaagcaa gctctagcat tacctcaagt     2280
aatggtcaga caactcttac agccaagaat ggcagtatcg caggaagtat tgatgccgct    2340
aatgtgacat taaataccac aggcacctta actactgtag cgggttcaaa cattaaggca    2400
accagtggca ctttagctat taacgcaaaa gatgctaagt tagatggtac tgcatcaggt    2460
gaccgcacag tagtaaatgc aactaacgca agtggctctg gtagtgtgac tgcggcaacc    2520
tcaagtaacg tgaatatcac tggagattta agcacaataa atggattaaa tatcatttcg    2580
aaaaatggta aaacaccgt agtgttaaaa ggtgctgaaa ttgatgtgaa atatattcaa     2640
ccaggtgtag caagtgcgaa tgaggttatt gaagcgaagc gtgcccttga aaagtaaaa     2700 gatttatctg atgaagaaag agaaacatta gctaaacttg gtgtaagtgc tgtacgtttt    2760
gttgagccaa ataatacaat tacagtcaat acacaaaatg aatttacaac cagaccgtca    2820
agtcaagtga caatttctga agacaaggcg tgtttctcaa gtggtaatgg tgcagcagta    2880
tgtactaatg ttactgacga tagacagtaa                                      2910
```

<210> SEQ ID NO 32
<211> LENGTH: 969
<212> TYPE: PRT
<213> ORGANISM: Haemophilus influenzae -continued

<400> SEQUENCE: 32

```
Pro Asp Asn Val Ser Ile Glu Asn Pro Ser Thr Glu Arg Asn Asp Ser
 1               5                  10                  15
Asn Glu Asp Leu Glu Tyr Thr Gly Thr Gly Glu Asn Ile Asn Asn Pro
             20                  25                  30
Lys Val Asn Asn Gln Ser Lys Lys Thr Leu Thr Ser Ser Ile Leu Glu
         35                  40                  45
Asn Ile Leu Lys Lys Gly Ser Phe Val Asn Ile Thr Ala Thr Asp Asn
     50                  55                  60
Ile Tyr Val Asn Ser Ser Ile Asn Ile Gly Asp Ser Gly His Leu Ile
 65                  70                  75                  80
Leu Ser Gly Gly Gly Arg Asn Gly Gly Val Lys Ile Asn Lys Asn
                 85                  90                  95
Ile Thr Ser Thr Gly Gly Ser Leu Thr Ile Asn Ser Lys Gly Trp Val
             100                 105                 110
Asp Ile His Ser Asn Ile Ser Leu Gly Thr Gly Phe Leu Asn Ile Thr
         115                 120                 125
Ser Asn Gly Ser Val Ala Phe Glu Lys Ala Asp Lys Asp Lys Ala Arg
     130                 135                 140
Ser Ala Asp Ala Gln Ile Val Ala Gln Gly Ile Ile Asn Leu Thr
145                 150                 155                 160
Gly Glu Asn Lys Thr Phe Arg Leu Asn Asn Val Ser Leu Asn Gly Val
                165                 170                 175
Gly Gln Gly Leu Ser Ile Thr Ser Asn Val Gly Asn Gln Thr His Lys
            180                 185                 190
Phe Asp Gly Glu Ile Asn Ile Thr Gly Asn Val Thr Ile Asn Gln Thr
        195                 200                 205
Ala Pro Ala Thr Thr Ala Tyr Trp Asn Phe Ser Tyr Asp Ser Tyr Trp
    210                 215                 220
Asn Val Ser Thr Leu Asn Val Gln Lys Asn Ser Ser Phe Thr Phe Ile
225                 230                 235                 240
Lys Arg Thr Glu Ser Asn Arg Phe Gly Pro Thr Thr Pro Leu Arg Ser
                245                 250                 255
Ser Gly Gly Val Phe Phe Asn Gly Thr Asn Gly Asn Met Val Leu Asn
            260                 265                 270
Val Gly Thr Asn Ser Arg Val Leu Phe Asn Leu Lys Pro Asn Glu Asn
        275                 280                 285
Thr Asn Asn Ser Lys Pro Leu Pro Leu Gln Phe Asn Ala Asn Ile Thr
    290                 295                 300
Ala Ile Gly Gly Gly Ser Val Ser Phe Asp Ile His Ala Asn His Ser
305                 310                 315                 320
Gly Arg Gly Ala Glu Leu Lys Met Asn Thr Ile Asn Ile Ser Asp Gly
                325                 330                 335
Thr Ser Leu Thr Leu Gln Ser His Val Arg Lys Asp Ser Ala Phe Ile
            340                 345                 350
Ile Ser Lys Asp Leu Thr Ile Asn Ala Thr Gly Ser Asn Phe Thr Leu
        355                 360                 365
Glu Gln Ser Pro Asp Ser Phe Thr Asp Lys Tyr Pro Gly Arg Ala Ile
    370                 375                 380
Ser Ser Thr Lys Asn Ile Thr Ile Ser Gly Gly Asn Val Ser Leu Gly
385                 390                 395                 400
Gly Gln Asn Ser Ser Ser Asp Ile Lys Gly Asn Ile Thr Ile Lys Ser
                405                 410                 415
```

```
Ser Thr Asn Val Thr Leu Lys Ala His Asn Ser Pro Arg Asp Phe Ala
            420                 425                 430

Ser Arg Thr Leu Thr Leu Gly Asn Leu Asn Val Glu Gly Asn Leu Thr
        435                 440                 445

Leu Thr Gly Ser Val Ala Asp Ile Lys Gly Asn Leu Ser Ile Leu Asn
    450                 455                 460

Asp Ala Thr Phe Lys Gly Glu Thr Ser Glu Asn Leu Asn Ile Thr Gly
465                 470                 475                 480

Asn Phe Thr Asn Asn Gly Thr Ala Asp Ile Asn Ile Lys Gln Gly Val
                485                 490                 495

Val Asn Ile Gln Gly Asn Ile Thr Asn Lys Gly Gly Leu Asn Ile Thr
            500                 505                 510

Thr Asn Ala Gln Asn Gln Lys Thr Ile Ile Asn Gly Asn Ile Thr
        515                 520                 525

Asn Glu Gly Gly Asp Leu Asn Ile Lys Asp Ser Asn Asn Ala Glu
        530                 535                 540

Ile Gln Ile Gly Gly Asn Ile Ser Gln Lys Lys Gly Asn Leu Thr Ile
545                 550                 555                 560

Ser Ser Asp Lys Ile Asn Ile Thr Lys Lys Ile Thr Ile Lys Ala Gly
                565                 570                 575

Val Asp Glu Gly Gly Ser Asp Ser Ser Pro Ala Ser Asn Ala Asn Leu
            580                 585                 590

Thr Ile Lys Thr Lys Thr Leu Glu Leu Thr Gly Asp Leu Asn Ile Ser
            595                 600                 605

Gly Phe Asn Lys Ala Glu Ile Thr Ala Lys Asn Gly Asn Asp Leu Thr
        610                 615                 620

Ile Gly Lys Ala Ser Asp Gly Asn Ala Asn Ala Lys Lys Val Thr Phe
625                 630                 635                 640

Asp Lys Val Lys Asp Ser Lys Ile Ser Ala Asn Gly His Asn Val Thr
                645                 650                 655

Leu Asn Ser Lys Val Glu Thr Ser Asn Ser Asp Ser Ser Ala Asp Asp
            660                 665                 670

Ser Asn Asp Asn Asn Thr Gly Leu Thr Ile Ser Ala Lys Asp Val Thr
        675                 680                 685

Val Asn Asn Asp Val Thr Ser His Lys Thr Ile Asn Ile Ser Ala Thr
        690                 695                 700

Thr Gly Asn Val Thr Thr Lys Glu Ser Thr Thr Ile Asn Ala Ala Thr
705                 710                 715                 720

Gly Ser Val Glu Val Thr Ala Lys Thr Gly Asp Ile Ser Gly Thr Ile
                725                 730                 735

Ser Gly Asn Thr Val Asn Val Thr Ala Thr Asp Ser Leu Thr Thr Gln
            740                 745                 750

Ala Ser Ser Ser Ile Thr Ser Ser Asn Gly Gln Thr Thr Leu Thr Ala
        755                 760                 765

Lys Asn Gly Ser Ile Ala Gly Ser Ile Asp Ala Ala Asn Val Thr Leu
        770                 775                 780

Asn Thr Thr Gly Thr Leu Thr Val Ala Gly Ser Asn Ile Lys Ala
785                 790                 795                 800

Thr Ser Gly Thr Leu Ala Ile Asn Ala Lys Asp Ala Lys Leu Asp Gly
                805                 810                 815

Thr Ala Ser Gly Asp Arg Thr Val Val Asn Ala Thr Asn Ala Ser Gly
            820                 825                 830
```

```
Ser Gly Ser Val Thr Ala Ala Thr Ser Ser Asn Val Asn Ile Thr Gly
        835                 840                 845

Asp Leu Ser Thr Ile Asn Gly Leu Asn Ile Ile Ser Lys Asn Gly Lys
        850                 855                 860

Asn Thr Val Val Leu Lys Gly Ala Glu Ile Asp Val Lys Tyr Ile Gln
865                 870                 875                 880

Pro Gly Val Ala Ser Ala Asn Glu Val Ile Glu Ala Lys Arg Ala Leu
                885                 890                 895

Glu Lys Val Lys Asp Leu Ser Asp Glu Glu Arg Glu Thr Leu Ala Lys
            900                 905                 910

Leu Gly Val Ser Ala Val Arg Phe Val Glu Pro Asn Asn Thr Ile Thr
        915                 920                 925

Val Asn Thr Gln Asn Glu Phe Thr Thr Arg Pro Ser Ser Gln Val Thr
930                 935                 940

Ile Ser Glu Asp Lys Ala Cys Phe Ser Ser Gly Asn Gly Ala Ala Val
945                 950                 955                 960

Cys Thr Asn Val Thr Asp Asp Arg Gln
                965
```

<210> SEQ ID NO 33
<211> LENGTH: 3686
<212> TYPE: DNA
<213> ORGANISM: Haemophilus influenzae

<400> SEQUENCE: 33

```
aaagagtggt tgttagaccc ggataatgta tctattaatg cacccgcact tggacgtact    60
gagagtaccc caaataacaa tgagtacgac tcgccaaatc aaattaacta taaaaacaaa   120
ccatccctaa gtacactaac aaacacaaca cttgagagaa tattaaaaag aaacacctct   180
gttaatatca ctgccaccaa acaatcaca gttaatagtg atatcaatat ggagacagc    240
tcccacttaa ccctttggag tgagggtcag gggagaggcg gcgttaatgt tacaggcaat   300
attacttcta ctaccaacgg aaacttaacc atttactctg gcggatgggt tgatgttcat   360
aaaaacatta cacttaaatc agggtactta acattacaa ctaaacaagg agacatcgcc   420
ttcgaagaca aaccagggct gagcaaccta accattacag ctaaagggac cattgccgtg   480
aacaacaaga aaggctttag gtttgataat gtcactctaa atggaacggg aggagggctc   540
tcttttaaat acatcgaaac cggaaataga gatagcaatt cgaaaccca ttttagagga   600
agattaaata tttcagggaa agtagatatc ttaatgcaag caaggcagga gaactggaac   660
cgcagacact ggggacgctc ccactggaat gtaacccgat tgaacgtttc tgaaaacagt   720
tattttaacg tcactattga tagcagtggc agtgcctctt ccctggcgc tggccctctg   780
aatgcccaat cgggtttaaa tggcatatcg tttaataatg acactgtttt taatattgca   840
gcaagttcgg cggttaactt taacatcaaa ccaccaatag tagacaaagt aaccaacggg   900
aatcacacat tattcaaagg gaatatttca gttttagggg ggggatgtc aactttcatt   960
ttaacgcctc ctccagcaac taccagactt atggcgtgat tatagagtca caaaacttta  1020
gtgcctcagg agggtcaagc ttaaaattca aaagcgaagg ttcgacacac gccgctttta  1080
caataaaaaa tgatttaatt ttaaatgcca ctgggggcaa tatatcattg aaccaagttg  1140
caggtattga tagtaatctc aaaaaaagcc ttatagccaa taaaaacata acctttgaag  1200
ggggcaatat caccttgca gccgataaaa accaatagaa atcaaaggt aatattactg  1260
ttaaagaagg agccaatgtc acccttcgta gcgcgaatta tggtaatgac aaatcagctt  1320
```

-continued

```
taagtataag aggaaatgtc actaataaag gcaatctcac cgttaccggc tccgctatca    1380
atatagaaaa aaatcttacc gttgaaggta gtgctaagtt tttagctaat ccaaattaca    1440
gctttaacgt atccggccta tttgacaacc aaggcaagtc aaacatttcc atcgctaagg    1500
gaggagctat ttttaaagat atcgagaata ctggcagtct gaatattacc actaaatccg    1560
actccaacca ccatactatt ataaagggta atataactaa cagaaaaggt gatttaaata    1620
tcacgaataa tggtgataat actgaaatcc aaattggcgg caatatctcg caaaagaag    1680 gcaatctcac aatttcttct gataaagtca atattaccga gcggataaca atcaaagcag    1740
gcgttaatgg ggataactct gattcaaatg aggcaacaag tgctaaccta accattaaaa    1800
ccaaagagtt aaaattaaca aacgacctaa atatttcagg ttttaataaa gcagaaatta    1860
cagctaaaga taacagtaat ttaactattg gcgataacag tgacgctggc aatactgacg    1920
ctaaaaaagt aacctttagc aatgttaaag attcaaaaat ctctgctagc gaccataatg    1980
taacgctaaa cagcaaagtg gaaacatctg gcgatactga cagcactgaa gatggcggca    2040
acaataacac cggcttaact attactgcaa aaaatgtaac agtaaacaac aatattactt    2100
ctcacaaaac agtaaatatc actgcgtcag aaaatgttac caccaaagcg ggcacaacca    2160
ttaatgcaac cacaggtagc gtagaagtaa cagccaaaac aggtgatatt aaaggtggaa    2220
ttgaatccaa ttccggtaat gtaaatatta cagcgagcgg cgacacgctt aatgtaagta    2280
acatcacagg tcaaaatgtg acagtggcag cagcctcagg tgccgtaaca accacaaaag    2340
gatcaactat taatgcaaca actggtaatg caaatattac aaccaaaaca ggtgaaatta    2400
atggcgaagt taaatcagct tccggtaatg taaatattac agcgagcggc aatacactta    2460
atgtaagtaa catcactggt caaaatgtaa cagtaacagc aaactcaggt gccataacaa    2520
ccacagaagg ctcaactatt aacgcgacaa caggtgatgc aaatattaca acccaaacag    2580
gtaatattaa tggtaaagtt gaatccagtt ctggttctgt gacgcttatt gcaactggac    2640
aaactcttgc tgtaggtaat atttcaggtg acactgttac cattactgcg gataaaggta    2700
aattaaccac acaaacaagc tctaagatta acggaactaa gagtgtaacc acctcaagcc    2760
aatcaggtga tattagtggc acaatttctg gtaatacggt aagcgttagt gcgaccggta    2820
gcttgaccac tcaagcaggc tcaaaaattg aagcaaaaac aggtgaggct aatgtaacaa    2880
gcgcaacagg tacaattggc ggtacaatct ctggcaatac agtaaatgtt acagcaaata    2940
ctgataattt aactattaaa gatggcgcaa gaattaaagc aacgggcgga gctgtgactt    3000
taaccgcaac aggaggtact ttaaccaccg aaacaagttc tgatattacc tcaagcaatg    3060
gtcagacaac tctcacggcc aaggatagca gtatcgcagg aagcatcaat gccgccaatg    3120
tgacattaaa taccacaggc actttaacta ctgtggcagg ttcaaaaatc gaggcagcca    3180
gtggcaccct ggttattaat gcaaaagatg ctcagttgga cggcgcggca tcaggtgacc    3240
acacagtagt aaatgcaacc aacgcaaacg gctccggcag cgtaatcgcg caaacctcaa    3300
gcagagtgaa catcactggg gatttaatca caataaatgg attaaatatc atttcaaaaa    3360
acggtaaaaa caccgtgctg ttaaaaggtg ttgaaattga tgtgaaatac attcaaccgg    3420
gcatagcgag cgtaaatgaa gtaattgaag cgaaacgcgc ccttgagaaa gtaaaagatt    3480
tatctgacga agaaagagaa acattagcta aacttggcgt gagcgctgta cgttttgctg    3540
agccaaataa tgccattacg attaatacac aaaatgagtt tacaaccaga ccattaagtc    3600
aagtgacaat ttctgaaggt aaggtatgtt tcttaatcgg caatggcgca acaatatgca    3660
ccaatattgc tgatattgag cggtag                                        3686
```

<210> SEQ ID NO 34
<211> LENGTH: 1228
<212> TYPE: PRT
<213> ORGANISM: Haemophilus influenzae

<400> SEQUENCE: 34

```
Lys Glu Trp Leu Leu Asp Pro Asp Asn Val Ser Ile Asn Ala Pro Ala
  1               5                  10                  15

Leu Gly Arg Thr Glu Ser Thr Pro Asn Asn Glu Tyr Asp Ser Pro
             20                  25                  30

Asn Gln Ile Asn Tyr Lys Asn Lys Pro Ser Leu Ser Thr Leu Thr Asn
             35                  40                  45

Thr Thr Leu Glu Arg Ile Leu Lys Arg Asn Thr Ser Val Asn Ile Thr
 50                  55                  60

Ala Thr Lys Thr Ile Thr Val Asn Ser Asp Ile Asn Ile Gly Asp Ser
 65                  70                  75                  80

Ser His Leu Thr Leu Trp Ser Glu Gly Gln Gly Arg Gly Gly Val Asn
                 85                  90                  95

Val Thr Gly Asn Ile Thr Ser Thr Thr Asn Gly Asn Leu Thr Ile Tyr
                100                 105                 110

Ser Gly Gly Trp Val Asp Val His Lys Asn Ile Thr Leu Lys Ser Gly
            115                 120                 125

Tyr Leu Asn Ile Thr Thr Lys Gln Gly Asp Ile Ala Phe Glu Asp Lys
        130                 135                 140

Pro Gly Leu Ser Asn Leu Thr Ile Thr Ala Lys Gly Thr Ile Ala Val
145                 150                 155                 160

Asn Asn Lys Lys Gly Phe Arg Phe Asp Asn Val Thr Leu Asn Gly Thr
                165                 170                 175

Gly Gly Gly Leu Ser Phe Lys Tyr Ile Glu Thr Gly Asn Arg Asp Ser
            180                 185                 190

Asn Phe Glu Thr His Phe Arg Gly Arg Leu Asn Ile Ser Gly Lys Val
        195                 200                 205

Asp Ile Leu Met Gln Ala Arg Gln Glu Asn Trp Asn Arg Arg His Trp
    210                 215                 220

Gly Arg Ser His Trp Asn Val Thr Arg Leu Asn Val Ser Glu Asn Ser
225                 230                 235                 240

Tyr Phe Asn Val Thr Ile Asp Ser Ser Gly Ser Ala Ser Ser Pro Gly
                245                 250                 255

Ala Gly Pro Leu Asn Ala Gln Ser Gly Leu Asn Gly Ile Ser Phe Asn
            260                 265                 270

Asn Asp Thr Val Phe Asn Ile Ala Ala Ser Ser Ala Val Asn Phe Asn
        275                 280                 285

Ile Lys Pro Pro Ile Val Asp Lys Val Thr Asn Gly Asn His Thr Leu
    290                 295                 300

Phe Lys Gly Asn Ile Ser Val Leu Gly Gly Met Ser Thr Phe Ile
305                 310                 315                 320

Phe Asn Ala Ser Ser Ser Asn Tyr Gln Thr Tyr Gly Val Ile Ile Glu
                325                 330                 335

Ser Gln Asn Phe Ser Ala Ser Gly Gly Ser Ser Leu Lys Phe Lys Ser
            340                 345                 350

Glu Gly Ser Thr His Ala Ala Phe Thr Ile Lys Asn Asp Leu Ile Leu
        355                 360                 365

Asn Ala Thr Gly Gly Asn Ile Ser Leu Asn Gln Val Ala Gly Ile Asp
```

-continued

```
                370                 375                 380
Ser Asn Leu Lys Lys Ser Leu Ile Ala Asn Lys Asn Ile Thr Phe Glu
385                 390                 395                 400
Gly Gly Asn Ile Thr Leu Ala Ala Asp Lys Lys Pro Ile Glu Ile Lys
                405                 410                 415
Gly Asn Ile Thr Val Lys Glu Gly Ala Asn Val Thr Leu Arg Ser Ala
                420                 425                 430
Asn Tyr Gly Asn Asp Lys Ser Ala Leu Ser Ile Arg Gly Asn Val Thr
                435                 440                 445
Asn Lys Gly Asn Leu Thr Val Thr Gly Ser Ala Ile Asn Ile Glu Lys
                450                 455                 460
Asn Leu Thr Val Glu Gly Ser Ala Lys Phe Leu Ala Asn Pro Asn Tyr
465                 470                 475                 480
Ser Phe Asn Val Ser Gly Leu Phe Asp Asn Gln Gly Lys Ser Asn Ile
                485                 490                 495
Ser Ile Ala Lys Gly Gly Ala Ile Phe Lys Asp Ile Glu Asn Thr Gly
                500                 505                 510
Ser Leu Asn Ile Thr Thr Lys Ser Asp Ser Asn His His Thr Ile Ile
                515                 520                 525
Lys Gly Asn Ile Thr Asn Arg Lys Gly Asp Leu Asn Ile Thr Asn Asn
530                 535                 540
Gly Asp Asn Thr Glu Ile Gln Ile Gly Gly Asn Ile Ser Gln Lys Glu
545                 550                 555                 560
Gly Asn Leu Thr Ile Ser Ser Asp Lys Val Asn Ile Thr Glu Arg Ile
                565                 570                 575
Thr Ile Lys Ala Gly Val Asn Gly Asp Asn Ser Asp Ser Asn Glu Ala
                580                 585                 590
Thr Ser Ala Asn Leu Thr Ile Lys Thr Lys Glu Leu Lys Leu Thr Asn
                595                 600                 605
Asp Leu Asn Ile Ser Gly Phe Asn Lys Ala Glu Ile Thr Ala Lys Asp
                610                 615                 620
Asn Ser Asn Leu Thr Ile Gly Asp Asn Ser Asp Ala Gly Asn Thr Asp
625                 630                 635                 640
Ala Lys Lys Val Thr Phe Ser Asn Val Lys Asp Ser Lys Ile Ser Ala
                645                 650                 655
Ser Asp His Asn Val Thr Leu Asn Ser Lys Val Glu Thr Ser Gly Asp
                660                 665                 670
Thr Asp Ser Thr Glu Asp Gly Asn Asn Thr Gly Leu Thr Ile
                675                 680                 685
Thr Ala Lys Asn Val Thr Val Asn Asn Ile Thr Ser His Lys Thr
                690                 695                 700
Val Asn Ile Thr Ala Ser Glu Asn Val Thr Thr Lys Ala Gly Thr Thr
705                 710                 715                 720
Ile Asn Ala Thr Thr Gly Ser Val Glu Val Thr Ala Lys Thr Gly Asp
                725                 730                 735
Ile Lys Gly Gly Ile Glu Ser Asn Ser Gly Asn Val Asn Ile Thr Ala
                740                 745                 750
Ser Gly Asp Thr Leu Asn Val Ser Asn Ile Thr Gly Gln Asn Val Thr
                755                 760                 765
Val Ala Ala Ala Ser Gly Ala Val Thr Thr Lys Gly Ser Thr Ile
                770                 775                 780
Asn Ala Thr Thr Gly Asn Ala Asn Ile Thr Thr Lys Thr Gly Glu Ile
785                 790                 795                 800
```

-continued

Asn Gly Glu Val Lys Ser Ala Ser Gly Asn Val Asn Ile Thr Ala Ser
                805                 810                 815
Gly Asn Thr Leu Asn Val Ser Asn Ile Thr Gly Gln Asn Val Thr Val
            820                 825                 830
Thr Ala Asn Ser Gly Ala Ile Thr Thr Thr Glu Gly Ser Thr Ile Asn
        835                 840                 845
Ala Thr Thr Gly Asp Ala Asn Ile Thr Thr Gln Thr Gly Asn Ile Asn
    850                 855                 860
Gly Lys Val Glu Ser Ser Gly Ser Val Thr Leu Ile Ala Thr Gly
865                 870                 875                 880
Gln Thr Leu Ala Val Gly Asn Ile Ser Gly Asp Thr Val Thr Ile Thr
                885                 890                 895
Ala Asp Lys Gly Lys Leu Thr Thr Gln Thr Ser Ser Lys Ile Asn Gly
            900                 905                 910
Thr Lys Ser Val Thr Thr Ser Ser Gln Ser Gly Asp Ile Ser Gly Thr
        915                 920                 925
Ile Ser Gly Asn Thr Val Ser Val Ser Ala Thr Gly Ser Leu Thr Thr
    930                 935                 940
Gln Ala Gly Ser Lys Ile Glu Ala Lys Thr Gly Glu Ala Asn Val Thr
945                 950                 955                 960
Ser Ala Thr Gly Thr Ile Gly Gly Thr Ile Ser Gly Asn Thr Val Asn
                965                 970                 975
Val Thr Ala Asn Thr Asp Asn Leu Thr Ile Lys Asp Gly Ala Arg Ile
            980                 985                 990
Lys Ala Thr Gly Gly Ala Val Thr Leu Thr Ala Thr Gly Gly Thr Leu
        995                 1000                1005
Thr Thr Glu Thr Ser Ser Asp Ile Thr Ser Ser Asn Gly Gln Thr Thr
    1010                1015                1020
Leu Thr Ala Lys Asp Ser Ser Ile Ala Gly Ser Ile Asn Ala Ala Asn
1025                1030                1035                1040
Val Thr Leu Asn Thr Thr Gly Thr Leu Thr Thr Val Ala Gly Ser Lys
                1045                1050                1055
Ile Glu Ala Ala Ser Gly Thr Leu Val Ile Asn Ala Lys Asp Ala Gln
            1060                1065                1070
Leu Asp Gly Ala Ala Ser Gly Asp His Thr Val Val Asn Ala Thr Asn
        1075                1080                1085
Ala Asn Gly Ser Gly Ser Val Ile Ala Thr Thr Ser Ser Arg Val Asn
    1090                1095                1100
Ile Thr Gly Asp Leu Ile Thr Ile Asn Gly Leu Asn Ile Ile Ser Lys
1105                1110                1115                1120
Asn Gly Lys Asn Thr Val Leu Leu Lys Gly Val Glu Ile Asp Val Lys
                1125                1130                1135
Tyr Ile Gln Pro Gly Ile Ala Ser Val Asn Glu Val Ile Glu Ala Lys
            1140                1145                1150
Arg Ala Leu Glu Lys Val Lys Asp Leu Ser Asp Glu Glu Arg Glu Thr
        1155                1160                1165
Leu Ala Lys Leu Gly Val Ser Ala Val Arg Phe Ala Glu Pro Asn Asn
    1170                1175                1180
Ala Ile Thr Ile Asn Thr Gln Asn Glu Phe Thr Thr Arg Pro Leu Ser
1185                1190                1195                1200
Gln Val Thr Ile Ser Glu Gly Lys Val Cys Phe Leu Ile Gly Asn Gly
                1205                1210                1215

-continued

```
Ala Thr Ile Cys Thr Asn Ile Ala Asp Ile Glu Arg
            1220                1225

<210> SEQ ID NO 35
<211> LENGTH: 915
<212> TYPE: PRT
<213> ORGANISM: Haemophilus influenzae

<400> SEQUENCE: 35

Gly Gly Asp Val Asn Phe His Phe Asn Ala Ser Ser Asn Tyr Gln
 1               5                  10                  15

Thr Tyr Gly Val Ile Ile Glu Ser Gln Asn Phe Ser Ala Ser Gly Gly
                20                  25                  30

Ser Ser Leu Lys Phe Lys Ser Glu Gly Ser Thr His Ala Ala Phe Thr
            35                  40                  45

Ile Lys Asn Asp Leu Ile Leu Asn Ala Thr Gly Gly Asn Ile Ser Leu
     50                  55                  60

Asn Gln Val Ala Gly Ile Asp Ser Asn Leu Lys Lys Ser Leu Ile Ala
 65                  70                  75                  80

Asn Lys Asn Ile Thr Phe Glu Gly Gly Asn Ile Thr Leu Ala Ala Asp
                85                  90                  95

Lys Lys Pro Ile Glu Ile Lys Gly Asn Ile Thr Val Lys Glu Gly Ala
            100                 105                 110

Asn Val Thr Leu Arg Ser Ala Asn Tyr Gly Asn Asp Lys Ser Ala Leu
        115                 120                 125

Ser Ile Arg Gly Asn Val Thr Asn Lys Gly Asn Leu Thr Val Thr Gly
    130                 135                 140

Ser Ala Ile Asn Ile Glu Lys Asn Leu Thr Val Glu Gly Ser Ala Lys
145                 150                 155                 160

Phe Leu Ala Asn Pro Asn Tyr Ser Phe Asn Val Ser Gly Leu Phe Asp
                165                 170                 175

Asn Gln Gly Lys Ser Asn Ile Ser Ile Ala Lys Gly Gly Ala Ile Phe
            180                 185                 190

Lys Asp Ile Glu Asn Thr Gly Ser Leu Asn Ile Thr Thr Lys Ser Asp
        195                 200                 205

Ser Asn His His Thr Ile Ile Lys Gly Asn Ile Thr Asn Arg Lys Gly
    210                 215                 220

Asp Leu Asn Ile Thr Asn Asn Gly Asp Asn Thr Glu Ile Gln Ile Gly
225                 230                 235                 240

Gly Asn Ile Ser Gln Lys Gly Asn Leu Thr Ile Ser Ser Asp Lys
                245                 250                 255

Val Asn Ile Thr Glu Arg Ile Thr Ile Lys Ala Gly Val Asn Gly Asp
            260                 265                 270

Asn Ser Asp Ser Asn Glu Ala Thr Ser Ala Asn Leu Thr Ile Lys Thr
        275                 280                 285

Lys Glu Leu Lys Leu Thr Asn Asp Leu Asn Ile Ser Gly Phe Asn Lys
    290                 295                 300

Ala Glu Ile Thr Ala Lys Asp Asn Ser Asn Leu Thr Ile Gly Asp Asn
305                 310                 315                 320

Ser Asp Ala Gly Asn Thr Asp Ala Lys Lys Val Thr Phe Ser Asn Val
                325                 330                 335

Lys Asp Ser Lys Ile Ser Ala Ser Asp His Asn Val Thr Leu Asn Ser
            340                 345                 350

Lys Val Glu Thr Ser Gly Asp Thr Asp Ser Thr Glu Asp Gly Gly Asn
        355                 360                 365
```

-continued

```
Asn Asn Thr Gly Leu Thr Ile Thr Ala Lys Asn Val Thr Asn Asn
    370                 375                 380
Asn Ile Thr Ser His Lys Thr Val Asn Ile Thr Ala Ser Glu Asn Val
385                 390                 395                 400
Thr Thr Lys Ala Gly Thr Thr Ile Asn Ala Thr Thr Gly Ser Val Glu
                405                 410                 415
Val Thr Ala Lys Thr Gly Asp Ile Lys Gly Ile Glu Ser Asn Ser
                420                 425                 430
Gly Asn Val Asn Ile Thr Ala Ser Gly Asp Thr Leu Asn Val Ser Asn
                435                 440                 445
Ile Thr Gly Gln Asn Val Thr Val Ala Ala Ser Gly Ala Val Thr
    450                 455                 460
Thr Thr Lys Gly Ser Thr Ile Asn Ala Thr Thr Gly Asn Ala Asn Ile
465                 470                 475                 480
Thr Thr Lys Thr Gly Glu Ile Asn Gly Glu Val Lys Ser Ala Ser Gly
                485                 490                 495
Asn Val Asn Ile Thr Ala Ser Gly Asn Thr Leu Asn Val Ser Asn Ile
                500                 505                 510
Thr Gly Gln Asn Val Thr Val Thr Ala Asn Ser Gly Ala Ile Thr Thr
    515                 520                 525
Thr Glu Gly Ser Thr Ile Asn Ala Thr Thr Gly Asp Ala Asn Ile Thr
    530                 535                 540
Thr Gln Thr Gly Asn Ile Asn Gly Lys Val Glu Ser Ser Ser Gly Ser
545                 550                 555                 560
Val Thr Leu Ile Ala Thr Gly Gln Thr Leu Ala Val Gly Asn Ile Ser
                565                 570                 575
Gly Asp Thr Val Thr Ile Thr Ala Asp Lys Gly Lys Leu Thr Thr Gln
                580                 585                 590
Thr Ser Ser Lys Ile Asn Gly Thr Lys Ser Val Thr Thr Ser Ser Gln
                595                 600                 605
Ser Gly Asp Ile Ser Gly Thr Ile Ser Gly Asn Thr Val Ser Val Ser
                610                 615                 620
Ala Thr Gly Ser Leu Thr Thr Gln Ala Gly Ser Lys Ile Glu Ala Lys
625                 630                 635                 640
Thr Gly Glu Ala Asn Val Thr Ser Ala Thr Gly Thr Ile Gly Thr
                645                 650                 655
Ile Ser Gly Asn Thr Val Asn Val Thr Ala Asn Thr Asp Asn Leu Thr
                660                 665                 670
Ile Lys Asp Gly Ala Arg Ile Lys Ala Thr Gly Gly Ala Val Thr Leu
                675                 680                 685
Thr Ala Thr Gly Gly Thr Leu Thr Thr Glu Thr Ser Ser Asp Ile Thr
    690                 695                 700
Ser Ser Asn Gly Gln Thr Thr Leu Thr Ala Lys Asp Ser Ser Ile Ala
705                 710                 715                 720
Gly Ser Ile Asn Ala Ala Asn Val Thr Leu Asn Thr Thr Gly Thr Leu
                725                 730                 735
Thr Thr Val Ala Gly Ser Lys Ile Glu Ala Ala Ser Gly Thr Leu Val
                740                 745                 750
Ile Asn Ala Lys Asp Ala Gln Leu Asp Gly Ala Ala Ser Gly Asp His
    755                 760                 765
Thr Val Val Asn Ala Thr Asn Ala Asn Gly Ser Gly Ser Val Ile Ala
    770                 775                 780
```

```
Thr Thr Ser Ser Arg Val Asn Ile Thr Gly Asp Leu Ile Thr Ile Asn
785                 790                 795                 800

Gly Leu Asn Ile Ile Ser Lys Asn Gly Lys Asn Thr Val Leu Leu Lys
            805                 810                 815

Gly Val Glu Ile Asp Val Lys Tyr Ile Gln Pro Gly Ile Ala Ser Val
            820                 825                 830

Asn Glu Val Ile Glu Ala Lys Arg Ala Leu Glu Lys Val Lys Asp Leu
            835                 840                 845

Ser Asp Glu Glu Arg Glu Thr Leu Ala Lys Leu Gly Val Ser Ala Val
        850                 855                 860

Arg Phe Ala Glu Pro Asn Asn Ala Ile Thr Ile Asn Thr Gln Asn Glu
865                 870                 875                 880

Phe Thr Thr Arg Pro Leu Ser Gln Val Thr Ile Ser Glu Gly Lys Val
                885                 890                 895

Cys Phe Leu Ile Gly Asn Gly Ala Thr Ile Cys Thr Asn Ile Ala Asp
            900                 905                 910

Ile Glu Arg
        915

<210> SEQ ID NO 36
<211> LENGTH: 3668
<212> TYPE: DNA
<213> ORGANISM: Haemophilus influenzae

<400> SEQUENCE: 36
ccggataatg tatctattaa tgcacccgca cttggacgta ctgagagtac cccaaataac      60
aatgagtacg actcgccaaa tcaaattaac tataaaaaca aaccatccct aagtacacta     120
acaaacacaa cacttgagag aatattaaaa agaaacacct ctgttaatat cactgccacc     180
aaaacaatca cagttaatag tgatatcaat attggagaca gctcccactt aacccttttgg     240 agtgagggtc aggggagagg cggcgttaat gttacaggca atattacttc tactaccaac     300
ggaaacttaa ccatttactc tggcggatgg gttgatgttc ataaaaacat tacacttaaa     360
tcagggtact taaacattac aactaaacaa ggagacatcg ccttcgaaga caaaccaggg     420
ctgagcaacc taaccattac agctaaaggg accattgccg tgaacaacaa gaaaggcttt     480
aggtttgata atgtcactct aaatggaacg ggaggagggc tctcttttaa atacatcgaa     540
accggaaata gagatagcaa tttcgaaacc catttagag gaagattaaa tatttcaggg     600
aaagtagata tcttaatgca agcaaggcag agagactgga accgcagaca ctggggacgc     660
tcccactgga atgtaacccg attgaacgtt tctgaaaaca gttatttaa cgtcactatt     720 gatagcagtg gcagtgcctc ttcccctggc gctggccctc tgaatgccca atcgggttta     780
aatggcatat cgtttaataa tgacactgtt tttaatattg cagcaagttc ggcggttaac     840
tttaacatca aaccaccaat agtagacaaa gtaaccaacg gaatcacac attattcaaa     900 gggaatattt cagttttagg ggggggatg tcaactttca tttaacgcc tcctccagca     960 actaccagac ttatggcgtg attatagagt cacaaaactt agtgcctca ggagggtcaa    1020 gcttaaaatt caaagcgaa ggttcgacac acgccgcttt tacaataaaa aatgatttaa    1080
ttttaaatgc cactgggggc aatatatcat tgaaccaagt tgcaggtatt gatagtaatc    1140
tcaaaaaaag ccttatagcc aataaaaaca taaccttga aggggggcaat atcacccttg    1200 cagccgataa aaaccaata gaaatcaaag gtaatattac tgttaaagaa ggagccaatg    1260
tcacccttcg tagcgcgaat tatggtaatg acaaatcagc tttaagtata agaggaaatg    1320
```

```
tcactaataa aggcaatctc accgttaccg gctccgctat caatatagaa aaaaatctta    1380
ccgttgaagg tagtgctaag ttttagcta atccaaatta cagctttaac gtatccggcc    1440
tatttgacaa ccaaggcaag tcaaacattt ccatcgctaa gggaggagct atttttaaag    1500
atatcgagaa tactggcagt ctgaatatta ccactaaatc cgactccaac caccatacta    1560
ttataaaggg taatataact aacagaaaag gtgatttaaa tatcacgaat aatggtgata    1620
atactgaaat ccaaattggc ggcaatatct cgcaaaaaga aggcaatctc acaatttctt    1680
ctgataaagt caatattacc gagcggataa caatcaaagc aggcgttaat ggggataact    1740
ctgattcaaa tgaggcaaca agtgctaacc taaccattaa aaccaaagag ttaaaattaa    1800
caaacgacct aaatatttca ggttttaata agcagaaaat tacagctaaa gataacagta    1860
atttaactat tggcgataac agtgacgctg gcaatactga cgctaaaaaa gtaaccttta    1920
gcaatgttaa agattcaaaa atctctgcta gcgaccataa tgtaacgcta aacagcaaag    1980
tggaaacatc tggcgatact gacagcactg aagatggcgg caacaataac accggcttaa    2040
ctattactgc aaaaaatgta acagtaaaca acaatattac ttctcacaaa acagtaaata    2100
tcactgcgtc agaaaatgtt accaccaaag cgggcacaac cattaatgca accacaggta    2160
gcgtagaagt aacagccaaa acaggtgata ttaaaggtgg aattgaatcc aattccggta    2220
atgtaaatat tacagcgagc ggcgacacgc ttaatgtaag taacatcaca ggtcaaaatg    2280
tgacagtggc agcagcctca ggtgccgtaa caaccacaaa aggatcaact attaatgcaa    2340
caactggtaa tgcaaatatt acaaccaaaa caggtgaaat taatggcgaa gttaaatcag    2400
cttccggtaa tgtaaatatt acagcgagcg gcaatacact taatgtaagt aacatcactg    2460
gtcaaaatgt aacagtaaca gcaaactcag gtgccataac aaccacagaa ggctcaacta    2520
ttaacgcgac aacaggtgat gcaaatatta caacccaaac aggtaatatt aatggtaaag    2580
ttgaatccag ttctggttct gtgacgctta ttgcaactgg acaaactctt gctgtaggta    2640
atatttcagg tgacactgtt accattactg cggataaagg taaattaacc acacaaacaa    2700
gctctaagat taacggaact aagagtgtaa ccacctcaag ccaatcaggt gatattagtg    2760
gcacaatttc tggtaatacg gtaagcgtta gtgcgaccgg tagcttgacc actcaagcag    2820
gctcaaaaat tgaagcaaaa acaggtgagg ctaatgtaac aagcgcaaca ggtacaattg    2880
gcggtacaat ctctggcaat acagtaaatg ttacagcaaa tactgataat ttaactatta    2940
aagatggcgc aagaattaaa gcaacgggcg gagctgtgac tttaaccgca acaggaggta    3000
ctttaaccac cgaaacaagt tctgatatta cctcaagcaa tggtcagaca actctcacgg    3060
ccaaggatag cagtatcgca ggaagcatca atgccgccaa tgtgacatta aataccacag    3120
gcactttaac tactgtggca ggttcaaaaa tcgaggcagc cagtggcacc ctggttatta    3180
atgcaaaaga tgctcagttg gacggcgcgg catcaggtga ccacacagta gtaaatgcaa    3240
ccaacgcaaa cggctccggc agcgtaatcg cgacaacctc aagcagagtg aacatcactg    3300
gggatttaat cacaataaat ggattaaata tcatttcaaa aaacggtaaa acaccgtgc    3360 tgttaaaagg tgttgaaatt gatgtgaaat acattcaacc gggcatagcg agcgtaaatg    3420
aagtaattga agcgaaacgc gcccttgaga agtaaaagaa tttatctgac gaagaaagag    3480
aaacattagc taaacttggc gtgagcgctg tacgttttgc tgagccaaat aatgccatta    3540
cgattaatac acaaaatgag tttacaacca gaccattaag tcaagtgaca atttctgaag    3600
gtaaggtatg tttcttaatc ggcaatggcg caacaatatg caccaatatt gctgatattg    3660
agcggtag                                                            3668
```

```
<210> SEQ ID NO 37
<211> LENGTH: 1222
<212> TYPE: PRT
<213> ORGANISM: Haemophilus influenzae

<400> SEQUENCE: 37

Pro Asp Asn Val Ser Ile Asn Ala Pro Ala Leu Gly Arg Thr Glu Ser
 1               5                  10                  15

Thr Pro Asn Asn Asn Glu Tyr Asp Ser Pro Asn Gln Ile Asn Tyr Lys
            20                  25                  30

Asn Lys Pro Ser Leu Ser Thr Leu Thr Asn Thr Thr Leu Glu Arg Ile
        35                  40                  45

Leu Lys Arg Asn Thr Ser Val Asn Ile Thr Ala Thr Lys Thr Ile Thr
 50                  55                  60

Val Asn Ser Asp Ile Asn Ile Gly Asp Ser Ser His Leu Thr Leu Trp
 65                  70                  75                  80

Ser Glu Gly Gln Gly Arg Gly Gly Val Asn Val Thr Gly Asn Ile Thr
                85                  90                  95

Ser Thr Thr Asn Gly Asn Leu Thr Ile Tyr Ser Gly Gly Trp Val Asp
            100                 105                 110

Val His Lys Asn Ile Thr Leu Lys Ser Gly Tyr Leu Asn Ile Thr Thr
        115                 120                 125

Lys Gln Gly Asp Ile Ala Phe Glu Asp Lys Pro Gly Leu Ser Asn Leu
130                 135                 140

Thr Ile Thr Ala Lys Gly Thr Ile Ala Val Asn Asn Lys Lys Gly Phe
145                 150                 155                 160

Arg Phe Asp Asn Val Thr Leu Asn Gly Thr Gly Gly Leu Ser Phe
                165                 170                 175

Lys Tyr Ile Glu Thr Gly Asn Arg Asp Ser Asn Phe Glu Thr His Phe
            180                 185                 190

Arg Gly Arg Leu Asn Ile Ser Gly Lys Val Asp Ile Leu Met Gln Ala
        195                 200                 205

Arg Gln Glu Asn Trp Asn Arg Arg His Trp Gly Arg Ser His Trp Asn
210                 215                 220

Val Thr Arg Leu Asn Val Ser Glu Asn Ser Tyr Phe Asn Val Thr Ile
225                 230                 235                 240

Asp Ser Ser Gly Ser Ala Ser Ser Pro Gly Ala Gly Pro Leu Asn Ala
                245                 250                 255

Gln Ser Gly Leu Asn Gly Ile Ser Phe Asn Asn Asp Thr Val Phe Asn
            260                 265                 270

Ile Ala Ala Ser Ser Ala Val Asn Phe Asn Ile Lys Pro Pro Ile Val
        275                 280                 285

Asp Lys Val Thr Asn Gly Asn His Thr Leu Phe Lys Gly Asn Ile Ser
290                 295                 300

Val Leu Gly Gly Gly Met Ser Thr Phe Ile Phe Asn Ala Ser Ser Ser
305                 310                 315                 320

Asn Tyr Gln Thr Tyr Gly Val Ile Ile Glu Ser Gln Asn Phe Ser Ala
                325                 330                 335

Ser Gly Gly Ser Ser Leu Lys Phe Lys Ser Glu Gly Ser Thr His Ala
            340                 345                 350

Ala Phe Thr Ile Lys Asn Asp Leu Ile Leu Asn Ala Thr Gly Gly Asn
        355                 360                 365

Ile Ser Leu Asn Gln Val Ala Gly Ile Asp Ser Asn Leu Lys Lys Ser
```

-continued

```
            370             375             380
Leu Ile Ala Asn Lys Asn Ile Thr Phe Glu Gly Gly Asn Ile Thr Leu
385             390             395             400
Ala Ala Asp Lys Lys Pro Ile Glu Ile Lys Gly Asn Ile Thr Val Lys
            405             410             415
Glu Gly Ala Asn Val Thr Leu Arg Ser Ala Asn Tyr Gly Asn Asp Lys
            420             425             430
Ser Ala Leu Ser Ile Arg Gly Asn Val Thr Asn Lys Gly Asn Leu Thr
            435             440             445
Val Thr Gly Ser Ala Ile Asn Ile Glu Lys Asn Leu Thr Val Glu Gly
            450             455             460
Ser Ala Lys Phe Leu Ala Asn Pro Asn Tyr Ser Phe Asn Val Ser Gly
465             470             475             480
Leu Phe Asp Asn Gln Gly Lys Ser Asn Ile Ser Ile Ala Lys Gly Gly
            485             490             495
Ala Ile Phe Lys Asp Ile Glu Asn Thr Gly Ser Leu Asn Ile Thr Thr
            500             505             510
Lys Ser Asp Ser Asn His His Thr Ile Ile Lys Gly Asn Ile Thr Asn
            515             520             525
Arg Lys Gly Asp Leu Asn Ile Thr Asn Asn Gly Asp Asn Thr Glu Ile
            530             535             540
Gln Ile Gly Gly Asn Ile Ser Gln Lys Glu Gly Asn Leu Thr Ile Ser
545             550             555             560
Ser Asp Lys Val Asn Ile Thr Glu Arg Ile Thr Ile Lys Ala Gly Val
            565             570             575
Asn Gly Asp Asn Ser Asp Ser Asn Glu Ala Thr Ser Ala Asn Leu Thr
            580             585             590
Ile Lys Thr Lys Glu Leu Lys Leu Thr Asn Asp Leu Asn Ile Ser Gly
            595             600             605
Phe Asn Lys Ala Glu Ile Thr Ala Lys Asp Asn Ser Asn Leu Thr Ile
            610             615             620
Gly Asp Asn Ser Asp Ala Gly Asn Thr Asp Ala Lys Lys Val Thr Phe
625             630             635             640
Ser Asn Val Lys Asp Ser Lys Ile Ser Ala Ser Asp His Asn Val Thr
            645             650             655
Leu Asn Ser Lys Val Glu Thr Ser Gly Asp Thr Asp Ser Thr Glu Asp
            660             665             670
Gly Gly Asn Asn Asn Thr Gly Leu Thr Ile Thr Ala Lys Asn Val Thr
            675             680             685
Val Asn Asn Asn Ile Thr Ser His Lys Thr Val Asn Ile Thr Ala Ser
            690             695             700
Glu Asn Val Thr Thr Lys Ala Gly Thr Thr Ile Asn Ala Thr Thr Gly
705             710             715             720
Ser Val Glu Val Thr Ala Lys Thr Gly Asp Ile Lys Gly Gly Ile Glu
            725             730             735
Ser Asn Ser Gly Asn Val Asn Ile Thr Ala Ser Gly Asp Thr Leu Asn
            740             745             750
Val Ser Asn Ile Thr Gly Gln Asn Val Thr Val Ala Ala Ala Ser Gly
            755             760             765
Ala Val Thr Thr Thr Lys Gly Ser Thr Ile Asn Ala Thr Thr Gly Asn
            770             775             780
Ala Asn Ile Thr Thr Lys Thr Gly Glu Ile Asn Gly Glu Val Lys Ser
785             790             795             800
```

-continued

```
Ala Ser Gly Asn Val Asn Ile Thr Ala Ser Gly Asn Thr Leu Asn Val
                805                 810                 815
Ser Asn Ile Thr Gly Gln Asn Val Thr Val Thr Ala Asn Ser Gly Ala
            820                 825                 830
Ile Thr Thr Thr Glu Gly Ser Thr Ile Asn Ala Thr Thr Gly Asp Ala
            835                 840                 845
Asn Ile Thr Thr Gln Thr Gly Asn Ile Asn Gly Lys Val Glu Ser Ser
    850                 855                 860
Ser Gly Ser Val Thr Leu Ile Ala Thr Gly Gln Thr Leu Ala Val Gly
865                 870                 875                 880
Asn Ile Ser Gly Asp Thr Val Thr Ile Thr Ala Asp Lys Gly Lys Leu
                885                 890                 895
Thr Thr Gln Thr Ser Ser Lys Ile Asn Gly Thr Lys Ser Val Thr Thr
                900                 905                 910
Ser Ser Gln Ser Gly Asp Ile Ser Gly Thr Ile Ser Gly Asn Thr Val
            915                 920                 925
Ser Val Ser Ala Thr Gly Ser Leu Thr Thr Gln Ala Gly Ser Lys Ile
    930                 935                 940
Glu Ala Lys Thr Gly Glu Ala Asn Val Thr Ser Ala Thr Gly Thr Ile
945                 950                 955                 960
Gly Gly Thr Ile Ser Gly Asn Thr Val Asn Val Thr Ala Asn Thr Asp
                965                 970                 975
Asn Leu Thr Ile Lys Asp Gly Ala Arg Ile Lys Ala Thr Gly Gly Ala
            980                 985                 990
Val Thr Leu Thr Ala Thr Gly Gly Thr Leu Thr Thr Glu Thr Ser Ser
    995                 1000                1005
Asp Ile Thr Ser Ser Asn Gly Gln Thr Thr Leu Thr Ala Lys Asp Ser
    1010                1015                1020
Ser Ile Ala Gly Ser Ile Asn Ala Ala Asn Val Thr Leu Asn Thr Thr
1025                1030                1035                1040
Gly Thr Leu Thr Thr Val Ala Gly Ser Lys Ile Glu Ala Ala Ser Gly
                1045                1050                1055
Thr Leu Val Ile Asn Ala Lys Asp Ala Gln Leu Asp Gly Ala Ala Ser
                1060                1065                1070
Gly Asp His Thr Val Val Asn Ala Thr Asn Ala Asn Gly Ser Gly Ser
            1075                1080                1085
Val Ile Ala Thr Thr Ser Ser Arg Val Asn Ile Thr Gly Asp Leu Ile
    1090                1095                1100
Thr Ile Asn Gly Leu Asn Ile Ile Ser Lys Asn Gly Lys Asn Thr Val
1105                1110                1115                1120
Leu Leu Lys Gly Val Glu Ile Asp Val Lys Tyr Ile Gln Pro Gly Ile
                1125                1130                1135
Ala Ser Val Asn Glu Val Ile Glu Ala Lys Arg Ala Leu Glu Lys Val
                1140                1145                1150
Lys Asp Leu Ser Asp Glu Glu Arg Glu Thr Leu Ala Lys Leu Gly Val
            1155                1160                1165
Ser Ala Val Arg Phe Ala Glu Pro Asn Asn Ala Ile Thr Ile Asn Thr
    1170                1175                1180
Gln Asn Glu Phe Thr Thr Arg Pro Leu Ser Gln Val Thr Ile Ser Glu
1185                1190                1195                1200
Gly Lys Val Cys Phe Leu Ile Gly Asn Gly Ala Thr Ile Cys Thr Asn
                1205                1210                1215
```

Ile Ala Asp Ile Glu Arg
         1220

<210> SEQ ID NO 38
<211> LENGTH: 3036
<212> TYPE: DNA
<213> ORGANISM: Haemophilus influenzae

<400> SEQUENCE: 38

| | | | | | |
|---|---|---|---|---|---|
| aaagagtggt | tgttagaccc | ggatgatata | aatattgtca | acggaagtaa | tattgatgct | 60 |
| caattacagc | caggtagagg | cgatacaccc | aacaaggttt | cagcagaagg | cttaacatcc | 120 |
| attaacaatg | ccacattatc | caccgcttta | caaagggta | ttgaggtcaa | catttctgcc | 180 |
| acaaaaaatg | taaccgtcaa | cgcggatgtt | gatgttaaaa | acggaacatt | agtattacat | 240 |
| tcacaaagga | atggagttaa | aattaacggt | aatattacct | caacacaaaa | tggtaattta | 300 |
| accattaaaa | caggtggcaa | ggttgatgtt | cataaaaata | tcacacttgg | tatgggtttt | 360 |
| ttgaatatta | cttccgataa | taacatcacc | tttgaaaaag | gtgataatct | aaccattacc | 420 |
| gcccaaggaa | atataatctc | taatcaagag | aataaacaac | ttagatttag | taatgtatct | 480 |
| ttaaatggga | tgggtgcggg | tttaactttt | actgcaaata | aaggtaatca | tacccataag | 540 |
| tttgatggca | cgcttaacat | ttccggaaag | gtagtaatta | atcaaaccac | acctcacaac | 600 |
| attgctccat | ggaatgcaag | tgcagactct | tactggaatg | taactactct | tactttaggt | 660 |
| aataatgcgc | aatttacctt | tattaaattt | gtcgatagca | accgctcggt | agctcttaat | 720 |
| agcggttcaa | gaagttttgc | ggggtaaag | ttctacggca | agaataatga | aatgaaattt | 780 |
| aatattggtg | ataatgctaa | tgttgaattc | aagttaaaat | caaatgataa | tacaagcaac | 840 |
| aacaaaccac | taccaattca | gttttatct | aatatctcag | ccactggtaa | tggcactgta | 900 |
| tcttttgata | tacatgccaa | cttgtcagca | aggtcaactg | agttaaatat | gagtttaatt | 960 |
| aacatttcta | tggggttaa | ttttccata | aactcccatg | ttcgcggtaa | taatgctttt | 1020 |
| gaaatcaaaa | aagatttaat | tataaatgca | actggctcga | attttaatct | taagcaaacg | 1080 |
| aaagataaat | ttgacaatag | ttacgaaaaa | aacgccattt | tctcaactca | taacctaacc | 1140 |
| attcttggcg | gcaatgttac | tctaggtggg | gaaaattcaa | gtagtaatat | taaggaaat | 1200 |
| atcaacatca | atagcaaggc | aaatgttaca | ttacaagctc | atgccggcac | gagtcacctt | 1260 |
| gataaaaaag | aaagaaccct | aacccttggc | aatgtatctg | ttgggggaaa | tttaaacata | 1320 |
| attggctcaa | atgcacatat | tgacggcaat | ctttctattg | cagaaagtgc | taaatttcaa | 1380 |
| ggaaaaacca | ataacaacct | aaatattacc | ggcacctta | ccaacaacgg | caccgccgac | 1440 |
| attaatataa | aacaaggagt | ggtaaaactc | caaggtgata | ttaccaataa | cggtaattta | 1500 |
| aatatcacta | ctaacgcctc | agtcaatcaa | aaaaccatta | ttaacggaaa | tataactaac | 1560 |
| aaaaaaggcg | acttaaacat | caaggatatt | aaagccaacc | ccgaaatcca | aattggcggc | 1620 |
| aatatctcgc | aaaagaagg | taatctcacg | atttcttctg | acaaaattaa | tatcaccaaa | 1680 |
| cggatagaaa | ttaaggcaga | tactgatcaa | gggaattctg | attcaggcgt | agcaagtaat | 1740 |
| gctaatctaa | ccattaaaac | caaagagtta | acattaacag | acaatctaaa | catttcaggt | 1800 |
| tttaataaag | cagaaattac | agctaaagat | aacagtgatt | taattattgg | caaggctagc | 1860 |
| agtgacaaca | gtaatgctaa | acaaataacc | tttgacaagg | ttaaagattc | aaaaatctca | 1920 |
| gctggcaatc | acaatgtaac | actaaatagc | aaagtggaaa | cgtctaatag | cgatggtagc | 1980 |
| accggaaacg | gtagcgatga | caacaatatc | ggcttaacta | tttccgcaaa | agatgtaacg | 2040 |

-continued

```
gtaaatagta atatcacctc tcacaaaaca gtaaatatct ctgcatcaga aggaggtatc    2100
actactaaag caggcacaac cattaatgcg accacaggta gcgtggaagt aactgctaaa    2160
acaggcgata ttagcggtac gatttccggt aagacagtaa gtgttacagc aaccaccgac    2220
agtttaactg ttaaaggtgg cgcaaaaatt aatgcgacag aaggaactgc aaccttaact    2280
gcatcatcgg gcaaattaac caccgaggcc aactctgcga ttagcgggc taacggtgta    2340 actgcctcaa gtcaatcagg cgatattagc ggtacgattt ccggtaagac agtaagtgtt    2400
acagcaagct ctggcagttt aactgttgga ggtgacgcaa aaattaatgc gacagaagga    2460
gctgcgactt taactgcaac aaaaggcact ttaactaccg tgaagggttc aaacattgac    2520
gcaaacgaag gcaccttagt tattaacgca aagacgcca cactaaatgg tgatgcatca    2580
ggcgaccgta cagaagtgaa tgcagtcaac gcaagcggct ctggtaacgt aactgcgaaa    2640
acctcaagca gtgtgaatat cactggagat ttaagcacaa taaatggatt aaatatcatt    2700
tcgaaaaatg gtaaaaacac cgtagtgtta aaaggtgctg aaattgatgt gaaatatatt    2760
caaccaggtg tagcaagtgc gaatgaggtt attgaagcga agcgtgccct tgaaaaagta    2820
aaagatttat ctgatgaaga aagagaaaca ttagctaaac ttggtgtaag tgctgtacgt    2880
tttattgaac caaataatac cattacggtt aacacacaaa atgagtttac aaccagacca    2940
tcaagtcaag tgacaatttc tgaaggtaag gcgtgtttct caagtggtaa tggcgcagca    3000
gtatgtacca atgttgctga cgatggacag cagtag                              3036
```

<210> SEQ ID NO 39
<211> LENGTH: 1011
<212> TYPE: PRT
<213> ORGANISM: Haemophilus influenzae

<400> SEQUENCE: 39

```
Lys Glu Trp Leu Leu Asp Pro Asp Asp Ile Asn Ile Val Asn Gly Ser
  1               5                  10                  15

Asn Ile Asp Ala Gln Leu Gln Pro Gly Arg Gly Asp Thr Pro Asn Lys
             20                  25                  30

Val Ser Ala Glu Gly Leu Thr Ser Ile Asn Asn Ala Thr Leu Ser Thr
         35                  40                  45

Ala Leu Gln Lys Gly Ile Glu Val Asn Ile Ser Ala Thr Lys Asn Val
     50                  55                  60

Thr Val Asn Ala Asp Val Asp Val Lys Asn Gly Thr Leu Val Leu His
 65                  70                  75                  80

Ser Gln Arg Asn Gly Val Lys Ile Asn Gly Asn Ile Thr Ser Thr Gln
                 85                  90                  95

Asn Gly Asn Leu Thr Ile Lys Thr Gly Gly Lys Val Asp Val His Lys
            100                 105                 110

Asn Ile Thr Leu Gly Met Gly Phe Leu Asn Ile Thr Ser Asp Asn Asn
        115                 120                 125

Ile Thr Phe Glu Lys Gly Asp Asn Leu Thr Ile Thr Ala Gln Gly Asn
    130                 135                 140

Ile Ile Ser Asn Gln Glu Asn Lys Gln Leu Arg Phe Ser Asn Val Ser
145                 150                 155                 160

Leu Asn Gly Met Gly Ala Gly Leu Thr Phe Thr Ala Asn Lys Gly Asn
                165                 170                 175

His Thr His Lys Phe Asp Gly Ser Leu Asn Ile Ser Gly Lys Val Val
            180                 185                 190

Ile Asn Gln Thr Thr Pro His Asn Ile Ala Pro Trp Asn Ala Ser Ala
```

-continued

```
            195                 200                     205
Asp Ser Tyr Trp Asn Val Thr Thr Leu Thr Leu Gly Asn Asn Ala Gln
    210             215             220

Phe Thr Phe Ile Lys Phe Val Asp Ser Asn Arg Ser Val Ala Leu Asn
225             230             235                 240

Ser Gly Ser Arg Ser Phe Ala Gly Val Lys Phe Tyr Gly Lys Asn Asn
            245             250                 255

Glu Met Lys Phe Asn Ile Gly Asp Asn Ala Asn Val Glu Phe Lys Leu
            260             265             270

Lys Ser Asn Asp Asn Thr Ser Asn Asn Lys Pro Leu Pro Ile Gln Phe
            275             280             285

Leu Ser Asn Ile Ser Ala Thr Gly Asn Gly Thr Val Ser Phe Asp Ile
    290             295             300

His Ala Asn Leu Ser Ala Arg Ser Thr Glu Leu Asn Met Ser Leu Ile
305             310             315             320

Asn Ile Ser Asn Gly Val Asn Phe Ser Ile Asn Ser His Val Arg Gly
            325             330             335

Asn Asn Ala Phe Glu Ile Lys Lys Asp Leu Ile Ile Asn Ala Thr Gly
            340             345             350

Ser Asn Phe Asn Leu Lys Gln Thr Lys Asp Lys Phe Asp Asn Ser Tyr
            355             360             365

Glu Lys Asn Ala Ile Phe Ser Thr His Asn Leu Thr Ile Leu Gly Gly
    370             375             380

Asn Val Thr Leu Gly Gly Glu Asn Ser Ser Ser Asn Ile Lys Gly Asn
385             390             395             400

Ile Asn Ile Asn Ser Lys Ala Asn Val Thr Leu Gln Ala His Ala Gly
            405             410             415

Thr Ser His Leu Asp Lys Lys Glu Arg Thr Leu Thr Leu Gly Asn Val
            420             425             430

Ser Val Gly Gly Asn Leu Asn Ile Ile Gly Ser Asn Ala His Ile Asp
            435             440             445

Gly Asn Leu Ser Ile Ala Glu Ser Ala Lys Phe Gln Gly Lys Thr Asn
    450             455             460

Asn Asn Leu Asn Ile Thr Gly Thr Phe Thr Asn Asn Gly Thr Ala Asp
465             470             475             480

Ile Asn Ile Lys Gln Gly Val Val Lys Leu Gln Gly Asp Ile Thr Asn
            485             490             495

Asn Gly Asn Leu Asn Ile Thr Thr Asn Ala Ser Val Asn Gln Lys Thr
            500             505             510

Ile Ile Asn Gly Asn Ile Thr Asn Lys Lys Gly Asp Leu Asn Ile Lys
            515             520             525

Asp Ile Lys Ala Asn Ala Glu Ile Gln Ile Gly Asn Ile Ser Gln
            530             535             540

Lys Glu Gly Asn Leu Thr Ile Ser Ser Asp Lys Ile Asn Ile Thr Lys
545             550             555             560

Arg Ile Glu Ile Lys Ala Asp Thr Asp Gln Gly Asn Ser Asp Ser Gly
            565             570             575

Val Ala Ser Asn Ala Asn Leu Thr Ile Lys Thr Lys Glu Leu Thr Leu
            580             585             590

Thr Asp Asn Leu Asn Ile Ser Gly Phe Asn Lys Ala Glu Ile Thr Ala
            595             600             605

Lys Asp Asn Ser Asp Leu Ile Ile Gly Lys Ala Ser Ser Asp Asn Ser
            610             615             620
```

-continued

Asn Ala Lys Gln Ile Thr Phe Asp Lys Val Lys Asp Ser Lys Ile Ser
625                 630                 635                 640

Ala Gly Asn His Asn Val Thr Leu Asn Ser Lys Val Glu Thr Ser Asn
            645                 650                 655

Ser Asp Gly Ser Thr Gly Asn Gly Ser Asp Asn Asn Ile Gly Leu
        660                 665                 670

Thr Ile Ser Ala Lys Asp Val Thr Val Asn Ser Asn Ile Thr Ser His
        675                 680                 685

Lys Thr Val Asn Ile Ser Ala Ser Glu Gly Gly Ile Thr Thr Lys Ala
    690                 695                 700

Gly Thr Thr Ile Asn Ala Thr Thr Gly Ser Val Glu Val Thr Ala Lys
705                 710                 715                 720

Thr Gly Asp Ile Ser Gly Thr Ile Ser Gly Lys Thr Val Ser Val Thr
            725                 730                 735

Ala Thr Thr Asp Ser Leu Thr Val Lys Gly Gly Ala Lys Ile Asn Ala
            740                 745                 750

Thr Glu Gly Thr Ala Thr Leu Thr Ala Ser Ser Gly Lys Leu Thr Thr
    755                 760                 765

Glu Ala Asn Ser Ala Ile Ser Gly Ala Asn Gly Val Thr Ala Ser Ser
770                 775                 780

Gln Ser Gly Asp Ile Ser Gly Thr Ile Ser Gly Lys Thr Val Ser Val
785                 790                 795                 800

Thr Ala Ser Ser Gly Ser Leu Thr Val Gly Gly Asp Ala Lys Ile Asn
            805                 810                 815

Ala Thr Glu Gly Ala Ala Thr Leu Thr Ala Thr Lys Gly Thr Leu Thr
            820                 825                 830

Thr Val Lys Gly Ser Asn Ile Asp Ala Asn Glu Gly Thr Leu Val Ile
    835                 840                 845

Asn Ala Gln Asp Ala Thr Leu Asn Gly Asp Ala Ser Gly Asp Arg Thr
850                 855                 860

Glu Val Asn Ala Val Asn Ala Ser Gly Ser Gly Asn Val Thr Ala Lys
865                 870                 875                 880

Thr Ser Ser Val Asn Ile Thr Gly Asp Leu Ser Thr Ile Asn Gly
            885                 890                 895

Leu Asn Ile Ile Ser Lys Asn Gly Lys Asn Thr Val Leu Lys Gly
        900                 905                 910

Ala Glu Ile Asp Val Lys Tyr Ile Gln Pro Gly Val Ala Ser Ala Asn
            915                 920                 925

Glu Val Ile Glu Ala Lys Arg Ala Leu Glu Lys Val Lys Asp Leu Ser
930                 935                 940

Asp Glu Glu Arg Glu Thr Leu Ala Lys Leu Gly Val Ser Ala Val Arg
945                 950                 955                 960

Phe Ile Glu Pro Asn Asn Thr Ile Thr Val Asn Thr Gln Asn Glu Phe
            965                 970                 975

Thr Thr Arg Pro Ser Ser Gln Val Thr Ile Ser Glu Gly Lys Ala Cys
            980                 985                 990

Phe Ser Ser Gly Asn Gly Ala Ala Val Cys Thr Asn Val Ala Asp Asp
            995                 1000                1005

Gly Gln Gln
    1010

<210> SEQ ID NO 40
<211> LENGTH: 3018

<212> TYPE: DNA
<213> ORGANISM: Haemophilus influenzae

<400> SEQUENCE: 40

| | | | | | |
|---|---|---|---|---|---|
| ccggatgata | taaatattgt | caacggaagt | aatattgatg | ctcaattaca | gccaggtaga | 60 |
| ggcgatacac | ccaacaaggt | ttcagcagaa | ggcttaacat | ccattaacaa | tgccacatta | 120 |
| tccaccgctt | tacaaaaggg | tattgaggtc | aacatttctg | ccacaaaaaa | tgtaaccgtc | 180 |
| aacgcggatg | ttgatgttaa | aaacggaaca | ttagtattac | attcacaaag | gaatggagtt | 240 |
| aaaattaacg | gtaatattac | ctcaacacaa | aatggtaatt | taaccattaa | aacaggtggc | 300 |
| aaggttgatg | ttcataaaaa | tatcacactt | ggtatggggtt | ttttgaatat | tacttccgat | 360 |
| aataacatca | cctttgaaaa | aggtgataat | ctaaccatta | ccgcccaagg | aaatataatc | 420 |
| tctaatcaag | agaataaaca | acttagattt | agtaatgtat | ctttaaatgg | gatgggtgcg | 480 |
| ggtttaactt | ttactgcaaa | taaggtaatt | cataccccata | agtttgatgg | cacgcttaac | 540 |
| atttccggaa | agtagtaatt | aatcaaacc | acacctcaca | acattgctcc | atggaatgca | 600 |
| agtgcagact | cttactggaa | tgtaactact | cttactttag | gtaataatgc | gcaatttacc | 660 |
| tttattaaat | ttgtcgatag | caaccgctcg | gtagctctta | atagcggttc | aagaagtttt | 720 |
| gcggggggtaa | agttctacgg | caagaataat | gaaatgaaat | ttaatattgg | tgataatgct | 780 |
| aatgttgaat | tcaagttaaa | atcaaatgat | aatacaagca | caacaaaacc | actaccaatt | 840 |
| cagttttttat | ctaatatctc | agccactggt | aatggcactg | tatcttttga | tatacatgcc | 900 |
| aacttgtcag | caaggtcaac | tgagttaaat | atgagtttaa | ttaacatttc | taatggggtt | 960 |
| aattttttcca | taaactccca | tgttcgcggt | aataatgctt | ttgaaatcaa | aaagatttta | 1020 |
| attataaatg | caactggctc | gaattttaat | cttaagcaaa | cgaaagataa | atttgacaat | 1080 |
| agttacgaaa | aaaacgccat | tttctcaact | cataacctaa | ccattcttgg | cggcaatgtt | 1140 |
| actctaggtg | gggaaaattc | aagtagtaat | attaaaggaa | atatcaacat | caatagcaag | 1200 |
| gcaaatgtta | cattacaagc | tcatgccggc | acgagtcacc | ttgataaaaa | agaaagaacc | 1260 |
| ctaacccttg | gcaatgtatc | tgttgggggga | aatttaaaca | taattggctc | aaatgcacat | 1320 |
| attgacggca | atctttctat | tgcagaaagt | gctaaatttc | aaggaaaaac | caataacaac | 1380 |
| ctaaatatta | ccggcaccctt | taccaacaac | ggcaccgccg | acattaatat | aaaacaagga | 1440 |
| gtggtaaaac | tccaaggtga | tattaccaat | aacggtaatt | taaatatcac | tactaacgcc | 1500 |
| tcagtcaatc | aaaaaaccat | tattaacgga | aatataacta | caaaaaagg | cgacttaaac | 1560 |
| atcaaggata | ttaaagccaa | cgccgaaatc | caaattggcg | gcaatatctc | gcaaaaagaa | 1620 |
| ggtaatctca | cgatttcttc | tgacaaaatt | aatatcacca | aacggataga | aattaaggca | 1680 |
| gatactgatc | aagggaattc | tgattcaggc | gtagcaagta | atgctaatct | aaccattaaa | 1740 |
| accaaagagt | taacattaac | agacaatcta | aacatttcag | gttttaataa | agcagaaatt | 1800 |
| acagctaaag | ataacagtga | tttaattatt | ggcaaggcta | gcagtgacaa | cagtaatgct | 1860 |
| aaacaaataa | cctttgacaa | ggttaaagat | tcaaaaatct | cagctggcaa | tcacaatgta | 1920 |
| acactaaata | gcaaagtgga | aacgtctaat | agcgatggta | gcaccggaaa | cggtagcgat | 1980 |
| gacaacaata | tcggcttaac | tatttccgca | aaagatgaa | cggtaaatag | taatatcacc | 2040 |
| tctcacaaaa | cagtaaatat | ctctgcatca | gaaggaggta | tcactactaa | agcaggcaca | 2100 |
| accattaatg | cgaccacagg | tagcgtggaa | gtaactgcta | aaacaggcga | tattagcggt | 2160 |
| acgatttccg | gtaagacagt | aagtgttaca | gcaaccaccg | acagtttaac | tgttaaaggt | 2220 |

-continued

```
ggcgcaaaaa ttaatgcgac agaaggaact gcaaccttaa ctgcatcatc gggcaaatta    2280
accaccgagg ccaactctgc gattagcggg gctaacggtg taactgcctc aagtcaatca    2340
ggcgatatta gcggtacgat ttccggtaag acagtaagtg ttacagcaag ctctggcagt    2400
ttaactgttg gaggtgacgc aaaaattaat gcgacagaag gagctgcgac tttaactgca    2460
acaaaaggca ctttaactac cgtgaagggt tcaaacattg acgcaaacga aggcaccttt    2520
gttattaacg cacaagacgc cacactaaat ggtgatgcat caggcgaccg tacagaagtg    2580
aatgcagtca acgcaagcgg ctctggtaac gtaactgcga aaacctcaag cagtgtgaat    2640
atcactggag atttaagcac aataaatgga ttaaatatca tttcgaaaaa tggtaaaaac    2700
accgtagtgt taaaggtgc tgaaattgat gtgaaatata ttcaaccagg tgtagcaagt    2760
gcgaatgagg ttattgaagc gaagcgtgcc cttgaaaaag taaagatttt atctgatgaa    2820
gaaagagaaa cattagctaa acttggtgta agtgctgtac gttttattga accaaataat    2880
accattacgg ttaacacaca aaatgagttt acaaccagac catcaagtca agtgacaatt    2940
tctgaaggta aggcgtgttt ctcaagtggt aatggcgcag cagtatgtac caatgttgct    3000
gacgatggac agcagtag                                                  3018
```

<210> SEQ ID NO 41
<211> LENGTH: 1005
<212> TYPE: PRT
<213> ORGANISM: Haemophilus influenzae

<400> SEQUENCE: 41

```
Pro Asp Asp Ile Asn Ile Val Asn Gly Ser Asn Ile Asp Ala Gln Leu
  1               5                  10                  15

Gln Pro Gly Arg Gly Asp Thr Pro Asn Lys Val Ser Ala Glu Gly Leu
             20                  25                  30

Thr Ser Ile Asn Asn Ala Thr Leu Ser Thr Ala Leu Gln Lys Gly Ile
         35                  40                  45

Glu Val Asn Ile Ser Ala Thr Lys Asn Val Thr Val Asn Ala Asp Val
     50                  55                  60

Asp Val Lys Asn Gly Thr Leu Val Leu His Ser Gln Arg Asn Gly Val
 65                  70                  75                  80

Lys Ile Asn Gly Asn Ile Thr Ser Thr Gln Asn Gly Asn Leu Thr Ile
                 85                  90                  95

Lys Thr Gly Gly Lys Val Asp Val His Lys Asn Ile Thr Leu Gly Met
            100                 105                 110

Gly Phe Leu Asn Ile Thr Ser Asp Asn Asn Ile Thr Phe Glu Lys Gly
        115                 120                 125

Asp Asn Leu Thr Ile Thr Ala Gln Gly Asn Ile Ile Ser Asn Gln Glu
    130                 135                 140

Asn Lys Gln Leu Arg Phe Ser Asn Val Ser Leu Asn Gly Met Gly Ala
145                 150                 155                 160

Gly Leu Thr Phe Thr Ala Asn Lys Gly Asn His Thr His Lys Phe Asp
                165                 170                 175

Gly Thr Leu Asn Ile Ser Gly Lys Val Val Ile Asn Gln Thr Thr Pro
            180                 185                 190

His Asn Ile Ala Pro Trp Asn Ala Ser Ala Asp Ser Tyr Trp Asn Val
        195                 200                 205

Thr Thr Leu Thr Leu Gly Asn Asn Ala Gln Phe Thr Phe Ile Lys Phe
    210                 215                 220

Val Asp Ser Asn Arg Ser Val Ala Leu Asn Ser Gly Ser Arg Ser Phe
```

```
                225                 230                 235                 240
Ala Gly Val Lys Phe Tyr Gly Lys Asn Asn Glu Met Lys Phe Asn Ile
                    245                 250                 255
Gly Asp Asn Ala Asn Val Glu Phe Lys Leu Lys Ser Asn Asp Asn Thr
            260                 265                 270
Ser Asn Asn Lys Pro Leu Pro Ile Gln Phe Leu Ser Asn Ile Ser Ala
        275                 280                 285
Thr Gly Asn Gly Thr Val Ser Phe Asp Ile His Ala Asn Leu Ser Ala
    290                 295                 300
Arg Ser Thr Glu Leu Asn Met Ser Leu Ile Asn Ile Ser Asn Gly Val
305                 310                 315                 320
Asn Phe Ser Ile Asn Ser His Val Arg Gly Asn Asn Ala Phe Glu Ile
                325                 330                 335
Lys Lys Asp Leu Ile Ile Asn Ala Thr Gly Ser Asn Phe Asn Leu Lys
            340                 345                 350
Gln Thr Lys Asp Lys Phe Asp Asn Ser Tyr Glu Lys Asn Ala Ile Phe
        355                 360                 365
Ser Thr His Asn Leu Thr Ile Leu Gly Gly Asn Val Thr Leu Gly Gly
    370                 375                 380
Glu Asn Ser Ser Asn Ile Lys Gly Asn Ile Asn Ile Asn Ser Lys
385                 390                 395                 400
Ala Asn Val Thr Leu Gln Ala His Ala Gly Thr Ser His Leu Asp Lys
                405                 410                 415
Lys Glu Arg Thr Leu Thr Leu Gly Asn Val Ser Val Gly Gly Asn Leu
            420                 425                 430
Asn Ile Ile Gly Ser Asn Ala His Ile Asp Gly Asn Leu Ser Ile Ala
        435                 440                 445
Glu Ser Ala Lys Phe Gln Gly Lys Thr Asn Asn Leu Asn Ile Thr
    450                 455                 460
Gly Thr Phe Thr Asn Asn Gly Thr Ala Asp Ile Asn Ile Lys Gln Gly
465                 470                 475                 480
Val Val Lys Leu Gln Gly Asp Ile Thr Asn Asn Gly Asn Leu Asn Ile
                485                 490                 495
Thr Thr Asn Ala Ser Val Asn Gln Lys Thr Ile Ile Asn Gly Asn Ile
            500                 505                 510
Thr Asn Lys Lys Gly Asp Leu Asn Ile Lys Asp Ile Lys Ala Asn Ala
        515                 520                 525
Glu Ile Gln Ile Gly Gly Asn Ile Ser Gln Lys Glu Gly Asn Leu Thr
    530                 535                 540
Ile Ser Ser Asp Lys Ile Asn Ile Thr Lys Arg Ile Glu Ile Lys Ala
545                 550                 555                 560
Asp Thr Asp Gln Gly Asn Ser Asp Ser Gly Val Ala Ser Asn Ala Asn
                565                 570                 575
Leu Thr Ile Lys Thr Lys Glu Leu Thr Leu Thr Asp Asn Leu Asn Ile
            580                 585                 590
Ser Gly Phe Asn Lys Ala Glu Ile Thr Ala Lys Asp Asn Ser Asp Leu
        595                 600                 605
Ile Ile Gly Lys Ala Ser Ser Asp Asn Ser Asn Ala Lys Gln Ile Thr
    610                 615                 620
Phe Asp Lys Val Lys Asp Ser Lys Ile Ser Ala Gly Asn His Asn Val
625                 630                 635                 640
Thr Leu Asn Ser Lys Val Glu Thr Ser Asn Ser Asp Gly Ser Thr Gly
                645                 650                 655
```

```
Asn Gly Ser Asp Asp Asn Asn Ile Gly Leu Thr Ile Ser Ala Lys Asp
            660                 665                 670

Val Thr Val Asn Ser Asn Ile Thr Ser His Lys Thr Val Asn Ile Ser
        675                 680                 685

Ala Ser Glu Gly Gly Ile Thr Thr Lys Ala Gly Thr Thr Ile Asn Ala
    690                 695                 700

Thr Thr Gly Ser Val Glu Val Thr Ala Lys Thr Gly Asp Ile Ser Gly
705                 710                 715                 720

Thr Ile Ser Gly Lys Thr Val Ser Val Thr Ala Thr Thr Asp Ser Leu
                725                 730                 735

Thr Val Lys Gly Gly Ala Lys Ile Asn Ala Thr Glu Gly Thr Ala Thr
            740                 745                 750

Leu Thr Ala Ser Ser Gly Lys Leu Thr Thr Glu Ala Asn Ser Ala Ile
        755                 760                 765

Ser Gly Ala Asn Gly Val Thr Ala Ser Ser Gln Ser Gly Asp Ile Ser
    770                 775                 780

Gly Thr Ile Ser Gly Lys Thr Val Ser Val Thr Ala Ser Ser Gly Ser
785                 790                 795                 800

Leu Thr Val Gly Gly Asp Ala Lys Ile Asn Ala Thr Glu Gly Ala Ala
                805                 810                 815

Thr Leu Thr Ala Thr Lys Gly Thr Leu Thr Thr Val Lys Gly Ser Asn
            820                 825                 830

Ile Asp Ala Asn Glu Gly Thr Leu Val Ile Asn Ala Gln Asp Ala Thr
        835                 840                 845

Leu Asn Gly Asp Ala Ser Gly Asp Arg Thr Glu Val Asn Ala Val Asn
    850                 855                 860

Ala Ser Gly Ser Gly Asn Val Thr Ala Lys Thr Ser Ser Ser Val Asn
865                 870                 875                 880

Ile Thr Gly Asp Leu Ser Thr Ile Asn Gly Leu Asn Ile Ile Ser Lys
                885                 890                 895

Asn Gly Lys Asn Thr Val Val Leu Lys Gly Ala Glu Ile Asp Val Lys
            900                 905                 910

Tyr Ile Gln Pro Gly Val Ala Ser Ala Asn Glu Val Ile Glu Ala Lys
        915                 920                 925

Arg Ala Leu Glu Lys Val Lys Asp Leu Ser Asp Glu Glu Arg Glu Thr
    930                 935                 940

Leu Ala Lys Leu Gly Val Ser Ala Val Arg Phe Ile Glu Pro Asn Asn
945                 950                 955                 960

Thr Ile Thr Val Asn Thr Gln Asn Glu Phe Thr Thr Arg Pro Ser Ser
                965                 970                 975

Gln Val Thr Ile Ser Glu Gly Lys Ala Cys Phe Ser Ser Gly Asn Gly
            980                 985                 990

Ala Ala Val Cys Thr Asn Val Ala Asp Asp Gly Gln Gln
        995                 1000                1005

<210> SEQ ID NO 42
<211> LENGTH: 3306
<212> TYPE: DNA
<213> ORGANISM: Haemophilus influenzae

<400> SEQUENCE: 42
aaagagtggc tactggaccc tgatgaagta actattggag caggtgacgt aggacgtagc      60
gatgattcaa gtgacactgc tttccctacc ggaacagggg aaagaaacag ccccaaaaca     120
```

```
aacgctcaaa acagaccaac aataacaaac acatctcttg agcaaatatt aaaaaatggc      180
acctttgtta acataaccgc caaaataaaa atcttagtta atagcgacat caatatcaaa      240
gagaactccc acctaatcct ctggagcgaa agagatggca acagcggcgt tcagattgat      300
ggcaatatta cttccgctac tggcggaagc ttaaccgttt actctagtgg ctgggttgat      360
gttcataaaa acattacact taattcaggg tacttaaaca ttacgactaa agtggagat       420 gtcgccttcg aacaagggaa tgacctaacc attacaggtc aaggaactat taccgcaagc     480
aaaaaaggtt ttagatttga taatgttact ctaagtggag tgaaaaaggg gttccttttt     540
aaatacagcc aaaccaacaa taataaagat agcaatttcg aaaaccattt tagaggaact     600
ttaaatattt cagggaaagt agatatctta atgcaagcaa ggcaggagaa ctggaaccgc     660
agacactcgg gacgctccca ctggaatgta acccgattga atgtttctac aaatagttat     720
ctcaacatca ctattgataa cagtggcagc cgtccatccc ctggtgccgg ccctctatat     780
agacgttcgg gtttaaatgg catatcgttt aacaatgaca ctgttttttaa tgttgcgtca     840 ggttcggcag ttaactttag catcaagcca ccaatagtaa gcaatgtaca cgacgggaat     900
cacacattat tcaatgggaa tgtttcagtt ttaggggag gggatgtcaa cttttcatttt    960 aacgcctcct ccagcaacca ctggactcat ggcgtggtta taaagtctca aaactttaat    1020
gcctcagaag ggtcaagctt aagattcaaa agcgaaggtt caacacgaac cgcttttaca    1080
atagaaagtg atttaacttt aaatgccact gggggcaata tatcattgaa ccaagttgca    1140
ggtattgatg gtaatctcca aaaagccctt gtagccaata aaaacataac ctttgaaggg    1200
ggcaatatca cccttgcagc cgataaaaaa ccaatagaaa tcaaaggtaa tattactgtt    1260
aaagaaggag ccaatgtcac ccttcgtagc gcgaattatg gtaatgacaa atcagcttta    1320
agtataagag gaaatgtcac taataaaggc aatctcaccg ttaccggctc cgctatcaat    1380
atagaaaaaa atcttaccgt tgaaggtagt gctaagtttt tagctaatcc aaattacagc    1440
tttaacgtat ccggcctatt tgacaaccaa ggcaagtcaa acatttccat tgccaaagga    1500
ggggctcact ttaaagacat taataacact aagagtttaa acattactac caactccgac    1560
tccgcttacc gcactattat agaaggcaat ataaccaaca gtaacgggga tttaaatatc    1620
actgataata aaaataacgc tgaatccaa attggcggca atatctcgca aaaagaaggt    1680
aatctcacga tttcttccga taaaattaat atcactaacc agataacaat caagaagggt    1740
gttaataaag aggattctga ttcaagcacg gcaaacaatg ctaatctaac cattaaaacc    1800
aaagaattgc aattaacggg agacctaaat atttcaggct tcgataaagc agaaatcaca    1860
gccaaagagg gtgccgattt aatcatcggt aatagtgata ataacaacaa tgctaatgct    1920
aaaaaagtaa cctttaacca ggttaaagat tcgaaaatct ctgctgacag tcacaatgta    1980
acactaaaca gtaaagtaga aacctctaat ggcaataatg acgctgaaag caataatggc    2040
gatggcacca gcttaactat taatgcaaaa aatataacag taaacaacaa tattacttct    2100
cacaaaacag taaatatcac tgcgtcagaa atgttaccac ccaaagcggg cacaaccatt    2160
aatgcaacca caggtagcgt agaagtaaca gccaaaacag gtgatattaa aggtaaagtt    2220
gaatccactt ccggctctgt aacacttact gcaaccggag aagctcttgc tgtaagcaac    2280
atttcaggca acactgttac catcactgca aataagggta aattaacaac tcaagcaggc    2340
tctacggtta gcgcgattaa cggtgtaact gcctcaagcc aatcaggcga tattagcggt    2400
acgatttccg gtaacacagt aaaagttagt gcgatcggtg atttgactac taaatccggc    2460
tcggaaatca aggcaaaaac aggtgaggct aacgtgacaa gtgcgacagg tacaattggt    2520
```

-continued

```
ggtacgattt ctggtaatgc agtaaatgtt acagcaaata ctggcgattt aactgttgaa   2580
gatgccgcaa aaattgatgc gacaggagga gccgcgaccc taactgcaac atcgggcaaa   2640
ttaaccacta aggctagttc aagcattact tcagctaata accaggtaaa cctttcagct   2700
aaggatggta gcattggggg aaatatcaat gctgctaatg taacactgaa tactacaggc   2760
gctctaacta ccgtgaaggg ttcaagcatt aacgcaaaca gcggcacctt ggttattaac   2820
gcaaaagacg ctgagctaaa tggtgaggca tcaggtaacc atacagtagt gaatgcaacc   2880
aacgcaaatg gctccggcag cgtaatcgcg acaacctcaa gcagagtgaa catcactggg   2940
gatttaatca caataaatgg attaaatatc atttcaaaaa acggtataaa caccgtactg   3000
ttaaaaggcg ttaaaattga tgtgaaatac attcaaccgg gtatagcaag cgtagatgaa   3060
gtaattgaag cgaaacgcat ccttgagaag gtaaaagatt tatctgatga agaaagagaa   3120
gcgttagcta aacttggcgt aagcgctgta cgttttgctg agccaaataa tgccattacg   3180
attaatacac aaaatgagtt tacaaccaga ccatcaagtc aagtgacaat ttctgaaggt   3240
aaggtatgtt tcttaatcgg caatggtgca acaatatgca ccaatattgc tgatattgag   3300
cggtag                                                              3306
```

<210> SEQ ID NO 43
<211> LENGTH: 1101
<212> TYPE: PRT
<213> ORGANISM: Haemophilus influenzae

<400> SEQUENCE: 43

```
Lys Glu Trp Leu Leu Asp Pro Asp Glu Val Thr Ile Gly Ala Gly Asp
  1               5                  10                  15

Val Gly Arg Ser Asp Asp Ser Ser Asp Thr Ala Phe Pro Thr Gly Thr
                 20                  25                  30

Gly Glu Arg Asn Ser Pro Lys Thr Asn Ala Gln Asn Arg Pro Thr Ile
             35                  40                  45

Thr Asn Thr Ser Leu Glu Gln Ile Leu Lys Asn Gly Thr Phe Val Asn
         50                  55                  60

Ile Thr Ala Lys Asn Lys Ile Leu Val Asn Ser Asp Ile Asn Ile Lys
 65                  70                  75                  80

Glu Asn Ser His Leu Ile Leu Trp Ser Glu Arg Asp Gly Asn Ser Gly
                 85                  90                  95

Val Gln Ile Asp Gly Asn Ile Thr Ser Ala Thr Gly Gly Ser Leu Thr
            100                 105                 110

Val Tyr Ser Ser Gly Trp Val Asp Val His Lys Asn Ile Thr Leu Asn
        115                 120                 125

Ser Gly Tyr Leu Asn Ile Thr Thr Lys Ser Gly Asp Val Ala Phe Glu
    130                 135                 140

Gln Gly Asn Asp Leu Thr Ile Thr Gly Gln Gly Thr Ile Thr Ala Ser
145                 150                 155                 160

Lys Lys Gly Phe Arg Phe Asp Asn Val Thr Leu Ser Gly Val Lys Lys
                165                 170                 175

Gly Phe Leu Phe Lys Tyr Ser Gln Thr Asn Asn Lys Asp Ser Asn
            180                 185                 190

Phe Glu Asn His Phe Arg Gly Thr Leu Asn Ile Ser Gly Lys Val Asp
        195                 200                 205

Ile Leu Met Gln Ala Arg Gln Gly Asn Trp Asn Arg Arg His Ser Gly
    210                 215                 220
```

```
Arg Ser His Trp Asn Val Thr Arg Leu Asn Val Ser Thr Asn Ser Tyr
225                 230                 235                 240

Leu Asn Ile Thr Ile Asp Asn Ser Gly Ser Arg Pro Ser Pro Gly Ala
            245                 250                 255

Gly Pro Leu Tyr Arg Arg Ser Gly Leu Asn Gly Ile Ser Phe Asn Asn
        260                 265                 270

Asp Thr Val Phe Asn Val Ala Ser Gly Ser Ala Val Asn Phe Ser Ile
    275                 280                 285

Lys Pro Pro Ile Val Ser Asn Val His Asp Gly Asn His Thr Leu Phe
290                 295                 300

Asn Gly Asn Val Ser Val Leu Gly Gly Asp Val Asn Phe His Phe
305                 310                 315                 320

Asn Ala Ser Ser Asn His Trp Thr His Gly Val Val Ile Lys Ser
                325                 330                 335

Gln Asn Phe Asn Ala Ser Glu Gly Ser Ser Leu Arg Phe Lys Ser Glu
            340                 345                 350

Gly Ser Thr Arg Thr Ala Phe Thr Ile Glu Ser Asp Leu Thr Leu Asn
        355                 360                 365

Ala Thr Gly Gly Asn Ile Ser Leu Asn Gln Val Ala Gly Ile Asp Gly
    370                 375                 380

Asn Leu Gln Lys Ser Leu Val Ala Asn Lys Asn Ile Thr Phe Glu Gly
385                 390                 395                 400

Gly Asn Ile Thr Leu Ala Ala Asp Lys Lys Pro Ile Glu Ile Lys Gly
            405                 410                 415

Asn Ile Thr Val Lys Glu Gly Ala Asn Val Thr Leu Arg Ser Ala Asn
        420                 425                 430

Tyr Gly Asn Asp Lys Ser Ala Leu Ser Ile Arg Gly Asn Val Thr Asn
    435                 440                 445

Lys Gly Asn Leu Thr Val Thr Gly Ser Ala Ile Asn Ile Glu Lys Asn
450                 455                 460

Leu Thr Val Glu Gly Ser Ala Lys Phe Leu Ala Asn Pro Asn Tyr Ser
465                 470                 475                 480

Phe Asn Val Ser Gly Leu Phe Asp Asn Gln Gly Lys Ser Asn Ile Ser
            485                 490                 495

Ile Ala Lys Gly Gly Ala His Phe Lys Asp Ile Asn Asn Thr Lys Ser
        500                 505                 510

Leu Asn Ile Thr Thr Asn Ser Asp Ser Ala Tyr Arg Thr Ile Ile Glu
    515                 520                 525

Gly Asn Ile Thr Asn Ser Asn Gly Asp Leu Asn Ile Thr Asp Asn Lys
530                 535                 540

Asn Asn Ala Glu Ile Gln Ile Gly Gly Asn Ile Ser Gln Lys Glu Gly
545                 550                 555                 560

Asn Leu Thr Ile Ser Ser Asp Lys Ile Asn Ile Thr Asn Gln Ile Thr
            565                 570                 575

Ile Lys Lys Gly Val Asn Lys Glu Asp Ser Asp Ser Ser Thr Ala Asn
        580                 585                 590

Asn Ala Asn Leu Thr Ile Lys Thr Lys Glu Leu Gln Leu Thr Gly Asp
    595                 600                 605

Leu Asn Ile Ser Gly Phe Asp Lys Ala Glu Ile Thr Ala Lys Glu Gly
    610                 615                 620

Ala Asp Leu Ile Ile Gly Asn Ser Asp Asn Asn Asn Ala Asn Ala
625                 630                 635                 640

Lys Lys Val Thr Phe Asn Gln Val Lys Asp Ser Lys Ile Ser Ala Asp
```

```
                 645                 650                 655
Ser His Asn Val Thr Leu Asn Ser Lys Val Glu Thr Ser Asn Gly Asn
                660                 665                 670

Asn Asp Ala Glu Ser Asn Asn Gly Asp Gly Thr Ser Leu Thr Ile Asn
                675                 680                 685

Ala Lys Asn Ile Thr Val Asn Asn Ile Thr Ser His Lys Thr Val
                690                 695                 700

Asn Ile Thr Ala Ser Glu Asn Val Thr Thr Lys Ala Gly Thr Thr Ile
705                 710                 715                 720

Asn Ala Thr Thr Gly Ser Val Glu Val Thr Ala Lys Thr Gly Asp Ile
                    725                 730                 735

Lys Gly Lys Val Glu Ser Thr Ser Gly Ser Val Thr Leu Thr Ala Thr
                740                 745                 750

Gly Glu Ala Leu Ala Val Ser Asn Ile Ser Gly Asn Thr Val Thr Ile
                755                 760                 765

Thr Ala Asn Lys Gly Lys Leu Thr Thr Gln Ala Gly Ser Thr Val Ser
                770                 775                 780

Ala Ile Asn Gly Val Thr Ala Ser Ser Gln Ser Gly Asp Ile Ser Gly
785                 790                 795                 800

Thr Ile Ser Gly Asn Thr Val Lys Val Ser Ala Ile Gly Asp Leu Thr
                    805                 810                 815

Thr Lys Ser Gly Ser Glu Ile Lys Ala Lys Thr Gly Glu Ala Asn Val
                820                 825                 830

Thr Ser Ala Thr Gly Thr Ile Gly Gly Thr Ile Ser Gly Asn Ala Val
                835                 840                 845

Asn Val Thr Ala Asn Thr Gly Asp Leu Thr Val Glu Asp Ala Ala Lys
850                 855                 860

Ile Asp Ala Thr Gly Gly Ala Ala Thr Leu Thr Ala Thr Ser Gly Lys
865                 870                 875                 880

Leu Thr Thr Lys Ala Ser Ser Ile Thr Ser Ala Asn Asn Gln Val
                    885                 890                 895

Asn Leu Ser Ala Lys Asp Gly Ser Ile Gly Gly Asn Ile Asn Ala Ala
                900                 905                 910

Asn Val Thr Leu Asn Thr Thr Gly Ala Leu Thr Thr Val Lys Gly Ser
                915                 920                 925

Ser Ile Asn Ala Asn Ser Gly Thr Leu Val Ile Asn Ala Lys Asp Ala
                930                 935                 940

Glu Leu Asn Gly Glu Ala Ser Gly Asn His Thr Val Val Asn Ala Thr
945                 950                 955                 960

Asn Ala Asn Gly Ser Gly Ser Val Ile Ala Thr Thr Ser Ser Arg Val
                965                 970                 975

Asn Ile Thr Gly Asp Leu Ile Thr Ile Asn Gly Leu Asn Ile Ile Ser
                980                 985                 990

Lys Asn Gly Ile Asn Thr Val Leu Leu Lys Gly Val Lys Ile Asp Val
                995                 1000                1005

Lys Tyr Ile Gln Pro Gly Ile Ala Ser Val Asp Glu Val Ile Glu Ala
                1010                1015                1020

Lys Arg Ile Leu Glu Lys Val Lys Asp Leu Ser Asp Glu Glu Arg Glu
1025                1030                1035                1040

Ala Leu Ala Lys Leu Gly Val Ser Ala Val Arg Phe Ala Glu Pro Asn
                    1045                1050                1055

Asn Ala Ile Thr Ile Asn Thr Gln Asn Glu Phe Thr Thr Arg Pro Ser
                1060                1065                1070
```

Ser Gln Val Thr Ile Ser Glu Gly Lys Val Cys Phe Leu Ile Gly Asn
      1075                    1080                   1085

Gly Ala Thr Ile Cys Thr Asn Ile Ala Asp Ile Glu Arg
      1090                    1095                1100

<210> SEQ ID NO 44
<211> LENGTH: 3288
<212> TYPE: DNA
<213> ORGANISM: Haemophilus influenzae

<400> SEQUENCE: 44

| | | | | | |
|---|---|---|---|---|---|
| cctgatgaag | taactattgg | agcaggtgac | gtaggacgta | gcgatgattc | aagtgacact |     60 |
| gctttcccta | ccggaacagg | ggaaagaaac | agccccaaaa | caaacgctca | aaacagacca |    120 |
| acaataacaa | acacatctct | tgagcaaata | ttaaaaaatg | gcacctttgt | taacataacc |    180 |
| gccaaaaata | aaatcttagt | taatagcgac | atcaatatca | aagagaactc | ccacctaatc |    240 |
| ctctggagcg | aaagagatgg | caacagcggc | gttcagattg | atggcaatat | tacttccgct |    300 |
| actggcggaa | gcttaaccgt | ttactctagt | ggctgggttg | atgttcataa | aaacattaca |    360 |
| cttaattcag | ggtacttaaa | cattacgact | aaaagtggag | atgtcgcctt | cgaacaaggg |    420 |
| aatgacctaa | ccattacagg | tcaaggaact | attaccgcaa | gcaaaaaagg | ttttagattt |    480 |
| gataatgtta | ctctaagtgg | agtgaaaaag | gggttccttt | ttaaatacag | ccaaaccaac |    540 |
| aataataaag | atagcaattt | cgaaaaccat | tttagaggaa | ctttaaatat | ttcagggaaa |    600 |
| gtagatatct | taatgcaagc | aaggcaggag | aactggaacc | gcagacactc | gggacgctcc |    660 |
| cactggaatg | taacccgatt | gaatgtttct | acaaatagtt | atctcaacat | cactattgat |    720 |
| aacagtggca | gccgtccatc | ccctggtgcc | ggccctctat | atagacgttc | gggtttaaat |    780 |
| ggcatatcgt | ttaacaatga | cactgttttt | aatgttgcgt | caggttcggc | agttaacttt |    840 |
| agcatcaagc | caccaatagt | aagcaatgta | cacgacggga | atcacacatt | attcaatggg |    900 |
| aatgtttcag | ttttaggggg | agggatgtc | aactttcatt | ttaacgcctc | ctccagcaac |    960 |
| cactggactc | atggcgtggt | tataaagtct | caaaacttta | atgcctcaga | agggtcaagc |   1020 |
| ttaagattca | aaagcgaagg | ttcaacacga | accgctttta | caatagaaag | tgatttaact |   1080 |
| ttaaatgcca | ctgggggcaa | tatatcattg | aaccaagttg | caggtattga | tggtaatctc |   1140 |
| caaaaaagcc | ttgtagccaa | taaaacata | acctttgaag | ggggcaatat | cacccttgca |   1200 |
| gccgataaaa | aaccaataga | aatcaaaggt | aatattactg | ttaaagaagg | agccaatgtc |   1260 |
| acccttcgta | gcgcgaatta | tggtaatgac | aaatcagctt | taagtataag | aggaaatgtc |   1320 |
| actaataaag | gcaatctcac | cgttaccggc | tccgctatca | atatagaaaa | aaatcttacc |   1380 |
| gttgaaggta | gtgctaagtt | tttagctaat | ccaaattaca | gctttaacgt | atccggccta |   1440 |
| tttgacaacc | aaggcaagtc | aaacatttcc | attgccaaag | gaggggctca | ctttaaagac |   1500 |
| attaataaca | ctaagagttt | aaacattact | accaactccg | actccgctta | ccgcactatt |   1560 |
| atagaaggca | atataaccaa | cagtaacggg | gatttaaata | tcactgataa | taaaaataac |   1620 |
| gctgaaatcc | aaattggcgg | caatatctcg | caaaaagaag | gtaatctcac | gatttcttcc |   1680 |
| gataaaatta | atatcactaa | ccagataaca | atcaagaagg | gtgttaataa | agaggattct |   1740 |
| gattcaagca | cggcaaacaa | tgctaatcta | accattaaaa | ccaaagaatt | gcaattaacg |   1800 |
| ggagacctaa | atatttcagg | cttcgataaa | gcagaaatca | cagccaaaga | gggtgccgat |   1860 |
| ttaatcatcg | gtaatagtga | taataacaac | aatgctaatg | ctaaaaaagt | aacctttaac |   1920 |

```
caggttaaag attcgaaaat ctctgctgac agtcacaatg taacactaaa cagtaaagta    1980
gaaacctcta atggcaataa tgacgctgaa agcaataatg gcgatggcac cagcttaact    2040
attaatgcaa aaaatataac agtaaacaac aatattactt ctcacaaaac agtaaatatc    2100
actgcgtcag aaaatgttac caccaaagcg ggcacaacca ttaatgcaac cacaggtagc    2160
gtagaagtaa cagccaaaac aggtgatatt aaaggtaaag ttgaatccac ttccggctct    2220
gtaacactta ctgcaaccgg agaagctctt gctgtaagca catttcagg caacactgtt     2280 accatcactg caaataaggg taaattaaca actcaagcag gctctacggt tagcgcgatt    2340
aacggtgtaa ctgcctcaag ccaatcaggc gatattagcg gtacgatttc cggtaacaca    2400
gtaaaagtta gtgcgatcgg tgatttgact actaaatccg gctcggaaat caaggcaaaa    2460
acaggtgagg ctaacgtgac aagtgcgaca ggtacaattg gtggtacgat tctggtaat    2520 gcagtaaatg ttacagcaaa tactggcgat ttaactgttg aagatgccgc aaaaattgat    2580
gcgacaggag gagccgcgac cctaactgca acatcgggca aattaaccac taaggctagt    2640
tcaagcatta cttcagctaa taaccaggta aacctttcag ctaaggatgg tagcattggg    2700
ggaaatatca atgctgctaa tgtaacactg aatactacag gcgctctaac taccgtgaag    2760
ggttcaagca ttaacgcaaa cagcggcacc ttggttatta acgcaaaaga cgctgagcta    2820
aatggtgagg catcaggtaa ccatacagta gtgaatgcaa ccaacgcaaa tggctccggc    2880
agcgtaatcg cgacaacctc aagcagagtg aacatcactg gggatttaat cacaataaat    2940
ggattaaata tcatttcaaa aaacggtata acaccgtac tgttaaaagg cgttaaaatt     3000
gatgtgaaat acattcaacc gggtatagca agcgtagatg aagtaattga agcgaaacgc    3060
atccttgaga aggtaaaaga tttatctgat gaagaaagag aagcgttagc taaacttggc    3120
gtaagcgctg tacgttttgc tgagccaaat aatgccatta cgattaatac acaaaatgag    3180
tttacaacca gaccatcaag tcaagtgaca atttctgaag gtaaggtatg tttcttaatc    3240
ggcaatggtg caacaatatg caccaatatt gctgatattg agcggtag                 3288
```

<210> SEQ ID NO 45
<211> LENGTH: 1095
<212> TYPE: PRT
<213> ORGANISM: Haemophilus influenzae

<400> SEQUENCE: 45

```
Pro Asp Glu Val Thr Ile Gly Ala Gly Asp Val Gly Arg Ser Asp Asp
  1               5                  10                  15

Ser Ser Asp Thr Ala Phe Pro Thr Gly Thr Gly Glu Arg Asn Ser Pro
             20                  25                  30

Lys Thr Asn Ala Gln Asn Arg Pro Thr Ile Thr Asn Thr Ser Leu Glu
         35                  40                  45

Gln Ile Leu Lys Asn Gly Thr Phe Val Asn Ile Thr Ala Lys Asn Lys
     50                  55                  60

Ile Leu Val Asn Ser Asp Ile Asn Ile Lys Glu Asn Ser His Leu Ile
 65                  70                  75                  80

Leu Trp Ser Glu Arg Asp Gly Asn Ser Gly Val Gln Ile Asp Gly Asn
                 85                  90                  95

Ile Thr Ser Ala Thr Gly Gly Ser Leu Thr Val Tyr Ser Ser Gly Trp
            100                 105                 110

Val Asp Val His Lys Asn Ile Thr Leu Asn Ser Gly Tyr Leu Asn Ile
        115                 120                 125

Thr Thr Lys Ser Gly Asp Val Ala Phe Glu Gln Gly Asn Asp Leu Thr
```

-continued

```
            130                 135                 140
Ile Thr Gly Gln Gly Thr Ile Thr Ala Ser Lys Lys Gly Phe Arg Phe
145                 150                 155                 160
Asp Asn Val Thr Leu Ser Gly Val Lys Lys Gly Phe Leu Phe Lys Tyr
                    165                 170                 175
Ser Gln Thr Asn Asn Asn Lys Asp Ser Asn Phe Glu Asn His Phe Arg
                180                 185                 190
Gly Thr Leu Asn Ile Ser Gly Lys Val Asp Ile Leu Met Gln Ala Arg
                195                 200                 205
Gln Glu Asn Trp Asn Arg Arg His Ser Gly Arg Ser His Trp Asn Val
        210                 215                 220
Thr Arg Leu Asn Val Ser Thr Asn Ser Tyr Leu Asn Ile Thr Ile Asp
225                 230                 235                 240
Asn Ser Gly Ser Arg Pro Ser Pro Gly Ala Gly Pro Leu Tyr Arg Arg
                    245                 250                 255
Ser Gly Leu Asn Gly Ile Ser Phe Asn Asn Asp Thr Val Phe Asn Val
                260                 265                 270
Ala Ser Gly Ser Ala Val Asn Phe Ser Ile Lys Pro Pro Ile Val Ser
            275                 280                 285
Asn Val His Asp Gly Asn His Thr Leu Phe Asn Gly Asn Val Ser Val
        290                 295                 300
Leu Gly Gly Gly Asp Val Asn Phe His Phe Asn Ala Ser Ser Ser Asn
305                 310                 315                 320
His Trp Thr His Gly Val Val Ile Lys Ser Gln Asn Phe Asn Ala Ser
                325                 330                 335
Glu Gly Ser Ser Leu Arg Phe Lys Ser Glu Gly Ser Thr Arg Thr Ala
                340                 345                 350
Phe Thr Ile Glu Ser Asp Leu Thr Leu Asn Ala Thr Gly Gly Asn Ile
                355                 360                 365
Ser Leu Asn Gln Val Ala Gly Ile Asp Gly Asn Leu Gln Lys Ser Leu
        370                 375                 380
Val Ala Asn Lys Asn Ile Thr Phe Glu Gly Gly Asn Ile Thr Leu Ala
385                 390                 395                 400
Ala Asp Lys Lys Pro Ile Glu Ile Lys Gly Asn Ile Thr Val Lys Glu
                    405                 410                 415
Gly Ala Asn Val Thr Leu Arg Ser Ala Asn Tyr Gly Asn Asp Lys Ser
                420                 425                 430
Ala Leu Ser Ile Arg Gly Asn Val Thr Asn Lys Gly Asn Leu Thr Val
            435                 440                 445
Thr Gly Ser Ala Ile Asn Ile Glu Lys Asn Leu Thr Val Glu Gly Ser
        450                 455                 460
Ala Lys Phe Leu Ala Asn Pro Asn Tyr Ser Phe Asn Val Ser Gly Leu
465                 470                 475                 480
Phe Asp Asn Gln Gly Lys Ser Asn Ile Ser Ile Ala Lys Gly Gly Ala
                    485                 490                 495
His Phe Lys Asp Ile Asn Asn Thr Lys Ser Leu Asn Ile Thr Thr Asn
                500                 505                 510
Ser Asp Ser Ala Tyr Arg Thr Ile Ile Glu Gly Asn Ile Thr Asn Ser
            515                 520                 525
Asn Gly Asp Leu Asn Ile Thr Asp Asn Lys Asn Asn Ala Glu Ile Gln
        530                 535                 540
Ile Gly Gly Asn Ile Ser Gln Lys Glu Gly Asn Leu Thr Ile Ser Ser
545                 550                 555                 560
```

-continued

```
Asp Lys Ile Asn Ile Thr Asn Gln Ile Thr Ile Lys Lys Gly Val Asn
                565                 570                 575
Lys Glu Asp Ser Asp Ser Ser Thr Ala Asn Asn Ala Asn Leu Thr Ile
            580                 585                 590
Lys Thr Lys Glu Leu Gln Leu Thr Gly Asp Leu Asn Ile Ser Gly Phe
        595                 600                 605
Asp Lys Ala Glu Ile Thr Ala Lys Glu Gly Ala Asp Leu Ile Ile Gly
    610                 615                 620
Asn Ser Asp Asn Asn Asn Ala Asn Ala Lys Lys Val Thr Phe Asn
625                 630                 635                 640
Gln Val Lys Asp Ser Lys Ile Ser Ala Asp Ser His Asn Val Thr Leu
            645                 650                 655
Asn Ser Lys Val Glu Thr Ser Asn Gly Asn Asn Asp Ala Glu Ser Asn
            660                 665                 670
Asn Gly Asp Gly Thr Ser Leu Thr Ile Asn Ala Lys Asn Ile Thr Val
        675                 680                 685
Asn Asn Asn Ile Thr Ser His Lys Thr Val Asn Ile Thr Ala Ser Glu
    690                 695                 700
Asn Val Thr Thr Lys Ala Gly Thr Thr Ile Asn Ala Thr Thr Gly Ser
705                 710                 715                 720
Val Glu Val Thr Ala Lys Thr Gly Asp Ile Lys Gly Lys Val Glu Ser
            725                 730                 735
Thr Ser Gly Ser Val Thr Leu Thr Ala Thr Gly Glu Ala Leu Ala Val
            740                 745                 750
Ser Asn Ile Ser Gly Asn Thr Val Thr Ile Thr Ala Asn Lys Gly Lys
        755                 760                 765
Leu Thr Thr Gln Ala Gly Ser Thr Val Ser Ala Ile Asn Gly Val Thr
    770                 775                 780
Ala Ser Ser Gln Ser Gly Asp Ile Ser Gly Thr Ile Ser Gly Asn Thr
785                 790                 795                 800
Val Lys Val Ser Ala Ile Gly Asp Leu Thr Thr Lys Ser Gly Ser Glu
            805                 810                 815
Ile Lys Ala Lys Thr Gly Glu Ala Asn Val Thr Ser Ala Thr Gly Thr
            820                 825                 830
Ile Gly Gly Thr Ile Ser Gly Asn Ala Val Asn Val Thr Ala Asn Thr
        835                 840                 845
Gly Asp Leu Thr Val Glu Asp Ala Ala Lys Ile Asp Ala Thr Gly Gly
    850                 855                 860
Ala Ala Thr Leu Thr Ala Thr Ser Gly Lys Leu Thr Thr Lys Ala Ser
865                 870                 875                 880
Ser Ser Ile Thr Ser Ala Asn Asn Gln Val Asn Leu Ser Ala Lys Asp
            885                 890                 895
Gly Ser Ile Gly Gly Asn Ile Asn Ala Ala Asn Val Thr Leu Asn Thr
        900                 905                 910
Thr Gly Ala Leu Thr Thr Val Lys Gly Ser Ser Ile Asn Ala Asn Ser
    915                 920                 925
Gly Thr Leu Val Ile Asn Ala Lys Asp Ala Glu Leu Asn Gly Glu Ala
    930                 935                 940
Ser Gly Asn His Thr Val Val Asn Ala Thr Asn Ala Asn Gly Ser Gly
945                 950                 955                 960
Ser Val Ile Ala Thr Thr Ser Ser Arg Val Asn Ile Thr Gly Asp Leu
            965                 970                 975
```

```
Ile Thr Ile Asn Gly Leu Asn Ile Ile Ser Lys Asn Gly Ile Asn Thr
        980                 985                 990

Val Leu Leu Lys Gly Val Lys Ile Asp Val Lys Tyr Ile Gln Pro Gly
        995                 1000                1005

Ile Ala Ser Val Asp Glu Val Ile Glu Ala Lys Arg Ile Leu Glu Lys
        1010                1015                1020

Val Lys Asp Leu Ser Asp Glu Glu Arg Glu Ala Leu Ala Lys Leu Gly
1025                1030                1035                1040

Val Ser Ala Val Arg Phe Ala Glu Pro Asn Asn Ala Ile Thr Ile Asn
                1045                1050                1055

Thr Gln Asn Glu Phe Thr Thr Arg Pro Ser Ser Gln Val Thr Ile Ser
        1060                1065                1070

Glu Gly Lys Val Cys Phe Leu Ile Gly Asn Gly Ala Thr Ile Cys Thr
        1075                1080                1085

Asn Ile Ala Asp Ile Glu Arg
        1090            1095
```

<210> SEQ ID NO 46
<211> LENGTH: 3240
<212> TYPE: DNA
<213> ORGANISM: Haemophilus influenzae

<400> SEQUENCE: 46

```
aaagagtggt tgttagaccc ggatgatgta tccattgacg caccttcggc tgaacgcact      60
gacactggcg aagacgtgga atacaccgga acagggctg atattaacca tcaaaaacaa     120
aacagcgaaa ccaagtcaac attaacaaac acaactcttg aggggatgtt aaaaggggg     180
cttttgtta atatcaccgc cagaaataaa atccgagtta atagcaccat caatatcggg     240
gatagcggcc atttaaccct ttacaaaaaa agaaaaaatc gtagcgatgg tattcaaatt     300
aacaaggata ttacttctac aggcggaagt ttaactatta ctccgacga ctgggttgat     360
attcatggaa atatcacgct tggtgagggc ttttaaata ttacctctag tgattccgtg     420
gctttcgagg gtggaaacgg caataaagga cgtagctcag caagtgctca aattatcgcg     480
cagggtacta taactcttac tggagaaaat aaaacctta gactcaacaa tgtgtcttta     540
aatgggacgg taatggtct aagtattatt caacagcaa gcaatttatc tcatagactt     600
gacggtgaaa ttaatgtatc tggaaatgta acaattaatc aaaccacgca gcaaaacatt     660
gaatactgga aggctagcag cgattcttat tggaatgtca cttcttttaa tttgagagaa     720
gattcaaagt ttacctttat caaatacgtt aactctgcca gaaatggtga tgtaagagga     780
agaagttttg caggtgtgat atttaatgct aaagtctca ctacaagctt taacgtcaag     840
aaaggctcga cagttgattt taaattaaag ccaaattcag gctataattc acaaaaaagg     900
attccaattc aattccaatc aacatctcg gtctcaggag gaggaaggg aaacattaac     960
acgctcgcca atcttacagg cggaggagtt gagataagat cgagttcaat taatgtttct    1020
gatggctcaa ccctctctat gacagctcag gctcgcgaca ggaatgcctt tgaaattacc    1080
aaagatttag ttataaacgc aagcaattca aacctatcta ttatacagca aatgatgga    1140
tttgataata atcaaaaggc aaatgccatt aactcaaaat ataacgtaac tattcaaggt    1200
ggtaatgtta cccttggcgg gcaaaattca agcagtacaa tcacagggag tgttaatatt    1260
ggcgctaatg caaatgttac tttgcaagcc cacaatggca atgatagaaa taaaaagcta    1320
accttcggta atgtatctgt tgaaggagaa ttaaggctag ttggcgcaag tgcaaacatt    1380
aacaacaatc ttagtgttaa gagcggtgct aaattcaaag cagaaacaaa tgacaaccta    1440
```

-continued

```
aacattaccg gcacctttac caacaacggc acctccataa ttgatgtaaa aaaggggcg    1500 gcaaaactag gcaatattac caatgatggt aatttaaata tcactactaa tgctaaaaac    1560
ggtcaaaaaa gcgttatcaa cggaaatata actaacaata aggtgctttt aaatattacg    1620
aataatggta atgacactga atccaaatt ggcggcaata tctcgcaaaa agaaggtaat    1680
ctcacgattt cttctgacaa aattaatatc accaaacgga tagaaattaa ggcaggtact    1740
gatcaaggga attctgattc aggcgtagca agtaatgcta atctaaccat taaaaccaaa    1800
gaattgaaat taacagaaaa cctaaatatt tcaggttttg ataaagcaga aattgtagcc    1860
aaagagaata acaatttaat tattggcaat aataatggcg acaatgctaa cgccaaaaca    1920 gtaacttta acaatgttaa agattcaaaa atctctgcta acggtcacaa tgtgacacta    1980
aatagcaaag tggaaacatc tgatggaaac agtaacactg aaggtaatag tgacaataac    2040
gccggcttaa ctatcgatgc aaaaaatgta acagtaaaca acgatatcac ttctcacaaa    2100 acagtaaaata tcactgcgtc agaaaggatt gatactaaag ctgatacaac cattaatgca    2160
accaccggca acgtgaaact aacagctgta acaagtgata tccaaggtgg aattaaatct    2220
aattctggtg atgtaaatat cacaaccagc acaggtagca ttaacggtaa aattgaatcc    2280
aagtctggct ctgtaacact taccgcaacc gaaaaaactc ttactgtagg caatgtttcg    2340
ggcaacaccg ttactgttac tgcaaataga ggtgcattaa ccactttggc aggctctacg    2400
attaacggga ctaacggtgt aactacctca agtcaatcag gcgagattgg cggtgaggtt    2460
actggtaaga cagtaagtgt tacagcaact gccggcagct taactgttaa aggtggcgca    2520
aaaattaatg cgacagaagg aactgcaacc ttaactgcat catcgggcaa attaaccacc    2580
gaggctagct caaacatcac ttcagccaaa ggtcaggtag accttcagc tcaggatggt    2640 agcattgcag acaaattag tgcagctaat gtaacactga atactacagg cactctaact    2700
accgtagagg gttcaagcat taacgcaaac gaaggcacct tggttattaa cgcaaacgac    2760
gccaagttag atggtaaggc atcaggtaac cgtacagaag taaatgcaac taacgcaagc    2820
ggctctggta gcgtgactgc gaaaacctca agcagcgtga atatcaccgg ggatttaaac    2880
acaataaatg ggtaaatat catttcggaa aatggtagaa acactgtgcg cttaagaggc    2940
aaggaaattg aggtgaaata tatccagcca ggtgtagcaa gtgtagaaga agtaattgaa    3000
gcgaaacgcg tccttgagaa agtgaaagat ttatctgatg aagaaagaga aacattagct    3060
aaacttggtg taagtgctgt acgttttatt gaaccaaata ataccattac ggttaacaca    3120
caaaatgagt ttacaaccag accatcaagt caagtgacaa tttctgaagg taaggcgtgt    3180
ttctcaagtg gtaatggcgc agcagtatgt accaatgttg ctgacgatgg acagcagtag    3240
```

<210> SEQ ID NO 47
<211> LENGTH: 1079
<212> TYPE: PRT
<213> ORGANISM: Haemophilus influenzae

<400> SEQUENCE: 47

Lys Glu Trp Leu Leu Asp Pro Asp Val Ser Ile Asp Ala Pro Ser
 1               5                  10                  15

Ala Glu Arg Thr Asp Thr Gly Glu Asp Val Glu Tyr Thr Gly Thr Gly
            20                  25                  30

Ala Asp Ile Asn His Gln Lys Gln Asn Ser Glu Thr Lys Ser Thr Leu
        35                  40                  45

Thr Asn Thr Thr Leu Glu Gly Met Leu Lys Arg Gly Leu Phe Val Asn

-continued

```
            50                  55                  60
Ile Thr Ala Arg Asn Lys Ile Arg Val Asn Ser Thr Ile Asn Ile Gly
65                  70                  75                  80
Asp Ser Gly His Leu Thr Leu Tyr Lys Lys Arg Lys Asn Arg Ser Asp
                85                  90                  95
Gly Ile Gln Ile Asn Lys Asp Ile Thr Ser Thr Gly Gly Ser Leu Thr
                100                 105                 110
Ile Asn Ser Asp Asp Trp Val Asp Ile His Gly Asn Ile Thr Leu Gly
                115                 120                 125
Glu Gly Phe Leu Asn Ile Thr Ser Ser Asp Ser Val Ala Phe Glu Gly
                130                 135                 140
Gly Asn Gly Asn Lys Gly Arg Ser Ser Ala Ser Ala Gln Ile Ile Ala
145                 150                 155                 160
Gln Gly Thr Ile Thr Leu Thr Gly Glu Asn Lys Thr Phe Arg Leu Asn
                165                 170                 175
Asn Val Ser Leu Asn Gly Thr Gly Asn Gly Leu Ser Ile Ile Ser Thr
                180                 185                 190
Ala Ser Asn Leu Ser His Arg Leu Asp Gly Glu Ile Asn Val Ser Gly
                195                 200                 205
Asn Val Thr Ile Asn Gln Thr Thr Gln Gln Asn Ile Glu Tyr Trp Lys
210                 215                 220
Ala Ser Ser Asp Ser Tyr Trp Asn Val Thr Ser Phe Asn Leu Arg Glu
225                 230                 235                 240
Asp Ser Lys Phe Thr Phe Ile Lys Tyr Val Asn Ser Ala Arg Asn Gly
                245                 250                 255
Asp Val Arg Gly Arg Ser Phe Ala Gly Val Ile Phe Asn Ala Lys Gly
                260                 265                 270
Leu Thr Thr Ser Phe Asn Val Lys Lys Gly Ser Thr Val Asp Phe Lys
                275                 280                 285
Leu Lys Pro Asn Ser Gly Tyr Asn Ser Gln Lys Arg Ile Pro Ile Gln
                290                 295                 300
Phe Gln Ser Asn Ile Ser Val Ser Gly Gly Arg Val Asn Ile Asn
305                 310                 315                 320
Thr Leu Ala Asn Leu Thr Gly Gly Val Glu Ile Arg Ser Ser Ser
                325                 330                 335
Ile Asn Val Ser Asp Gly Ser Thr Leu Ser Met Thr Ala Gln Ala Arg
                340                 345                 350
Asp Arg Asn Ala Phe Glu Ile Thr Lys Asp Leu Val Ile Asn Ala Ser
                355                 360                 365
Asn Ser Asn Leu Ser Ile Ile Gln Gln Asn Asp Gly Phe Asp Asn Asn
                370                 375                 380
Gln Lys Ala Asn Ala Ile Asn Ser Lys Tyr Asn Val Thr Ile Gln Gly
385                 390                 395                 400
Gly Asn Val Thr Leu Gly Gly Gln Asn Ser Ser Thr Ile Thr Gly
                405                 410                 415
Ser Val Asn Ile Gly Ala Asn Ala Val Thr Leu Gln Ala His Asn
                420                 425                 430
Gly Asn Asp Arg Asn Lys Lys Leu Thr Phe Gly Asn Val Ser Val Glu
                435                 440                 445
Gly Glu Leu Arg Leu Val Gly Ala Ser Ala Asn Ile Asn Asn Asn Leu
                450                 455                 460
Ser Val Lys Ser Gly Ala Lys Phe Lys Ala Glu Thr Asn Asp Asn Leu
465                 470                 475                 480
```

-continued

```
Asn Ile Thr Gly Thr Phe Thr Asn Asn Gly Thr Ser Ile Ile Asp Val
                485                 490                 495
Lys Lys Gly Ala Ala Lys Leu Gly Asn Ile Thr Asn Asp Gly Asn Leu
            500                 505                 510
Asn Ile Thr Thr Asn Ala Lys Asn Gly Gln Lys Ser Val Ile Asn Gly
            515                 520                 525
Asn Ile Thr Asn Asn Lys Gly Ala Leu Asn Ile Thr Asn Asn Gly Asn
        530                 535                 540
Asp Thr Glu Ile Gln Ile Gly Gly Asn Ile Ser Gln Lys Gly Asn
545                 550                 555                 560
Leu Thr Ile Ser Ser Asp Lys Ile Asn Ile Thr Lys Arg Ile Glu Ile
                565                 570                 575
Lys Ala Gly Thr Asp Gln Gly Asn Ser Asp Ser Gly Val Ala Ser Asn
                580                 585                 590
Ala Asn Leu Thr Ile Lys Thr Lys Glu Leu Lys Leu Thr Glu Asn Leu
            595                 600                 605
Asn Ile Ser Gly Phe Asp Lys Ala Glu Ile Val Ala Lys Glu Asn Asn
        610                 615                 620
Asn Leu Ile Ile Gly Asn Asn Asn Gly Asp Asn Ala Asn Ala Lys Thr
625                 630                 635                 640
Val Thr Phe Asn Asn Val Lys Asp Ser Lys Ile Ser Ala Asn Gly His
                645                 650                 655
Asn Val Thr Leu Asn Ser Lys Val Glu Thr Ser Asp Gly Asn Ser Asn
                660                 665                 670
Thr Glu Gly Asn Ser Asp Asn Asn Ala Gly Leu Thr Ile Asp Ala Lys
            675                 680                 685
Asn Val Thr Val Asn Asn Asp Ile Thr Ser His Lys Thr Val Asn Ile
        690                 695                 700
Thr Ala Ser Glu Arg Ile Asp Thr Lys Ala Asp Thr Thr Ile Asn Ala
705                 710                 715                 720
Thr Thr Gly Asn Val Lys Leu Thr Ala Val Thr Ser Asp Ile Gln Gly
                725                 730                 735
Gly Ile Lys Ser Asn Ser Gly Asp Val Asn Ile Thr Thr Ser Thr Gly
                740                 745                 750
Ser Ile Asn Gly Lys Ile Glu Ser Lys Ser Gly Ser Val Thr Leu Thr
            755                 760                 765
Ala Thr Glu Lys Thr Leu Thr Val Gly Asn Val Ser Gly Asn Thr Val
        770                 775                 780
Thr Val Thr Ala Asn Arg Gly Ala Leu Thr Thr Leu Ala Gly Ser Thr
785                 790                 795                 800
Ile Asn Gly Thr Asn Gly Val Thr Thr Ser Gln Ser Gly Glu Ile
                805                 810                 815
Gly Gly Glu Val Thr Gly Lys Thr Val Ser Val Thr Ala Thr Ala Gly
                820                 825                 830
Ser Leu Thr Val Lys Gly Ala Lys Ile Asn Ala Thr Glu Gly Thr
            835                 840                 845
Ala Thr Leu Thr Ala Ser Ser Gly Lys Leu Thr Thr Glu Ala Ser Ser
850                 855                 860
Asn Ile Thr Ser Ala Lys Gly Gln Val Asp Leu Ser Ala Gln Asp Gly
865                 870                 875                 880
Ser Ile Ala Gly Gln Ile Ser Ala Asn Val Thr Leu Asn Thr Thr
                885                 890                 895
```

-continued

```
Gly Thr Leu Thr Thr Val Glu Gly Ser Ser Ile Asn Ala Asn Glu Gly
            900                 905                 910
Thr Leu Val Ile Asn Ala Asn Asp Ala Lys Leu Asp Gly Lys Ala Ser
            915                 920                 925
Gly Asn Arg Thr Glu Val Asn Ala Thr Asn Ala Ser Gly Ser Gly Ser
            930                 935                 940
Val Thr Ala Lys Thr Ser Ser Ser Val Asn Ile Thr Gly Asp Leu Asn
945                 950                 955                 960
Thr Ile Asn Gly Leu Asn Ile Ile Ser Glu Asn Gly Arg Asn Thr Val
            965                 970                 975
Arg Leu Arg Gly Lys Glu Ile Glu Val Lys Tyr Ile Gln Pro Gly Val
            980                 985                 990
Ala Ser Val Glu Glu Val Ile Glu Ala Lys Arg Val Leu Glu Lys Val
            995                 1000                1005
Lys Asp Leu Ser Asp Glu Glu Arg Glu Thr Leu Ala Lys Leu Gly Val
        1010                1015                1020
Ser Ala Val Arg Phe Ile Glu Pro Asn Asn Thr Ile Thr Val Asn Thr
1025                1030                1035                1040
Gln Asn Glu Phe Thr Thr Arg Pro Ser Ser Gln Val Thr Ile Ser Glu
            1045                1050                1055
Gly Lys Ala Cys Phe Ser Ser Gly Asn Gly Ala Ala Val Cys Thr Asn
            1060                1065                1070
Val Ala Asp Asp Gly Gln Gln
        1075
```

<210> SEQ ID NO 48
<211> LENGTH: 3222
<212> TYPE: DNA
<213> ORGANISM: Haemophilus influenzae

<400> SEQUENCE: 48

```
ccggatgatg tatccattga cgcaccttcg gctgaacgca ctgacactgg cgaagacgtg      60
gaatacaccg aacagggggc tgatattaac catcaaaaac aaaacagcga aaccaagtca     120
acattaacaa acacaactct tgagggggatg ttaaaaaggg ggcttttttgt taatatcacc     180
gccagaaata aaatccgagt taatagcacc atcaatatcg gggggatagcgg ccattttaacc     240
ctttacaaaa aaagaaaaaa tcgtagcgat ggtattcaaa ttaacaagga tattacttct     300
acaggcggaa gtttaactat taactccgac gactggggttg atattcatgg aaatatcacg     360
cttggtgagg ctttttttaaa tattacctct agtgattccg tggctttcga gggtggaaac     420
ggcaataaag gacgtagctc agcaagtgct caaattatcg cgcagggtac tataactctt     480
actggagaaa ataaaacctt tagactcaac aatgtgtctt taaatgggac gggtaatggt     540
ctaagtatta tttcaacagc aagcaattta tctcatagac ttgacggtga attaatgta     600
tctggaaatg taacaattaa tcaaaccacg cagcaaaaca ttgaatactg gaaggctagc     660
agcgattctt attggaatgt cacttctttt aatttgagag aagattcaaa gtttaccttt     720
atcaaatacg ttaactctgc cagaaatggt gatgtaagag gaagaagttt tgcaggtgtg     780
atatttaatg ctaaaggtct cactacaagc tttaacgtca agaaaggctc gacagttgat     840
tttaaattaa agccaaattc aggctataat tcacaaaaaa ggattccaat tcaattccaa     900
tccaacatct cggtctcagg aggaggaagg gtaaacatta acacgctcgc caatcttaca     960
ggcggaggag ttgagataag atcgagttca attaatgttt ctgatggctc aaccctctct    1020
atgacagctc aggctcgcga caggaatgcc tttgaaatta ccaaagattt agttataaac    1080
```

```
gcaagcaatt caaacctatc tattatacag caaaatgatg gatttgataa taatcaaaag    1140
gcaaatgcca ttaactcaaa atataacgta actattcaag gtggtaatgt taccettggc    1200 gggcaaaatt caagcagtac aatcacaggg agtgttaata ttggcgctaa tgcaaatgtt    1260
actttgcaag cccacaatgg caatgataga aataaaaagc taaccttcgg taatgtatct    1320
gttgaaggag aattaaggct agttggcgca agtgcaaaca ttaacaacaa tcttagtgtt    1380
aagagcggtg ctaaattcaa agcagaaaca atgacaacc taaacattac cggcaccttt     1440
accaacaacg gcacctccat aattgatgta aaaaagggg cggcaaaact aggcaatatt     1500
accaatgatg gtaatttaaa tatcactact aatgctaaaa acggtcaaaa aagcgttatc    1560
aacgaaaata taactaacaa taaaggtgct ttaaatatta cgaataatgg taatgacact    1620
gaaatccaaa ttggcggcaa tatctcgcaa aaagaaggta atctcacgat ttcttctgac    1680
aaaattaata tcaccaaacg gatagaaatt aaggcaggta ctgatcaagg gaattctgat    1740
tcaggcgtag caagtaatgc taatctaacc attaaaacca aagaattgaa attaacagaa    1800
aacctaaata tttcaggttt tgataaagca gaaattgtag ccaaagagaa taacaattta    1860
attattggca ataataatgg cgacaatgct aacgccaaaa cagtaacttt taacaatgtt    1920
aaagattcaa aaatctctgc taacggtcac aatgtgacac taaatagcaa agtggaaaca    1980
tctgatggaa acagtaacac tgaaggtaat agtgacaata acgccggctt aactatcgat    2040
gcaaaaaatg taacagtaaa caacgatatc acttctcaca aaacagtaaa tatcactgcg    2100
tcagaaagga ttgatactaa agctgataca accattaatg caaccaccgg caacgtgaaa    2160
ctaacagctg taacaagtga tatccaaggt ggaattaaat ctaattctgg tgatgtaaat    2220
atcacaacca gcacaggtag cattaacggt aaaattgaat ccaagtctgg ctctgtaaca    2280
cttaccgcaa ccgaaaaaac tcttactgta ggcaatgttt cgggcaacac cgttactgtt    2340
actgcaaata gaggtgcatt aaccactttg gcaggctcta cgattaacgg gactaacggt    2400
gtaactacct caagtcaatc aggcgagatt ggcggtgagg ttactggtaa gacagtaagt    2460
gttacagcaa ctgccggcag cttaactgtt aaaggtggcg caaaaattaa tgcgacagaa    2520
ggaactgcaa ccttaactgc atcatcgggc aaattaacca ccgaggctag ctcaaacatc    2580
acttcagcca aaggtcaggt agacctttca gctcaggatg gtagcattgc aggacaaatt    2640
agtgcagcta atgtaacact gaatactaca ggcactctaa ctaccgtaga gggttcaagc    2700
attaacgcaa acgaaggcac cttggttatt aacgcaaacg acgccaagtt agatggtaag    2760
gcatcaggta accgtacaga agtaaatgca actaacgcaa gcggctctgg tagcgtgact    2820
gcgaaaacct caagcagcgt gaatatcacc ggggatttaa acacaataaa tgggttaaat    2880
atcatttcgg aaaatggtag aaacactgtg cgcttaagag gcaaggaaat tgaggtgaaa    2940
tatatccagc caggtgtagc aagtgtagaa gaagtaattg aagcgaaacg cgtccttgag    3000
aaagtgaaag atttatctga tgaagaaaga gaaacattag ctaaacttgg tgtaagtgct    3060
gtacgtttta ttgaaccaaa taataccatt acggttaaca cacaaaatga gtttacaacc    3120
agaccatcaa gtcaagtgac aatttctgaa ggtaaggcgt gttttctcaag tggtaatggc    3180 gcagcagtat gtaccaatgt tgctgacgat ggacagcagt ag                      3222
```

<210> SEQ ID NO 49
<211> LENGTH: 1073
<212> TYPE: PRT
<213> ORGANISM: Haemophilus influenzae -continued

```
<400> SEQUENCE: 49

Pro Asp Asp Val Ser Ile Asp Ala Pro Ser Ala Glu Arg Thr Asp Thr
 1               5                  10                  15

Gly Glu Asp Val Glu Tyr Thr Gly Thr Gly Ala Asp Ile Asn His Gln
             20                  25                  30

Lys Gln Asn Ser Glu Thr Lys Ser Thr Leu Thr Asn Thr Thr Leu Glu
         35                  40                  45

Gly Met Leu Lys Arg Gly Leu Phe Val Asn Ile Thr Ala Arg Asn Lys
 50                  55                  60

Ile Arg Val Asn Ser Thr Ile Asn Ile Gly Asp Ser Gly His Leu Thr
 65                  70                  75                  80

Leu Tyr Lys Lys Arg Lys Asn Arg Ser Asp Gly Ile Gln Ile Asn Lys
                 85                  90                  95

Asp Ile Thr Ser Thr Gly Gly Ser Leu Thr Ile Asn Ser Asp Asp Trp
             100                 105                 110

Val Asp Ile His Gly Asn Ile Thr Leu Gly Glu Gly Phe Leu Asn Ile
             115                 120                 125

Thr Ser Ser Asp Ser Val Ala Phe Glu Gly Gly Asn Gly Asn Lys Gly
     130                 135                 140

Arg Ser Ser Ala Ser Ala Gln Ile Ile Ala Gln Gly Thr Ile Thr Leu
145                 150                 155                 160

Thr Gly Glu Asn Lys Thr Phe Arg Leu Asn Asn Val Ser Leu Asn Gly
                 165                 170                 175

Thr Gly Asn Gly Leu Ser Ile Ile Ser Thr Ala Ser Asn Leu Ser His
             180                 185                 190

Arg Leu Asp Gly Glu Ile Asn Val Ser Gly Asn Val Thr Ile Asn Gln
         195                 200                 205

Thr Thr Gln Gln Asn Ile Glu Tyr Trp Lys Ala Ser Ser Asp Ser Tyr
210                 215                 220

Trp Asn Val Thr Ser Phe Asn Leu Arg Glu Asp Ser Lys Phe Thr Phe
225                 230                 235                 240

Ile Lys Tyr Val Asn Ser Ala Arg Asn Gly Asp Val Arg Gly Arg Ser
                 245                 250                 255

Phe Ala Gly Val Ile Phe Asn Ala Lys Gly Leu Thr Thr Ser Phe Asn
             260                 265                 270

Val Lys Lys Gly Ser Thr Val Asp Phe Lys Leu Lys Pro Asn Ser Gly
         275                 280                 285

Tyr Asn Ser Gln Lys Arg Ile Pro Ile Gln Phe Gln Ser Asn Ile Ser
     290                 295                 300

Val Ser Gly Gly Arg Val Asn Ile Asn Thr Leu Ala Asn Leu Thr
305                 310                 315                 320

Gly Gly Gly Val Glu Ile Arg Ser Ser Ile Asn Val Ser Asp Gly
                 325                 330                 335

Ser Thr Leu Ser Met Thr Ala Gln Ala Arg Asp Arg Asn Ala Phe Glu
             340                 345                 350

Ile Thr Lys Asp Leu Val Ile Asn Ala Ser Asn Ser Leu Ser Ile
         355                 360                 365

Ile Gln Gln Asn Asp Gly Phe Asp Asn Asn Gln Lys Ala Asn Ala Ile
     370                 375                 380

Asn Ser Lys Tyr Asn Val Thr Ile Gln Gly Gly Asn Val Thr Leu Gly
385                 390                 395                 400

Gly Gln Asn Ser Ser Ser Thr Ile Thr Gly Ser Val Asn Ile Gly Ala
                 405                 410                 415
```

```
Asn Ala Asn Val Thr Leu Gln Ala His Asn Gly Asn Asp Arg Asn Lys
            420                 425                 430

Lys Leu Thr Phe Gly Asn Val Ser Val Glu Gly Glu Leu Arg Leu Val
            435                 440                 445

Gly Ala Ser Ala Asn Ile Asn Asn Leu Ser Val Lys Ser Gly Ala
            450                 455                 460

Lys Phe Lys Ala Glu Thr Asn Asp Asn Leu Asn Ile Thr Gly Thr Phe
465                 470                 475                 480

Thr Asn Asn Gly Thr Ser Ile Ile Asp Val Lys Lys Gly Ala Ala Lys
            485                 490                 495

Leu Gly Asn Ile Thr Asn Asp Gly Asn Leu Asn Ile Thr Thr Asn Ala
            500                 505                 510

Lys Asn Gly Gln Lys Ser Val Ile Asn Gly Asn Ile Thr Asn Asn Lys
            515                 520                 525

Gly Ala Leu Asn Ile Thr Asn Gly Asn Asp Thr Glu Ile Gln Ile
            530                 535                 540

Gly Gly Asn Ile Ser Gln Lys Glu Gly Asn Leu Thr Ile Ser Ser Asp
545                 550                 555                 560

Lys Ile Asn Ile Thr Lys Arg Ile Glu Ile Lys Ala Gly Thr Asp Gln
            565                 570                 575

Gly Asn Ser Asp Ser Gly Val Ala Ser Asn Ala Asn Leu Thr Ile Lys
            580                 585                 590

Thr Lys Glu Leu Lys Leu Thr Glu Asn Leu Asn Ile Ser Gly Phe Asp
            595                 600                 605

Lys Ala Glu Ile Val Ala Lys Glu Asn Asn Asn Leu Ile Ile Gly Asn
            610                 615                 620

Asn Asn Gly Asp Asn Ala Asn Ala Lys Thr Val Thr Phe Asn Asn Val
625                 630                 635                 640

Lys Asp Ser Lys Ile Ser Ala Asn Gly His Asn Val Thr Leu Asn Ser
            645                 650                 655

Lys Val Glu Thr Ser Asp Gly Asn Ser Asn Thr Glu Gly Asn Ser Asp
            660                 665                 670

Asn Asn Ala Gly Leu Thr Ile Asp Ala Lys Asn Val Thr Val Asn Asn
            675                 680                 685

Asp Ile Thr Ser His Lys Thr Val Asn Ile Thr Ala Ser Glu Arg Ile
            690                 695                 700

Asp Thr Lys Ala Asp Thr Thr Ile Asn Ala Thr Thr Gly Asn Val Lys
705                 710                 715                 720

Leu Thr Ala Val Thr Ser Asp Ile Gln Gly Gly Ile Lys Ser Asn Ser
            725                 730                 735

Gly Asp Val Asn Ile Thr Thr Ser Thr Gly Ser Ile Asn Gly Lys Ile
            740                 745                 750

Glu Ser Lys Ser Gly Ser Val Thr Leu Thr Ala Thr Glu Lys Thr Leu
            755                 760                 765

Thr Val Gly Asn Val Ser Gly Asn Thr Val Thr Val Thr Ala Asn Arg
            770                 775                 780

Gly Ala Leu Thr Thr Leu Ala Gly Ser Thr Ile Asn Gly Thr Asn Gly
785                 790                 795                 800

Val Thr Thr Ser Ser Gln Ser Gly Glu Ile Gly Gly Glu Val Thr Gly
            805                 810                 815

Lys Thr Val Ser Val Thr Ala Thr Ala Gly Ser Leu Thr Val Lys Gly
            820                 825                 830
```

```
Gly Ala Lys Ile Asn Ala Thr Glu Gly Thr Ala Thr Leu Thr Ala Ser
        835                 840                 845

Ser Gly Lys Leu Thr Thr Glu Ala Ser Ser Asn Ile Thr Ser Ala Lys
        850                 855                 860

Gly Gln Val Asp Leu Ser Ala Gln Asp Gly Ser Ile Ala Gly Gln Ile
865                 870                 875                 880

Ser Ala Ala Asn Val Thr Leu Asn Thr Thr Gly Thr Leu Thr Thr Val
                885                 890                 895

Glu Gly Ser Ser Ile Asn Ala Asn Glu Gly Thr Leu Val Ile Asn Ala
        900                 905                 910

Asn Asp Ala Lys Leu Asp Gly Lys Ala Ser Gly Asn Arg Thr Glu Val
        915                 920                 925

Asn Ala Thr Asn Ala Ser Gly Ser Gly Ser Val Thr Ala Lys Thr Ser
        930                 935                 940

Ser Ser Val Asn Ile Thr Gly Asp Leu Asn Thr Ile Asn Gly Leu Asn
945                 950                 955                 960

Ile Ile Ser Glu Asn Gly Arg Asn Thr Val Arg Leu Arg Gly Lys Glu
        965                 970                 975

Ile Glu Val Lys Tyr Ile Gln Pro Gly Val Ala Ser Val Glu Glu Val
        980                 985                 990

Ile Glu Ala Lys Arg Val Leu Glu Lys Val Lys Asp Leu Ser Asp Glu
        995                 1000                1005

Glu Arg Glu Thr Leu Ala Lys Leu Gly Val Ser Ala Val Arg Phe Ile
        1010                1015                1020

Glu Pro Asn Asn Thr Ile Thr Val Asn Thr Gln Asn Glu Phe Thr Thr
1025                1030                1035                1040

Arg Pro Ser Ser Gln Val Thr Ile Ser Glu Gly Lys Ala Cys Phe Ser
                1045                1050                1055

Ser Gly Asn Gly Ala Ala Val Cys Thr Asn Val Ala Asp Asp Gly Gln
                1060                1065                1070

Gln

<210> SEQ ID NO 50
<211> LENGTH: 2952
<212> TYPE: DNA
<213> ORGANISM: Haemophilus influenzae

<400> SEQUENCE: 50
aaagagtggt tgttagaccc ggataatgtc aatattgtta aaggaaccga attacagaat      60
gatttggttg ttaggggcga tagtattgag aaaaagaatg cccctaccaa gactacaatt    120
catgcaggct ctatagaaca atctttgatg aagggtggtg cagttaatat ttctgctaca    180
aataaagtaa atgttactac agatattaat gtttataatg gagcattaac gttacactca    240
gaacgagatg gagttgaaat taacggtaat attacctcag aaaaaaatgg taatttaacc    300
attaaagcag gtagctgggt tgatgttcat aaaaatatca cacttggcga gggttttttg    360
aatattactt ccggtgatat cgccttcgaa aaggtaataa atctaaccat taccgctcaa    420
ggaaatataa cctctaataa agacggaaaa caacttagac ttaataatgt atcttttaaat   480 ggaacaggtg caggtttaaa ctttattgca aatcaaaata attttacaca caacattagt    540
ggcgcgatta acatttccgg agtagtaacg attaatcaaa ctacgaaaaa aaacgctaag    600
gcatggaata caagctatga ctcttactgg aacgtatcta ctcttacttt aagcaatgat    660
gcgaaattta cctttattaa atatgtcgac agcaatcatt cgacaaactc cagtgattca    720
```

-continued

```
cgaagttttg cgggagtaaa gttccacggc aagaataatg aaatgaaatt taatattggt    780
aataatgcca aggctgaatt taggttaaaa ccaaatgaga agacaactcc taacagacca    840
ctaccaattc agtttttatc taatatttcg gtcactggcg gaggttctgt gttttttcgat   900
atatacgcta acctttgggg taaagggact gagctaaaga tggattcaat taacgtttct    960
agcggctcta atcttacctt aaattcccat gttcgcaagt ataatgcttt tgaaatcaat   1020
aaagacttaa ctataaacgc aactaattca aatttcaacc tcagacagac gtcagatagt   1080
tttcgtaacg ggtaccgcaa taatgccatc aattcaaccc acaacatatc catcttgggc   1140
ggcaacgtca ctctcggcgg acaaaactca agcagcagca ttatggggaa tatcatcatc   1200
aagcgagcag caaatgttac gctagaagcc gataatagtc acaattctga caacgtaaag   1260
gatagaacta taaatcttgg caacttgacc gttgagggga atttaagttt aattggcgaa   1320
aatgcaaata ttaacggcaa tctctccatt gaaaagaag ccatctttaa aggaaaaacc    1380
aaggacagcc taaacatcac cggcaacttt accaataatg gcactgccga aattaatata   1440
agccaaggag tggtaagtct tggcgatatt accaatgatg gcaaattaaa catcaccact   1500
cacgccaaga gcggtcaaaa aagcattatc cgcggagata taattaacaa acaagggaat   1560
ttaaatatta cggacaataa tagtaatgct gaaattgaaa ttggcggcaa tatctcgcaa   1620
aaagaaggta atctcaccat ttcttctgat aaagtcaata ttaccaaaca gataacaatc   1680
aaagcaggcg ttgatgggga gagttctagt tcaagcacag caagtgatgc caatctaacc   1740
attaaaacca aagagttaac attaacagac aatctaaaca tttcaggttt taataaagca   1800
gaaattacag ctaaagataa cagtgattta attattggca aggctagcag tgacaacagt   1860
aatgctaaac aagtaacctt tgacaaggtt aaagattcaa aaatctcagc tggcaatcac   1920
aatgtaacac taaatagcaa agtggaaacg tctaatagcg atggtagcac cggaaacggt   1980
agcgatgaca caatatcgg cttaactatt tccgcaaaag atgtaacggt aaatagtaat   2040
atcacctctc acaaaacagt aaatatctct gcatcagaag gaggtatcac tactaaagca   2100
ggcacaacca ttaatgcgac cacaggtagc gtggaagtaa ctgctaaaac aggcgatatt   2160
agcggtacga tttccggtaa gacagtaagt gttacagcaa gcactggcga tttaactgtt   2220
aggaaagctg caaccattag tgcgacagaa ggagctgcaa ccttaaccgc aacagggaat   2280
accttgacta ctgaagccgg ttctagcatc acttcaacta agggtcaggt agacctttca   2340
gctcaggatg gtagcattgc aggacaaatt agtgcagcta atgtgacatt aaataccaca   2400
ggcaccttaa ctactgtaga aggttcaaac attaaggcaa ccagtggcac cttagctatt   2460
aacgcaaaag acgctaagct agatggtacg gcatcaggta accgtacaga agtaaatgca   2520
actaacgcaa gtggttctgg tagcgtgact gcgaaaacct caagtaatgt gaatatcacc   2580
ggggatttaa gcacaataaa tgggttaaat atcatttcgg aaaatggtag aaacactgtg   2640
cgcttaagag gcaaggaaat tgatgtgaaa tatatccaac caggtgtagc aagcgtagaa   2700
gaggtaattg aagcgaaacg cgtccttgag aaagtaaaag atttatctga cgaagaaaga   2760
gaaacactag ccaaacttgg tgtaagtgct gtacgtttcg ttgagccaaa taatgccatt   2820
acgattaata cacaaaatga atttacaacc agaccgtcaa gtcaagtgat aatttctgaa   2880
ggtaaggcgt gtttctcaag tggtaatggc gcagcagtat gtaccaatgt tgctgacgat   2940
ggacagccgt ag                                                       2952
```

<210> SEQ ID NO 51
<211> LENGTH: 983

```
<212> TYPE: PRT
<213> ORGANISM: Haemophilus influenzae

<400> SEQUENCE: 51

Lys Glu Trp Leu Leu Asp Pro Asp Asn Val Asn Ile Val Lys Gly Thr
 1               5                  10                  15

Glu Leu Gln Asn Asp Leu Val Val Arg Gly Asp Ser Ile Glu Lys Lys
             20                  25                  30

Asn Ala Pro Thr Lys Thr Thr Ile His Ala Gly Ser Ile Glu Gln Ser
         35                  40                  45

Leu Met Lys Gly Gly Ala Val Asn Ile Ser Ala Thr Asn Lys Val Asn
     50                  55                  60

Val Thr Thr Asp Ile Asn Val Tyr Asn Gly Ala Leu Thr Leu His Ser
 65                  70                  75                  80

Glu Arg Asp Gly Val Glu Ile Asn Gly Asn Ile Thr Ser Glu Lys Asn
                 85                  90                  95

Gly Asn Leu Thr Ile Lys Ala Gly Ser Trp Val Asp Val His Lys Asn
            100                 105                 110

Ile Thr Leu Gly Glu Gly Phe Leu Asn Ile Thr Ser Gly Asp Ile Ala
        115                 120                 125

Phe Glu Lys Gly Asn Asn Leu Thr Ile Thr Ala Gln Gly Asn Ile Thr
    130                 135                 140

Ser Asn Lys Asp Gly Lys Gln Leu Arg Leu Asn Asn Val Ser Leu Asn
145                 150                 155                 160

Gly Thr Gly Ala Gly Leu Asn Phe Ile Ala Asn Gln Asn Asn Phe Thr
                165                 170                 175

His Asn Ile Ser Gly Ala Ile Asn Ile Ser Gly Val Val Thr Ile Asn
            180                 185                 190

Gln Thr Thr Lys Lys Asn Ala Lys Ala Trp Asn Thr Ser Tyr Asp Ser
        195                 200                 205

Tyr Trp Asn Val Ser Thr Leu Thr Leu Ser Asn Asp Ala Lys Phe Thr
    210                 215                 220

Phe Ile Lys Tyr Val Asp Ser Asn His Ser Thr Asn Ser Ser Asp Ser
225                 230                 235                 240

Arg Ser Phe Ala Gly Val Lys Phe His Gly Lys Asn Asn Glu Met Lys
                245                 250                 255

Phe Asn Ile Gly Asn Asn Ala Lys Ala Glu Phe Arg Leu Lys Pro Asn
            260                 265                 270

Glu Lys Thr Thr Pro Asn Arg Pro Leu Pro Ile Gln Phe Leu Ser Asn
        275                 280                 285

Ile Ser Val Thr Gly Gly Ser Val Phe Phe Asp Ile Tyr Ala Asn
    290                 295                 300

Leu Trp Gly Lys Gly Thr Glu Leu Lys Met Asp Ser Ile Asn Val Ser
305                 310                 315                 320

Ser Gly Ser Asn Leu Thr Leu Asn Ser His Val Arg Lys Tyr Asn Ala
                325                 330                 335

Phe Glu Ile Asn Lys Asp Leu Thr Ile Asn Ala Thr Asn Ser Asn Phe
            340                 345                 350

Asn Leu Arg Gln Thr Ser Asp Ser Phe Arg Asn Gly Tyr Arg Asn Asn
        355                 360                 365

Ala Ile Asn Ser Thr His Asn Ile Ser Ile Leu Gly Asn Val Thr
    370                 375                 380

Leu Gly Gly Gln Asn Ser Ser Ser Ile Met Gly Asn Ile Ile Ile
385                 390                 395                 400
```

-continued

```
Lys Arg Ala Ala Asn Val Thr Leu Glu Ala Asp Asn Ser His Asn Ser
                405                 410                 415
Asp Asn Val Lys Asp Arg Thr Ile Asn Leu Gly Asn Leu Thr Val Glu
                420                 425                 430
Gly Asn Leu Ser Leu Ile Gly Glu Asn Ala Asn Ile Asn Gly Asn Leu
                435                 440                 445
Ser Ile Glu Lys Glu Ala Ile Phe Lys Gly Lys Thr Lys Asp Ser Leu
            450                 455                 460
Asn Ile Thr Gly Asn Phe Thr Asn Asn Gly Thr Ala Glu Ile Asn Ile
465                 470                 475                 480
Ser Gln Gly Val Val Ser Leu Gly Asp Ile Thr Asn Asp Gly Lys Leu
                485                 490                 495
Asn Ile Thr Thr His Ala Lys Ser Gly Gln Lys Ser Ile Ile Arg Gly
                500                 505                 510
Asp Ile Ile Asn Lys Gln Gly Asn Leu Asn Ile Thr Asp Asn Asn Ser
            515                 520                 525
Asn Ala Glu Ile Glu Ile Gly Gly Asn Ile Ser Gln Lys Glu Gly Asn
            530                 535                 540
Leu Thr Ile Ser Ser Asp Lys Val Asn Ile Thr Lys Gln Ile Thr Ile
545                 550                 555                 560
Lys Ala Gly Val Asp Gly Glu Ser Ser Ser Ser Thr Ala Ser Asp
                565                 570                 575
Ala Asn Leu Thr Ile Lys Thr Lys Glu Leu Thr Leu Thr Asp Asn Leu
                580                 585                 590
Asn Ile Ser Gly Phe Asn Lys Ala Glu Ile Thr Ala Lys Asp Asn Ser
            595                 600                 605
Asp Leu Ile Ile Gly Lys Ala Ser Ser Asp Asn Ser Asn Ala Lys Gln
            610                 615                 620
Val Thr Phe Asp Lys Val Lys Asp Ser Lys Ile Ser Ala Gly Asn His
625                 630                 635                 640
Asn Val Thr Leu Asn Ser Lys Val Glu Thr Ser Asn Ser Asp Gly Ser
                645                 650                 655
Thr Gly Asn Gly Ser Asp Asp Asn Asn Ile Gly Leu Thr Ile Ser Ala
            660                 665                 670
Lys Asp Val Thr Val Asn Ser Asn Ile Thr Ser His Lys Thr Val Asn
            675                 680                 685
Ile Ser Ala Ser Glu Gly Gly Ile Thr Thr Lys Ala Gly Thr Thr Ile
            690                 695                 700
Asn Ala Thr Thr Gly Ser Val Glu Val Thr Ala Lys Thr Gly Asp Ile
705                 710                 715                 720
Ser Gly Thr Ile Ser Gly Lys Thr Val Ser Val Thr Ala Ser Thr Gly
                725                 730                 735
Asp Leu Thr Val Arg Lys Ala Ala Thr Ile Ser Ala Thr Glu Gly Ala
                740                 745                 750
Ala Thr Leu Thr Ala Thr Gly Asn Thr Leu Thr Thr Glu Ala Gly Ser
            755                 760                 765
Ser Ile Thr Ser Thr Lys Gly Gln Val Asp Leu Ser Ala Gln Asp Gly
            770                 775                 780
Ser Ile Ala Gly Gln Ile Ser Ala Ala Asn Val Thr Leu Asn Thr Thr
785                 790                 795                 800
Gly Thr Leu Thr Thr Val Glu Gly Ser Asn Ile Lys Ala Thr Ser Gly
                805                 810                 815
```

```
Thr Leu Ala Ile Asn Ala Lys Asp Ala Lys Leu Asp Gly Thr Ala Ser
            820                 825                 830
Gly Asn Arg Thr Glu Val Asn Ala Thr Asn Ala Ser Gly Ser Gly Ser
            835                 840                 845
Val Thr Ala Lys Thr Ser Ser Asn Val Asn Ile Thr Gly Asp Leu Ser
    850                 855                 860
Thr Ile Asn Gly Leu Asn Ile Ile Ser Glu Asn Gly Arg Asn Thr Val
865                 870                 875                 880
Arg Leu Arg Gly Lys Glu Ile Asp Val Lys Tyr Ile Gln Pro Gly Val
                885                 890                 895
Ala Ser Val Glu Glu Val Ile Glu Ala Lys Arg Val Leu Glu Lys Val
            900                 905                 910
Lys Asp Leu Ser Asp Glu Glu Arg Glu Thr Leu Ala Lys Leu Gly Val
            915                 920                 925
Ser Ala Val Arg Phe Val Glu Pro Asn Asn Ala Ile Thr Ile Asn Thr
    930                 935                 940
Gln Asn Glu Phe Thr Thr Arg Pro Ser Ser Gln Val Ile Ile Ser Glu
945                 950                 955                 960
Gly Lys Ala Cys Phe Ser Ser Gly Asn Gly Ala Ala Val Cys Thr Asn
                965                 970                 975
Val Ala Asp Asp Gly Gln Pro
            980

<210> SEQ ID NO 52
<211> LENGTH: 2934
<212> TYPE: DNA
<213> ORGANISM: Haemophilus influenzae

<400> SEQUENCE: 52
ccggataatg tcaatattgt taaaggaacc gaattacaga atgatttggt tgttaggggc      60
gatagtattg agaaaaagaa tgcccctacc aagactacaa ttcatgcagg ctctatagaa     120
caatctttga tgaagggtgg tgcagttaat atttctgcta caaataaagt aaatgttact     180
acagatatta atgtttataa tggagcatta acgttacact cagaacgaga tggagttgaa     240
attaacggta atattcctc agaaaaaaat ggtaatttaa ccattaaagc aggtagctgg     300
gttgatgttc ataaaaatat cacacttggc gagggttttt tgaatattac ttccggtgat     360
atcgccttcg aaaaggtaa taatctaacc attaccgctc aaggaaatat aacctctaat     420
aaagacggaa acaacttag acttaataat gtatctttaa atggaacagg tgcaggttta     480
aactttattg caaatcaaaa taattttaca cacaacatta gtggcgcgat taacatttcc     540
ggagtagtaa cgattaatca aactacgaaa aaaaacgcta aggcatggaa tacaagctat     600
gactcttact ggaacgtatc tactcttact ttaagcaatg atgcgaaatt tacctttatt     660
aaatatgtcg acagcaatca ttcgacaaac tccagtgatt cacgaagttt tgcgggagta     720
aagttccacg gcaagaataa tgaaatgaaa tttaatattg gtaataatgc caaggctgaa     780
tttaggttaa aaccaaatga gaagacaact cctaacagac cactaccaat tcagttttta     840
tctaatattt cggtcactgg cggaggttct gtgttttcg atatatacgc taacctttgg     900
ggtaaaggga ctgagctaaa gatggattca attaacgttt ctagcggctc taatcttacc     960
ttaaattccc atgttcgcaa gtataatgct tttgaaatca taaagactt aactataaac    1020
gcaactaatt caaatttcaa cctcagacag acgtcagata gtttcgtaa cgggtaccgc    1080
aataatgcca tcaattcaac ccacaacata tccatcttgg gcggcaacgt cactctcggc    1140
```

-continued

```
ggacaaaact caagcagcag cattatgggg aatatcatca tcaagcgagc agcaaatgtt    1200
acgctagaag ccgataatag tcacaattct gacaacgtaa aggatagaac tataaatctt    1260
ggcaacttga ccgttgaggg gaatttaagt ttaattggcg aaaatgcaaa tattaacggc    1320
aatctctcca ttgaaaaaga agccatcttt aaaggaaaaa ccaaggacag cctaaacatc    1380
accggcaact ttaccaataa tggcactgcc gaaattaata taagccaagg agtggtaagt    1440
cttggcgata ttaccaatga tggcaaatta acatcacca ctcacgccaa gagcggtcaa    1500
aaaagcatta tccgcggaga tataattaac aaacaaggga attaaatat tacgacaat    1560
aatagtaatg ctgaaattga aattggcggc aatatctcgc aaaaagaagg taatctcacc    1620
atttcttctg ataaagtcaa tattaccaaa cagataacaa tcaaagcagg cgttgatggg    1680
gagagttcta gttcaagcac agcaagtgat gccaatctaa ccattaaaac caaagagtta    1740
acattaacag acaatctaaa catttcaggt tttaataaag cagaaattac agctaaagat    1800
aacagtgatt taattattgg caaggctagc agtgacaaca gtaatgctaa acaagtaacc    1860
tttgacaagg ttaaagattc aaaaatctca gctggcaatc acaatgtaac actaaatagc    1920
aaagtggaaa cgtctaatag cgatggtagc accggaaacg gtagcgatga caacaatatc    1980
ggcttaacta tttccgcaaa agatgtaacg gtaaatagta atatcacctc tcacaaaaca    2040
gtaaatatct ctgcatcaga aggaggtatc actactaaag caggcacaac cattaatgcg    2100
accacaggta gcgtggaagt aactgctaaa acaggcgata ttagcggtac gatttccggt    2160
aagacagtaa gtgttacagc aagcactggc gatttaactg ttaggaaagc tgcaaccatt    2220
agtgcgacag aaggagctgc aaccttaacc gcaacaggga ataccttgac tactgaagcc    2280
ggttctagca tcacttcaac taagggtcag gtagaccttt cagctcagga tggtagcatt    2340
gcaggacaaa ttagtgcagc taatgtgaca ttaaatacca caggcacctt aactactgta    2400
gaaggttcaa acattaaggc aaccagtggc accttagcta ttaacgcaaa agacgctaag    2460
ctagatggta cggcatcagg taaccgtaca gaagtaaatg caactaacgc aagtggttct    2520
ggtagcgtga ctgcgaaaac ctcaagtaat gtgaatatca ccggggattt aagcacaata    2580
aatgggttaa atatcatttc ggaaatggt agaaacactg tgcgcttaag aggcaaggaa    2640
attgatgtga aatatatcca accaggtgta gcaagcgtag aagaggtaat tgaagcgaaa    2700
cgcgtccttg agaaagtaaa agatttatct gacgaagaaa gagaaacact agccaaactt    2760
ggtgtaagtg ctgtacgttt cgttgagcca aataatgcca ttacgattaa tacacaaaat    2820
gaatttacaa ccagaccgtc aagtcaagtg ataatttctg aaggtaaggc gtgtttctca    2880
agtggtaatg gcgcagcagt atgtaccaat gttgctgacg atggacagcc gtag          2934
```

<210> SEQ ID NO 53
<211> LENGTH: 977
<212> TYPE: PRT
<213> ORGANISM: Haemophilus influenzae

<400> SEQUENCE: 53

```
Pro Asp Asn Val Asn Ile Val Lys Gly Thr Glu Leu Gln Asn Asp Leu
  1               5                  10                  15

Val Val Arg Gly Asp Ser Ile Glu Lys Lys Asn Ala Pro Thr Lys Thr
             20                  25                  30

Thr Ile His Ala Gly Ser Ile Glu Gln Ser Leu Met Lys Gly Gly Ala
         35                  40                  45

Val Asn Ile Ser Ala Thr Asn Lys Val Asn Val Thr Thr Asp Ile Asn
     50                  55                  60
```

```
Val Tyr Asn Gly Ala Leu Thr Leu His Ser Glu Arg Asp Gly Val Glu
 65                  70                  75                  80

Ile Asn Gly Asn Ile Thr Ser Glu Lys Asn Gly Asn Leu Thr Ile Lys
                 85                  90                  95

Ala Gly Ser Trp Val Asp Val His Lys Asn Ile Thr Leu Gly Glu Gly
            100                 105                 110

Phe Leu Asn Ile Thr Ser Gly Asp Ile Ala Phe Glu Lys Gly Asn Asn
            115                 120                 125

Leu Thr Ile Thr Ala Gln Gly Asn Ile Thr Ser Asn Lys Asp Gly Lys
    130                 135                 140

Gln Leu Arg Leu Asn Asn Val Ser Leu Asn Gly Thr Gly Ala Gly Leu
145                 150                 155                 160

Asn Phe Ile Ala Asn Gln Asn Asn Phe Thr His Asn Ile Ser Gly Ala
                165                 170                 175

Ile Asn Ile Ser Gly Val Val Thr Ile Asn Gln Thr Thr Lys Lys Asn
            180                 185                 190

Ala Lys Ala Trp Asn Thr Ser Tyr Asp Ser Tyr Trp Asn Val Ser Thr
            195                 200                 205

Leu Thr Leu Ser Asn Asp Ala Lys Phe Thr Phe Ile Lys Tyr Val Asp
    210                 215                 220

Ser Asn His Ser Thr Asn Ser Ser Asp Ser Arg Ser Phe Ala Gly Val
225                 230                 235                 240

Lys Phe His Gly Lys Asn Asn Glu Met Lys Phe Asn Ile Gly Asn Asn
                245                 250                 255

Ala Lys Ala Glu Phe Arg Leu Lys Pro Asn Glu Lys Thr Thr Pro Asn
            260                 265                 270

Arg Pro Leu Pro Ile Gln Phe Leu Ser Asn Ile Ser Val Thr Gly Gly
    275                 280                 285

Gly Ser Val Phe Phe Asp Ile Tyr Ala Asn Leu Trp Gly Lys Gly Thr
    290                 295                 300

Glu Leu Lys Met Asp Ser Ile Asn Val Ser Ser Gly Ser Asn Leu Thr
305                 310                 315                 320

Leu Asn Ser His Val Arg Lys Tyr Asn Ala Phe Glu Ile Asn Lys Asp
                325                 330                 335

Leu Thr Ile Asn Ala Thr Asn Ser Asn Phe Asn Leu Arg Gln Thr Ser
            340                 345                 350

Asp Ser Phe Arg Asn Gly Tyr Arg Asn Asn Ala Ile Asn Ser Thr His
            355                 360                 365

Asn Ile Ser Ile Leu Gly Gly Asn Val Thr Leu Gly Gly Gln Asn Ser
    370                 375                 380

Ser Ser Ser Ile Met Gly Asn Ile Ile Lys Arg Ala Ala Asn Val
385                 390                 395                 400

Thr Leu Glu Ala Asp Asn Ser His Asn Ser Asp Asn Val Lys Asp Arg
            405                 410                 415

Thr Ile Asn Leu Gly Asn Leu Thr Val Glu Gly Asn Leu Ser Leu Ile
            420                 425                 430

Gly Glu Asn Ala Asn Ile Asn Gly Asn Leu Ser Ile Glu Lys Glu Ala
            435                 440                 445

Ile Phe Lys Gly Lys Thr Lys Asp Ser Leu Asn Ile Thr Gly Asn Phe
    450                 455                 460

Thr Asn Asn Gly Thr Ala Glu Ile Asn Ile Ser Gln Gly Val Val Ser
465                 470                 475                 480
```

-continued

```
Leu Gly Asp Ile Thr Asn Asp Gly Lys Leu Asn Ile Thr Thr His Ala
            485                 490                 495

Lys Ser Gly Gln Lys Ser Ile Ile Arg Gly Asp Ile Ile Asn Lys Gln
        500                 505                 510

Gly Asn Leu Asn Ile Thr Asp Asn Ser Asn Ala Glu Ile Glu Ile
        515                 520                 525

Gly Gly Asn Ile Ser Gln Lys Glu Gly Asn Leu Thr Ile Ser Ser Asp
    530                 535                 540

Lys Val Asn Ile Thr Lys Gln Ile Thr Ile Lys Ala Gly Val Asp Gly
545                 550                 555                 560

Glu Ser Ser Ser Ser Thr Ala Ser Asp Ala Asn Leu Thr Ile Lys
            565                 570                 575

Thr Lys Glu Leu Thr Leu Thr Asp Asn Leu Asn Ile Ser Gly Phe Asn
            580                 585                 590

Lys Ala Glu Ile Thr Ala Lys Asp Asn Ser Asp Leu Ile Ile Gly Lys
        595                 600                 605

Ala Ser Ser Asp Asn Ser Asn Ala Lys Gln Val Thr Phe Asp Lys Val
    610                 615                 620

Lys Asp Ser Lys Ile Ser Ala Gly Asn His Asn Val Thr Leu Asn Ser
625                 630                 635                 640

Lys Val Glu Thr Ser Asn Ser Asp Gly Ser Thr Gly Asn Gly Ser Asp
            645                 650                 655

Asp Asn Asn Ile Gly Leu Thr Ile Ser Ala Lys Asp Val Thr Val Asn
            660                 665                 670

Ser Asn Ile Thr Ser His Lys Thr Val Asn Ile Ser Ala Ser Glu Gly
        675                 680                 685

Gly Ile Thr Thr Lys Ala Gly Thr Thr Ile Asn Ala Thr Thr Gly Ser
    690                 695                 700

Val Glu Val Thr Ala Lys Thr Gly Asp Ile Ser Gly Thr Ile Ser Gly
705                 710                 715                 720

Lys Thr Val Ser Val Thr Ala Ser Thr Gly Asp Leu Thr Val Arg Lys
            725                 730                 735

Ala Ala Thr Ile Ser Ala Thr Glu Gly Ala Ala Thr Leu Thr Ala Thr
            740                 745                 750

Gly Asn Thr Leu Thr Thr Glu Ala Gly Ser Ser Ile Thr Ser Thr Lys
        755                 760                 765

Gly Gln Val Asp Leu Ser Ala Gln Asp Gly Ser Ile Ala Gly Gln Ile
    770                 775                 780

Ser Ala Ala Asn Val Thr Leu Asn Thr Thr Gly Thr Leu Thr Thr Val
785                 790                 795                 800

Glu Gly Ser Asn Ile Lys Ala Thr Ser Gly Thr Leu Ala Ile Asn Ala
            805                 810                 815

Lys Asp Ala Lys Leu Asp Gly Thr Ala Ser Gly Asn Arg Thr Glu Val
        820                 825                 830

Asn Ala Thr Asn Ala Ser Gly Ser Gly Ser Val Thr Ala Lys Thr Ser
    835                 840                 845

Ser Asn Val Asn Ile Thr Gly Asp Leu Ser Thr Ile Asn Gly Leu Asn
    850                 855                 860

Ile Ile Ser Glu Asn Gly Arg Asn Thr Val Arg Leu Arg Gly Lys Glu
865                 870                 875                 880

Ile Asp Val Lys Tyr Ile Gln Pro Gly Val Ala Ser Val Glu Glu Val
            885                 890                 895

Ile Glu Ala Lys Arg Val Leu Glu Lys Val Lys Asp Leu Ser Asp Glu
```

```
                    900               905               910
Glu Arg Glu Thr Leu Ala Lys Leu Gly Val Ser Ala Val Arg Phe Val
            915               920               925
Glu Pro Asn Asn Ala Ile Thr Ile Asn Thr Gln Asn Glu Phe Thr Thr
    930               935               940
Arg Pro Ser Ser Gln Val Ile Ile Ser Glu Gly Lys Ala Cys Phe Ser
945               950               955               960
Ser Gly Asn Gly Ala Ala Val Cys Thr Asn Val Ala Asp Asp Gly Gln
                965               970               975
Pro

<210> SEQ ID NO 54
<211> LENGTH: 3033
<212> TYPE: DNA
<213> ORGANISM: Haemophilus influenzae

<400> SEQUENCE: 54
```

| | | | | | |
|---|---|---|---|---|---|
| aaagagtggt | tgttagaccc | ggatgatgta | actattgccg | caggcgcgcc | aggacgtaac | 60 |
| gatggttcag | tagacgactt | ttttcccact | ggaagagggg | atgatgctag | taatgcaaaa | 120 |
| acaaaccatc | cagacaagcc | gacattaaca | aacacaactg | ttgagaacgc | attaaaaaac | 180 |
| aacacctttg | ttaacataac | cgccaaaaat | aaaatcacag | ttaatagcga | catcaatatc | 240 |
| aaaggtggcg | cccacctaac | cctctatagc | aaaaacaata | aaaaaagtag | cgttaagatt | 300 |
| aatggcaata | ttacttctac | cactaacgga | aacttaacta | tttactccag | cggctgggtt | 360 |
| gatatccata | aaaacattac | gcttaacaca | ggttacctga | atattaccgc | tgggggttct | 420 |
| gtagccttcg | agaaagccgg | aaatgagaaa | gggcgccaag | tatcagaatc | tgtaatcaaa | 480 |
| gcccagggag | ttatcacctc | aggtgtaggg | aaggcttta  | ggtttaataa | cgtctcccta | 540 |
| aatggcgttg | gcgcaggact | gcgcttcgtt | ggtcagaaaa | atatcagtag | caactcttgg | 600 |
| agagaaaaca | ccatcaaaaa | cagattcgat | gggaatttaa | atatctcagg | aaaggtaaat | 660 |
| gtttcaatgg | atgtatccgg | gacaaagtgg | catacaagaa | ttaacgggcg | cacctactgg | 720 |
| aatgtaacca | ctctaaacgt | tgcctcaggt | agtagtttca | atctcagtat | cgacgccagt | 780 |
| ggaatttctt | caggtaacca | ggacgacata | acaaataggg | gtttaaatgg | cataacattt | 840 |
| aatggagaaa | acactttaa  | tatcgcacag | ggctcaacag | ctaactttca | tatcaaaacg | 900 |
| tcagtaatga | cccctaaacc | caactcgaac | tacgcattat | ttaatggaaa | tatttcagtt | 960 |
| ttaggaggag | gaactgtcaa | ctttgaactt | aatgcctcat | ctagcaccca | cacaacttct | 1020 |
| ggcgcaatta | taaattctca | aaattttaat | gtctcaggtg | ggtcaaaatt | aaatctcaag | 1080 |
| gcttcaggct | caacaaatac | cgcttttta  | ataaaaaata | atttaacttt | aaacgctact | 1140 |
| ggaggtaata | tagaaattaa | acaggttgag | ggtaccgatt | cgcgcattca | aaaaggtgtt | 1200 |
| gtagccgaac | aaaacataat | ttttgaaggg | ggtaacatca | cccttggctc | ccaaaaagcc | 1260 |
| ccaacagaaa | taaaggcga  | tgttaccgtc | aaacaaggaa | ccaacgccac | tctcagaagc | 1320 |
| gcgaattttg | acaaccacaa | aggtgcctta | attgtgaatg | gaaacgttac | cgccaatggc | 1380 |
| aaccttactg | cggacggcga | cactattaaa | ataaaaggca | atcttgatgt | tgcacaaggc | 1440 |
| gctaaattta | acggcagcac | aaaaaacaac | ctaaacatta | ctggcacctt | taccaacaac | 1500 |
| ggcacttcta | taatcgatat | aacacaaggg | gtggtaaacc | ttggtaatgt | taccaatgac | 1560 |
| ggcaaattaa | acatcaccac | tcacgccaag | agcggtcaaa | aaagcattat | ccgcggagat | 1620 |
| ataattaaca | aacaagggaa | tttaaatatt | acggacaata | atagtaatgc | tgaaattgaa | 1680 |

```
attggcggca atatctcgca aaagaaggt aatctcacca tttcttctga taaagtcaat    1740
attaccaaac agataacaat caaagcaggc gttgatgggg agagttctag ttcaagcaca    1800
gcaagtgatg ccaatctaac cattaaaacc aaagagttaa cattcacaga caatctaaac    1860
atttcaggtt ttaataaagc agaaattaca gctaaagata acagtgattt aattattggc    1920
aaggctagca gtgacaacag taatgctaaa caagtaacct tgacaaggt taaagattca    1980 aaaatctcag ctggcaatca caatgtaaca ctaaatagca agtggaaac gtctaatagc    2040 gatggtagca ccggaaacgg tagcgatgac aacaatatcg gcttaactat ttccgcaaaa    2100
gatgtaacgg taaatagtaa tatcacctct cacaaaacag taaatatctc tgcatcagaa    2160
ggaggtatca ctactaaagc aggcacaacc attaatgcga ccacaggtag cgtggaagta    2220
actgctaaaa caggcgatat tagcggtacg atttccggta agacagtaag tgttacagca    2280
agcactggcg atttaactgt taggaaagct gcaaccatta gtgtgacaga aggagctgca    2340
accttaaccg caacagggaa taccttgact actgaagccg gttctagcat cacttcaact    2400
aagggtcagg tagcccttc agctcaggat ggtagcattg caggacaaat tagtgcagct    2460
aatgtgacat taaataccac aggcacctta actactgtag aaggttcaaa cattaaggca    2520
accagtggca ccttagctat taacgcaaaa gacgctaagc tagatggtac ggcatcaggt    2580
aaccgtacag aagtaaatgc aactaacgca agtggttctg gtagcgtgac tgcgaaaacc    2640
tcaagtaatg tgaatatcac cggggattta agcacaataa atgggttaaa tatcatttcg    2700
gaaaatggta gaaacactgt gcgcttaaga ggcaaggaaa ttgatgtgaa atatatccaa    2760
ccaggtgtag caagcgtaga agaggtaatt gaagcgaaac gcgtccttga gaaagtaaaa    2820
gatttatctg acgaagaaag agaaacacta gccaaacttg gtgtaagtgc tgtacgtttc    2880
gttgagccaa ataatgccat tacgattaat acacaaaatg aatttacaac agaccgtca     2940 agtcaagtga taatttctga aggtaaggcg tgtttctcaa gtggtaatgg cgcagcagta    3000
tgtaccaatg ttgctgacga tggacagccg tag                                  3033
```

<210> SEQ ID NO 55
<211> LENGTH: 1010
<212> TYPE: PRT
<213> ORGANISM: Haemophilus influenzae

<400> SEQUENCE: 55

```
Lys Glu Trp Leu Leu Asp Pro Asp Val Thr Ile Ala Ala Gly Ala
 1               5                  10                  15

Pro Gly Arg Asn Asp Gly Ser Val Asp Asp Phe Phe Pro Thr Gly Arg
                20                  25                  30

Gly Asp Asp Ala Ser Asn Ala Lys Thr Asn His Pro Asp Lys Pro Thr
            35                  40                  45

Leu Thr Asn Thr Thr Val Glu Asn Ala Leu Lys Asn Asn Thr Phe Val
        50                  55                  60

Asn Ile Thr Ala Lys Asn Lys Ile Thr Val Asn Ser Asp Ile Asn Ile
    65                  70                  75                  80

Lys Gly Gly Ala His Leu Thr Leu Tyr Ser Lys Asn Lys Lys Ser
                85                  90                  95

Ser Val Lys Ile Asn Gly Asn Ile Thr Ser Thr Thr Asn Gly Asn Leu
               100                 105                 110

Thr Ile Tyr Ser Ser Gly Trp Val Asp Ile His Lys Asn Ile Thr Leu
           115                 120                 125
```

```
Asn Thr Gly Tyr Leu Asn Ile Thr Ala Gly Gly Ser Val Ala Phe Glu
    130                 135                 140

Lys Ala Gly Asn Glu Lys Gly Arg Gln Val Ser Glu Ser Val Ile Lys
145                 150                 155                 160

Ala Gln Gly Val Ile Thr Ser Gly Val Gly Glu Gly Phe Arg Phe Asn
                    165                 170                 175

Asn Val Ser Leu Asn Gly Val Gly Ala Gly Leu Arg Phe Val Gly Gln
                180                 185                 190

Lys Asn Ile Ser Ser Asn Ser Trp Arg Glu Asn Thr Ile Lys Asn Arg
        195                 200                 205

Phe Asp Gly Asn Leu Asn Ile Ser Gly Lys Val Asn Val Ser Met Asp
    210                 215                 220

Val Ser Gly Thr Lys Trp His Thr Arg Ile Asn Gly Arg Thr Tyr Trp
225                 230                 235                 240

Asn Val Thr Thr Leu Asn Val Ala Ser Gly Ser Ser Phe Asn Leu Ser
                    245                 250                 255

Ile Asp Ala Ser Gly Ile Ser Ser Gly Asn Gln Asp Asp Ile Thr Asn
                260                 265                 270

Arg Gly Leu Asn Gly Ile Thr Phe Asn Gly Glu Asn Thr Phe Asn Ile
        275                 280                 285

Ala Gln Gly Ser Thr Ala Asn Phe His Ile Lys Thr Ser Val Met Thr
    290                 295                 300

Pro Lys Pro Asn Ser Asn Tyr Ala Leu Phe Asn Gly Asn Ile Ser Val
305                 310                 315                 320

Leu Gly Gly Gly Thr Val Asn Phe Glu Leu Asn Ala Ser Ser Ser Thr
                    325                 330                 335

His Thr Thr Ser Gly Ala Ile Ile Asn Ser Gln Asn Phe Asn Val Ser
                340                 345                 350

Gly Gly Ser Lys Leu Asn Leu Lys Ala Ser Gly Ser Thr Asn Thr Ala
        355                 360                 365

Phe Leu Ile Lys Asn Asn Leu Thr Leu Asn Ala Thr Gly Gly Asn Ile
    370                 375                 380

Glu Ile Lys Gln Val Glu Gly Thr Asp Ser Arg Ile Gln Lys Gly Val
385                 390                 395                 400

Val Ala Glu Gln Asn Ile Ile Phe Glu Gly Gly Asn Ile Thr Leu Gly
                    405                 410                 415

Ser Gln Lys Ala Pro Thr Glu Ile Lys Gly Asp Val Thr Val Lys Gln
                420                 425                 430

Gly Thr Asn Ala Thr Leu Arg Ser Ala Asn Phe Asp Asn His Lys Gly
        435                 440                 445

Ala Leu Ile Val Asn Gly Asn Val Thr Ala Asn Gly Asn Leu Thr Ala
    450                 455                 460

Asp Gly Asp Thr Ile Lys Ile Lys Gly Asn Leu Asp Val Ala Gln Gly
465                 470                 475                 480

Ala Lys Phe Asn Gly Ser Thr Lys Asn Leu Asn Ile Thr Gly Thr
                    485                 490                 495

Phe Thr Asn Asn Gly Thr Ser Ile Ile Asp Ile Thr Gln Gly Val Val
                500                 505                 510

Asn Leu Gly Asn Val Thr Asn Asp Gly Lys Leu Asn Ile Thr Thr His
        515                 520                 525

Ala Lys Ser Gly Gln Lys Ser Ile Ile Arg Gly Asp Ile Ile Asn Lys
    530                 535                 540

Gln Gly Asn Leu Asn Ile Thr Asp Asn Asn Ser Asn Ala Glu Ile Glu
```

```
545                 550                 555                 560
Ile Gly Gly Asn Ile Ser Gln Lys Glu Gly Asn Leu Thr Ile Ser Ser
                565                 570                 575
Asp Lys Val Asn Ile Thr Lys Gln Ile Thr Ile Lys Ala Gly Val Asp
                580                 585                 590
Gly Glu Ser Ser Ser Ser Thr Ala Ser Asp Ala Asn Leu Thr Ile
                595                 600             605
Lys Thr Lys Glu Leu Thr Phe Thr Asp Asn Leu Asn Ile Ser Gly Phe
            610                 615                 620
Asn Lys Ala Glu Ile Thr Ala Lys Asp Asn Ser Asp Leu Ile Ile Gly
625                 630                 635                 640
Lys Ala Ser Ser Asp Asn Ser Asn Ala Lys Gln Val Thr Phe Asp Lys
                645                 650                 655
Val Lys Asp Ser Lys Ile Ser Ala Gly Asn His Asn Val Thr Leu Asn
                660                 665                 670
Ser Lys Val Glu Thr Ser Asn Ser Asp Gly Ser Thr Gly Asn Gly Ser
            675                 680                 685
Asp Asp Asn Asn Ile Gly Leu Thr Ile Ser Ala Lys Asp Val Thr Val
            690                 695                 700
Asn Ser Asn Ile Thr Ser His Lys Thr Val Asn Ile Ser Ala Ser Glu
705                 710                 715                 720
Gly Gly Ile Thr Thr Lys Ala Gly Thr Thr Ile Asn Ala Thr Thr Gly
                725                 730                 735
Ser Val Glu Val Thr Ala Lys Thr Gly Asp Ile Ser Gly Thr Ile Ser
                740                 745                 750
Gly Lys Thr Val Ser Val Thr Ala Ser Thr Gly Asp Leu Thr Val Arg
            755                 760                 765
Lys Ala Ala Thr Ile Ser Val Thr Glu Gly Ala Ala Thr Leu Thr Ala
            770                 775                 780
Thr Gly Asn Thr Leu Thr Thr Glu Ala Gly Ser Ser Ile Thr Ser Thr
785                 790                 795                 800
Lys Gly Gln Val Asp Leu Ser Ala Gln Asp Gly Ser Ile Ala Gly Gln
                805                 810                 815
Ile Ser Ala Ala Asn Val Thr Leu Asn Thr Thr Gly Thr Leu Thr Thr
                820                 825                 830
Val Glu Gly Ser Asn Ile Lys Ala Thr Ser Gly Thr Leu Ala Ile Asn
                835                 840                 845
Ala Lys Asp Ala Lys Leu Asp Gly Thr Ala Ser Gly Asn Arg Thr Glu
            850                 855                 860
Val Asn Ala Thr Asn Ala Ser Gly Ser Gly Ser Val Thr Ala Lys Thr
865                 870                 875                 880
Ser Ser Asn Val Asn Ile Thr Gly Asp Leu Ser Thr Ile Asn Gly Leu
                885                 890                 895
Asn Ile Ile Ser Glu Asn Gly Arg Asn Thr Val Arg Leu Arg Gly Lys
                900                 905                 910
Glu Ile Asp Val Lys Tyr Ile Gln Pro Gly Val Ala Ser Val Glu Glu
            915                 920                 925
Val Ile Glu Ala Lys Arg Val Leu Glu Lys Val Lys Asp Leu Ser Asp
            930                 935                 940
Glu Glu Arg Glu Thr Leu Ala Lys Leu Gly Val Ser Ala Val Arg Phe
945                 950                 955                 960
Val Glu Pro Asn Asn Ala Ile Thr Ile Asn Thr Gln Asn Glu Phe Thr
                965                 970                 975
```

Thr Arg Pro Ser Ser Gln Val Ile Ile Ser Glu Gly Lys Ala Cys Phe
         980                 985               990

Ser Ser Gly Asn Gly Ala Ala Val Cys Thr Asn Val Ala Asp Asp Gly
         995              1000             1005

Gln Pro
    1010

<210> SEQ ID NO 56
<211> LENGTH: 3015
<212> TYPE: DNA
<213> ORGANISM: Haemophilus influenzae

<400> SEQUENCE: 56

```
ccggatgatg taactattgc cgcaggcgcg ccaggacgta acgatggttc agtagacgac     60
ttttttccca ctggaagagg ggatgatgct agtaatgcaa aaacaaacca tccagacaag    120
ccgacattaa caaacacaac tgttgagaac gcattaaaaa acaacacctt tgttaacata    180
accgccaaaa ataaaatcac agttaatagc gacatcaata tcaaaggtgg cgcccaccta    240
accctctata gcaaaaacaa taaaaaaagt agcgttaaga ttaatggcaa tattacttct    300
accactaacg gaaacttaac tatttactcc agcggctggg ttgatatcca taaaaacatt    360
acgcttaaca caggttacct gaatattacc gctgggggtt ctgtagcctt cgagaaagcc    420
ggaaatgaga aagggcgcca agtatcagaa tctgtaatca agcccaggg  agttatcacc    480
tcaggtgtag gggaaggctt taggtttaat aacgtctccc taaatggcgt tggcgcagga    540
ctgcgcttcg ttggtcagaa aaatatcagt agcaactctt ggagagaaaa caccatcaaa    600
aacagattcg atgggaattt aaatatctca ggaaaggtaa atgtttcaat ggatgtatcc    660
gggacaaagt ggcatacaag aattaacggg cgcacctact ggaatgtaac cactctaaac    720
gttgcctcag gtagtagttt caatctcagt atcgacgcca gtggaatttc ttcaggtaac    780
caggacgaca taacaaatag gggtttaaat ggcataacat ttaatggaga aaacactttt    840
aatatcgcac agggctcaac agctaacttt catatcaaaa cgtcagtaat gaccctaaa     900
cccaactcga actacgcatt atttaatgga atatttcag ttttaggagg aggaactgtc     960
aactttgaac ttaatgcctc atctagcacc cacacaactc tggcgcaat tataaattct    1020
caaaatttta atgtctcagg tgggtcaaaa ttaaatctca aggcttcagg ctcaacaaat    1080
accgctttt  taataaaaaa taatttaact ttaaacgcta ctggaggtaa tatagaaatt    1140
aaacaggttg agggtaccga ttcgcgcatt caaaaaggtg ttgtagccga caaaacata     1200
attttgaag ggggtaacat cacccttggc tcccaaaaag ccccaacaga ataaaaggc     1260
gatgttaccg tcaaacaagg aaccaacgcc actctcagaa gcgcgaattt tgacaaccac    1320
aaaggtgcct taattgtgaa tggaaacgtt accgccaatg caaccttac tgcggacggc    1380
gacactatta aataaaagg caatcttgat gttgcacaag gcgctaaatt taacggcagc    1440
acaaaaaaca acctaaacat tactggcacc tttaccaaca acggcacttc tataatcgat    1500
ataacacaag gggtggtaaa ccttggtaat gttaccaatg acggcaaatt aaacatcacc    1560
actcacgcca agagcggtca aaaagcatt atccgcggag atataattaa caaacaaggg    1620
aatttaaata ttacggacaa taatagtaat gctgaaattg aaattggcgg caatatctcg    1680
caaaaagaag gtaatctcac catttcttct gataaagtca atattaccaa acagataaca    1740
atcaaagcag gcgttgatgg ggagagttct agttcaagca cagcaagtga tgccaatcta    1800
accattaaaa ccaaagagtt aacattcaca gacaatctaa acatttcagg ttttaataaa    1860
```

-continued

```
gcagaaatta cagctaaaga taacagtgat ttaattattg gcaaggctag cagtgacaac    1920
agtaatgcta aacaagtaac ctttgacaag gttaaagatt caaaaatctc agctggcaat    1980
cacaatgtaa cactaaatag caaagtggaa acgtctaata gcgatggtag caccggaaac    2040
ggtagcgatg acaacaatat cggcttaact atttccgcaa aagatgtaac ggtaaatagt    2100
aatatcacct ctcacaaaac agtaaatatc tctgcatcag aaggaggtat cactactaaa    2160
gcaggcacaa ccattaatgc gaccacaggt agcgtggaag taactgctaa acaggcgat    2220 attagcggta cgatttccgg taagacagta agtgttacag caagcactgg cgatttaact    2280
gttaggaaag ctgcaaccat tagtgtgaca gaaggagctg caaccttaac cgcaacaggg    2340
aataccttga ctactgaagc cggttctagc atcacttcaa ctaagggtca ggtagacctt    2400
tcagctcagg atggtagcat tgcaggacaa attagtgcag ctaatgtgac attaaatacc    2460
acaggcacct taactactgt agaaggttca aacattaagg caaccagtgg cacccttagc    2520
attaacgcaa aagacgctaa gctagatggt acggcatcag gtaaccgtac agaagtaaat    2580
gcaactaacg caagtggttc tggtagcgtg actgcgaaaa cctcaagtaa tgtgaatatc    2640 accgggatt taagcacaat aaatgggtta aatatcattt cggaaaatgg tagaaacact    2700
gtgcgcttaa gaggcaagga aattgatgtg aaatatatcc aaccaggtgt agcaagcgta    2760
gaagaggtaa ttgaagcgaa acgcgtcctt gagaaagtaa aagatttatc tgacgaagaa    2820
agagaaacac tagccaaact tggtgtaagt gctgtacgtt tcgttgagcc aaataatgcc    2880
attacgatta atacacaaaa tgaatttaca accagaccgt caagtcaagt gataatttct    2940
gaaggtaagg cgtgtttctc aagtggtaat ggcgcagcag tatgtaccaa tgttgctgac    3000
gatggacagc cgtag                                                    3015
```

<210> SEQ ID NO 57
<211> LENGTH: 1004
<212> TYPE: PRT
<213> ORGANISM: Haemophilus influenzae

<400> SEQUENCE: 57

```
Pro Asp Asp Val Thr Ile Ala Ala Gly Ala Pro Gly Arg Asn Asp Gly
  1               5                  10                  15

Ser Val Asp Asp Phe Phe Pro Thr Gly Arg Gly Asp Asp Ala Ser Asn
                 20                  25                  30

Ala Lys Thr Asn His Pro Asp Lys Pro Thr Leu Thr Asn Thr Thr Val
             35                  40                  45

Glu Asn Ala Leu Lys Asn Asn Thr Phe Val Asn Ile Thr Ala Lys Asn
         50                  55                  60

Lys Ile Thr Val Asn Ser Asp Ile Asn Ile Lys Gly Gly Ala His Leu
     65                  70                  75                  80

Thr Leu Tyr Ser Lys Asn Asn Lys Lys Ser Val Lys Ile Asn Gly
                 85                  90                  95

Asn Ile Thr Ser Thr Thr Asn Gly Asn Leu Thr Ile Tyr Ser Ser Gly
            100                 105                 110

Trp Val Asp Ile His Lys Asn Ile Thr Leu Asn Thr Gly Tyr Leu Asn
            115                 120                 125

Ile Thr Ala Gly Gly Ser Val Ala Phe Glu Lys Ala Gly Asn Glu Lys
        130                 135                 140

Gly Arg Gln Val Ser Glu Ser Val Ile Lys Ala Gln Gly Val Ile Thr
    145                 150                 155                 160
```

-continued

```
Ser Gly Val Gly Glu Gly Phe Arg Phe Asn Asn Val Ser Leu Asn Gly
                165                 170                 175
Val Gly Ala Gly Leu Arg Phe Val Gly Gln Lys Asn Ile Ser Ser Asn
            180                 185                 190
Ser Trp Arg Glu Asn Thr Ile Lys Asn Arg Phe Asp Gly Asn Leu Asn
        195                 200                 205
Ile Ser Gly Lys Val Asn Val Ser Met Asp Val Ser Gly Thr Lys Trp
210                 215                 220
His Thr Arg Ile Asn Gly Arg Thr Tyr Trp Asn Val Thr Thr Leu Asn
225                 230                 235                 240
Val Ala Ser Gly Ser Ser Phe Asn Leu Ser Ile Asp Ala Ser Gly Ile
                245                 250                 255
Ser Ser Gly Asn Gln Asp Asp Ile Thr Asn Arg Gly Leu Asn Gly Ile
            260                 265                 270
Thr Phe Asn Gly Glu Asn Thr Phe Asn Ile Ala Gln Gly Ser Thr Ala
        275                 280                 285
Asn Phe His Ile Lys Thr Ser Val Met Thr Pro Lys Pro Asn Ser Asn
290                 295                 300
Tyr Ala Leu Phe Asn Gly Asn Ile Ser Val Leu Gly Gly Thr Val
305                 310                 315                 320
Asn Phe Glu Leu Asn Ala Ser Ser Ser Thr His Thr Thr Ser Gly Ala
                325                 330                 335
Ile Ile Asn Ser Gln Asn Phe Asn Val Ser Gly Gly Ser Lys Leu Asn
            340                 345                 350
Leu Lys Ala Ser Gly Ser Thr Asn Thr Ala Phe Leu Ile Lys Asn Asn
        355                 360                 365
Leu Thr Leu Asn Ala Thr Gly Gly Asn Ile Glu Ile Lys Gln Val Glu
370                 375                 380
Gly Thr Asp Ser Arg Ile Gln Lys Gly Val Val Ala Glu Gln Asn Ile
385                 390                 395                 400
Ile Phe Glu Gly Gly Asn Ile Thr Leu Gly Ser Gln Lys Ala Pro Thr
                405                 410                 415
Glu Ile Lys Gly Asp Val Thr Val Lys Gln Gly Thr Asn Ala Thr Leu
            420                 425                 430
Arg Ser Ala Asn Phe Asp Asn His Lys Gly Ala Leu Ile Val Asn Gly
        435                 440                 445
Asn Val Thr Ala Asn Gly Asn Leu Thr Ala Asp Gly Asp Thr Ile Lys
450                 455                 460
Ile Lys Gly Asn Leu Asp Val Ala Gln Gly Ala Lys Phe Asn Gly Ser
465                 470                 475                 480
Thr Lys Asn Asn Leu Asn Ile Thr Gly Thr Phe Thr Asn Asn Gly Thr
                485                 490                 495
Ser Ile Ile Asp Ile Thr Gln Gly Val Val Asn Leu Gly Asn Val Thr
            500                 505                 510
Asn Asp Gly Lys Leu Asn Ile Thr Thr His Ala Lys Ser Gly Gln Lys
        515                 520                 525
Ser Ile Ile Arg Gly Asp Ile Asn Lys Gln Gly Asn Leu Asn Ile
530                 535                 540
Thr Asp Asn Asn Ser Asn Ala Glu Ile Glu Ile Gly Gly Asn Ile Ser
545                 550                 555                 560
Gln Lys Glu Gly Asn Leu Thr Ile Ser Ser Asp Lys Val Asn Ile Thr
                565                 570                 575
Lys Gln Ile Thr Ile Lys Ala Gly Val Asp Gly Glu Ser Ser Ser Ser
```

-continued

```
              580                 585                 590
Ser Thr Ala Ser Asp Ala Asn Leu Thr Ile Lys Thr Lys Glu Leu Thr
            595                 600                 605

Phe Thr Asp Asn Leu Asn Ile Ser Gly Phe Asn Lys Ala Glu Ile Thr
610                 615                 620

Ala Lys Asp Asn Ser Asp Leu Ile Ile Gly Lys Ala Ser Ser Asp Asn
625                 630                 635                 640

Ser Asn Ala Lys Gln Val Thr Phe Asp Lys Val Lys Asp Ser Lys Ile
                645                 650                 655

Ser Ala Gly Asn His Asn Val Thr Leu Asn Ser Lys Val Glu Thr Ser
                660                 665                 670

Asn Ser Asp Gly Ser Thr Gly Asn Gly Ser Asp Asp Asn Asn Ile Gly
                675                 680                 685

Leu Thr Ile Ser Ala Lys Asp Val Thr Val Asn Ser Asn Ile Thr Ser
690                 695                 700

His Lys Thr Val Asn Ile Ser Ala Ser Glu Gly Gly Ile Thr Thr Lys
705                 710                 715                 720

Ala Gly Thr Thr Ile Asn Ala Thr Thr Gly Ser Val Glu Val Thr Ala
                725                 730                 735

Lys Thr Gly Asp Ile Ser Gly Thr Ile Ser Gly Lys Thr Val Ser Val
                740                 745                 750

Thr Ala Ser Thr Gly Asp Leu Thr Val Arg Lys Ala Ala Thr Ile Ser
                755                 760                 765

Val Thr Glu Gly Ala Ala Thr Leu Thr Ala Thr Gly Asn Thr Leu Thr
            770                 775                 780

Thr Glu Ala Gly Ser Ser Ile Thr Ser Thr Lys Gly Gln Val Asp Leu
785                 790                 795                 800

Ser Ala Gln Asp Gly Ser Ile Ala Gly Gln Ile Ser Ala Ala Asn Val
                805                 810                 815

Thr Leu Asn Thr Thr Gly Thr Leu Thr Thr Val Glu Gly Ser Asn Ile
                820                 825                 830

Lys Ala Thr Ser Gly Thr Leu Ala Ile Asn Ala Lys Asp Ala Lys Leu
                835                 840                 845

Asp Gly Thr Ala Ser Gly Asn Arg Thr Glu Val Asn Ala Thr Asn Ala
                850                 855                 860

Ser Gly Ser Gly Ser Val Thr Ala Lys Thr Ser Ser Asn Val Asn Ile
865                 870                 875                 880

Thr Gly Asp Leu Ser Thr Ile Asn Gly Leu Asn Ile Ile Ser Glu Asn
                885                 890                 895

Gly Arg Asn Thr Val Arg Leu Arg Gly Lys Glu Ile Asp Val Lys Tyr
                900                 905                 910

Ile Gln Pro Gly Val Ala Ser Val Glu Glu Val Ile Glu Ala Lys Arg
                915                 920                 925

Val Leu Glu Lys Val Lys Asp Leu Ser Asp Glu Glu Arg Glu Thr Leu
            930                 935                 940

Ala Lys Leu Gly Val Ser Ala Val Arg Phe Val Glu Pro Asn Asn Ala
945                 950                 955                 960

Ile Thr Ile Asn Thr Gln Asn Glu Phe Thr Thr Arg Pro Ser Ser Gln
                965                 970                 975

Val Ile Ile Ser Glu Gly Lys Ala Cys Phe Ser Ser Gly Asn Gly Ala
                980                 985                 990

Ala Val Cys Thr Asn Val Ala Asp Asp Gly Gln Pro
                995                 1000
```

<210> SEQ ID NO 58
<211> LENGTH: 2997
<212> TYPE: DNA
<213> ORGANISM: Haemophilus influenzae

<400> SEQUENCE: 58

```
aaagagtggt tgttagaccc ggataatgta acaattgaag ccccttccta ttctcgcggt      60
aatgccggta tagatagtga attcccgggc ggttcgggca caaggaaag ccctaaaaca     120
aacggcgaac agccgacagt attaaccaat gaaaccattt caaattatct gaaaagcggc    180
acctgggtaa tgaatataac agccaagaaa atcttaccg ttaacagctc aattaacatt     240
ggagacagct cccacttaat ccttcatagt gaaggcaaga ataacggcgg tgttaagatt    300
aaagaagaca ttacctctaa tggcggaaac ttaaccattc aatccggcgg atgggttgat    360
gttcacaaaa atattacgct tggcacaggc accttgaata ttacagctaa aggatccata    420
gcctttgagg gaaacggtac agaaaaagcc cgcaacgcat caagcgctca aatcaccgcg    480
cagggaacta taaccaatac tggcgatcaa aaacaactca gacttaataa tgtatctatt    540
aatgggacgg gtataggttt aaattttgtt tcaattcagc ctaacacttc tcacagattt    600
gatggggagc ttattatttc agggagagta catgttaatc aaaccacacc taaaaacctg    660
tcttttttgga aggtatccga tgaatcttat tggaatgtca gccatcttac cgtaaaagag    720
aagtcagcat tctcatttac caagtttgcg ttaaataaca atcatggccg agagacttcc    780
agataccgca aggtggagg tgtaatcttt cgctcaccta ccggtcacac aaatttcaca    840
gttaaacaag gctcagtggc taattttttca ttcaaggcaa aaaatgatac aaatcatgca    900
aatcaactcc cgattcagtt taactctaat atctcagtcg atggaggagg gaaagtcctt    960
ttttgtataa cctccaacta ctccggcaga tcagtgggga taggaatgtc tagcattaat   1020
gtttctgatg gctcaaacct tactttaat tcttccattc gcggccagga agcctttaat   1080
atcagtaaag atttaaccat aaatgcaacc ggttcatttt ttgaacttgg caatactcg    1140
gataccttta atggtaatgg ctttaaccac gacgccatta aatcaactca caatatatcc   1200
atcttaggtg gcaatgttac ccttggcggg caagattcaa gcagtaccat tacaggtaat   1260
atcaatatct ctcaggcagc aaatgttacc ttgcgagctt ataatggtaa cggtcgaaac   1320
aaacaactaa cccttggcaa tgtatctatt gaagggaatt taagtttaat cggtgcaagt   1380
gcaaatatta acggcaacct ttccgttaaa gaaaatgcta aatttaaagg ggaaacccaa   1440
gacaacttga acatcaccgg cacctttatc aataacggcg actctaaaat caatatatct   1500
caaggagtgg taaaacttgg caatgttacc aatgatggtg atttaaacat taccactcac   1560
gctaaacaca accaaagaag catcatcggc ggagatataa tcaacaaaaa aggaagctta   1620
aatattacag acagtaataa gaatgctgaa atccaaattg gcggcaatat ctcgcaaaaa   1680
gaaggcaatc tcacgatttc ttccgataaa atcaatatta ccaatcagat aacaatcaaa   1740
gcaggtgttg atgggagaa ttccgattca gacgcgacaa caatgccaa tctaaccatt    1800
aaaccaaag aattgaaatt aacgcaagac ctaaatattt caggtttcaa taaagcagag   1860
attacagcta aagatggtag tgatttaact attggtaaca ccaatagtgc tgatagtact   1920
aatgccaaaa aagtaacctt taaccaggtt aaagattcaa aaatctctgc tggcgaccat   1980
aatgtgcacac taaatagcaa agtggaaaca tctggtaata ctgacaacac tggagacggc   2040
agtggcaata atgccggctt aactattgcc gcgaaaaatg tagaagtaaa aaacaacatt   2100
```

-continued

```
acttctaaca aaacagtaaa tatcaccgcg tcagaaaaac ttaccaccaa agcggatgca   2160
accattaatg caaccactgg taacgtagaa gtgacagcca aaacaggtga tattaaggt    2220 gaagtcaaat ccacttccgg taatgtaaat attacagcaa acggcgacac gcttaatgta   2280
agtaatgttt caggcaatgc tgttaccatc actgcagata agggcaaatt aaccacccaa   2340
gcaagctcta gcattacctc aaacaatggc cagacaactc ttacagccaa ggatggcagt   2400
atcgcaggaa gcatcaatgc cgccaatgtg acattaaata ccacaggcac tttaactact   2460
gtagaaggtt caaacattaa cgcagccagt ggtaccttgg ttattaatgc aaaagatgct   2520
aagttgaacg gcgcggcatc aggtgaccac acagtagtaa atgcaactaa cgcaagtggc   2580
tctggtagtg tgactgcggt aacctcaagt aatgtgaata tcaccgggga tttaagtaca   2640
gtaaatggat taaatatcat ttcgaaaaat ggtagaaaca ccgtagtgtt aaaaggtact   2700
gaaattgagg tgaaatatat ccagccaggt gtagcaagtg tagaagaagt aattgaagcg   2760
aaacgcgtcc ttgagaaagt gaaagattta tctgatgaag aaagagaaac attagctaaa   2820
cttggtgtaa gtgctgtacg tttattgaa ccaaataata ccattacggt taacacacaa   2880
aatgagttta caaccagacc atcaagtcaa gtgacaattt ctgaaggtaa ggcgtgtttc   2940
tcaagtggta atggcgcagc agtatgtacc aatgttgctg acgatggaca gcagtag      2997
```

<210> SEQ ID NO 59
<211> LENGTH: 998
<212> TYPE: PRT
<213> ORGANISM: Haemophilus influenzae

<400> SEQUENCE: 59

```
Lys Glu Trp Leu Leu Asp Pro Asp Asn Val Thr Ile Glu Ala Pro Ser
  1               5                  10                  15

Tyr Ser Arg Gly Asn Ala Gly Ile Asp Ser Glu Phe Pro Gly Gly Ser
                 20                  25                  30

Gly Thr Lys Glu Ser Pro Lys Thr Asn Gly Glu Gln Pro Thr Val Leu
             35                  40                  45

Thr Asn Glu Thr Ile Ser Asn Tyr Leu Lys Ser Gly Thr Trp Val Met
         50                  55                  60

Asn Ile Thr Ala Lys Lys Asn Leu Thr Val Asn Ser Ser Ile Asn Ile
 65                  70                  75                  80

Gly Asp Ser Ser His Leu Ile Leu His Ser Glu Gly Lys Asn Asn Gly
                 85                  90                  95

Gly Val Lys Ile Lys Glu Asp Ile Thr Ser Asn Gly Gly Asn Leu Thr
            100                 105                 110

Ile Gln Ser Gly Gly Trp Val Asp Val His Lys Asn Ile Thr Leu Gly
            115                 120                 125

Thr Gly Thr Leu Asn Ile Thr Ala Lys Gly Ser Ile Ala Phe Glu Gly
        130                 135                 140

Asn Gly Thr Glu Lys Ala Arg Asn Ala Ser Ser Ala Gln Ile Thr Ala
145                 150                 155                 160

Gln Gly Thr Ile Thr Asn Thr Gly Asp Gln Lys Gln Leu Arg Leu Asn
                165                 170                 175

Asn Val Ser Ile Asn Gly Thr Gly Ile Gly Leu Asn Phe Val Ser Ile
            180                 185                 190

Gln Pro Asn Thr Ser His Arg Phe Asp Gly Glu Leu Ile Ile Ser Gly
        195                 200                 205

Arg Val His Val Asn Gln Thr Thr Pro Lys Asn Leu Ser Phe Trp Lys
    210                 215                 220
```

-continued

Val Ser Asp Glu Ser Tyr Trp Asn Val Ser His Leu Thr Val Lys Glu
225                 230                 235                 240

Lys Ser Ala Phe Ser Phe Thr Lys Phe Ala Leu Asn Asn Asn His Gly
            245                 250                 255

Arg Glu Thr Ser Arg Tyr Arg Lys Gly Gly Val Ile Phe Arg Ser
        260                 265                 270

Pro Thr Gly His Thr Asn Phe Thr Val Lys Gln Gly Ser Val Ala Asn
            275                 280                 285

Phe Ser Phe Lys Ala Lys Asn Asp Thr Asn His Ala Asn Gln Leu Pro
290                 295                 300

Ile Gln Phe Asn Ser Asn Ile Ser Val Asp Gly Gly Lys Val Leu
305                 310                 315                 320

Phe Cys Ile Thr Ser Asn Tyr Ser Gly Arg Ser Val Gly Ile Gly Met
                325                 330                 335

Ser Ser Ile Asn Val Ser Asp Gly Ser Asn Leu Thr Phe Asn Ser Ser
                340                 345                 350

Ile Arg Gly Gln Glu Ala Phe Asn Ile Ser Lys Asp Leu Thr Ile Asn
        355                 360                 365

Ala Thr Gly Ser Phe Phe Glu Leu Gly Gln Tyr Ser Asp Thr Phe Asn
370                 375                 380

Gly Asn Gly Phe Asn His Asp Ala Ile Lys Ser Thr His Asn Ile Ser
385                 390                 395                 400

Ile Leu Gly Gly Asn Val Thr Leu Gly Gly Gln Asp Ser Ser Ser Thr
                405                 410                 415

Ile Thr Gly Asn Ile Asn Ile Ser Gln Ala Ala Asn Val Thr Leu Arg
            420                 425                 430

Ala Tyr Asn Gly Asn Gly Arg Asn Lys Gln Leu Thr Leu Gly Asn Val
        435                 440                 445

Ser Ile Glu Gly Asn Leu Ser Leu Ile Gly Ala Ser Ala Asn Ile Asn
450                 455                 460

Gly Asn Leu Ser Val Lys Glu Asn Ala Lys Phe Lys Gly Glu Thr Gln
465                 470                 475                 480

Asp Asn Leu Asn Ile Thr Gly Thr Phe Ile Asn Asn Gly Asp Ser Lys
            485                 490                 495

Ile Asn Ile Ser Gln Gly Val Val Lys Leu Gly Asn Val Thr Asn Asp
                500                 505                 510

Gly Asp Leu Asn Ile Thr His Ala Lys His Asn Gln Arg Ser Ile
        515                 520                 525

Ile Gly Gly Asp Ile Ile Asn Lys Lys Gly Ser Leu Asn Ile Thr Asp
530                 535                 540

Ser Asn Lys Asn Ala Glu Ile Gln Ile Gly Asn Ile Ser Gln Lys
545                 550                 555                 560

Glu Gly Asn Leu Thr Ile Ser Ser Asp Lys Ile Asn Ile Thr Asn Gln
            565                 570                 575

Ile Thr Ile Lys Ala Gly Val Asp Gly Glu Asn Ser Asp Ser Asp Ala
            580                 585                 590

Thr Asn Asn Ala Asn Leu Thr Ile Lys Thr Lys Glu Leu Lys Leu Thr
            595                 600                 605

Gln Asp Leu Asn Ile Ser Gly Phe Asn Lys Ala Glu Ile Thr Ala Lys
        610                 615                 620

Asp Gly Ser Asp Leu Thr Ile Gly Asn Thr Asn Ser Ala Asp Ser Thr
625                 630                 635                 640

-continued

```
Asn Ala Lys Lys Val Thr Phe Asn Gln Val Lys Asp Ser Lys Ile Ser
                645                 650                 655
Ala Gly Asp His Asn Val Thr Leu Asn Ser Lys Val Glu Thr Ser Gly
            660                 665                 670
Asn Thr Asp Asn Thr Gly Asp Gly Ser Gly Asn Asn Ala Gly Leu Thr
        675                 680                 685
Ile Ala Ala Lys Asn Val Glu Val Lys Asn Asn Ile Thr Ser Asn Lys
    690                 695                 700
Thr Val Asn Ile Thr Ala Ser Glu Lys Leu Thr Thr Lys Ala Asp Ala
705                 710                 715                 720
Thr Ile Asn Ala Thr Thr Gly Asn Val Glu Val Thr Ala Lys Thr Gly
                725                 730                 735
Asp Ile Lys Gly Glu Val Lys Ser Thr Ser Gly Asn Val Asn Ile Thr
            740                 745                 750
Ala Asn Gly Asp Thr Leu Asn Val Ser Asn Val Ser Gly Asn Ala Val
        755                 760                 765
Thr Ile Thr Ala Asp Lys Gly Lys Leu Thr Thr Gln Ala Ser Ser Ser
    770                 775                 780
Ile Thr Ser Asn Asn Gly Gln Thr Thr Leu Thr Ala Lys Asp Gly Ser
785                 790                 795                 800
Ile Ala Gly Ser Ile Asn Ala Ala Asn Val Thr Leu Asn Thr Thr Gly
                805                 810                 815
Thr Leu Thr Thr Val Glu Gly Ser Asn Ile Asn Ala Ala Ser Gly Thr
            820                 825                 830
Leu Val Ile Asn Ala Lys Asp Ala Lys Leu Asn Gly Ala Ala Ser Gly
        835                 840                 845
Asp His Thr Val Val Asn Ala Thr Asn Ala Ser Gly Ser Gly Ser Val
    850                 855                 860
Thr Ala Val Thr Ser Ser Asn Val Asn Ile Thr Gly Asp Leu Ser Thr
865                 870                 875                 880
Val Asn Gly Leu Asn Ile Ile Ser Lys Asn Gly Arg Asn Thr Val Val
                885                 890                 895
Leu Lys Gly Thr Glu Ile Glu Val Lys Tyr Ile Gln Pro Gly Val Ala
            900                 905                 910
Ser Val Glu Glu Val Ile Glu Ala Lys Arg Val Leu Lys Val Lys
        915                 920                 925
Asp Leu Ser Asp Glu Glu Arg Glu Thr Leu Ala Lys Leu Gly Val Ser
    930                 935                 940
Ala Val Arg Phe Ile Glu Pro Asn Asn Thr Ile Thr Val Asn Thr Gln
945                 950                 955                 960
Asn Glu Phe Thr Thr Arg Pro Ser Ser Gln Val Thr Ile Ser Glu Gly
                965                 970                 975
Lys Ala Cys Phe Ser Ser Gly Asn Gly Ala Ala Val Cys Thr Asn Val
            980                 985                 990
Ala Asp Asp Gly Gln Gln
        995
```

<210> SEQ ID NO 60
<211> LENGTH: 2979
<212> TYPE: DNA
<213> ORGANISM: Haemophilus influenzae

<400> SEQUENCE: 60
ccggataatg taacaattga agccccttcc tattctcgcg gtaatgccgg tatagatagt    60

-continued

| | |
|---|---|
| gaattcccgg gcggttcggg cacaaaggaa agccctaaaa caaacggcga acagccgaca | 120 |
| gtattaacca atgaaaccat ttcaaattat ctgaaaagcg gcacctgggt aatgaatata | 180 |
| acagccaaga aaaatcttac cgttaacagc tcaattaaca ttggagacag ctcccactta | 240 |
| atccttcata gtgaaggcaa gaataacggc ggtgttaaga ttaaagaaga cattacctct | 300 |
| aatggcggaa acttaaccat tcaatccggc ggatgggttg atgttcacaa aaatattacg | 360 |
| cttggcacag gcaccttgaa tattacagct aaaggatcca tagcctttga gggaaacggt | 420 |
| acagaaaaag cccgcaacgc atcaagcgct caaatcaccg cgcagggaac tataaccaat | 480 |
| actggcgatc aaaaacaact cagacttaat aatgtatcta ttaatgggac gggtataggt | 540 |
| ttaaattttg tttcaattca gcctaacact tctcacagat ttgatgggga gcttattatt | 600 |
| tcagggagag tacatgttaa tcaaaccaca cctaaaaacc tgtctttttg gaaggtatcc | 660 |
| gatgaatctt attggaatgt cagccatctt accgtaaaag agaagtcagc attctcattt | 720 |
| accaagtttg cgttaaataa caatcatggc cgagagactt ccagataccg caaaggtgga | 780 |
| ggtgtaatct ttcgctcacc taccggtcac acaaatttca cagttaaaca aggctcagtg | 840 |
| gctaattttt cattcaaggc aaaaaatgat acaaatcatg caaatcaact cccgattcag | 900 |
| tttaactcta atatctcagt cgatggagga gggaaagtcc ttttttgtat aacctccaac | 960 |
| tactccggca gatcagtggg gataggaatg tctagcatta atgtttctga tggctcaaac | 1020 |
| cttactttta attcttccat tcgcggccag gaagccttta atatcagtaa agatttaacc | 1080 |
| ataaatgcaa ccgttcatt ttttgaactt gggcaatact cggataccttt taatggtaat | 1140 |
| ggctttaacc acgacgccat taatcaact cacaatatat ccatcttagg tggcaatgtt | 1200 |
| acccttggcg ggcaagattc aagcagtacc attacaggta atatcaatat ctctcaggca | 1260 |
| gcaaatgtta ccttgcgagc ttataatggt aacggtcgaa acaaacaact aacccttggc | 1320 |
| aatgtatcta ttgaagggaa tttaagttta atcggtgcaa gtgcaaatat taacggcaac | 1380 |
| ctttccgtta aagaaaatgc taaatttaaa ggggaaaccc aagacaactt gaacatcacc | 1440 |
| ggcaccttta tcaataacgg cgactctaaa atcaatatat ctcaaggagt ggtaaaactt | 1500 |
| ggcaatgtta ccaatgatgg tgatttaaac attaccactc acgctaaaca caaccaaaga | 1560 |
| agcatcatcg gcggagatat aatcaacaaa aaaggaagct taaatattac agacagtaat | 1620 |
| aagaatgctg aaatccaaat tggcggcaat atctcgcaaa aagaaggcaa tctcacgatt | 1680 |
| tcttccgata aaatcaatat taccaatcag ataacaatca aagcaggtgt tgatggggag | 1740 |
| aattccgatt cagacgcgac aaacaatgcc aatctaacca ttaaaaccaa agaattgaaa | 1800 |
| ttaacgcaag acctaaatat ttcaggtttc aataaagcag agattacagc taaagatggt | 1860 |
| agtgatttaa ctattggtaa caccaatagt gctgatagta ctaatgccaa aaaagtaacc | 1920 |
| tttaaccagg ttaagattc aaaaatctct gctggcgacc ataatgtgac actaaatagc | 1980 |
| aaagtggaaa catctggtaa tactgacaac actggagacg gcagtggcaa taatgccggc | 2040 |
| ttaactattg ccgcgaaaaa tgtagaagta aaaaacaaca ttacttctaa caaacagta | 2100 |
| aatatcaccg cgtcagaaaa acttaccacc aaagcggatg caaccattaa tgcaaccact | 2160 |
| ggtaacgtag aagtgacagc caaaacaggt gatattaaag gtgaagtcaa atccacttcc | 2220 |
| ggtaatgtaa atattacagc aaacggcgac acgcttaatg taagtaatgt ttcaggcaat | 2280 |
| gctgttacca tcactgcaga taagggcaaa ttaccaccc aagcaagctc tagcattacc | 2340 |
| tcaaacaatg gccagacaac tcttacagcc aaggatggca gtatcgcagg aagcatcaat | 2400 |
| gccgccaatg tgacattaaa taccacaggc actttaacta ctgtagaagg ttcaaacatt | 2460 |

-continued

```
aacgcagcca gtggtacctt ggttattaat gcaaagatg ctaagttgaa cggcgcggca    2520
tcaggtgacc acacagtagt aaatgcaact aacgcaagtg gctctggtag tgtgactgcg    2580
gtaacctcaa gtaatgtgaa tatcaccggg gatttaagta cagtaaatgg attaaatatc    2640
atttcgaaaa atggtagaaa caccgtagtg ttaaaaggta ctgaaattga ggtgaaatat    2700
atccagccag gtgtagcaag tgtagaagaa gtaattgaag cgaaacgcgt ccttgagaaa    2760
gtgaaagatt tatctgatga agaaagagaa acattagcta aacttggtgt aagtgctgta    2820
cgttttattg aaccaaataa taccattacg gttaacacac aaaatgagtt tacaaccaga    2880
ccatcaagtc aagtgacaat ttctgaaggt aaggcgtgtt tctcaagtgg taatggcgca    2940
gcagtatgta ccaatgttgc tgacgatgga cagcagtag                           2979
```

<210> SEQ ID NO 61
<211> LENGTH: 992
<212> TYPE: PRT
<213> ORGANISM: Haemophilus influenzae

<400> SEQUENCE: 61

```
Pro Asp Asn Val Thr Ile Glu Ala Pro Ser Tyr Ser Arg Gly Asn Ala
  1               5                  10                  15

Gly Ile Asp Ser Glu Phe Pro Gly Gly Ser Gly Thr Lys Glu Ser Pro
             20                  25                  30

Lys Thr Asn Gly Glu Gln Pro Thr Val Leu Thr Asn Glu Thr Ile Ser
         35                  40                  45

Asn Tyr Leu Lys Ser Gly Thr Trp Val Met Asn Ile Thr Ala Lys Lys
     50                  55                  60

Asn Leu Thr Val Asn Ser Ser Ile Asn Ile Gly Asp Ser Ser His Leu
 65                  70                  75                  80

Ile Leu His Ser Glu Gly Lys Asn Asn Gly Val Lys Ile Lys Glu
                 85                  90                  95

Asp Ile Thr Ser Asn Gly Gly Asn Leu Thr Ile Gln Ser Gly Gly Trp
             100                 105                 110

Val Asp Val His Lys Asn Ile Thr Leu Gly Thr Gly Thr Leu Asn Ile
         115                 120                 125

Thr Ala Lys Gly Ser Ile Ala Phe Glu Gly Asn Gly Thr Glu Lys Ala
     130                 135                 140

Arg Asn Ala Ser Ser Ala Gln Ile Thr Ala Gln Gly Thr Ile Thr Asn
145                 150                 155                 160

Thr Gly Asp Gln Lys Gln Leu Arg Leu Asn Asn Val Ser Ile Asn Gly
                 165                 170                 175

Thr Gly Ile Gly Leu Asn Phe Val Ser Ile Gln Pro Asn Thr Ser His
             180                 185                 190

Arg Phe Asp Gly Glu Leu Ile Ile Ser Gly Arg Val His Val Asn Gln
         195                 200                 205

Thr Thr Pro Lys Asn Leu Ser Phe Trp Lys Val Ser Asp Glu Ser Tyr
     210                 215                 220

Trp Asn Val Ser His Leu Thr Val Lys Glu Lys Ser Ala Phe Ser Phe
225                 230                 235                 240

Thr Lys Phe Ala Leu Asn Asn Asn His Gly Arg Glu Thr Ser Arg Tyr
                 245                 250                 255

Arg Lys Gly Gly Gly Val Ile Phe Arg Ser Pro Thr Gly His Thr Asn
             260                 265                 270

Phe Thr Val Lys Gln Gly Ser Val Ala Asn Phe Ser Phe Lys Ala Lys
```

-continued

```
              275                 280                 285
Asn Asp Thr Asn His Ala Asn Gln Leu Pro Ile Gln Phe Asn Ser Asn
            290                 295                 300

Ile Ser Val Asp Gly Gly Lys Val Leu Phe Cys Ile Thr Ser Asn
305                 310                 315                 320

Tyr Ser Gly Arg Ser Val Gly Ile Gly Met Ser Ser Ile Asn Val Ser
                325                 330                 335

Asp Gly Ser Asn Leu Thr Phe Asn Ser Ser Ile Arg Gly Gln Glu Ala
            340                 345                 350

Phe Asn Ile Ser Lys Asp Leu Thr Ile Asn Ala Thr Gly Ser Phe Phe
            355                 360                 365

Glu Leu Gly Gln Tyr Ser Asp Thr Phe Asn Gly Asn Gly Phe Asn His
370                 375                 380

Asp Ala Ile Lys Ser Thr His Asn Ile Ser Ile Leu Gly Gly Asn Val
385                 390                 395                 400

Thr Leu Gly Gly Gln Asp Ser Ser Thr Ile Thr Gly Asn Ile Asn
                405                 410                 415

Ile Ser Gln Ala Ala Asn Val Thr Leu Arg Ala Tyr Asn Gly Asn Gly
            420                 425                 430

Arg Asn Lys Gln Leu Thr Leu Gly Asn Val Ser Ile Glu Gly Asn Leu
            435                 440                 445

Ser Leu Ile Gly Ala Ser Ala Asn Ile Asn Gly Asn Leu Ser Val Lys
450                 455                 460

Glu Asn Ala Lys Phe Lys Gly Glu Thr Gln Asp Asn Leu Asn Ile Thr
465                 470                 475                 480

Gly Thr Phe Ile Asn Asn Gly Asp Ser Lys Ile Asn Ile Ser Gln Gly
                485                 490                 495

Val Val Lys Leu Gly Asn Val Thr Asn Asp Gly Asp Leu Asn Ile Thr
                500                 505                 510

Thr His Ala Lys His Asn Gln Arg Ser Ile Ile Gly Gly Asp Ile Ile
            515                 520                 525

Asn Lys Lys Gly Ser Leu Asn Ile Thr Asp Ser Asn Lys Asn Ala Glu
            530                 535                 540

Ile Gln Ile Gly Gly Asn Ile Ser Gln Lys Glu Gly Asn Leu Thr Ile
545                 550                 555                 560

Ser Ser Asp Lys Ile Asn Ile Thr Asn Gln Ile Thr Ile Lys Ala Gly
                565                 570                 575

Val Asp Gly Glu Asn Ser Asp Ser Asp Ala Thr Asn Asn Ala Asn Leu
            580                 585                 590

Thr Ile Lys Thr Lys Glu Leu Lys Leu Thr Gln Asp Leu Asn Ile Ser
            595                 600                 605

Gly Phe Asn Lys Ala Glu Ile Thr Ala Lys Asp Gly Ser Asp Leu Thr
610                 615                 620

Ile Gly Asn Thr Asn Ser Ala Asp Ser Thr Asn Ala Lys Lys Val Thr
625                 630                 635                 640

Phe Asn Gln Val Lys Asp Ser Lys Ile Ser Ala Gly Asp His Asn Val
                645                 650                 655

Thr Leu Asn Ser Lys Val Glu Thr Ser Gly Asn Thr Asp Asn Thr Gly
            660                 665                 670

Asp Gly Ser Gly Asn Asn Ala Gly Leu Thr Ile Ala Ala Lys Asn Val
            675                 680                 685

Glu Val Lys Asn Asn Ile Thr Ser Asn Lys Thr Val Asn Ile Thr Ala
690                 695                 700
```

-continued

```
Ser Glu Lys Leu Thr Thr Lys Ala Asp Ala Thr Ile Asn Ala Thr Thr
705                 710                 715                 720

Gly Asn Val Glu Val Thr Ala Lys Thr Gly Asp Ile Lys Gly Glu Val
            725                 730                 735

Lys Ser Thr Ser Gly Asn Val Asn Ile Thr Ala Asn Gly Asp Thr Leu
        740                 745                 750

Asn Val Ser Asn Val Ser Gly Asn Ala Val Thr Ile Thr Ala Asp Lys
    755                 760                 765

Gly Lys Leu Thr Thr Gln Ala Ser Ser Ile Thr Ser Asn Asn Gly
770                 775                 780

Gln Thr Thr Leu Thr Ala Lys Asp Gly Ser Ile Ala Gly Ser Ile Asn
785                 790                 795                 800

Ala Ala Asn Val Thr Leu Asn Thr Thr Gly Thr Leu Thr Thr Val Glu
            805                 810                 815

Gly Ser Asn Ile Asn Ala Ala Ser Gly Thr Leu Val Ile Asn Ala Lys
        820                 825                 830

Asp Ala Lys Leu Asn Gly Ala Ala Ser Gly Asp His Thr Val Val Asn
    835                 840                 845

Ala Thr Asn Ala Ser Gly Ser Gly Ser Val Thr Ala Val Thr Ser Ser
850                 855                 860

Asn Val Asn Ile Thr Gly Asp Leu Ser Thr Val Asn Gly Leu Asn Ile
865                 870                 875                 880

Ile Ser Lys Asn Gly Arg Asn Thr Val Val Leu Lys Gly Thr Glu Ile
            885                 890                 895

Glu Val Lys Tyr Ile Gln Pro Gly Val Ala Ser Val Glu Glu Val Ile
        900                 905                 910

Glu Ala Lys Arg Val Leu Glu Lys Val Lys Asp Leu Ser Asp Glu Glu
    915                 920                 925

Arg Glu Thr Leu Ala Lys Leu Gly Val Ser Ala Val Arg Phe Ile Glu
930                 935                 940

Pro Asn Asn Thr Ile Thr Val Asn Thr Gln Asn Glu Phe Thr Thr Arg
945                 950                 955                 960

Pro Ser Ser Gln Val Thr Ile Ser Glu Gly Lys Ala Cys Phe Ser Ser
            965                 970                 975

Gly Asn Gly Ala Ala Val Cys Thr Asn Val Ala Asp Asp Gly Gln Gln
        980                 985                 990
```

<210> SEQ ID NO 62
<211> LENGTH: 3568
<212> TYPE: DNA
<213> ORGANISM: Haemophilus influenzae

<400> SEQUENCE: 62

```
gaattcggct tcgggatccc atatgccgga gaatgtatat attaatgcag gagacgcagg    60
gcgtagtgac actaatttag aaaacgaaga atacacagga acaggagaga gtgctgatac   120
tccaaaacga aacaataaca caaagacaac actaacaaac tcaacgcttg agaagatatt   180
agcaagaggc tcttttgtta atatcactgc caacaatgaa atcagagtta atagtgatat   240
caatatcgga ggcaactccc acctaaccct ctggagcagc aaaaataaaa acagtggcgt   300
tctgattaat ggcaatatca cttctactgc taacggaaac ttaaccattt actctagcgg   360
atgggttgat attcataaaa atattacgct tgaatcagga cgcttaaaca ttacaactaa   420
agaaggagat gtcgcctttg aaaaagggaa taacctaacc attacaggtc aaggaactat   480
```

```
tacagcaggc aataataaag gctttagatt tgaaaatgtc tctctaaatg gcactgggac    540
tggcttgctt tttaatctca gtagaccaca aaaaaacaat agtctcgtca caaactattt    600
taatgggact ttaaatattt caggaagcgt aaatatctca atgattccac ctaatgctac    660
aagcaattgg tacagcagat acaaagggcg aacctattgg aatataaccc acttaaatgc    720
ctccgaagat agcaactttt aaccttactat tgactcctcg gcagaggatg gctcagcccc    780
tcttttatcc agttatacct taaacggcat atcattcacc acagatacca cctttaatgt    840
taataaaaat gcaaaagtca actttaacat caaagcacca ataqggacta taaatcaata    900 caataacctg aattacgcat tattcaatgg gaacatttca gtttcaggag ggggaatgt     960 caccttcagg cttaacgctt catcctctaa ccagcaaacc cctggcgtaa ttataaattc   1020
taaacacctt aatgcttcaa aagggtcgag cttaagattt gaaactacag gttcaacaaa   1080
agtcggtttt ttaataaata atgatttaac tttaaacgcc actggaggca atatatcgct   1140
cttgcaggtt gaaggcattg acgggatgat tggtgaaggc gttgtagcta aaaaaaacat   1200 aaccttact ggaggcaata tcacctttgg ctccaagaaa gccataacag aaatcaaagg   1260
caatgttact atcaatgaaa acaccaacgc cactcttatc ggttcggatt taacgatca   1320 taaaaaacct ttaaatataa aaggagatgt cgtcaataga ggcaacctta ccgctggcgg   1380
caatgttatc aatataggcg gaaatcttac cgttgaaaat ggcgccaatc ttaaagctat   1440
cacaaatttc acttttaatg taggcggctt gtttaacaac aaaggcaatt caaatatctc   1500
cattgctaga ggagggcta aatttaaaga tatcaataac accagtagct aaatattac   1560 caccaactcc gacaccactt accgtaccat tatagaaggt aatataacca acaaagcagg   1620
tgatttgaat atcattgata ataaaggtaa cgctgaaatc caaattggcg gcaacatctc   1680
gcaaaaagaa ggtaacctca cgatttcctc cgataaaatc aatattacca aacagataac   1740
aatcaagaag ggtgttaacg gagagaactc tgattcaagt acgaaaagtc aagccaatct   1800
aaccattaaa accaaagaat tgaaattaac acaagaccta aatatttcag gcttcaacaa   1860
agcaaagatt gtagctaaag atagtagtaa tttaactatt ggtaatagtg atgatagcgg   1920
caatactagc gctaaaacag taactttaa caatgttaaa gattcaaaaa tctctgctga   1980
cggtcacaag gtgacactaa atagcaaagt gaaaacactt agtgataatg ataacaacac   2040
tgaaggtggc agtgacaaca ataccggttt aactattact gcaaaagatg tagaagtaaa   2100
caacaatatt acttctcaca aaacagtgaa cgtctctgcg gcaaatggag ggattaccac   2160
taaaacaggt acaaccatta atgcaaccgc cggtaacgtg gagataaccg ctcatacagg   2220
cagtatccaa ggcggaattg agtccaagcc tggctctgtg acaattgtgg caggcggcga   2280
tactcttgct gtaggtaata tttcaggcaa cgccgttact gttactgcaa atagcggtgc   2340
attaaccact ttggcaggct ctacaattaa aggaaccgag agtataacca cttcaagtca   2400
atcaggtaat atcggcggta aaatttccgg caagacagta acgttaaag caactaatag   2460 tttaaccacc caagcagact caaaaattga agcgactgaa ggcgaggcta atgtaacaag   2520
caaaacaagc ataattggcg gtacaatttc tggtggcaca gtagaagtta ccgcgaccga   2580
aggtttaacc acccaagcag gctctacgat tactggaacc gagagcgtga ccacttcaag   2640
ccaatcaggt aatatcggcg gcatgatttc tggtggcaaa gtagaagtta gcgcaaccaa   2700
agatttaatt actaaatccg gttcagagat taaagcaacg gcgggcgagg tgaatgtaac   2760
aagtgcaaca ggtacaattg acggtacgat ttccggtaat acggtaaatg ttacagcaaa   2820
tactggcgat ttaactgttg aagatgccgc aaaaattgat gcgacaggag gagccgcgac   2880
```

-continued

```
cctaactgca acatcgggca aattaaccac taaggctagt tcaagcatta cttcagctaa      2940
taaccaggta aacctttcag ctaaggatgg tagcattggg ggaaatatca atgctgctaa      3000
tgtaacactg aatactacag gcgctctaac taccgtgaag ggttcaagca ttaacgcaaa      3060
cagcggcacc ttggttatta acgcaaaaga cgctgagcta aatggtgagg catcaggtaa      3120
ccatacagta gtgaatgcaa ccaacgcaaa tggctccggc agcgtaatcg cgacaacctc      3180
aagcagagtg aacatcactg gggatttaat cacaataaat ggattaaata tcatttcaaa      3240
aaacggtata aacaccgtac tgttaaaagg cgttaaaatt gatgtgaaat acattcaacc      3300
gggtatagca agcgtagatg aagtaattga agcgaaacgc atccttgaga aggtaaaaga      3360
tttatctgat gaagaaagag aagcgttagc taaacttggc gtaagcgctg tacgttttgc      3420
tgagccaaat aatgccatta cgattaatac acaaaatgag tttacaacca gaccatcaag      3480
tcaagtgaca atttctgaag gtaaggtatg tttcttaatc ggcaatggtg caacaatatg      3540
caccaatatt gctgatattg agcggtag                                        3568
```

<210> SEQ ID NO 63
<211> LENGTH: 1188
<212> TYPE: PRT
<213> ORGANISM: Haemophilus influenzae

<400> SEQUENCE: 63

```
Asn Ser Ala Ser Gly Ser His Met Pro Glu Asn Val Tyr Ile Asn Ala
  1               5                  10                  15

Gly Asp Ala Gly Arg Ser Asp Thr Asn Leu Glu Asn Glu Glu Tyr Thr
                 20                  25                  30

Gly Thr Gly Glu Ser Ala Asp Thr Pro Lys Arg Asn Asn Asn Thr Lys
             35                  40                  45

Thr Thr Leu Thr Asn Ser Thr Leu Glu Lys Ile Leu Ala Arg Gly Ser
         50                  55                  60

Phe Val Asn Ile Thr Ala Asn Asn Glu Ile Arg Val Asn Ser Asp Ile
 65                  70                  75                  80

Asn Ile Gly Gly Asn Ser His Leu Thr Leu Trp Ser Ser Lys Asn Lys
                 85                  90                  95

Asn Ser Gly Val Leu Ile Asn Gly Asn Ile Thr Ser Thr Ala Asn Gly
            100                 105                 110

Asn Leu Thr Ile Tyr Ser Ser Gly Trp Val Asp Ile His Lys Asn Ile
        115                 120                 125

Thr Leu Glu Ser Gly Arg Leu Asn Ile Thr Thr Lys Glu Gly Asp Val
    130                 135                 140

Ala Phe Glu Lys Gly Asn Asn Leu Thr Ile Thr Gly Gln Gly Thr Ile
145                 150                 155                 160

Thr Ala Gly Asn Asn Lys Gly Phe Arg Phe Glu Asn Val Ser Leu Asn
                165                 170                 175

Gly Thr Gly Thr Gly Leu Leu Phe Asn Leu Ser Arg Pro Gln Lys Asn
            180                 185                 190

Asn Ser Leu Val Thr Asn Tyr Phe Asn Gly Thr Leu Asn Ile Ser Gly
        195                 200                 205

Ser Val Asn Ile Ser Met Ile Pro Pro Asn Ala Thr Ser Asn Trp Tyr
    210                 215                 220

Ser Arg Tyr Lys Gly Arg Thr Tyr Trp Asn Ile Thr His Leu Asn Ala
225                 230                 235                 240

Ser Glu Asp Ser Asn Phe Asn Leu Thr Ile Asp Ser Ser Ala Glu Asp
```

```
                   245                 250                 255
Gly Ser Ala Pro Leu Ser Ser Tyr Thr Leu Asn Gly Ile Ser Phe
                260                 265                 270
Thr Thr Asp Thr Thr Phe Asn Val Asn Lys Asn Ala Lys Val Asn Phe
                275                 280                 285
Asn Ile Lys Ala Pro Ile Gly Thr Ile Asn Gln Tyr Asn Asn Leu Asn
                290                 295                 300
Tyr Ala Leu Phe Asn Gly Asn Ile Ser Val Ser Gly Gly Asn Val
305                 310                 315                 320
Thr Phe Arg Leu Asn Ala Ser Ser Asn Gln Gln Thr Pro Gly Val
                325                 330                 335
Ile Ile Asn Ser Lys His Leu Asn Ala Ser Lys Gly Ser Ser Leu Arg
                340                 345                 350
Phe Glu Thr Thr Gly Ser Thr Lys Val Gly Phe Leu Ile Asn Asn Asp
                355                 360                 365
Leu Thr Leu Asn Ala Thr Gly Gly Asn Ile Ser Leu Leu Gln Val Glu
    370                 375                 380
Gly Ile Asp Gly Met Ile Gly Glu Gly Val Val Ala Lys Lys Asn Ile
385                 390                 395                 400
Thr Phe Thr Gly Gly Asn Ile Thr Phe Gly Ser Lys Lys Ala Ile Thr
                405                 410                 415
Glu Ile Lys Gly Asn Val Thr Ile Asn Glu Asn Thr Asn Ala Thr Leu
                420                 425                 430
Ile Gly Ser Asp Phe Asn Asp His Lys Lys Pro Leu Asn Ile Lys Gly
                435                 440                 445
Asp Val Val Asn Arg Gly Asn Leu Thr Ala Gly Gly Asn Val Ile Asn
450                 455                 460
Ile Gly Gly Asn Leu Thr Val Glu Asn Gly Ala Asn Leu Lys Ala Ile
465                 470                 475                 480
Thr Asn Phe Thr Phe Asn Val Gly Gly Leu Phe Asn Asn Lys Gly Asn
                485                 490                 495
Ser Asn Ile Ser Ile Ala Arg Gly Gly Ala Lys Phe Lys Asp Ile Asn
                500                 505                 510
Asn Thr Ser Ser Leu Asn Ile Thr Thr Asn Ser Asp Thr Thr Tyr Arg
                515                 520                 525
Thr Ile Ile Glu Gly Asn Ile Thr Asn Lys Ala Gly Asp Leu Asn Ile
                530                 535                 540
Ile Asp Asn Lys Gly Asn Ala Glu Ile Gln Ile Gly Gly Asn Ile Ser
545                 550                 555                 560
Gln Lys Glu Gly Asn Leu Thr Ile Ser Ser Asp Lys Ile Asn Ile Thr
                565                 570                 575
Lys Gln Ile Thr Ile Lys Lys Gly Val Asn Gly Glu Asn Ser Asp Ser
                580                 585                 590
Ser Thr Lys Ser Gln Ala Asn Leu Thr Ile Lys Thr Lys Glu Leu Lys
                595                 600                 605
Leu Thr Gln Asp Leu Asn Ile Ser Gly Phe Asn Lys Ala Lys Ile Val
                610                 615                 620
Ala Lys Asp Ser Ser Asn Leu Thr Ile Gly Asn Ser Asp Asp Ser Gly
625                 630                 635                 640
Asn Thr Ser Ala Lys Thr Val Thr Phe Asn Asn Val Lys Asp Ser Lys
                645                 650                 655
Ile Ser Ala Asp Gly His Lys Val Thr Leu Asn Ser Lys Val Lys Thr
                660                 665                 670
```

```
Leu Ser Asp Asn Asp Asn Asn Thr Glu Gly Ser Asp Asn Asn Thr
            675                 680                 685
Gly Leu Thr Ile Thr Ala Lys Asp Val Glu Val Asn Asn Asn Ile Thr
    690                 695                 700
Ser His Lys Thr Val Asn Val Ser Ala Ala Asn Gly Gly Ile Thr Thr
705                 710                 715                 720
Lys Thr Gly Thr Thr Ile Asn Ala Thr Ala Gly Asn Val Glu Ile Thr
                725                 730                 735
Ala His Thr Gly Ser Ile Gln Gly Gly Ile Glu Ser Lys Pro Gly Ser
            740                 745                 750
Val Thr Ile Val Ala Gly Gly Asp Thr Leu Ala Val Gly Asn Ile Ser
        755                 760                 765
Gly Asn Ala Val Thr Val Thr Ala Asn Ser Gly Ala Leu Thr Thr Leu
    770                 775                 780
Ala Gly Ser Thr Ile Lys Gly Thr Glu Ser Ile Thr Thr Ser Ser Gln
785                 790                 795                 800
Ser Gly Asn Ile Gly Gly Lys Ile Ser Gly Lys Thr Val Asn Val Lys
                805                 810                 815
Ala Thr Asn Ser Leu Thr Thr Gln Ala Asp Ser Lys Ile Glu Ala Thr
            820                 825                 830
Glu Gly Glu Ala Asn Val Thr Ser Lys Thr Ser Ile Ile Gly Gly Thr
        835                 840                 845
Ile Ser Gly Gly Thr Val Glu Val Thr Ala Thr Glu Gly Leu Thr Thr
    850                 855                 860
Gln Ala Gly Ser Thr Ile Thr Gly Thr Glu Ser Val Thr Thr Ser Ser
865                 870                 875                 880
Gln Ser Gly Asn Ile Gly Gly Met Ile Ser Gly Gly Lys Val Glu Val
                885                 890                 895
Ser Ala Thr Lys Asp Leu Ile Thr Lys Ser Gly Ser Glu Ile Lys Ala
            900                 905                 910
Thr Ala Gly Glu Val Asn Val Thr Ser Ala Thr Gly Thr Ile Asp Gly
        915                 920                 925
Thr Ile Ser Gly Asn Thr Val Asn Val Thr Ala Asn Thr Gly Asp Leu
    930                 935                 940
Thr Val Glu Asp Ala Ala Lys Ile Asp Ala Thr Gly Gly Ala Ala Thr
945                 950                 955                 960
Leu Thr Ala Thr Ser Gly Lys Leu Thr Thr Lys Ala Ser Ser Ser Ile
                965                 970                 975
Thr Ser Ala Asn Asn Gln Val Asn Leu Ser Ala Lys Asp Gly Ser Ile
            980                 985                 990
Gly Gly Asn Ile Asn Ala Ala Asn Val Thr Leu Asn Thr Thr Gly Ala
        995                 1000                1005
Leu Thr Thr Val Lys Gly Ser Ser Ile Asn Ala Asn Ser Gly Thr Leu
    1010                1015                1020
Val Ile Asn Ala Lys Asp Ala Glu Leu Asn Gly Glu Ala Ser Gly Asn
1025                1030                1035                1040
His Thr Val Val Asn Ala Thr Asn Ala Asn Gly Ser Gly Ser Val Ile
                1045                1050                1055
Ala Thr Thr Ser Ser Arg Val Asn Ile Thr Gly Asp Leu Ile Thr Ile
            1060                1065                1070
Asn Gly Leu Asn Ile Ile Ser Lys Asn Gly Ile Asn Thr Val Leu Leu
        1075                1080                1085
```

```
Lys Gly Val Lys Ile Asp Val Lys Tyr Ile Gln Pro Gly Ile Ala Ser
    1090                1095                1100

Val Asp Glu Val Ile Glu Ala Lys Arg Ile Leu Glu Lys Val Lys Asp
1105                1110                1115                1120

Leu Ser Asp Glu Glu Arg Glu Ala Leu Ala Lys Leu Gly Val Ser Ala
                1125                1130                1135

Val Arg Phe Ala Glu Pro Asn Asn Ala Ile Thr Ile Asn Thr Gln Asn
            1140                1145                1150

Glu Phe Thr Thr Arg Pro Ser Ser Gln Val Thr Ile Ser Glu Gly Lys
        1155                1160                1165

Val Cys Phe Leu Ile Gly Asn Gly Ala Thr Ile Cys Thr Asn Ile Ala
    1170                1175                1180

Asp Ile Glu Arg
1185

<210> SEQ ID NO 64
<211> LENGTH: 3543
<212> TYPE: DNA
<213> ORGANISM: Haemophilus influenzae

<400> SEQUENCE: 64
ccggagaatg tatatattaa tgcaggagac gcagggcgta gtgacactaa tttagaaaac      60
gaagaataca caggaacagg agagagtgct gatactccaa acgaaacaa taacacaaag      120
acaacactaa caaactcaac gcttgagaag atattagcaa gaggctcttt tgttaatatc     180
actgccaaca atgaaatcag agttaatagt gatatcaata tcggaggcaa ctcccaccta    240
accctctgga gcagcaaaaa taaaaacagt ggcgttctga ttaatggcaa tatcacttct    300
actgctaacg gaaacttaac catttactct agcggatggg ttgatattca taaaaatatt    360
acgcttgaat caggacgctt aaacattaca actaaagaag gagatgtcgc ctttgaaaaa    420
gggaataacc taaccattac aggtcaagga actattacag caggcaataa taaaggcttt    480
agatttgaaa atgtctctct aaatggcact gggactggct tgcttttaa tctcagtaga     540
ccacaaaaaa acaatagtct cgtcacaaac tattttaatg ggactttaaa tatttcagga    600
agcgtaaata tctcaatgat tccacctaat gctacaagca attggtacag cagatacaaa    660
gggcgaacct attggaatat aacccactta aatgcctccg aagatagcaa ctttaacctt    720
actattgact cctcggcaga ggatggctca gcccctcttt tatccagtta taccttaaac    780
ggcatatcat tcaccacaga taccaccttt aatgttaata aaaatgcaaa agtcaacttt    840
aacatcaaag caccaatagg gactataaat caatacaata acctgaatta cgcattattc    900
aatgggaaca tttcagtttc aggagggggg aatgtcacct tcaggcttaa cgcttcatcc    960
tctaaccagc aaacccctgg cgtaattata aattctaaac accttaatgc ttcaaagggg   1020
tcgagcttaa gatttgaaac tacaggttca acaaaagtcg gttttttaat aaataatgat   1080
ttaactttaa acgccactgg aggcaatata tcgctcttgc aggttgaagg cattgacggg   1140
atgattggtg aaggcgttgt agctaaaaaa aacataaacct ttactggagg caatatcacc   1200
tttggctcca agaaagccat aacagaaatc aaaggcaatg ttactatcaa tgaaaacacc   1260
aacgccactc ttatcggttc ggattttaac gatcataaaa aacctttaaa tataaaagga   1320
gatgtcgtca atagaggcaa ccttaccgct ggcggcaatg ttatcaatat aggcggaaat   1380
cttaccgttg aaaatggcgc caatcttaaa gctatcacaa atttcacttt taatgtaggc   1440
ggcttgttta acaacaaagg caattcaat atctccattg ctagaggagg ggctaaattt   1500
```

-continued

```
aaagatatca ataacaccag tagcttaaat attaccacca actccgacac cacttaccgt      1560
accattatag aaggtaatat aaccaacaaa gcaggtgatt tgaatatcat tgataataaa      1620
ggtaacgctg aaatccaaat tggcggcaac atctcgcaaa aagaaggtaa cctcacgatt      1680
tcctccgata aaatcaatat taccaaacag ataacaatca agaagggtgt taacggagag      1740
aactctgatt caagtacgaa aagtcaagcc aatctaacca ttaaaaccaa agaattgaaa      1800
ttaacacaag acctaaatat ttcaggcttc aacaaagcaa agattgtagc taaagatagt      1860
agtaatttaa ctattggtaa tagtgatgat agcggcaata ctagcgctaa aacagtaact      1920
tttaacaatg ttaaagattc aaaaatctct gctgacggtc acaaggtgac actaaatagc      1980
aaagtgaaaa cacttagtga taatgataac aacactgaag gtggcagtga caacaatacc      2040
ggtttaacta ttactgcaaa agatgtagaa gtaaacaaca atattacttc tcacaaaaca      2100
gtgaacgtct ctgcggcaaa tggagggatt accactaaaa caggtacaac cattaatgca      2160
accgccggta acgtggagat aaccgctcat acaggcagta tccaaggcgg aattgagtcc      2220
aagcctggct ctgtgacaat tgtggcaggc ggcgatactc ttgctgtagg taatatttca      2280
ggcaacgccg ttactgttac tgcaaatagc ggtgcattaa ccactttggc aggctctaca      2340
attaaaggaa ccgagagtat aaccacttca agtcaatcag gtaatatcgg cggtaaaatt      2400
tccggcaaga cagtaaacgt taaagcaact aatagtttaa ccacccaagc agactcaaaa      2460
attgaagcga ctgaaggcga ggctaatgta acaagcaaaa caagcataat tggcggtaca      2520
atttctggtg gcacagtaga agttaccgcg accgaaggtt taaccaccca agcaggctct      2580
acgattactg gaaccgagag cgtgaccact tcaagccaat caggtaatat cggcggcatg      2640
atttctggtg gcaaagtaga agttagcgca accaaagatt taattactaa atccggttca      2700
gagattaaag caacggcggg cgaggtgaat gtaacaagtg caacaggtac aattgacggt      2760
acgatttccg gtaatacggt aaatgttaca gcaaatactg gcgatttaac tgttgaagat      2820
gccgcaaaaa ttgatgcgac aggaggagcc gcgaccctaa ctgcaacatc gggcaaatta      2880
accactaagg ctagttcaag cattacttca gctaataacc aggtaaacct ttcagctaag      2940
gatggtagca ttgggggaaa tatcaatgct gctaatgtaa cactgaatac tacaggcgct      3000
ctaactaccg tgaagggttc aagcattaac gcaaacagcg gcaccttggt tattaacgca      3060
aaagacgctg agctaaatgg tgaggcatca ggtaaccata cagtagtgaa tgcaaccaac      3120
gcaaatggct ccggcagcgt aatcgcgaca acctcaagca gagtgaacat cactggggat      3180
ttaatcacaa taaatggatt aaatatcatt tcaaaaaacg gtataaacac cgtactgtta      3240
aaaggcgtta aaattgatgt gaaatacatt caaccgggta tagcaagcgt agatgaagta      3300
attgaagcga aacgcatcct tgagaaggta aaagatttat ctgatgaaga aagagaagcg      3360
ttagctaaac ttggcgtaag cgctgtacgt tttgctgagc caataatgc cattacgatt      3420 aatacacaaa atgagtttac aaccagacca tcaagtcaag tgacaatttc tgaaggtaag      3480
gtatgtttct taatcggcaa tggtgcaaca atatgcacca atattgctga tattgagcgg      3540
tag                                                                    3543
```

<210> SEQ ID NO 65
<211> LENGTH: 1180
<212> TYPE: PRT
<213> ORGANISM: Haemophilus influenzae

<400> SEQUENCE: 65

Pro Glu Asn Val Tyr Ile Asn Ala Gly Asp Ala Gly Arg Ser Asp Thr

-continued

```
  1               5               10              15
Asn Leu Glu Asn Glu Tyr Thr Gly Thr Gly Glu Ser Ala Asp Thr
            20              25              30

Pro Lys Arg Asn Asn Thr Lys Thr Leu Thr Asn Ser Thr Leu
        35              40              45

Glu Lys Ile Leu Ala Arg Gly Ser Phe Val Asn Ile Thr Ala Asn Asn
        50              55              60

Glu Ile Arg Val Asn Ser Asp Ile Asn Ile Gly Gly Asn Ser His Leu
65              70              75              80

Thr Leu Trp Ser Ser Lys Asn Lys Asn Ser Gly Val Leu Ile Asn Gly
                85              90              95

Asn Ile Thr Ser Thr Ala Asn Gly Asn Leu Thr Ile Tyr Ser Ser Gly
            100             105             110

Trp Val Asp Ile His Lys Asn Ile Thr Leu Glu Ser Gly Arg Leu Asn
            115             120             125

Ile Thr Thr Lys Glu Gly Asp Val Ala Phe Glu Lys Gly Asn Asn Leu
        130             135             140

Thr Ile Thr Gly Gln Gly Thr Ile Thr Ala Gly Asn Asn Lys Gly Phe
145             150             155             160

Arg Phe Glu Asn Val Ser Leu Asn Gly Thr Gly Thr Gly Leu Leu Phe
            165             170             175

Asn Leu Ser Arg Pro Gln Lys Asn Asn Ser Leu Val Thr Asn Tyr Phe
            180             185             190

Asn Gly Thr Leu Asn Ile Ser Gly Ser Val Asn Ile Ser Met Ile Pro
            195             200             205

Pro Asn Ala Thr Ser Asn Trp Tyr Ser Arg Tyr Lys Gly Arg Thr Tyr
        210             215             220

Trp Asn Ile Thr His Leu Asn Ala Ser Glu Asp Ser Asn Phe Asn Leu
225             230             235             240

Thr Ile Asp Ser Ser Ala Glu Asp Gly Ser Ala Pro Leu Leu Ser Ser
            245             250             255

Tyr Thr Leu Asn Gly Ile Ser Phe Thr Thr Asp Thr Thr Phe Asn Val
            260             265             270

Asn Lys Asn Ala Lys Val Asn Phe Asn Ile Lys Ala Pro Ile Gly Thr
        275             280             285

Ile Asn Gln Tyr Asn Asn Leu Asn Tyr Ala Leu Phe Asn Gly Asn Ile
        290             295             300

Ser Val Ser Gly Gly Gly Asn Val Thr Phe Arg Leu Asn Ala Ser Ser
305             310             315             320

Ser Asn Gln Gln Thr Pro Gly Val Ile Ile Asn Ser Lys His Leu Asn
            325             330             335

Ala Ser Lys Gly Ser Ser Leu Arg Phe Glu Thr Thr Gly Ser Thr Lys
            340             345             350

Val Gly Phe Leu Ile Asn Asn Asp Leu Thr Leu Asn Ala Thr Gly Gly
            355             360             365

Asn Ile Ser Leu Leu Gln Val Glu Gly Ile Asp Gly Met Ile Gly Glu
        370             375             380

Gly Val Val Ala Lys Lys Asn Ile Thr Phe Thr Gly Gly Asn Ile Thr
385             390             395             400

Phe Gly Ser Lys Lys Ala Ile Thr Glu Ile Lys Gly Asn Val Thr Ile
            405             410             415

Asn Glu Asn Thr Asn Ala Thr Leu Ile Gly Ser Asp Phe Asn Asp His
        420             425             430
```

```
Lys Lys Pro Leu Asn Ile Lys Gly Asp Val Val Asn Arg Gly Asn Leu
        435                 440                 445

Thr Ala Gly Gly Asn Val Ile Asn Ile Gly Gly Asn Leu Thr Val Glu
    450                 455                 460

Asn Gly Ala Asn Leu Lys Ala Ile Thr Asn Phe Thr Phe Asn Val Gly
465                 470                 475                 480

Gly Leu Phe Asn Asn Lys Gly Asn Ser Asn Ile Ser Ile Ala Arg Gly
                485                 490                 495

Gly Ala Lys Phe Lys Asp Ile Asn Asn Thr Ser Ser Leu Asn Ile Thr
                500                 505                 510

Thr Asn Ser Asp Thr Thr Tyr Arg Thr Ile Ile Glu Gly Asn Ile Thr
            515                 520                 525

Asn Lys Ala Gly Asp Leu Asn Ile Ile Asp Asn Lys Gly Asn Ala Glu
530                 535                 540

Ile Gln Ile Gly Gly Asn Ile Ser Gln Lys Glu Gly Asn Leu Thr Ile
545                 550                 555                 560

Ser Ser Asp Lys Ile Asn Ile Thr Lys Gln Ile Thr Ile Lys Lys Gly
                565                 570                 575

Val Asn Gly Glu Asn Ser Asp Ser Ser Thr Lys Ser Gln Ala Asn Leu
            580                 585                 590

Thr Ile Lys Thr Lys Glu Leu Lys Leu Thr Gln Asp Leu Asn Ile Ser
        595                 600                 605

Gly Phe Asn Lys Ala Lys Ile Val Ala Lys Asp Ser Ser Asn Leu Thr
        610                 615                 620

Ile Gly Asn Ser Asp Asp Ser Gly Asn Thr Ser Ala Lys Thr Val Thr
625                 630                 635                 640

Phe Asn Asn Val Lys Asp Ser Lys Ile Ser Ala Asp Gly His Lys Val
                645                 650                 655

Thr Leu Asn Ser Lys Val Lys Thr Leu Ser Asp Asn Asp Asn Asn Thr
            660                 665                 670

Glu Gly Gly Ser Asp Asn Asn Thr Gly Leu Thr Ile Thr Ala Lys Asp
        675                 680                 685

Val Glu Val Asn Asn Asn Ile Thr Ser His Lys Thr Val Asn Val Ser
    690                 695                 700

Ala Ala Asn Gly Gly Ile Thr Thr Lys Thr Gly Thr Thr Ile Asn Ala
705                 710                 715                 720

Thr Ala Gly Asn Val Glu Ile Thr Ala His Thr Gly Ser Ile Gln Gly
                725                 730                 735

Gly Ile Glu Ser Lys Pro Gly Ser Val Thr Ile Val Ala Gly Gly Asp
            740                 745                 750

Thr Leu Ala Val Gly Asn Ile Ser Gly Asn Ala Val Thr Val Thr Ala
        755                 760                 765

Asn Ser Gly Ala Leu Thr Thr Leu Ala Gly Ser Thr Ile Lys Gly Thr
770                 775                 780

Glu Ser Ile Thr Thr Ser Ser Gln Ser Gly Asn Ile Gly Gly Lys Ile
785                 790                 795                 800

Ser Gly Lys Thr Val Asn Val Lys Ala Thr Asn Ser Leu Thr Thr Gln
                805                 810                 815

Ala Asp Ser Lys Ile Glu Ala Thr Glu Gly Glu Ala Asn Val Thr Ser
            820                 825                 830

Lys Thr Ser Ile Ile Gly Gly Thr Ile Ser Gly Gly Thr Val Glu Val
        835                 840                 845
```

```
Thr Ala Thr Glu Gly Leu Thr Thr Gln Ala Gly Ser Thr Ile Thr Gly
    850                 855                 860
Thr Glu Ser Val Thr Thr Ser Gln Ser Gly Asn Ile Gly Gly Met
865                 870                 875                 880
Ile Ser Gly Gly Lys Val Glu Val Ser Ala Thr Lys Asp Leu Ile Thr
                885                 890                 895
Lys Ser Gly Ser Glu Ile Lys Ala Thr Ala Gly Glu Val Asn Val Thr
            900                 905                 910
Ser Ala Thr Gly Thr Ile Asp Gly Thr Ile Ser Gly Asn Thr Val Asn
            915                 920                 925
Val Thr Ala Asn Thr Gly Asp Leu Thr Val Glu Asp Ala Ala Lys Ile
    930                 935                 940
Asp Ala Thr Gly Gly Ala Ala Thr Leu Thr Ala Thr Ser Gly Lys Leu
945                 950                 955                 960
Thr Thr Lys Ala Ser Ser Ser Ile Thr Ser Ala Asn Asn Gln Val Asn
                965                 970                 975
Leu Ser Ala Lys Asp Gly Ser Ile Gly Gly Asn Ile Asn Ala Ala Asn
            980                 985                 990
Val Thr Leu Asn Thr Thr Gly Ala Leu Thr Thr Val Lys Gly Ser Ser
            995                 1000                1005
Ile Asn Ala Asn Ser Gly Thr Leu Val Ile Asn Ala Lys Asp Ala Glu
    1010                1015                1020
Leu Asn Gly Glu Ala Ser Gly Asn His Thr Val Val Asn Ala Thr Asn
1025                1030                1035                1040
Ala Asn Gly Ser Gly Ser Val Ile Ala Thr Thr Ser Ser Arg Val Asn
                1045                1050                1055
Ile Thr Gly Asp Leu Ile Thr Ile Asn Gly Leu Asn Ile Ile Ser Lys
            1060                1065                1070
Asn Gly Ile Asn Thr Val Leu Leu Lys Gly Val Lys Ile Asp Val Lys
            1075                1080                1085
Tyr Ile Gln Pro Gly Ile Ala Ser Val Asp Glu Val Ile Glu Ala Lys
    1090                1095                1100
Arg Ile Leu Glu Lys Val Lys Asp Leu Ser Asp Glu Glu Arg Glu Ala
1105                1110                1115                1120
Leu Ala Lys Leu Gly Val Ser Ala Val Arg Phe Ala Glu Pro Asn Asn
                1125                1130                1135
Ala Ile Thr Ile Asn Thr Gln Asn Glu Phe Thr Thr Arg Pro Ser Ser
            1140                1145                1150
Gln Val Thr Ile Ser Glu Gly Lys Val Cys Phe Leu Ile Gly Asn Gly
            1155                1160                1165
Ala Thr Ile Cys Thr Asn Ile Ala Asp Ile Glu Arg
    1170                1175                1180

<210> SEQ ID NO 66
<211> LENGTH: 5116
<212> TYPE: DNA
<213> ORGANISM: Haemophilus influenzae

<400> SEQUENCE: 66
acagcgttct cttaatacta gtacaaaccc acaataaaat atgacaaaca acaattacaa      60
cacctttttt gcagtctata tgcaaatatt ttaaaaaata gtataaatcc gccatataaa     120
atggtataat ctttcatctt tcatctttca tctttcatct ttcatctttc atctttcatc     180
tttcatcttt catctttcat ctttcatctt tcatctttca tctttcatct ttcatctttc     240
```

-continued

```
acatgccctg atgaaccgag ggaagggagg gaggggcaag aatgaagagg gagctgaacg      300
aacgcaaatg ataaagtaat ttaattgttc aactaacctt aggagaaaat atgaacaagc      360
tatatcgtct caaattcagc aaacgcctga atgctttggt tgctgtgtct gaattggcac      420
ggggttgtga ccattccaca gaaaaaggca gcgaaaaacc tgctcgcatg aaagtgcgtc      480
acttagcgtt aaagccactt tccgctatgt tactatcttt aggtgtaaca tctattccac      540
aatctgtttt agcaagcggc ttacaaggaa tggatgtagt acacggcaca gccactatgc      600
aagtagatgg taataaaacc attatccgca acagtgttga cgatatcatt aattggaaac      660
aatttaacat cgaccaaaat gaaatggtgc agtttttaca agaaacaac aactccgccg       720 tattcaaccg tgttacatct aaccaaatct cccaattaaa agggatttta gattctaacg      780
gacaagtctt tttaatcaac ccaatggta tcacaatagg taaagacgca attattaaca       840
ctaatggctt tacggcttct acgctagaca tttctaacga aaacatcaag gcgcgtaatt      900
tcaccttcga gcaaaccaaa gataaagcgc tcgctgaaat tgtgaatcac ggtttaatta      960
ctgtcggtaa agacggcagt gtaaatctta ttggtggcaa agtgaaaaac gagggtgtga     1020
ttagcgtaaa tggtggcagc atttctttac tcgcagggca aaaaatcacc atcagcgata     1080
taataaaccc aaccattact tacagcattg ccgcgcctga aatgaagcg gtcaatctgg      1140 gcgatatttt tgccaaaggc ggtaacatta atgtccgtgc tgccactatt cgaaaccaag     1200
gtaaactttc tgctgattct gtaagcaaag ataaaagcgg caatattgtt ctttccgcca     1260
aagagggtga agcggaaatt ggcggtgtaa tttccgctca aaatcagcaa gctaaaggcg     1320
gcaagctgat gattacaggc gataaagtca cattaaaaac aggtgcagtt atcgaccttt     1380
caggtaaaga aggggagaa acttaccttg gcggtgacga gcgcggcgaa ggtaaaaagg      1440
gcattcaatt agcaaagaaa acctctttag aaaaaggctc aaccatcaat gtatcaggca     1500
aagaaaaagg cggacgcgct attgtgtggg gcgatattgc gttaattgac ggcaatatta     1560
acgctcaagg tagtggtgat atcgctaaaa ccggtggttt tgtggagacg tcgggcatg      1620 atttattcat caaagacaat gcaattgttg acgccaaaga gtggttgtta gacccggata     1680
atgtatctat taatgcagaa acagcaggac gcagcaatac ttcagaagac gatgaataca     1740
cgggatccgg gaatagtgcc agcaccccaa aacgaaacaa agaaaagaca acattaacaa     1800
acacaactct tgagagtata ctaaaaaaag gtacctttgt taacatcact gctaatcaac     1860
gcatctatgt caatagctcc attaatttat ccaatggcag cttaactctt tggagtgagg     1920
gtcggagcgg tggcggcgtt gagattaaca acgatattac caccggtgat gataccagag     1980
gtgcaaactt aacaatttac tcaggcggct gggttgatgt tcataaaaat atctcactcg     2040
gggcgcaagg taacataaac attacagcta aacaagatat cgcctttgag aaaggaagca     2100
accaagtcat tacaggtcaa gggactatta cctcaggcaa tcaaaaaggt tttagattta     2160
ataatgtctc tctaaacggc actggcagcg gactgcaatt caccactaaa agaaccaata     2220
aatacgctat cacaaataaa tttgaaggga ctttaaatat ttcagggaaa gtgaacatct     2280
caatggtttt acctaaaaat gaaagtggat atgataaatt caaaggacgc acttactgga     2340
atttaacctc cttaaatgtt tccgagagtg gcgagtttaa cctcactatt gactccagag     2400
gaagcgatag tgcaggcaca cttacccagc cttataattt aaacggtata tcattcaaca     2460
aagacactac ctttaatgtt gaacgaaatg caagagtcaa ctttgacatc aaggcaccaa     2520
tagggataaa taagtattct agtttgaatt acgcatcatt taatgaaac atttcagttt      2580 cgggaggggg gagtgttgat ttcacacttc tcgcctcatc ctctaacgtc caaaccccg      2640
```

```
gtgtagttat aaattctaaa tactttaatg tttcaacagg gtcaagttta agatttaaaa   2700
cttcaggctc aacaaaaact ggcttctcaa tagagaaaga tttaacttta aatgccaccg   2760
gaggcaacat aacacttttg caagttgaag gcaccgatgg aatgattggt aaaggcattg   2820
tagccaaaaa aaacataacc tttgaaggag gtaacatcac ctttggctcc aggaaagccg   2880
taacagaaat cgaaggcaat gttactatca ataacaacg taacgtcact cttatcggtt   2940
cggattttga caaccatcaa aaacctttaa ctattaaaaa agatgtcatc attaatagcg   3000
gcaaccttac cgctggaggc aatattgtca atatagccgg aaatcttacc gttgaaagta   3060
acgctaattt caaagctatc acaaatttca cttttaatgt aggcggcttg tttgacaaca   3120
aaggcaattc aaatatttcc attgccaaag gaggggctcg ctttaaagac attgataatt   3180
ccaagaattt aagcatcacc accaactcca gctccactta ccgcactatt ataagcggca   3240
atataaccaa taaaaacggt gatttaaata ttacgaacga aggtagtgat actgaaatgc   3300
aaattggcgg cgatgtctcg caaaagaag gtaatctcac gatttcttct gacaaaatca   3360
atattaccaa acagataaca atcaaggcag gtgttgatgg ggagaattcc gattcagacg   3420
cgacaaacaa tgccaatcta accattaaaa ccaaagaatt gaaattaacg caagacctaa   3480
atatttcagg tttcaataaa gcagagatta cagctaaaga tggtagtgat ttaactattg   3540
gtaacaccaa tagtgctgat ggtactaatg ccaaaaaagt aacctttaac caggttaaag   3600
attcaaaaat ctctgctgac ggtcacaagg tgacactaca cagcaaagtg gaaacatccg   3660
gtagtaataa caacactgaa gatagcagtg acaataatgc cggcttaact atcgatgcaa   3720
aaaatgtaac agtaaacaac aatattactt ctcacaaagc agtgagcatc tctgcgacaa   3780
gtggagaaat taccactaaa acaggtacaa ccattaacgc aaccactggt aacgtggaga   3840
taaccgctca aacaggtagt atcctaggtg gaattgagtc cagctctggc tctgtaacac   3900
ttactgcaac cgagggcgct cttgctgtaa gcaatatttc gggcaacacc gttactgtta   3960
ctgcaaatag cggtgcatta accactttgg caggctctac aattaaagga accgagagtg   4020
taaccacttc aagtcaatca ggcgatatcg gcggtacgat ttctggtggc acagtagagg   4080
ttaaagcaac cgaaagttta accactcaat ccaattcaaa aattaaagca acaacaggcg   4140
aggctaacgt aacaagtgca acaggtacaa ttggtggtac gatttccggt aatacggtaa   4200
atgttacggc aaacgctggc gatttaacag ttgggaatgg cgcagaaatt aatgcgacag   4260
aaggagctgc aaccttaact acatcatcgg gcaaattaac taccgaagct agttcacaca   4320
ttacttcagc caagggtcag gtaaatcttt cagctcagga tggtagcgtt gcaggaagta   4380
ttaatgccgc caatgtgaca ctaaatacta caggcacttt aactaccgtg aagggttcaa   4440
acattaatgc aaccagcggt accttggtta ttaacgcaaa agacgctgag ctaaatggcg   4500
cagcattggg taaccacaca gtggtaaatg caaccaacgc aaatggctcc ggcagcgtaa   4560
tcgcgacaac ctcaagcaga gtgaacatca ctggggattt aatcacaata aatggattaa   4620
atatcatttc aaaaaacggt ataaacaccg tactgttaaa aggcgttaaa attgatgtga   4680
aatacattca accgggtata gcaagcgtag atgaagtaat tgaagcgaaa cgcatccttg   4740
agaaggtaaa agatttatct gatgaagaaa gagaagcgtt agctaaactt ggagtaagtg   4800
ctgtacgttt tattgagcca aataatacaa ttacagtcga tacacaaaat gaatttgcaa   4860
ccagaccatt aagtcgaata gtgatttctg aaggcagggc gtgtttctca aacagtgatg   4920
gcgcgacggt gtgcgttaat atcgctgata acgggcggta gcggtcagta attgacaagg   4980
```

```
tagatttcat cctgcaatga agtcatttta ttttcgtatt atttactgtg tgggttaaag    5040
ttcagtacgg gctttaccca tcttgtaaaa aattacggag aatacaataa agtattttta    5100
acaggttatt attatg                                                    5116
```

<210> SEQ ID NO 67
<211> LENGTH: 1536
<212> TYPE: PRT
<213> ORGANISM: Haemophilus influenzae

<400> SEQUENCE: 67

```
Met Asn Lys Leu Tyr Arg Leu Lys Phe Ser Lys Arg Leu Asn Ala Leu
 1               5                  10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Asp Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350
```

-continued

```
Leu Gly Gly Asp Glu Arg Gly Glu Gly Lys Lys Gly Ile Gln Leu Ala
        355                 360                 365
Lys Lys Thr Ser Leu Glu Lys Gly Ser Thr Ile Asn Val Ser Gly Lys
    370                 375                 380
Glu Lys Gly Gly Arg Ala Ile Val Trp Gly Asp Ile Ala Leu Ile Asp
385                 390                 395                 400
Gly Asn Ile Asn Ala Gln Gly Ser Gly Asp Ile Ala Lys Thr Gly Gly
                405                 410                 415
Phe Val Glu Thr Ser Gly His Asp Leu Phe Ile Lys Asp Asn Ala Ile
                420                 425                 430
Val Asp Ala Lys Glu Trp Leu Leu Asp Pro Asp Asn Val Ser Ile Asn
            435                 440                 445
Ala Glu Thr Ala Gly Arg Ser Asn Thr Ser Glu Asp Asp Glu Tyr Thr
    450                 455                 460
Gly Ser Gly Asn Ser Ala Ser Thr Pro Lys Arg Asn Lys Glu Lys Thr
465                 470                 475                 480
Thr Leu Thr Asn Thr Thr Leu Glu Ser Ile Leu Lys Lys Gly Thr Phe
                485                 490                 495
Val Asn Ile Thr Ala Asn Gln Arg Ile Tyr Val Asn Ser Ser Ile Asn
                500                 505                 510
Leu Ser Asn Gly Ser Leu Thr Leu Trp Ser Glu Gly Arg Ser Gly Gly
            515                 520                 525
Gly Val Glu Ile Asn Asn Asp Ile Thr Thr Gly Asp Asp Thr Arg Gly
    530                 535                 540
Ala Asn Leu Thr Ile Tyr Ser Gly Gly Trp Val Asp Val His Lys Asn
545                 550                 555                 560
Ile Ser Leu Gly Ala Gln Gly Asn Ile Asn Ile Thr Ala Lys Gln Asp
                565                 570                 575
Ile Ala Phe Glu Lys Gly Ser Asn Gln Val Ile Thr Gly Gln Gly Thr
                580                 585                 590
Ile Thr Ser Gly Asn Gln Lys Gly Phe Arg Phe Asn Asn Val Ser Leu
            595                 600                 605
Asn Gly Thr Gly Ser Gly Leu Gln Phe Thr Thr Lys Arg Thr Asn Lys
    610                 615                 620
Tyr Ala Ile Thr Asn Lys Phe Glu Gly Thr Leu Asn Ile Ser Gly Lys
625                 630                 635                 640
Val Asn Ile Ser Met Val Leu Pro Lys Asn Glu Ser Gly Tyr Asp Lys
                645                 650                 655
Phe Lys Gly Arg Thr Tyr Trp Asn Leu Thr Ser Leu Asn Val Ser Glu
                660                 665                 670
Ser Gly Glu Phe Asn Leu Thr Ile Asp Ser Arg Gly Ser Asp Ser Ala
            675                 680                 685
Gly Thr Leu Thr Gln Pro Tyr Asn Leu Asn Gly Ile Ser Phe Asn Lys
    690                 695                 700
Asp Thr Thr Phe Asn Val Glu Arg Asn Ala Arg Val Asn Phe Asp Ile
705                 710                 715                 720
Lys Ala Pro Ile Gly Ile Asn Lys Tyr Ser Ser Leu Asn Tyr Ala Ser
                725                 730                 735
Phe Asn Gly Asn Ile Ser Val Ser Gly Gly Ser Val Asp Phe Thr
                740                 745                 750
Leu Leu Ala Ser Ser Ser Asn Val Gln Thr Pro Gly Val Val Ile Asn
            755                 760                 765
```

```
Ser Lys Tyr Phe Asn Val Ser Thr Gly Ser Ser Leu Arg Phe Lys Thr
    770                 775                 780

Ser Gly Ser Thr Lys Thr Gly Phe Ser Ile Glu Lys Asp Leu Thr Leu
785                 790                 795                 800

Asn Ala Thr Gly Gly Asn Ile Thr Leu Leu Gln Val Glu Gly Thr Asp
                805                 810                 815

Gly Met Ile Gly Lys Gly Ile Val Ala Lys Lys Asn Ile Thr Phe Glu
            820                 825                 830

Gly Gly Asn Ile Thr Phe Gly Ser Arg Lys Ala Val Thr Glu Ile Glu
        835                 840                 845

Gly Asn Val Thr Ile Asn Asn Asn Ala Asn Val Thr Leu Ile Gly Ser
    850                 855                 860

Asp Phe Asp Asn His Gln Lys Pro Leu Thr Ile Lys Lys Asp Val Ile
865                 870                 875                 880

Ile Asn Ser Gly Asn Leu Thr Ala Gly Gly Asn Ile Val Asn Ile Ala
                885                 890                 895

Gly Asn Leu Thr Val Glu Ser Asn Ala Asn Phe Lys Ala Ile Thr Asn
            900                 905                 910

Phe Thr Phe Asn Val Gly Gly Leu Phe Asp Asn Lys Gly Asn Ser Asn
        915                 920                 925

Ile Ser Ile Ala Lys Gly Gly Ala Arg Phe Lys Asp Ile Asp Asn Ser
    930                 935                 940

Lys Asn Leu Ser Ile Thr Thr Asn Ser Ser Thr Tyr Arg Thr Ile
945                 950                 955                 960

Ile Ser Gly Asn Ile Thr Asn Lys Asn Gly Asp Leu Asn Ile Thr Asn
                965                 970                 975

Glu Gly Ser Asp Thr Glu Met Gln Ile Gly Gly Asp Val Ser Gln Lys
            980                 985                 990

Glu Gly Asn Leu Thr Ile Ser Ser Asp Lys Ile Asn Ile Thr Lys Gln
        995                 1000                1005

Ile Thr Ile Lys Ala Gly Val Asp Gly Glu Asn Ser Asp Ser Asp Ala
    1010                1015                1020

Thr Asn Asn Ala Asn Leu Thr Ile Lys Thr Lys Glu Leu Lys Leu Thr
1025                1030                1035                1040

Gln Asp Leu Asn Ile Ser Gly Phe Asn Lys Ala Glu Ile Thr Ala Lys
                1045                1050                1055

Asp Gly Ser Asp Leu Thr Ile Gly Asn Thr Asn Ser Ala Asp Gly Thr
            1060                1065                1070

Asn Ala Lys Lys Val Thr Phe Asn Gln Val Lys Asp Ser Lys Ile Ser
        1075                1080                1085

Ala Asp Gly His Lys Val Thr Leu His Ser Lys Val Glu Thr Ser Gly
    1090                1095                1100

Ser Asn Asn Asn Thr Glu Asp Ser Ser Asp Asn Asn Ala Gly Leu Thr
1105                1110                1115                1120

Ile Asp Ala Lys Asn Val Thr Val Asn Asn Ile Thr Ser His Lys
                1125                1130                1135

Ala Val Ser Ile Ser Ala Thr Ser Gly Glu Ile Thr Thr Lys Thr Gly
            1140                1145                1150

Thr Thr Ile Asn Ala Thr Gly Asn Val Glu Ile Thr Ala Gln Thr
        1155                1160                1165

Gly Ser Ile Leu Gly Gly Ile Glu Ser Ser Gly Ser Val Thr Leu
    1170                1175                1180

Thr Ala Thr Glu Gly Ala Leu Ala Val Ser Asn Ile Ser Gly Asn Thr
```

```
                1185                1190                1195                1200
Val Thr Val Thr Ala Asn Ser Gly Ala Leu Thr Leu Ala Gly Ser
                    1205                1210                1215
Thr Ile Lys Gly Thr Glu Ser Val Thr Thr Ser Ser Gln Ser Gly Asp
                1220                1225                1230
Ile Gly Gly Thr Ile Ser Gly Gly Thr Val Glu Val Lys Ala Thr Glu
            1235                1240                1245
Ser Leu Thr Thr Gln Ser Asn Ser Lys Ile Lys Ala Thr Thr Gly Glu
        1250                1255                1260
Ala Asn Val Thr Ser Ala Thr Gly Thr Ile Gly Gly Thr Ile Ser Gly
1265                1270                1275                1280
Asn Thr Val Asn Val Thr Ala Asn Ala Gly Asp Leu Thr Val Gly Asn
                1285                1290                1295
Gly Ala Glu Ile Asn Ala Thr Glu Gly Ala Ala Thr Leu Thr Thr Ser
                    1300                1305                1310
Ser Gly Lys Leu Thr Thr Glu Ala Ser Ser His Ile Thr Ser Ala Lys
                1315                1320                1325
Gly Gln Val Asn Leu Ser Ala Gln Asp Gly Ser Val Ala Gly Ser Ile
        1330                1335                1340
Asn Ala Ala Asn Val Thr Leu Asn Thr Thr Gly Thr Leu Thr Thr Val
1345                1350                1355                1360
Lys Gly Ser Asn Ile Asn Ala Thr Ser Gly Thr Leu Val Ile Asn Ala
                1365                1370                1375
Lys Asp Ala Glu Leu Asn Gly Ala Ala Leu Gly Asn His Thr Val Val
                    1380                1385                1390
Asn Ala Thr Asn Ala Asn Gly Ser Gly Ser Val Ile Ala Thr Thr Ser
                1395                1400                1405
Ser Arg Val Asn Ile Thr Gly Asp Leu Ile Thr Ile Asn Gly Leu Asn
        1410                1415                1420
Ile Ile Ser Lys Asn Gly Ile Asn Thr Val Leu Leu Lys Gly Val Lys
1425                1430                1435                1440
Ile Asp Val Lys Tyr Ile Gln Pro Gly Ile Ala Ser Val Asp Glu Val
                1445                1450                1455
Ile Glu Ala Lys Arg Ile Leu Glu Lys Val Lys Asp Leu Ser Asp Glu
            1460                1465                1470
Glu Arg Glu Ala Leu Ala Lys Leu Gly Val Ser Ala Val Arg Phe Ile
        1475                1480                1485
Glu Pro Asn Asn Thr Ile Thr Val Asp Thr Gln Asn Glu Phe Ala Thr
    1490                1495                1500
Arg Pro Leu Ser Arg Ile Val Ile Ser Glu Gly Arg Ala Cys Phe Ser
1505                1510                1515                1520
Asn Ser Asp Gly Ala Thr Val Cys Val Asn Ile Ala Asp Asn Gly Arg
                1525                1530                1535
```

<210> SEQ ID NO 68
<211> LENGTH: 3285
<212> TYPE: DNA
<213> ORGANISM: Haemophilus influenzae

<400> SEQUENCE: 68
ccggataatg tatctattaa tgcagaaaca gcaggacgca gcaatacttc agaagacgat    60
gaatacacgg gatccgggaa tagtgccagc accccaaaac gaaacaaaga aaagacaaca   120
ttaacaaaca caactcttga gagtatacta aaaaaaggta cctttgttaa catcactgct   180

-continued

| | |
|---|---|
| aatcaacgca tctatgtcaa tagctccatt aatttatcca atggcagctt aactctttgg | 240 |
| agtgagggtc ggagcggtgg cggcgttgag attaacaacg atattaccac cggtgatgat | 300 |
| accagaggtc caaacttaac aatttactca ggcggctggg ttgatgttca taaaaatatc | 360 |
| tcactcgggg cgcaaggtaa cataaacatt acagctaaac aagatatcgc ctttgagaaa | 420 |
| ggaagcaacc aagtcattac aggtcaaggg actattaccT caggcaatca aaaggtttt | 480 |
| agatttaata atgtctctct aaacggcact ggcagcggac tgcaattcac cactaaaaga | 540 |
| accaataaat acgctatcac aaataaattt gaagggactt taaatatttc agggaaagtg | 600 |
| aacatctcaa tggttttacc taaaaatgaa agtggatatg ataaattcaa aggacgcact | 660 |
| tactggaatt taacctcctt aaatgtttcc gagagtggcg agtttaacct cactattgac | 720 |
| tccagaggaa gcgatagtgc aggcacactt acccagcctt ataatttaaa cggtatatca | 780 |
| ttcaacaaag acactacctt taatgttgaa cgaaatgcaa gagtcaactt tgacatcaag | 840 |
| gcaccaatag ggataaataa gtattctagt ttgaattacg catcatttaa tggaaacatt | 900 |
| tcagtttcgg gaggggggag tgttgatttc acacttctcg cctcatcctc taacgtccaa | 960 |
| accccggtg tagttataaa ttctaaatac tttaatgttt caacagggtc aagtttaaga | 1020 |
| tttaaaactt caggctcaac aaaaactggc ttctcaatag agaaagattt aactttaaat | 1080 |
| gccaccggag gcaacataac acttttgcaa gttgaaggca ccgatggaat gattggtaaa | 1140 |
| ggcattgtag ccaaaaaaaa cataacctt gaaggaggta acatcacctt tggctccagg | 1200 |
| aaagccgtaa cagaaatcga aggcaatgtt actatcaata caacgctaa cgtcactctt | 1260 |
| atcggttcgg attttgacaa ccatcaaaaa cctttaacta ttaaaaaaga tgtcatcatt | 1320 |
| aatagcggca accttaccgc tggaggcaat attgtcaata tagccggaaa tcttaccgtt | 1380 |
| gaaagtaacg ctaatttcaa agctatcaca aatttcactt ttaatgtagg cggcttgttt | 1440 |
| gacaacaaag gcaattcaaa tatttccatt gccaaaggag gggctcgctt taagacatt | 1500 |
| gataattcca agaatttaag catcaccacc aactccagct ccacttaccg cactattata | 1560 |
| agcggcaata taaccaataa aaacggtgat ttaaatatta cgaacgaagg tagtgatact | 1620 |
| gaaatgcaaa ttggcggcga tgtctcgcaa aaagaaggta atctcacgat ttcttctgac | 1680 |
| aaaatcaata ttaccaaaca gataacaatc aaggcaggtt tgatgggga gaattccgat | 1740 |
| tcagacgcga caaacaatgc caatctaacc attaaaacca aagaattgaa attaacgcaa | 1800 |
| gacctaaata tttcaggttt caataaagca gagattacag ctaaagatgg tagtgatta | 1860 |
| actattggta acaccaatag tgctgatggt actaatgcca aaaaagtaac ctttaaccag | 1920 |
| gttaaagatt caaaaatctc tgctgacggt cacaaggtga cactacacag caaagtggaa | 1980 |
| acatccggta gtaataacaa cactgaagat agcagtgaca ataatgccgg cttaactatc | 2040 |
| gatgcaaaaa atgtaacagt aaacaacaat attacttctc acaaagcagt gagcatctct | 2100 |
| gcgacaagtg gagaaattac cactaaaaca ggtacaacca ttaacgcaac cactggtaac | 2160 |
| gtggagataa ccgctcaaac aggtagtatc ctaggtggaa ttgagtccag ctctggctct | 2220 |
| gtaacactta ctgcaaccga gggcgctctt gctgtaagca atatttcggg caacaccgtt | 2280 |
| actgttactg caaatagcgg tgcattaacc actttggcag gctctacaat taaaggaacc | 2340 |
| gagagtgtaa ccacttcaag tcaatcaggc gatatcggcg tacgatttc tggtggcaca | 2400 |
| gtagaggtta aagcaaccga aagtttaacc actcaatcca attcaaaaat taaagcaaca | 2460 |
| acaggcgagg ctaacgtaac aagtgcaaca ggtacaattg tgtgtacgat ttccggtaat | 2520 |
| acggtaaatg ttacggcaaa cgctggcgat ttaacagttg ggaatggcgc agaaattaat | 2580 |

-continued

```
gcgacagaag gagctgcaac cttaactaca tcatcgggca aattaactac cgaagctagt   2640
tcacacatta cttcagccaa gggtcaggta aatctttcag ctcaggatgg tagcgttgca   2700
ggaagtatta atgccgccaa tgtgacacta aatactacag gcactttaac taccgtgaag   2760
ggttcaaaca ttaatgcaac cagcggtacc ttggttatta acgcaaaaga cgctgagcta   2820
aatggcgcag cattgggtaa ccacacagtg gtaaatgcaa ccaacgcaaa tggctccggc   2880
agcgtaatcg cgacaacctc aagcagagtg aacatcactg gggatttaat cacaataaat   2940
ggattaaata tcatttcaaa aaacggtata acaccgtact tgttaaaagg cgttaaaatt   3000
gatgtgaaat acattcaacc gggtatagca agcgtagatg aagtaattga agcgaaacgc   3060
atccttgaga aggtaaaaga tttatctgat gaagaaagag aagcgttagc taaacttgga   3120
gtaagtgctg tacgttttat tgagccaaat aatacaatta cagtcgatac acaaaatgaa   3180
tttgcaacca gaccattaag tcgaatagtg atttctgaag gcagggcgtg tttctcaaac   3240
agtgatggcg cgacggtgtg cgttaatatc gctgataacg ggcgg               3285
```

<210> SEQ ID NO 69
<211> LENGTH: 1095
<212> TYPE: PRT
<213> ORGANISM: Haemophilus influenzae

<400> SEQUENCE: 69

| Pro | Asp | Asn | Val | Ser | Ile | Asn | Ala | Glu | Thr | Ala | Gly | Arg | Ser | Asn | Thr |
|---|---|---|---|---|---|---|---|---|---|---|---|---|---|---|---|
| 1 | | | | 5 | | | | | 10 | | | | | 15 | |

| Ser | Glu | Asp | Asp | Glu | Tyr | Thr | Gly | Ser | Gly | Asn | Ser | Ala | Ser | Thr | Pro |
| | | | 20 | | | | | 25 | | | | | 30 | | |

| Lys | Arg | Asn | Lys | Glu | Lys | Thr | Thr | Leu | Thr | Asn | Thr | Thr | Leu | Glu | Ser |
| | | 35 | | | | | 40 | | | | | 45 | | | |

| Ile | Leu | Lys | Lys | Gly | Thr | Phe | Val | Asn | Ile | Thr | Ala | Asn | Gln | Arg | Ile |
| | 50 | | | | | 55 | | | | | 60 | | | | |

| Tyr | Val | Asn | Ser | Ser | Ile | Asn | Leu | Ser | Asn | Gly | Ser | Leu | Thr | Leu | Trp |
| 65 | | | | | 70 | | | | | 75 | | | | | 80 |

| Ser | Glu | Gly | Arg | Ser | Gly | Gly | Val | Glu | Ile | Asn | Asn | Asp | Ile | Thr |
| | | | | 85 | | | | | 90 | | | | | 95 |

| Thr | Gly | Asp | Asp | Thr | Arg | Gly | Ala | Asn | Leu | Thr | Ile | Tyr | Ser | Gly | Gly |
| | | | 100 | | | | | 105 | | | | | 110 | | |

| Trp | Val | Asp | Val | His | Lys | Asn | Ile | Ser | Leu | Gly | Ala | Gln | Gly | Asn | Ile |
| | | 115 | | | | | 120 | | | | | 125 | | | |

| Asn | Ile | Thr | Ala | Lys | Gln | Asp | Ile | Ala | Phe | Glu | Lys | Gly | Ser | Asn | Gln |
| | 130 | | | | | 135 | | | | | 140 | | | | |

| Val | Ile | Thr | Gly | Gln | Gly | Thr | Ile | Thr | Ser | Gly | Asn | Gln | Lys | Gly | Phe |
| 145 | | | | | 150 | | | | | 155 | | | | | 160 |

| Arg | Phe | Asn | Asn | Val | Ser | Leu | Asn | Gly | Thr | Gly | Ser | Gly | Leu | Gln | Phe |
| | | | | 165 | | | | | 170 | | | | | 175 |

| Thr | Thr | Lys | Arg | Thr | Asn | Lys | Tyr | Ala | Ile | Thr | Asn | Lys | Phe | Glu | Gly |
| | | | 180 | | | | | 185 | | | | | 190 | | |

| Thr | Leu | Asn | Ile | Ser | Gly | Lys | Val | Asn | Ile | Ser | Met | Val | Leu | Pro | Lys |
| | | 195 | | | | | 200 | | | | | 205 | | | |

| Asn | Glu | Ser | Gly | Tyr | Asp | Lys | Phe | Lys | Gly | Arg | Thr | Tyr | Trp | Asn | Leu |
| | 210 | | | | | 215 | | | | | 220 | | | | |

| Thr | Ser | Leu | Asn | Val | Ser | Glu | Ser | Gly | Glu | Phe | Asn | Leu | Thr | Ile | Asp |
| 225 | | | | | 230 | | | | | 235 | | | | | 240 |

| Ser | Arg | Gly | Ser | Asp | Ser | Ala | Gly | Thr | Leu | Thr | Gln | Pro | Tyr | Asn | Leu |

-continued

```
                    245                 250                 255
Asn Gly Ile Ser Phe Asn Lys Asp Thr Thr Phe Asn Val Glu Arg Asn
                260                 265                 270
Ala Arg Val Asn Phe Asp Ile Lys Ala Pro Ile Gly Ile Asn Lys Tyr
            275                 280                 285
Ser Ser Leu Asn Tyr Ala Ser Phe Asn Gly Asn Ile Ser Val Ser Gly
        290                 295                 300
Gly Gly Ser Val Asp Phe Thr Leu Leu Ala Ser Ser Ser Asn Val Gln
305                 310                 315                 320
Thr Pro Gly Val Val Ile Asn Ser Lys Tyr Phe Asn Val Ser Thr Gly
                325                 330                 335
Ser Ser Leu Arg Phe Lys Thr Ser Gly Ser Thr Lys Thr Gly Phe Ser
            340                 345                 350
Ile Glu Lys Asp Leu Thr Leu Asn Ala Thr Gly Gly Asn Ile Thr Leu
        355                 360                 365
Leu Gln Val Glu Gly Thr Asp Gly Met Ile Gly Lys Gly Ile Val Ala
    370                 375                 380
Lys Lys Asn Ile Thr Phe Glu Gly Gly Asn Ile Thr Phe Gly Ser Arg
385                 390                 395                 400
Lys Ala Val Thr Glu Ile Glu Gly Asn Val Thr Ile Asn Asn Asn Ala
                405                 410                 415
Asn Val Thr Leu Ile Gly Ser Asp Phe Asp Asn His Gln Lys Pro Leu
            420                 425                 430
Thr Ile Lys Lys Asp Val Ile Asn Ser Gly Asn Leu Thr Ala Gly
        435                 440                 445
Gly Asn Ile Val Asn Ile Ala Gly Asn Leu Thr Val Glu Ser Asn Ala
    450                 455                 460
Asn Phe Lys Ala Ile Thr Asn Phe Thr Phe Asn Val Gly Gly Leu Phe
465                 470                 475                 480
Asp Asn Lys Gly Asn Ser Asn Ile Ser Ile Ala Lys Gly Gly Ala Arg
                485                 490                 495
Phe Lys Asp Ile Asp Asn Ser Lys Asn Leu Ser Ile Thr Thr Asn Ser
            500                 505                 510
Ser Ser Thr Tyr Arg Thr Ile Ile Ser Gly Asn Ile Thr Asn Lys Asn
        515                 520                 525
Gly Asp Leu Asn Ile Thr Asn Glu Gly Ser Asp Thr Glu Met Gln Ile
    530                 535                 540
Gly Gly Asp Val Ser Gln Lys Glu Gly Asn Leu Thr Ile Ser Ser Asp
545                 550                 555                 560
Lys Ile Asn Ile Thr Lys Gln Ile Thr Ile Lys Ala Gly Val Asp Gly
                565                 570                 575
Glu Asn Ser Asp Ser Asp Ala Thr Asn Asn Ala Asn Leu Thr Ile Lys
            580                 585                 590
Thr Lys Glu Leu Lys Leu Thr Gln Asp Leu Asn Ile Ser Gly Phe Asn
        595                 600                 605
Lys Ala Glu Ile Thr Ala Lys Asp Gly Ser Asp Leu Thr Ile Gly Asn
    610                 615                 620
Thr Asn Ser Ala Asp Gly Thr Asn Ala Lys Lys Val Thr Phe Asn Gln
625                 630                 635                 640
Val Lys Asp Ser Lys Ile Ser Ala Asp Gly His Lys Val Thr Leu His
                645                 650                 655
Ser Lys Val Glu Thr Ser Gly Ser Asn Asn Thr Glu Asp Ser Ser
            660                 665                 670
```

```
Asp Asn Asn Ala Gly Leu Thr Ile Asp Ala Lys Asn Val Thr Val Asn
            675                 680                 685
Asn Asn Ile Thr Ser His Lys Ala Val Ser Ile Ser Ala Thr Ser Gly
        690                 695                 700
Glu Ile Thr Thr Lys Thr Gly Thr Thr Ile Asn Ala Thr Thr Gly Asn
705                 710                 715                 720
Val Glu Ile Thr Ala Gln Thr Gly Ser Ile Leu Gly Gly Ile Glu Ser
                725                 730                 735
Ser Ser Gly Ser Val Thr Leu Thr Ala Thr Glu Gly Ala Leu Ala Val
            740                 745                 750
Ser Asn Ile Ser Gly Asn Thr Val Thr Val Thr Ala Asn Ser Gly Ala
            755                 760                 765
Leu Thr Thr Leu Ala Gly Ser Thr Ile Lys Gly Thr Glu Ser Val Thr
770                 775                 780
Thr Ser Ser Gln Ser Gly Asp Ile Gly Gly Thr Ile Ser Gly Gly Thr
785                 790                 795                 800
Val Glu Val Lys Ala Thr Glu Ser Leu Thr Thr Gln Ser Asn Ser Lys
                805                 810                 815
Ile Lys Ala Thr Thr Gly Glu Ala Asn Val Thr Ser Ala Thr Gly Thr
            820                 825                 830
Ile Gly Gly Thr Ile Ser Gly Asn Thr Val Asn Val Thr Ala Asn Ala
            835                 840                 845
Gly Asp Leu Thr Val Gly Asn Gly Ala Glu Ile Asn Ala Thr Glu Gly
            850                 855                 860
Ala Ala Thr Leu Thr Thr Ser Ser Gly Lys Leu Thr Thr Glu Ala Ser
865                 870                 875                 880
Ser His Ile Thr Ser Ala Lys Gly Gln Val Asn Leu Ser Ala Gln Asp
                885                 890                 895
Gly Ser Val Ala Gly Ser Ile Asn Ala Asn Val Thr Leu Asn Thr
            900                 905                 910
Thr Gly Thr Leu Thr Thr Val Lys Gly Ser Asn Ile Asn Ala Thr Ser
            915                 920                 925
Gly Thr Leu Val Ile Asn Ala Lys Asp Ala Glu Leu Asn Gly Ala Ala
            930                 935                 940
Leu Gly Asn His Thr Val Val Asn Ala Thr Asn Ala Asn Gly Ser Gly
945                 950                 955                 960
Ser Val Ile Ala Thr Thr Ser Ser Arg Val Asn Ile Thr Gly Asp Leu
                965                 970                 975
Ile Thr Ile Asn Gly Leu Asn Ile Ile Ser Lys Asn Gly Ile Asn Thr
            980                 985                 990
Val Leu Leu Lys Gly Val Lys Ile Asp Val Lys Tyr Ile Gln Pro Gly
            995                 1000                1005
Ile Ala Ser Val Asp Glu Val Ile Glu Ala Lys Arg Ile Leu Glu Lys
            1010                1015                1020
Val Lys Asp Leu Ser Asp Glu Arg Glu Ala Leu Ala Lys Leu Gly
1025                1030                1035                1040
Val Ser Ala Val Arg Phe Ile Glu Pro Asn Asn Thr Ile Thr Val Asp
                1045                1050                1055
Thr Gln Asn Glu Phe Ala Thr Arg Pro Leu Ser Arg Ile Val Ile Ser
            1060                1065                1070
Glu Gly Arg Ala Cys Phe Ser Asn Ser Asp Gly Ala Thr Val Cys Val
            1075                1080                1085
```

```
Asn Ile Ala Asp Asn Gly Arg
   1090            1095

<210> SEQ ID NO 70
<211> LENGTH: 4937
<212> TYPE: DNA
<213> ORGANISM: Haemophilus influenzae

<400> SEQUENCE: 70
taaatataca agataataaa aataaatcaa gattttgtg atgacaaaca acaattacaa      60
cacctttttt gcagtctata tgcaaatatt ttaaaaaaat agtataaatc cgccatataa     120
aatggtataa tctttcatct ttcatcttta atctttcatc tttcatcttt catctttcat     180
cttttcatct tcatctttca tctttcatct ttcatctttc atctttcatc tttcatcttt     240
cacatgaaat gatgaaccga gggaagggag ggaggggcaa gaatgaagag ggagctgaac     300
gaacgcaaat gataaagtaa tttaattgtt caactaacct taggagaaaa tatgaacaag     360
atatatcgtc tcaaattcag caaacgcctg aatgctttgg ttgctgtgtc tgaattggca     420
cggggttgtg accattccac agaaaaaggc ttccgctatg ttactatctt taggtgtaac     480
cacttagcgt taaagccact ttccgctatg ttactatctt taggtgtaac atctattcca     540
caatctgttt tagcaagcgg cttacaagga atggatgtag tacacggcac agccactatg     600
caagtagatg gtaataaaac cattatccgc aacagtgttg acgctatcat taattggaaa     660
caatttaaca tcgaccaaaa tgaaatggtg cagtttttac aagaaaacaa caactccgcc     720
gtattcaacc gtgttacatc taaccaaatc tcccaattaa aagggatttt agattctaac     780
ggacaagtct ttttaatcaa cccaaatggt atcacaatag gtaaagacgc aattattaac     840
actaatggct ttacggcttc tacgctagac atttctaacg aaaacatcaa ggcgcgtaat     900
ttcaccttcg agcaaaccaa agataaagcg ctcgctgaaa ttgtgaatca cggtttaatt     960
actgtcggta agacggcag tgtaaatctt attggtggca agtgaaaaa cgagggtgtg    1020 attagcgtaa atggtggcag catttcttta ctcgcagggc aaaaaatcac catcagcgat    1080
ataataaacc caaccattac ttacagcatt gccgcgcctg aaaatgaagc ggtcaatctg    1140
ggcgatattt tgccaaaagg cggtaacatt aatgtccgtg ctgccactat tcgaaaccaa    1200
ggtaaacttt ctgctgattc tgtaagcaaa gataaaagcg gcaatattgt tctttccgcc    1260
aaagagggtg aagcggaaat tggcggtgta atttccgctc aaaatcagca agctaaaggc    1320
ggcaagctga tgattacagg cgataaagtc acattaaaaa caggtgcagt tatcgacctt    1380
tcaggtaaag aagggggaga aacttacctt ggcggtgacg agcgcggcga aggtaaaaac    1440
ggcattcaat tagcaaagaa aacctcttta gaaaaaggct caaccatcaa tgtatcaggc    1500
aaagaaaaag gcggacgcgc tattgtgtgg ggcgatattg cgttaattga cggcaatatt    1560
aacgctcaag gtagtggtga tatcgctaaa accggtggtt ttgtggagac atcggggcat    1620
tatttatcca ttgacagcaa tgcaattgtt aaaacaaaag agtggttgct agaccctgat    1680
gatgtaacaa ttgaagccga agacccccct cgcaataata ccgtataaaa tgatgaattc    1740
ccaacaggca ccggtgaagc aagcgaccct aaaaaaaata gcgaactcaa acaacgcta    1800 accaatacaa ctatttcaaa ttatctgaaa acgcctgga caatgaatat aacggcatca    1860
agaaaactta ccgttaatag ctcaatcaac atcggaagca actcccactt aattctccat    1920
agtaaaggtc agcgtggcgg aggcgttcag attgatggag atattacttc taaggcgga    1980 aatttaacca tttattctgg cggatgggtt gatgttcata aaaatattac gcttgatcag    2040
```

-continued

```
ggttttttaa atattaccgc cgcttccgta gcttttgaag gtggaaataa caaagcacgc    2100
gacgcggcaa atgctaaaat tgtcgcccag ggcactgtaa ccattacagg agagggaaaa    2160
gatttcaggg ctaacaacgt atcttttaaac ggaacgggta aaggtctgaa tatcatttca   2220
tcagtgaata atttaaccca caatcttagt ggcacaatta acatatctgg aatataaca    2280 attaaccaaa ctacgagaaa gaacacctcg tattggcaaa ccagccatga ttcgcactgg    2340
aacgtcagtg ctcttaatct agagacaggc gcaaatttta cctttattaa atacatttca   2400
agcaatagca aaggcttaac aacacagtat agaagctctg caggggtgaa ttttaacggc    2460
gtaaatggca acatgtcatt caatctcaaa gaaggagcga aagttaattt caaattaaaa    2520
ccaaacgaga acatgaacac aagcaaacct ttaccaattc ggttttttagc caatatcaca   2580 gccactggtg ggggctctgt ttttttttgat atatatgcca accattctgg cagaggggct    2640
gagttaaaaa tgagtgaaat taatatctct aacggcgcta attttacctt aaattcccat    2700
gttcgcggcg atgacgcttt taaaatcaac aaagacttaa ccataaatgc aaccaattca    2760
aatttcagcc tcagacagac gaaagatgat ttttatgacg ggtacgcacg caatgccatc    2820
aattcaacct acaacatatc cattctgggc ggtaatgtca cccttggtgg acaaaactca    2880
agcagcagca ttacggggaa tattactatc gagaaagcag caaatgttac gctagaagcc    2940
aataacgccc ctaatcagca aaacataagg gatagagtta taaaacttgg cagcttgctc    3000
gttaatggga gtttaagttt aactggcgaa aatgcagata ttaaaggcaa tctcactatt    3060
tcagaaagcg ccacttttaa aggaaagact agagatacccc taaatatcac cggcaatttt   3120
accaataatg gcactgccga aattaatata acacaaggag tggtaaaact tggcaatgtt    3180
accaatgatg gtgattttaaa cattaccact cacgctaaac gcaaccaaag aagcatcatc    3240
ggcggagata taatcaacaa aaaggaagc ttaaatatta cagacagtaa taatgatgct    3300
gaaatccaaa ttggcggcaa tatctcgcaa aaagaaggca acctcacgat ttcttccgat    3360
aaaattaata tcaccaaaca gataacaatc aaaaagggta ttgatggaga ggactctagt    3420
tcagatgcga caagtaatgc caacctaact attaaaacca aagaattgaa attgacagaa    3480
gacctaagta tttcaggttt caataaagca gagattacag ccaaagatgg tagagattta    3540
actattggca acagtaatga cggtaacagc ggtgccgaag ccaaaacagt aactttttaac   3600 aatgttaaag attcaaaaat ctctgctgac ggtcacaatg tgacactaaa tagcaaagtg    3660
aaaacatcta gcagcaatgg cggacgtgaa agcaatagcg acaacgatac cggcttaact    3720
attactgcaa aaaatgtaga agtaaacaaa gatattactt ctctcaaaac agtaaatatc    3780
accgcgtcgg aaaaggttac caccacagca ggctcgacca ttaacgcaac aaatggcaaa    3840
gcaagtatta caaccaaaac aggtgatatc agcggtacga tttccggtaa cacggtaagt    3900
gttagcgcga ctggtgattt aaccactaaa tccggctcaa aaattgaagc gaaatcgggt    3960
gaggctaatg taacaagtgc aacaggtaca attggcggta caatttccgg taatacggta    4020
aatgttacgg caaacgctgg cgatttaaca gttgggaatg gcgcagaaat taatgcgaca    4080
gaaggagctg caaccttaac cgcaacaggg aatacctga ctactgaagc cggttctagc     4140
atcacttcaa ctaagggtca ggtagacctc ttggctcaga atggtagcat cgcaggaagc    4200
attaatgctg ctaatgtgac attaaatact acaggcacct taaccaccgt ggcaggctcg    4260
gatattaaag caaccagcgg caccttggtt attaacgcaa aagatgctaa gctaaatggt    4320
gatgcatcag gtgatagtac agaagtgaat gcagtcaacg caagcggctc tggtagtgtg    4380
actgcggcaa cctcaagcag tgtgaatatc actggggatt taaacacagt aaatggggtta   4440
```

-continued

```
aatatcattt cgaaagatgg tagaaacact gtgcgcttaa gaggcaagga aattgaggtg   4500
aaatatatcc agccaggtgt agcaagtgta gaagaagtaa ttgaagcgaa acgcgtcctt   4560
gaaaaagtaa aagatttatc tgatgaagaa agagaaacat tagctaaact tggtgtaagt   4620
gctgtacgtt tgttgagcc aaataataca attacagtca atacacaaaa tgaatttaca    4680
accagaccgt caagtcaagt gataaatttct gaaggtaagg cgtgtttctc aagtggtaat  4740
ggcgcacgag tatgtaccaa tgttgctgac gatggacagc cgtagtcagt aattgacaag   4800
gtagatttca tcctgcaatg aagtcatttt attttcgtat tatttactgt gtgggttaaa   4860
gttcagtacg ggctttaccc atcttgtaaa aaattacgga gaatacaata aagtattttt   4920
aacaggttat tattatg                                                  4937
```

<210> SEQ ID NO 71
<211> LENGTH: 1477
<212> TYPE: PRT
<213> ORGANISM: Haemophilus influenzae

<400> SEQUENCE: 71

```
Met Asn Lys Ile Tyr Arg Leu Lys Phe Ser Lys Arg Leu Asn Ala Leu
 1               5                  10                  15

Val Ala Val Ser Glu Leu Ala Arg Gly Cys Asp His Ser Thr Glu Lys
            20                  25                  30

Gly Phe Arg Tyr Val Thr Ile Phe Arg Cys Asn His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
```

-continued

```
                275                 280                 285
Asp Ser Val Ser Lys Asp Lys Ser Gly Asn Ile Val Leu Ser Ala Lys
    290                 295                 300
Glu Gly Glu Ala Glu Ile Gly Gly Val Ile Ser Ala Gln Asn Gln Gln
305                 310                 315                 320
Ala Lys Gly Gly Lys Leu Met Ile Thr Gly Asp Lys Val Thr Leu Lys
                325                 330                 335
Thr Gly Ala Val Ile Asp Leu Ser Gly Lys Glu Gly Gly Glu Thr Tyr
                340                 345                 350
Leu Gly Gly Asp Glu Arg Gly Glu Gly Lys Asn Gly Ile Gln Leu Ala
                355                 360                 365
Lys Lys Thr Ser Leu Glu Lys Gly Ser Thr Ile Asn Val Ser Gly Lys
                370                 375                 380
Glu Lys Gly Gly Arg Ala Ile Val Trp Gly Asp Ile Ala Leu Ile Asp
385                 390                 395                 400
Gly Asn Ile Asn Ala Gln Gly Ser Gly Asp Ile Ala Lys Thr Gly Gly
                405                 410                 415
Phe Val Glu Thr Ser Gly His Tyr Leu Ser Ile Asp Ser Asn Ala Ile
                420                 425                 430
Val Lys Thr Lys Glu Trp Leu Leu Asp Pro Asp Val Thr Ile Glu
                435                 440                 445
Ala Glu Asp Pro Leu Arg Asn Asn Thr Gly Ile Asn Asp Glu Phe Pro
450                 455                 460
Thr Gly Thr Gly Glu Ala Ser Asp Pro Lys Lys Asn Ser Glu Leu Lys
465                 470                 475                 480
Thr Thr Leu Thr Asn Thr Thr Ile Ser Asn Tyr Leu Lys Asn Ala Trp
                485                 490                 495
Thr Met Asn Ile Thr Ala Ser Arg Lys Leu Thr Val Asn Ser Ser Ile
                500                 505                 510
Asn Ile Gly Ser Asn Ser His Leu Ile Leu His Ser Lys Gly Gln Arg
                515                 520                 525
Gly Gly Gly Val Gln Ile Asp Gly Asp Ile Thr Ser Lys Gly Gly Asn
                530                 535                 540
Leu Thr Ile Tyr Ser Gly Gly Trp Val Asp Val His Lys Asn Ile Thr
545                 550                 555                 560
Leu Asp Gln Gly Phe Leu Asn Ile Thr Ala Ala Ser Val Ala Phe Glu
                565                 570                 575
Gly Gly Asn Asn Lys Ala Arg Asp Ala Ala Asn Ala Lys Ile Val Ala
                580                 585                 590
Gln Gly Thr Val Thr Ile Thr Gly Glu Gly Lys Asp Phe Arg Ala Asn
                595                 600                 605
Asn Val Ser Leu Asn Gly Thr Gly Lys Gly Leu Asn Ile Ile Ser Ser
                610                 615                 620
Val Asn Asn Leu Thr His Asn Leu Ser Gly Thr Ile Asn Ile Ser Gly
625                 630                 635                 640
Asn Ile Thr Ile Asn Gln Thr Thr Arg Lys Asn Thr Ser Tyr Trp Gln
                645                 650                 655
Thr Ser His Asp Ser His Trp Asn Val Ser Ala Leu Asn Leu Glu Thr
                660                 665                 670
Gly Ala Asn Phe Thr Phe Ile Lys Tyr Ile Ser Ser Asn Ser Lys Gly
                675                 680                 685
Leu Thr Thr Gln Tyr Arg Ser Ser Ala Gly Val Asn Phe Asn Gly Val
                690                 695                 700
```

-continued

```
Asn Gly Asn Met Ser Phe Asn Leu Lys Glu Gly Ala Lys Val Asn Phe
705                 710                 715                 720
Lys Leu Lys Pro Asn Glu Asn Met Asn Thr Ser Lys Pro Leu Pro Ile
            725                 730                 735
Arg Phe Leu Ala Asn Ile Thr Ala Thr Gly Gly Ser Val Phe Phe
        740                 745                 750
Asp Ile Tyr Ala Asn His Ser Arg Gly Ala Glu Leu Lys Met Ser
        755                 760                 765
Glu Ile Asn Ile Ser Asn Gly Ala Asn Phe Thr Leu Asn Ser His Val
    770                 775                 780
Arg Gly Asp Asp Ala Phe Lys Ile Asn Lys Asp Leu Thr Ile Asn Ala
785                 790                 795                 800
Thr Asn Ser Asn Phe Ser Leu Arg Gln Thr Lys Asp Asp Phe Tyr Asp
                805                 810                 815
Gly Tyr Ala Arg Asn Ala Ile Asn Ser Thr Tyr Asn Ile Ser Ile Leu
            820                 825                 830
Gly Gly Asn Val Thr Leu Gly Gly Gln Asn Ser Ser Ser Ile Thr
            835                 840                 845
Gly Asn Ile Thr Ile Glu Lys Ala Ala Asn Val Thr Leu Glu Ala Asn
    850                 855                 860
Asn Ala Pro Asn Gln Gln Asn Ile Arg Asp Arg Val Ile Lys Leu Gly
865                 870                 875                 880
Ser Leu Leu Val Asn Gly Ser Leu Ser Leu Thr Gly Glu Asn Ala Asp
                885                 890                 895
Ile Lys Gly Asn Leu Thr Ile Ser Glu Ser Ala Thr Phe Lys Gly Lys
            900                 905                 910
Thr Arg Asp Thr Leu Asn Ile Thr Gly Asn Phe Thr Asn Asn Gly Thr
            915                 920                 925
Ala Glu Ile Asn Ile Thr Gln Gly Val Val Lys Leu Gly Asn Val Thr
            930                 935                 940
Asn Asp Gly Asp Leu Asn Ile Thr Thr His Ala Lys Arg Asn Gln Arg
945                 950                 955                 960
Ser Ile Ile Gly Gly Asp Ile Ile Asn Lys Lys Gly Ser Leu Asn Ile
                965                 970                 975
Thr Asp Ser Asn Asn Asp Ala Glu Ile Gln Ile Gly Gly Asn Ile Ser
            980                 985                 990
Gln Lys Glu Gly Asn Leu Thr Ile Ser Ser Asp Lys Ile Asn Ile Thr
            995                 1000                1005
Lys Gln Ile Thr Ile Lys Lys Gly Ile Asp Gly Glu Asp Ser Ser Ser
    1010                1015                1020
Asp Ala Thr Ser Asn Ala Asn Leu Thr Ile Lys Thr Lys Glu Leu Lys
1025                1030                1035                1040
Leu Thr Glu Asp Leu Ser Ile Ser Gly Phe Asn Lys Ala Glu Ile Thr
                1045                1050                1055
Ala Lys Asp Gly Arg Asp Leu Thr Ile Gly Asn Ser Asn Asp Gly Asn
            1060                1065                1070
Ser Gly Ala Glu Ala Lys Thr Val Thr Phe Asn Asn Val Lys Asp Ser
        1075                1080                1085
Lys Ile Ser Ala Asp Gly His Asn Val Thr Leu Asn Ser Lys Val Lys
    1090                1095                1100
Thr Ser Ser Ser Asn Gly Gly Arg Glu Ser Asn Ser Asp Asn Asp Thr
1105                1110                1115                1120
```

```
Gly Leu Thr Ile Thr Ala Lys Asn Val Glu Val Asn Lys Asp Ile Thr
            1125                1130                1135

Ser Leu Lys Thr Val Asn Ile Thr Ala Ser Glu Lys Val Thr Thr Thr
            1140                1145                1150

Ala Gly Ser Thr Ile Asn Ala Thr Asn Gly Lys Ala Ser Ile Thr Thr
            1155                1160                1165

Lys Thr Gly Asp Ile Ser Gly Thr Ile Ser Gly Asn Thr Val Ser Val
    1170                1175                1180

Ser Ala Thr Gly Asp Leu Thr Thr Lys Ser Gly Ser Lys Ile Glu Ala
1185                1190                1195                1200

Lys Ser Gly Glu Ala Asn Val Thr Ser Ala Thr Gly Thr Ile Gly Gly
            1205                1210                1215

Thr Ile Ser Gly Asn Thr Val Asn Val Thr Ala Asn Ala Gly Asp Leu
            1220                1225                1230

Thr Val Gly Asn Gly Ala Glu Ile Asn Ala Thr Glu Gly Ala Ala Thr
            1235                1240                1245

Leu Thr Ala Thr Gly Asn Thr Leu Thr Thr Glu Ala Gly Ser Ser Ile
    1250                1255                1260

Thr Ser Thr Lys Gly Gln Val Asp Leu Leu Ala Gln Asn Gly Ser Ile
1265                1270                1275                1280

Ala Gly Ser Ile Asn Ala Ala Asn Val Thr Leu Asn Thr Gly Thr
            1285                1290                1295

Leu Thr Thr Val Ala Gly Ser Asp Ile Lys Ala Thr Ser Gly Thr Leu
            1300                1305                1310

Val Ile Asn Ala Lys Asp Ala Lys Leu Asn Gly Asp Ala Ser Gly Asp
            1315                1320                1325

Ser Thr Glu Val Asn Ala Val Asn Ala Ser Gly Ser Gly Ser Val Thr
    1330                1335                1340

Ala Ala Thr Ser Ser Val Asn Ile Thr Gly Asp Leu Asn Thr Val
1345                1350                1355                1360

Asn Gly Leu Asn Ile Ile Ser Lys Asp Gly Arg Asn Thr Val Arg Leu
            1365                1370                1375

Arg Gly Lys Glu Ile Glu Val Lys Tyr Ile Gln Pro Gly Val Ala Ser
            1380                1385                1390

Val Glu Glu Val Ile Glu Ala Lys Arg Val Leu Glu Lys Val Lys Asp
    1395                1400                1405

Leu Ser Asp Glu Glu Arg Glu Thr Leu Ala Lys Leu Gly Val Ser Ala
    1410                1415                1420

Val Arg Phe Val Glu Pro Asn Asn Thr Ile Thr Val Asn Thr Gln Asn
1425                1430                1435                1440

Glu Phe Thr Thr Arg Pro Ser Ser Gln Val Ile Ile Ser Glu Gly Lys
            1445                1450                1455

Ala Cys Phe Ser Ser Gly Asn Gly Ala Arg Val Cys Thr Asn Val Ala
            1460                1465                1470

Asp Asp Gly Gln Pro
        1475

<210> SEQ ID NO 72
<211> LENGTH: 3108
<212> TYPE: DNA
<213> ORGANISM: Haemophilus influenzae

<400> SEQUENCE: 72
cctgatgatg taacaattga agccgaagac ccccttcgca ataataccgg tataaatgat      60
```

-continued

```
gaattcccaa caggcaccgg tgaagcaagc gaccctaaaa aaaatagcga actcaaaaca    120
acgctaacca atacaactat ttcaaattat ctgaaaaacg cctggacaat gaatataacg    180
gcatcaagaa aacttaccgt taatagctca atcaacatcg gaagcaactc ccacttaatt    240
ctccatagta aaggtcagcg tggcggaggc gttcagattg atggagatat acttctaaa    300
ggcggaaatt taaccattta ttctggcgga tgggttgatg ttcataaaaa tattacgctt    360
gatcagggtt ttttaaatat taccgccgct tccgtagctt ttgaaggtgg aaataacaaa    420
gcacgcgacg cggcaaatgc taaaattgtc gcccagggca ctgtaaccat tacaggagag    480
ggaaaagatt tcagggctaa caacgtatct ttaaacgaa cgggtaaagg tctgaatatc     540
atttcatcag tgaataattt aacccacaat cttagtggca caattaacat atctgggaat    600
ataacaatta accaaactac gagaaagaac acctcgtatt ggcaaaccag ccatgattcg    660
cactggaacg tcagtgctct taatctagag acaggcgcaa atttaccctt tattaaatac    720
atttcaagca atagcaaagg cttaacaaca cagtatagaa gctctgcagg ggtgaatttt    780
aacggcgtaa atgcaacat gtcattcaat ctcaaagaag gagcgaaagt taatttcaaa     840
ttaaaaccaa acgagaacat gaacacaagc aaacctttac caattcggtt tttagccaat    900
atcacagcca ctggtggggg ctctgttttt tttgatatat atgccaacca ttctggcaga    960
ggggctgagt taaaaatgag tgaaattaat atctctaacg cgctaatttt taccttaaat   1020
tcccatgttc gcgcgatga cgcttttaaa atcaacaaag acttaaccat aaatgcaacc    1080
aattcaaatt tcagcctcag acagacgaaa gatgattttt atgacgggta cgcacgcaat   1140
gccatcaatt caacctacaa catatccatt ctgggcggta atgtcaccct tggtggacaa   1200
aactcaagca gcagcattac ggggaatatt actatcgaga aagcagcaaa tgttacgcta   1260
gaagccaata acgcccctaa tcagcaaaac ataagggata gagttataaa acttggcagc   1320
ttgctcgtta atgggagttt aagtttaact ggcgaaaatg cagatattaa aggcaatctc   1380
actatttcag aaagcgccac ttttaaagga aagactagag atacctaaa tatcaccggc    1440
aatttttacca ataatggcac tgccgaaatt aatataacac aaggagtggt aaaacttggc   1500
aatgttacca atgatggtga tttaaacatt accactcacg ctaaacgcaa ccaaagaagc   1560
atcatcggcg gagatataat caacaaaaaa ggaagcttaa atattacaga cagtaataat   1620
gatgctgaaa tccaaattgg cggcaatatc tcgcaaaaag aaggcaaccct cacgatttct   1680
tccgataaaa ttaatatcac caaacagata acaatcaaaa agggtattga tggagaggac   1740
tctagttcag atgcgacaag taatgccaac ctaactatta aaaccaaaga attgaaattg   1800
acagaagacc taagtatttc aggtttcaat aaagcagaga ttacagccaa agatggtaga   1860
gatttaacta ttggcaacag taatgacggt aacagcggtg ccgaagccaa aacagtaact   1920
tttaacaatg ttaaagattc aaaaatctct gctgacggtc acaatgtgac actaaatagc   1980
aaagtgaaaa catctagcag caatggcgga cgtgaaagca atagcgacaa cgataccggc   2040
ttaactatta ctgcaaaaaa tgtagaagta aacaaagata ttacttctct caaaacagta   2100
aatatcaccg cgtcggaaaa ggttaccacc acagcaggct cgaccattaa cgcaacaaat   2160
ggcaaagcaa gtattacaac caaaacaggt gatatcagcg gtacgatttc cggtaacacg   2220
gtaagtgtta gcgcgactgg tgatttaacc actaaatccg gctcaaaaat tgaagcgaaa   2280
tcgggtgagg ctaatgtaac aagtgcaaca ggtacaattg gcggtacaat ttccggtaat   2340
acggtaaatg ttacggcaaa cgctggcgat ttaacagttg gaatggcgc agaaattaat    2400
gcgacagaag gagctgcaac cttaaccgca acagggaata ccttgactac tgaagccggt   2460
```

```
tctagcatca cttcaactaa gggtcaggta gacctcttgg ctcagaatgg tagcatcgca    2520
ggaagcatta atgctgctaa tgtgacatta aatactacag gcaccttaac caccgtggca    2580
ggctcggata ttaaagcaac cagcggcacc ttggttatta acgcaaaaga tgctaagcta    2640
aatggtgatg catcaggtga tagtacagaa gtgaatgcag tcaacgcaag cggctctggt    2700
agtgtgactg cggcaacctc aagcagtgtg aatatcactg gggatttaaa cacagtaaat    2760
gggttaaata tcatttcgaa agatggtaga acactgtgc gcttaagagg caaggaaatt    2820
gaggtgaaat atatccagcc aggtgtagca agtgtagaaa agtaattga agcgaaacgc    2880 gtccttgaaa aagtaaaaga tttatctgat gaagaaagag aaacattagc taaacttggt    2940
gtaagtgctg tacgttttgt tgagccaaat aatacaatta cagtcaatac acaaaatgaa    3000
tttacaacca gaccgtcaag tcaagtgata atttctgaag gtaaggcgtg tttctcaagt    3060
ggtaatggcg cacgagtatg taccaatgtt gctgacgatg gacagccg                 3108
```

<210> SEQ ID NO 73
<211> LENGTH: 1036
<212> TYPE: PRT
<213> ORGANISM: Haemophilus influenzae

<400> SEQUENCE: 73

```
Pro Asp Asp Val Thr Ile Glu Ala Glu Asp Pro Leu Arg Asn Asn Thr
 1               5                  10                  15

Gly Ile Asn Asp Glu Phe Pro Thr Gly Thr Gly Glu Ala Ser Asp Pro
            20                  25                  30

Lys Lys Asn Ser Glu Leu Lys Thr Thr Leu Thr Asn Thr Thr Ile Ser
        35                  40                  45

Asn Tyr Leu Lys Asn Ala Trp Thr Met Asn Ile Thr Ala Ser Arg Lys
    50                  55                  60

Leu Thr Val Asn Ser Ser Ile Asn Ile Gly Ser Asn Ser His Leu Ile
65                  70                  75                  80

Leu His Ser Lys Gly Gln Arg Gly Gly Gly Val Gln Ile Asp Gly Asp
                85                  90                  95

Ile Thr Ser Lys Gly Gly Asn Leu Thr Ile Tyr Ser Gly Gly Trp Val
            100                 105                 110

Asp Val His Lys Asn Ile Thr Leu Asp Gln Gly Phe Leu Asn Ile Thr
        115                 120                 125

Ala Ala Ser Val Ala Phe Glu Gly Gly Asn Asn Lys Ala Arg Asp Ala
    130                 135                 140

Ala Asn Ala Lys Ile Val Ala Gln Gly Thr Val Thr Ile Thr Gly Glu
145                 150                 155                 160

Gly Lys Asp Phe Arg Ala Asn Asn Val Ser Leu Asn Gly Thr Gly Lys
                165                 170                 175

Gly Leu Asn Ile Ile Ser Ser Val Asn Asn Leu Thr His Asn Leu Ser
            180                 185                 190

Gly Thr Ile Asn Ile Ser Gly Asn Ile Thr Ile Asn Gln Thr Thr Arg
        195                 200                 205

Lys Asn Thr Ser Tyr Trp Gln Thr Ser His Asp Ser His Trp Asn Val
    210                 215                 220

Ser Ala Leu Asn Leu Glu Thr Gly Ala Asn Phe Thr Phe Ile Lys Tyr
225                 230                 235                 240

Ile Ser Ser Asn Ser Lys Gly Leu Thr Thr Gln Tyr Arg Ser Ser Ala
                245                 250                 255
```

```
Gly Val Asn Phe Asn Gly Val Asn Gly Asn Met Ser Phe Asn Leu Lys
            260                 265                 270

Glu Gly Ala Lys Val Asn Phe Lys Leu Lys Pro Asn Glu Asn Met Asn
            275                 280                 285

Thr Ser Lys Pro Leu Pro Ile Arg Phe Leu Ala Asn Ile Thr Ala Thr
            290                 295                 300

Gly Gly Gly Ser Val Phe Phe Asp Ile Tyr Ala Asn His Ser Gly Arg
305                 310                 315                 320

Gly Ala Glu Leu Lys Met Ser Glu Ile Asn Ile Ser Asn Gly Ala Asn
                325                 330                 335

Phe Thr Leu Asn Ser His Val Arg Gly Asp Asp Ala Phe Lys Ile Asn
            340                 345                 350

Lys Asp Leu Thr Ile Asn Ala Thr Asn Ser Asn Phe Ser Leu Arg Gln
            355                 360                 365

Thr Lys Asp Asp Phe Tyr Asp Gly Tyr Ala Arg Asn Ala Ile Asn Ser
            370                 375                 380

Thr Tyr Asn Ile Ser Ile Leu Gly Gly Asn Val Thr Leu Gly Gly Gln
385                 390                 395                 400

Asn Ser Ser Ser Ile Thr Gly Asn Ile Thr Ile Glu Lys Ala Ala
                405                 410                 415

Asn Val Thr Leu Glu Ala Asn Asn Ala Pro Asn Gln Gln Asn Ile Arg
            420                 425                 430

Asp Arg Val Ile Lys Leu Gly Ser Leu Leu Val Asn Gly Ser Leu Ser
            435                 440                 445

Leu Thr Gly Glu Asn Ala Asp Ile Lys Gly Asn Leu Thr Ile Ser Glu
450                 455                 460

Ser Ala Thr Phe Lys Gly Lys Thr Arg Asp Thr Leu Asn Ile Thr Gly
465                 470                 475                 480

Asn Phe Thr Asn Asn Gly Thr Ala Glu Ile Asn Ile Thr Gln Gly Val
                485                 490                 495

Val Lys Leu Gly Asn Val Thr Asn Asp Gly Asp Leu Asn Ile Thr Thr
            500                 505                 510

His Ala Lys Arg Asn Gln Arg Ser Ile Ile Gly Gly Asp Ile Ile Asn
            515                 520                 525

Lys Lys Gly Ser Leu Asn Ile Thr Asp Ser Asn Asn Asp Ala Glu Ile
            530                 535                 540

Gln Ile Gly Gly Asn Ile Ser Gln Lys Glu Gly Asn Leu Thr Ile Ser
545                 550                 555                 560

Ser Asp Lys Ile Asn Ile Thr Lys Gln Ile Thr Ile Lys Lys Gly Ile
                565                 570                 575

Asp Gly Glu Asp Ser Ser Ser Asp Ala Thr Ser Asn Ala Asn Leu Thr
            580                 585                 590

Ile Lys Thr Lys Glu Leu Lys Leu Thr Glu Asp Leu Ser Ile Ser Gly
            595                 600                 605

Phe Asn Lys Ala Glu Ile Thr Ala Lys Asp Gly Arg Asp Leu Thr Ile
            610                 615                 620

Gly Asn Ser Asn Asp Gly Asn Ser Gly Ala Glu Ala Lys Thr Val Thr
625                 630                 635                 640

Phe Asn Asn Val Lys Asp Ser Lys Ile Ser Ala Asp Gly His Asn Val
                645                 650                 655

Thr Leu Asn Ser Lys Val Lys Thr Ser Ser Asn Gly Gly Arg Glu
            660                 665                 670

Ser Asn Ser Asp Asn Asp Thr Gly Leu Thr Ile Thr Ala Lys Asn Val
```

-continued

|   | 675 |   |   |   | 680 |   |   |   | 685 |   |   |
|---|---|---|---|---|---|---|---|---|---|---|---|

Glu Val Asn Lys Asp Ile Thr Ser Leu Lys Thr Val Asn Ile Thr Ala
690                  695                  700

Ser Glu Lys Val Thr Thr Thr Ala Gly Ser Thr Ile Asn Ala Thr Asn
705                  710                  715                  720

Gly Lys Ala Ser Ile Thr Thr Lys Thr Gly Asp Ile Ser Gly Thr Ile
                    725                  730                  735

Ser Gly Asn Thr Val Ser Val Ser Ala Thr Gly Asp Leu Thr Thr Lys
                    740                  745                  750

Ser Gly Ser Lys Ile Glu Ala Lys Ser Gly Glu Ala Asn Val Thr Ser
                    755                  760                  765

Ala Thr Gly Thr Ile Gly Gly Thr Ile Ser Gly Asn Thr Val Asn Val
770                  775                  780

Thr Ala Asn Ala Gly Asp Leu Thr Val Gly Asn Gly Ala Glu Ile Asn
785                  790                  795                  800

Ala Thr Glu Gly Ala Ala Thr Leu Thr Ala Thr Gly Asn Thr Leu Thr
                    805                  810                  815

Thr Glu Ala Gly Ser Ser Ile Thr Ser Thr Lys Gly Gln Val Asp Leu
                    820                  825                  830

Leu Ala Gln Asn Gly Ser Ile Ala Gly Ser Ile Asn Ala Ala Asn Val
                    835                  840                  845

Thr Leu Asn Thr Thr Gly Thr Leu Thr Thr Val Ala Gly Ser Asp Ile
850                  855                  860

Lys Ala Thr Ser Gly Thr Leu Val Ile Asn Ala Lys Asp Ala Lys Leu
865                  870                  875                  880

Asn Gly Asp Ala Ser Gly Asp Ser Thr Glu Val Asn Ala Val Asn Ala
                    885                  890                  895

Ser Gly Ser Gly Ser Val Thr Ala Ala Thr Ser Ser Val Asn Ile
                    900                  905                  910

Thr Gly Asp Leu Asn Thr Val Asn Gly Leu Asn Ile Ile Ser Lys Asp
                    915                  920                  925

Gly Arg Asn Thr Val Arg Leu Arg Gly Lys Glu Ile Glu Val Lys Tyr
930                  935                  940

Ile Gln Pro Gly Val Ala Ser Val Glu Glu Val Ile Glu Ala Lys Arg
945                  950                  955                  960

Val Leu Glu Lys Val Lys Asp Leu Ser Asp Glu Glu Arg Glu Thr Leu
                    965                  970                  975

Ala Lys Leu Gly Val Ser Ala Val Arg Phe Val Glu Pro Asn Asn Thr
                    980                  985                  990

Ile Thr Val Asn Thr Gln Asn Glu Phe Thr Thr Arg Pro Ser Ser Gln
                    995                  1000                 1005

Val Ile Ile Ser Glu Gly Lys Ala Cys Phe Ser Ser Gly Asn Gly Ala
     1010                 1015                 1020

Arg Val Cys Thr Asn Val Ala Asp Asp Gly Gln Pro
1025                 1030                 1035

<210> SEQ ID NO 74
<211> LENGTH: 25
<212> TYPE: DNA
<213> ORGANISM: Haemophilus influenzae

<400> SEQUENCE: 74
tcttttgctg tggctgatgc ccta                                    25

```
<210> SEQ ID NO 75
<211> LENGTH: 25
<212> TYPE: DNA
<213> ORGANISM: Haemophilus influenzae

<400> SEQUENCE: 75
cactgatagg ttgctcatat tcgcc                                    25

<210> SEQ ID NO 76
<211> LENGTH: 6
<212> TYPE: PRT
<213> ORGANISM: Haemophilus influenzae

<400> SEQUENCE: 76

Val Gly Val His Lys Asn
  1               5

<210> SEQ ID NO 77
<211> LENGTH: 20
<212> TYPE: DNA
<213> ORGANISM: Haemophilus influenzae

<400> SEQUENCE: 77
ggtgatgttc ataaaaatat                                          20

<210> SEQ ID NO 78
<211> LENGTH: 21
<212> TYPE: DNA
<213> ORGANISM: Haemophilus influenzae

<400> SEQUENCE: 78
atatttttat gaacatcaac c                                        21

<210> SEQ ID NO 79
<211> LENGTH: 8
<212> TYPE: PRT
<213> ORGANISM: Haemophilus influenzae

<400> SEQUENCE: 79

Gly Gly Ser Leu Thr Ile Asn Ser
  1               5

<210> SEQ ID NO 80
<211> LENGTH: 22
<212> TYPE: DNA
<213> ORGANISM: Haemophilus influenzae

<400> SEQUENCE: 80
ggcggagttt aactattaac tc                                       22

<210> SEQ ID NO 81
<211> LENGTH: 23
<212> TYPE: DNA
<213> ORGANISM: Haemophilus influenzae

<400> SEQUENCE: 81
gagttaatag ttaaacttcc gcc                                      23

<210> SEQ ID NO 82
<211> LENGTH: 10
<212> TYPE: PRT
<213> ORGANISM: Haemophilus influenzae

<400> SEQUENCE: 82
```

-continued

```
Gly Val Asp Gly Glu Asn Ser Asp Ser Asp
 1               5                  10
```

<210> SEQ ID NO 83
<211> LENGTH: 31
<212> TYPE: DNA
<213> ORGANISM: Haemophilus influenzae

<400> SEQUENCE: 83
ggtgttgatg gggagaattc cgattcagac g                           31

<210> SEQ ID NO 84
<211> LENGTH: 10
<212> TYPE: PRT
<213> ORGANISM: Haemophilus influenzae

<400> SEQUENCE: 84

```
Val Cys Val Asn Ile Ala Asp Asn Gly Arg
 1               5                  10
```

<210> SEQ ID NO 85
<211> LENGTH: 33
<212> TYPE: DNA
<213> ORGANISM: Haemophilus influenzae

<400> SEQUENCE: 85
gtgtgcgtta atatcgctga taacgggcgg tag                         33

<210> SEQ ID NO 86
<211> LENGTH: 43
<212> TYPE: DNA
<213> ORGANISM: Haemophilus influenzae

<400> SEQUENCE: 86
ggcctctaga ctaccgcccg ttatcagcga tattaacgca cac              43

<210> SEQ ID NO 87
<211> LENGTH: 41
<212> TYPE: DNA
<213> ORGANISM: Haemophilus influenzae

<400> SEQUENCE: 87
ggcctctaga cggtcagtaa ttgacaaggt agatttcatc c                41

<210> SEQ ID NO 88
<211> LENGTH: 13
<212> TYPE: PRT
<213> ORGANISM: Haemophilus influenzae

<400> SEQUENCE: 88

```
Gly Arg Gln Trp Phe Asp Leu Arg Glu Phe Asn Met Ala
 1               5                  10
```

<210> SEQ ID NO 89
<211> LENGTH: 39
<212> TYPE: DNA
<213> ORGANISM: Haemophilus influenzae

<400> SEQUENCE: 89
ggtcgtcagt ggttcgattt gcgtgaattc aatatggca                   39

<210> SEQ ID NO 90
<211> LENGTH: 39
<212> TYPE: DNA

```
<213> ORGANISM: Haemophilus influenzae

<400> SEQUENCE: 90
tgccatattg aattcacgca aatcgaacca ctgacgacc                                 39

<210> SEQ ID NO 91
<211> LENGTH: 13
<212> TYPE: PRT
<213> ORGANISM: Haemophilus influenzae

<400> SEQUENCE: 91

Met Pro Asp Asp Val Ser Ile Asp Ala Pro Ser Ala Glu
  1               5                  10

<210> SEQ ID NO 92
<211> LENGTH: 50
<212> TYPE: DNA
<213> ORGANISM: Haemophilus influenzae

<400> SEQUENCE: 92
cgggatccca tatgccggat gatgtatcca ttgacgcacc ttcggctgaa                     50

<210> SEQ ID NO 93
<211> LENGTH: 13
<212> TYPE: PRT
<213> ORGANISM: Haemophilus influenzae

<400> SEQUENCE: 93

Ala Ala Val Cys Thr Asn Val Ala Asp Asp Gly Gln Gln
  1               5                  10

<210> SEQ ID NO 94
<211> LENGTH: 43
<212> TYPE: DNA
<213> ORGANISM: Haemophilus influenzae

<400> SEQUENCE: 94
gcagcagtat gtaccaatgt tgctgacgat ggacagcagt agt                            43

<210> SEQ ID NO 95
<211> LENGTH: 49
<212> TYPE: DNA
<213> ORGANISM: Haemophilus influenzae

<400> SEQUENCE: 95
gtctagacta ctgctgtcca tcgtcagcaa cattggtaca tactgctgc                      49
```